(12) United States Patent
Bhattacharjee et al.

(10) Patent No.: US 12,152,031 B2
(45) Date of Patent: *Nov. 26, 2024

(54) BIODEFENSE AGENTS

(71) Applicant: BIOVERSYS AG, Basel (CH)

(72) Inventors: Ashoke Bhattacharjee, Cheshire, CT (US); Erin M. Duffy, Deep River, CT (US); Trudy Grossman, New Haven, CT (US); Joseph A. Ippolito, Guilford, CT (US); Zoltan F. Kanyo, North Haven, CT (US)

(73) Assignee: BIOVERSYS AG, Basel (CH)

( * ) Notice: Subject to any disclaimer, the term of this patent is extended or adjusted under 35 U.S.C. 154(b) by 994 days.

This patent is subject to a terminal disclaimer.

(21) Appl. No.: 16/972,775

(22) PCT Filed: Jun. 6, 2019

(86) PCT No.: PCT/IB2019/000808
§ 371 (c)(1),
(2) Date: Dec. 7, 2020

(87) PCT Pub. No.: WO2019/234508
PCT Pub. Date: Dec. 12, 2019

(65) Prior Publication Data
US 2021/0253577 A1    Aug. 19, 2021

Related U.S. Application Data

(60) Provisional application No. 62/681,627, filed on Jun. 6, 2018.

(51) Int. Cl.
*C07D 487/04* (2006.01)
*A61P 31/04* (2006.01)

(52) U.S. Cl.
CPC ............ *C07D 487/04* (2013.01); *A61P 31/04* (2018.01)

(58) Field of Classification Search
CPC .............................. C07D 487/04; A61P 31/04
See application file for complete search history.

(56) References Cited

U.S. PATENT DOCUMENTS 10,815,237 B2 * 10/2020 Duffy .................. C07D 487/04

FOREIGN PATENT DOCUMENTS

WO    WO-2017193017 A1 * 11/2017 .............. A61P 31/04

* cited by examiner

*Primary Examiner* — James D. Anderson
(74) *Attorney, Agent, or Firm* — Withers Bergman LLP; Thomas C. Meyers

(57) ABSTRACT

The present disclosure relates to methods of treating, preventing, reducing the risk of, or delaying the onset of microbial infections in humans and animals that are caused by or involves one or more microorganisms which are capable of being used as biological weapons, the method including administering a pyrrolocytosine compound or a tautomer thereof or a pharmaceutically acceptable salt of the compound or tautomer.

29 Claims, 5 Drawing Sheets

BIODEFENSE AGENTS

CROSS-REFERENCE TO RELATED APPLICATION

This application claims the benefit of U.S. Provisional Application Ser. No. 62/681,627, filed Jun. 6, 2018, the contents of which are incorporated herein by reference.

GOVERNMENT SUPPORT

This invention was made with U.S. Government support under Defense Threat Reduction Agency (DTRA), Project 922141, MRMC Control Number W81XWH-12-0162. The U.S. Government has certain rights in the invention.

TECHNICAL FIELD

This disclosure relates to antimicrobial compounds, and more particularly to pyrrolocytosines, and methods for treating, preventing, reducing the risk of, and delaying the onset of microbial infections caused by biological agents, including those that can be used as weapons.

BACKGROUND

Biological agents, including various types of bacteria such as *Bacillus anthracis* and multidrug-resistant (MDR) anthrax, *Francisella tularensis, Yersinia pestis, Burkholderia mallei, Burkholderia pseudomallei*, and other category A or B biodefense pathogens, can be used as weapons, which pose a material threat to the national security and public health in the United States.

Therefore, there is a need for effective anti-bacterial agents for the prevention, prophylaxis, and treatment of infections caused by biological agents, including those that can be used as weapons.

SUMMARY

The present disclosure relates generally to the field of antimicrobial compounds and to methods of making and using them. These compounds and tautomers thereof are useful for treating, preventing, reducing the risk of, or delaying the onset of microbial infections caused by biological agents in humans and animals.

The present disclosure also describes methods of using these compounds and tautomers in treating, preventing, reducing the risk of, or delaying the onset of microbial infections caused by biological agents.

In some embodiments, provided is a method of treating, preventing, reducing the risk of, or delaying the onset of a microbial infection in a subject, the method including administering to the subject a therapeutically effective amount of a compound of Formula (I):

(I)

or a tautomer thereof or a pharmaceutically acceptable salt of the compound or tautomer, wherein:

$R_1$ is selected from H and halo;

$R_2$ is selected from H, halo, $C_{1-6}$ alkyl, $C_{1-4}$ haloalkyl, and $OR^{a1}$;

$R_3$ is selected from H, $C_{1-6}$ alkyl, and $C_{1-4}$ haloalkyl;

W is selected from N and $CR_4$;

$R_4$ is selected from H, halo, $OR^{a2}$, $SR^{a2}$, 5-6 membered heterocycloalkyl, $S(O)_2R^{b2}$, $C_{1-6}$ alkyl, and $C_{2-6}$ alkenyl, wherein the $C_{1-6}$ alkyl is optionally substituted with $OR^{a2}$;

$R_5$ is selected from H, halo, $C_{1-6}$ alkyl, and $C_{2-6}$ alkenyl, wherein the $C_{1-6}$ alkyl is optionally substituted with $OR^{a2}$ $R_6$ is selected from H, $C_{1-6}$ alkyl, and $C_{2-6}$ alkenyl, wherein the $C_{1-6}$ alkyl is optionally substituted with $OR^{a3}$;

$R_7$ is selected from H and $C_{1-6}$ alkyl; or $R_6$ and $R_7$ together with the carbon atoms to which they are attached and the nitrogen atom connecting the two carbon atoms forms a ring of the formula:

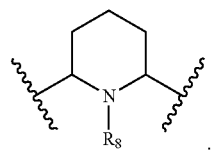

$R_8$ is selected from H, $C_{1-6}$ alkyl, and $C_{1-4}$ haloalkyl;

X is selected from O and $NR^N$;

$R^N$ is selected from H and $C_{1-4}$ alkyl;

$R_A$ is H;

$R_B$ is H; or $R_A$ and $R_B$ together with the nitrogen atom to which they are attached form a 5- to 6-membered heterocycloalkyl ring containing 1 or 2 heteroatoms selected from N, O and S, wherein the 5- to 6-membered heterocycloalkyl is optionally substituted with halo;

$R_9$ is selected from $C_{1-6}$ alkyl, $C_{2-6}$ alkenyl, $C_{3-5}$ cycloalkyl, wherein the $C_{1-6}$ alkyl is optionally substituted with a substituent selected from $OR^{a3}$ and $SR^{a3}$;

$R_{10}$ is selected from H, $C_{2-4}$ alkenyl, $C_{1-4}$ haloalkyl and $C_{1-4}$ alkyl optionally substituted with a substituent selected from amino, $C_{1-4}$ alkoxy, $C_{3-5}$ cycloalkyl, and 3- to 6-membered heterocycloalkyl;

$R_{11}$ is H or $C_{1-3}$ alkyl, wherein the $C_{1-3}$ alkyl is optionally substituted with OH; and each $R^{a1}$, $R^{a2}$, and $R^{a3}$ is independently selected from H, $C_{1-6}$ alkyl and $C_{1-4}$ haloalkyl; and wherein the infection is caused by or involves one or more microorganisms which are capable of being used as biological weapons, or the infection is caused by or involves one or more microorganisms which are extremely-drug resistant Gram-positive or Gram-negative pathogens.

In some embodiments of the method, the compound of Formula (I) has the Formula (A):

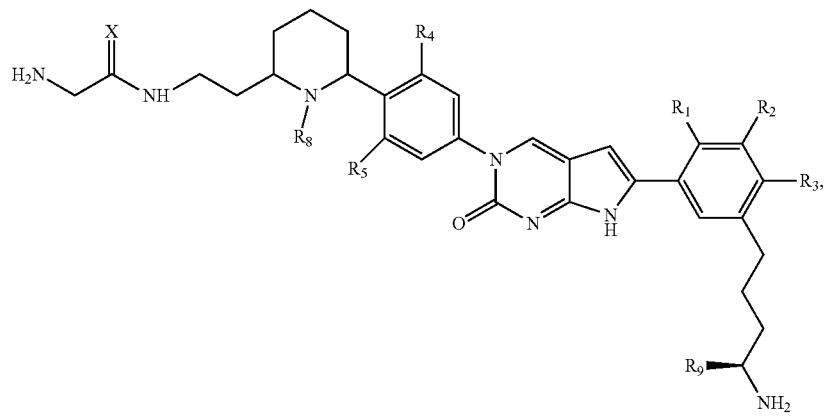

(A)

or a tautomer thereof or a pharmaceutically acceptable salt of the compound or tautomer.

In some embodiments of the method, the compound of Formula (I) has the Formula (Ia):

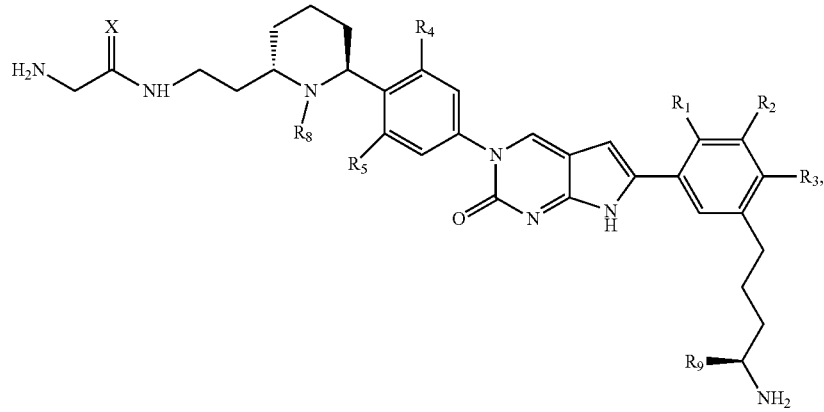

(Ia)

or a tautomer thereof or a pharmaceutically acceptable salt of the compound or tautomer.
In some embodiments of the method, the compound of Formula (I) has a formula selected from Formulae (Ib)-(Id):
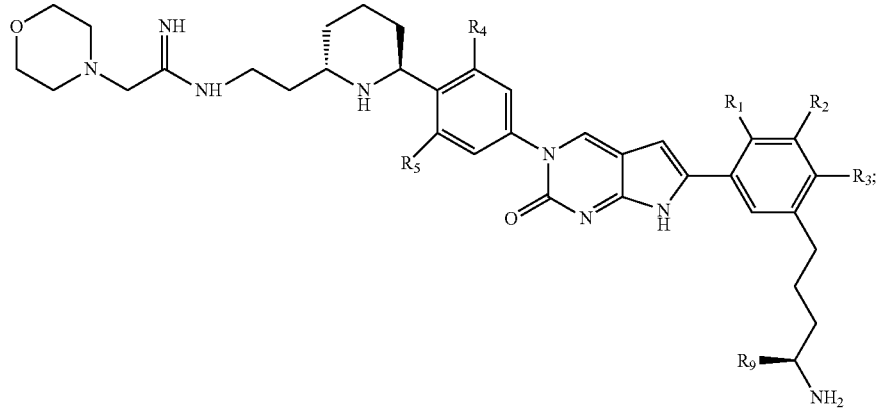
(Ib)
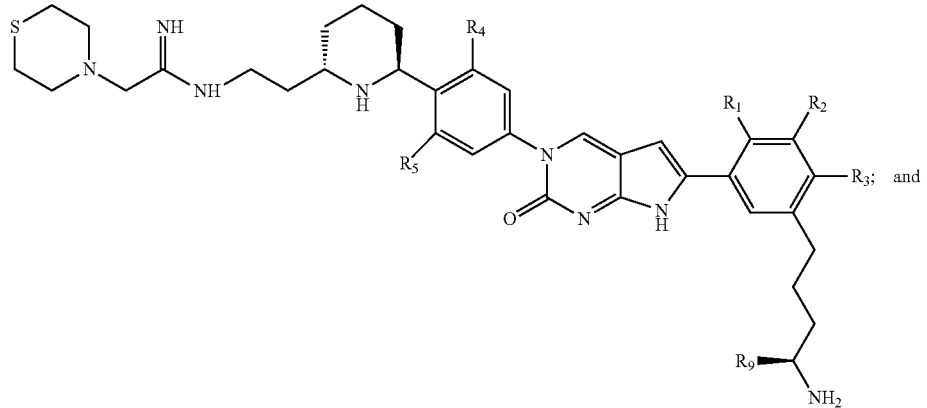
(Ic)
and
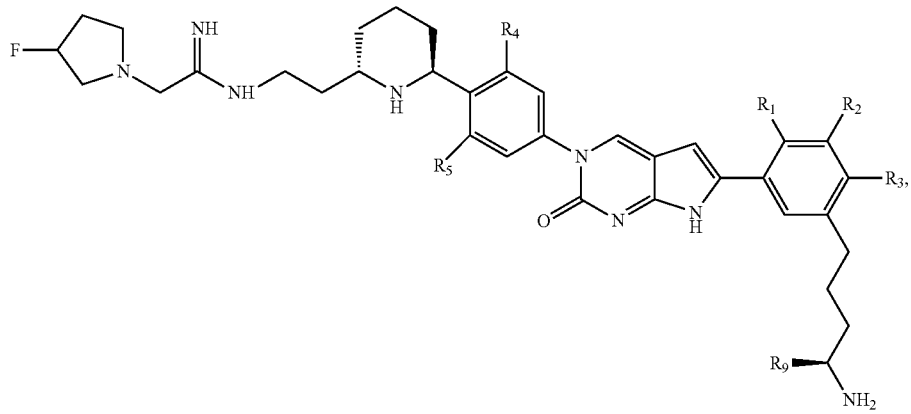
(Id)

or a tautomer thereof or a pharmaceutically acceptable salt of the compound or tautomer.

In some embodiments, provided is a method of treating, preventing, reducing the risk of, or delaying the onset of a microbial infection in a subject, the method including administering to the subject a therapeutically effective amount of a compound of Formula (II):

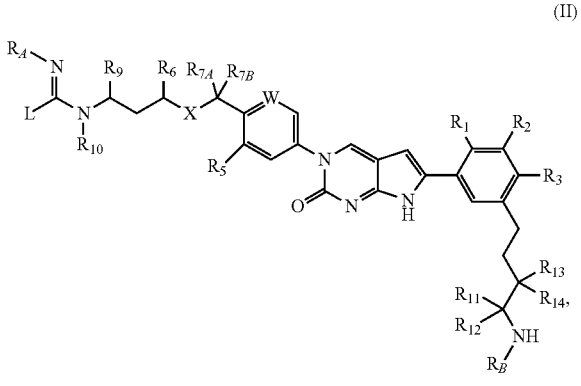

(II)

or a tautomer thereof or a pharmaceutically acceptable salt of the compound or tautomer, wherein:

$R_1$ is selected from H, halo, and $C_{1-4}$ alkoxy;

$R_2$ is selected from H, halo, $C_{1-6}$ alkyl, $C_{1-4}$ haloalkyl, and $OR^{a1}$;

$R_3$ is selected from H, $C_{1-6}$ alkyl, $C_{1-4}$ haloalkyl, and $C(O)OR^{a1}$; W is selected from N and $CR_4$;

$R_4$ is selected from H, halo, $OR^{a2}$, $SR^{a2}$, 5-6 membered heterocycloalkyl, $S(O)_2R^{b2}$, $C_{1-6}$ alkyl, and $C_{2-6}$ alkenyl, wherein the $C_{1-6}$ alkyl is optionally substituted with $OR^{a2}$;

$R_5$ is selected from H, halo, $C_{1-6}$ alkyl, and $C_{2-6}$ alkenyl, wherein the $C_{1-6}$ alkyl is optionally substituted with $OR^{a2}$ $R_6$ is selected from H, $C_{1-6}$ alkyl, $C_{3-5}$ cycloalkyl, and $C_{2-6}$ alkenyl, wherein the $C_{1-6}$ alkyl is optionally substituted with a substituent selected from $OR^{a3}$, $SR^{a3}$, and $NR^{c3}R^{d3}$;

$R_{7A}$ is selected from H, $C_{1-6}$ alkyl, $C_{1-4}$ haloalkyl, and $C_{2-6}$ alkenyl, wherein the $C_{1-6}$ alkyl is optionally substituted with a substituent selected from $OR^{a3}$ and $SR^{a3}$ $R_{7B}$ is H; or $R_{7A}$ and $R_{7B}$ together with the carbon atom to which they are attached form a group selected from oxo and $C_{3-6}$ cycloalkyl; or $R_6$ and $R_{7A}$ together with the carbon atoms to which they are attached and the X atom connecting the two carbon atoms form a 5- to 6-membered heterocycloalkyl containing 1-3 heteroatoms selected from N, O, and S;

X is selected from O and $NR_8$;

$R_8$ is selected from H, $C_{1-6}$ alkyl, and $C_{1-4}$ haloalkyl, wherein the $C_{1-6}$ alkyl is optionally substituted with $R_{8A}$;

$R_{8A}$ is selected from $OR^{a3}$ and 5- to 6-membered heteroaryl, wherein the 5- to 6-membered heteroaryl is optionally substituted with one or two $C_{1-6}$ alkyl;

$R_9$ is selected from H, $C_{2-4}$ alkenyl, $C_{1-4}$ haloalkyl, and $C_{1-4}$ alkyl optionally substituted with a substituent selected from amino, $C_{1-4}$ alkoxy, $C_{3-5}$ cycloalkyl, and 3- to 6-membered heterocycloalkyl;

$R_{10}$ is selected from H and $C_{2-6}$ alkenyl;

$R_A$ is selected from H and $C_{1-6}$ alkyl;

L is selected from $C_{1-6}$ alkyl and $C_{2-6}$ alkenyl, wherein the $C_{1-6}$ alkyl is optionally substituted with 1, 2, or 3 substituents independently selected from halo, $OR^{a4}$, $SR^{a4}$, and Z;

$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with 1, 2, or 3 substituents independently selected from CN, $OR^{a5}$, $SR^{a5}$, $C(O)NR^{c5}R^{d5}$, $NR^{c5}R^{d5}$, and $S(O)_2R^{b5}$;

$R_{12}$ is selected from H and $C_{1-6}$ alkyl; or $R_{11}$ and $R_{12}$ together with the carbon atom to which they are attached form a $C_{3-5}$ cycloalkyl;

$R_{13}$ is selected from H, halo, and $C_{1-6}$ alkyl;

$R_{14}$ is selected from H, halo, and $C_{1-6}$ alkyl; and $R_B$ is selected from H and $C(=NR^{e5})R^{b5}$; or $R_{11}$ and $R_B$ together with the carbon atom to which $R_{11}$ is attached and the nitrogen atom to which $R_B$ is attached form a 5- to 6-membered heterocycloalkyl containing 1-3 heteroatoms selected from N, O, and S, wherein the 5- to 6-membered heterocycloalkyl is optionally substituted with oxo;

each $R^{a1}$, $R^{a2}$, $R^{a3}$, $R^{a4}$, $R^{a5}$, $R^{b2}$, $R^{b5}$, $R^{c3}$, $R^{d3}$, $R^{c5}$ and $R^{d5}$ are independently selected from H, $C_{1-6}$ alkyl, $C_{1-4}$ haloalkyl, and 5-membered heteroaryl;

$R^{e5}$ is independently selected from H and $C_{1-4}$ alkyl; and

Z is $-O(CH_2CH_2O)CH_3$; and wherein the infection is caused by or involves one or more microorganisms which are capable of being used as biological weapons, or the infection is caused by or involves one or more microorganisms which are extremely-drug resistant Gram-positive or Gram-negative pathogens.

In some embodiments of the methods, the compound of Formula (II) has the Formula (IIa):

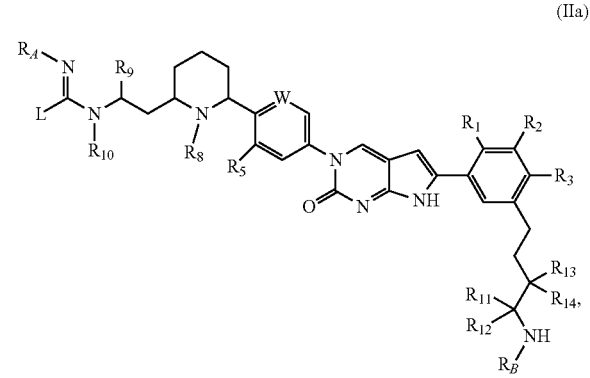

(IIa)

or a tautomer thereof or a pharmaceutically acceptable salt of the compound or tautomer.

In some embodiments of the method, the compound of Formula (II) has the Formula (IIb):

In some embodiments of the method, the compound of Formula (II) has the Formula (IIc):

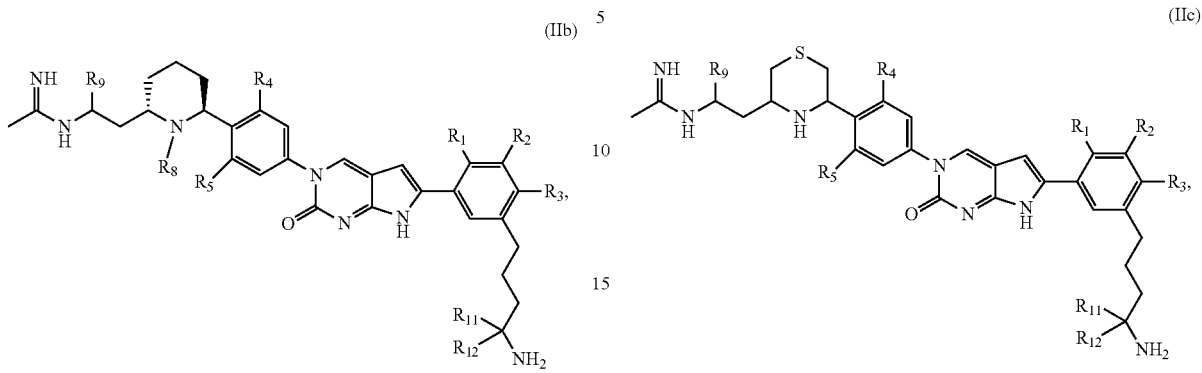

(IIb)

(IIc)

or a tautomer thereof or a pharmaceutically acceptable salt of the compound or tautomer.

or a tautomer thereof or a pharmaceutically acceptable salt of the compound or tautomer.

In some embodiments of the method, the compound of Formula (II) has a formula selected from Formulae (IId)-(IIg):

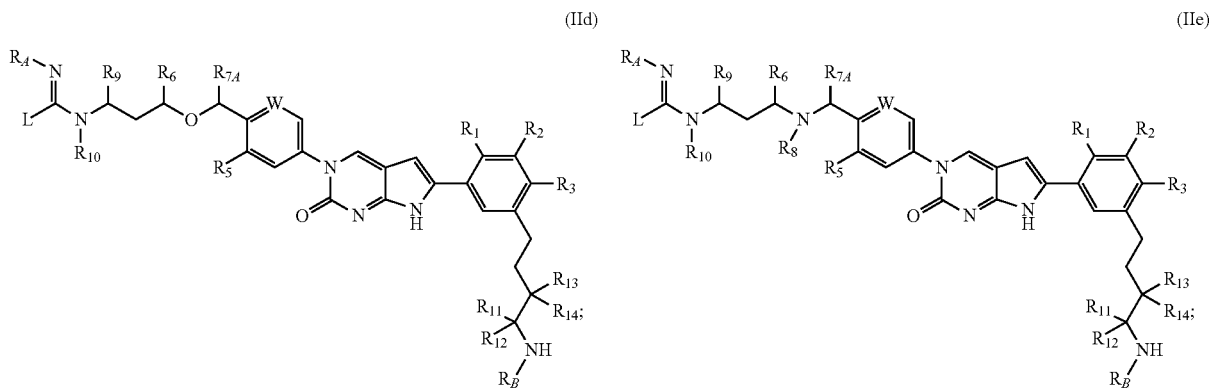

(IId)

(IIe)

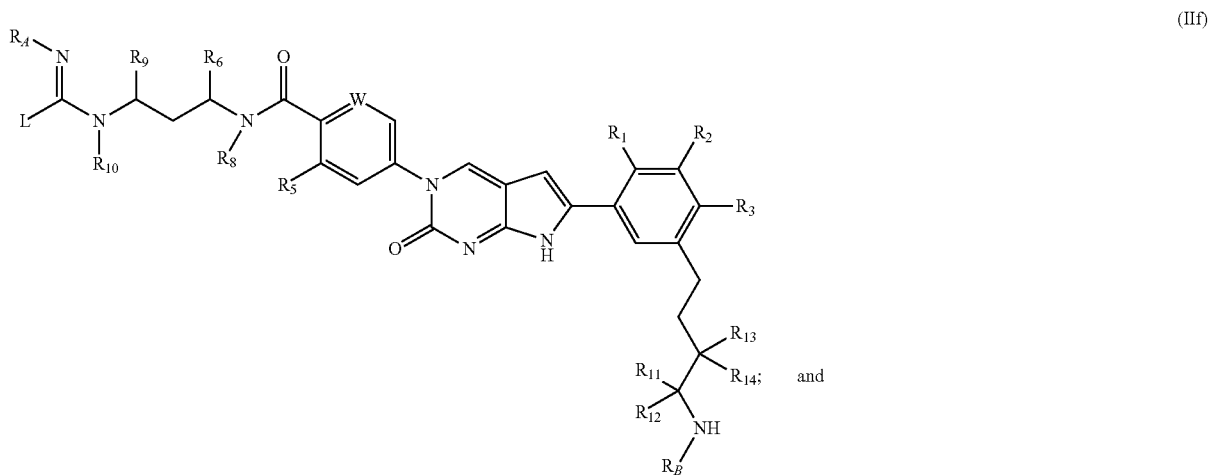

(IIf)

and

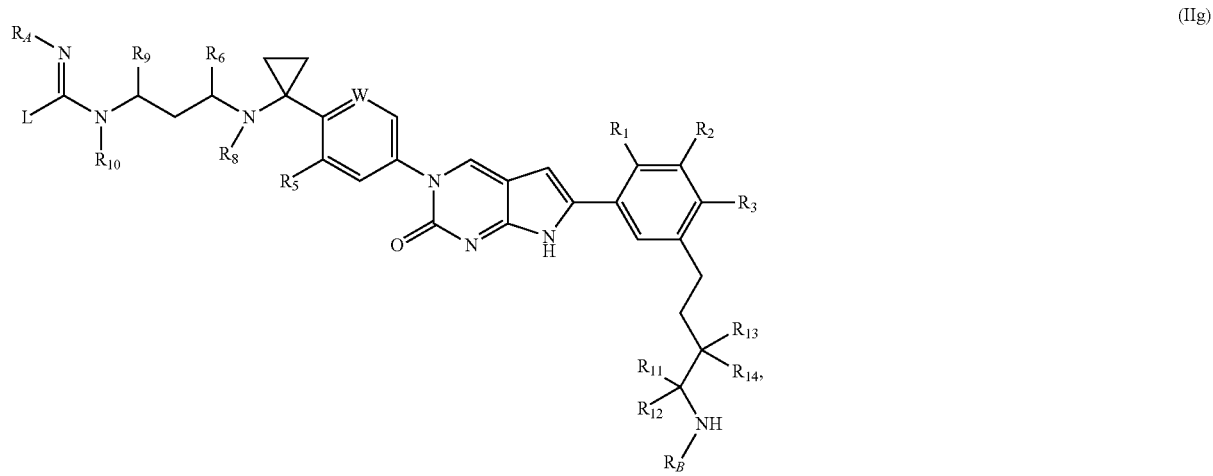
(IIg)
or a tautomer thereof or a pharmaceutically acceptable salt of the compound or tautomer.
In some embodiments of the method, the compound of Formula (II) has a formula selected from Formulae (IIh)-(IIk):
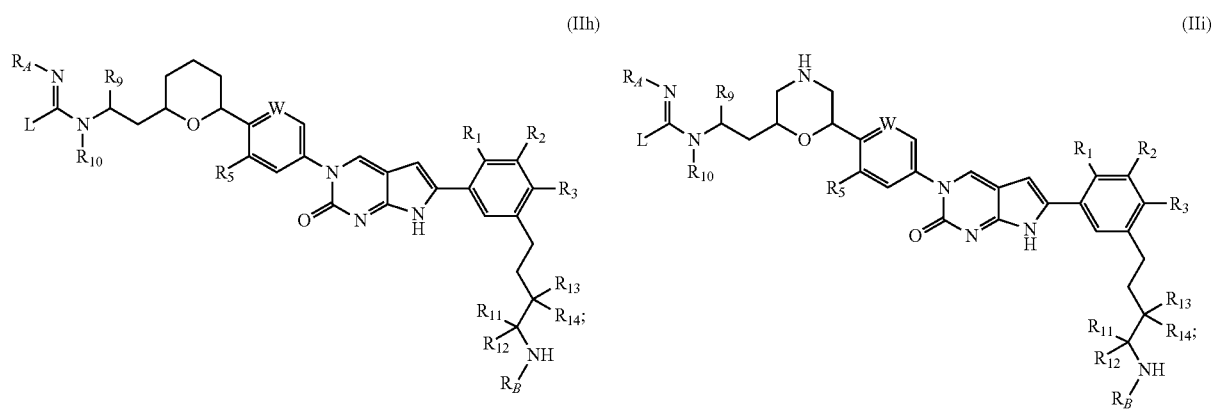
(IIh) (IIi)
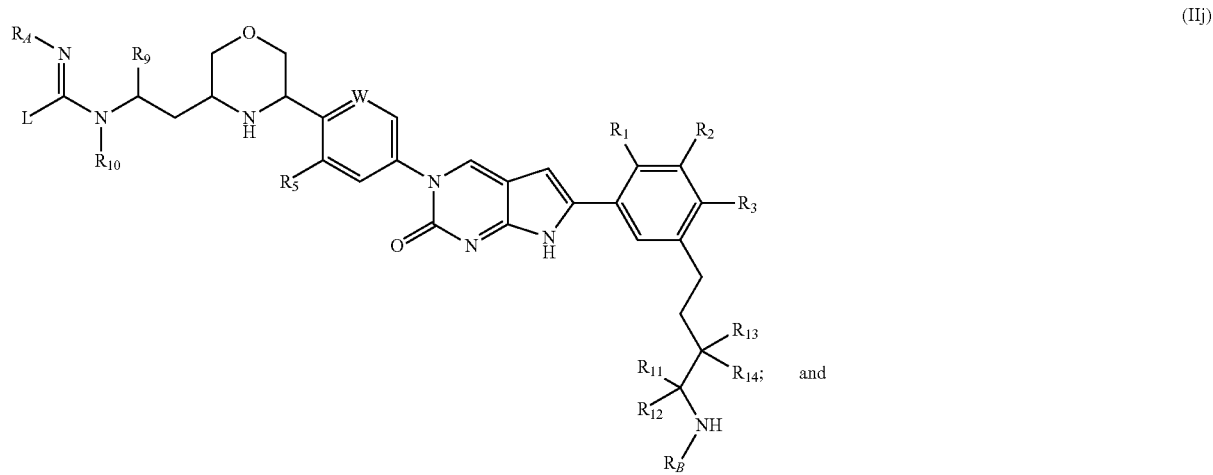
(IIj)
and (IIk)

[Chemical structure of Formula (IIk)]

or a tautomer thereof or a pharmaceutically acceptable salt of the compound or tautomer.

In some embodiments, provided is a method of treating, preventing, reducing the risk of, or delaying the onset of a microbial infection in a subject, the method including administering to the subject a therapeutically effective amount of a compound of Formula (III):

(III)

[Chemical structure of Formula (III)]

or a tautomer thereof or a pharmaceutically acceptable salt of the compound or tautomer, wherein the infection is caused by or involves one or more microorganisms which are capable of being used as biological weapons, or the infection is caused by or involves one or more microorganisms which are extremely-drug resistant Gram-positive or Gram-negative pathogens.

In some embodiments of the provided methods, the one or more microorganisms are selected from the group consisting of biodefense category A pathogens *Bacillus anthracis* (anthrax), *Yersinia pestis* (plague), and *Francisella tularensis* (tularemia).

In some embodiments of the provided methods, the one or more microorganisms are selected from the group consisting of biodefense category B pathogens *Burkholderia pseudomallei* (melioidosis), *Coxiella burnetii* (Q fever), *Brucella* species (brucellosis), *Burkholderia mallei* (glanders), *Chlamydia psittaci* (psittacosis), *Rickettsia prowazekii* (typhus fever), diarrheagenic *E. coli*, pathogenic *Vibrios*, *Shigella* species, *Salmonella*, *Listeria monocytogenes*, *Campylobacter jejuni*, and *Yersinia enterocolitica*.

In some embodiments, the one or more microorganisms are selected from *Bacillus anthracis*, *Franciscella tularensis*, *Yersinia pestis*, *Burkholderia mallei*, and *Burkholderia pseudomallei*. In some embodiments, the one or more microorganisms are selected from *Burkholderia mallei* and *Burkholderia pseudomallei*. In some embodiments, the one or more microorganisms are *Burkholderia pseudomallei*.

In some embodiments, the one or more microorganisms are extremely-drug resistant Gram-positive or Gram-negative pathogens.

Also provided are kit comprising a container, a compound selected from a compound of Formula (I), Formula (II), and Formula (III) and stereoisomers, tautomers, and salts thereof, and instructions for use in the treatment, prevention, or reducing the risk of a microbial infection that is caused by or involves one or more microorganisms which are capable of being used as biological weapons.

The foregoing and other aspects and embodiments of the disclosure can be more fully understood by reference to the following detailed description and claims.

DETAILED DESCRIPTION

Figure 1:
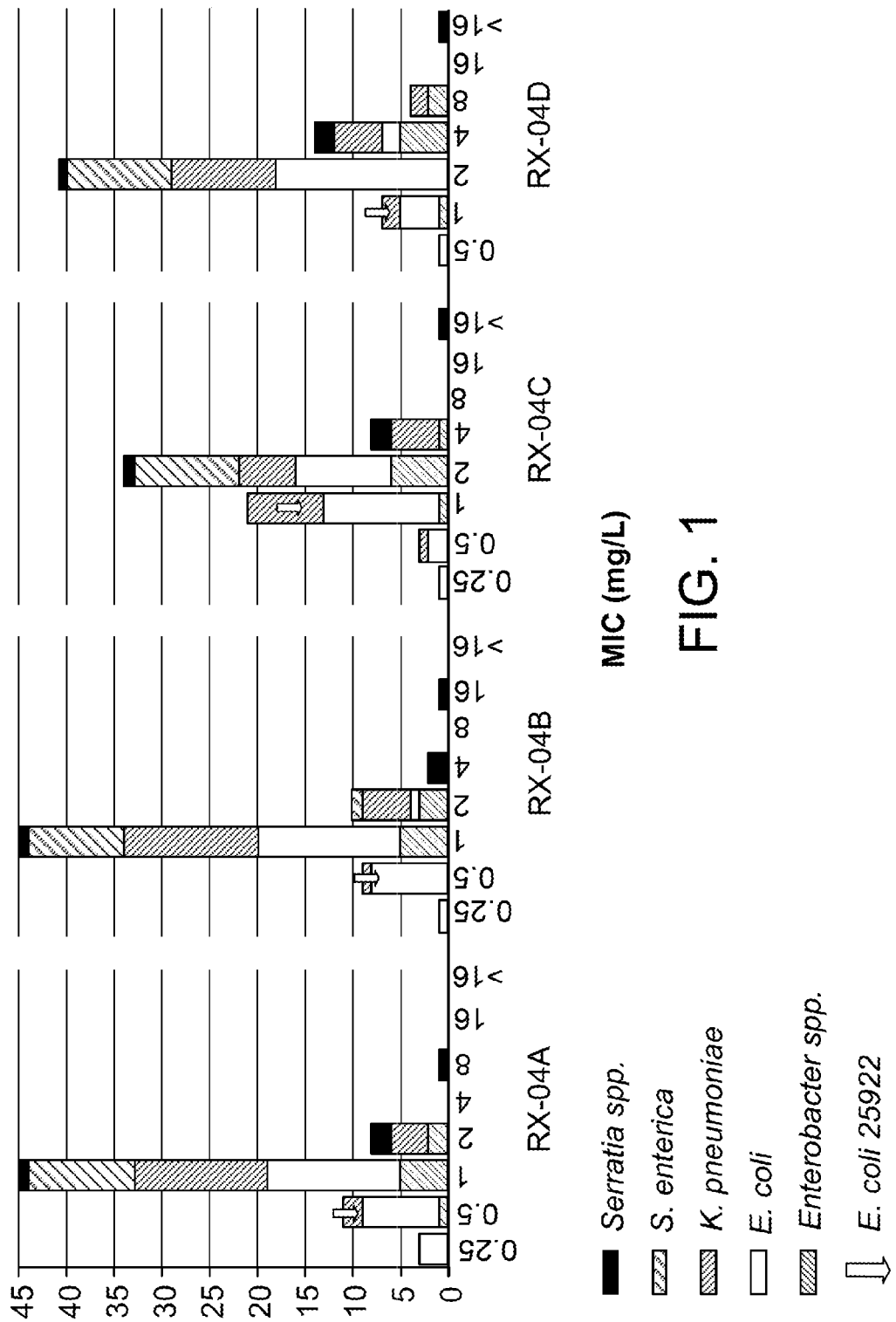
FIG. 1 provides bar graphs illustrating the MIC distribution of RX-04A-RX-04D for all Enterobacteriaceae tested by species (n=68).

The present disclosure describes methods of treating, preventing, reducing the risk of, or delaying the onset of a microbial infection in a subject that is caused by or involves one or more microorganisms which are capable of being used as biological weapons, or caused by or involves one or more microorganisms which are extremely-drug resistant Gram-positive or Gram-negative pathogens. The method includes administering a therapeutically effective amount of an antimicrobial compound, such as a pyrrolocytosine compound presently disclosed.

Certain pyrrolocytosine compounds are effective for treating, preventing, reducing the risk of, and/or delaying the onset of infections caused by various types of microorganisms (e.g., bacteria) that can be used as biological weapons. In some embodiments, the compounds of the present disclosure are modulators, for example, inhibitors, of ribosome function.

Ribosomes are ribonucleoproteins, which are present in both prokaryotes and eukaryotes. Ribosomes are the cellular organelles responsible for protein synthesis. During gene expression, ribosomes translate the genetic information encoded in a messenger RNA into protein (Garrett et al. (2000) "*The Ribosome: Structure, Function, Antibiotics and Cellular Interactions*," American Society for Microbiology, Washington, D.C.).

Ribosomes comprise two nonequivalent ribonucleoprotein subunits. The larger subunit (also known as the "large ribosomal subunit") is about twice the size of the smaller subunit (also known as the "small ribosomal subunit"). The small ribosomal subunit binds messenger RNA (mRNA) and mediates the interactions between mRNA and transfer RNA (tRNA) anticodons on which the fidelity of translation depends. The large ribosomal subunit catalyzes peptide bond formation (the peptidyl-transferase reaction of protein synthesis), and includes, at least, three different tRNA binding sites known as the aminoacyl, peptidyl, and exit sites. The aminoacyl site or A-site accommodates the incoming aminoacyl-tRNA that is to contribute its amino acid to the growing peptide chain. Also, the A space of the A-site is important. The peptidyl site or P-site accommodates the peptidyl-tRNA complex (the tRNA with its amino acid that is part of the growing peptide chain). The exit or E-site accommodates the deacylated tRNA after it has donated its amino acid to the growing polypeptide chain.

In some embodiments, the compounds of the present disclosure target a naive site of the bacterial 50S ribosome, resulting in protein synthesis inhibition. Owing to the chemical structures and uniqueness in binding locus, the pyrrolocytosines are not impacted by cross-resistance to current therapies. In some embodiments, the pyrrolocytosines presently disclosed exhibit equivalent or improved in vitro efficacy compared to comparator antibiotics against a number of potential biothreats, including *Yersinia pestis* (YP), *Francisella tularensis* (FT), *Bacillus anthracis* (BA), *Burkholderia mallei* (BM), and *Burkholderia pseudomallei* (BP).

1. DEFINITIONS

"Isomerism" means compounds that have identical molecular formulae but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four nonidentical substituents is termed a "chiral center."

"Chiral isomer" means a compound with at least one chiral center. A compound with one chiral center has two enantiomeric forms of opposite chirality and may exist either as an individual enantiomer or as a mixture of enantiomers. A mixture containing equal amounts of individual enantiomeric forms of opposite chirality is termed a "racemic mixture." A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J., Chem. Educ.* 1964, 41, 116).

"Geometric isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

The compounds disclosed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however, as a result of recent advances in chromatography techniques, it has been possible to separate mixtures of two atropic isomers in select cases.

Some compounds of the present disclosure can exist in a tautomeric form which is also intended to be encompassed within the scope of the present disclosure. "Tautomers" refers to compounds whose structures differ markedly in the arrangement of atoms, but which exist in easy and rapid equilibrium. It is to be understood that compounds of the present disclosure may be depicted as different tautomers. It should also be understood that when compounds have tautomeric forms, all tautomeric forms are intended to be within the scope of the disclosure, and the naming of the compounds does not exclude any tautomeric form.

The compounds and pharmaceutically acceptable salts of the present disclosure can exist in one or more tautomeric forms, including the enol and imine form and the keto and enamine form, and geometric isomers and mixtures thereof. All such tautomeric forms are included within the scope of the present disclosure. Tautomers exist as mixtures of a tautomeric set in solution. In solid form, usually one tautomer predominates. Even though one tautomer may be described, the present disclosure includes all tautomers of the compounds disclosed herein.

A tautomer is one of two or more structural isomers that exist in equilibrium and are readily converted from one isomeric form to another. This reaction results in the formal migration of a hydrogen atom accompanied by a shift of adjacent conjugated double bonds. In solutions where tautomerization is possible, a chemical equilibrium of the tautomers can be reached. The exact ratio of the tautomers depends on several factors, including temperature, solvent, and pH. The concept of tautomers that are interconvertible by tautomerizations is called tautomerism.

Of the various types of tautomerism that are possible, two are commonly observed. In keto-enol tautomerism, a simultaneous shift of electrons and a hydrogen atom occurs. Ring-chain tautomerism, exhibited by glucose and other sugars, arises as a result of the aldehyde group (—CHO) in a sugar chain molecule reacting with one of the hydroxy groups (—OH) in the same molecule to give it a cyclic (ring-shaped) form.

Tautomerizations can be catalyzed by: Base: 1. deprotonation; 2. formation of a delocalized anion (e.g., an enolate); 3. protonation at a different position of the anion; or Acid: 1. protonation; 2. formation of a delocalized cation; 3. deprotonation at a different position adjacent to the cation.

Common tautomeric pairs include: ketone-enol, amide-nitrile, lactam-lactim, amide-imidic acid tautomerism in heterocyclic rings (e.g., in the nucleobases guanine, thymine, and cytosine), amine-enamine, and enamine-enamine. Examples below are included for illustrative purposes, and the present disclosure is not limited to the examples:

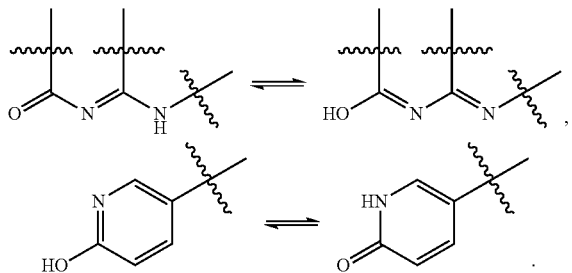

The term "substituted," as used herein, means that any one or more hydrogens on the designated atom, usually a carbon, oxygen, or nitrogen atom, is replaced with a selection from the indicated group, provided that the designated atom's normal valency is not exceeded, and that the substitution results in a stable compound. When a substituent is keto or oxo (=O), then two hydrogens on the atom are replaced. Ring double bonds, as used herein, are double bonds that are formed between two adjacent ring atoms (e.g., C=C, C=N, N=N, etc.).

As used herein, "alkyl" is intended to include both branched and straight-chain saturated aliphatic hydrocarbon groups having the specified number of carbon atoms. For example, $C_{1-4}$ is intended to include $C_1$, $C_2$, $C_3$, and $C_4$. $C_{1-6}$ alkyl is intended to include $C_1$, $C_2$, $C_3$, $C_4$, $C_5$, and $C_6$ alkyl groups and $C_{1-8}$ is intended to include $C_1$, $C_2$, $C_3$, $C_4$, $C_5$, $C_6$, $C_7$, and $C_8$. Some examples of alkyl groups include, but are not limited to, methyl, ethyl, n-propyl, i-propyl, n-butyl, s-butyl, t-butyl, n-pentyl, s-pentyl, n-hexyl, n-heptyl, and n-octyl.

As used herein, "alkenyl" is intended to include hydrocarbon chains of either straight or branched configuration and one or more unsaturated carbon-carbon bonds that can occur in any stable point along the chain, such as ethenyl and propenyl. For example, $C_{2-6}$ alkenyl is intended to include $C_2$, $C_3$, $C_4$, $C_5$, and $C_6$ alkenyl groups and $C_{2-8}$ alkenyl is intended to include $C_2$, $C_3$, $C_4$, $C_5$, $C_6$, $C_7$, and $C_8$.

As used herein, "alkylene" is intended to include moieties which are diradicals (having two points of attachment). A non-limiting example of such alkylene moiety that is a diradical is —CH$_2$CH$_2$—, a $C_2$ alkyl group that is covalently bonded via each terminal carbon atom to the remainder of the molecule. The alkylene diradicals are also known as "alkylenyl" radicals. Alkylene groups can be saturated or unsaturated (e.g., containing —CH=CH— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms). Some examples of alkylene groups include, but are not limited to, methylene, ethylene, n-propylene, iso-propylene, n-butylene, iso-butylene, sec-butylene, tert-butylene, n-pentylene, iso-pentylene, sec-pentylene and neo-pentylene.

As used herein, "cycloalkyl" is intended to include saturated or unsaturated nonaromatic ring groups, such as cyclopropyl, cyclobutyl, or cyclopentyl. $C_{3-8}$ cycloalkyl is intended to include $C_3$, $C_4$, $C_5$, $C_6$, $C_7$, and $C_8$ cycloalkyl groups. Cycloalkyl can include multiple spiro- or fused rings.

As used herein, the term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. A heterocycloalkyl group containing a fused aromatic ring can be attached through any ring-forming atom, including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

As used herein, "amine" or "amino" refers to unsubstituted —NH$_2$ unless otherwise specified.

As used herein, "halo" or "halogen" refers to fluoro, chloro, bromo, and iodo substituents.

As used herein, "haloalkyl" is intended to include both branched and straight-chain saturated aliphatic hydrocarbon groups having the specified number of carbon atoms, substituted with one or more halogen (for example —C$_v$FWH$_{2v-w+1}$ wherein v=1 to 3 and w=1 to (2v+1)). Examples of haloalkyl groups include, but are not limited to, trifluoromethyl, trichloromethyl, pentafluoroethyl, and pentachloroethyl.

The term "haloalkoxy" as used herein refers to an alkoxy group, as defined herein, which is substituted one or more halogen. Examples of haloalkoxy groups include, but are not limited to, trifluoromethoxy, difluoromethoxy, pentafluoroethoxy, and trichloromethoxy.

As used herein, "alkoxyl" or "alkoxy" refers to an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "aryl" includes groups with aromaticity, including conjugated or multicyclic systems with at least one aromatic ring and do not contain any heteroatom in the ring structure. Aryl groups can be monocyclic or polycyclic (e.g., having 2, 3, or 4 fused rings). The term "$C_{n-m}$ aryl" refers to an aryl group having from n to m ring carbon atoms. In some embodiments, aryl groups have from 6 to 10 carbon atoms. In some embodiments, the aryl group is phenyl or naphthyl.

As used herein, the term "aromatic heterocycle," "aromatic heterocyclic," or "heteroaryl" ring is intended to mean a stable 5, 6, 7, 8, 9, 10, 11, or 12-membered monocyclic or bicyclic aromatic ring which consists of carbon atoms and one or more heteroatoms, e.g., 1 or 1-2 or 1-3 or 1-4 or 1-5 or 1-6 heteroatoms independently selected from nitrogen, oxygen, and sulfur. In the case of bicyclic aromatic heterocyclic or heterocycle or heteroaryl rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (N or NR wherein R is H or another substituent, as defined). The nitrogen and sulfur heteroatoms can optionally be oxidized (N→O and S(O)$_p$, wherein p=1 or 2). In certain compounds, the total number of S and O atoms in the aromatic heterocycle is not more than 1.

Examples of aromatic heterocycles, aromatic heterocyclics or heteroaryls include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, benzooxadiazoly, carbazolyl, 4aH-carbazolyl, carbolinyl, cinnolinyl, furazanyl, imidazolyl, imidazolonyl, 1H-indazolyl, indolizinyl, indolyl, 3H-indolyl, isobenzofuranyl, isochromanyl, isoindazolyl, isoindolyl, isoquinolinyl, isothiazolyl, isoxazolyl, methylbenztriazolyl, methylfuranyl, methylimidazolyl, methylthiazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, phenanthridinyl, phenanthrolinyl, phenazinyl, phenothiazinyl, phenoxathinyl, phenoxazinyl, phthalazinyl, pteridinyl, purinyl, pyrazinyl, pyrazolyl, pyridazinyl, pyridooxazolyl, pyridoimidazolyl, pyridothiazolyl, pyridinyl, pyridinonyl, pyridyl, pyrimidinyl, 2H-pyrrolyl, pyrrolyl, quinazolinyl, quinolinyl, 4H-quinolizinyl, quinoxalinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, triazolopyrimidinyl, 1,2,3-triazolyl, 1,2,4-triazolyl, 1,2,5-triazolyl, and 1,3,4-triazolyl.

The term "hydroxyalkyl" means an alkyl group as defined above, where the alkyl group is substituted with one or more OH groups. Examples of hydroxyalkyl groups include HO—CH$_2$—, HO—CH$_2$—CH$_2$— and CH$_3$—CH(OH)—.

The term "cyano" as used herein means a substituent having a carbon atom joined to a nitrogen atom by a triple bond, represented by the formula C≡N.

As used herein, "oxo" means a group represented by the formula "=O."

As used herein, "unsaturated" refers to compounds having at least one degree of unsaturation (e.g., at least one multiple bond) and includes partially and fully unsaturated compounds.

As used herein, the phrase "pharmaceutically acceptable" refers to those compounds or tautomers thereof, or salts thereof, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds or tautomers thereof, wherein the parent compound or a tautomer thereof, is modified by making of the acid or base salts thereof of the parent compound or a tautomer thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound, or a tautomer thereof, formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present disclosure can be synthesized by conventional chemical methods from the parent compound or a tautomer thereof that contains a basic or acidic moiety. Generally, such pharmaceutically acceptable salts can be prepared by reacting the free acid or base forms of these compounds or tautomers thereof with a stoichiometric amount of the appropriate base or acid in water or in an organic solvent, or in a mixture of the two; In some embodiments, non-aqueous media like ether, ethyl acetate, ethanol, isopropanol, or acetonitrile are used. Lists of suitable salts can be found in Remington's Pharmaceutical Sciences, 18th ed., Mack Publishing Company, Easton, PA, USA, p. 1445 (1990).

As used herein, "stable compound" and "stable structure" are meant to indicate a compound that is sufficiently robust to survive isolation to a useful degree of purity from a reaction mixture, and formulation into an efficacious therapeutic agent.

As used herein, the terms "treating" or "treatment" means to provide a therapeutic intervention to cure or ameliorate an infection. In some embodiments, "treating" refers to administering a compound or pharmaceutical composition as provided herein for therapeutic purposes. The term "therapeutic treatment" refers to administering treatment to a patient already suffering from a disease thus causing a therapeutically beneficial effect, such as ameliorating or diminishing one or more existing symptoms, ameliorating or diminishing the underlying metabolic causes of symptoms, postponing or preventing the further development of a disorder, and/or reducing the severity of symptoms that will or are expected to develop. In some embodiments, the disorder to be treated is a microbial infection, such as a bacterial infection.

As used herein, the terms "prevent," "preventing," or "prevention" mean to completely or almost completely stop an infection from occurring, for example when the patient or subject is predisposed to an infection or at risk of contracting an infection. Preventing can also include inhibiting, or arresting the development, of an infection.

As used herein, the term "reducing the risk of" means to lower the likelihood or probability of an infection occurring, for example when the patient or subject is predisposed to an infection or at risk of contracting an infection.

As used herein, the term "effective amount" or "therapeutically effective amount" refers to an amount of a compound or a tautomer thereof, or a pharmaceutically acceptable salt of the compound or tautomer (including combinations of compounds and/or tautomers thereof, and/or pharmaceutically acceptable salts of the compound or tautomer) of the present disclosure that is effective when administered alone or in combination as an antimicrobial agent. For example, an effective amount refers to an amount of the compound or tautomer thereof, or a pharmaceutically acceptable salt of the compound or tautomer that is present in a composition, a formulation or on a medical device given to a recipient patient or subject sufficient to elicit biological activity, for example, anti-infective activity, such as e.g., anti-microbial activity, anti-bacterial activity, anti-fungal activity, anti-viral activity, or anti-parasitic activity. In some embodiments, the term "effective amount" includes the amount of a compound of the present invention that produces an efficacious level sufficient to achieve the desired therapeutic effect through the killing of bacteria and/or inhibition of bacterial growth. In one embodiment, the effective amount is sufficient to eradicate the bacterium or bacteria causing the infection.

The term "prophylactically effective amount" means an amount of a compound or a tautomer of the compound, or a pharmaceutically acceptable salt of the compound or tautomer (including combinations of compounds and/or tautomers thereof, and/or pharmaceutically acceptable salts thereof), of the present disclosure that is effective prophylactically when administered alone or in combination as an antimicrobial agent. For example, a prophylactically effective amount refers to an amount of the compound or tautomer thereof, or a pharmaceutically acceptable salt of the compound or tautomer that is present in a composition, a formulation, or on a medical device given to a recipient patient or subject sufficient to prevent or reduce the risk of an infection due to a surgical procedure or an invasive medical procedure.

As used herein, the terms "expose," "exposure," or "exposed" means that a subject comes in contact in any way with a bacterium or any component thereof (e.g., bacterial cell wall, bacterial cell membrane, a bacterial nucleic acid, a bacterial polynucleotide, a bacterial protein, a bacterial polypeptide, a bacterial spore, and a bacterial toxin). For example, a subject can be exposed to a bacterium or any component thereof by ingesting, inhaling, or touching anything which contains the bacterium or any component thereof. Bacterium, as well as components of a bacterium (e.g., bacterial cell wall, bacterial cell membrane, a bacterial nucleic acid, a bacterial polynucleotide, a bacterial protein, a bacterial polypeptide, a bacterial spore, and a bacterial toxin), can cause an infection or symptoms of an infection in a subject. An example of a bacterial component that can cause an infection is a bacterial spore.

"Suspected exposure," as used herein, means that there is certain possibility, although it is not known, that a subject has been exposed to a microorganism, for example, a bacterium, and thus is at the risk of a microbial (bacterial) infection, such as a bacterial infection. In some embodiments, "suspected exposure" means that there is greater than 50% possibility that a subject has been exposed to a microorganism, for example, a bacterium.

As used herein, a "symptom" of a microbial infection, for example, a bacterial infection, can be any indication that the subject exposed or suspected of being exposed to the bacterium is not normal, well, or comfortable, regardless of the subject's subjective perception or feeling. "Symptom" includes, but is not limited to, headache, stomachache, abdominal cramps, abdominal pain, muscle pain, fever, diarrhea, vomiting, coughing, weakness, tiredness, soreness, rash or bumps on skin, wounds in any parts of the body (skin, head, eye, ear, nose, mouth, torso, limbs, arm, hand, leg, foot, etc.), and an abnormality in any tissue or organ (skin, bone, blood, lymph, intestine, stomach, pancreas, brain, heart, lung, liver, spleen, kidney, bladder, ovary, etc.).

A bacterium is "easily produced or disseminated" if the bacterium can be produced or disseminated by routine methods, processes, or techniques and with common materials, reagents, and equipment available in the art, or by methods, processes, or techniques and with materials, reagents, and equipment which are accessible to and can be operated or used by a lay person having little or no training in the art.

The term "moderate morbidity" refers to morbidity of no less than 10%, no less than 15%, no less than 20%, no less than 25%, no less than 30%, no less than 35%, no less than 40%, or no less than 45%. The term "high morbidity" refers to morbidity of no less than 50%, no less than 55%, no less than 60%, no less than 65%, no less than 70%, no less than 75%, no less than 80%, no less than 85%, no less than 90%, or no less than 95%.

The term "moderate mortality" refers to mortality of no less than 10%, no less than 15%, no less than 20%, no less than 25%, no less than 30%, no less than 35%, no less than 40%, or no less than 45%. The term "high mortality" refers to mortality of no less than 50%, no less than 55%, no less than 60%, no less than 65%, no less than 70%, no less than 75%, no less than 80%, no less than 85%, no less than 90%, or no less than 95%.

The terms "resistance" or "resistant" refer to the antibiotic/organism standards as defined by the Clinical and Laboratories Standards Institute (CLSI) and/or the Food and Drug Administration (FDA).

As used herewith, the terms "multi-drug resistance," "multi-drug resistant," or "MDR" refer to acquired non-susceptibility to at least two antimicrobial agents, e.g., resistance to one agent in three or more antimicrobial categories. The terms "extremely-drug resistant," "extensive drug resistance," or "XDR," as used herein, refer to acquired non-susceptibility to at least one agent in all but two or fewer antimicrobial categories. For example, bacterial isolates remain susceptible to only one or two categories. Accordingly, an XDR bacterial isolate is always an MDR bacterial isolate, but an MDR bacterial isolate is not necessarily an XDR bacterial isolate. For example, an XDR microorganism is a *Pseudomonas aeruginosa* isolate that is susceptible to only one or two antimicrobial categories, such as a *Pseudomonas aeruginosa* isolate that is only susceptible to polymyxins (for example, colistin) or only susceptible to a pyrrolocytosine compound described herein. See, for example, Magiorakos et al., *Clin. Microbial Infect.* 2012; 18: 268-281, the content of which is hereby incorporated by reference in its entirety.

The term "subject" includes animals which either have or are susceptible or are suspected to have acquired a microbial infection (e.g., a bacterial infection). Examples of subjects include animals such as farm animals (e.g., cows, pigs, horses, goats, rabbits, sheep, chickens, etc.), lab animals (mice, rats, monkeys, chimpanzees, etc.), pets (e.g., dogs, cats, ferrets, hamsters, etc.), birds (e.g., chickens, turkeys, ducks, geese, crows, ravens, sparrows, etc.), primates (e.g., monkeys, gorillas, chimpanzees, bonobos, and humans), and other animals (e.g., squirrels, raccoons, mice, rats, etc.). In some embodiments, the subject is a mouse or rat. In yet another embodiment, the subject is a cow, a pig, or a chicken. In another embodiment, the subject is a human.

As used herein, the term ESBL is extended spectrum beta-lactamase. The term KPC is *Klebsiella pneumoniae* carbapenemase.

As used herein, the term acute bacterial skin and skin structure infection (ABSSSI) encompasses complicated skin and skin structure infections (cSSSI) and complication skin and soft tissue infections (cSSTI), which have been used interchangeably. The terms uncomplicated skin and skin structure infections (uCSSSI) and uncomplicated skin and soft tissue infections (uCSSTI) have been used interchangeably.

As used herein, the term "spp." is the abbreviation for species.

As used herein, the term "formulae of the disclosure" or "formulae disclosed herein" includes one or more of the Formulae: (I), (I-1), (A), (Ia), (Ia-1), (Ia-2), (Ib), (Ic), (I-A), (Ib-2), (Ic-2), (Id-2), (Id), (II), (IIa), (IIa-1), (IIa-2), (IIb-a), (IIb), (IIa-3), (IIc), (IIc-1), (IId), (IIe), (IIf), (IIg), (IIe-1), (IIh), (IIi), (IIj), (IIk), and (III).

As used herein, the term "compound of the disclosure" or "compound disclosed herein" includes one or more compounds of the formulae of the disclosure or a compound explicitly disclosed herein.

The term "about," when used in conjunction with a numerical range, modifies that range by extending the boundaries above and below the numerical values set forth. In general, the term "about" is used herein to modify a numerical value above and below the stated value by a variance of 10%. Thus, "about 10" means 9 to 11.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present disclosure also consist essentially of, or consist of, the recited components, and that the processes of the present disclosure also consist essentially of, or consist of, the recited processing steps. Further, it should be understood that the order of steps or order for performing certain actions are immaterial so long as the invention remains operable. Moreover, two or more steps or actions can be conducted simultaneously.

2. COMPOUNDS OF THE DISCLOSURE

In some embodiments, the present disclosure provides a method of treating, preventing, reducing the risk of, or delaying the onset of a microbial infection in a subject, the method comprising administering to the subject a therapeutically effective amount of a compound of Formula (I):

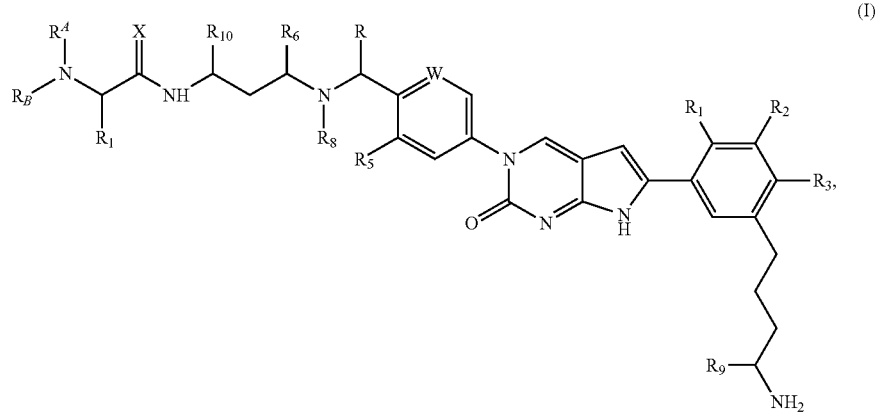

(I)

or a tautomer thereof or a pharmaceutically acceptable salt of the compound or tautomer, wherein:

$R_1$ is selected from H and halo;

$R_2$ is selected from H, halo, $C_{1-6}$ alkyl, $C_{1-4}$ haloalkyl, and $OR^{a1}$;

$R_3$ is selected from H, $C_{1-6}$ alkyl, and $C_{1-4}$ haloalkyl;

W is selected from N and $CR_4$;

$R_4$ is selected from H, halo, $OR^{a2}$, $SR^{a2}$, 5-6 membered heterocycloalkyl, $S(O)_2R^{b2}$, $C_{1-6}$ alkyl, and $C_{2-6}$ alkenyl, wherein the $C_{1-6}$ alkyl is optionally substituted with $OR^{a2}$;

$R_5$ is selected from H, halo, $C_{1-6}$ alkyl, and $C_{2-6}$ alkenyl, wherein the $C_{1-6}$ alkyl is optionally substituted with $OR^{a2}$ $R_6$ is selected from H, $C_{1-6}$ alkyl, and $C_{2-6}$ alkenyl, wherein the $C_{1-6}$ alkyl is optionally substituted with $OR^{a3}$;

$R_7$ is selected from H and $C_{1-6}$ alkyl; or $R_6$ and $R_7$ together with the carbon atoms to which they are attached and the nitrogen atom connecting the two carbon atoms form a ring of the formula:

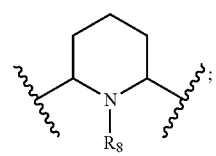

$R_8$ is selected from H, $C_{1-6}$ alkyl, and $C_{1-4}$ haloalkyl;

X is selected from O and $NR^N$;

$R^N$ is selected from H and $C_{1-4}$ alkyl; $R_A$ is H;
$R_B$ is H; or
$R_A$ and $R_B$ together with the nitrogen atom to which they are attached form a 5- to 6-membered heterocycloalkyl ring containing 1 or 2 heteroatoms selected from N, O, and S, wherein the 5- to 6-membered heterocycloalkyl is optionally substituted with halo;
$R_9$ is selected from $C_{1-6}$ alkyl, $C_{2-6}$ alkenyl, $C_{3-5}$ cycloalkyl, wherein the $C_{1-6}$ alkyl is optionally substituted with a substituent selected from $OR^{a3}$ and $SR^{a3}$;
$R_{10}$ is selected from H, $C_{2-4}$ alkenyl, $C_{1-4}$ haloalkyl, and $C_{1-4}$ alkyl optionally substituted with a substituent selected from amino, $C_{1-4}$ alkoxy, $C_{3-5}$ cycloalkyl, and 3- to 6-membered heterocycloalkyl;
$R_{11}$ is H or $C_{1-3}$ alkyl, wherein the $C_{1-3}$ alkyl is optionally substituted with OH; and
each $R^{a1}$, $R^{a2}$, and $R^{a3}$ is independently selected from H, $C_{1-6}$ alkyl, and $C_{1-4}$ haloalkyl.

In some embodiments of the method, the compound is a compound of Formula (I-1):

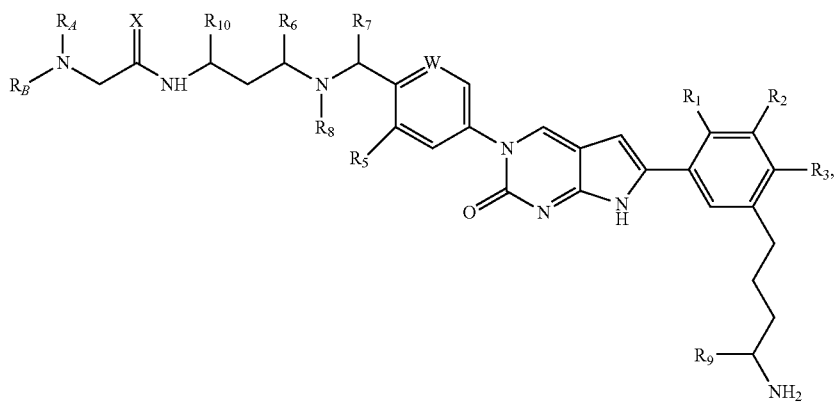

(I-1)

or a tautomer thereof or a pharmaceutically acceptable salt of the compound or tautomer, wherein:
$R_1$ is selected from H and halo;
$R_2$ is selected from H, halo, $C_{1-6}$ alkyl, $C_{1-4}$ haloalkyl, and $OR^{a1}$;
$R_3$ is selected from H, $C_{1-6}$ alkyl, and $C_{1-4}$ haloalkyl;
W is selected from N and $CR_4$;
$R_4$ is selected from H, halo, $C_{1-6}$ alkyl, $OR^{a2}$, $SR^{a2}$, 5-6 membered heterocycloalkyl, and $S(O)_2R^{b2}$;
$R_5$ is selected from H and halo;
$R_6$ is selected from H, $C_{1-6}$ alkyl, and $C_{2-6}$ alkenyl, wherein the $C_{1-6}$ alkyl is optionally substituted with $OR^{a3}$;
$R_7$ is H and $C_{1-6}$ alkyl; or
$R_6$ and $R_7$ together with the carbon atoms to which they are attached and the nitrogen atom connecting the two carbon atoms form a ring of the formula:

$R_8$ is selected from H, $C_{1-6}$ alkyl, and $C_{1-4}$ haloalkyl;
X is selected from O and $NR^N$
$R^N$ is selected from H and $C_{1-4}$ alkyl;
$R_A$ is H;
$R_B$ is H; or
$R_A$ and $R_B$ together with the nitrogen atom to which they are attached form a 5- to 6-membered heterocycloalkyl ring containing 1 or 2 heteroatoms independently selected from N, O, and S, wherein the 5- to 6-membered heterocycloalkyl is optionally substituted with halo;
$R_9$ is selected from $C_{1-6}$ alkyl and $C_{3-5}$ cycloalkyl, wherein the $C_{1-6}$ alkyl is optionally substituted with a substituent selected from $OR^{a3}$ and $SR^{a3}$
$R^{10}$ is selected from H, $C_{1-4}$ alkenyl, $C_{1-4}$ haloalkyl, and $C_{1-4}$ alkyl optionally substituted with a substituent selected from amino, $C_{1-4}$ alkoxy, $C_{3-5}$ cycloalkyl, and 3- to 6-membered heterocycloalkyl; and
each $R^{a1}$, $R^{a2}$, and $R^{a3}$ is independently selected from H, $C_{1-6}$ alkyl, and $C_{1-4}$ haloalkyl.

In some embodiments of Formula (I) or Formula (I-1), $R_1$ is H. In some embodiments, $R_1$ is halo. In some embodiments, $R_1$ is selected from H and fluoro. In some embodiments, $R_1$ is fluoro.

In some embodiments of Formula (I) or Formula (I-1), $R_2$ is selected from H, halo, $C_{1-4}$ haloalkyl, and $C_{1-4}$ haloalkoxy. In some embodiments, $R_2$ is halo. In some embodiments, $R_2$ is $C_{1-4}$ haloalkyl. In some embodiments, $R_2$ is $C_{1-4}$ haloalkoxy. In some embodiments, $R_2$ is selected from H, chloro, trifluoromethyl, and trifluoromethoxy. For example, $R_2$ can be selected from H and chloro. In some embodiments, $R_2$ is selected from chloro, trifluoromethyl, and trifluoromethoxy. In some embodiments, $R_2$ is selected from H and trifluoromethyl. In some embodiments, $R_2$ is chloro. In some embodiments, $R_2$ is H. In some embodiments, $R_2$ is trifluoromethyl. In some embodiments, $R_2$ is trifluoromethoxy.

In some embodiments of Formula (I) or Formula (I-1), $R_1$ is halo and $R_2$ is halo. In some embodiments, $R_1$ is halo and $R_2$ is $C_{1-4}$ haloalkoxy. In some embodiments, $R_1$ is H and $R_2$ is $C_{1-4}$ haloalkyl. In some embodiments, $R_1$ is H and $R_2$ is H. In some embodiments, $R_1$ is fluoro and $R_2$ is chloro. In some embodiments, $R_1$ is fluoro and $R_2$ is trifluoromethoxy. In some embodiments, $R_1$ is H and $R_2$ is trifluoromethyl.

In some embodiments of Formula (I) or Formula (I-1), $R_3$ is selected from H and $C_{1-4}$ haloalkyl. In some embodiments, $R_3$ is $C_{1-4}$ haloalkyl. In some embodiments, $R_3$ is selected from H, and trifluoromethyl. In some embodiments, $R_3$ is trifluoromethyl. In some embodiments, $R_3$ is H.

In some embodiments of Formula (I) or Formula (I-1), $R_1$ is H, $R_2$ is H and $R_3$ is $C_{1-4}$ haloalkyl. For example, $R_1$ can be H, $R_2$ can be H and $R_3$ can be trifluoromethyl. In some embodiments, $R_1$ is halo, $R_2$ is halo, and $R_3$ is H. For example, $R_1$ can be fluoro, $R_2$ can be chloro, and $R_3$ can be H. In some embodiments, $R_1$ is H, $R_2$ is $C_{1-4}$ haloalkyl and $R_3$ is H. For example, $R_1$ can be H, $R_2$ can be trifluoromethyl and $R_3$ can be H.

In some embodiments of Formula (I) or Formula (I-1), W is N. In some embodiments, W is $CR_4$.

In some embodiments of Formula (I) or Formula (I-1), $R_4$ is selected from H, halo, and $S(C_{1-4}$ alkyl). In some embodiments, $R_4$ is selected from halo and $S(C_{1-4}$ alkyl). In some embodiments, $R_4$ is H. In some embodiments, $R_4$ is halo. In some embodiments, $R_4$ is $S(C_{1-4}$ alkyl). In some embodiments, $R_4$ is selected from H, fluoro, and methylthio. In some embodiments, $R_4$ is selected from fluoro and methylthio. In some embodiments, $R_4$ is fluoro. In some embodiments, $R_4$ is methylthio.

In some embodiments of Formula (I) or Formula (I-1), $R_5$ is selected from H and halo. For example, $R_5$ can be selected from H and fluoro. In some embodiments, $R_5$ is halo. For example, $R_5$ can be fluoro. In some embodiments, $R_5$ is H.

In some embodiments of Formula (I) or Formula (I-1), $R_6$ is selected from H, $C_{2-6}$ alkenyl, and $C_{1-6}$ hydroxyalkyl. In some embodiments, $R_6$ is $C_{2-6}$ alkenyl. In some embodiments, $R_6$ is $C_{1-6}$ hydroxyalkyl. In some embodiments, $R_6$ is selected from H, ethenyl, and hydroxymethyl. In some embodiments, $R_6$ is ethenyl. In some embodiments, $R_6$ is hydroxymethyl.

In some embodiments of Formula (I) or Formula (I-1), $R_7$ is selected from H and methyl. In some embodiments, $R_7$ is methyl. In some embodiments, $R_7$ is H.

In some embodiments of Formula (I) or Formula (I-1), $R_6$ is $C_{2-6}$ alkenyl and $R_7$ is H. For example, $R_6$ can be ethenyl and $R_7$ can be H. In some embodiments, $R_6$ is $C_{1-6}$ hydroxyalkyl and $R_7$ is H. For example, $R_6$ can be hydroxymethyl and $R_7$ can be H. In some embodiments, $R_6$ is H and $R_7$ is $C_{1-6}$ alkyl. For example, $R_6$ can be H and $R_7$ can be methyl.

In some embodiments of Formula (I) or Formula (I-1), the carbon atom to which $R_6$ is attached is in (S) configuration according to Cahn-Ingold-Prelog nomenclature. In some embodiments, the carbon atom to which $R_6$ is attached is in (R) configuration according to Cahn-Ingold-Prelog nomenclature. In some embodiments, the stereochemistry at the carbon atom bound to $R_6$ is as shown below:

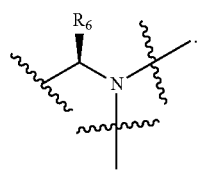

In some embodiments, the stereochemistry at the carbon atom bound to $R_6$ is as shown below: 1

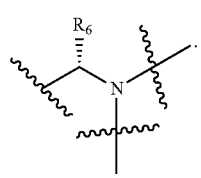

In some embodiments, the carbon atom to which $R_7$ is attached is in (S) configuration according to Cahn-Ingold-Prelog nomenclature. In some embodiments, the carbon atom to which $R_7$ is attached is in (R) configuration according to Cahn-Ingold-Prelog nomenclature.

In some embodiments, the stereochemistry at the carbon atom bound to $R_7$ is as shown below:

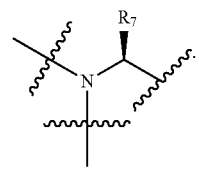

In some embodiments of Formula (I) or Formula (II), the stereochemistry at the carbon atom bound to $R_7$ is as shown below:

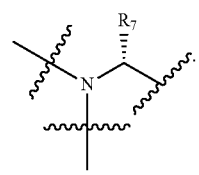

In some embodiments, $R_6$ and $R_7$ form a ring of the formula:

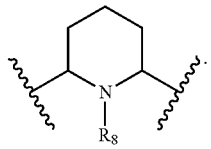

In some embodiments, $R_6$ and $R_7$ form a ring of the formula:

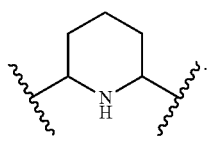 [SMILES: *C1CCCC(*)N1]

In some embodiments, $R_6$ and $R_7$ form a ring of the formula:

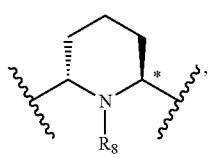

wherein the * indicates the ring carbon that is attached to the ring containing W.

In some embodiments of Formula (I) or Formula (I-1), $R_6$ and $R_7$ form a ring of the formula:

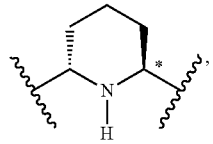 [SMILES: *[C@@H]1CCC[C@@H](*)N1]

wherein the * indicates the ring carbon that is attached to the ring containing W.

In some embodiments of Formula (I) or Formula (I-1), $R_8$ is selected from H, and 3-fluoropropyl. In some embodiments, $R_8$ is H. In some embodiments, $R_8$ is $C_{1-4}$ haloalkyl. For example, $R_8$ can be 3-fluoropropyl.

In some embodiments of Formula (I) or Formula (I-1), X is O. In some embodiments, X is $NR^N$. In some embodiments, X is selected from O, NH and N-(methyl). In some embodiments, X is selected from O and NH. In some embodiments, X is NH. In some embodiments, X is N-(methyl).

In some embodiments of Formula (I) or Formula (I-1), $R^N$ is selected from H and methyl. In some embodiments of Formula (I) or Formula (I-1), $R^N$ is H. In some embodiments, $R^N$ is methyl.

In some embodiments of Formula (I) or Formula (I-1), $R_A$ is H and $R_B$ is H.

In some embodiments of Formula (I) or Formula (I-1), $R_A$ and $R_B$ together with the nitrogen atom to which they are attached form a 5-membered heterocycloalkyl optionally substituted with halo. In some embodiments, $R_A$ and $R_B$ together with the nitrogen atom to which they are attached form a 6-membered heterocycloalkyl optionally substituted with halo.

In some embodiments of Formula (I) or Formula (I-1), $R_A$ and $R_B$ together with the nitrogen atom to which they are attached form a ring of the formula:

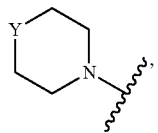

wherein Y is selected from O, S and NH. In some embodiments, Y is O. In some embodiments, Y is S. In some embodiments, $R_A$ and $R_B$ together with the nitrogen atom to which they are attached form a ring of any one of the following formulae:

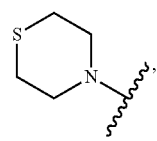
(i)

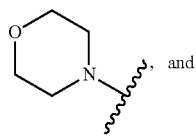 and
(ii)

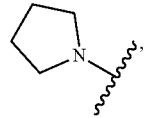,
(iii)

wherein any one of the formulae (i)-(iii) is optionally substituted with halo.

In some embodiments of Formula (I) or Formula (I-1), $R_A$ and $R_B$ together with the nitrogen atom to which they are attached form a ring of the formula:

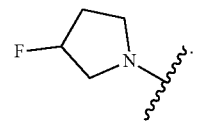
(iiia)

In some embodiments of Formula (I) or Formula (I-1), $R_9$ is selected from $C_{1-6}$ alkyl, $C_{2-6}$ alkenyl, $C_{1-6}$ hydroxyalkyl, and $C_{3-5}$ cycloalkyl, wherein the $C_{1-6}$ alkyl is optionally substituted with a substituent selected from $C_{1-6}$ alkoxy and $S(C_{1-6}$ alkyl). In some embodiments, $R_9$ is selected from $C_{1-6}$ alkyl, $C_{1-6}$ hydroxyalkyl, and $C_{3-5}$ cycloalkyl, wherein the $C_{1-6}$ alkyl is optionally substituted with a substituent selected from $C_{1-6}$ alkoxy and $S(C_{1-6}$ alkyl). In some embodiments, $R_9$ is $C_{1-6}$ alkyl. In some embodiments, $R_9$ is $C_{2-6}$ alkenyl. In some embodiments, $R_9$ is $C_{1-6}$ hydroxyalkyl. In some embodiments, $R_9$ is $C_{3-5}$ cycloalkyl. In some embodiments, $R_9$ is $C_{1-6}$ alkyl substituted with $C_{1-6}$ alkoxy or $S(C_{1-6}$ alkyl). In some embodiments, $R_9$ is $C_{1-6}$ alkyl substituted with $C_{1-6}$ alkoxy. In some embodiments, $R_9$ is $C_{1-6}$ alkyl substituted with $S(C_{1-6}$ alkyl). In some embodiments, $R_9$ is $C_{1-6}$ alkyl optionally substituted with $S(C_{1-6}$ alkyl). In some embodiments, $R_9$ is selected from methyl, ethenyl, hydroxymethyl, methoxymethyl, methylthiomethyl and cyclopropyl. In some embodiments, $R_9$ is selected from methyl, hydroxymethyl, methoxymethyl, methylthiomethyl and cyclopropyl. In some embodiments, $R_9$ is selected from methyl, and hydroxymethyl.

In some embodiments, $R_9$ is selected from methyl, and methoxymethyl. In some embodiments, $R_9$ is selected from methyl, and methylthiomethyl. In some embodiments, $R_9$ is selected from methyl, ethenyl, and cyclopropyl. In some embodiments, $R_9$ is selected from methyl, and cyclopropyl. In some embodiments, $R_9$ is methyl. In some embodiments, $R_9$ is ethenyl. In some embodiments, $R_9$ is $C_{1-6}$ hydroxymethyl. In some embodiments, $R_9$ is methoxymethyl. In some embodiments, $R_9$ is methylthiomethyl. In some embodiments, $R_9$ is cyclopropyl.

In some embodiments of Formula (I) or Formula (I-1), $R^{10}$ is selected from H, $C_{1-4}$ alkenyl, $C_{1-4}$ haloalkyl, $C_{3-5}$ cycloalkyl and $C_{1-4}$ alkyl optionally substituted with a substituent selected from amino, $C_{1-4}$ alkoxy, $C_{3-5}$ cycloalkyl, and 3- to 6-membered heterocycloalkyl. In some embodiments, $R^{10}$ is selected from H, allyl, fluoromethyl, cyclopropyl, methoxymethyl, aminomethyl, (N-azetidinyl) methyl, oxetanyl-methyl, cyclopropyl-methyl, vinyl, propyl and isopropyl. In some embodiments, $R^{10}$ is H. In some embodiments, $R^{10}$ is $C_{1-4}$ alkyl. In some embodiments, $R^{10}$ is methyl. In some embodiments, $R^{10}$ is ethyl. In some embodiments, $R^{10}$ is n-propyl. In some embodiments, $R^{10}$ is i-propyl.

In some embodiments of Formula (I), $R_{11}$ is H or $C_{1-3}$ alkyl, wherein the $C_{1-3}$ alkyl is optionally substituted with OH. In some embodiments, $R_1$ is H. In some embodiments, $R_1$ is $C_{1-3}$ alkyl, wherein the $C_{1-3}$ alkyl is optionally substituted with OH. For example, Ru can be —CH$_2$OH. In some embodiments, $R_{11}$ is CH$_3$.

In some embodiments of Formula (I) or Formula (I-1), the carbon atom to which $R_9$ is attached is in (S) configuration according to Cahn-Ingold-Prelog nomenclature. In some embodiments, the carbon atom to which $R_9$ is attached is in (R) configuration according to Cahn-Ingold-Prelog nomenclature. In some embodiments, the stereochemistry at the carbon atom bound to $R_9$ is as shown below:

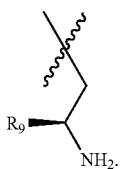

In some embodiments, the stereochemistry at the carbon atom bound to $R_9$ is as shown below:

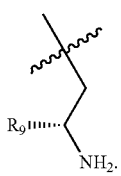

In some embodiments of Formula (I) or Formula (I-1), the carbon atom to which $R_{10}$ is attached is in (S) configuration according to Cahn-Ingold-Prelog nomenclature. In some embodiments, the carbon atom to which $R_{10}$ is attached is in (R) configuration according to Cahn-Ingold-Prelog nomenclature. In some embodiments, the stereochemistry at the carbon atom bound to $R_{10}$ is as shown below:

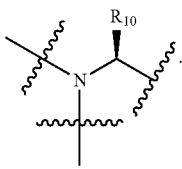

In some embodiments, the stereochemistry at the carbon atom bound to $R_{10}$ is as shown below:

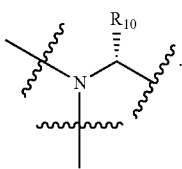

In some embodiments of Formula (I):
$R_1$ is selected from H, and fluoro;
$R_2$ is selected from H, halo, $C_{1-4}$ haloalkyl, and $C_{1-4}$ haloalkoxy;
$R_3$ is selected from H, and $C_{1-4}$ haloalkyl;
W is $CR_4$ and $R_4$ is selected from H, halo, $C_{1-6}$ alkyl, $C_{1-4}$ alkoxy, $C_{1-4}$ haloalkoxy, S($C_{1-4}$ alkyl), 6-membered heterocycloalkyl, and S(O)$_2$C$_{1-4}$ alkyl;
$R_5$ is selected from H and fluoro;
$R_6$ is selected from H, ethenyl, and $C_{1-6}$ hydroxyalkyl;
$R_7$ is selected from H, and methyl; or
$R_6$ and $R_7$ form a ring of the formula:

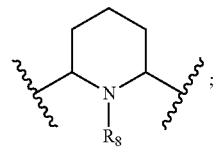

$R_8$ is selected from H, and $C_{1-4}$ haloalkyl;
$R^N$ is selected from H and methyl;
$R_A$ is H and $R_B$ is H;
$R_9$ is selected from $C_{1-6}$ alkyl, $C_{2-6}$ alkenyl, $C_{1-6}$ hydroxyalkyl, and $C_{3-5}$ cycloalkyl, wherein the $C_{1-6}$ alkyl is optionally substituted with a substituent selected from $C_{1-6}$ alkoxy and S($C_{1-6}$ alkyl);
$R_{10}$ is selected from H, methyl, ethyl, n-propyl and i-propyl; and
$R_{11}$ is H.

In some embodiments of Formula (I):
$R_1$ is selected from H, and fluoro;
$R_2$ is selected from H, chloro, trifluoromethyl, and trifluoromethoxy;
$R_3$ is selected from H, and trifluoromethyl;
W is $CR_4$ and $R_4$ is selected from H, fluoro, chloro, methylthio, methoxy, methyl, S(=O)$_2$(methyl), trifluoromethoxy, and N-morpholino;
$R_5$ is selected from H and fluoro;
$R_6$ is selected from H, ethenyl, and hydroxymethyl;
$R_7$ is selected from H, and methyl; or
$R_6$ and $R_7$ form a ring of the formula:

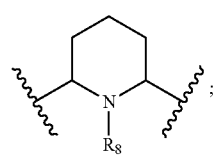

$R_8$ is selected from H, and 3-fluoropropyl;
$R^N$ is selected from H, and methyl;
$R_A$ is H and $R_B$ is H;
$R_9$ is selected from methyl, $C_{1-6}$ hydroxymethyl, methoxymethyl, methylthiomethyl, ethenyl, and cyclopropyl;
$R_{10}$ is selected from H, methyl, ethyl, n-propyl and i-propyl; and
$R_{11}$ is H.

In some embodiments of Formula (I):
$R_1$ is selected from H, and fluoro;
$R_2$ is selected from H, halo, $C_{1-4}$ haloalkyl, and $C_{1-4}$ haloalkoxy;
$R_3$ is selected from H, and $C_{1-4}$ haloalkyl;
W is $CR_4$ and $R_4$ is selected from H, halo, $C_{1-6}$ alkyl, $C_{1-4}$ alkoxy, $C_{1-4}$ haloalkoxy, S($C_{1-4}$ alkyl), 6-membered heterocycloalkyl, and S(O)$_2$C$_{1-4}$ alkyl;
$R_5$ is selected from H and fluoro;
$R_6$ is selected from H, ethenyl, and $C_{1-6}$ hydroxyalkyl;

$R_7$ is selected from H, and methyl; or
$R_6$ and $R_7$ form a ring of the formula:

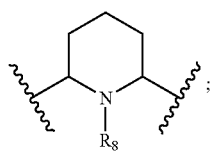

$R_8$ is selected from H, and $C_{1-4}$ haloalkyl;
$R^N$ is selected from H and methyl;
$R_A$ is H and $R_B$ is H; or
$R_A$ and $R_B$ together with the nitrogen atom to which they are attached form a ring of any one of the following formulae:

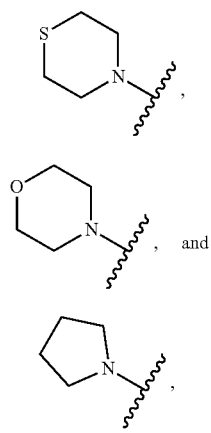

wherein any one of the formulae (i)-(iii) is optionally substituted with halo;
$R_9$ is selected from $C_{1-6}$ alkyl, $C_{1-6}$ hydroxyalkyl, and $C_{3-5}$ cycloalkyl, wherein the $C_{1-6}$ alkyl is optionally substituted with a substituent selected from $C_{1-6}$ alkoxy and $S(C_{1-6}$ alkyl);
$R_{10}$ is selected from H, methyl, ethyl, n-propyl and i-propyl; and
$R_{11}$ is H.
In some embodiments of Formula (I):
$R_1$ is selected from H, and fluoro;
$R_2$ is selected from H, halo, $C_{1-4}$ haloalkyl, and $C_{1-4}$ haloalkoxy;
$R_3$ is selected from H, and $C_{1-4}$ haloalkyl;
W is $CR_4$ and $R_4$ is selected from H, halo, $C_{1-6}$ alkyl, $C_{1-4}$ alkoxy, $C_{1-4}$ haloalkoxy, $S(C_{1-4}$ alkyl), 6-membered heterocycloalkyl, and $S(O)_2C_{1-4}$ alkyl;
$R_5$ is selected from H and fluoro;
$R_6$ is selected from H, ethenyl, and $C_{1-6}$ hydroxyalkyl;
$R_7$ is selected from H, and methyl; or
$R_6$ and $R_7$ form a ring of the formula:

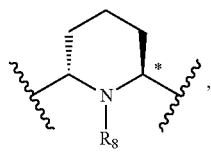

wherein the * indicates the ring carbon that is attached to the ring containing W;
$R_8$ is selected from H, and $C_{1-4}$ haloalkyl;
$R^N$ is selected from H and methyl;
$R_A$ is H and $R_B$ is H; or
$R_A$ and $R_B$ together with the nitrogen atom to which they are attached form a ring of any one of the following formulae:

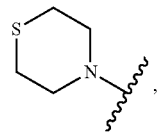

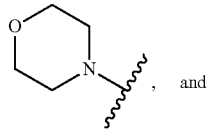

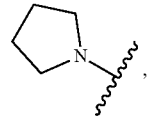

wherein any one of the formulae (i)-(iii) is optionally substituted with halo;
$R_9$ is selected from $C_{1-6}$ alkyl, $C_{1-6}$ hydroxyalkyl, and $C_{3-5}$ cycloalkyl, wherein the $C_{1-6}$ alkyl is optionally substituted with a substituent selected from $C_{1-6}$ alkoxy and $S(C_{1-6}$ alkyl);
$R_{10}$ is selected from H, methyl, ethyl, n-propyl and i-propyl; and
$R_{11}$ is H.
In some embodiments of Formula (I):
$R_1$ is selected from H, and fluoro;
$R_2$ is selected from H, chloro, trifluoromethyl, and trifluoromethoxy;
$R_3$ is selected from H, and trifluoromethyl;
W is $CR_4$ and $R_4$ is selected from H, fluoro, chloro, methylthio, methoxy, methyl, $S(=O)_2$(methyl), trifluoromethoxy, and N-morpholino;
$R_5$ is selected from H and fluoro;
$R_6$ is selected from H, ethenyl, and hydroxymethyl;
$R_7$ is selected from H, and methyl; or
$R_6$ and $R_7$ form a ring of the formula:

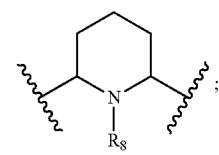

$R_8$ is selected from H, and 3-fluoropropyl;
$R^N$ is selected from H, and methyl;
$R_A$ is H and $R_B$ is H; or
$R_A$ and $R_B$ together with the nitrogen atom to which they are attached form a ring of any one of the following formulae:

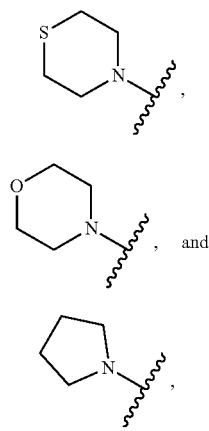

(i), (ii), (iii)

wherein any one of the formulae (i)-(iii) is optionally substituted with halo;
R$_9$ is selected from methyl, C$_{1-6}$ hydroxymethyl, methoxymethyl, methylthiomethyl and cyclopropyl;
R$_{10}$ is selected from H, methyl, ethyl, n-propyl and i-propyl; and
R$_{11}$ is H.
In some embodiments of Formula (I):
R$_1$ is selected from H, and fluoro;
R$_2$ is selected from H, chloro, trifluoromethyl, and trifluoromethoxy;
R$_3$ is selected from H, and trifluoromethyl;
W is CR$_4$ and R$_4$ is selected from H, fluoro, chloro, methylthio, methoxy, methyl, S(=O)$_2$(methyl), trifluoromethoxy, and N-morpholino;
R$_5$ is selected from H and fluoro;
R$_6$ is selected from H, ethenyl, and hydroxymethyl;
R$_7$ is selected from H, and methyl; or
R$_6$ and R$_7$ form a ring of the formula:

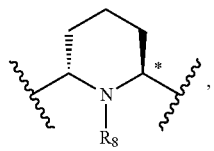

wherein the * indicates the ring carbon that is attached to the ring containing W;
R$_8$ is selected from H, and 3-fluoropropyl;
R$^N$ is selected from H, and methyl;
R$_A$ is H and R$_B$ is H; or
R$_A$ and R$_B$ together with the nitrogen atom to which they are attached form a ring of any one of the following formulae:

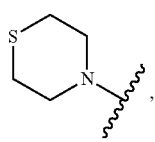

(i)

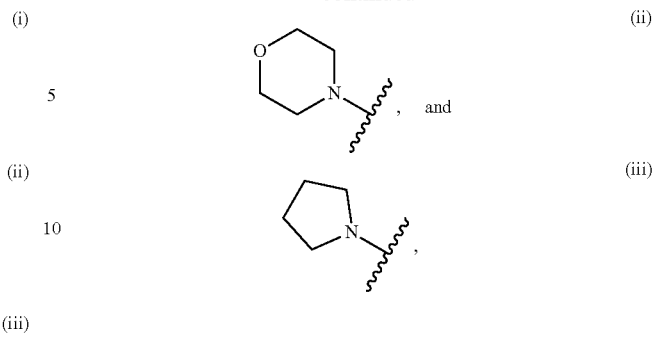

(ii), (iii)

wherein any one of the formulae (i)-(iii) is optionally substituted with halo;
R$_9$ is selected from methyl, C$_{1-6}$ hydroxymethyl, methoxymethyl, methylthiomethyl and cyclopropyl;
R$_{10}$ is selected from H, methyl, ethyl, n-propyl and i-propyl; and
R$_{11}$ is H.
In some embodiments of Formula (I):
R$_1$ is selected from H, and fluoro;
R$_2$ is selected from chloro, and trifluoromethyl;
R$_3$ is H;
W is CR$_4$ and R$_4$ is selected from H, fluoro, chloro, methylthio, methoxy, methyl, S(=O)$_2$(methyl), trifluoromethoxy, and N-morpholino;
R$_5$ is H;
R$_6$ and R$_7$ form a ring of the formula:

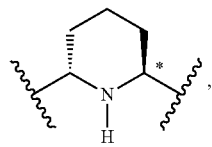 [SMILES: *[C@@H]1CCC[C@@H](*)N1]

wherein the * indicates the ring carbon that is attached to the ring containing W;
X is NH;
R$_A$ is H and R$_B$ is H; and
R$_9$ is selected from methyl, and methylthiomethyl;
R$_{10}$ is selected from H, methyl, ethyl, n-propyl and i-propyl; and
R$_{11}$ is H.
In some embodiments of Formula (I-1):
R$_1$ is selected from H, and fluoro;
R$_2$ is selected from H, halo, C$_{1-4}$ haloalkyl, and C$_{1-4}$ haloalkoxy;
R$_3$ is selected from H, and C$_{1-4}$ haloalkyl;
W is CR$_4$ and R$_4$ is selected from H, halo, C$_{1-6}$ alkyl, C$_{1-4}$ alkoxy, C$_{1-4}$ haloalkoxy, S(C$_{1-4}$ alkyl), 6-membered heterocycloalkyl, and S(O)$_2$C$_{1-4}$ alkyl;
R$_5$ is selected from H and fluoro;
R$_6$ is selected from H, ethenyl, and C$_{1-6}$ hydroxyalkyl;
R$_7$ is selected from H, and methyl; or
R$_6$ and R$_7$ form a ring of the formula:

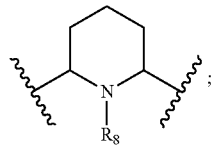

$R_8$ is selected from H, and $C_{1-4}$ haloalkyl;

$R^N$ is selected from H and methyl;

$R_A$ is H and $R_B$ is H; or $R_A$ and $R_B$ together with the nitrogen atom to which they are attached form a ring of any one of the following formulae:

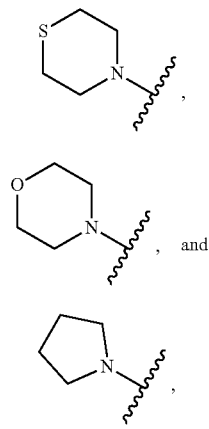

(i), (ii), and (iii)

wherein any one of the formulae (i)-(iii) is optionally substituted with halo;

$R_9$ is selected from $C_{1-6}$ alkyl, $C_{1-6}$ hydroxyalkyl, and $C_{3-5}$ cycloalkyl, wherein the $C_{1-6}$ alkyl is optionally substituted with a substituent selected from $C_{1-6}$ alkoxy and $S(C_{1-6}$ alkyl); and $R_{10}$ is selected from H, methyl, ethyl, n-propyl and i-propyl.

In some embodiments of Formula (I-1):

$R_1$ is selected from H, and fluoro;

$R_2$ is selected from H, halo, $C_{1-4}$ haloalkyl, and $C_{1-4}$ haloalkoxy;

$R_3$ is selected from H, and $C_{1-4}$ haloalkyl;

W is $CR_4$ and $R_4$ is selected from H, halo, $C_{1-6}$ alkyl, $C_{1-4}$ alkoxy, $C_{1-4}$ haloalkoxy, $S(C_{1-4}$ alkyl), 6-membered heterocycloalkyl, and $S(O)_2C_{1-4}$ alkyl;

$R_5$ is selected from H and fluoro;

$R_6$ is selected from H, ethenyl, and $C_{1-6}$ hydroxyalkyl;

$R_7$ is selected from H, and methyl; or $R_6$ and $R_7$ form a ring of the formula:

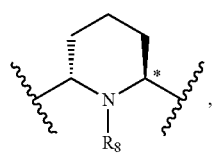

wherein the * indicates the ring carbon that is attached to the ring containing W;

$R_8$ is selected from H, and $C_{1-4}$ haloalkyl;

$R^N$ is selected from H and methyl;

$R_A$ is H and $R_B$ is H; or $R_A$ and $R_B$ together with the nitrogen atom to which they are attached form a ring of any one of the following formulae:

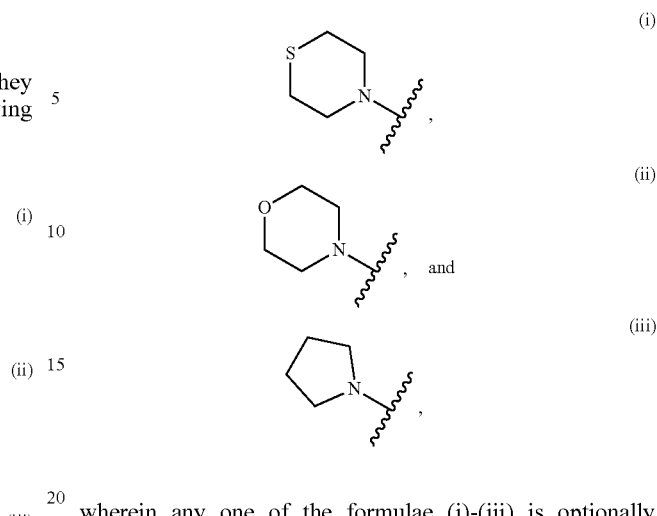

(i), (ii) and, (iii)

wherein any one of the formulae (i)-(iii) is optionally substituted with halo;

$R_9$ is selected from $C_{1-6}$ alkyl, $C_{1-6}$ hydroxyalkyl, and $C_{3-5}$ cycloalkyl, wherein the $C_{1-6}$ alkyl is optionally substituted with a substituent selected from $C_{1-6}$ alkoxy and $S(C_{1-6}$ alkyl); and $R_{10}$ is selected from H, methyl, ethyl, n-propyl and i-propyl.

In some embodiments of Formula (I-1):

$R_1$ is selected from H, and fluoro;

$R_2$ is selected from H, chloro, trifluoromethyl, and trifluoromethoxy;

$R_3$ is selected from H, and trifluoromethyl;

W is $CR_4$ and $R_4$ is selected from H, fluoro, chloro, methylthio, methoxy, methyl, $S(=O)_2$(methyl), trifluoromethoxy, and N-morpholino;

$R_5$ is selected from H and fluoro;

$R_6$ is selected from H, ethenyl, and hydroxymethyl;

$R_7$ is selected from H, and methyl; or $R_6$ and $R_7$ form a ring of the formula:

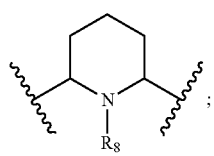

$R_8$ is selected from H, and 3-fluoropropyl;

$R^N$ is selected from H, and methyl;

$R_A$ is H and $R_B$ is H; or $R_A$ and $R_B$ together with the nitrogen atom to which they are attached form a ring of any one of the following formulae:

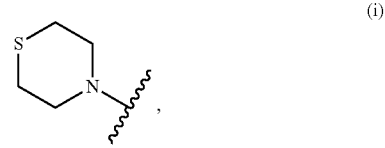

(i)

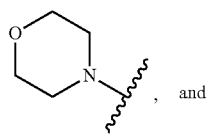, and

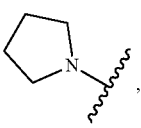, wherein any one of the formulae (i)-(iii) is optionally substituted with halo;

$R_9$ is selected from methyl, $C_{1-6}$ hydroxymethyl, methoxymethyl, methylthiomethyl and cyclopropyl; and $R_{10}$ is selected from H, methyl, ethyl, n-propyl and i-propyl.

In some embodiments of Formula (I-1):

$R_1$ is selected from H, and fluoro;

$R_2$ is selected from H, chloro, trifluoromethyl, and trifluoromethoxy;

$R_3$ is selected from H, and trifluoromethyl;

W is $CR_4$ and $R_4$ is selected from H, fluoro, chloro, methylthio, methoxy, methyl, $S(=O)_2(methyl)$, trifluoromethoxy, and N-morpholino;

$R_5$ is selected from H and fluoro;

$R_6$ is selected from H, ethenyl, and hydroxymethyl;

$R_7$ is selected from H, and methyl; or $R_6$ and $R_7$ form a ring of the formula:

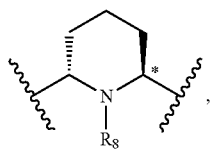, wherein the * indicates the ring carbon that is attached to the ring containing W;

$R_8$ is selected from H, and 3-fluoropropyl;

$R^N$ is selected from H, and methyl;

$R_A$ is H and $R_B$ is H; or $R_A$ and $R_B$ together with the nitrogen atom to which they are attached form a ring of any one of the following formulae:

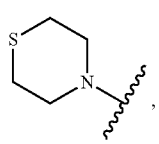,

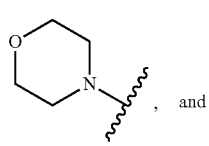, and

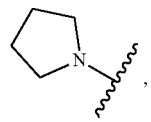, wherein any one of the formulae (i)-(iii) is optionally substituted with halo;

$R_9$ is selected from methyl, $C_{1-6}$ hydroxymethyl, methoxymethyl, methylthiomethyl and cyclopropyl; and $R_{10}$ is selected from H, methyl, ethyl, n-propyl and i-propyl.

In some embodiments of Formula (I-1):

$R_1$ is selected from H, and fluoro;

$R_2$ is selected from chloro, and trifluoromethyl;

$R_3$ is H;

W is $CR_4$ and $R_4$ is selected from H, fluoro, chloro, methylthio, methoxy, methyl, $S(=O)_2(methyl)$, trifluoromethoxy, and N-morpholino;

$R_5$ is H;

$R_6$ and $R_7$ form a ring of the formula:

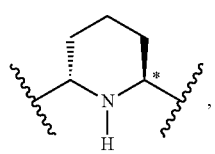, wherein the * indicates the ring carbon that is attached to the ring containing W;

X is NH;

$R_A$ is H and $R_B$ is H; and $R_9$ is selected from methyl, and methylthiomethyl; and $R_{10}$ is selected from H, methyl, ethyl, n-propyl, and i-propyl.

In some embodiments of any one of the Formulae (I), (I-1), (A), (Ia), (Ia-1), (Ia-2), (Ib), (Ic), (I-A), (Ib-2), (Ic-2), (Id-2), (Id) disclosed herein, the fragment

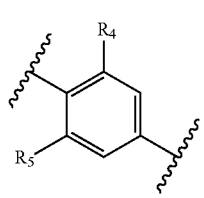

is selected from any one the following fragments:

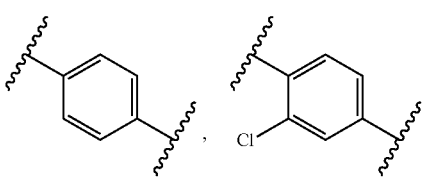

-continued

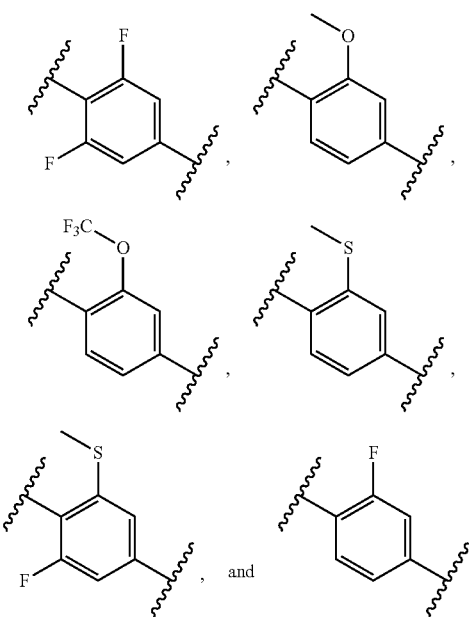

In some embodiments of any one of the Formulae (I), (I-1), (A), (Ia), (Ia-1), (Ia-2), (Ib), (Ic), (I-A), (Ib-2), (Ic-2), (Id-2), (Id) disclosed herein, the fragment

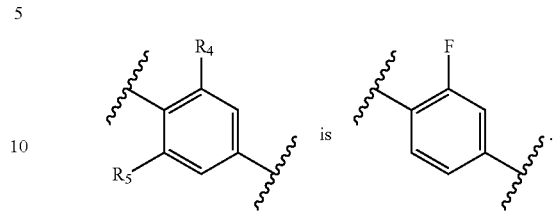

In some embodiments of any one of the Formulae (I), (I-1), (A), (Ia), (Ia-1), (Ia-2), (Ib), (Ic), (I-A), (Ib-2), (Ic-2), (Id-2), (Id) disclosed herein, the fragment

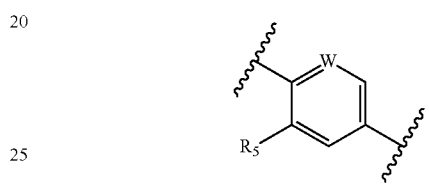

is selected from any one the following fragments:

In some embodiments of any one of the Formulae (I), (I-1), (A), (Ia), (Ia-1), (Ia-2), (Ib), (Ic), (I-A), (Ib-2), (Ic-2), (Id-2), (Id) disclosed herein, the fragment

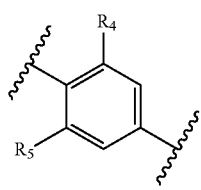

is selected from any one the following fragments:

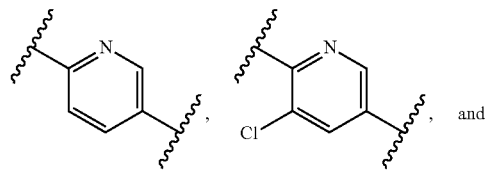

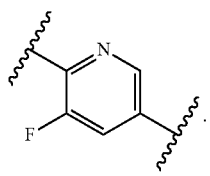

In some embodiments of any one of the Formulae (I), (I-1), (A), (Ia), (Ia-1), (Ia-2), (Ib), (Ic), (I-A), (Ib-2), (Ic-2), (Id-2), (Id) disclosed herein, the fragment

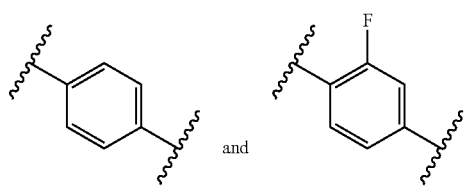

In some embodiments of any one of the Formulae (I), (I-1), (A), (Ia), (Ia-1), (Ia-2), (Ib), (Ic), (I-A), (Ib-2), (Ic-2), (Id-2), (Id) described herein, the fragment:

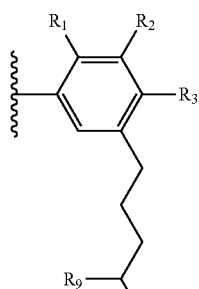

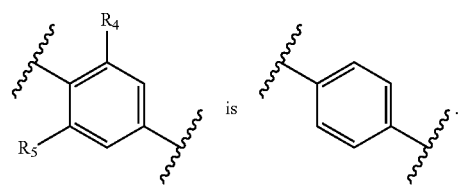

is selected from any one the following fragments:
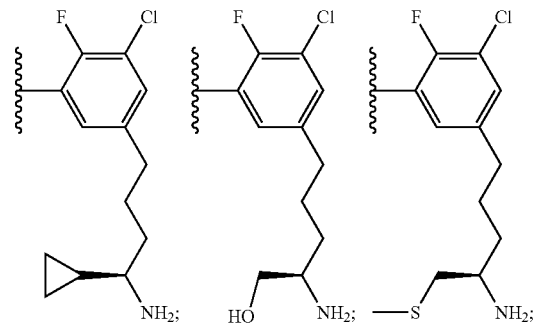
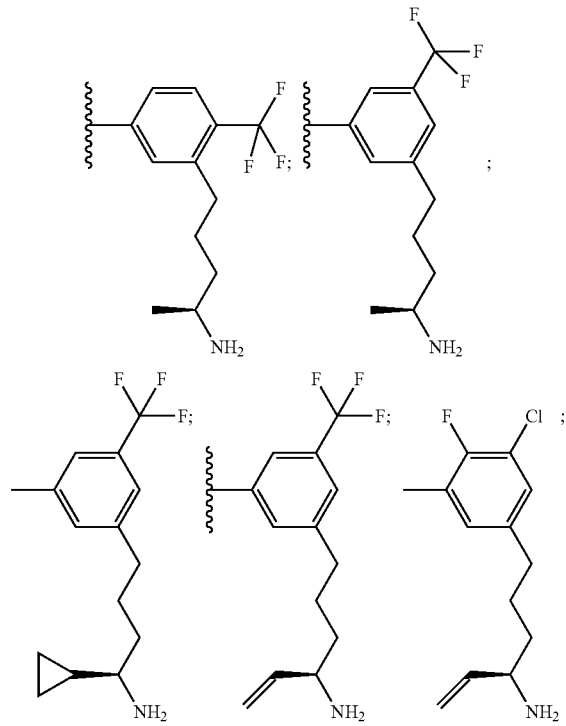
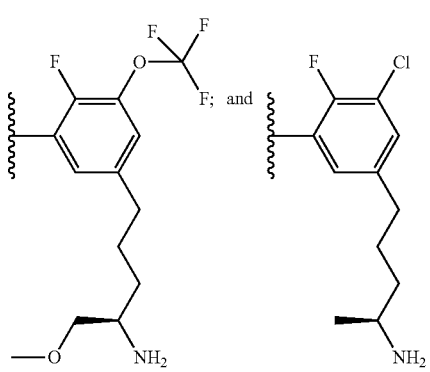
In some embodiments of any one of the Formulae (I), (I-1), (A), (Ia), (Ia-1), (Ia-2), (Ib), (Ic), (I-A), (Ib-2), (Ic-2), (Id-2), (Id) described herein, the fragment:
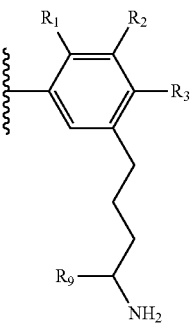
is selected from any one the following fragments:
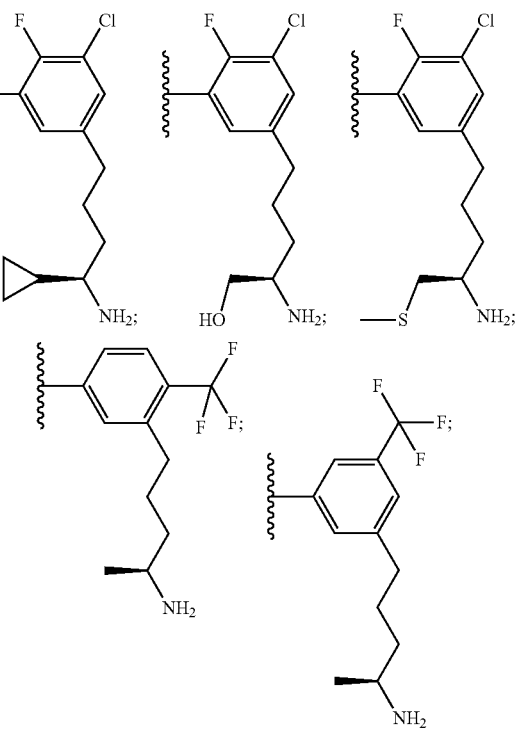
In some embodiments of any one of the Formulae (I), (I-1), (A), (Ia), (Ia-1), (Ia-2), (Ib), (Ic), (I-A), (Ib-2), (Ic-2), (Id-2), (Id) described herein, the fragment is selected from any one the following fragments:

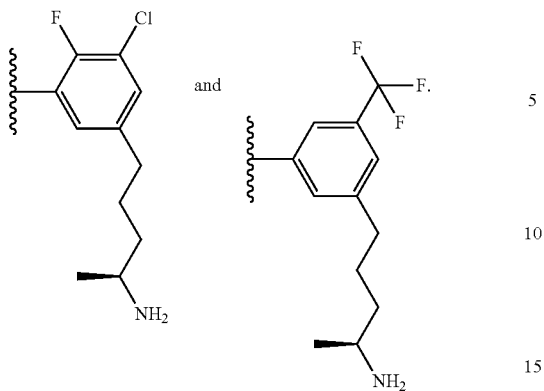

In some embodiments of the method, the compound of Formula (I) or Formula (I-1) is a compound of Formula (I-A):

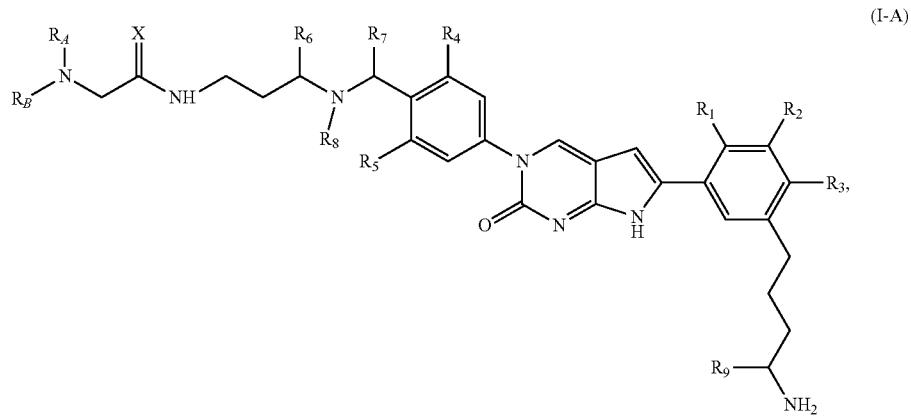

or a tautomer thereof or a pharmaceutically acceptable salt of the compound or tautomer, wherein X, $R_1$, $R_2$, $R_3$, $R_4$, $R_5$, $R_6$, $R_7$, $R_8$, $R_9$, $R_A$ and $R_B$ are as described herein for the compounds of Formula (I) or Formula (I-1).

In some embodiments of the method, the compound of Formula (I) or Formula (I-1) is a compound of Formula (A):

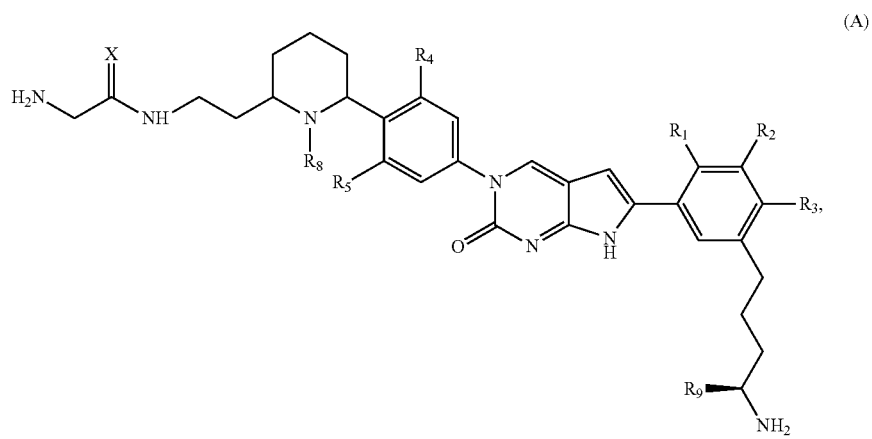

or a tautomer thereof or a pharmaceutically acceptable salt of the compound or tautomer, wherein X, $R_1$, $R_2$, $R_3$, $R_4$, $R_5$, $R_8$, and $R_9$ are as described herein for the compounds of Formula (I) or Formula (I-1).

In some embodiments of the method, the compound of Formula (I) or Formula (I-1) is a compound of Formula (Ia):

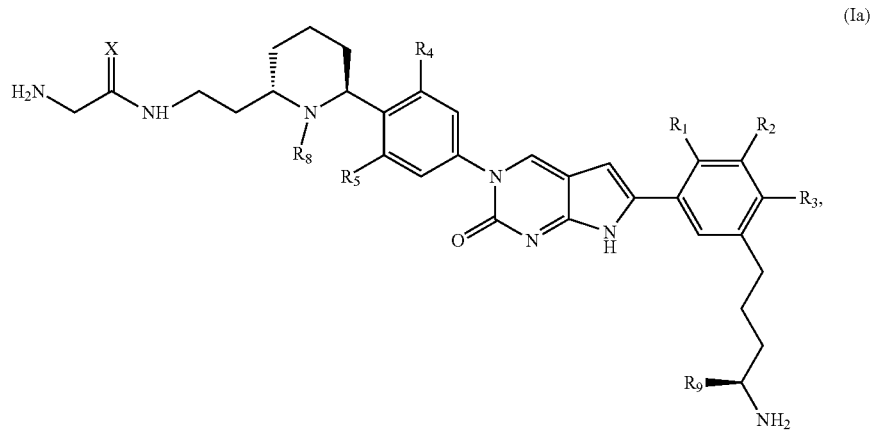

(Ia)

or a tautomer thereof or a pharmaceutically acceptable salt of the compound or tautomer, wherein X, $R_1$, $R_2$, $R_3$, $R_4$, $R_5$, $R_8$, and $R_9$ are as described herein for the compounds of Formula (I) or Formula (I-1).

In some embodiments of the method, the compound of Formula (I) or Formula (I-1) is a compound of Formula (Ia-1):

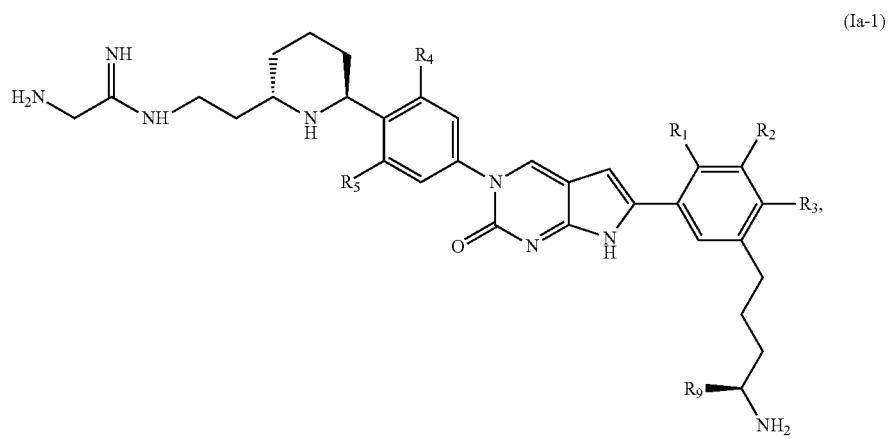

(Ia-1)

or a tautomer thereof or a pharmaceutically acceptable salt of the compound or tautomer, wherein $R_1$, $R_2$, $R_3$, $R_4$, $R_5$, and $R_9$ are as described herein for the compounds of Formula (I) or Formula (I-1).

In some embodiments of the method, the compound of Formula (I) or Formula (I-1) is a compound of Formula (Ia-2):

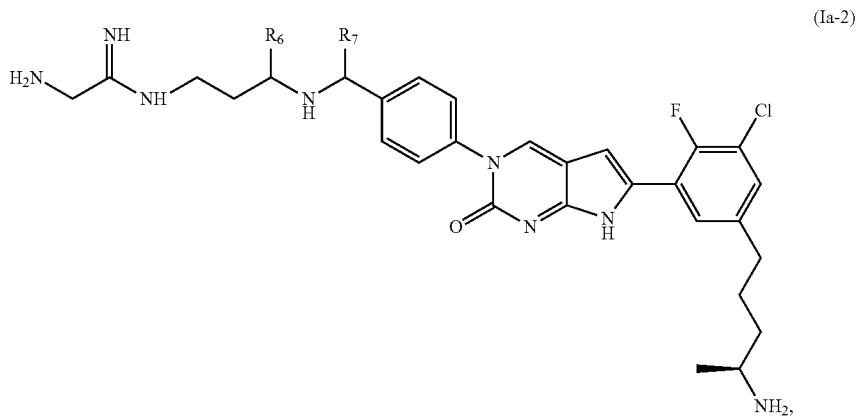

or a tautomer thereof or a pharmaceutically acceptable salt of the compound or tautomer, wherein $R_6$ and $R_7$ are as described herein for the compounds of Formula (I) or Formula (I-1).

In some embodiments of the method, the compound of Formula (I) or Formula (I-1) is a compound of Formula (Ib):

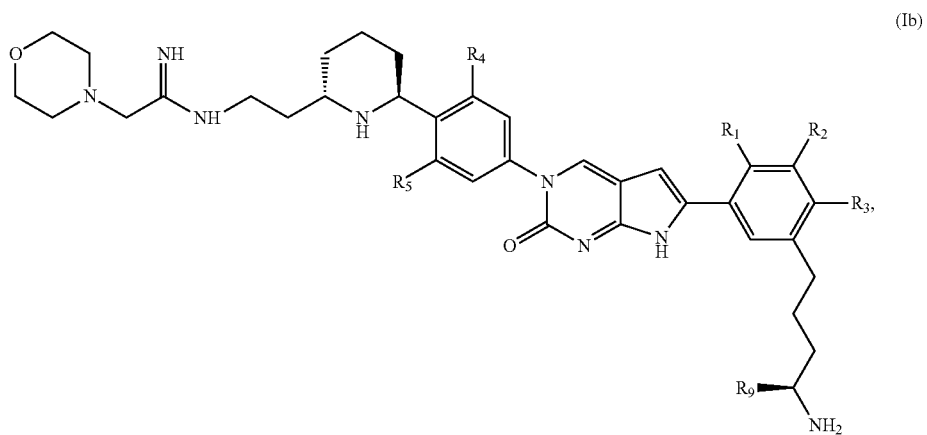

or a tautomer thereof or a pharmaceutically acceptable salt of the compound or tautomer, wherein $R_6$, $R_7$, and $R_8$ are as described herein for the compounds of Formula (I) or Formula (I-1).

In some embodiments of the method, the compound of Formula (I) or Formula (I-1) is a compound of Formula (Ic):

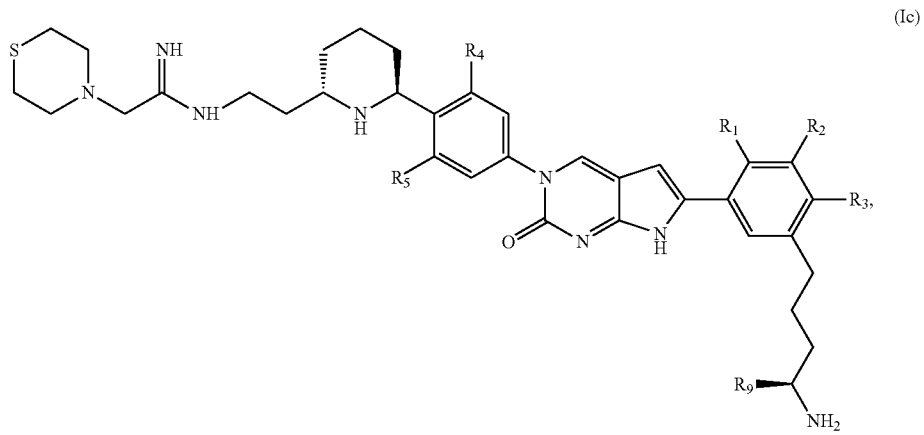

(Ic)

or a tautomer thereof or a pharmaceutically acceptable salt of the compound or tautomer, wherein $R_6$, $R_7$, and $R_8$ are as described herein for the compounds of Formula (I) or Formula (I-1).

In some embodiments of the method, the compound of Formula (I) or Formula (I-1) is a compound of Formula (Id):

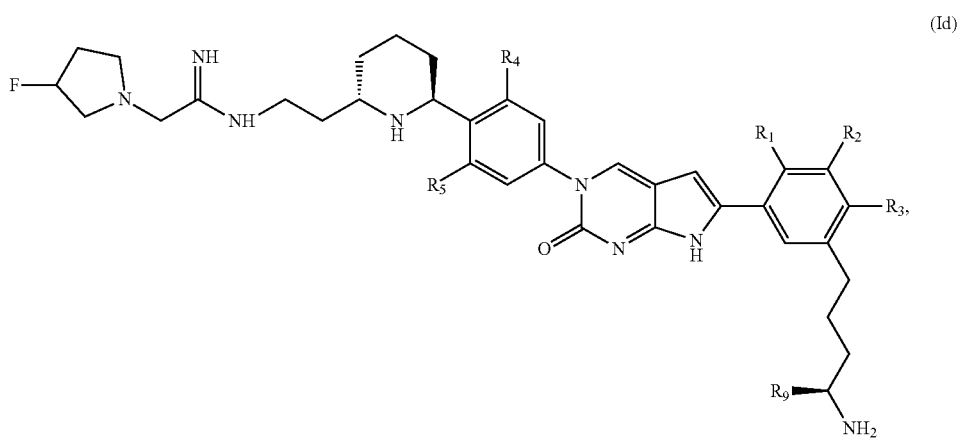

(Id)

or a tautomer thereof or a pharmaceutically acceptable salt of the compound or tautomer, wherein $R_6$, $R_7$, and $R_8$ are as described herein for the compounds of Formula (I) or Formula (I-1).

In some embodiments of the method, the compound of Formula (I) or Formula (I-1) is a compound of Formula (Ib-2):

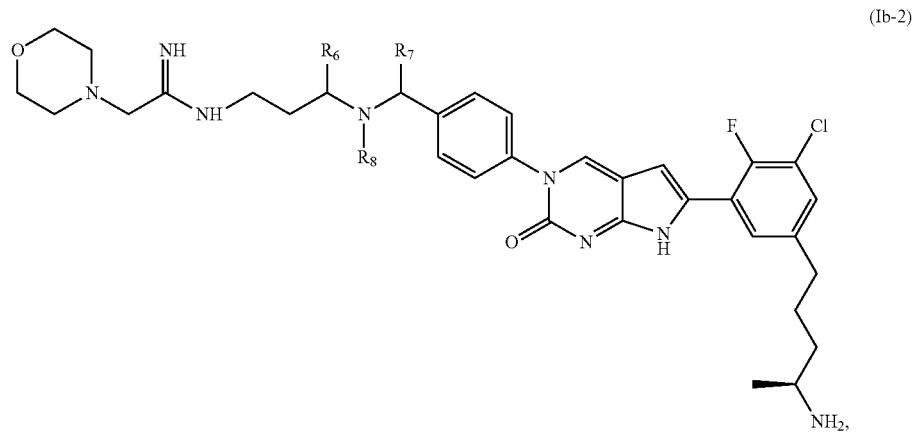

(Ib-2)

or a tautomer thereof or a pharmaceutically acceptable salt of the compound or tautomer, wherein $R_6$, $R_7$, and $R_8$ are as described herein for the compounds of Formula (I) or Formula (I-1).

In some embodiments of the method, the compound of Formula (I) or Formula (I-1) is a compound of Formula (Ic-2):

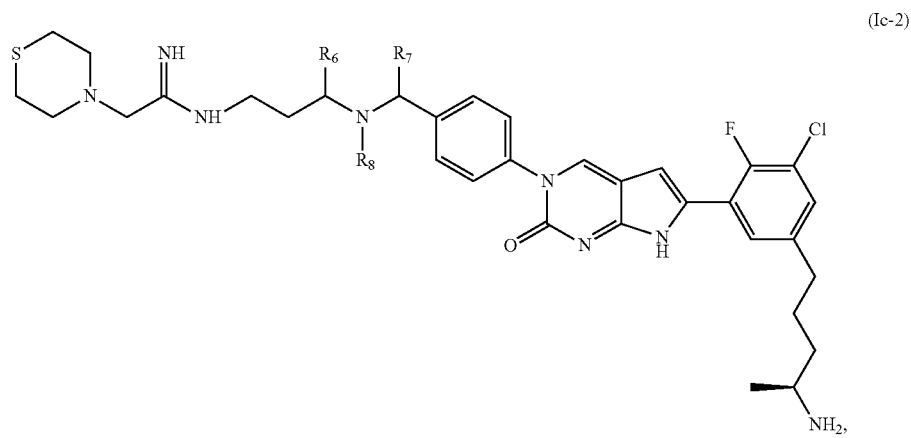

(Ic-2)

or a tautomer thereof or a pharmaceutically acceptable salt of the compound or tautomer, wherein $R_6$, $R_7$, and $R_8$ are as described herein for the compounds of Formula (I) or Formula (I-1).

In some embodiments of the method, the compound of Formula (I) or Formula (I-1) is a compound of Formula (Id-2):

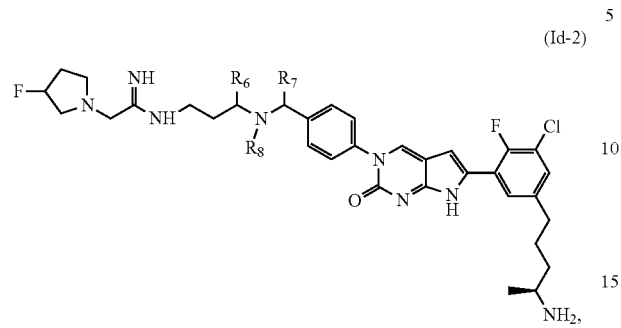

(Id-2)

or a tautomer thereof or a pharmaceutically acceptable salt of the compound or tautomer, wherein $R_6$, $R_7$, and $R_8$ are as described herein for the compounds of Formula (I) or Formula (I-1).

In some embodiments of the disclosed methods, the compound of Formula (I) or Formula (I-1) includes any one of compounds listed in Table 1, or a tautomer thereof or a pharmaceutically acceptable salt of the compound or tautomer.

TABLE 1

| # | Structure | ESI, m/z [M + H]+ |
|---|-----------|-------------------|
| 1 | 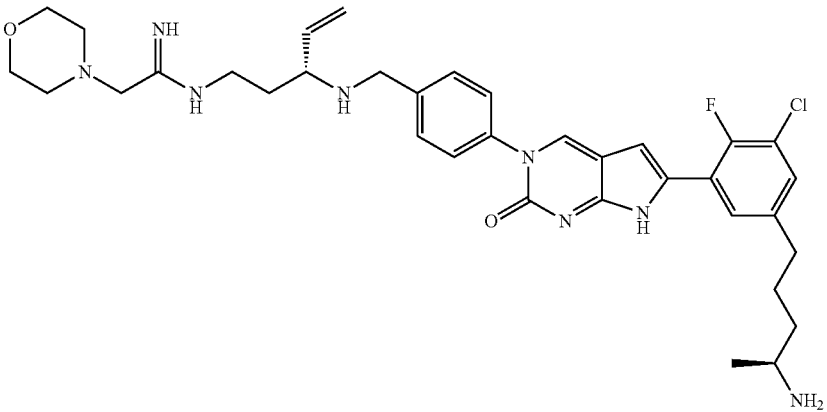 [SMILES: C=C[C@@H](CCNC(=N)CN1CCOCC1)NCc1ccc(-n2cc3cc(-c4cc(CCC[C@H](C)N)cc(Cl)c4F)[nH]c3nc2=O)cc1] | 663.6 |
| 2 | 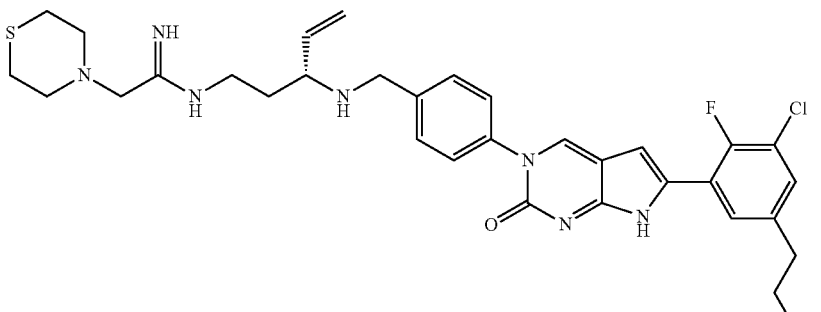 | 679.5 |

TABLE 1-continued
| # | Structure | ESI, m/z [M + H]+ |
|---|-----------|-------------------|
| 3 | 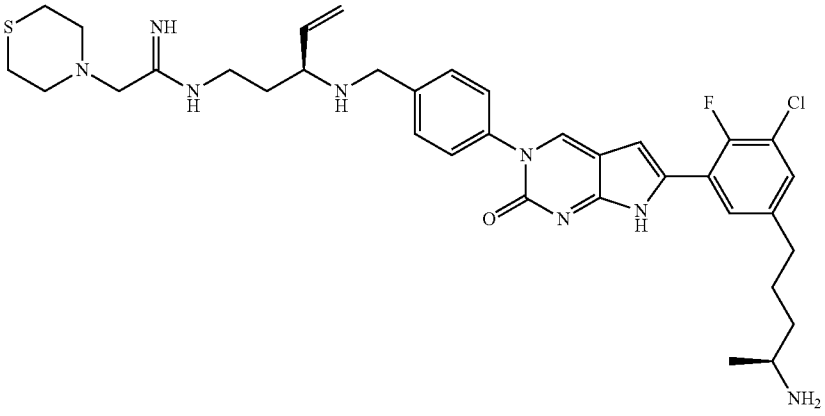 [SMILES: C=C[C@H](CCNC(=N)CN1CCSCC1)NCc1ccc(-n2cc3cc(-c4cc(CCC[C@H](C)N)cc(Cl)c4F)[nH]c3nc2=O)cc1] | 679.8 |
| 4 | 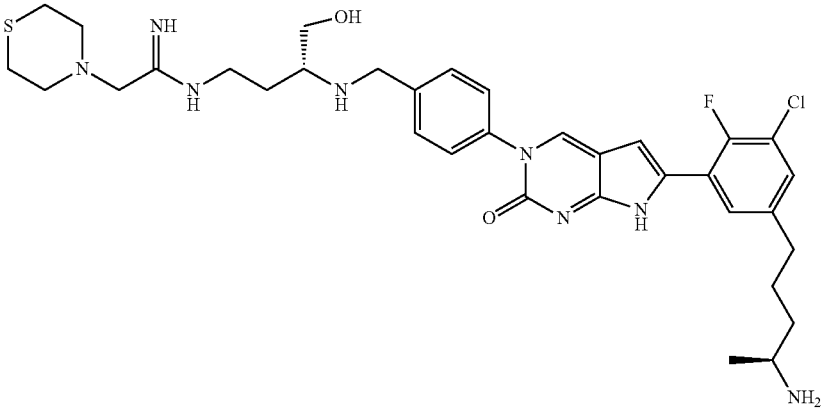 [SMILES: C[C@H](N)CCCc1cc(Cl)c(F)c(-c2cc3cn(-c4ccc(CN[C@@H](CO)CCNC(=N)CN5CCSCC5)cc4)c(=O)nc3[nH]2)c1] | 683.7 |
| 5 | 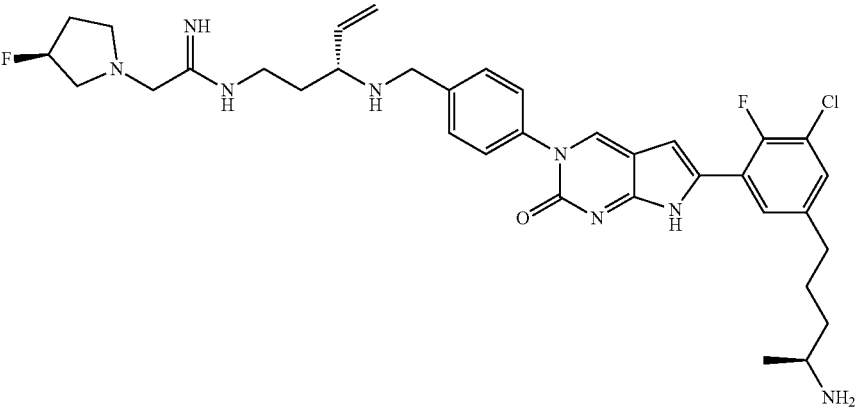 [SMILES: C=C[C@@H](CCNC(=N)CN1CC[C@H](F)C1)NCc1ccc(-n2cc3cc(-c4cc(CCC[C@H](C)N)cc(Cl)c4F)[nH]c3nc2=O)cc1] | 665.6 |

TABLE 1-continued
| # | Structure | ESI, m/z [M + H]+ |
|---|-----------|-------------------|
| 6 | 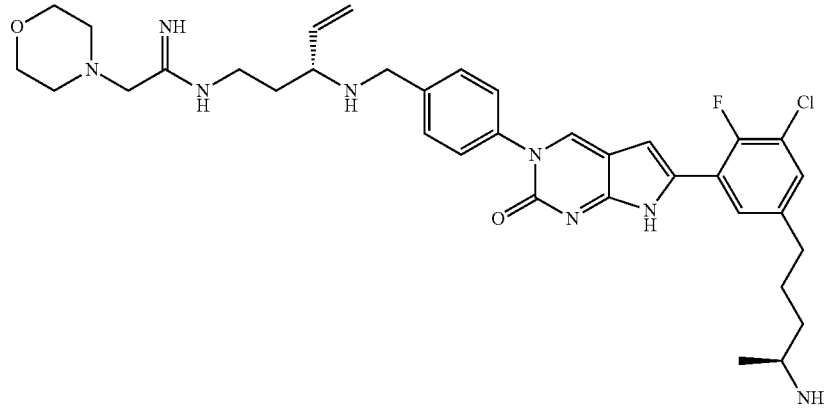 | 663.6 |
| 7 | 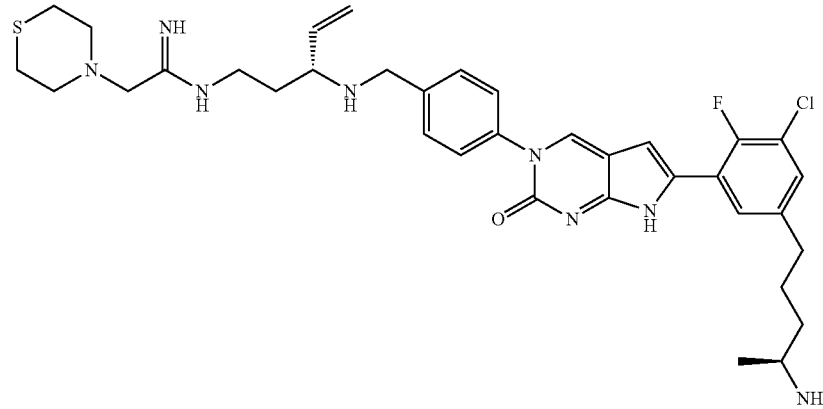 | 679.6 |
| 8 | 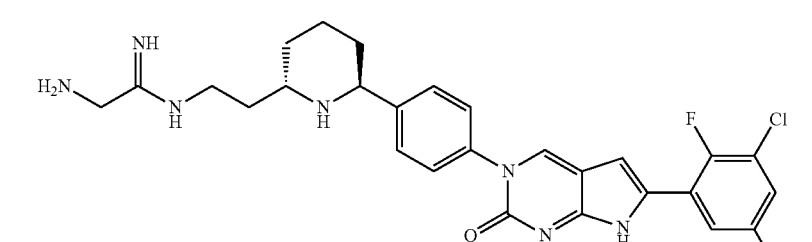 | 607.4 |

TABLE 1-continued
| # | Structure | ESI, m/z [M + H]+ |
|---|-----------|-------------------|
| 9 | 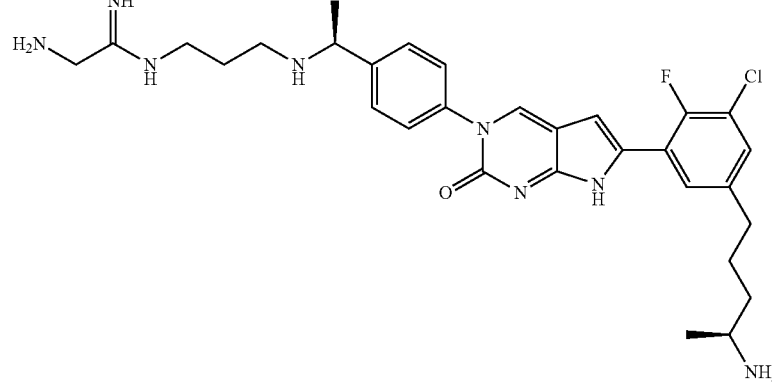 | 581.4 |
| 10 | 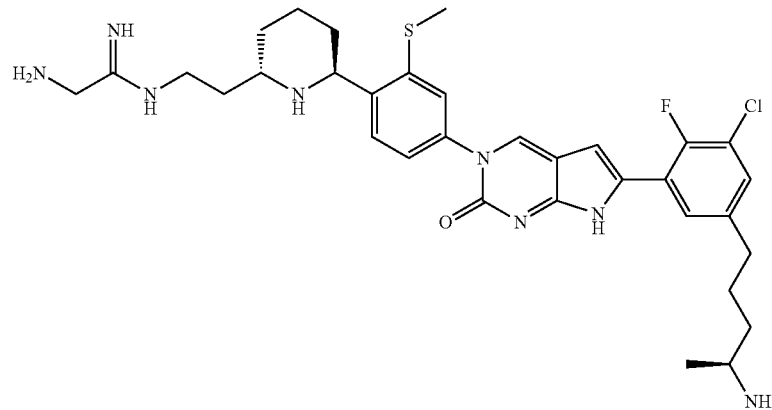 | 653.5 |
| 11 | 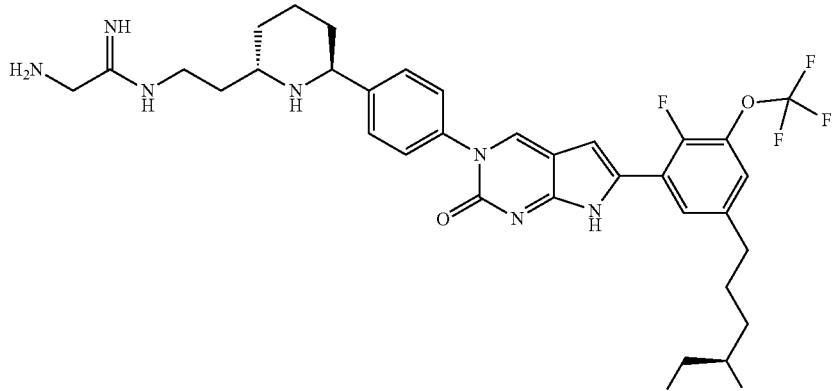 | 687.4 |

TABLE 1-continued
| # | Structure | ESI, m/z [M + H]+ |
|---|---|---|
| 12 | 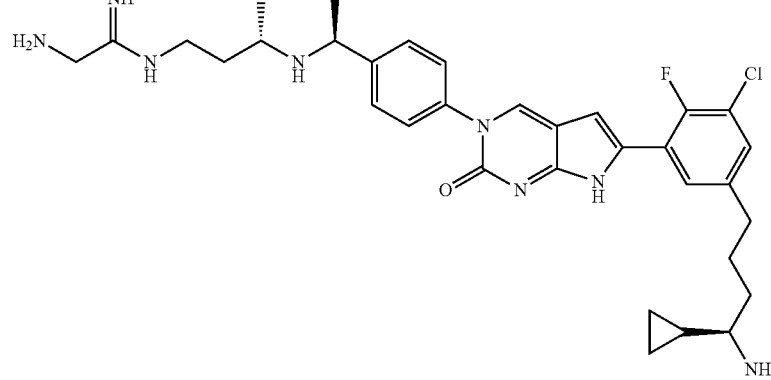 | 634.5 |
| 13 | 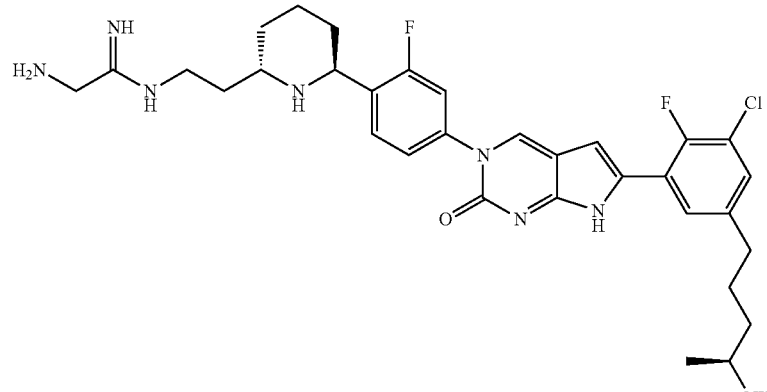 | 625.3 |
| 14 | 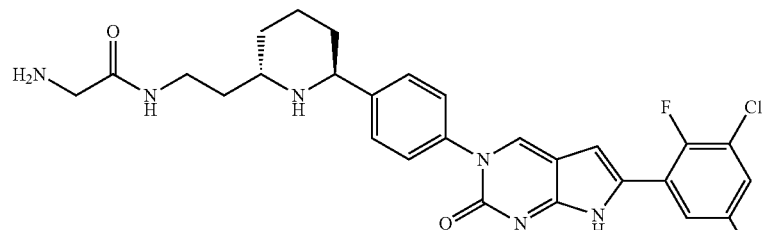 | 608.4 |

TABLE 1-continued
| # | Structure | ESI, m/z [M + H]+ |
|---|---|---|
| 15 | 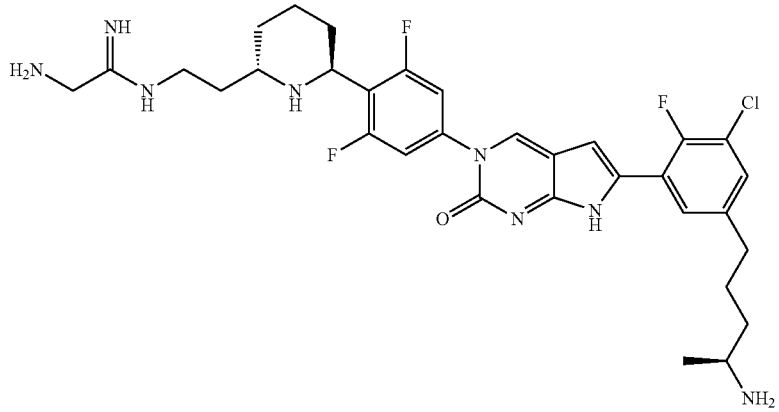 [SMILES: C[C@H](N)CCCc1cc(Cl)c(F)c(-c2cc3cn(-c4cc(F)c([C@@H]5CCC[C@@H](CCNC(=N)CN)N5)c(F)c4)c(=O)nc3[nH]2)c1] | 643.3 |
| 16 | 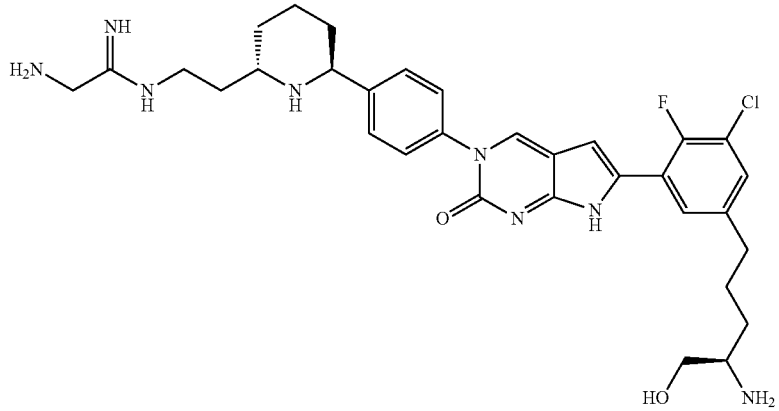 | 623.4 |
| 17 | 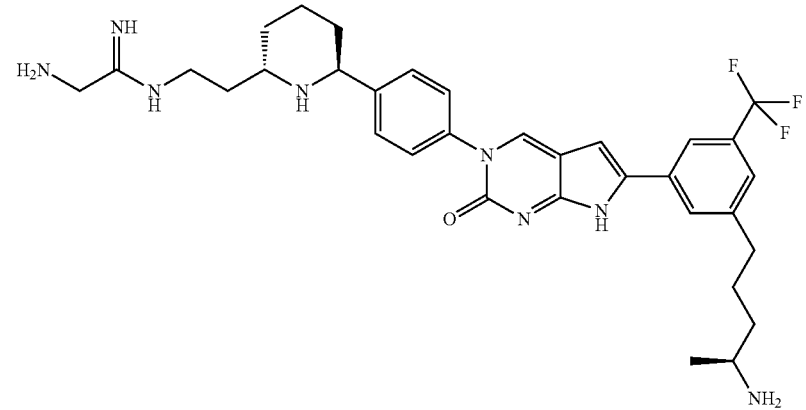 [SMILES: C[C@H](N)CCCc1cc(-c2cc3cn(-c4ccc([C@@H]5CCC[C@@H](CCNC(=N)CN)N5)cc4)c(=O)nc3[nH]2)cc(C(F)(F)F)c1] | 623.4 |

TABLE 1-continued
| # | Structure | ESI, m/z [M + H]+ |
|---|---|---|
| 18 | 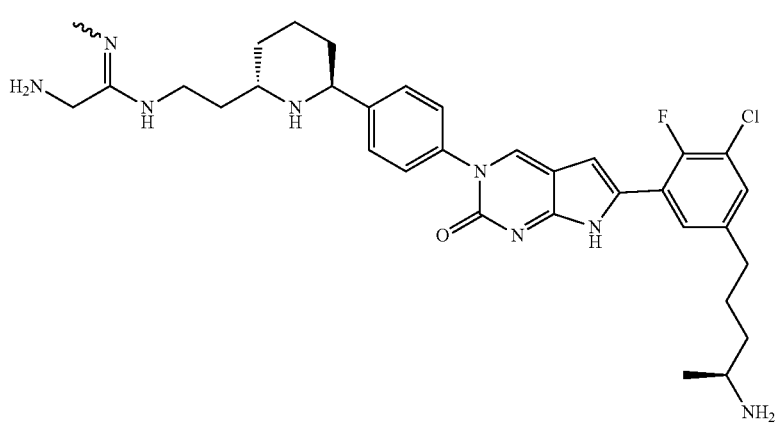 | 621.4 |
| 19 | 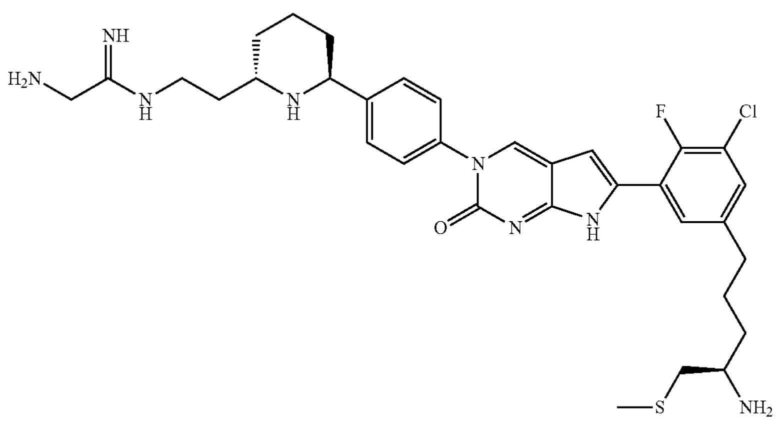 [SMILES: CSC[C@H](N)CCCc1cc(Cl)c(F)c(-c2cc3cn(-c4ccc([C@@H]5CCC[C@@H](CCNC(=N)CN)N5)cc4)c(=O)nc3[nH]2)c1] | 653.4 |
| 20 | 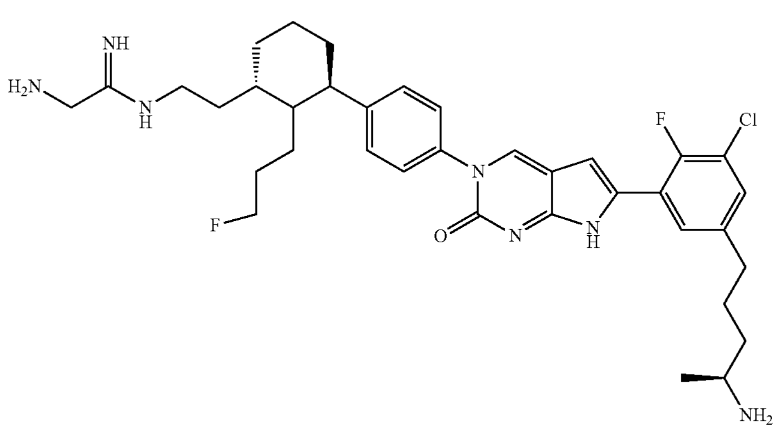 | 667 |

TABLE 1-continued

| # | Structure | ESI, m/z [M + H]+ |
|---|-----------|-------------------|
| 21 | 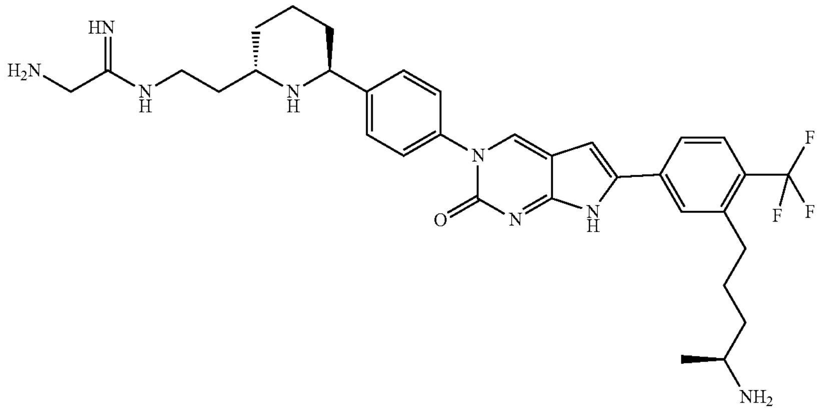 [SMILES: C[C@H](N)CCCc1cc(-c2cc3cn(-c4ccc([C@@H]5CCC[C@@H](CCNC(=N)CN)N5)cc4)c(=O)nc3[nH]2)ccc1C(F)(F)F] | 623.4 |
| 22 | 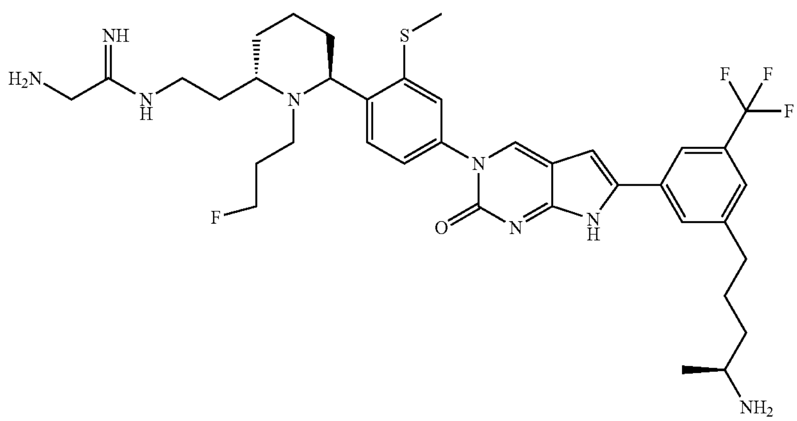 [SMILES: CSc1cc(-n2cc3cc(-c4cc(CCC[C@H](C)N)cc(C(F)(F)F)c4)[nH]c3nc2=O)ccc1[C@@H]1CCC[C@@H](CCNC(=N)CN)N1CCCF] | 729 |
| 23 | 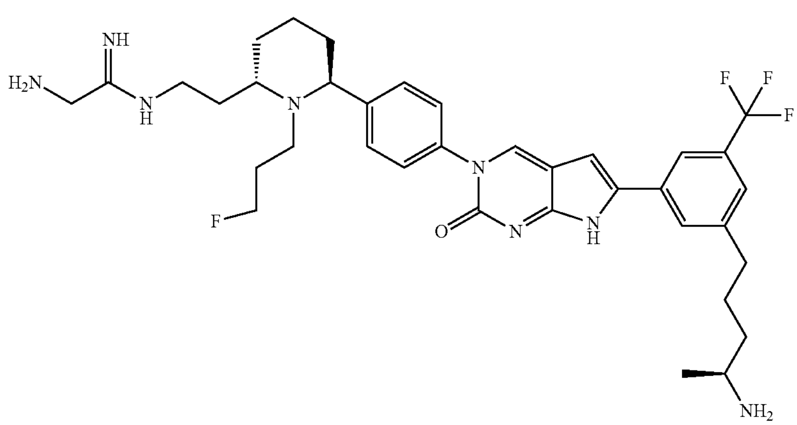 [SMILES: C[C@H](N)CCCc1cc(-c2cc3cn(-c4ccc([C@@H]5CCC[C@@H](CCNC(=N)CN)N5CCCF)cc4)c(=O)nc3[nH]2)cc(C(F)(F)F)c1] | 683 |

In some embodiments of the disclosed methods, the compound of Formula (I) or Formula (I-1) includes any one of compounds listed in Table 1a, or a tautomer thereof or a pharmaceutically acceptable salt of the compound or tautomer.
TABLE 1a
| # | Structure |
| --- | --- |
| 24 | 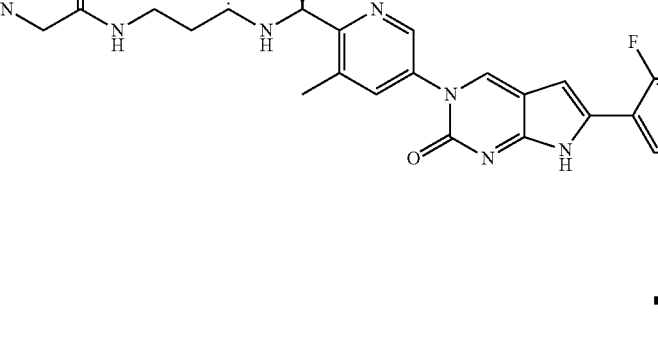 |
| 25 | 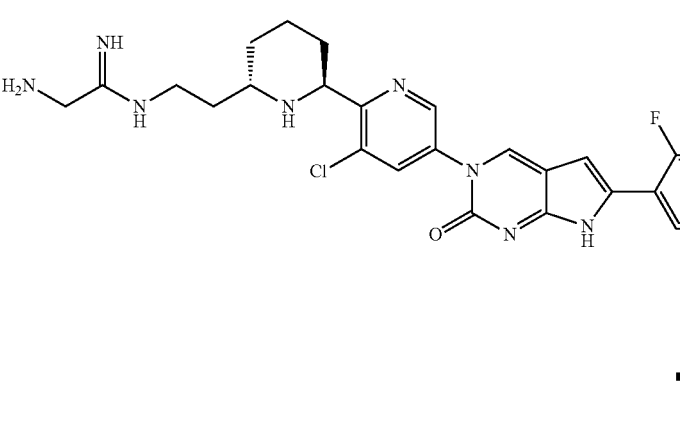 |
| 26 | 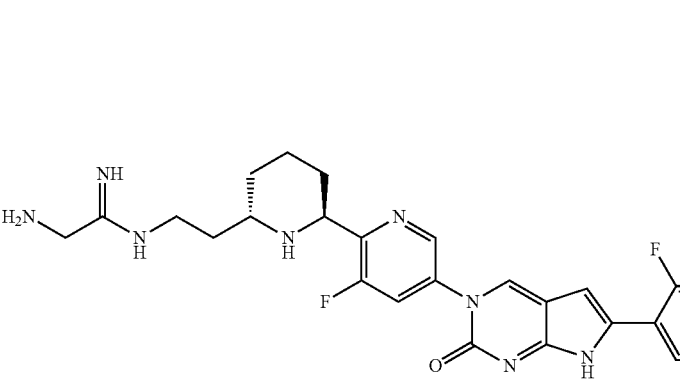 |

TABLE 1a-continued
| # | Structure |
|---|---|
| 27 | 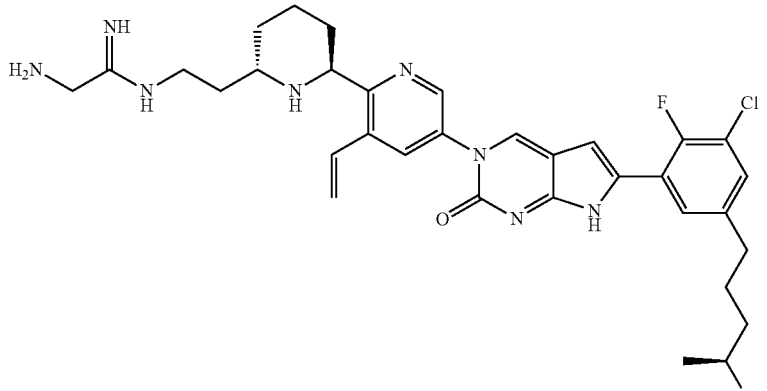 |
| 28 | 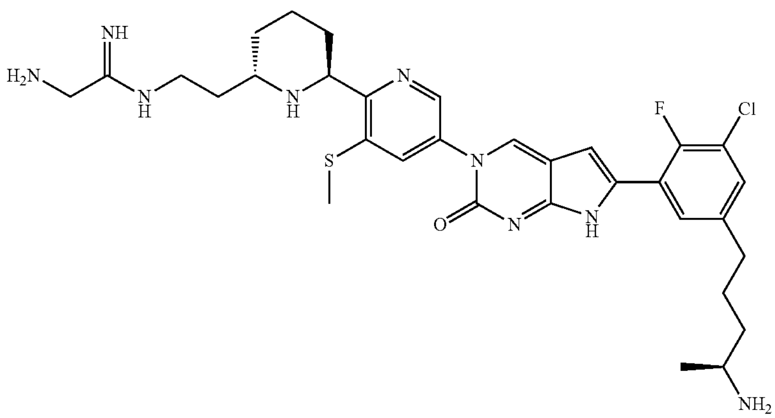 [SMILES: CSc1cc(-n2cc3cc(-c4cc(CCC[C@H](C)N)cc(Cl)c4F)[nH]c3nc2=O)cnc1[C@@H]1CCC[C@@H](CCNC(=N)CN)N1] |
| 29 | 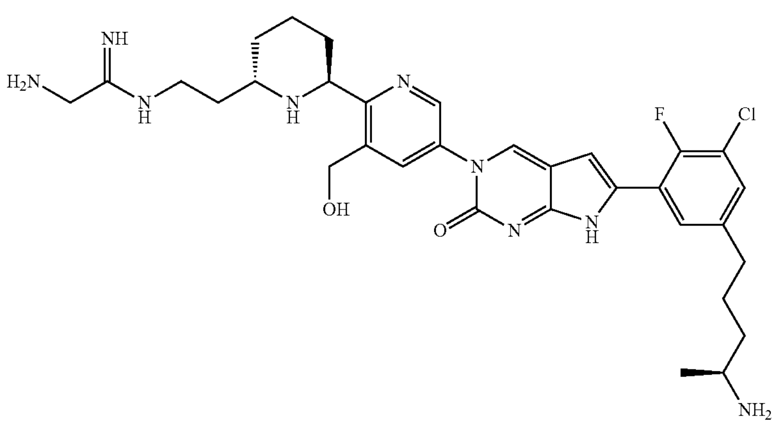 [SMILES: C[C@H](N)CCCc1cc(Cl)c(F)c(-c2cc3cn(-c4cnc([C@@H]5CCC[C@@H](CCNC(=N)CN)N5)c(CO)c4)c(=O)nc3[nH]2)c1] |

In some embodiments of the disclosed methods, the compound of Formula (I) or Formula (I-1) includes any one of compounds listed in Table 1b, or a tautomer thereof or a pharmaceutically acceptable salt of the compound or tautomer.
TABLE 1b
| # | Structure |
|---|-----------|
| 30 | 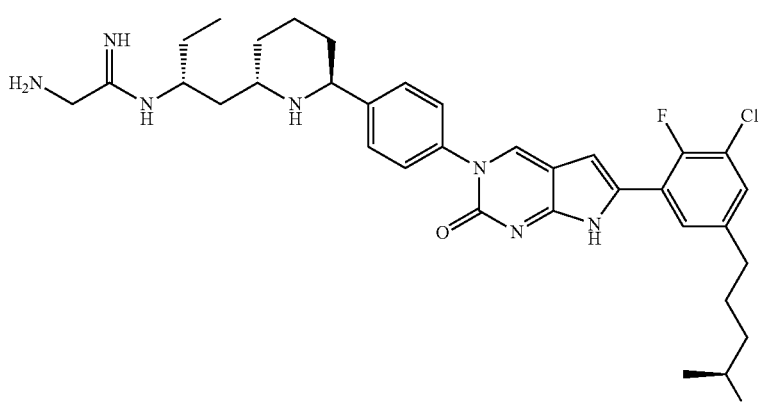 |
| 31 | 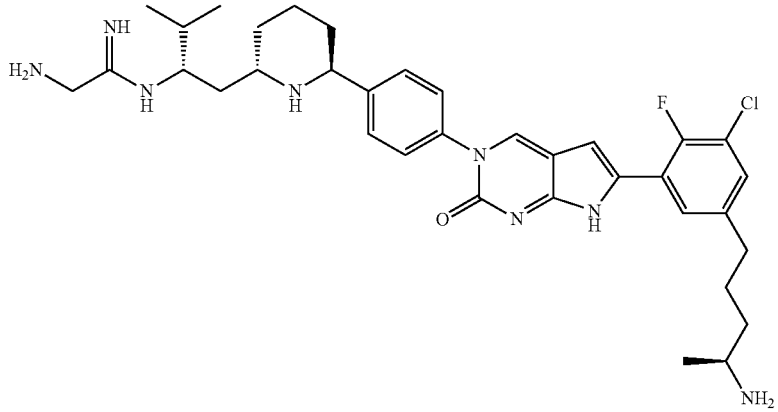 [SMILES: CC(C)[C@H](C[C@@H]1CCC[C@@H](c2ccc(-n3cc4cc(-c5cc(CCC[C@H](C)N)cc(Cl)c5F)[nH]c4nc3=O)cc2)N1)NC(=N)CN] |
| 32 | 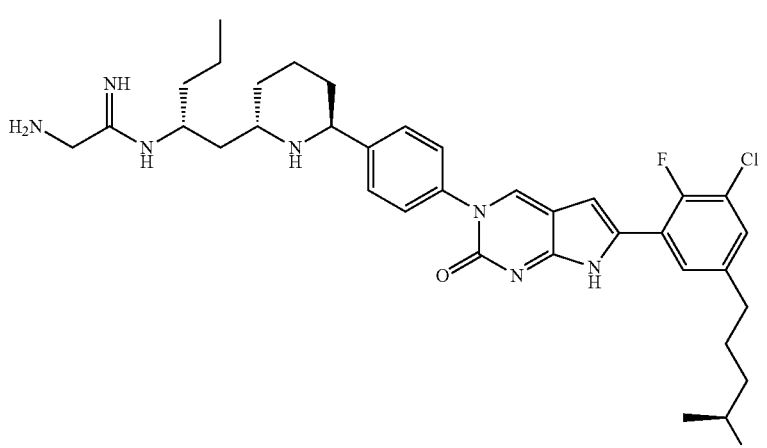 |

TABLE 1b-continued
| # | Structure |
|---|---|
| 33 | 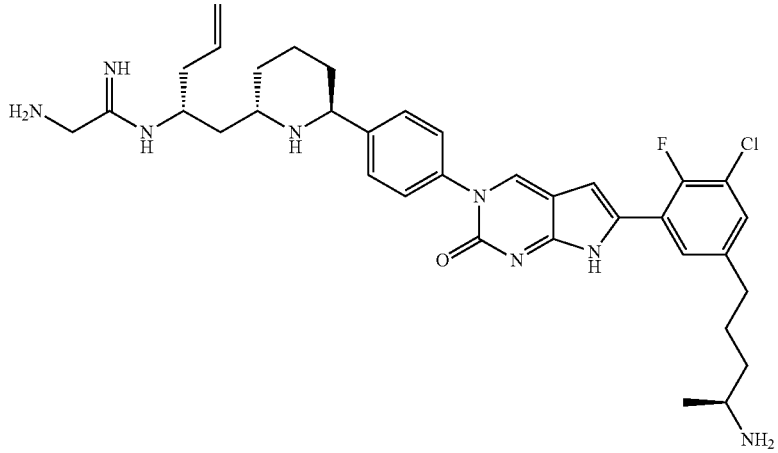 |
| 34 | 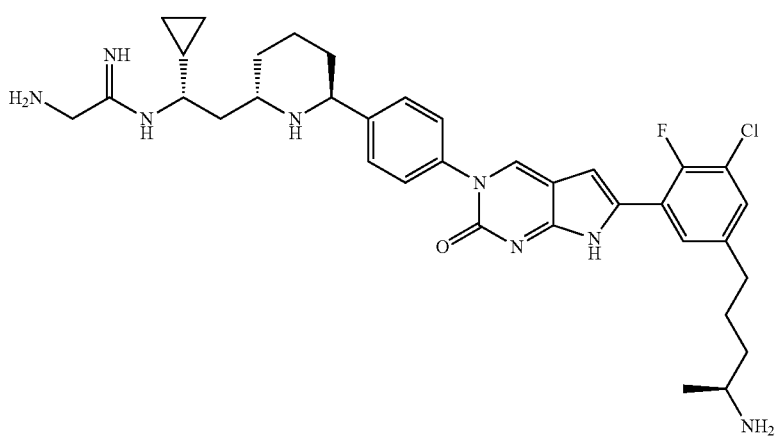 [SMILES: C[C@H](N)CCCc1cc(Cl)c(F)c(-c2cc3cn(-c4ccc([C@@H]5CCC[C@@H](C[C@H](NC(=N)CN)C6CC6)N5)cc4)c(=O)nc3[nH]2)c1] |
| 35 | 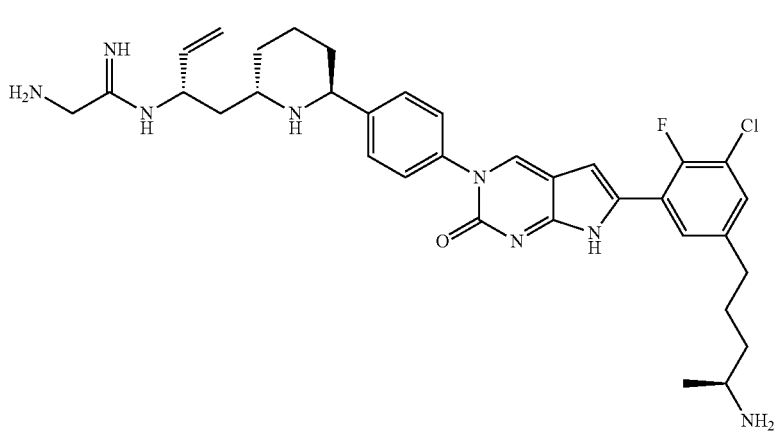 [SMILES: C=C[C@H](C[C@@H]1CCC[C@@H](c2ccc(-n3cc4cc(-c5cc(CCC[C@H](C)N)cc(Cl)c5F)[nH]c4nc3=O)cc2)N1)NC(=N)CN] |

TABLE 1b-continued
| # | Structure |
|---|---|
| 36 | 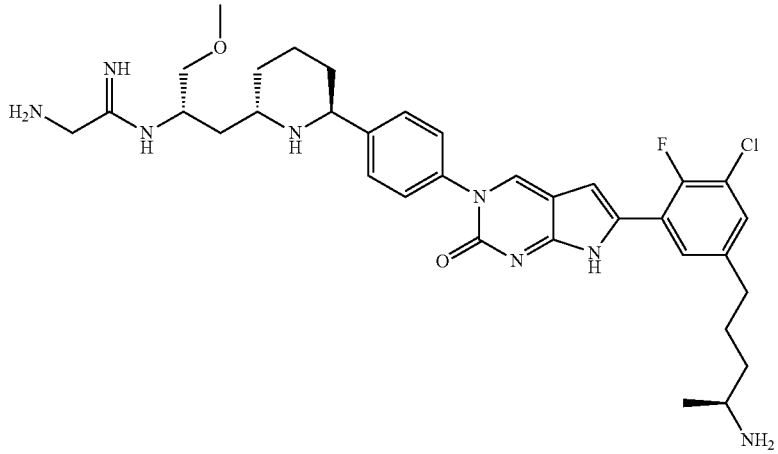 [SMILES: COC[C@H](C[C@@H]1CCC[C@@H](c2ccc(-n3cc4cc(-c5cc(CCC[C@H](C)N)cc(Cl)c5F)[nH]c4nc3=O)cc2)N1)NC(=N)CN] |
| 37 | 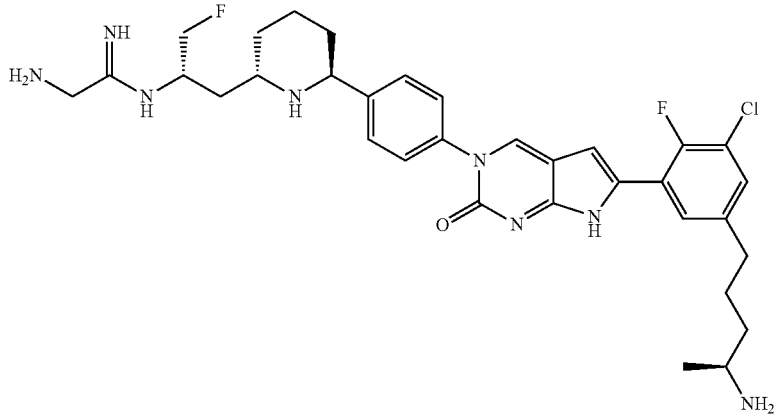 [SMILES: C[C@H](N)CCCc1cc(Cl)c(F)c(-c2cc3cn(-c4ccc([C@@H]5CCC[C@@H](C[C@@H](CF)NC(=N)CN)N5)cc4)c(=O)nc3[nH]2)c1] |
| 38 | 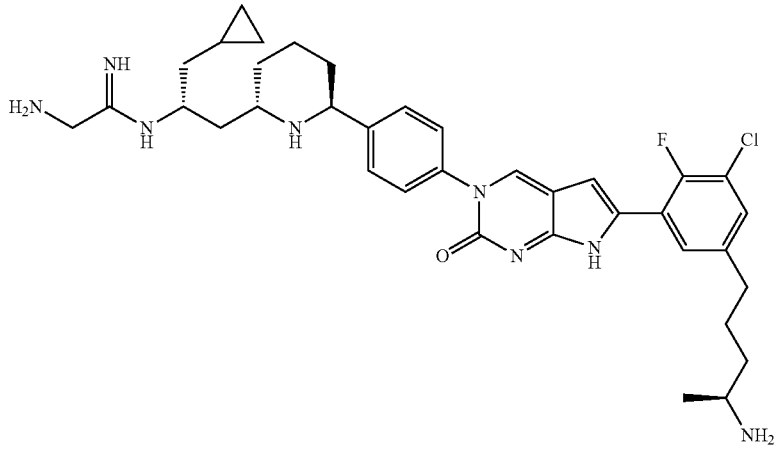 [SMILES: C[C@H](N)CCCc1cc(Cl)c(F)c(-c2cc3cn(-c4ccc([C@@H]5CCC[C@@H](C[C@@H](CC6CC6)NC(=N)CN)N5)cc4)c(=O)nc3[nH]2)c1] |

TABLE 1b-continued
| # | Structure |
|---|-----------|
| 39 | 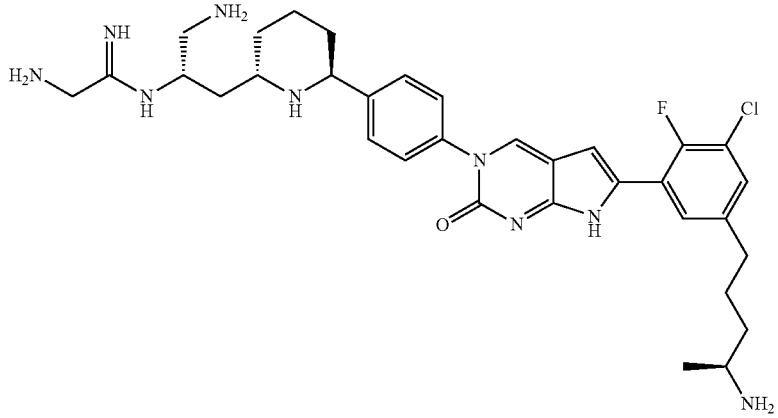 [SMILES: C[C@H](N)CCCc1cc(Cl)c(F)c(-c2cc3cn(-c4ccc([C@@H]5CCC[C@@H](C[C@@H](CN)NC(=N)CN)N5)cc4)c(=O)nc3[nH]2)c1] |
| 40 | 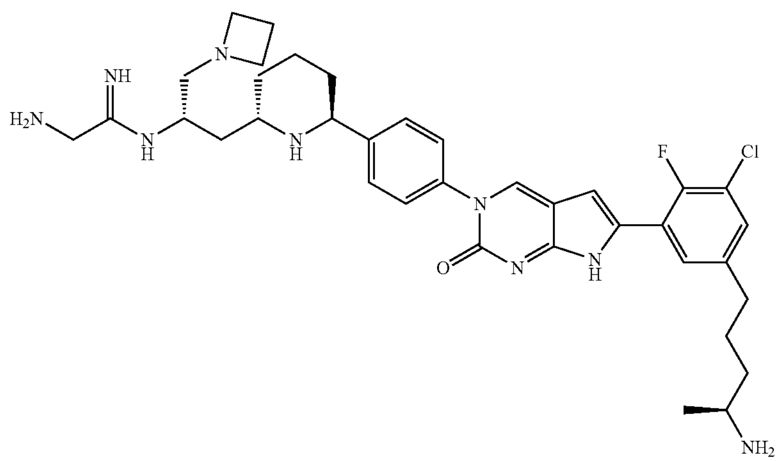 |
| 41 | 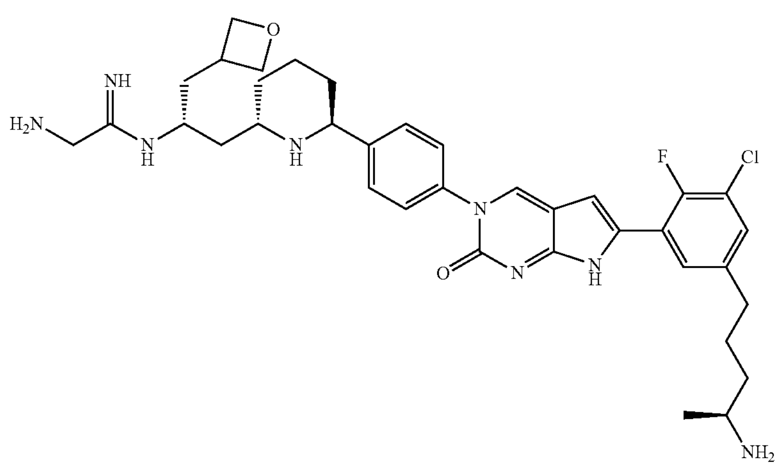 [SMILES: C[C@H](N)CCCc1cc(Cl)c(F)c(-c2cc3cn(-c4ccc([C@@H]5CCC[C@@H](C[C@@H](CC6COC6)NC(=N)CN)N5)cc4)c(=O)nc3[nH]2)c1] |

In some embodiments of the disclosed methods, the compound of Formula (I) or Formula (I-1) includes any one of compounds listed in Table Ic, or a tautomer thereof or a pharmaceutically acceptable salt of the compound or tautomer.

TABLE 1c

| # | Structure | ESI, m/z [M + H]+ |
|---|-----------|-------------------|
| 42 | 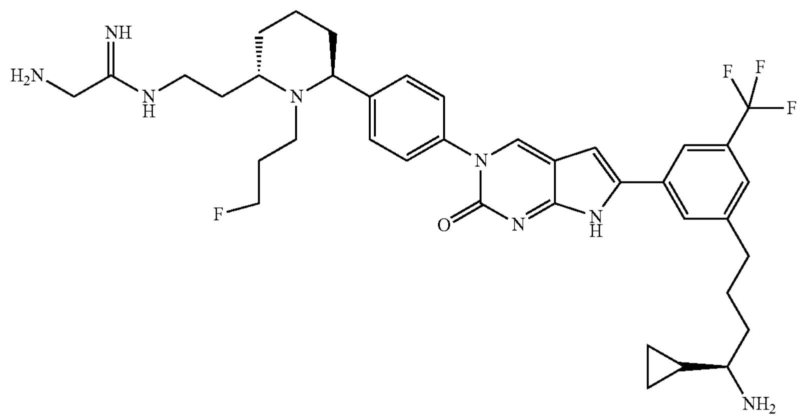 [SMILES: N=C(CN)NCC[C@@H]1CCC[C@@H](c2ccc(-n3cc4cc(-c5cc(CCC[C@@H](N)C6CC6)cc(C(F)(F)F)c5)[nH]c4nc3=O)cc2)N1CCCF] | 709 |
| 43 | 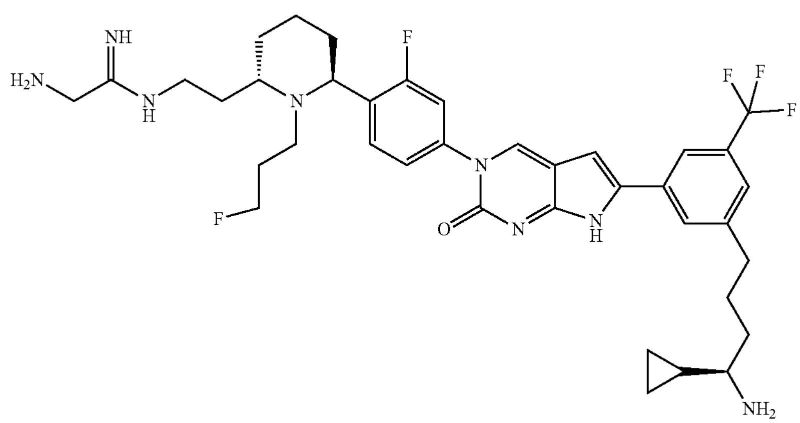 [SMILES: N=C(CN)NCC[C@@H]1CCC[C@@H](c2ccc(-n3cc4cc(-c5cc(CCC[C@@H](N)C6CC6)cc(C(F)(F)F)c5)[nH]c4nc3=O)cc2F)N1CCCF] | 727 |
| 44 | 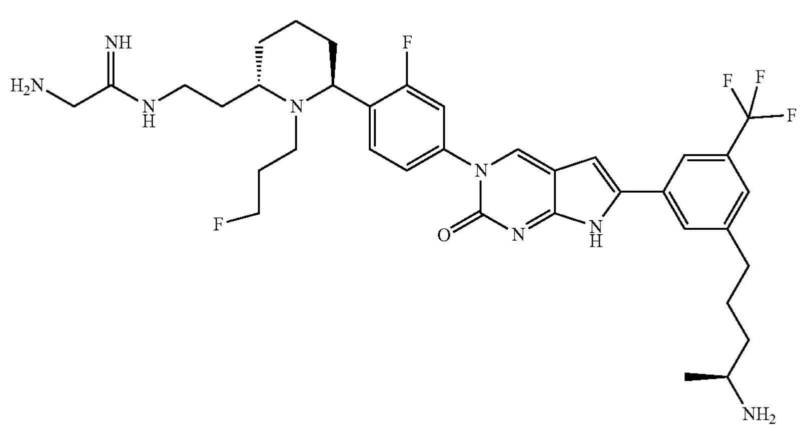 [SMILES: C[C@H](N)CCCc1cc(-c2cc3cn(-c4ccc([C@@H]5CCC[C@@H](CCNC(=N)CN)N5CCCF)c(F)c4)c(=O)nc3[nH]2)cc(C(F)(F)F)c1] | 701 |

TABLE 1c-continued
| # | Structure | ESI, m/z [M + H]+ |
|---|---|---|
| 45 | 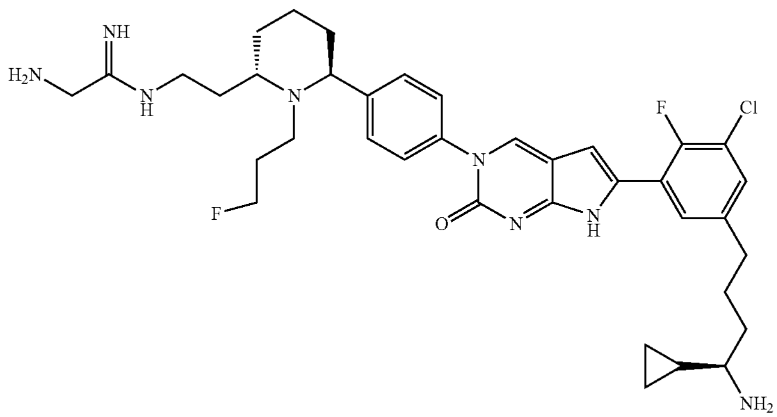 [SMILES: N=C(CN)NCC[C@@H]1CCC[C@@H](c2ccc(-n3cc4cc(-c5cc(CCC[C@@H](N)C6CC6)cc(Cl)c5F)[nH]c4nc3=O)cc2)N1CCCF] | 693 |
| 46 | 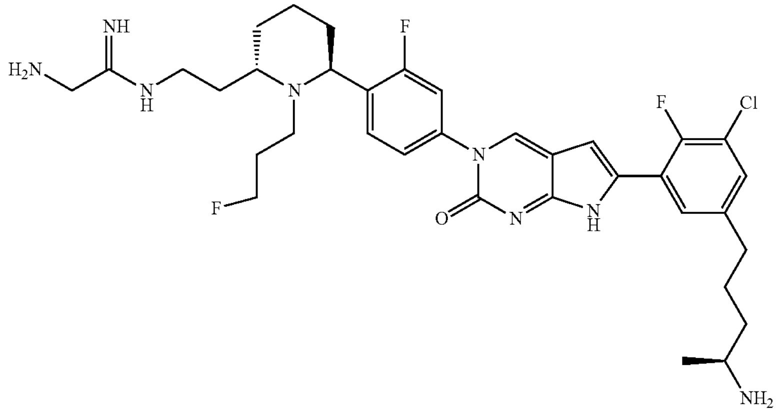 [SMILES: C[C@H](N)CCCc1cc(Cl)c(F)c(-c2cc3cn(-c4ccc([C@@H]5CCC[C@@H](CCNC(=N)CN)N5CCCF)c(F)c4)c(=O)nc3[nH]2)c1] | 685 |
| 47 | 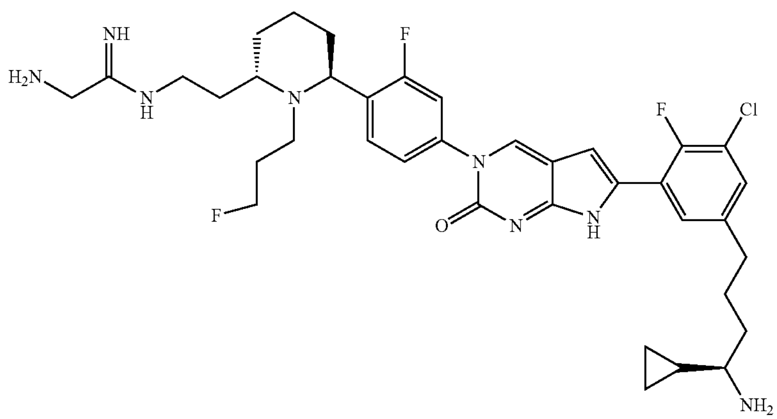 | 711 |

TABLE 1c-continued
| # | Structure | ESI, m/z [M + H]+ |
|---|-----------|-------------------|
| 48 | 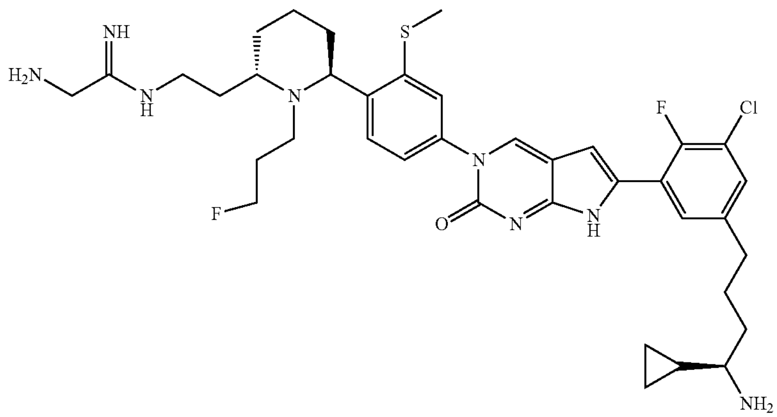 [SMILES: CSc1cc(-n2cc3cc(-c4cc(CCC[C@@H](N)C5CC5)cc(Cl)c4F)[nH]c3nc2=O)ccc1[C@@H]1CCC[C@@H](CCNC(=N)CN)N1CCCF] | 739 |
| 49 | 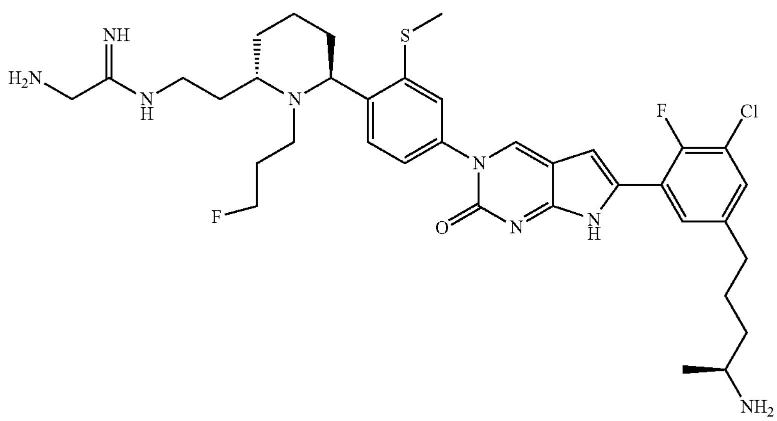 [SMILES: CSc1cc(-n2cc3cc(-c4cc(CCC[C@H](C)N)cc(Cl)c4F)[nH]c3nc2=O)ccc1[C@@H]1CCC[C@@H](CCNC(=N)CN)N1CCCF] | 713 |
| 50 | 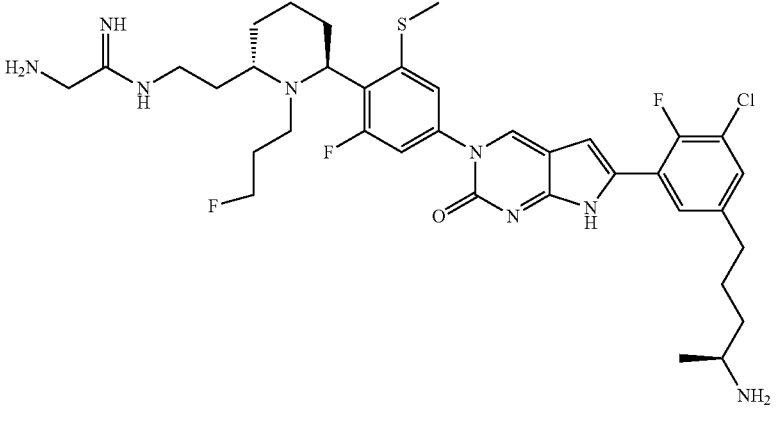 [SMILES: CSc1cc(-n2cc3cc(-c4cc(CCC[C@H](C)N)cc(Cl)c4F)[nH]c3nc2=O)cc(F)c1[C@@H]1CCC[C@@H](CCNC(=N)CN)N1CCCF] | 731 |

TABLE 1c-continued
| # | Structure | ESI, m/z [M + H]+ |
|---|---|---|
| 51 | 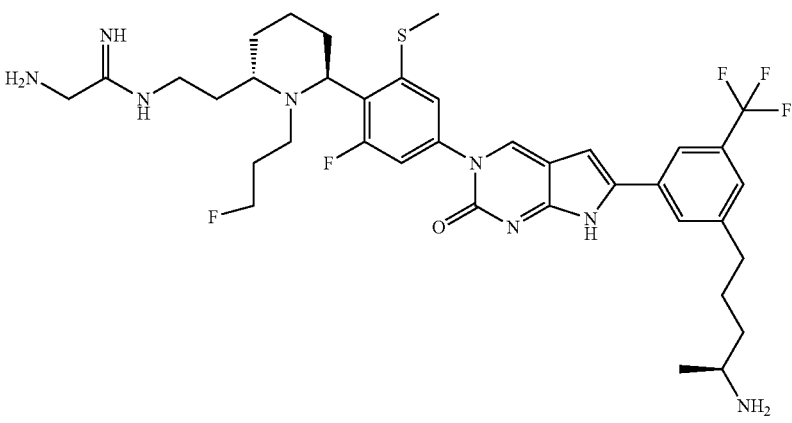 [SMILES: CSc1cc(-n2cc3cc(-c4cc(CCC[C@H](C)N)cc(C(F)(F)F)c4)[nH]c3nc2=O)cc(F)c1[C@@H]1CCC[C@@H](CCNC(=N)CN)N1CCCF] | 747 |
| 52 | 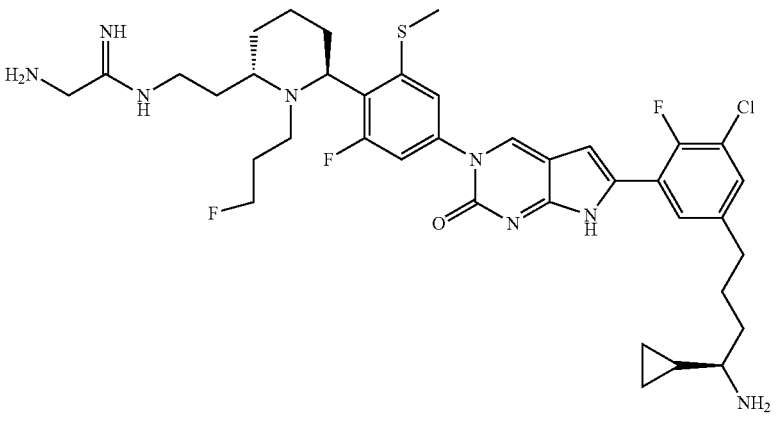 [SMILES: CSc1cc(-n2cc3cc(-c4cc(CCC[C@@H](N)C5CC5)cc(Cl)c4F)[nH]c3nc2=O)cc(F)c1[C@@H]1CCC[C@@H](CCNC(=N)CN)N1CCCF] | 757 |
| 53 | 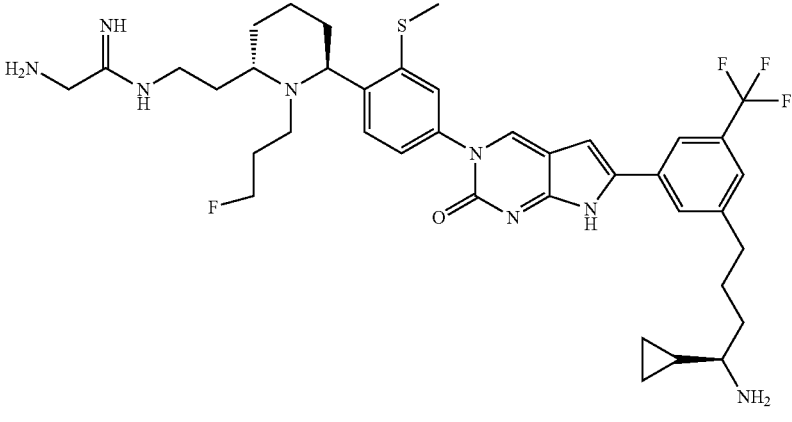 [SMILES: CSc1cc(-n2cc3cc(-c4cc(CCC[C@@H](N)C5CC5)cc(C(F)(F)F)c4)[nH]c3nc2=O)ccc1[C@@H]1CCC[C@@H](CCNC(=N)CN)N1CCCF] | 755 |

TABLE 1c-continued
| # | Structure | ESI, m/z [M + H]+ |
|---|---|---|
| 54 | 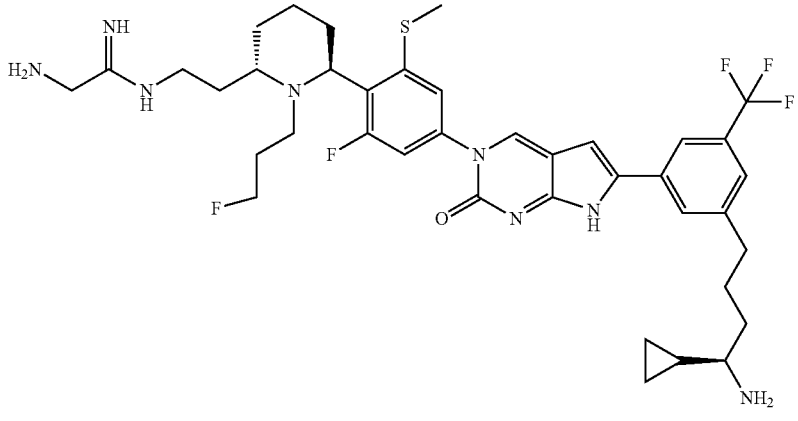 [SMILES: CSc1cc(-n2cc3cc(-c4cc(CCC[C@@H](N)C5CC5)cc(C(F)(F)F)c4)[nH]c3nc2=O)cc(F)c1[C@@H]1CCC[C@@H](CCNC(=N)CN)N1CCCF] | 773 |
| 55 | 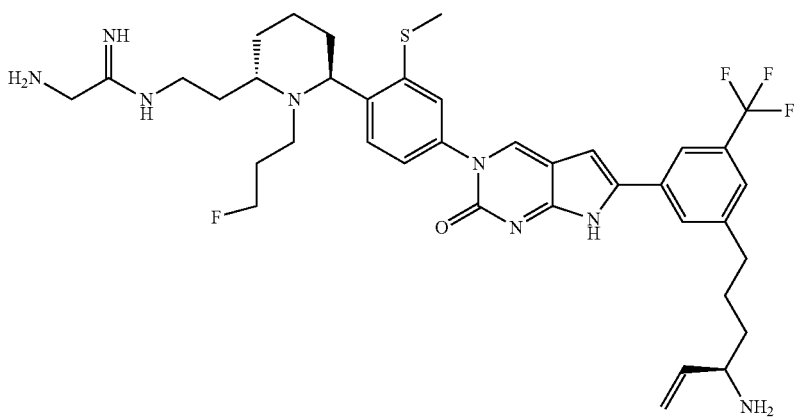 [SMILES: C=C[C@H](N)CCCc1cc(-c2cc3cn(-c4ccc([C@@H]5CCC[C@@H](CCNC(=N)CN)N5CCCF)c(SC)c4)c(=O)nc3[nH]2)cc(C(F)(F)F)c1] | 741 |
| 56 | 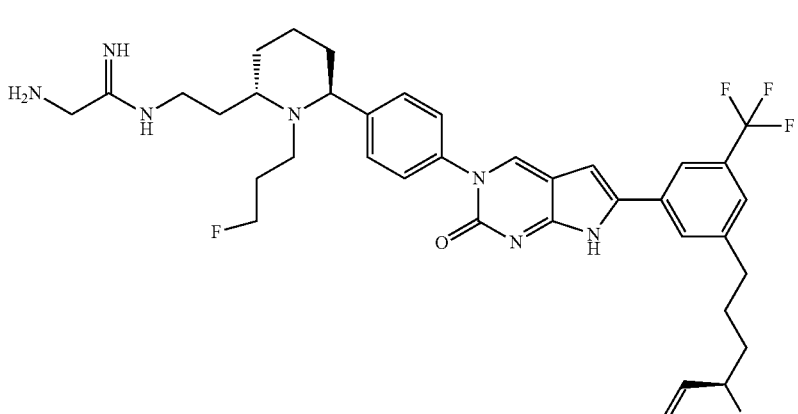 | 695 |

TABLE 1c-continued
| # | Structure | ESI, m/z [M + H]+ |
|---|---|---|
| 57 | 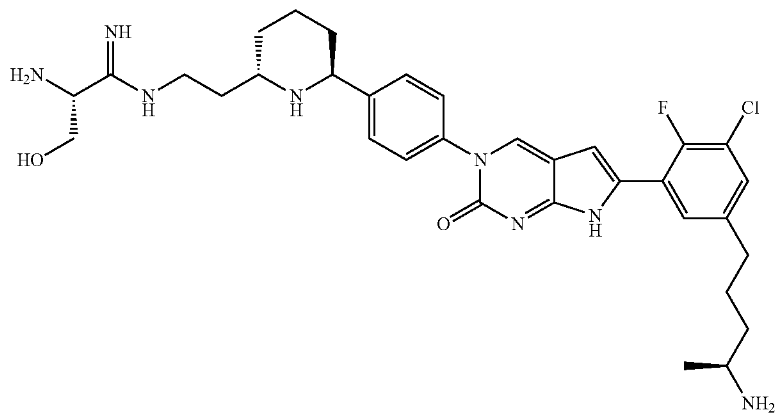 [SMILES: C[C@H](N)CCCc1cc(Cl)c(F)c(-c2cc3cn(-c4ccc([C@@H]5CCC[C@@H](CCNC(=N)[C@@H](N)CO)N5)cc4)c(=O)nc3[nH]2)c1] | 637 |
| 58 | 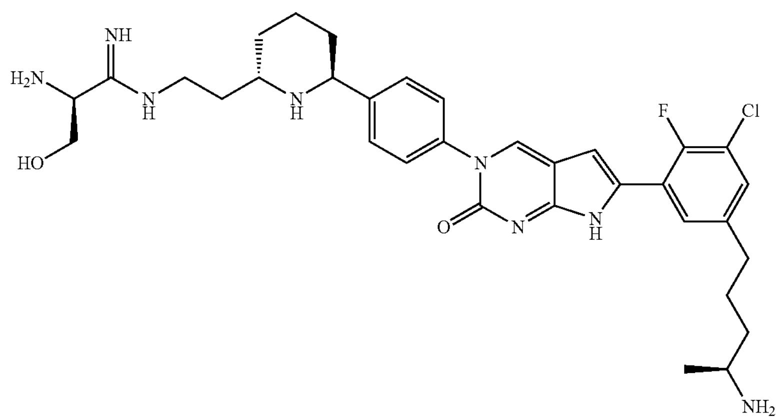 [SMILES: C[C@H](N)CCCc1cc(Cl)c(F)c(-c2cc3cn(-c4ccc([C@@H]5CCC[C@@H](CCNC(=N)[C@H](N)CO)N5)cc4)c(=O)nc3[nH]2)c1] | 637 |
| 59 | 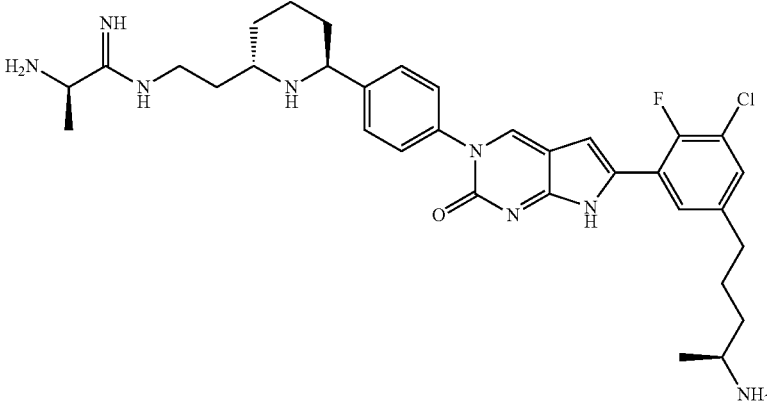 | 621 |

TABLE 1c-continued
| # | Structure | ESI, m/z [M + H]+ |
|---|---|---|
| 60 | 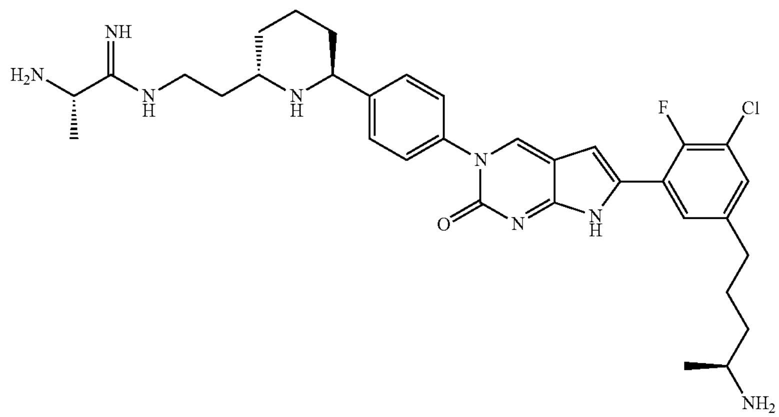 [SMILES: C[C@H](N)CCCc1cc(Cl)c(F)c(-c2cc3cn(-c4ccc([C@@H]5CCC[C@@H](CCNC(=N)[C@H](C)N)N5)cc4)c(=O)nc3[nH]2)c1] | 621 |
| 61 | 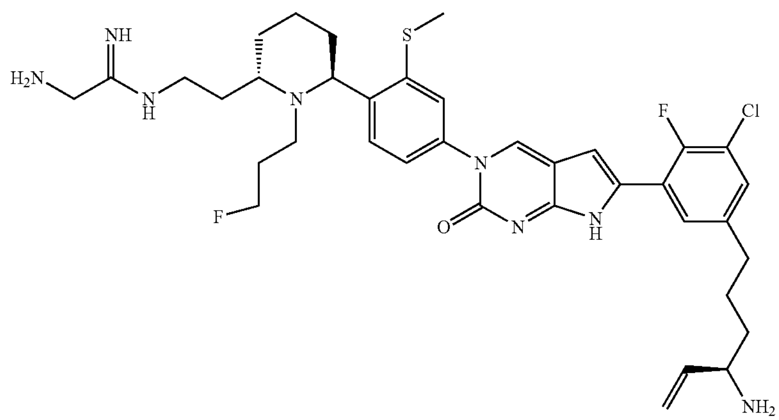 | 725 |
| 62 | 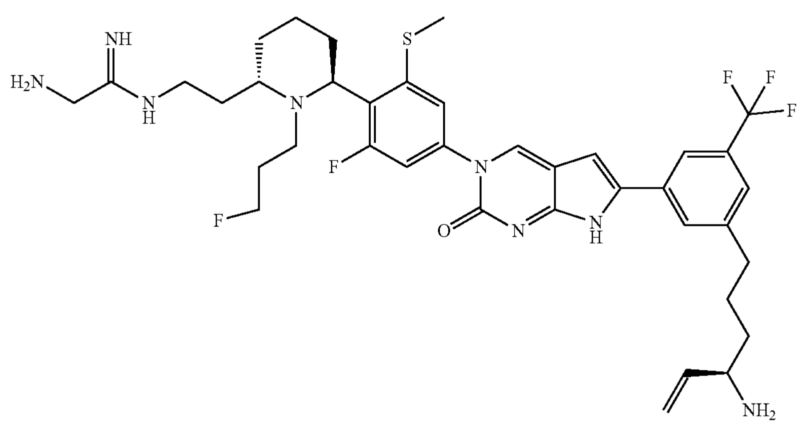 [SMILES: C=C[C@H](N)CCCc1cc(-c2cc3cn(-c4cc(F)c([C@@H]5CCC[C@@H](CCNC(=N)CN)N5CCCF)c(SC)c4)c(=O)nc3[nH]2)cc(C(F)(F)F)c1] | 759 |

TABLE 1c-continued
| # | Structure | ESI, m/z [M + H]+ |
|---|---|---|
| 63 | 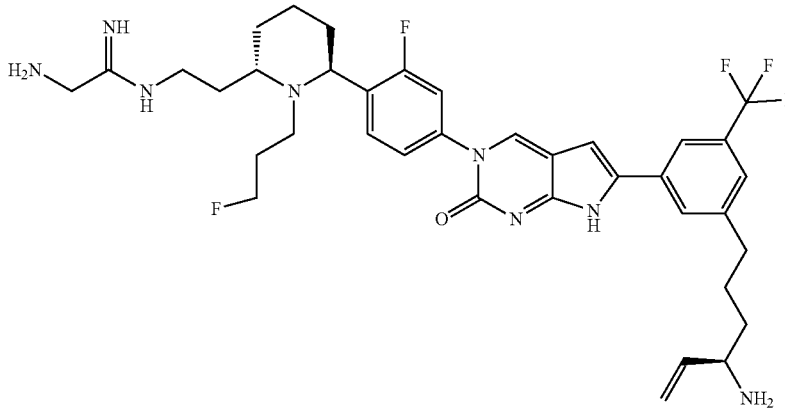 | 713 |
| 64 | 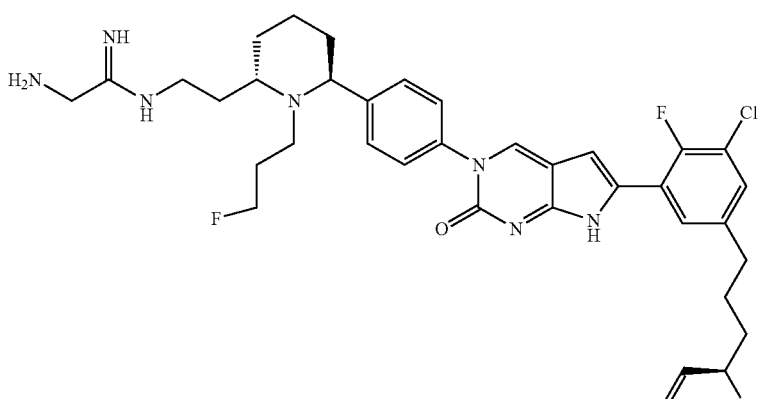 | 679 |
| 65 | 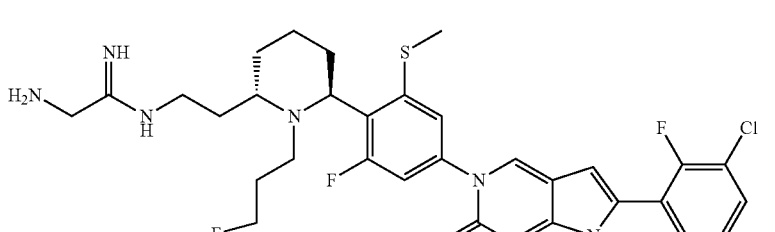 | 743 |

TABLE 1c-continued
| # | Structure | ESI, m/z [M + H]+ |
|---|---|---|
| 66 | 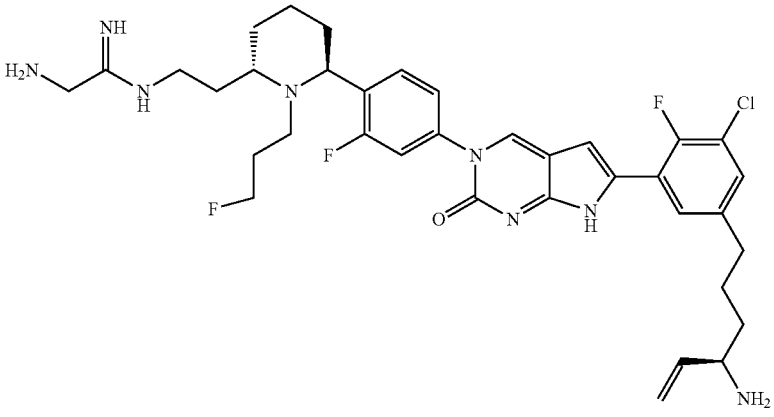 [SMILES: C=C[C@H](N)CCCc1cc(Cl)c(F)c(-c2cc3cn(-c4ccc([C@@H]5CCC[C@@H](CCNC(=N)CN)N5CCCF)c(F)c4)c(=O)nc3[nH]2)c1] | 697 |
| 67 | 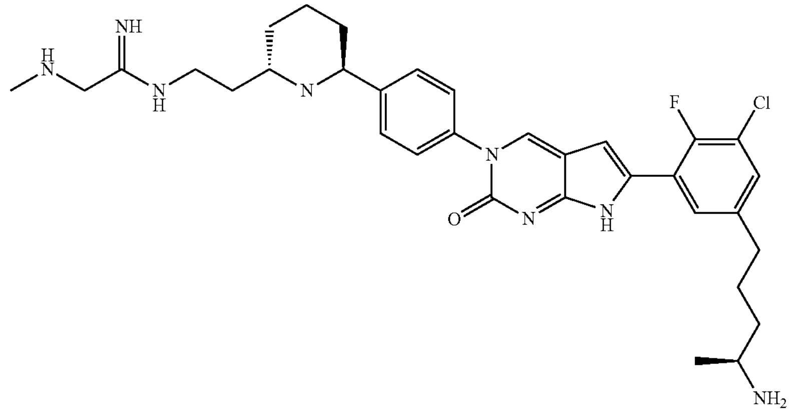 [SMILES: CNCC(=N)NCC[C@@H]1CCC[C@@H](c2ccc(-n3cc4cc(-c5cc(CCC[C@H](C)N)cc(Cl)c5F)[nH]c4nc3=O)cc2)N1] | 621.3 |
| 68 | 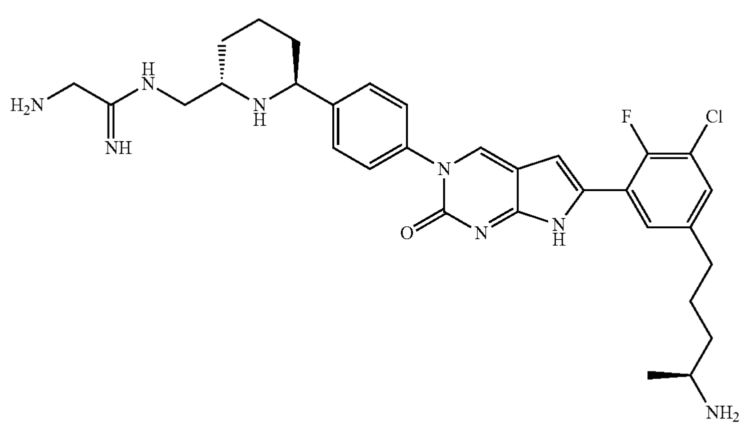 [SMILES: C[C@H](N)CCCc1cc(Cl)c(F)c(-c2cc3cn(-c4ccc([C@@H]5CCC[C@@H](CNC(=N)CN)N5)cc4)c(=O)nc3[nH]2)c1] | 593.1 |

TABLE 1c-continued

| # | Structure | ESI, m/z [M + H]+ |
|---|---|---|
| 69 | 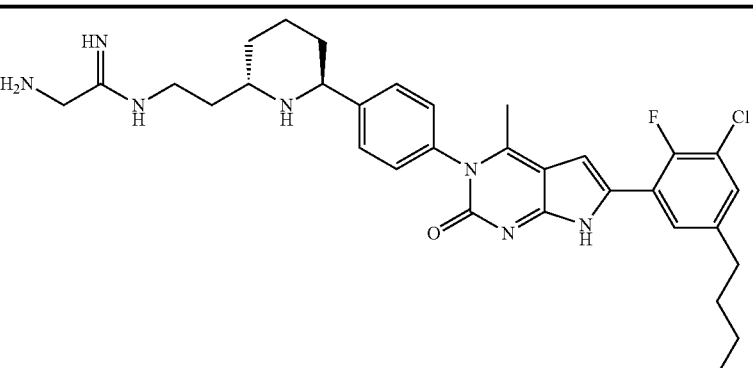 | 621 |

In some embodiments, the present disclosure provides a method of treating, preventing, reducing the risk of, or delaying the onset of a microbial infection in a subject, the method comprising administering to the subject a therapeutically effective amount of a compound of Formula (II):

(II)

or a tautomer thereof or a pharmaceutically acceptable salt of the compound or tautomer, wherein:
$R_1$ is selected from H, halo, and $C_{1-4}$ alkoxy;
$R_2$ is selected from H, halo, $C_{1-6}$ alkyl, $C_{1-4}$ haloalkyl, and $OR^{a1}$;
$R_3$ is selected from H, $C_{1-6}$ alkyl, $C_{1-4}$ haloalkyl, and $C(O)OR^{a1}$;
W is selected from N and $CR_4$;
$R_4$ is selected from H, halo, $OR^{a2}$, $SR^{a2}$, 5-6 membered heterocycloalkyl, $S(O)_2R^{b2}$, $C_{1-6}$ alkyl, and $C_{2-6}$ alkenyl, wherein the $C_{1-6}$ alkyl is optionally substituted with a substituent selected from $OR^{a2}$;
$R_5$ is selected from H, halo, $C_{1-6}$ alkyl, and $C_{2-6}$ alkenyl, wherein the $C_{1-6}$ alkyl is optionally substituted with a substituent selected from $OR^{a2}$;
$R_6$ is selected from H, $C_{1-6}$ alkyl, $C_{3-5}$ cycloalkyl, and $C_{2-6}$ alkenyl, wherein the $C_{1-6}$ alkyl is optionally substituted with a substituent selected from $OR^{a3}$, $SR^{a3}$, and $NR^{c3}R^{d3}$;
$R_{7A}$ is selected from H, $C_{1-6}$ alkyl, $C_{1-4}$ haloalkyl, and $C_{2-6}$ alkenyl, wherein the $C_{1-6}$ alkyl is optionally substituted with a substituent selected from $OR^{a3}$ and $SR^{a3}$ $R_{7B}$ is H; or
$R_{7A}$ and $R_{7B}$ together with the carbon atom to which they are attached form a group selected from oxo, and $C_{3-6}$ cycloalkyl; or
$R_6$ and $R_{7A}$ together with the carbon atoms to which they are attached and the X atom connecting the two carbon atoms form a 5- to 6-membered heterocycloalkyl containing 1-3 heteroatoms selected from N, O and S;
X is selected from O and NRs;
$R_8$ is selected from H, $C_{1-6}$ alkyl, and $C_{1-4}$ haloalkyl, wherein the $C_{1-6}$ alkyl is optionally substituted with $R_{8A}$;
$R_{8A}$ is selected from $OR^{a3}$ and 5- to 6-membered heteroaryl, wherein the 5- to 6-membered heteroaryl is optionally substituted with one or two $C_{1-6}$ alkyl;
$R_9$ is selected from H, $C_{2-4}$ alkenyl, $C_{1-4}$ haloalkyl and $C_{1-4}$ alkyl optionally substituted with a substituent selected from amino, $C_{1-4}$ alkoxy, $C_{3-5}$ cycloalkyl, and 3- to 6-membered heterocycloalkyl;
$R_{10}$ is selected from H and $C_{2-6}$ alkenyl;
$R_A$ is selected from H and $C_{1-6}$ alkyl;
L is selected from $C_{1-6}$ alkyl and $C_{2-6}$ alkenyl, wherein the $C_{1-6}$ alkyl is optionally substituted with 1, 2, or 3 substituents independently selected from halo, $OR^{a4}$, $SR^{a4}$, and Z;
$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with 1, 2, or 3 substituents independently selected from CN, $OR^{a5}$, $SR^{a5}$, $C(O)NR^{c5}R^{d5}$, $NR^{c5}R^{d5}$, and $S(O)_2R^{b5}$;
$R_{12}$ is selected from H and $C_{1-6}$ alkyl; or
$R_{11}$ and $R_{12}$ together with the carbon atom to which they are attached form a $C_{3-5}$ cycloalkyl;
$R_{13}$ is selected from H, halo, and $C_{1-6}$ alkyl;
$R_{14}$ is selected from H, halo, and $C_{1-6}$ alkyl; and
$R_B$ is selected from H and $C(=NR^{e5})R^{b5}$; or
$R_{11}$ and $R_B$ together with the carbon atom to which $R_{11}$ is attached and the nitrogen atom to which $R_B$ is attached form a 5- to 6-membered heterocycloalkyl containing 1-3 heteroatoms selected from N, O and S, wherein the 5- to 6-membered heterocycloalkyl is optionally substituted with oxo;
each $R^{a1}$, $R^{a2}$, $R^{a3}$, $R^{a4}$, $R^{a5}$, $R^{b2}$, $R^{b5}$, $R^{c3}$, $R^{d3}$, $R^{c5}$, and $R^{d5}$ is independently selected from H, $C_{1-6}$ alkyl, $C_{1-4}$ haloalkyl, and 5-membered heteroaryl;

$R^{e5}$ is selected from H and $C_{1-4}$ alkyl; and Z is —O(CH$_2$CH$_2$O)CH$_3$.

In some embodiments of the method, the compound is a compound of Formula (II-1):

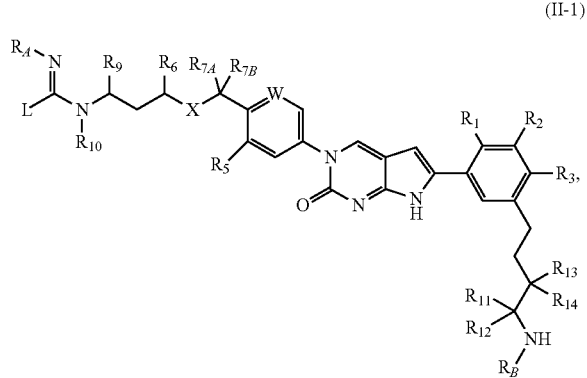

(II-1)

or tautomer thereof or a pharmaceutically acceptable salt of the compound or tautomer, wherein:
$R_1$ is selected from H and halo;
$R_2$ is selected from H, halo, $C_{1-6}$ alkyl, $C_{1-4}$ haloalkyl, and OR$^{a1}$;
$R_3$ is selected from H, $C_{1-6}$ alkyl, $C_{1-4}$ haloalkyl, and C(O)OR$^{a1}$;
W is selected from N and CR$_4$;
$R_4$ is selected from H, halo, $C_{1-6}$ alkyl, OR$^{a2}$, SR$^{a2}$, 5-6 membered heterocycloalkyl, and S(O)$_2$R$^{b2}$;
$R_5$ is selected from H and halo;
$R_6$ is selected from H, $C_{1-6}$ alkyl, $C_{3-5}$ cycloalkyl, and $C_{2-6}$ alkenyl, wherein the $C_{1-6}$ alkyl is optionally substituted with a substituent selected from OR$^{a3}$, SR$^{a3}$, and NR$^{c3}$R$^{d3}$;
$R_{7A}$ is selected from H, $C_{1-6}$ alkyl, $C_{1-4}$ haloalkyl, and $C_{2-6}$ alkenyl, wherein the $C_{1-6}$ alkyl is optionally substituted with a substituent selected from OR$^{a3}$, and SR$^{a3}$; $R_{7B}$ is H; or
$R_{7A}$ and $R_{7B}$ together with the carbon atom to which they are attached form a group selected from oxo and $C_{3-6}$ cyclopropyl; or
$R_6$ and $R_{7A}$ together with the carbon atoms to which they are attached and the X atom connecting the two carbon atoms form a 5- to 6-membered heterocycloalkyl containing 1-3 heteroatoms independently selected from N, O and S, wherein the 5- to 6-membered heterocycloalkyl is optionally substituted with a substituent selected from C(=NR$^{e3}$)R$^{b3}$, and NR$^{c3}$R$^{d3}$;
X is selected from O and NR$_8$;
$R_8$ is selected from H, $C_{1-6}$ alkyl, and $C_{1-4}$ haloalkyl, wherein the $C_{1-6}$ alkyl is optionally substituted with $R_{8A}$;
$R_{8A}$ is selected from 5- to 6-membered heteroaryl, and OR$^{a3}$, wherein the 5- to 6-membered heteroaryl is optionally substituted with 1, or 2 $C_{1-6}$ alkyl;
$R_9$ is selected from H, $C_{2-4}$ alkenyl, $C_{1-4}$ haloalkyl and $C_{1-4}$ alkyl optionally substituted with a substituent selected from amino, $C_{1-4}$ alkoxy, $C_{3-5}$ cycloalkyl, and 3- to 6-membered heterocycloalkyl;
$R_{10}$ is selected from H and $C_{2-6}$ alkenyl;
$R_A$ is selected from H and $C_{1-6}$ alkyl;
L is selected from $C_{1-6}$ alkyl and $C_{2-6}$ alkenyl, wherein the $C_{1-6}$ alkyl is optionally substituted with 1, 2, or 3 substituents independently selected from halo, OR$^{a4}$, and SR$^{a4}$;

$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with 1, 2, or 3 substituents independently selected from CN, OR$^{a5}$, SR$^{a5}$, C(O)NR$^{c5}$R$^{d5}$, NR$^{c5}$R$^{d5}$, and S(O)$_2$R$^{b5}$;
$R_{12}$ is selected from H and $C_{1-6}$ alkyl; or
$R_{11}$ and $R_{12}$ together with the carbon atom to which they are attached form a $C_{3-5}$ cycloalkyl;
$R_{13}$ is selected from H, halo, and $C_{1-6}$ alkyl;
$R_{14}$ is selected from H, halo, and $C_{1-6}$ alkyl; and
$R_B$ is selected from H and C(=NR$^{e5}$)R$^{b5}$; or
$R_{11}$ and $R_B$ together with the carbon atom to which $R_{11}$ is attached and the nitrogen atom to which $R_B$ is attached form a 5- to 6-membered heterocycloalkyl containing 1-3 heteroatoms selected from N, O and S, wherein the 5- to 6-membered heterocycloalkyl is optionally substituted with oxo;
each R$^{a1}$, R$^{a2}$, R$^{a3}$, R$^{a4}$, R$^{a5}$, R$^{b2}$, R$^{b3}$, R$^{b5}$, R$^{c3}$, R$^{d3}$, R$^{c5}$, and R$^{d5}$ is independently selected from H, $C_{1-6}$ alkyl, $C_{1-4}$ haloalkyl, and 5-membered heteroaryl; and
each R$^{e3}$ and R$^{55}$ is independently selected from H and $C_{1-4}$ alkyl.

In some embodiments of Formula (II) or Formula (II-1), $R_1$ is halo. In some embodiments, $R_1$ is selected from H and fluoro. In some embodiments, $R_1$ is fluoro. In some embodiments, $R_1$ is H.

In some embodiments of Formula (II), $R_1$ is $C_{1-4}$ alkoxy. For example, $R_1$ can be methoxy.

In some embodiments of Formula (II) or Formula (II-1), $R_2$ is selected from H, halo, $C_{1-4}$ haloalkyl, and $C_{1-4}$ haloalkoxy. In some embodiments, $R_2$ is halo. In some embodiments, $R_2$ is $C_{1-4}$ haloalkyl. In some embodiments, $R_2$ is $C_{1-4}$ haloalkoxy. In some embodiments, $R_2$ is selected from halo, $C_{1-4}$ haloalkyl, and $C_{1-4}$ haloalkoxy. In some embodiments, $R_2$ is selected from H, trifluoromethoxy, trifluoromethyl and chloro. In some embodiments, $R_2$ is selected from trifluoromethoxy, trifluoromethyl and chloro. In some embodiments, $R_2$ is trifluoromethoxy. In some embodiments, $R_2$ is trifluoromethyl. In some embodiments, $R_2$ is chloro. In some embodiments, $R_2$ is H. In some embodiments of Formula (II) or Formula (II-1), $R_1$ is halo and $R_2$ is halo. In some embodiments, $R_1$ is fluoro and $R_2$ is chloro. In some embodiments, $R_1$ is fluoro and $R_2$ is trifluoromethoxy. In some embodiments, $R_1$ is fluoro and $R_2$ is trifluoromethyl. In some embodiments, $R_1$ is H and $R_2$ is trifluoromethyl.

In some embodiments of Formula (II) or Formula (II-1), $R_1$ is H, $R_2$ is H, and $R_3$ is not H.

In some embodiments of Formula (II) or Formula (II-1), $R_3$ is selected from H, $C_{1-4}$ haloalkyl, and C(O)OR$^{a1}$. In some embodiments, $R_3$ is selected from H, $C_{1-4}$ haloalkyl, and C(O)$C_{1-4}$ alkoxy. In some embodiments, $R_3$ is selected from H, trifluoromethyl, and C(=O)(methoxy). In some embodiments, $R_3$ is trifluoromethyl. In some embodiments, $R_3$ is C(=O)(methoxy). In some embodiments, $R_3$ is H.

In some embodiments of Formula (II) or Formula (II-1), $R_1$ is H, $R_2$ is H, and $R_3$ is trifluoromethyl. In some embodiments, $R_1$ is H, $R_2$ is H, and $R_3$ is C(=O)(methoxy).

In some embodiments of Formula (II) or Formula (II-1), W is N.

In some embodiments of Formula (II) or Formula (II-1), W is CR$_4$.

In some embodiments of Formula (II) or Formula (II-1), $R_4$ is selected from H, halo, $C_{1-6}$ alkyl, $C_{1-4}$ alkoxy, $C_{1-4}$ haloalkoxy, S($C_{1-4}$ alkyl), 6-membered heterocycloalkyl, and S(O)$_2$$C_{1-4}$ alkyl. In some embodiments, $R_4$ is selected from halo, $C_{1-6}$ alkyl, $C_{1-4}$ alkoxy, $C_{1-4}$ haloalkoxy, S($C_{1-4}$ alkyl), 6-membered heterocycloalkyl, and $S(O)_2C_{1-4}$ alkyl. In some embodiments, $R_4$ is halo. In some embodiments, $R_4$ is $C_{1-4}$ alkoxy. In some embodiments, $R_4$ is $C_{1-4}$ haloalkoxy. In some embodiments, $R_4$ is $S(C_{1-4}$ alkyl). In some embodiments, $R_4$ is 6-membered heterocycloalkyl. In some embodiments, $R_4$ is $S(O)_2C_{1-4}$ alkyl. In some embodiments, $R_4$ is selected from H, fluoro, chloro, methylthio, methoxy, methyl, $S(=O)_2$(methyl), trifluoromethoxy, and N-morpholino. In some embodiments, $R_4$ is selected from fluoro, chloro, methylthio, methoxy, methyl, $S(=O)_2$(methyl), trifluoromethoxy, and N-morpholino. In some embodiments, $R_4$ is fluoro. In some embodiments, $R_4$ is chloro. In some embodiments, $R_4$ is methylthio. In some embodiments, $R_4$ is methoxy. In some embodiments, $R_4$ is methyl. In some embodiments, $R_4$ is $S(=O)_2$(methyl). In some embodiments, $R_4$ is trifluoromethoxy. In some embodiments, $R_4$ is N-morpholino. In some embodiments, $R_4$ is H. In some embodiments, $R_4$ is not H.

In some embodiments of Formula (II) or Formula (II-1), $R_5$ is halo. In some embodiments, $R_5$ is selected from H and F. In some embodiments, $R_5$ is F. In some embodiments, $R_5$ is H.

In some embodiments of Formula (II) or Formula (II-1), $R_5$ is halo and $R_4$ is selected from halo, $S(C_{1-4}$ alkyl), and 6-membered heterocycloalkyl. In some embodiments, $R_5$ is halo, and $R_4$ is $S(C_{1-4}$ alkyl). In some embodiments, $R_5$ is fluoro and $R_4$ is selected from fluoro, methylthio, and N-morpholino. In some embodiments, $R_5$ is fluoro and $R_4$ is methylthio. In some embodiments, $R_5$ is fluoro and $R_4$ is fluoro. In some embodiments, $R_5$ is fluoro and $R_4$ is 6-membered heterocycloalkyl. In some embodiments, $R_5$ is halo and $R_4$ is N-morpholino. In some embodiments, $R_5$ is fluoro and $R_4$ is N-morpholino. In some embodiments of Formula (II) or Formula (II-1), $R_6$ is selected from H, $C_{3-5}$ cycloalkyl, $C_{2-6}$ alkenyl, and $C_{1-6}$ alkyl optionally substituted with a substituent selected from hydroxyl, $C_{1-4}$ alkoxy, $S(C_{1-4}$ alkyl), amino, and NH(5-membered heteroaryl). In some embodiments, $R_6$ is selected from $C_{3-5}$ cycloalkyl, $C_{2-6}$ alkenyl, and $C_{1-6}$ alkyl optionally substituted with a substituent selected from hydroxyl, $C_{1-4}$ alkoxy, $S(C_{1-4}$ alkyl), amino, and NH(5-membered heteroaryl). In some embodiments, $R_6$ is $C_{3-5}$ cycloalkyl. In some embodiments, $R_6$ is $C_{2-6}$ alkenyl. In some embodiments, $R_6$ is $C_{1-6}$ alkyl optionally substituted with a substituent selected from hydroxyl, $C_{1-4}$ alkoxy, $S(C_{1-4}$ alkyl), amino, and NH(5-membered heteroaryl). In some embodiments, $R_6$ is selected from H, cyclopropyl, ethenyl, aminomethyl, hydroxymethyl, $CH_2NH$-imidazolyl, methylthiomethyl, and methoxymethyl. In some embodiments, $R_6$ is cyclopropyl. In some embodiments, $R_6$ is ethenyl. In some embodiments, $R_6$ is aminomethyl. In some embodiments, $R_6$ is hydroxymethyl. In some embodiments, $R_6$ is $CH_2NH$-imidazole. In some embodiments, $R_6$ is methylthiomethyl. In some embodiments, $R_6$ is methoxymethyl.

In some embodiments, $R_6$ is selected from cyclopropyl, ethenyl, aminomethyl, hydroxymethyl, $CH_2NH$-imidazolyl, methylthiomethyl, and methoxymethyl. In some embodiments, $R_6$ is H.

In some embodiments of Formula (II) or Formula (II-1), $R_{7A}$ is selected from H, $C_{1-6}$ alkyl, $C_{1-4}$ haloalkyl, $C_{1-4}$ hydroxyalkyl, and $C_{2-6}$ alkenyl. In some embodiments, $R_{7A}$ is selected from $C_{1-6}$ alkyl, $C_{1-4}$ haloalkyl, $C_{1-4}$ hydroxyalkyl, and $C_{2-6}$ alkenyl. In some embodiments, $R_{7A}$ is $C_{1-6}$ alkyl. In some embodiments, $R_{7A}$ is $C_{1-4}$ haloalkyl. In some embodiments, $R_{7A}$ is $C_{1-4}$ hydroxyalkyl. In some embodiments, $R_{7A}$ is $C_{2-6}$ alkenyl. In some embodiments, $R_{7A}$ is selected from H, methyl, trifluoromethyl, hydroxymethyl, difluoromethyl, and ethenyl. In some embodiments, $R_{7A}$ is selected from methyl, trifluoromethyl, hydroxymethyl, difluoromethyl, and ethenyl. In some embodiments, $R_{7A}$ is methyl. In some embodiments, $R_{7A}$ is trifluoromethyl. In some embodiments, $R_{7A}$ is hydroxymethyl. In some embodiments, $R_{7A}$ difluoromethyl. In some embodiments, $R_{7A}$ is ethenyl. In some embodiments, $R_{7A}$ is H.

In some embodiments of Formula (II) or Formula (II-1), $R_{7A}$ and $R_{7B}$ together with the carbon atom to which they are attached form oxo. In some embodiments, $R_{7A}$ and $R_{7B}$ together with the carbon atom to which they are attached form $C_{3-6}$ cyclopropyl.

In some embodiments of Formula (II) or Formula (II-1), $R_6$ is selected from $C_{2-6}$ alkenyl, $C_{1-6}$ hydroxyalkyl, and $C_{1-6}$ alkylene-NH(5-membered heteroaryl), and $R_{7A}$ is $C_{1-6}$ alkyl. In some embodiments, $R_6$ is selected from ethenyl, hydroxymethyl, and $CH_2NH$-imidazole, and $R_{7A}$ is $C_{1-6}$ alkyl. In some embodiments, $R_6$ is selected from ethenyl and $R_{7A}$ is methyl. In some embodiments, $R_6$ is hydroxymethyl, and $R_{7A}$ is methyl. In some embodiments, $R_6$ is $CH_2NH$-imidazole, and $R_{7A}$ is methyl. In some embodiments, $R_6$ is H and $R_{7A}$ is $C_{1-6}$ alkyl. In some embodiments, $R_6$ is H and $R_{7A}$ is methyl.

In some embodiments of Formula (II) or Formula (II-1), the carbon atom to which $R_6$ is attached is in (S) configuration according to Cahn-Ingold-Prelog nomenclature. In some embodiments, the carbon atom to which $R_6$ is attached is in (R) configuration according to Cahn-Ingold-Prelog nomenclature. In some embodiments, the stereochemistry at the carbon atom bound to $R_6$ is as shown below:

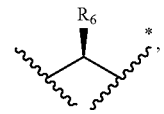

wherein the * indicates a point of attachment to the X atom.

In some embodiments, the stereochemistry at the carbon atom bound to $R_6$ is as shown below:

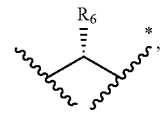

wherein the * indicates a point of attachment to the X atom.

In some embodiments of Formula (II) or Formula (II-1), the carbon atom to which $R_{7A}$ is attached is in (S) configuration according to Cahn-Ingold-Prelog nomenclature. In some embodiments, the carbon atom to which $R_{7A}$ is attached is in (R) configuration according to Cahn-Ingold-Prelog nomenclature.

In some embodiments, the stereochemistry at the carbon atom bound to $R_{7A}$ is as shown below:

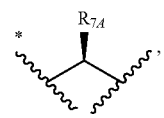

wherein the * indicates a point of attachment to the X atom.

In some embodiments, the stereochemistry at the carbon atom bound to $R_{7A}$ is as shown below:

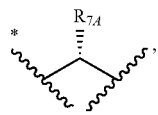

wherein the * indicates a point of attachment to the X atom.

In some embodiments of Formula (II) or Formula (II-1), $R_6$ and $R_{7A}$ together with the carbon atoms to which they are attached and the X atom connecting the two carbon atoms form a 6-membered heterocycloalkyl containing 1-3 heteroatoms selected from N, O and S, wherein the 6-membered heterocycloalkyl is optionally substituted with a substituent selected from C(=NH)C$_{1-6}$ alkyl, and di(C$_{1-6}$ alkyl)amino.

In some embodiments of Formula (II) or Formula (II-1), $R_6$ and $R_{7A}$ together with the carbon atoms to which they are attached and the X atom connecting the two carbon atoms form a ring of any one of the following formulae:

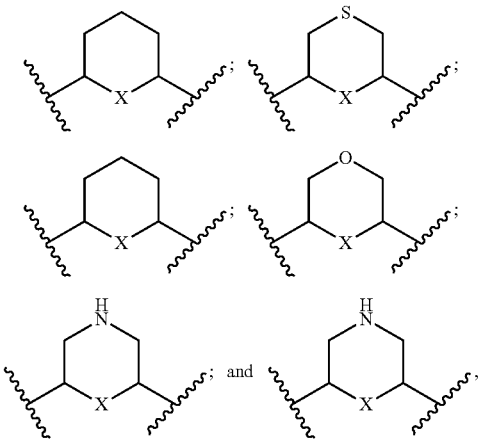

wherein any one of the formulae is optionally substituted with C(=NH)C$_{1-6}$ alkyl or di(C$_{1-6}$ alkyl)amino.

In some embodiments of Formula (II) or Formula (II-1), $R_6$ and $R_{7A}$ together with the carbon atoms to which they are attached and the X atom connecting the two carbon atoms form a ring of the following formulae:

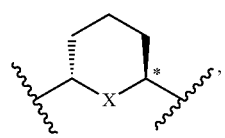

wherein the * indicates the ring carbon that is attached to the ring containing W atom and substituted with $R_5$.

In some embodiments of Formula (II) or Formula (II-1), $R_6$ and $R_{7A}$ together with the carbon atoms to which they are attached and the X atom connecting the two carbon atoms form a ring of any one of the following formulae:

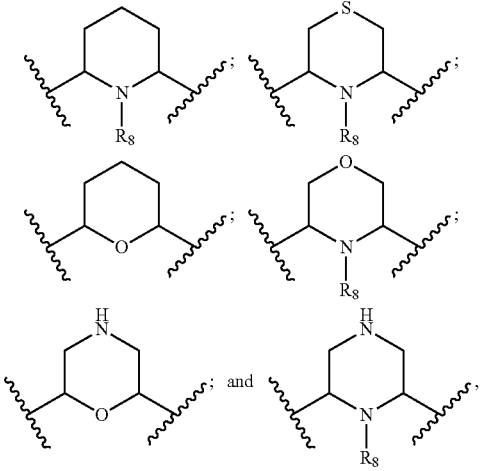

wherein any one of the formulae is optionally substituted with C(=NH)methyl, or dimethylamino.

In some embodiments of Formula (II) or Formula (II-1), $R_6$ and $R_{7A}$ together with the carbon atoms to which they are attached and the X atom connecting the two carbon atoms form a ring of any one of the following formulae:

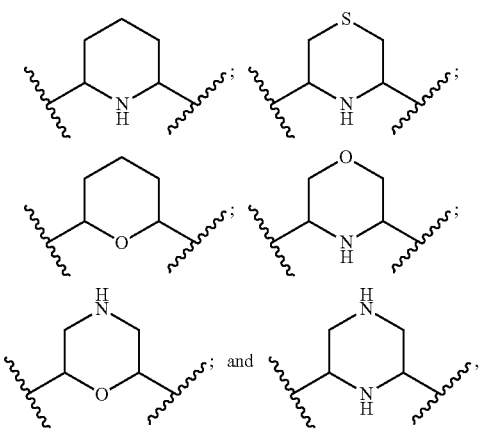

wherein any one of the formulae is optionally substituted with C(=NH)methyl, or dimethylamino.

In some embodiments of Formula (II) or Formula (II-1), $R_6$ and $R_{7A}$ together with the carbon atoms to which they are attached and the X atom connecting the two carbon atoms form a ring of formula:

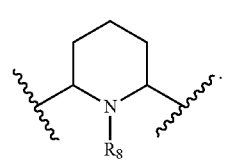

In some embodiments of Formula (II) or Formula (II-1), $R_6$ and $R_{7A}$ together with the carbon atoms to which they are attached and the X atom connecting the two carbon atoms form a ring of formula:

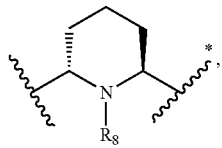

wherein the * indicates a point of attachment to the ring containing the W atom and substituted with $R_5$.

In some embodiments of Formula (II) or Formula (II-1), $R_6$ and $R_{7A}$ together with the carbon atoms to which they are attached and the X atom connecting the two carbon atoms form a ring of formula:

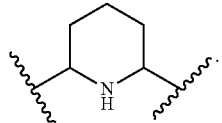 [SMILES: *C1CCCC(*)N1]

In some embodiments of Formula (II) or Formula (II-1), $R_6$ and $R_{7A}$ together with the carbon atoms to which they are attached and the X atom connecting the two carbon atoms form a ring of formula:

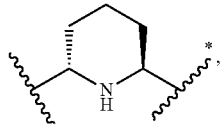 [SMILES: *[C@@H]1CCC[C@@H](*)N1]

wherein the * indicates a point of attachment to the ring containing the W atom and substituted with $R_5$.

In some embodiments of Formula (II) or Formula (II-1), $R_6$ and $R_{7A}$ together with the carbon atoms to which they are attached and the X atom connecting the two carbon atoms form a ring of any one of the following formulae:

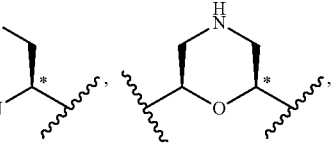

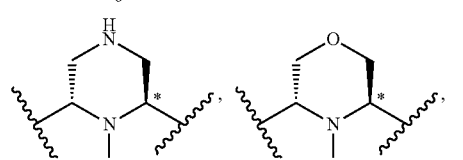

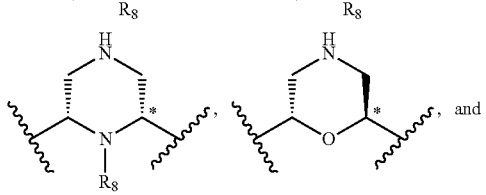

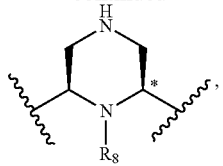

wherein the * indicates a point of attachment to the ring containing the W atom and substituted with $R_5$.

In some embodiments of Formula (II) or Formula (II-1), $R_6$ and $R_{7A}$ together with the carbon atoms to which they are attached and the X atom connecting the two carbon atoms form a ring of any one of the following formulae:

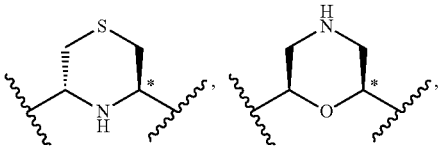

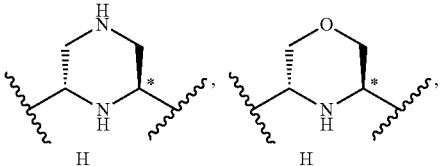

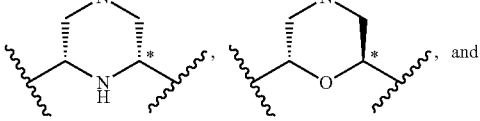

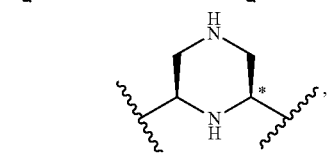

wherein the * indicates a point of attachment to the ring containing the W atom and substituted with $R_5$.

In some embodiments of Formula (II) or Formula (II-1), $R_6$ and $R_{7A}$ together with the carbon atoms to which they are attached and the X atom connecting the two carbon atoms form a ring of any one of the following formulae:

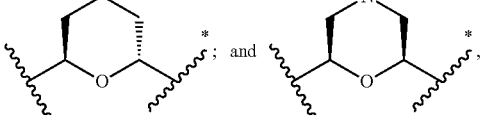

wherein the * indicates a point of attachment to the ring containing the W atom and substituted with $R_5$.

In some embodiments of Formula (II) or Formula (II-1), X is O. In some embodiments of Formula (II) or Formula (II-1), X is NRs.

In some embodiments of Formula (II) or Formula (II-1), $R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy, and $C_{1-6}$ alkyl substituted with 5- to 6-membered heteroaryl, wherein the 5- to 6-membered heteroaryl is optionally substituted with one or two $C_{1-6}$ alkyl. In some embodiments, $R_8$ is $C_{1-6}$ alkyl. In some embodiments, $R_8$ is $C_{1-4}$ haloalkyl. In some embodiments, $R_8$ is $C_{1-4}$ hydroxyalkyl. In some embodiments, $R_8$ is $C_{1-6}$ alkyl substituted with $C_{1-6}$ alkoxy. In some embodiments, $R_8$ is $C_{1-6}$ alkyl substituted with 5- to 6-membered heteroaryl, wherein the 5- to 6-membered heteroaryl is optionally substituted with 1, or 2 $C_{1-6}$ alkyl.

In some embodiments of Formula (II), $R_8$ is selected from H, methyl, tert-butyl, 2-fluoroethenyl, 3-fluoropropyl, 2-methoxyethyl, 3-hydroxypropyl, 2-methyl-3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl.

In some embodiments of Formula (II) or Formula (II-1), $R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl.

In some embodiments of Formula (II) or Formula (II-1), $R_8$ is selected from any one of the following formulae:

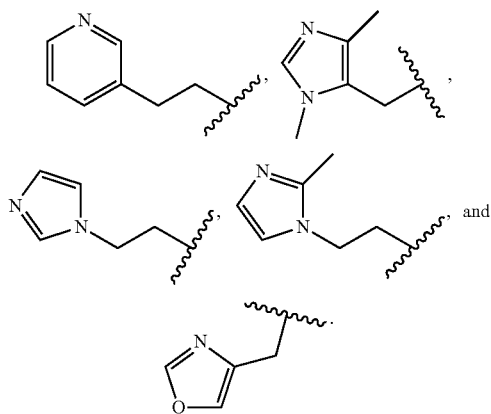

In some embodiments of Formula (II) or Formula (II-1), $R_8$ is selected from methyl, 3-fluoropropyl, 2-methoxyethyl, and 3-hydroxypropyl. In some embodiments, $R_8$ is methyl. In some embodiments, $R_8$ is 3-fluoropropyl. In some embodiments, $R_8$ is 2-methoxyethyl. In some embodiments, $R_8$ is 3-hydroxypropyl. In some embodiments, $R_8$ is H.

In some embodiments of Formula (II) or Formula (II-1), $R_9$ is selected from H and $C_{1-6}$ alkyl. In some embodiments, $R_9$ is H. In some embodiments, $R_9$ is $C_{1-6}$ alkyl. In some embodiments, $R_9$ is methyl. In some embodiments, $R_9$ is ethyl. In some embodiments, $R_9$ is n-propyl. In some embodiments, $R_9$ is i-propyl.

In some embodiments of Formula (II) or Formula (II-1), the carbon atom to which $R_9$ is attached is in (S) configuration according to Cahn-Ingold-Prelog nomenclature. In some embodiments, the carbon atom to which $R_9$ is attached is in (R) configuration according to Cahn-Ingold-Prelog nomenclature.

In some embodiments, the stereochemistry at the carbon atom bound to $R_9$ is as shown below:

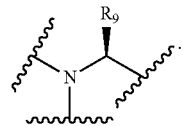

In some embodiments, the stereochemistry at the carbon atom bound to $R_9$ is as shown below:

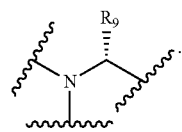

In some embodiments of Formula (II) or Formula (II-1), $R_{10}$ is H. In some embodiments, $R_{10}$ is $C_{2-6}$ alkenyl. In some embodiments, $R_{10}$ is allyl.

In some embodiments of Formula (II) or Formula (II-1), $R_A$ is selected from H and methyl. In some embodiments, $R_A$ is H.

In some embodiments of Formula (II), L is selected from $C_{1-6}$ alkyl, $C_{1-6}$ haloalkyl, $C_{1-6}$ hydroxyalkyl, $C_{2-6}$ alkenyl, and —O(CH$_2$CH$_2$O)CH$_3$, wherein the $C_{1-6}$ alkyl is optionally substituted with a substituent selected from $C_{1-6}$ alkoxy, and S($C_{1-6}$ alkyl).

In some embodiments of Formula (II) or Formula (II-1), L is selected from $C_{1-6}$ alkyl, $C_{1-6}$ haloalkyl, $C_{1-6}$ hydroxyalkyl, and $C_{2-6}$ alkenyl, wherein the $C_{1-6}$ alkyl is optionally substituted with a substituent selected from $C_{1-6}$ alkoxy, and S($C_{1-6}$ alkyl). In some embodiments, L is $C_{1-6}$ alkyl. In some embodiments, L is not $C_{1-6}$ alkyl. In some embodiments, L is $C_{1-6}$ haloalkyl. In some embodiments, L is not $C_{1-6}$ haloalkyl. In some embodiments, L is $C_{1-6}$ hydroxyalkyl. In some embodiments, L is $C_{2-6}$ alkenyl. In some embodiments, L is $C_{1-6}$ alkyl substituted with $C_{1-6}$ alkoxy. In some embodiments, L is $C_{1-6}$ alkyl substituted with S($C_{1-6}$ alkyl). In some embodiments, L is selected from $C_{1-6}$ hydroxyalkyl, and $C_{1-6}$ alkyl substituted with a substituent selected from $C_{1-6}$ alkoxy, and S($C_{1-6}$ alkyl). In some embodiments, L is selected from methyl, fluoromethyl, 2,2,2-trifluoroethyl, trichloromethyl, methylthiomethyl, methoxymethyl, hydroxyethyl, ethoxyethyl, and allyl. In some embodiments, L is fluoromethyl. In some embodiments, L is 2,2,2-trifluoroethyl. In some embodiments, L is trichloromethyl. In some embodiments, L is methylthiomethyl. In some embodiments, L is methoxymethyl. In some embodiments, L is hydroxyethyl. In some embodiments, L is ethoxyethyl. In some embodiments, L is allyl. In some embodiments, L is selected from 2,2,2-trifluoroethyl, trichloromethyl, methylthiomethyl, methoxymethyl, hydroxyethyl, and ethoxyethyl. In some embodiments, L is selected from methylthiomethyl, methoxymethyl, hydroxyethyl, and ethoxyethyl. In some embodiments, L is methyl. In some embodiments, L is not methyl. In some embodiments, L is not 3-chloropropyl, ethyl, isopropyl, fluoromethyl, or chloromethyl. In some embodiments, L is not 3-chloropropyl, fluoromethyl, or chloromethyl. In some embodiments, L is not ethyl or isopropyl.

In some embodiments of Formula (II) or Formula (II-1), $R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from CN, OH, $C_{1-6}$ alkoxy, $S(C_{1-6}$ alkyl), amino, $C(O)NH_2$, and $S(O)_2C_{1-6}$ alkyl. In some embodiments, $R_1$ is selected from $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from OH, $C_{1-6}$ alkoxy, $S(O)_2C_{1-6}$ alkyl, and $S(C_{1-6}$ alkyl). In some embodiments, $R_1$ is $C_{1-6}$ alkyl. In some embodiments, $R_{11}$ is not $C_{1-6}$ alkyl. In some embodiments, $R_{11}$ is $C_{3-5}$ cycloalkyl. In some embodiments, $R_{11}$ is $C_{1-4}$ haloalkyl. In some embodiments, $R_{11}$ is $C_{2-6}$ alkenyl. In some embodiments, $R_{11}$ is $C_{1-6}$ alkyl substituted with a substituent selected from OH, $C_{1-6}$ alkoxy, $S(O)_2C_{1-6}$ alkyl, and $S(C_{1-6}$ alkyl). In some embodiments, $R_{11}$ is $C_{1-6}$ alkyl substituted with $C_{1-6}$ alkoxy. In some embodiments, $R_{11}$ is selected from $C_{1-6}$ alkyl, $C_{3-5}$ cycloalkyl, $C_{2-6}$ alkenyl, and $C_{1-6}$ alkyl substituted with $C_{1-6}$ alkoxy. In some embodiments, $R_{11}$ is selected from H, methyl, ethenyl, fluoromethyl, difluoromethyl, trifluoromethyl, hydroxymethyl, methoxymethyl, methylthiomethyl, cyanomethyl, aminomethyl, cyclopropyl, $CH_2S(O)_2CH_3$, and $CH_2C(O)NH_2$. In some embodiments, $R_{11}$ is methyl. In some embodiments, $R_{11}$ is not methyl. In some embodiments, $R_{11}$ is ethenyl. In some embodiments, $R_{11}$ is fluoromethyl. In some embodiments, $R_{11}$ is difluoromethyl. In some embodiments, $R_{11}$ is trifluoromethyl. In some embodiments, $R_{11}$ is hydroxymethyl. In some embodiments, Ru is methoxymethyl. In some embodiments, $R_{11}$ is methylthiomethyl. In some embodiments, $R_{11}$ is cyanomethyl. In some embodiments, $R_{11}$ is aminomethyl. In some embodiments, $R_{11}$ is cyclopropyl. In some embodiments, $R_{11}$ is $CH_2S(O)_2CH_3$.

In some embodiments, $R_{11}$ is $CH_2C(O)NH_2$. In some embodiments, $R_{11}$ is selected from methyl, ethenyl, $CH_2S(O)_2CH_3$, methylthiomethyl, fluoromethyl, methoxymethyl, hydroxymethyl, and cyclopropyl. In some embodiments, $R_{11}$ is selected from methyl, cyclopropyl, ethenyl, and methoxymethyl.

In some embodiments of Formula (II) or Formula (II-1), the carbon atom to which $R_{11}$ is attached is in (S) configuration according to Cahn-Ingold-Prelog nomenclature. In some embodiments, the carbon atom to which $R_{11}$ is attached is in (R) configuration according to Cahn-Ingold-Prelog nomenclature.

In some embodiments, the stereochemistry at the carbon atom bound to Ru is as shown below:

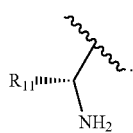

In some embodiments, the stereochemistry at the carbon atom bound to Ru is as shown below:

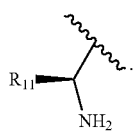

In some embodiments of Formula (II) or Formula (II-1), $R_{12}$ is selected from H and methyl. In some embodiments, $R_{12}$ is methyl. In some embodiments, $R_{12}$ is H.

In some embodiments of Formula (II) or Formula (II-1), $R_{11}$ and $R_{12}$ together with the carbon atom to which they are attached form a cyclopropyl ring. In some embodiments, $R_1$ is methyl and $R_{12}$ is methyl. In some embodiments of Formula (II) or Formula (II-1), $R_{13}$ is selected from H, fluoro, and methyl. In some embodiments, $R_{13}$ is fluoro. In some embodiments, $R_{13}$ is methyl. In some embodiments, $R_{13}$ is H.

In some embodiments of Formula (II) or Formula (II-1), $R_{14}$ is selected from H, fluoro, and methyl. In some embodiments, $R_{14}$ is fluoro. In some embodiments, $R_{14}$ is methyl. In some embodiments, $R_{14}$ is H.

In some embodiments of Formula (II) or Formula (II-1), $R_{13}$ is fluoro and $R_{14}$ is fluoro. In some embodiments, $R_{13}$ is methyl and $R_{14}$ is methyl.

In some embodiments of Formula (II) or Formula (II-1), $R_B$ is selected from H and $C(=NH)CH_3$. In some embodiments, $R_B$ is $C(=NH)CH_3$. In some embodiments, $R_B$ is H.

In some embodiments of Formula (II) or Formula (II-1), $R_{11}$ and $R_B$ together with the carbon atom to which $R_{11}$ is attached and the nitrogen atom to which $R_B$ is attached form a 6-membered heterocycloalkyl containing 1-3 heteroatoms selected from N and O, wherein the 6-membered heterocycloalkyl is optionally substituted with oxo.

In some embodiments of Formula (II) or Formula (II-1), $R_{11}$ and $R_B$ together with the carbon atom to which $R_{11}$ is attached and the nitrogen atom to which $R_B$ is attached form a ring of any one of the following formulae:

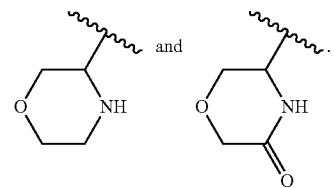 [SMILES: *C1COCCN1 ; *C1COCC(=O)N1]

In some embodiments of Formula (II) or Formula (II-1), $R_{11}$ and $R_B$ together with the carbon atom to which $R_{11}$ is attached and the nitrogen atom to which $R_B$ is attached form a ring of formula:

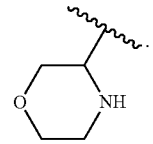

In some embodiments of Formula (II) or Formula (II-1):
$R_2$ is selected from H, halo, $C_{1-4}$ haloalkyl, and $C_{1-4}$ haloalkoxy;
$R_3$ is selected from H, $C_{1-4}$ haloalkyl, and $C(O)C_{1-4}$ alkoxy;
$R_4$ is selected from H, halo, $C_{1-6}$ alkyl, $C_{1-4}$ alkoxy, $C_{1-4}$ haloalkoxy, $S(C_{1-4}$ alkyl), 6-membered heterocycloalkyl, and $S(O)_2C_{1-4}$ alkyl;
$R_5$ is selected from H and fluoro;
$R_6$ is selected from H, $C_{3-5}$ cycloalkyl, $C_{2-6}$ alkenyl, and $C_{1-6}$ alkyl optionally substituted with a substituent selected from hydroxyl, $C_{1-4}$ alkoxy, $S(C_{1-6}$ alkyl), amino, and NH(5-membered heteroaryl);
$R_{7A}$ is selected from H, $C_{1-6}$ alkyl, $C_{1-4}$ haloalkyl, $C_{1-4}$ hydroxyalkyl, and $C_{2-6}$ alkenyl;

$R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy, and $C_{1-6}$ alkyl substituted with 5- to 6-membered heteroaryl, wherein the 5- to 6-membered heteroaryl is optionally substituted with 1, or 2 $C_{1-6}$ alkyl;

$R_9$ is selected from H, methyl, ethyl, n-propyl and i-propyl;

$R_{10}$ is selected from H and allyl;

$R_A$ is selected from H and methyl;

L is selected from $C_{1-6}$ alkyl, $C_{1-6}$ haloalkyl, $C_{1-6}$ hydroxyalkyl, and $C_{2-6}$ alkenyl, wherein the $C_{1-6}$ alkyl is optionally substituted with a substituent selected from $C_{1-6}$ alkoxy, and $S(C_{1-6}$ alkyl);

$R_{11}$ is selected from H, $C_{1-6}$ alkyl, $C_{3-5}$ cycloalkyl, Cia haloalkyl, and $C_{2-6}$ alkenyl, wherein the $C_{1-6}$ alkyl is optionally substituted with a substituent selected from CN, OH, $C_{1-6}$ alkoxy, $S(C_{1-6}$ alkyl), amino, $C(O)NH_2$, and $S(O)_2C_{1-6}$ alkyl;

$R_{12}$ is selected from H and methyl;

$R_{13}$ is selected from H, fluoro, and methyl;

$R_{14}$ is selected from H, fluoro, and methyl; and $R_B$ is selected from H and $C(=NH)CH_3$.

In some embodiments of Formula (II) or Formula (II-1):

$R_2$ is selected from H, halo, $C_{1-4}$ haloalkyl, and $C_{1-4}$ haloalkoxy;

$R_3$ is selected from H, $C_{1-4}$ haloalkyl, and $C(O)C_{1-4}$ alkoxy;

$R_4$ is selected from halo, $C_{1-6}$ alkyl, $C_{1-4}$ alkoxy, $C_{1-4}$ haloalkoxy, $S(C_{1-4}$ alkyl), 6-membered heterocycloalkyl, and $S(O)_2C_{1-4}$ alkyl;

$R_5$ is selected from H and fluoro;

$R_6$ is selected from H, $C_{3-5}$ cycloalkyl, $C_{2-6}$ alkenyl, and $C_{1-6}$ alkyl optionally substituted with a substituent selected from hydroxyl, $C_{1-4}$ alkoxy, $S(C_{1-4}$ alkyl), amino, and NH(5-membered heteroaryl);

$R_{7A}$ is selected from H, $C_{1-6}$ alkyl, $C_{1-4}$ haloalkyl, $C_{1-4}$ hydroxyalkyl, and $C_{2-6}$ alkenyl;

$R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy, and $C_{1-6}$ alkyl substituted with 5- to 6-membered heteroaryl, wherein the 5- to 6-membered heteroaryl is optionally substituted with 1, or 2 $C_{1-6}$ alkyl;

$R_9$ is selected from H, methyl, ethyl, n-propyl and i-propyl;

$R_{10}$ is selected from H and allyl;

$R_A$ is selected from H and methyl;

L is selected from $C_{1-6}$ alkyl, $C_{1-6}$ haloalkyl, $C_{1-6}$ hydroxyalkyl, and $C_{2-6}$ alkenyl, wherein the $C_{1-6}$ alkyl is optionally substituted with a substituent selected from $C_{1-6}$ alkoxy, and $S(C_{1-6}$ alkyl);

$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from CN, OH, $C_{1-6}$ alkoxy, $S(C_{1-6}$ alkyl), amino, $C(O)NH_2$, and $S(O)_2C_{1-6}$ alkyl;

$R_{12}$ is selected from H and methyl;

$R_{13}$ is selected from H, fluoro, and methyl;

$R_{14}$ is selected from H, fluoro, and methyl; and $R_B$ is selected from H and $C(=NH)CH_3$.

In some embodiments of Formula (II) or Formula (II-1):

$R_2$ is selected from H, halo, $C_{1-4}$ haloalkyl, and $C_{1-4}$ haloalkoxy;

$R_3$ is selected from H, $C_{1-4}$ haloalkyl, and $C(O)C_{1-4}$ alkoxy;

$R_4$ is selected from H, halo, $C_{1-6}$ alkyl, $C_{1-4}$ alkoxy, $C_{1-4}$ haloalkoxy, $S(C_{1-4}$ alkyl), 6-membered heterocycloalkyl, and $S(O)_2C_{1-4}$ alkyl;

$R_5$ is selected from H and fluoro;

$R_6$ and $R_{7A}$ together with the carbon atoms to which they are attached and the X atom connecting the two carbon atoms form a ring of any one of the following formulae:

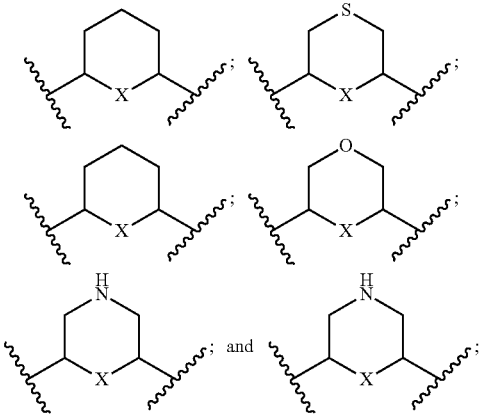

$R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy, and $C_{1-6}$ alkyl substituted with 5- to 6-membered heteroaryl, wherein the 5- to 6-membered heteroaryl is optionally substituted with 1, or 2 $C_{1-6}$ alkyl;

$R_9$ is selected from H, methyl, ethyl, n-propyl and i-propyl;

$R_{10}$ is selected from H and allyl;

$R_A$ is selected from H and methyl;

L is selected from $C_{1-6}$ alkyl, $C_{1-6}$ haloalkyl, $C_{1-6}$ hydroxyalkyl, and $C_{2-6}$ alkenyl, wherein the $C_{1-6}$ alkyl is optionally substituted with a substituent selected from $C_{1-6}$ alkoxy, and $S(C_{1-6}$ alkyl);

$R_{11}$ is selected from H, $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from CN, OH, $C_{1-6}$ alkoxy, $S(C_{1-6}$ alkyl), amino, $C(O)NH_2$, and $S(O)_2C_{1-6}$ alkyl;

$R_{12}$ is selected from H and methyl;

$R_{13}$ is selected from H, fluoro, and methyl;

$R_{14}$ is selected from H, fluoro, and methyl; and $R_B$ is selected from H and $C(=NH)CH_3$.

In some embodiments of Formula (II) or Formula (II-1):

$R_2$ is selected from H, halo, $C_{1-4}$ haloalkyl, and $C_{1-4}$ haloalkoxy;

$R_3$ is selected from H, $C_{1-4}$ haloalkyl, and $C(O)C_{1-4}$ alkoxy;

$R_4$ is selected from halo, $C_{1-6}$ alkyl, $C_{1-4}$ alkoxy, $C_{1-4}$ haloalkoxy, $S(C_{1-4}$ alkyl), 6-membered heterocycloalkyl, and $S(O)_2C_{1-4}$ alkyl;

$R_5$ is selected from H and fluoro;

$R_6$ and $R_{7A}$ together with the carbon atoms to which they are attached and the X atom connecting the two carbon atoms form a ring of any one of the following formulae:

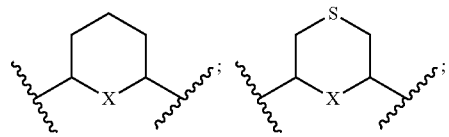

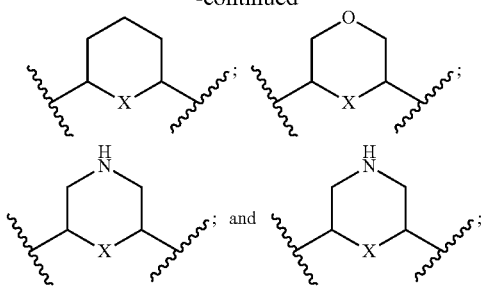

R$_8$ is selected from H, C$_{1-6}$ alkyl, C$_{1-4}$ haloalkyl, C$_{1-4}$ hydroxyalkyl, C$_{1-6}$ alkyl substituted with C$_{1-6}$ alkoxy, and C$_{1-6}$ alkyl substituted with 5- to 6-membered heteroaryl, wherein the 5- to 6-membered heteroaryl is optionally substituted with 1, or 2 C$_{1-6}$ alkyl;

R$_9$ is selected from H, methyl, ethyl, n-propyl and i-propyl;

R$_{10}$ is selected from H and allyl;

R$_A$ is selected from H and methyl;

L is selected from C$_{1-6}$ alkyl, C$_{1-6}$ haloalkyl, C$_{1-6}$ hydroxyalkyl, and C$_{2-6}$ alkenyl, wherein the C$_{1-6}$ alkyl is optionally substituted with a substituent selected from C$_{1-6}$ alkoxy and S(C$_{1-6}$ alkyl);

R$_{11}$ is selected from H, C$_{1-6}$ alkyl, C$_{3-5}$ cycloalkyl, C$_{1-4}$ haloalkyl, and C$_{2-6}$ alkenyl, wherein the C$_{1-6}$ alkyl is optionally substituted with a substituent selected from CN, OH, C$_{1-6}$ alkoxy, S(C$_{1-6}$ alkyl), amino, C(O)NH$_2$, and S(O)$_2$C$_{1-6}$ alkyl;

R$_{12}$ is selected from H and methyl;

R$_{13}$ is selected from H, fluoro, and methyl;

R$_{14}$ is selected from H, fluoro, and methyl; and

R$_B$ is selected from H and C(=NH)CH$_3$.

In some embodiments of Formula (II) or Formula (II-1):

R$_1$ is selected from H and fluoro;

R$_2$ is selected from H, trifluoromethoxy, trifluoromethyl, and chloro;

R$_3$ is selected from H, trifluoromethyl, and C(=O)(methoxy);

W is CR$_4$;

R$_4$ is selected from H, fluoro, chloro, methylthio, methoxy, methyl, S(=O)$_2$(methyl), trifluoromethoxy, and N-morpholino;

R$_5$ is selected from H and fluoro;

R$_6$ is selected from H, cyclopropyl, ethenyl, aminomethyl, hydroxymethyl, CH$_2$NH-imidazole, methylthiomethyl, and methoxymethyl;

R$_{7A}$ is selected from H, methyl, trifluoromethyl, hydroxymethyl, difluoromethyl, and ethenyl;

R$_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;

R$_9$ is selected from H and methyl;

R$_{10}$ is selected from H and allyl;

R$_A$ is selected from H and methyl;

L is selected from methyl, fluoromethyl, 2,2,2-trifluoroethyl, trichloromethyl, methylthiomethyl, methoxymethyl, hydroxyethyl, ethoxyethyl, and allyl;

R$_{11}$ is selected from H, methyl, ethenyl, fluoromethyl, difluoromethyl, trifluoromethyl, hydroxymethyl, methoxymethyl, methylthiomethyl, cyanomethyl, aminomethyl, cyclopropyl, CH$_2$S(O)$_2$CH$_3$, and CH$_2$C(O)NH$_2$;

R$_{12}$ is selected from H and methyl;

R$_{13}$ is selected from H, fluoro, and methyl;

R$_{14}$ is selected from H, fluoro, and methyl; and

R$_B$ is selected from H and C(=NH)CH$_3$.

In some embodiments of Formula (II) or Formula (II-1):

R$_1$ is selected from H and fluoro;

R$_2$ is selected from H, trifluoromethoxy, trifluoromethyl and chloro;

R$_3$ is selected from H, trifluoromethyl, and C(=O)(methoxy);

W is CR$_4$;

R$_4$ is selected from H, fluoro, chloro, methylthio, methoxy, methyl, S(=O)$_2$(methyl), trifluoromethoxy, and N-morpholino;

R$_5$ is selected from H and fluoro;

R$_6$ and R$_{7A}$ together with the carbon atoms to which they are attached and the X atom connecting the two carbon atoms form a ring of any one of the following formulae:

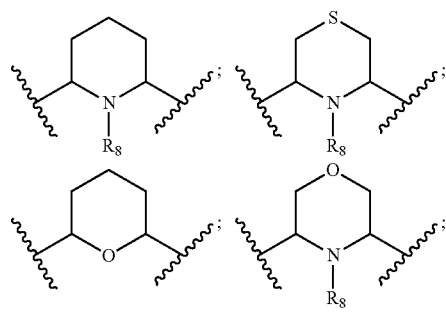

-continued

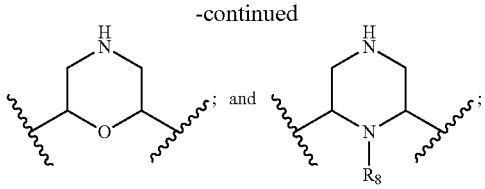

$R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;

$R_9$ is selected from H, methyl, ethyl, n-propyl and i-propyl;

$R_{10}$ is selected from H and allyl;

$R_A$ is selected from H and methyl;

L is selected from methyl, fluoromethyl, 2,2,2-trifluoroethyl, trichloromethyl, methylthiomethyl, methoxymethyl, hydroxyethyl, ethoxyethyl, and allyl;

$R_{11}$ is selected from H, methyl, ethenyl, fluoromethyl, difluoromethyl, trifluoromethyl, hydroxymethyl, methoxymethyl, methylthiomethyl, cyanomethyl, aminomethyl, cyclopropyl, $CH_2S(O)_2CH_3$, and $CH_2C(O)NH_2$;

$R_{12}$ is selected from H and methyl;

$R_{13}$ is selected from H, fluoro, and methyl;

$R_{14}$ is selected from H, fluoro, and methyl; and $R_B$ is selected from H and $C(=NH)CH_3$.

In some embodiments of Formula (II) or Formula (II-1):

$R_1$ is selected from H and fluoro;

$R_2$ is selected from H, trifluoromethoxy, trifluoromethyl and chloro;

$R_3$ is selected from H, trifluoromethyl, and $C(=O)$(methoxy);

W is $CR_4$;

$R_4$ is selected from fluoro, chloro, methylthio, methoxy, methyl, $S(=O)_2$(methyl), trifluoromethoxy, and N-morpholino;

$R_5$ is selected from H and fluoro;

$R_6$ and $R_{7A}$ together with the carbon atoms to which they are attached and the X atom connecting the two carbon atoms form a ring of any one of the following formulae:

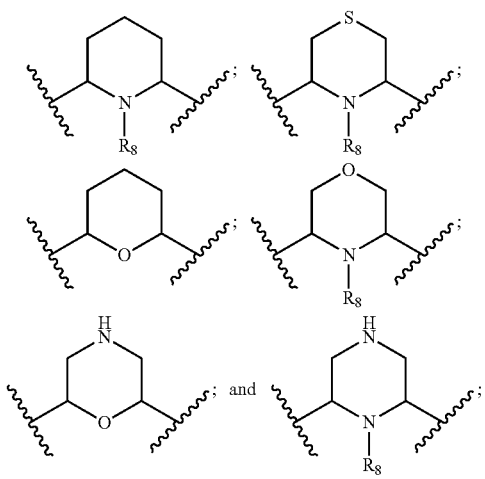

$R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;

$R_9$ is selected from H and methyl;

$R_{10}$ is selected from H and allyl;

$R_A$ is selected from H and methyl;

L is selected from methyl, fluoromethyl, 2,2,2-trifluoroethyl, trichloromethyl, methylthiomethyl, methoxymethyl, hydroxyethyl, ethoxyethyl, and allyl;

$R_{11}$ is selected from H, methyl, ethenyl, fluoromethyl, difluoromethyl, trifluoromethyl, hydroxymethyl, methoxymethyl, methylthiomethyl, cyanomethyl, aminomethyl, cyclopropyl, $CH_2S(O)_2CH_3$, and $CH_2C(O)NH_2$;

$R_{12}$ is selected from H and methyl;

$R_{13}$ is selected from H, fluoro, and methyl;

$R_{14}$ is selected from H, fluoro, and methyl; and $R_B$ is selected from H and $C(=NH)CH_3$.

In some embodiments of Formula (II) or Formula (II-1):

$R_1$ is fluoro;

$R_2$ is selected from $OCF_3$, $CF_3$ and Cl;

$R_3$ is H;

$R_4$ is selected from H, fluoro, chloro, methylthio, methoxy, and methyl;

$R_5$ is selected from H and fluoro;

$R_6$ is selected from H, cyclopropyl, ethenyl, aminomethyl, hydroxymethyl, $CH_2NH$-imidazolyl, methylthiomethyl, and methoxymethyl;

$R_{7A}$ is selected from H, methyl, trifluoromethyl, hydroxymethyl, difluoromethyl, and ethenyl;

$R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;

$R_9$ is selected from H and methyl;

$R_{10}$ is H;

$R_A$ is H;

L is selected from methyl, fluoromethyl, 2,2,2-trifluoroethyl, trichloromethyl, methylthiomethyl, methoxymethyl, hydroxyethyl, and ethoxyethyl;

$R_{12}$ is selected from H and methyl;

$R_{11}$ is selected from methyl, cyclopropyl, ethenyl, and methoxymethyl;

$R_{13}$ is selected from H, fluoro, and methyl;

$R_{14}$ is selected from H, fluoro, and methyl; and $R_B$ is H.

In some embodiments of Formula (II) or Formula (II-1):

$R_1$ is fluoro;

$R_2$ is selected from $OCF_3$, $CF_3$ and Cl;

$R_3$ is H;

$R_4$ is selected from fluoro, chloro, methylthio, methoxy, and methyl;

$R_5$ is selected from H and fluoro;

$R_6$ is selected from H, cyclopropyl, ethenyl, aminomethyl, hydroxymethyl, $CH_2NH$-imidazole, methylthiomethyl, and methoxymethyl;

$R_{7A}$ is selected from H, methyl, trifluoromethyl, hydroxymethyl, difluoromethyl, and ethenyl;

$R_8$ is selected from H, methyl, 3-fluoropropyl, 2-methoxyethyl, 3-hydroxypropyl, 2-(pyridinyl)ethyl, 2-(imidazolyl)ethyl, (imidazolyl)methyl, and (oxazolyl)methyl, wherein each pyridinyl, imidazolyl, and oxazolyl is optionally substituted with 1 or 2 methyl;

$R_9$ is selected from H, methyl, ethyl, n-propyl and i-propyl;

$R_{10}$ is H;
$R_A$ is H;
L is selected from methyl, fluoromethyl, 2,2,2-trifluoroethyl, trichloromethyl, methylthiomethyl, methoxymethyl, hydroxyethyl, and ethoxyethyl;
$R_{12}$ is selected from H and methyl;
$R_{11}$ is selected from methyl, cyclopropyl, ethenyl, and methoxymethyl;
$R_{13}$ is selected from H, fluoro, and methyl;
$R_{14}$ is selected from H, fluoro, and methyl; and
$R_B$ is H.

In some embodiments of Formula (II) or Formula (II-1):
$R_1$ is selected from H and halo;
$R_2$ is selected from H, $OR^{a1}$, $C_{1-4}$ haloalkyl and halo;
$R_3$ is selected from H and $C_{1-4}$ haloalkyl;
$R_4$ is selected from H, halo, $S(C_{1-4}$ alkyl), $C_{1-6}$ alkoxy, and $C_{1-6}$ alkyl;
$R_5$ is selected from H and halo;
$R_6$ and $R_{7A}$ together with the carbon atoms to which they are attached and the X atom connecting the two carbon atoms form a ring of any one of the following formulae:

wherein the * indicates a point of attachment to the ring containing the W atom and substituted with $R_5$;
$R_8$ is selected from H, $C_{1-6}$ alkyl, and $C_{1-4}$ haloalkyl, wherein the $C_{1-6}$ alkyl is optionally substituted with $OR^{a3}$;
$R_9$ is selected from H, methyl, ethyl, n-propyl and i-propyl;
$R_{10}$ is H;
$R_A$ is H;
L is $C_{1-6}$ alkyl;
$R_{11}$ is selected from selected from $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from OH, $C_{1-6}$ alkoxy, $S(O)_2C_{1-6}$ alkyl, and $S(C_{1-6}$ alkyl);
$R_{12}$ is H;
$R_{13}$ is H;
$R_{14}$ is H;
$R_B$ is H; or
$R_{11}$ and $R_B$ together with the carbon atom to which $R_{11}$ is attached and the nitrogen atom to which $R_B$ is attached form a ring of formula:

In some embodiments of Formula (II) or Formula (II-1):
$R_1$ is selected from H and fluoro;
$R_2$ is selected from H, $OCF_3$, $CF_3$ and Cl;
$R_3$ is selected from H and trifluoromethyl;
$R_4$ is selected from H, fluoro, chloro, methylthio, methoxy, and methyl;
$R_5$ is selected from H and fluoro;
$R_6$ and $R_{7A}$ together with the carbon atoms to which they are attached and the X atom connecting the two carbon atoms form a ring of any one of the following formulae:

wherein the * indicates a point of attachment to the ring containing the W atom and substituted with $R_5$;
$R_8$ is selected from H, methyl, 3-fluoropropyl, 2-methoxyethyl, and 3-hydroxypropyl;
$R_9$ is selected from H and methyl;
$R_{10}$ is H;
$R_A$ is H;
L is methyl;
$R_{11}$ is selected from methyl, ethenyl, $CH_2S(O)_2CH_3$, methylthiomethyl, fluoromethyl, methoxymethyl, hydroxymethyl, and cyclopropyl;
$R_{12}$ is H;
$R_{13}$ is H; and
$R_{14}$ is H.

In some embodiments of the method, the compounds of Formula (II) or Formula (II-1) are compounds of Formula (IIaa):

(IIaa)

or a tautomer thereof or a pharmaceutically acceptable salt of the compound or tautomer, wherein:
$R_2$ is selected from H, halo, $C_{1-4}$ haloalkyl, and $C_{1-4}$ haloalkoxy;
$R_4$ is selected from H, fluoro, methyl, ethyl, n-propyl, isopropyl, methylthio, and methoxy; and
$R_{11}$ is selected from H, methyl, ethyl, isopropyl, cyclopropyl, cyclobutyl, cyclopentyl, fluoromethyl, and cyanomethyl.

In some embodiments of Formula (IIaa), $R_2$ is selected from H, $OCF_3$, $CF_3$ and Cl. In some embodiments of Formula (IIaa), $R_2$ is Cl.

In some embodiments of Formula (IIaa), $R_4$ is selected from H, methyl, methylthio, and methoxy.

In some embodiments of Formula (IIaa), $R_{11}$ is selected from H, methyl, isopropyl, cyclopropyl, and fluoromethyl.

In some embodiments of Formula (IIaa), $R_2$ is selected from $OCF_3$, $CF_3$ and Cl; $R_4$ is selected from methylthio and methoxy; and $R_{11}$ is selected from methyl, cyclopropyl and fluoromethyl. In some embodiments of Formula (IIaa), $R_2$ is Cl; R₄ is selected from methylthio and methoxy; and $R_{11}$ is selected from cyclopropyl and methyl. In some embodiments of Formula (IIaa), $R_2$ is Cl; $R_4$ is methylthio; and Ru is methyl. In some embodiments of Formula (IIaa), $R_2$ is Cl; $R_4$ is methoxy; and $R_{11}$ is methyl. In some embodiments of Formula (IIaa), $R_2$ is Cl; $R_4$ is methylthio; and $R_{11}$ is cyclopropyl. In some embodiments of Formula (IIaa), $R_2$ is Cl; $R_4$ is methoxy; and $R_{11}$ is cyclopropyl.

In some embodiments of the method, the compounds of Formula (II) or Formula (II-1) are compounds of Formula (IIab):

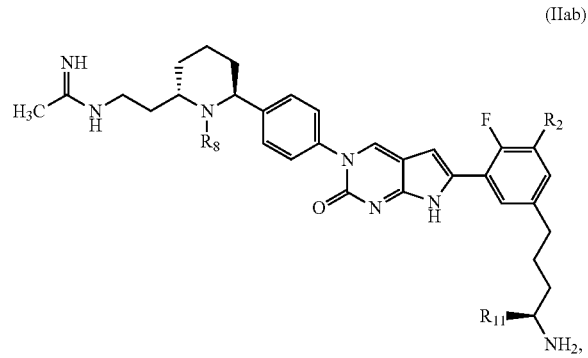

(IIab)

or a tautomer thereof or a pharmaceutically acceptable salt of the compound or tautomer, wherein:
- $R_2$ is selected from H, halo, $C_{1-4}$ haloalkyl, and $C_{1-4}$ haloalkoxy;
- $R_8$ is selected from H, methyl, n-propyl, n-butyl, 2-chloroethyl, 3,3,3-trifluoropropyl, 3-fluoropropyl, 2-methoxyethyl, 2-hydroxypropyl, and 3-hydroxypropyl.
- $R_{11}$ is selected from H, methyl, ethyl, isopropyl, cyclopropyl, cyclobutyl, cyclopentyl, fluoromethyl, and cyanomethyl.

In some embodiments of Formula (IIab), $R_2$ is selected from H, $OCF_3$, $CF_3$ and Cl. In some embodiments of Formula (IIab), $R_2$ is Cl.

In some embodiments of Formula (IIab), $R_8$ is selected from H, methyl, n-propyl, 3,3,3-trifluoropropyl, 3-fluoropropyl, 2-methoxyethyl, and 3-hydroxypropyl. In some embodiments of Formula (IIab), $R_8$ is selected from n-propyl, 3,3,3-trifluoropropyl, 3-fluoropropyl, and 3-hydroxypropyl.

In some embodiments of Formula (IIab), $R_2$ is selected from $OCF_3$, $CF_3$ and Cl; $R_8$ is selected from 3-fluoropropyl and 3-hydroxypropyl; and $R_1$ is selected from methyl, cyclopropyl and fluoromethyl. In some embodiments of Formula (IIab), $R_2$ is Cl; $R_8$ is selected from 3-fluoropropyl and 3-hydroxypropyl; and $R_{11}$ is selected from cyclopropyl and methyl. In some embodiments of Formula (IIab), $R_2$ is Cl; $R_8$ is 3-fluoropropyl; and $R_{11}$ is methyl. In some embodiments of Formula (IIab), $R_2$ is Cl; $R_8$ is 3-hydroxypropyl; and $R_{11}$ is methyl. In some embodiments of Formula (IIab), $R_2$ is Cl; $R_8$ is 3-fluoropropyl; and $R_{11}$ is cyclopropyl. In some embodiments of Formula (IIab), $R_2$ is Cl; $R_8$ is 3-hydroxypropyl; and $R_{11}$ is cyclopropyl.

In some embodiments of Formula (II-1):
- $R_1$ is selected from H and halo;
- $R_2$ is selected from H, $OR^{a1}$, $C_{1-4}$ haloalkyl and halo;
- $R_3$ is selected from H and $C_{1-4}$ haloalkyl;
- $R_4$ is selected from halo, $S(C_{1-4}$ alkyl), $C_{1-6}$ alkoxy, and $C_{1-6}$ alkyl;
- $R_5$ is selected from H and halo;
- $R_6$ and $R_{7A}$ together with the carbon atoms to which they are attached and the X atom connecting the two carbon atoms form a ring of any one of the following formulae:

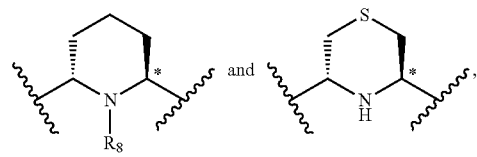

wherein the * indicates a point of attachment to the ring containing the W atom and substituted with $R_5$;
- $R_8$ is selected from H, $C_{1-6}$ alkyl, and $C_{1-4}$ haloalkyl, wherein the $C_{1-6}$ alkyl is optionally substituted with $OR^{a3}$;
- $R_9$ is selected from H, methyl, ethyl, n-propyl and i-propyl;
- $R_{10}$ is H;
- $R_A$ is H;
- L is $C_{1-6}$ alkyl;
- $R_{11}$ is selected from selected from $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from OH, $C_{1-6}$ alkoxy, $S(O)_2C_{1-6}$ alkyl, and $S(C_{1-6}$ alkyl);
- $R_{12}$ is H;
- $R_{13}$ is H;
- $R_{14}$ is H;
- $R_B$ is H; or
- $R_{11}$ and $R_B$ together with the carbon atom to which $R_{11}$ is attached and the nitrogen atom to which $R_B$ is attached form a ring of formula:

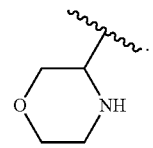

In some embodiments of Formula (II-1):
- $R_1$ is selected from H and fluoro;
- $R_2$ is selected from H, $OCF_3$, $CF_3$ and Cl;
- $R_3$ is selected from H and trifluoromethyl;
- $R_4$ is selected from fluoro, chloro, methylthio, methoxy, and methyl;
- $R_5$ is selected from H and fluoro;
- $R_6$ and $R_{7A}$ together with the carbon atoms to which they are attached and the X atom connecting the two carbon atoms form a ring of any one of the following formulae:

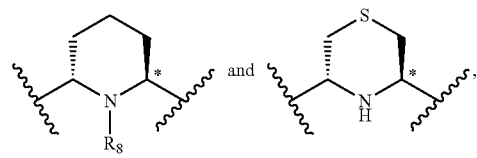

wherein the * indicates a point of attachment to the ring containing the W atom and substituted with $R_5$;
- $R_8$ is selected from H, methyl, 3-fluoropropyl, 2-methoxyethyl, and 3-hydroxypropyl;

$R_9$ is selected from H and methyl;
$R_{10}$ is H;
$R_A$ is H;
L is methyl;
$R_{11}$ is selected from methyl, ethenyl, $CH_2S(O)_2CH_3$, methylthiomethyl, fluoromethyl, methoxymethyl, hydroxymethyl, and cyclopropyl;
$R_{12}$ is H;
$R_{13}$ is H;
$R_{14}$ is H;
$R_B$ is H; or
$R_{11}$ and $R_B$ together with the carbon atom to which $R_{11}$ is attached and the nitrogen atom to which $R_B$ is attached form a ring of formula:

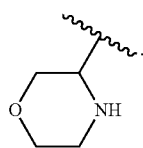 [SMILES: *C1COCCN1]

In some embodiments of Formula (II-1):
$R_1$ is selected from H and halo;
$R_2$ is selected from H, halo, $C_{1-4}$ haloalkyl, and $C_{1-4}$ haloalkoxy;
$R_3$ is selected from H and $C_{1-4}$ haloalkyl;
$R_4$ is selected from halo, $S(C_{1-4}$ alkyl), $C_{1-4}$ alkoxy, and $C_{1-6}$ alkyl;
$R_5$ is selected from H and halo;
$R_6$ and $R_{7A}$ together with the carbon atoms to which they are attached and the X atom connecting the two carbon atoms form a ring of formula:

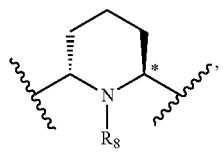

wherein the * indicates a point of attachment to the ring containing the W atom and substituted with $R_5$;
$R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy;
$R_9$ is selected from H, methyl, ethyl, n-propyl and i-propyl;
$R_{10}$ is H;
$R_A$ is H;
L is $C_{1-6}$ alkyl;
$R_{11}$ is selected from $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from OH, $C_{1-6}$ alkoxy, $S(O)_2C_{1-6}$ alkyl, and $S(C_{1-6}$ alkyl)
$R_{12}$ is H;
$R_{13}$ is H;
$R_{14}$ is H; and
$R_B$ is H; or
$R_{11}$ and $R_B$ together with the carbon atom to which $R_{11}$ is attached and the nitrogen atom to which $R_B$ is attached form a ring of formula:

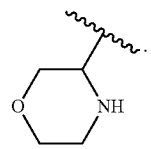

In some embodiments of Formula (II-1):
$R_1$ is selected from H and fluoro;
$R_2$ is selected from H, $OCF_3$, $CF_3$ and Cl;
$R_3$ is selected from H and trifluoromethyl;
$R_4$ is selected from fluoro, chloro, methylthio, methoxy, and methyl;
$R_5$ is selected from H and fluoro;
$R_6$ and $R_{7A}$ together with the carbon atoms to which they are attached and the X atom connecting the two carbon atoms form a ring of formula:

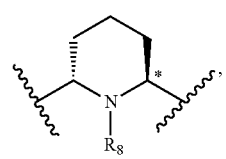

wherein the * indicates a point of attachment to the ring containing the W atom and substituted with $R_5$;
$R_8$ is selected from H, methyl, 3-fluoropropyl, 2-methoxyethyl, and 3-hydroxypropyl;
$R_9$ is selected from H and methyl;
$R_{10}$ is H;
$R_A$ is H;
L is methyl;
$R_{11}$ is selected from methyl, ethenyl, $CH_2S(O)_2CH_3$, methylthiomethyl, fluoromethyl, methoxymethyl, hydroxymethyl, and cyclopropyl;
$R_{12}$ is H;
$R_{13}$ is H;
$R_{14}$ is H; and
$R_B$ is H; or
$R_{11}$, and $R_B$ together with the carbon atom to which $R_1$ is attached and the nitrogen atom to which $R_B$ is attached form a ring of formula:

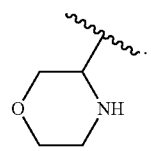

In some embodiments of Formula (II-1):
$R_1$ is selected from H and halo;
$R_2$ is selected from H, halo, $C_{1-4}$ haloalkyl, and $C_{1-4}$ haloalkoxy;
$R_3$ is selected from H and $C_{1-4}$ haloalkyl;
$R_4$ is selected from H, halo, $S(C_{1-4}$ alkyl), $C_{1-4}$ alkoxy, and $C_{1-6}$ alkyl;
$R_5$ is selected from H and halo;
$R_6$ and $R_{7A}$ together with the carbon atoms to which they are attached and the X atom connecting the two carbon atoms form a ring of formula:

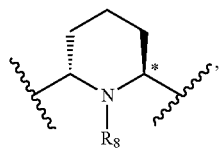

wherein the * indicates a point of attachment to the ring containing the W atom and substituted with $R_5$;
$R_8$ is selected from H, $C_{1-6}$ alkyl, $C_{1-4}$ haloalkyl, $C_{1-4}$ hydroxyalkyl, $C_{1-6}$ alkyl substituted with $C_{1-6}$ alkoxy;
$R_9$ is selected from H, methyl, ethyl, n-propyl and i-propyl;
$R_{10}$ is H;
$R_A$ is H;
L is $C_{1-6}$ alkyl;
$R_{11}$ is selected from $C_{1-6}$ alkyl, $C_{3-5}$ cycloalkyl, $C_{1-4}$ haloalkyl, and $C_{2-6}$ alkenyl, wherein the $C_{1-6}$ alkyl is optionally substituted with a substituent selected from OH, $C_{1-6}$ alkoxy, $S(O)_2C_{1-6}$ alkyl, and $S(C_{1-6}$ alkyl)
$R_{12}$ is H;
$R_{13}$ is H;
$R_{14}$ is H; and
$R_B$ is H; or
$R_{11}$ and $R_B$ together with the carbon atom to which $R_{11}$ is attached and the nitrogen atom to which $R_B$ is attached form a ring of formula:

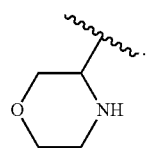 [SMILES: *C1COCCN1]

In some embodiments of Formula (II-1):
$R_1$ is selected from H and fluoro;
$R_2$ is selected from H, $OCF_3$, $CF_3$ and Cl;
$R_3$ is selected from H and trifluoromethyl;
$R_4$ is selected from H, fluoro, chloro, methylthio, methoxy, and methyl;
$R_5$ is selected from H and fluoro;

$R_6$ and $R_{7A}$ together with the carbon atoms to which they are attached and the X atom connecting the two carbon atoms form a ring of formula:

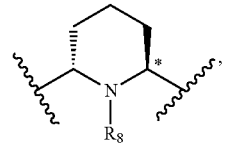

wherein the * indicates a point of attachment to the ring containing the W atom and substituted with $R_5$;
$R_8$ is selected from H, methyl, 3-fluoropropyl, 2-methoxyethyl, and 3-hydroxypropyl;
$R_9$ is selected from H and methyl;
$R_{10}$ is H;
$R_A$ is H;
L is methyl;
$R_{11}$ is selected from methyl, ethenyl, $CH_2S(O)_2CH_3$, methylthiomethyl, fluoromethyl, methoxymethyl, hydroxymethyl, and cyclopropyl;
$R_{12}$ is selected from H;
$R_{13}$ is H;
$R_{14}$ is H; and
$R_B$ is H; or
$R_{11}$ and $R_B$ together with the carbon atom to which $R_{11}$ is attached and the Nitrogen atom to which $R_B$ is attached form a ring of formula:

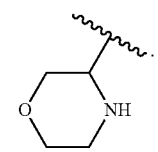

In some embodiments of the method, the compounds of Formula (II) or Formula (II-1) are compounds of Formula (IIa):

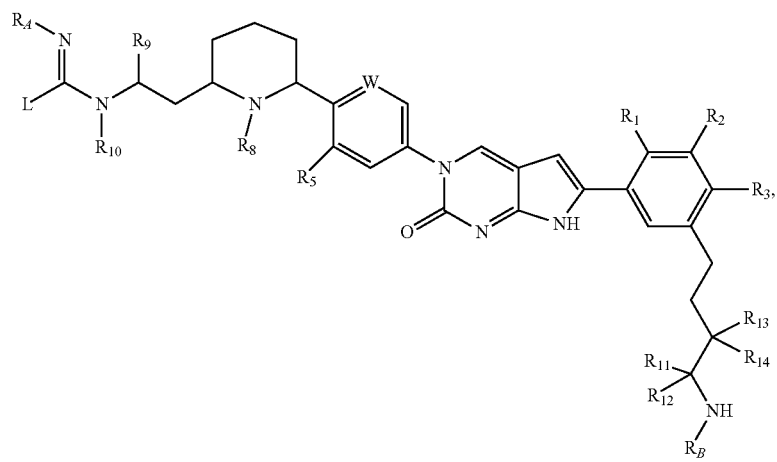

(IIa)

or a tautomer thereof or a pharmaceutically acceptable salt of the compound or tautomer, wherein $R_1$, $R_2$, $R_3$, $R_4$, $R_5$, $R_8$, $R_9$, $R_{10}$, $R_{11}$, $R_{12}$, $R_{13}$, $R_{14}$, $R_A$, $R_B$, L and W are as described herein for the compounds of Formula (II).

In some embodiments of the method, the compounds of Formula (II) or Formula (II-1) are compounds of Formula (IIa-1):

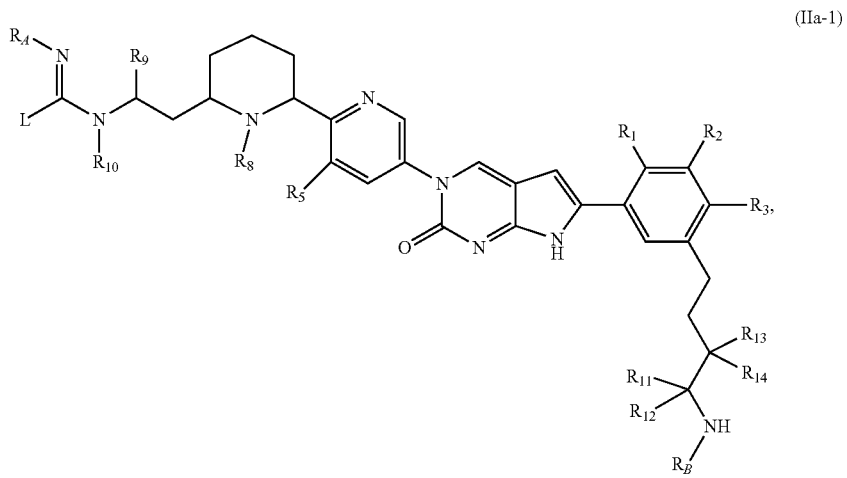

(IIa-1)

or a tautomer thereof or a pharmaceutically acceptable salt of the compound or tautomer, wherein $R_1$, $R_2$, $R_3$, $R_5$, $R_8$, $R_9$, $R_{10}$, $R_{11}$, $R_{12}$, $R_{13}$, $R_{14}$, $R_A$, $R_B$, and L are as described herein for the compounds of Formula (II).

In some embodiments of the method, the compounds of Formula (II) or Formula (II-1) are compounds of Formula (IIa-2):

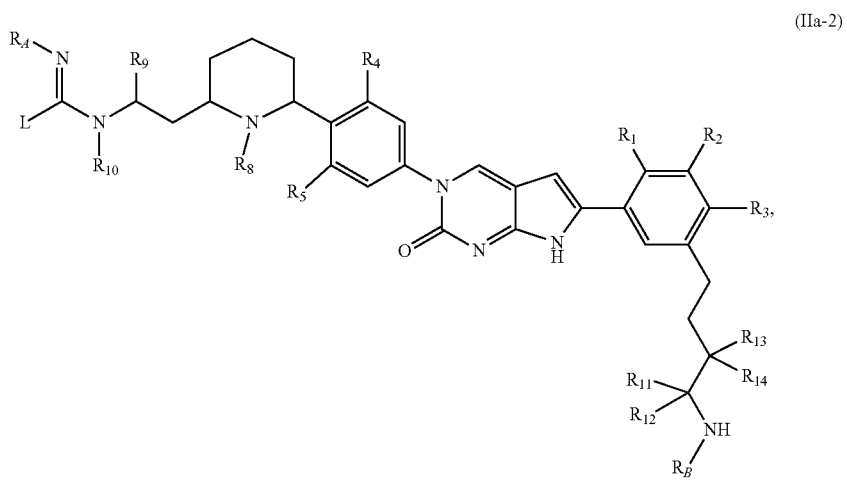

(IIa-2)

or a tautomer thereof or a pharmaceutically acceptable salt of the compound or tautomer, wherein $R_1$, $R_2$, $R_3$, $R_4$, $R_5$, $R_8$, $R_9$, $R_{10}$, $R_{11}$, $R_{12}$, $R_{13}$, $R_{14}$, $R_A$, $R_B$, and L are as described herein for the compounds of Formula (II).

In some embodiments of the method, the compounds of Formula (II) or Formula (II-1) are compounds of Formula (IIb-a):

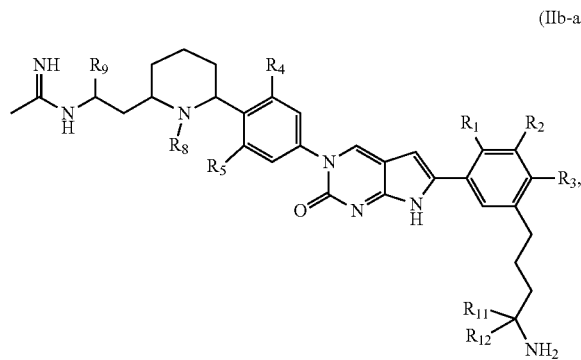

(IIb-a)

or a tautomer thereof or a pharmaceutically acceptable salt of the compound or tautomer, wherein $R_1$, $R_2$, $R_3$, $R_4$, $R_5$, $R_8$, $R_9$, $R_{11}$, and $R_{12}$ are as described herein for the compounds of Formula (II).

In some embodiments of the method, the compounds of Formula (II) or Formula (II-1) are compounds of Formula (IIb):

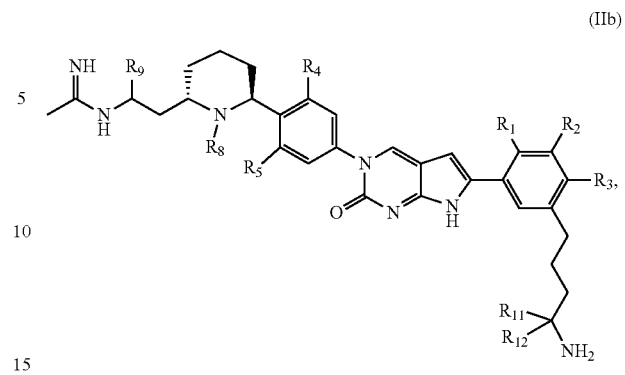

(IIb)

or a tautomer thereof or a pharmaceutically acceptable salt of the compound or tautomer, wherein $R_1$, $R_2$, $R_3$, $R_4$, $R_5$, $R_8$, $R_9$, $R_{11}$, and $R_{12}$ are as described herein for the compounds of Formula (II).

In some embodiments of the method, the compound of Formula (II) or Formula (II-1) has Formula (IIa-3):

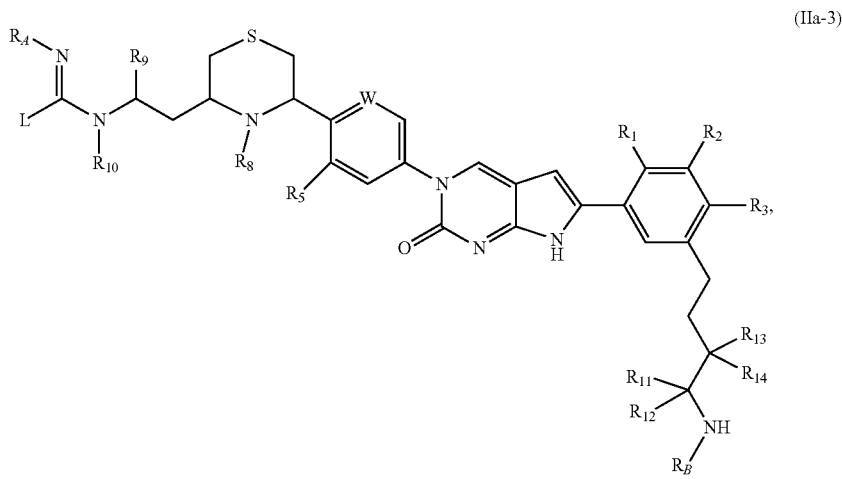

(IIa-3)

or a tautomer thereof or a pharmaceutically acceptable salt of the compound or tautomer, wherein $R_1$, $R_2$, $R_3$, $R_5$, $R_8$, $R_9$, $R_{10}$, $R_{11}$, $R_{12}$, $R_{13}$, $R_{14}$, $R_A$, $R_B$, L and W are as described herein for the compounds of Formula (II).

In some embodiments of the method, the compounds of Formula (II) or Formula (II-1) are compounds of Formula (IIc):

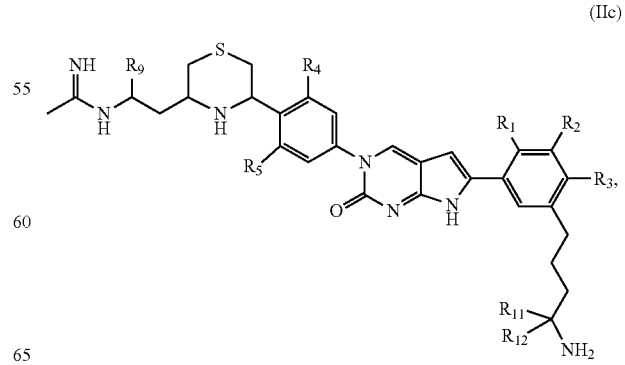

(IIc)

or a tautomer thereof or a pharmaceutically acceptable salt of the compound or tautomer, wherein $R_1$, $R_2$, $R_3$, $R_4$, $R_5$, $R_9$, $R_{11}$, and $R_{12}$ are as described herein for the compounds of Formula (II).

In some embodiments of the method, the compounds of Formula (II) or Formula (II-1) are compounds of Formula (IIc-1):

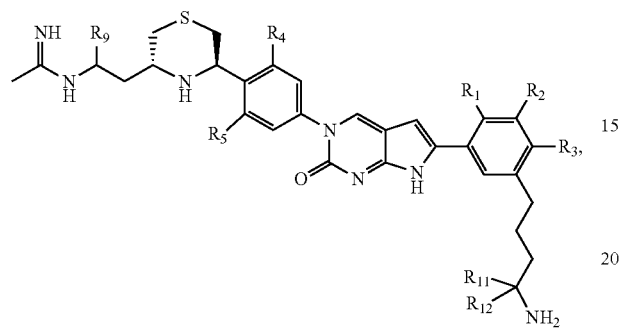

(IIc-1)

or a tautomer thereof or a pharmaceutically acceptable salt of the compound or tautomer, wherein $R_1$, $R_2$, $R_3$, $R_4$, $R_5$, $R_9$, $R_{11}$, and $R_{12}$ are as described herein for the compounds of Formula (II).

In some embodiments of the method, the compounds of Formula (II) or Formula (II-1) are compounds of any one of Formulae (IId)-(IIg):

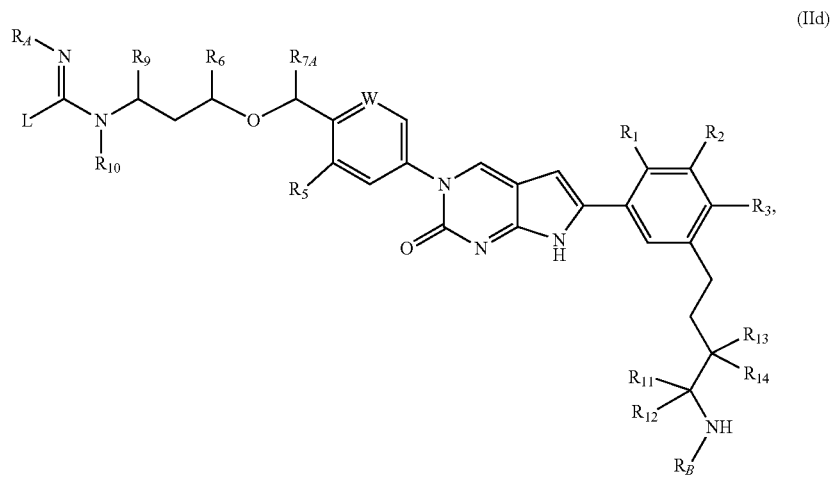

(IId)

or a tautomer thereof or a pharmaceutically acceptable salt of the compound or tautomer;
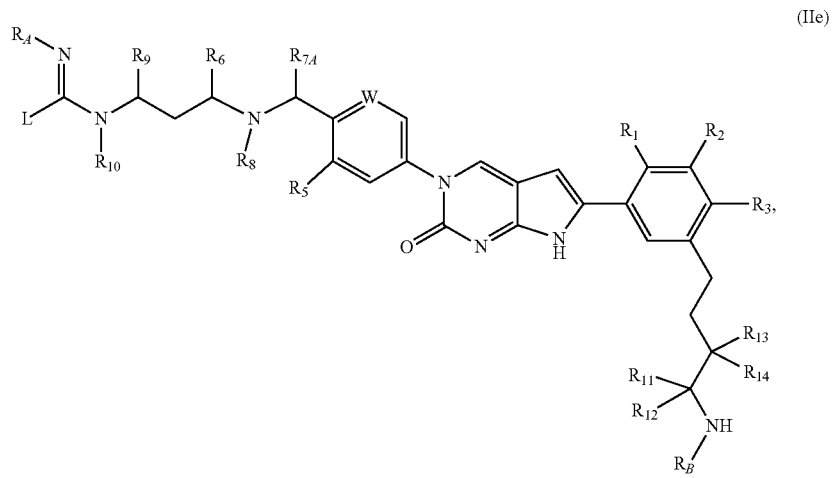
(IIe)
or a tautomer thereof or a pharmaceutically acceptable salt of the compound or tautomer;
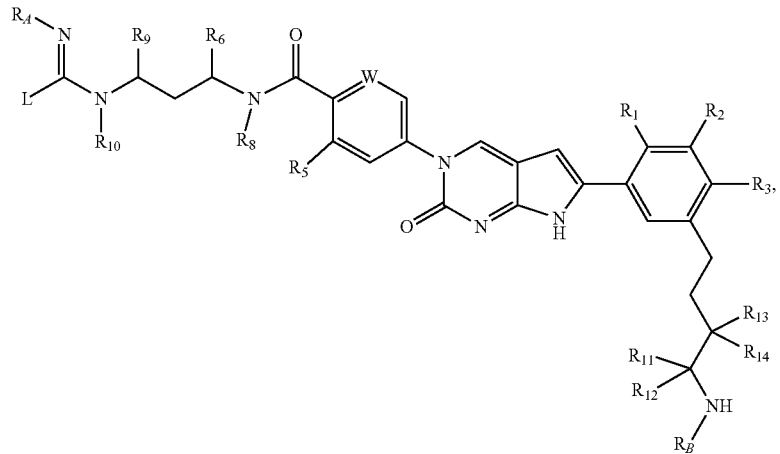
(IIf)

or a tautomer thereof or a pharmaceutically acceptable salt of the compound or tautomer; and (IIg)

[Structural formula IIg]

or a tautomer thereof or a pharmaceutically acceptable salt of the compound or tautomer, wherein $R_1$, $R_2$, $R_3$, $R_4$, $R_5$, $R_8$, $R_9$, $R_{10}$, $R_{11}$, $R_{12}$, $R_{13}$, $R_{14}$, $R_A$, $R_B$, L and W are as described herein for the compounds of Formula (II).

In some embodiments of the method, the compounds of Formula (II) or Formula (II-1) are compounds of Formula (IIe-1):

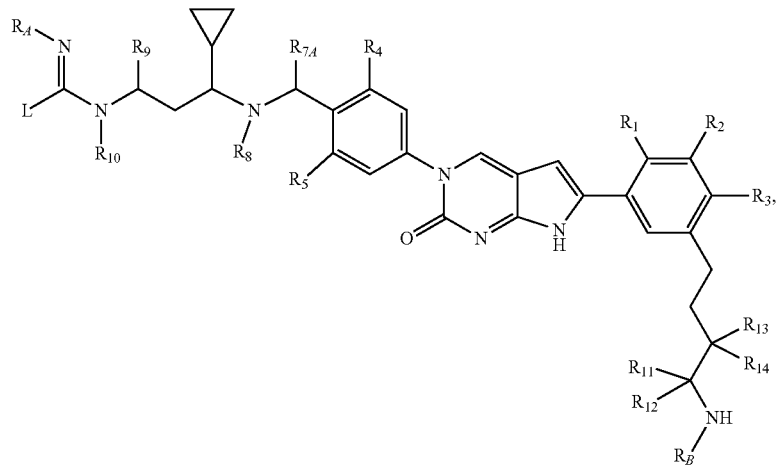

or a tautomer thereof or a pharmaceutically acceptable salt of the compound or tautomer, wherein $R_1$, $R_2$, $R_3$, $R_4$, $R_5$, $R_{7A}$, $R_8$, $R_9$, $R_{10}$, $R_{11}$, $R_{12}$, $R_{13}$, $R_{14}$, $R_A$, $R_B$, L and W are as described herein for the compounds of Formula (II).

In some embodiments of the method, the compounds of Formula (II) or Formula (II-1) are compounds of any one of Formulae (IIh)-(IIk):

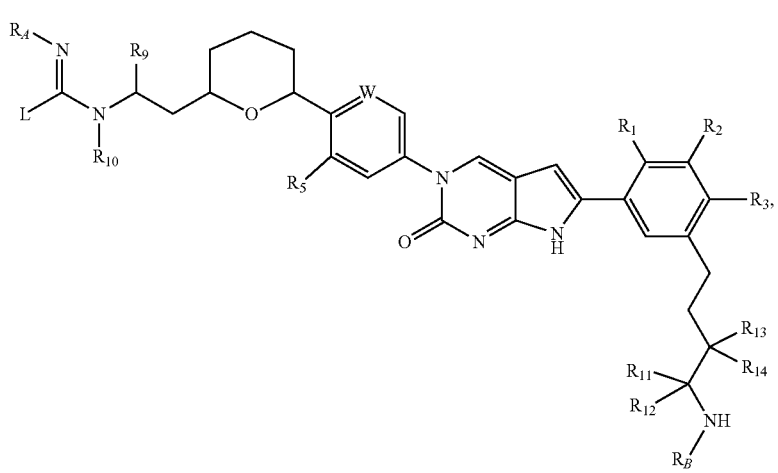

(IIh)

or a tautomer thereof or a pharmaceutically acceptable salt of the compound or tautomer;

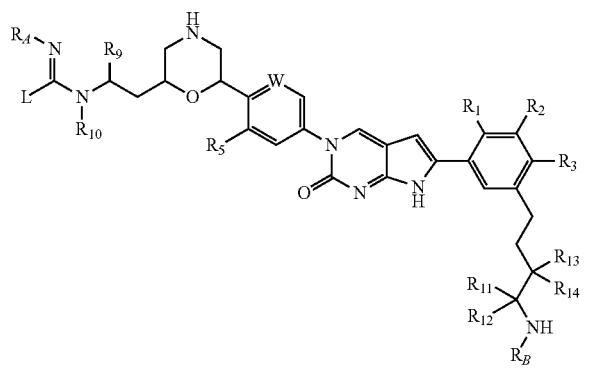

(IIi)

or a tautomer thereof or a pharmaceutically acceptable salt of the compound or tautomer;

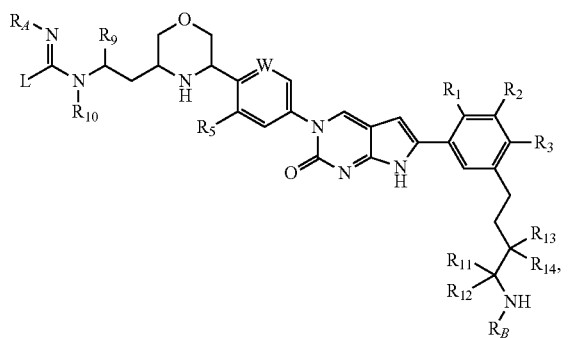

(IIj)

or a tautomer thereof or a pharmaceutically acceptable salt of the compound or tautomer; and

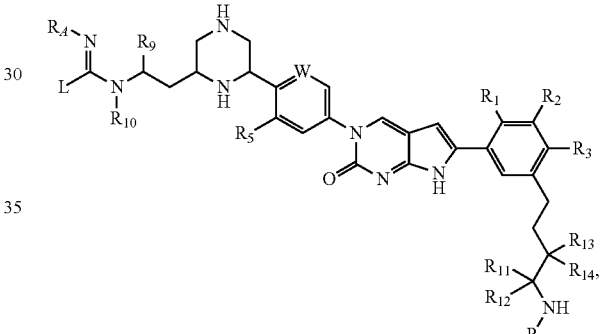

(IIk)

or a tautomer thereof or a pharmaceutically acceptable salt of the compound or tautomer, wherein $R_1$, $R_2$, $R_3$, $R_4$, $R_5$, $R_8$, $R_9$, $R_{10}$, $R_{11}$, $R_{12}$, $R_{13}$, $R_{14}$, $R_A$, $R_B$, L and W are as described herein for the compounds of Formula (II).

In some embodiments of any one of Formulae (II), (IIa), (IIa-1), (IIa-2), (IIb-a), (IIb), (IIa-3), (IIc), (IIc-1), (IId), (IIe), (IIf), (IIg), (IIe-1), (IIh), (IIi), (IIj), and (IIk) disclosed herein, the fragment:

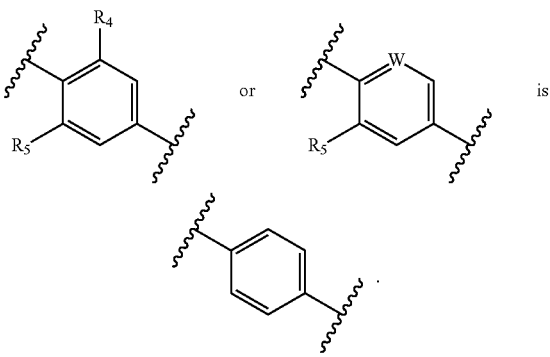

is

In some embodiments of any one of Formulae (II), (IIa), (IIa-1), (IIa-2), (IIb-a), (IIb), (IIa-3), (IIc), (IIc-1), (IId), (IIe), (IIf), (IIg), (IIe-1), (IIh), (IIi), (IIj), and (IIk) disclosed herein, the fragment

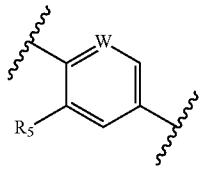

is

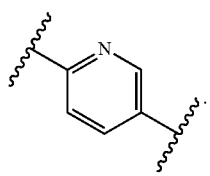 [SMILES: *c1ccc(*)nc1]

In some embodiments of any one of Formulae (II), (IIa), (IIa-1), (IIa-2), (IIb-a), (IIb), (IIa-3), (IIc), (IIc-1), (IId), (IIe), (IIf), (IIg), (IIe-1), (IIh), (IIi), (IIj), and (IIk) disclosed herein, the fragment:

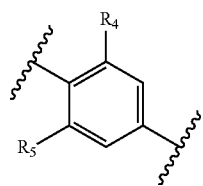 or 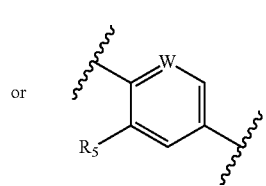

is selected from any one the following fragments:

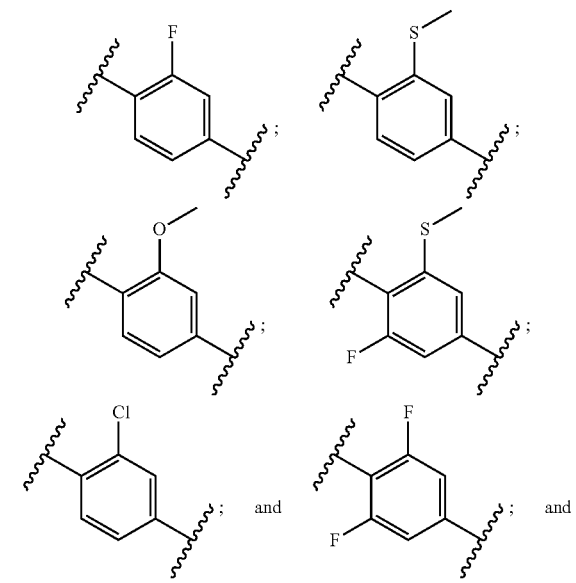

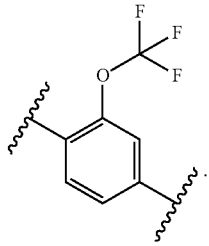

In some embodiments of any one of Formulae (II), (IIa), (IIa-1), (IIa-2), (IIb-a), (IIb), (IIa-3), (IIc), (IIc-1), (IId), (IIe), (IIf), (IIg), (IIe-1), (IIh), (IIi), (IIj), and (IIk) described herein, the fragment:

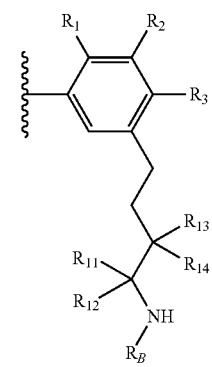 or 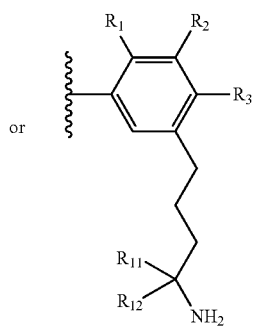

is selected from any one the following fragments:

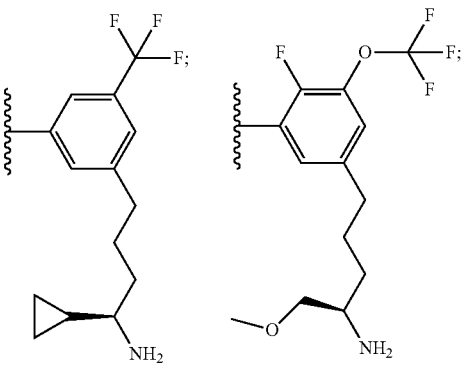

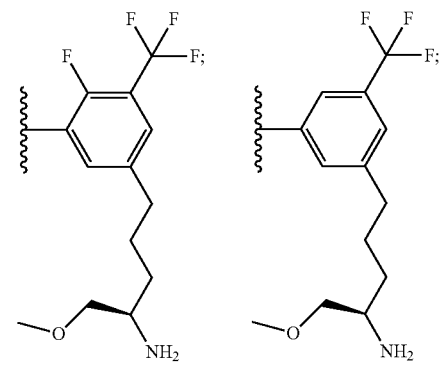

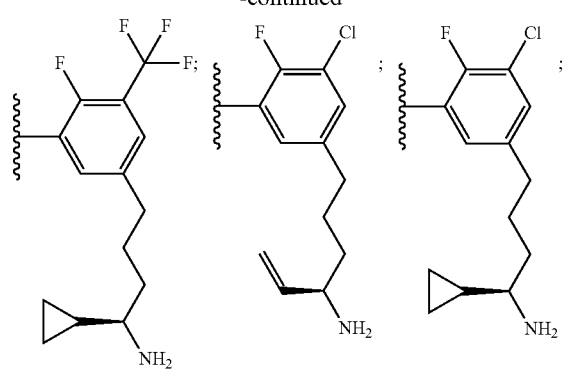
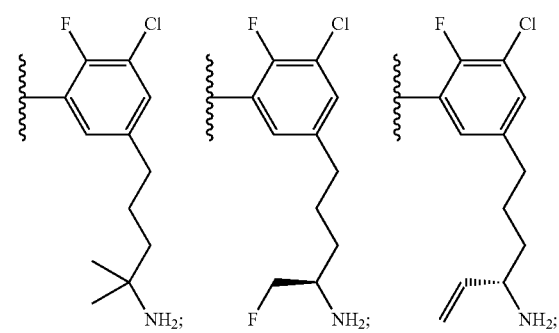
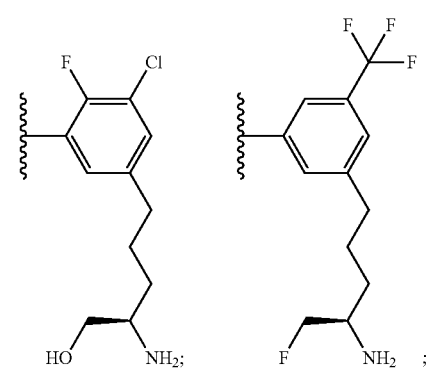
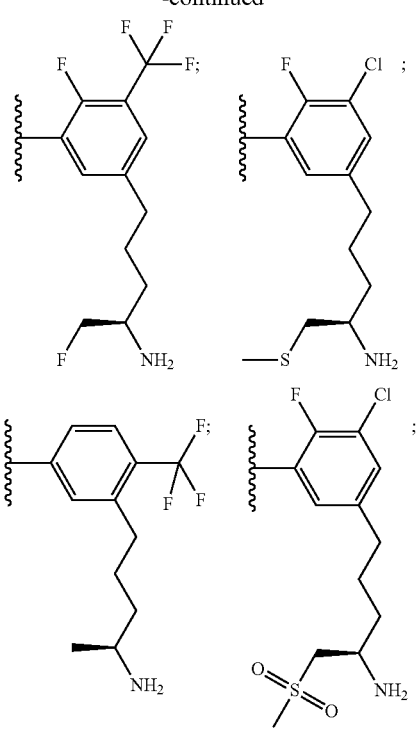
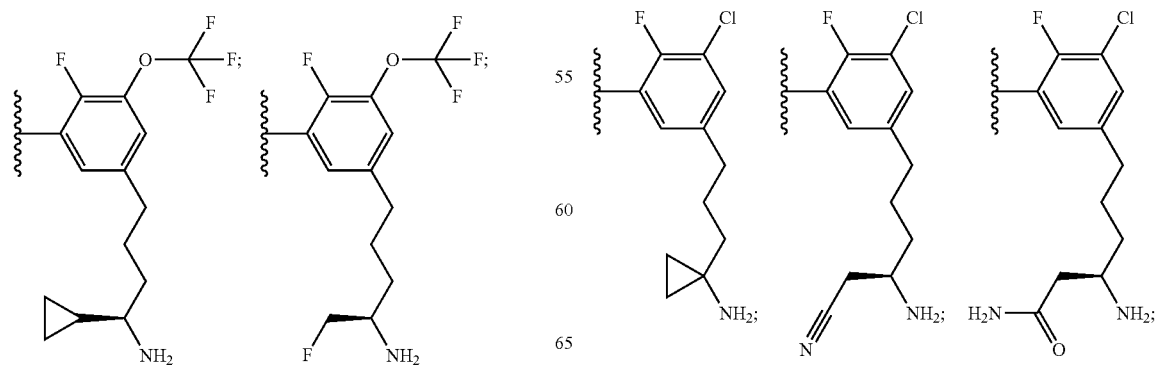

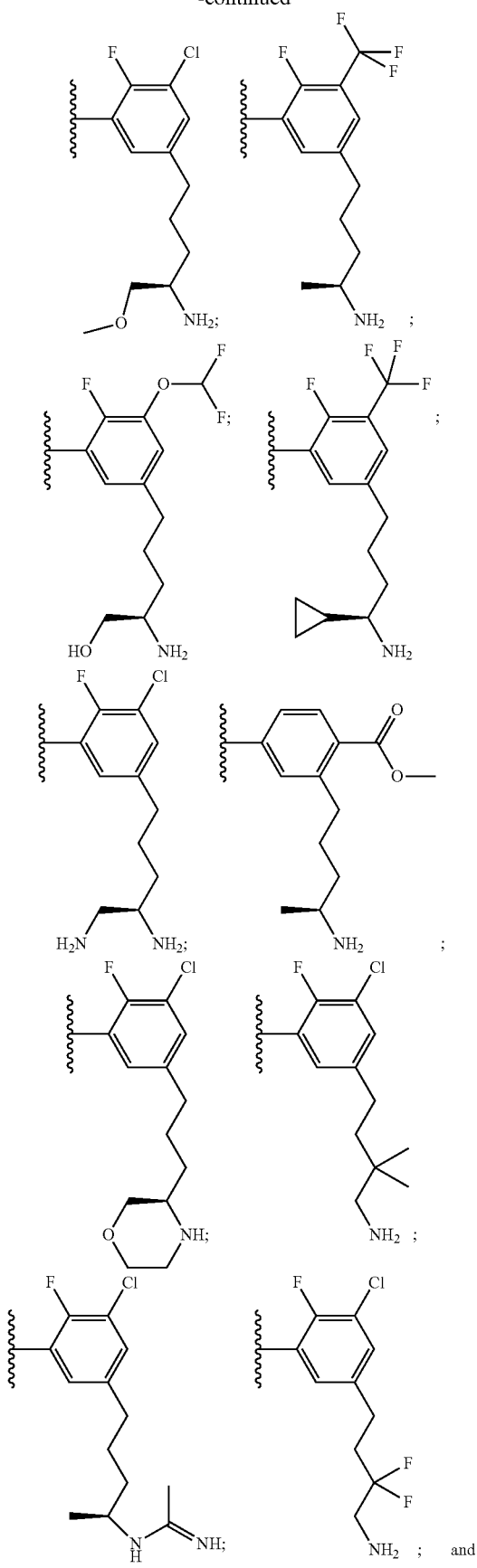
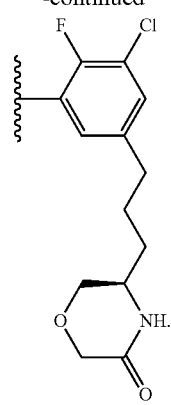
In some embodiments of any one of Formulae (II), (IIa), (IIa-1), (IIa-2), (IIb-a), (IIb), (IIa-3), (IIc), (IIc-1), (IId), (IIe), (IIf), (IIg), (IIe-1), (IIh), (IIi), (IIj), and (IIk) described herein, the fragment
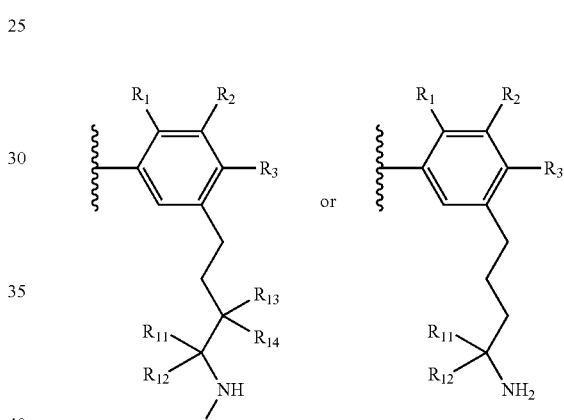
is selected from any one the following fragments:
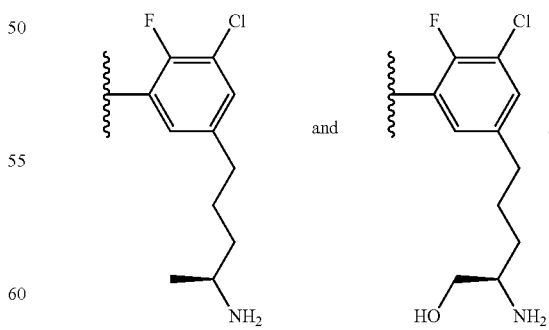
In some embodiments of any one of Formulae (II), (IIa), (IIa-1), (IIa-2), (IIb-a), (IIb), (IIa-3), (IIc), (IIc-1), (IId), (IIe), (IIf), (IIg), (IIe-1), (IIh), (IIi), (IIj), and (IIk) described herein, the fragment:

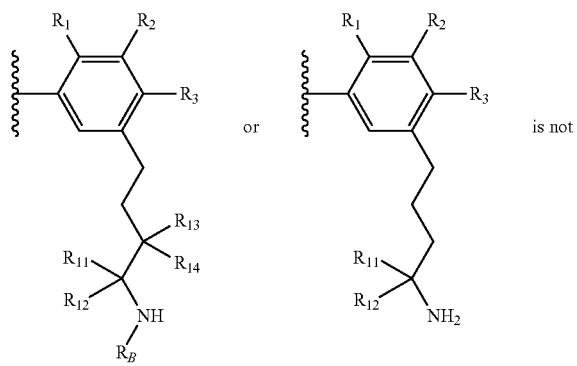 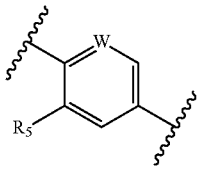

In some embodiments of any one of the Formulae (II), (IIa), (IIa-1), (IIa-2), (IIb-a), (IIb), (IIa-3), (IIc), (IIc-1), (IId), (IIe), (IIf), (IIg), (IIe-1), (IIh), (IIi), (IIj), and (IIk) disclosed herein, the fragment

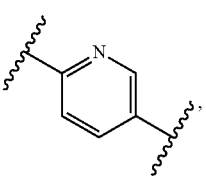

is selected from any one the following fragments:

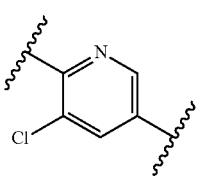

In some embodiments of any one of Formulae (II), (IIa), (IIa-1), (IIa-2), (IIb-a), (IIb), (IIa-3), (IIc), (IIc-1), (IId), (IIe), (IIf), (IIg), (IIe-1), (IIh), (IIi), (IIj), and (IIk) described herein, the fragment

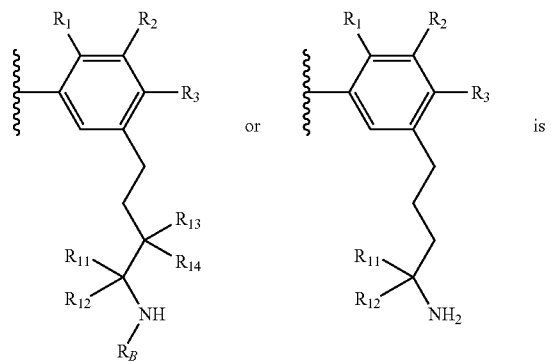

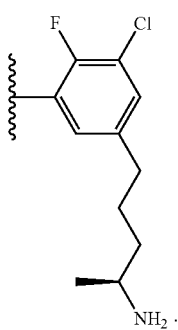

In some embodiments of the method, the compounds of Formula (II) or Formula (II-1) are not any of the compounds explicitly disclosed in PCT application No. PCT/US2010/052922 (published as WO 2011/047319), PCT application No. PCT/US2012/032994 (published as WO 2012/173689), PCT application No. PCT/US2014/054869 (published as WO 2015/035426), PCT application No. PCT/US2014/054860 (published as WO 2015/035421); or PCT application No. PCT/US2016/022216.

In some embodiments of the method, a compound of Formula (II) or Formula (II-1) is not compound 516 disclosed in Table 1 of PCT application No. PCT/US2014/054869 (published as WO 2015/035426). In some embodiments, the compounds of Formula (II) or Formula (II-1) are not compound 1, 28, 72, 81, 82, 85, 86, 97, 120, 137, 150, or 151 disclosed in Table 1 of PCT application No. PCT/US2016/022216.

In some embodiments of the disclosed methods, the compound of Formula (II) or Formula (II-1) includes any one of the compounds listed in Table 2, or a tautomer thereof or a pharmaceutically acceptable salt of the compound or tautomer.

TABLE 2

| # | Structure | ESI, m/z [M + H]+ |
|---|---|---|
| 2 | 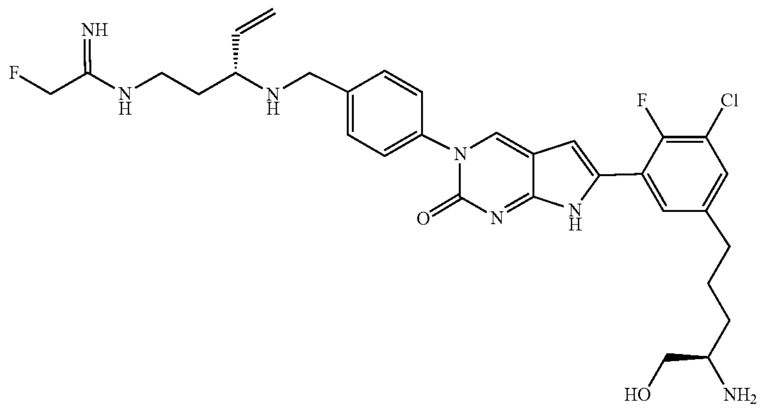 [SMILES: C=C[C@@H](CCNC(=N)CF)NCc1ccc(-n2cc3cc(-c4cc(CCC[C@@H](N)CO)cc(Cl)c4F)[nH]c3nc2=O)cc1] | 612.6 |
| 3 | 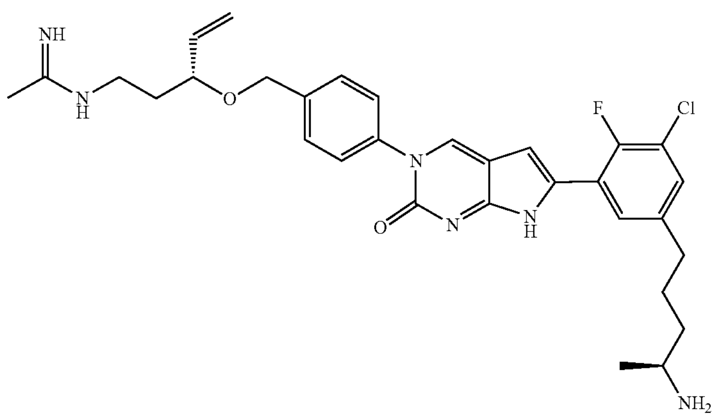 [SMILES: C=C[C@@H](CCNC(C)=N)OCc1ccc(-n2cc3cc(-c4cc(CCC[C@H](C)N)cc(Cl)c4F)[nH]c3nc2=O)cc1] | 579 |
| 4 | 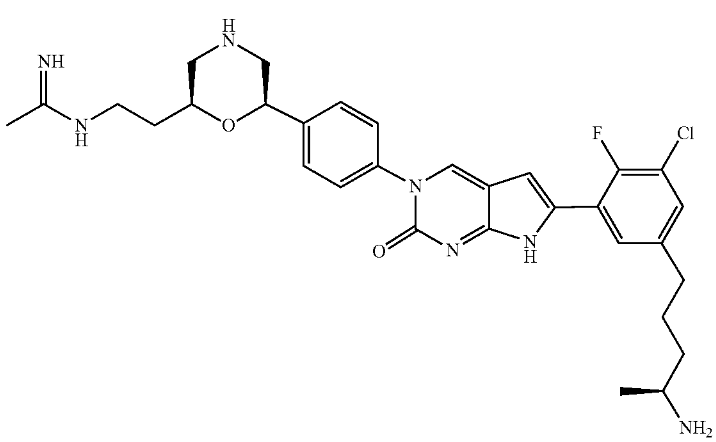 [SMILES: CC(=N)NCC[C@H]1CNC[C@@H](c2ccc(-n3cc4cc(-c5cc(CCC[C@H](C)N)cc(Cl)c5F)[nH]c4nc3=O)cc2)O1] | 594.7 |

TABLE 2-continued
| # | Structure | ESI, m/z [M + H]+ |
|---|---|---|
| 6 | 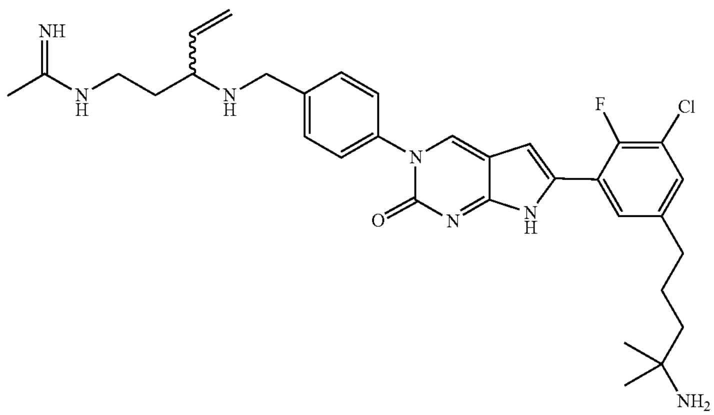 [SMILES: C=CC(CCNC(C)=N)NCc1ccc(-n2cc3cc(-c4cc(CCCC(C)(C)N)cc(Cl)c4F)[nH]c3nc2=O)cc1] | 592.7 |
| 5 | 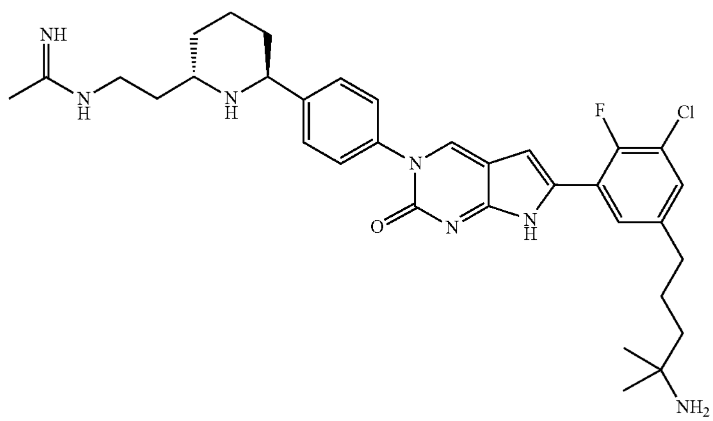 [SMILES: CC(=N)NCC[C@@H]1CCC[C@@H](c2ccc(-n3cc4cc(-c5cc(CCCC(C)(C)N)cc(Cl)c5F)[nH]c4nc3=O)cc2)N1] | 606.7 |
| 8 | 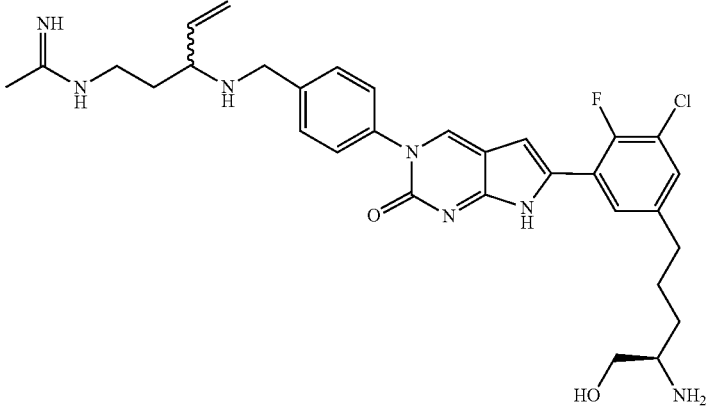 [SMILES: C=CC(CCNC(C)=N)NCc1ccc(-n2cc3cc(-c4cc(CCC[C@@H](N)CO)cc(Cl)c4F)[nH]c3nc2=O)cc1] | 594.7 |

TABLE 2-continued
| # | Structure | ESI, m/z [M + H]+ |
|---|---|---|
| 9 | 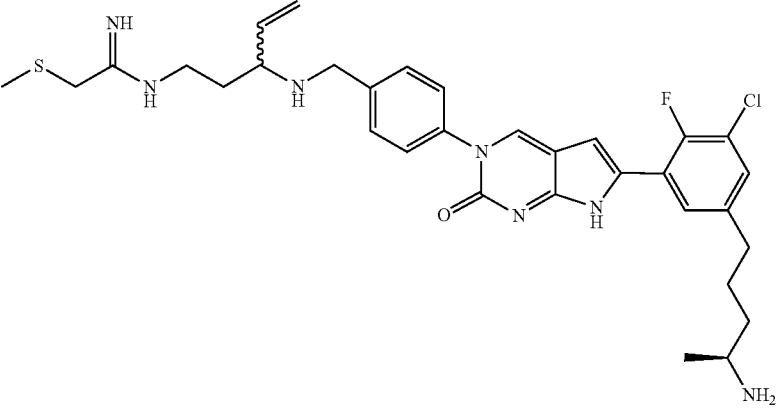 [SMILES: C=CC(CCNC(=N)CSC)NCc1ccc(-n2cc3cc(-c4cc(CCC[C@H](C)N)cc(Cl)c4F)[nH]c3nc2=O)cc1] | 624.27 |
| 10 | 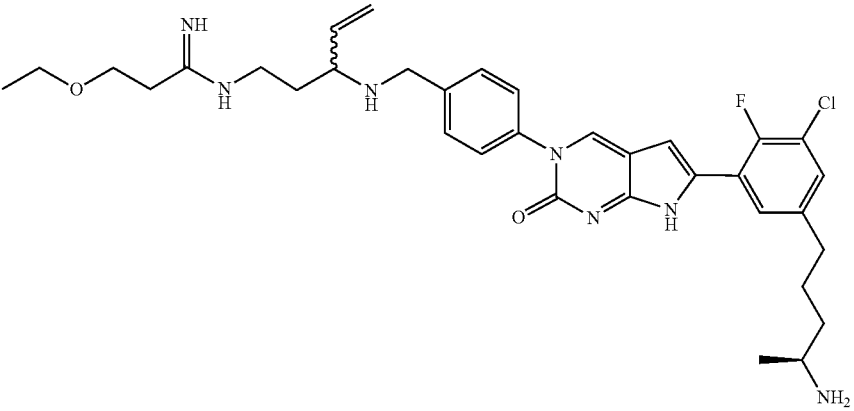 [SMILES: C=CC(CCNC(=N)CCOCC)NCc1ccc(-n2cc3cc(-c4cc(CCC[C@H](C)N)cc(Cl)c4F)[nH]c3nc2=O)cc1] | 636.32 |
| 11 | 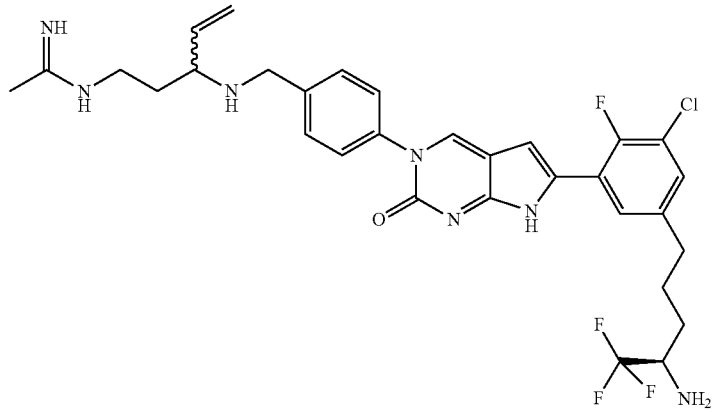 [SMILES: C=CC(CCNC(C)=N)NCc1ccc(-n2cc3cc(-c4cc(CCC[C@@H](N)C(F)(F)F)cc(Cl)c4F)[nH]c3nc2=O)cc1] | 632.6 |

TABLE 2-continued
| # | Structure | ESI, m/z [M + H]+ |
|---|---|---|
| 12 | 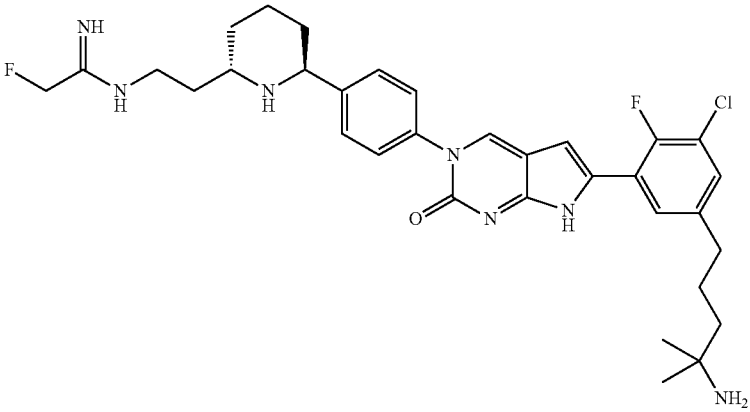 [SMILES: CC(C)(N)CCCc1cc(Cl)c(F)c(-c2cc3cn(-c4ccc([C@@H]5CCC[C@@H](CCNC(=N)CF)N5)cc4)c(=O)nc3[nH]2)c1] | 624.7 |
| 13 | 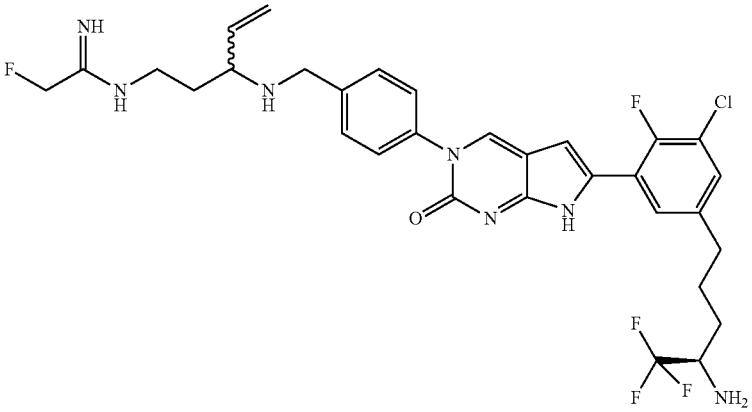 [SMILES: C=CC(CCNC(=N)CF)NCc1ccc(-n2cc3cc(-c4cc(CCC[C@@H](N)C(F)(F)F)cc(Cl)c4F)[nH]c3nc2=O)cc1] | 650.6 |
| 14 | 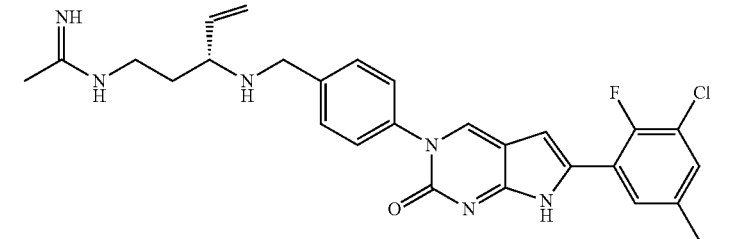 | 578 |

TABLE 2-continued

| # | Structure | ESI, m/z [M + H]+ |
|---|---|---|
| 15 | 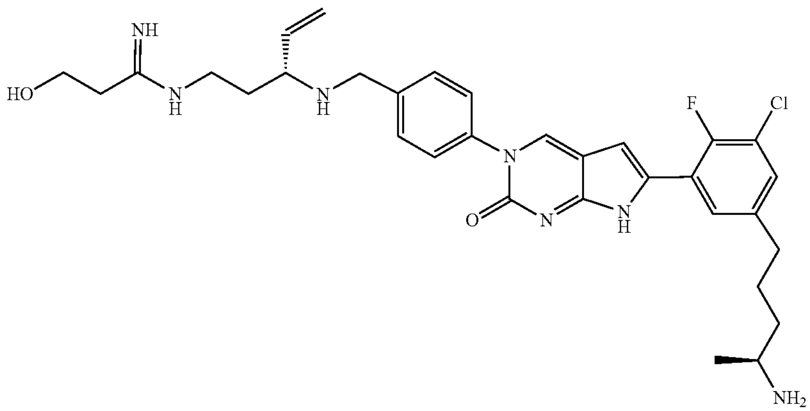 [SMILES: C=C[C@@H](CCNC(=N)CCO)NCc1ccc(-n2cc3cc(-c4cc(CCC[C@H](C)N)cc(Cl)c4F)[nH]c3nc2=O)cc1] | 608.7 |
| 16 | 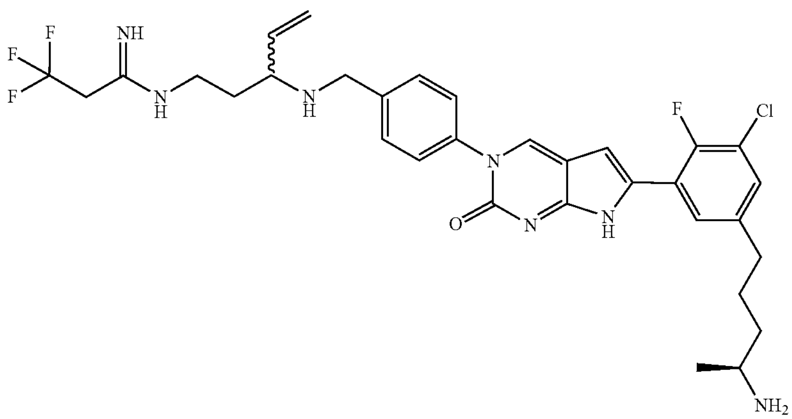 [SMILES: C=CC(CCNC(=N)CC(F)(F)F)NCc1ccc(-n2cc3cc(-c4cc(CCC[C@H](C)N)cc(Cl)c4F)[nH]c3nc2=O)cc1] | 647.13 |
| 17 | 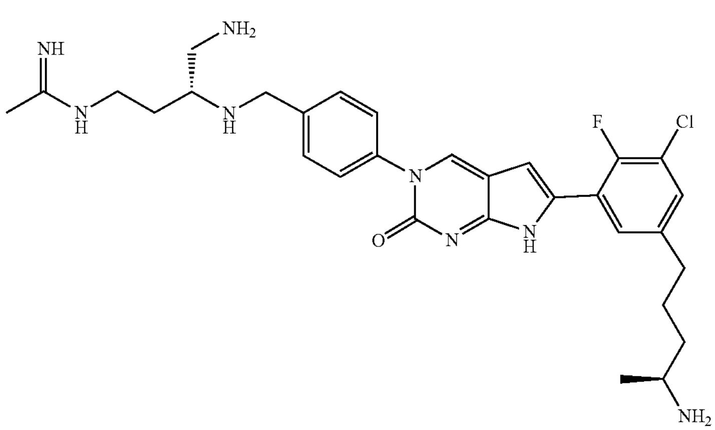 [SMILES: CC(=N)NCC[C@H](CN)NCc1ccc(-n2cc3cc(-c4cc(CCC[C@H](C)N)cc(Cl)c4F)[nH]c3nc2=O)cc1] | 581 |

TABLE 2-continued

| # | Structure | ESI, m/z [M + H]+ |
|---|---|---|
| 18 | 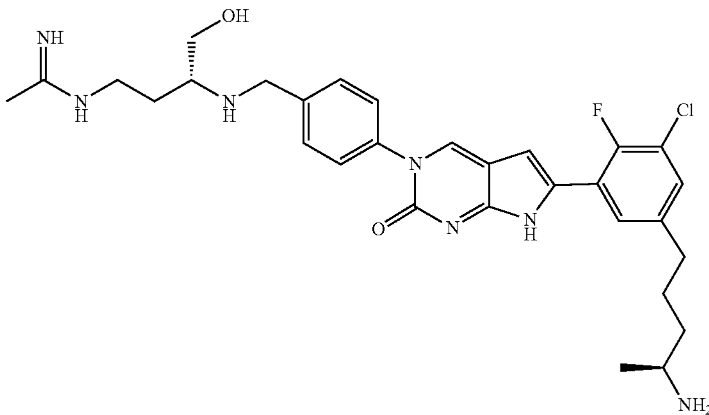 [SMILES: CC(=N)NCC[C@H](CO)NCc1ccc(-n2cc3cc(-c4cc(CCC[C@H](C)N)cc(Cl)c4F)[nH]c3nc2=O)cc1] | 582 |
| 19 | 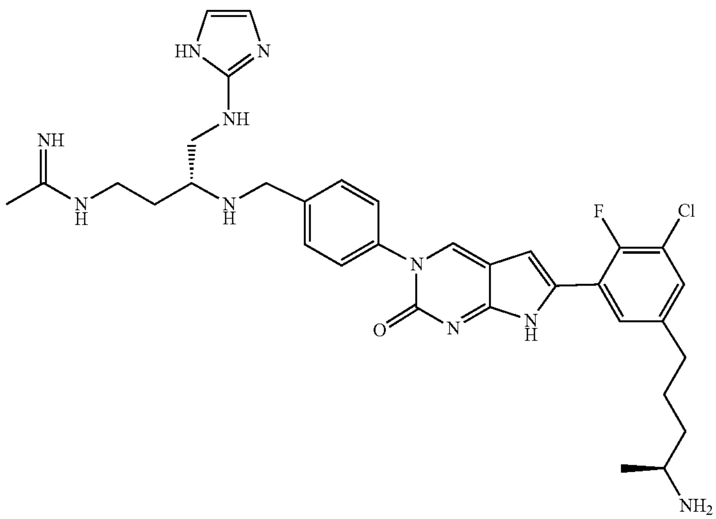 [SMILES: CC(=N)NCC[C@H](CNc1ncc[nH]1)NCc1ccc(-n2cc3cc(-c4cc(CCC[C@H](C)N)cc(Cl)c4F)[nH]c3nc2=O)cc1] | 647 |
| 20 | 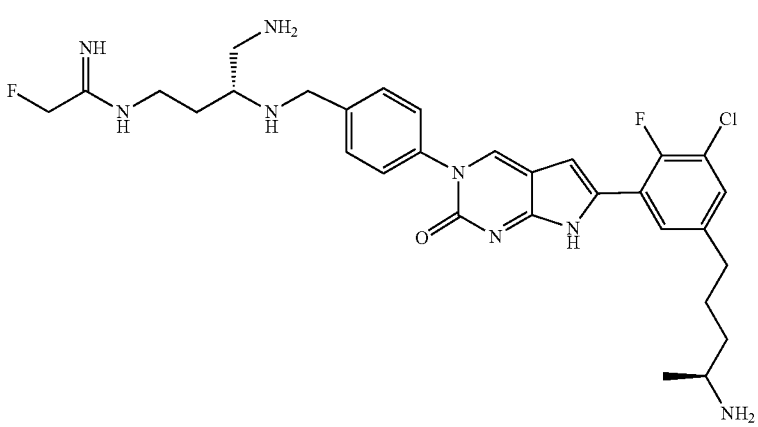 [SMILES: C[C@H](N)CCCc1cc(Cl)c(F)c(-c2cc3cn(-c4ccc(CN[C@@H](CN)CCNC(=N)CF)cc4)c(=O)nc3[nH]2)c1] | 599 |

TABLE 2-continued
| # | Structure | ESI, m/z [M + H]+ |
|---|---|---|
| 21 | 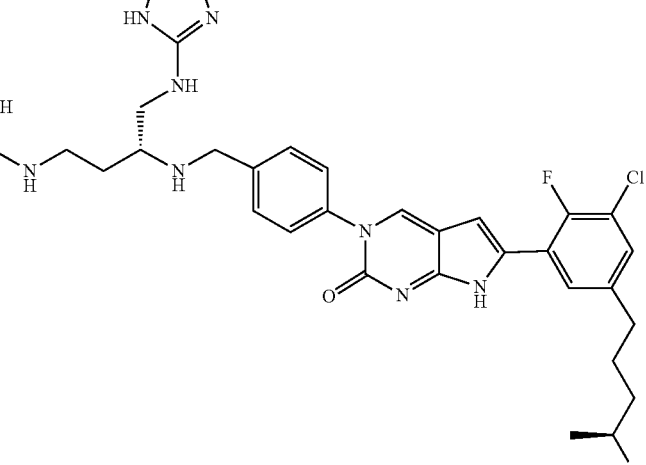 | 665 |
| 22 | 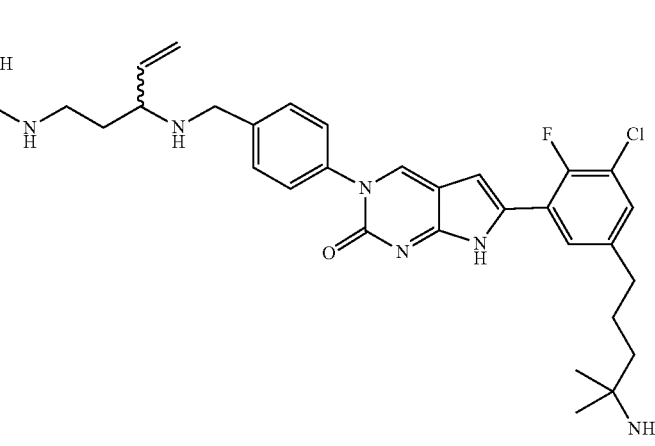 | 610.6 |
| 23 | 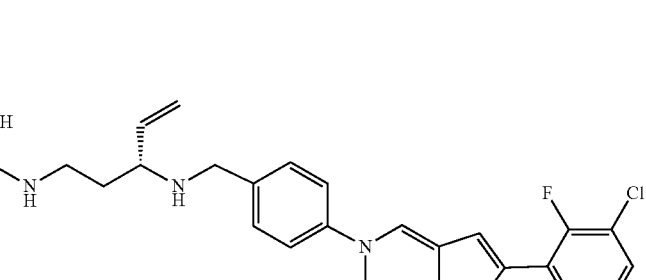 | 596 |

TABLE 2-continued
| # | Structure | ESI, m/z [M + H]+ |
|---|---|---|
| 24 | 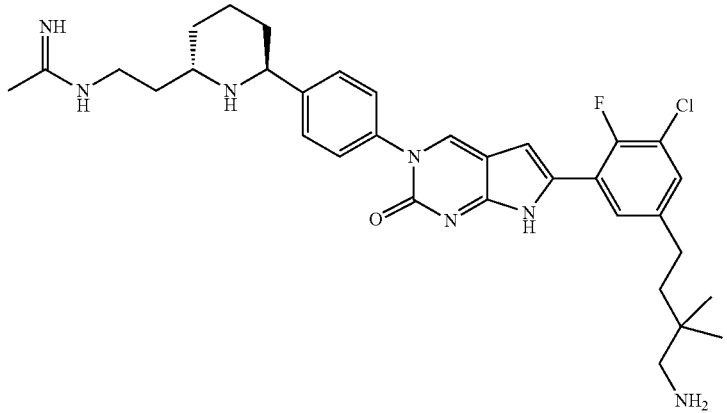 [SMILES: CC(=N)NCC[C@@H]1CCC[C@@H](c2ccc(-n3cc4cc(-c5cc(CCC(C)(C)CN)cc(Cl)c5F)[nH]c4nc3=O)cc2)N1] | 606.6 |
| 25 | 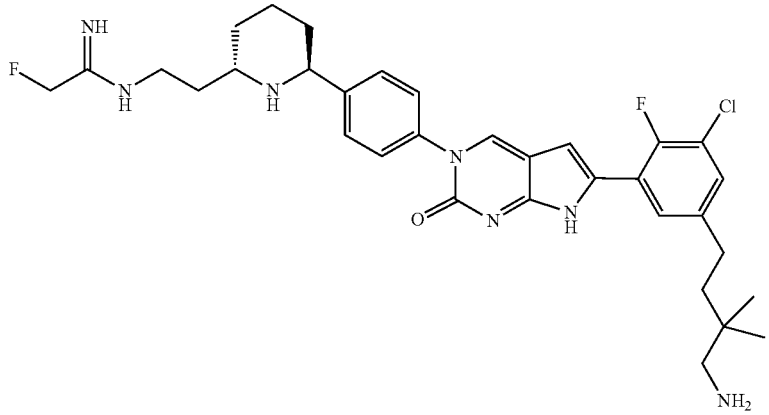 [SMILES: CC(C)(CN)CCc1cc(Cl)c(F)c(-c2cc3cn(-c4ccc([C@@H]5CCC[C@@H](CCNC(=N)CF)N5)cc4)c(=O)nc3[nH]2)c1] | 624.6 |
| 26 | 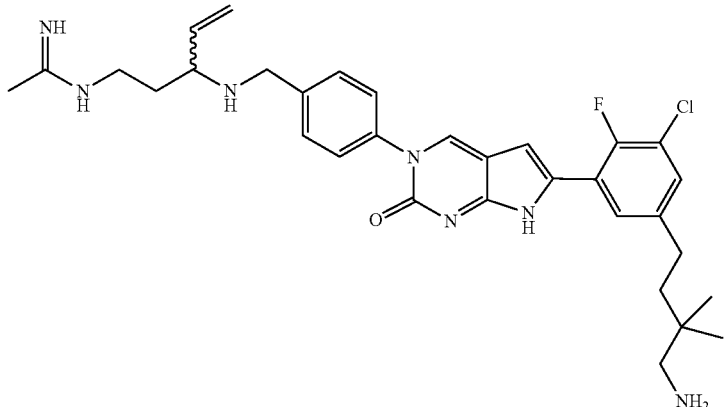 [SMILES: C=CC(CCNC(C)=N)NCc1ccc(-n2cc3cc(-c4cc(CCC(C)(C)CN)cc(Cl)c4F)[nH]c3nc2=O)cc1] | 592.6 |

TABLE 2-continued

| # | Structure | ESI, m/z [M + H]+ |
|---|---|---|
| 27 | 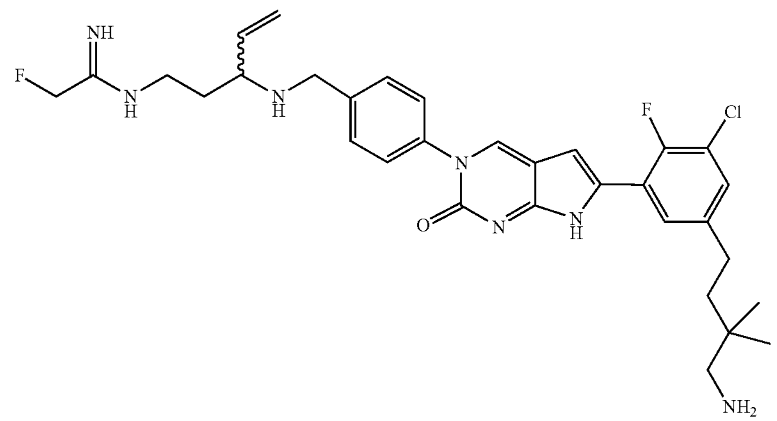 [SMILES: C=CC(CCNC(=N)CF)NCc1ccc(-n2cc3cc(-c4cc(CCC(C)(C)CN)cc(Cl)c4F)[nH]c3nc2=O)cc1] | 610.6 |
| 28 | 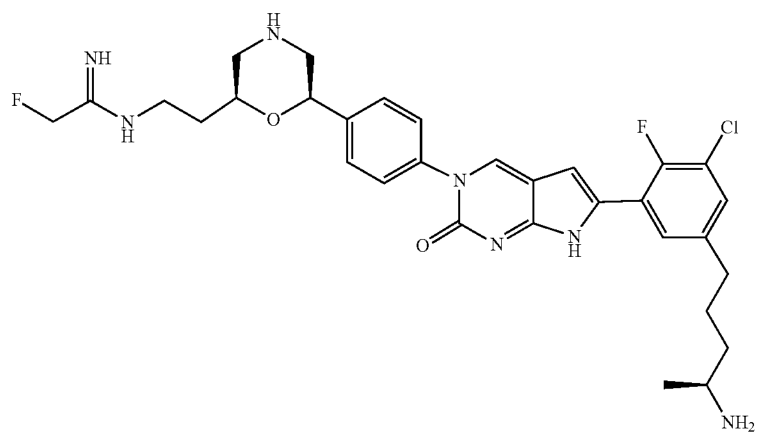 [SMILES: C[C@H](N)CCCc1cc(Cl)c(F)c(-c2cc3cn(-c4ccc([C@@H]5CNC[C@H](CCNC(=N)CF)O5)cc4)c(=O)nc3[nH]2)c1] | 612.6 |
| 29 | 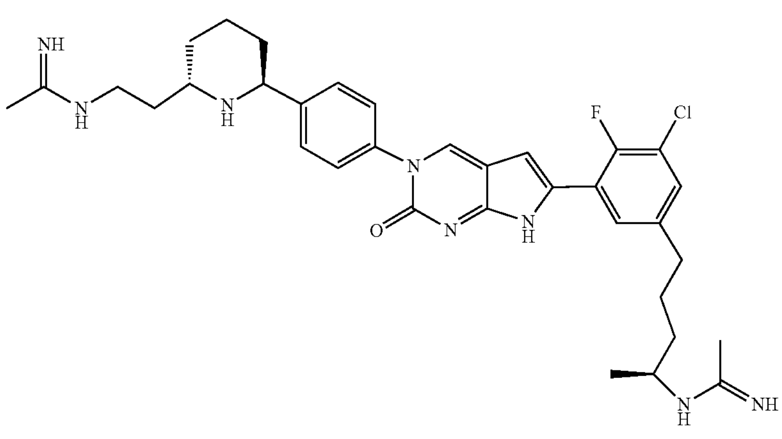 [SMILES: CC(=N)NCC[C@@H]1CCC[C@@H](c2ccc(-n3cc4cc(-c5cc(CCC[C@H](C)NC(C)=N)cc(Cl)c5F)[nH]c4nc3=O)cc2)N1] | 633.7 |

TABLE 2-continued
| # | Structure | ESI, m/z [M + H]+ |
|---|-----------|-------------------|
| 30 | 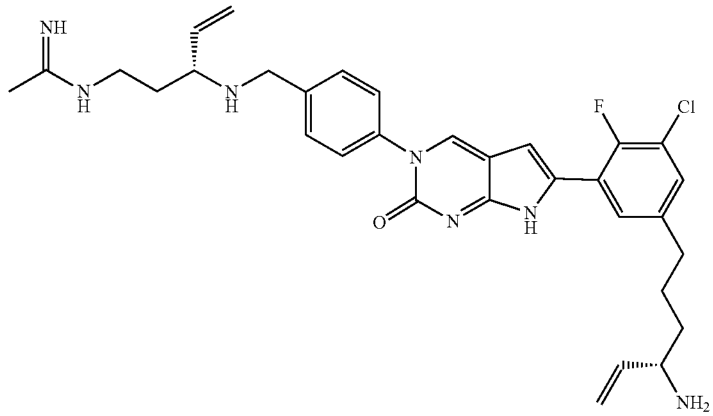 [SMILES: C=C[C@@H](N)CCCc1cc(Cl)c(F)c(-c2cc3cn(-c4ccc(CN[C@@H](C=C)CCNC(C)=N)cc4)c(=O)nc3[nH]2)c1] | 590.6 |
| 31 | 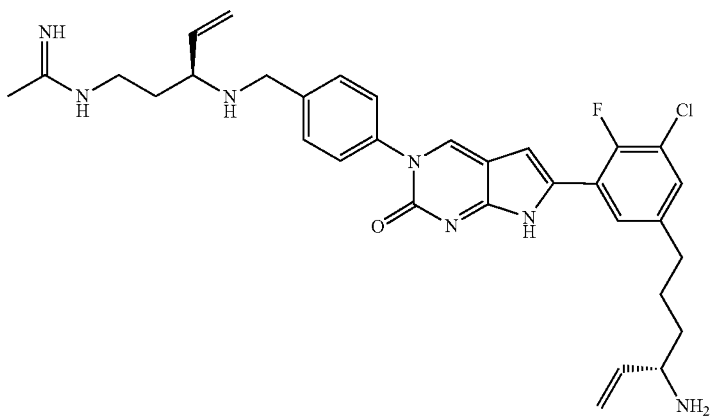 [SMILES: C=C[C@@H](N)CCCc1cc(Cl)c(F)c(-c2cc3cn(-c4ccc(CN[C@H](C=C)CCNC(C)=N)cc4)c(=O)nc3[nH]2)c1] | 590.6 |
| 32 | 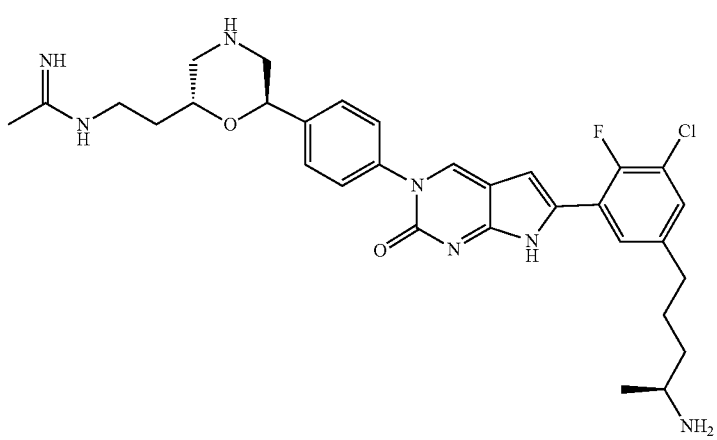 [SMILES: CC(=N)NCC[C@@H]1CNC[C@@H](c2ccc(-n3cc4cc(-c5cc(CCC[C@H](C)N)cc(Cl)c5F)[nH]c4nc3=O)cc2)O1] | 594.6 |

TABLE 2-continued

| # | Structure | ESI, m/z [M + H]+ |
|---|-----------|-------------------|
| 33 | 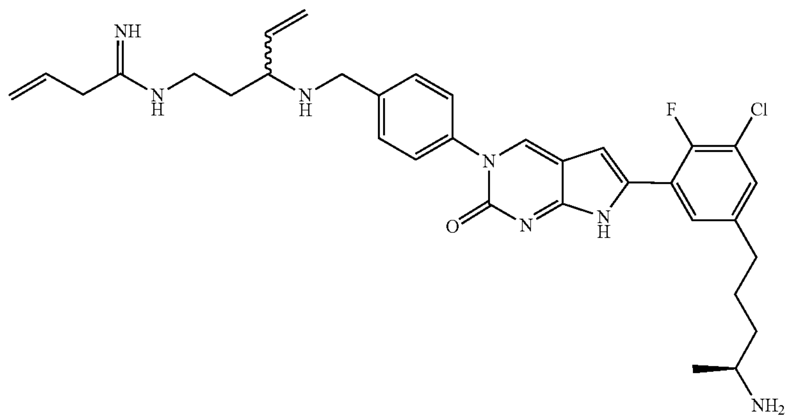 [SMILES: C=CCC(=N)NCCC(C=C)NCc1ccc(-n2cc3cc(-c4cc(CCC[C@H](C)N)cc(Cl)c4F)[nH]c3nc2=O)cc1] | 605.17 |
| 34 | 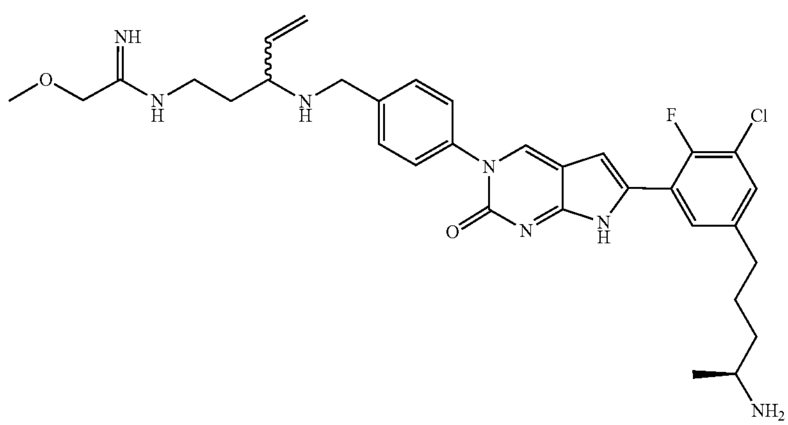 [SMILES: C=CC(CCNC(=N)COC)NCc1ccc(-n2cc3cc(-c4cc(CCC[C@H](C)N)cc(Cl)c4F)[nH]c3nc2=O)cc1] | 609.16 |
| 35 | 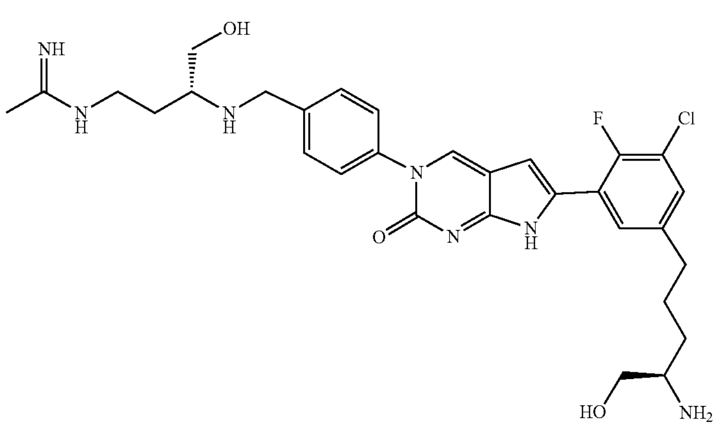 [SMILES: CC(=N)NCC[C@H](CO)NCc1ccc(-n2cc3cc(-c4cc(CCC[C@@H](N)CO)cc(Cl)c4F)[nH]c3nc2=O)cc1] | 598.6 |

TABLE 2-continued
| # | Structure | ESI, m/z [M + H]+ |
|---|---|---|
| 36 | 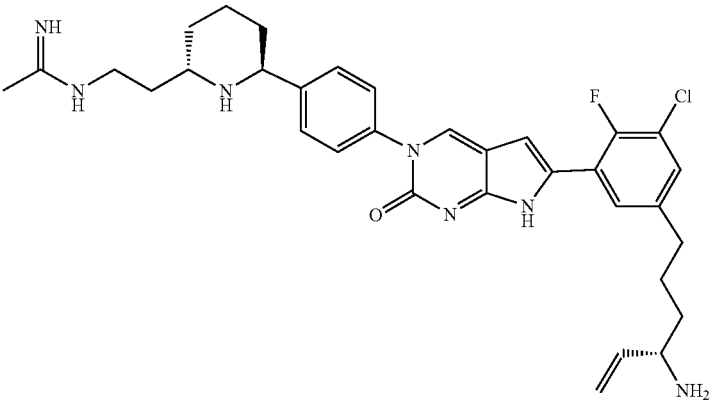 [SMILES: C=C[C@@H](N)CCCc1cc(Cl)c(F)c(-c2cc3cn(-c4ccc([C@@H]5CCC[C@@H](CCNC(C)=N)N5)cc4)c(=O)nc3[nH]2)c1] | 604.6 |
| 37 | 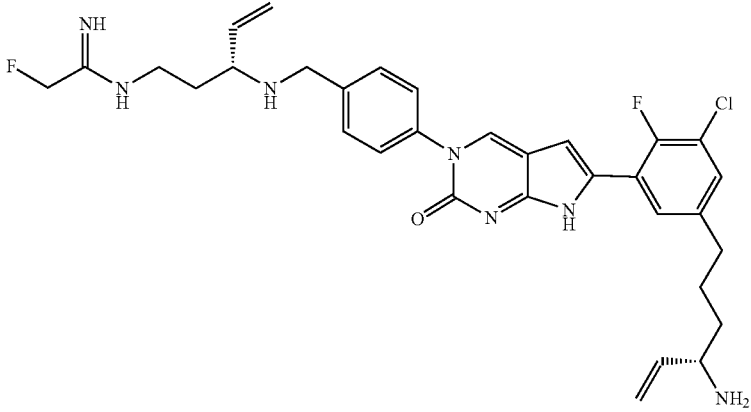 [SMILES: C=C[C@@H](N)CCCc1cc(Cl)c(F)c(-c2cc3cn(-c4ccc(CN[C@@H](C=C)CCNC(=N)CF)cc4)c(=O)nc3[nH]2)c1] | 608.6 |
| 38 | 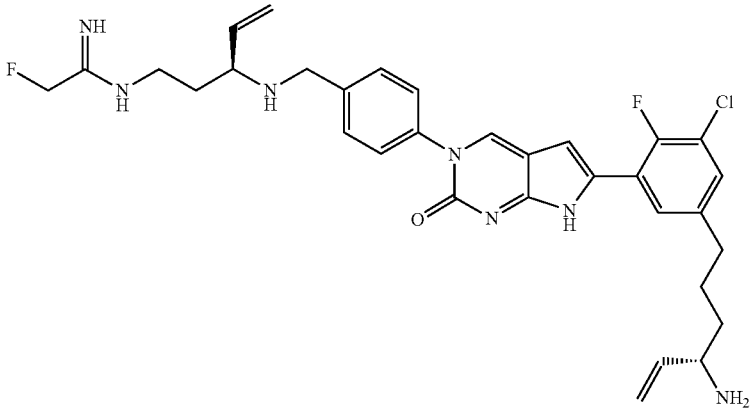 [SMILES: C=C[C@@H](N)CCCc1cc(Cl)c(F)c(-c2cc3cn(-c4ccc(CN[C@H](C=C)CCNC(=N)CF)cc4)c(=O)nc3[nH]2)c1] | 608.6 |

TABLE 2-continued
| # | Structure | ESI, m/z [M + H]+ |
|---|---|---|
| 39 | 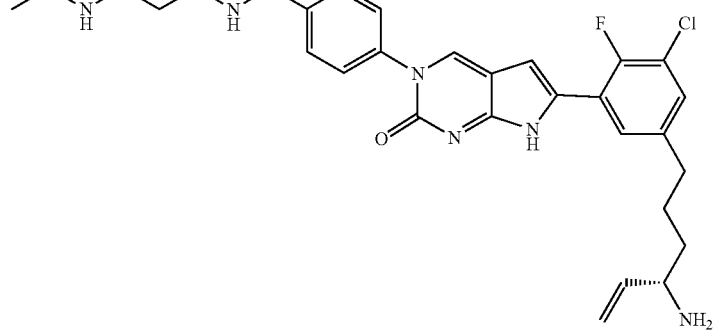 | 596.6 |
| 40 | 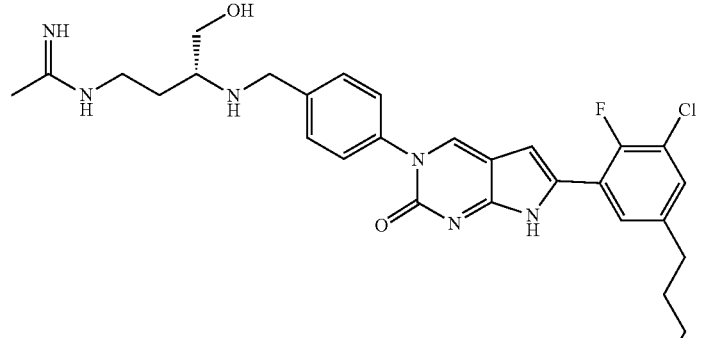 | 639.3 |
| 41 | 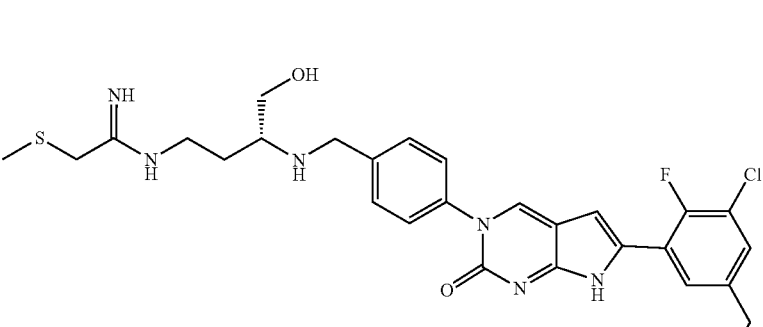 | 629.21 |

TABLE 2-continued
| # | Structure | ESI, m/z [M + H]+ |
|---|---|---|
| 42 | 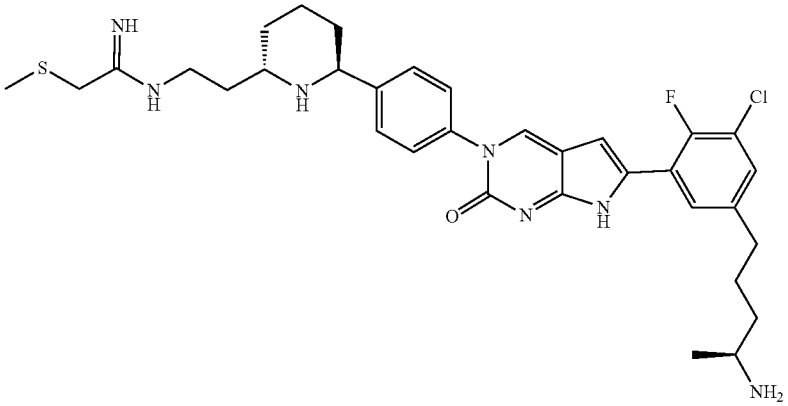 [SMILES: CSCC(=N)NCC[C@@H]1CCC[C@@H](c2ccc(-n3cc4cc(-c5cc(CCC[C@H](C)N)cc(Cl)c5F)[nH]c4nc3=O)cc2)N1] | 639.3 |
| 43 | 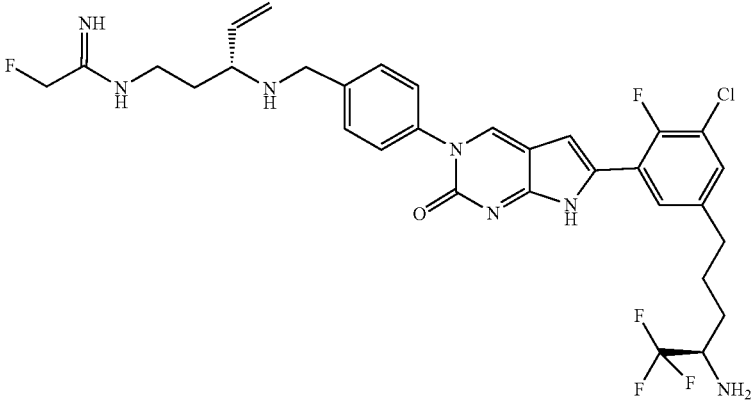 | 650.6 |
| 44 | 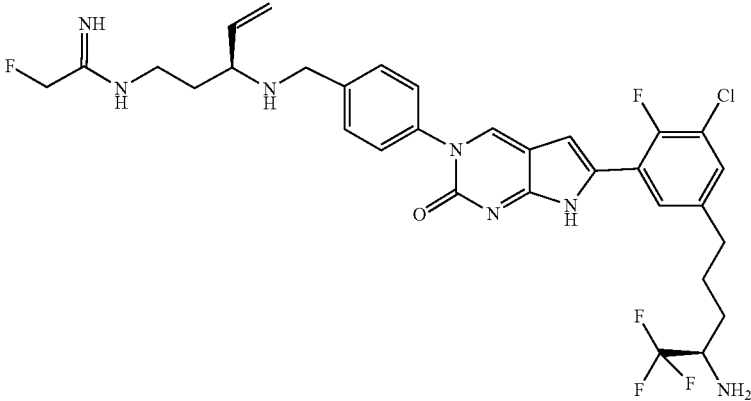 | 650.6 |

TABLE 2-continued

| # | Structure | ESI, m/z [M + H]+ |
|---|---|---|
| 45 | 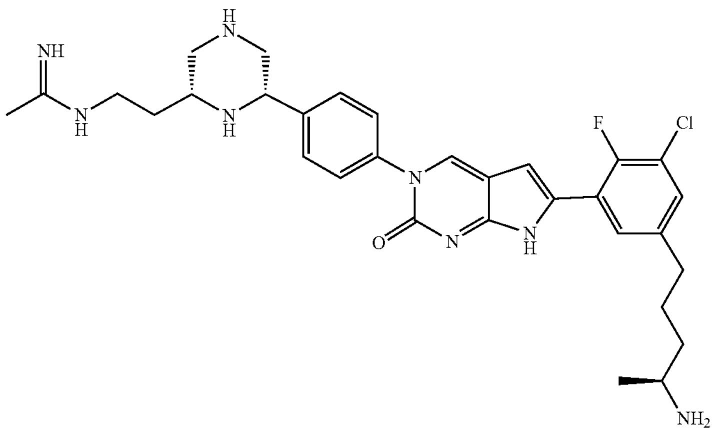 [SMILES: CC(=N)NCC[C@@H]1CNC[C@H](c2ccc(-n3cc4cc(-c5cc(CCC[C@H](C)N)cc(Cl)c5F)[nH]c4nc3=O)cc2)N1] | 593.6 |
| 46 | 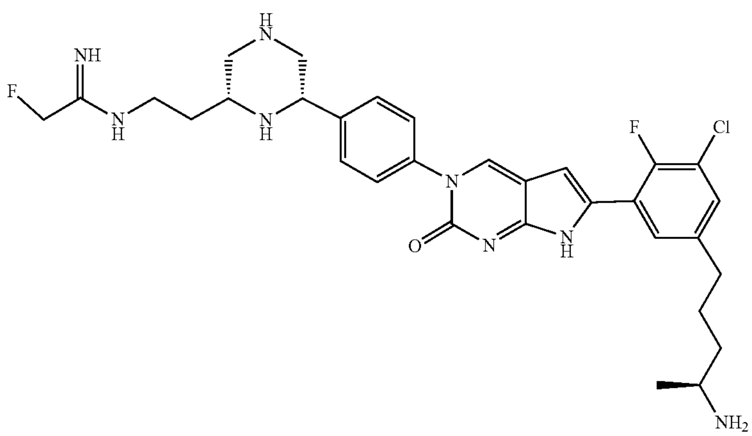 [SMILES: C[C@H](N)CCCc1cc(Cl)c(F)c(-c2cc3cn(-c4ccc([C@H]5CNC[C@@H](CCNC(=N)CF)N5)cc4)c(=O)nc3[nH]2)c1] | 611.6 |
| 47 | 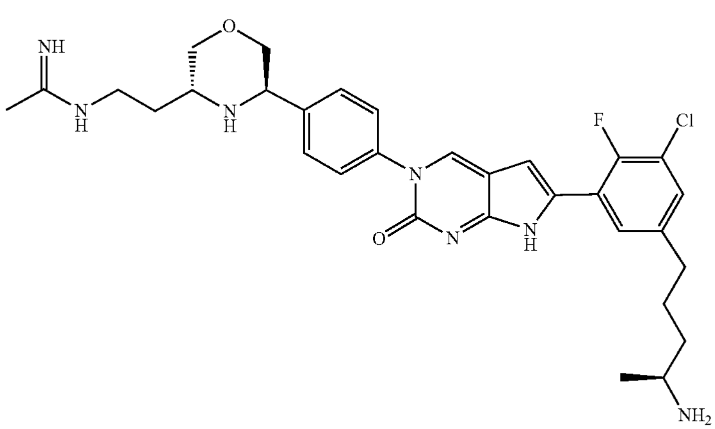 [SMILES: CC(=N)NCC[C@@H]1COC[C@@H](c2ccc(-n3cc4cc(-c5cc(CCC[C@H](C)N)cc(Cl)c5F)[nH]c4nc3=O)cc2)N1] | 594.5 |

TABLE 2-continued

| # | Structure | ESI, m/z [M + H]+ |
|---|---|---|
| 48 | 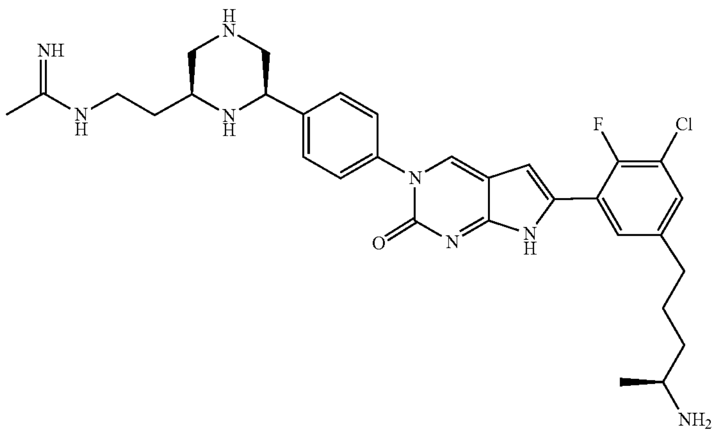 [SMILES: CC(=N)NCC[C@H]1CNC[C@@H](c2ccc(-n3cc4cc(-c5cc(CCC[C@H](C)N)cc(Cl)c5F)[nH]c4nc3=O)cc2)N1] | 593.5 |
| 49 | 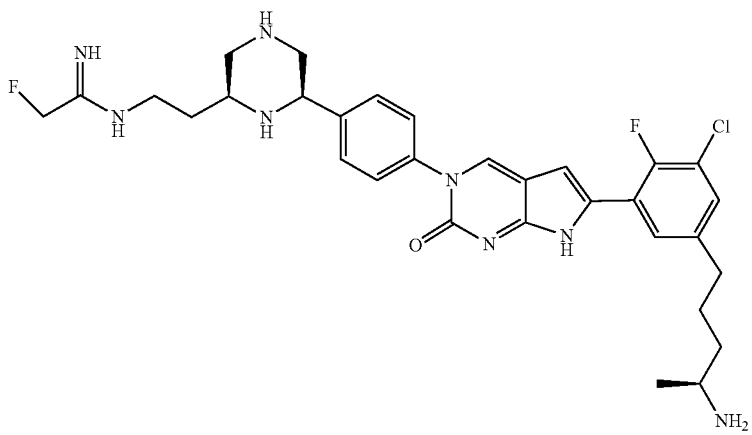 [SMILES: C[C@H](N)CCCc1cc(Cl)c(F)c(-c2cc3cn(-c4ccc([C@@H]5CNC[C@H](CCNC(=N)CF)N5)cc4)c(=O)nc3[nH]2)c1] | 611.4 |
| 50 | 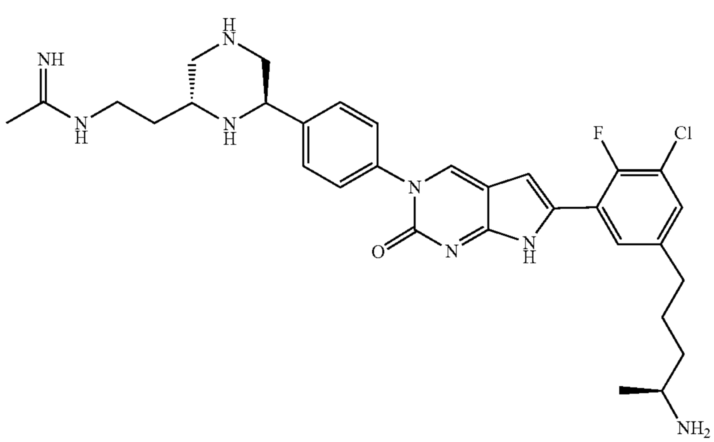 [SMILES: CC(=N)NCC[C@@H]1CNC[C@@H](c2ccc(-n3cc4cc(-c5cc(CCC[C@H](C)N)cc(Cl)c5F)[nH]c4nc3=O)cc2)N1] | 593.5 |

TABLE 2-continued
| # | Structure | ESI, m/z [M + H]+ |
|---|---|---|
| 51 | 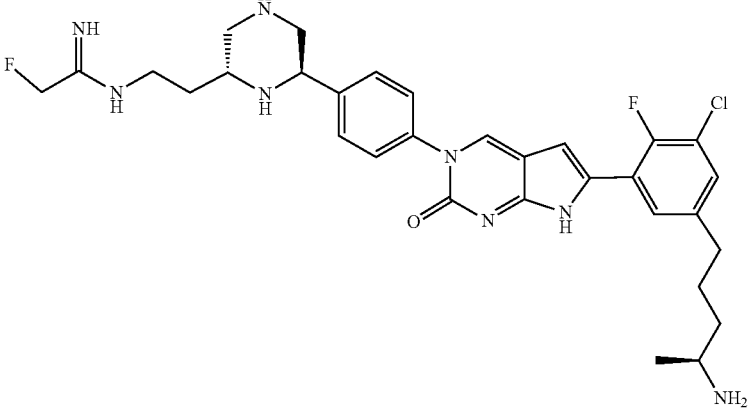 | 611.5 |
| 52 | 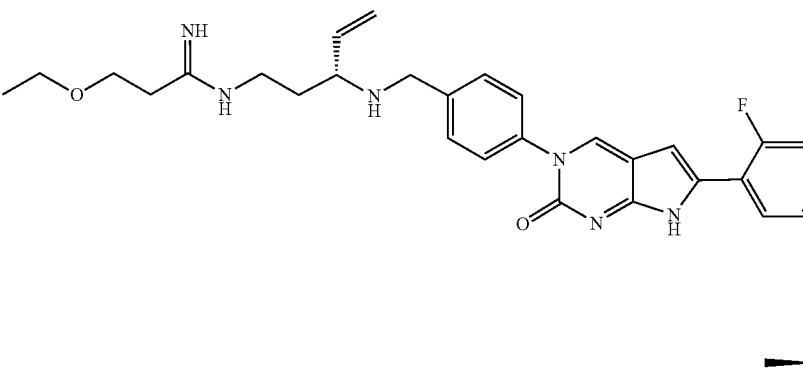 | 637.2 |
| 53 | 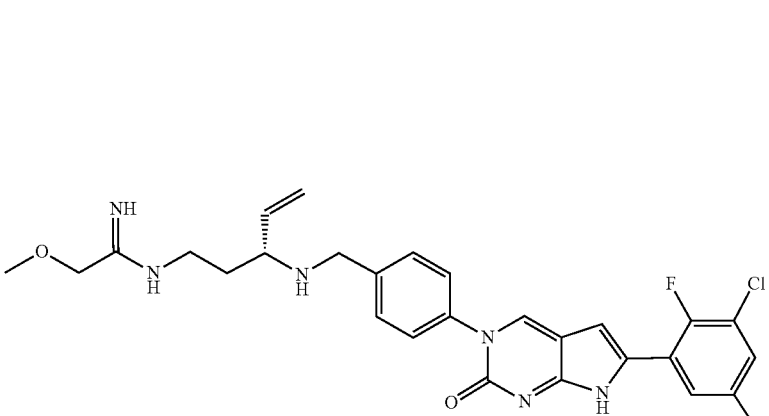 | 609.2 |

TABLE 2-continued

| # | Structure | ESI, m/z [M + H]+ |
|---|---|---|
| 54 | 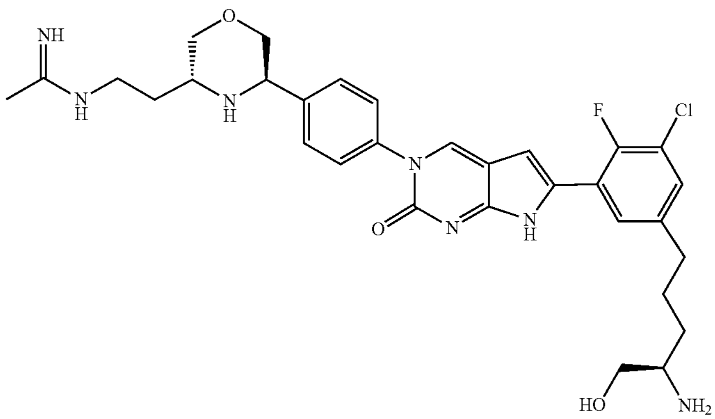 [SMILES: CC(=N)NCC[C@@H]1COC[C@@H](c2ccc(-n3cc4cc(-c5cc(CCC[C@@H](N)CO)cc(Cl)c5F)[nH]c4nc3=O)cc2)N1] | 610.6 |
| 55 | 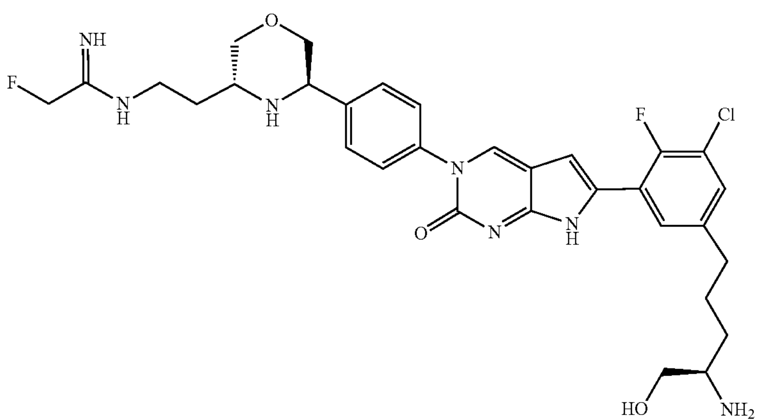 [SMILES: N=C(CF)NCC[C@@H]1COC[C@@H](c2ccc(-n3cc4cc(-c5cc(CCC[C@@H](N)CO)cc(Cl)c5F)[nH]c4nc3=O)cc2)N1] | 628.6 |
| 56 | 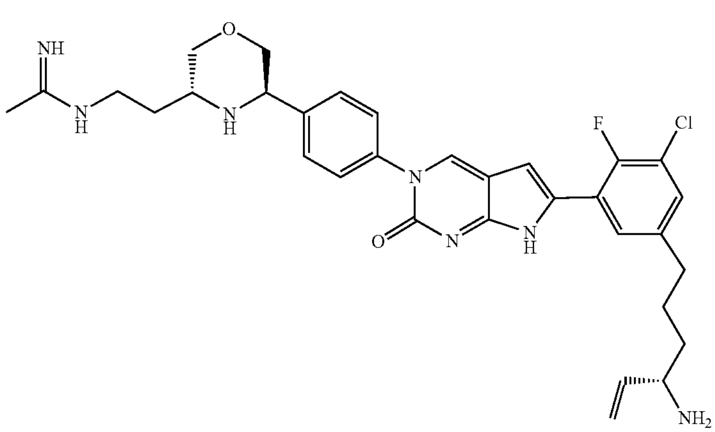 [SMILES: C=C[C@@H](N)CCCc1cc(Cl)c(F)c(-c2cc3cn(-c4ccc([C@@H]5COC[C@@H](CCNC(C)=N)N5)cc4)c(=O)nc3[nH]2)c1] | 606.6 |

TABLE 2-continued
| # | Structure | ESI, m/z [M + H]+ |
|---|---|---|
| 57 | 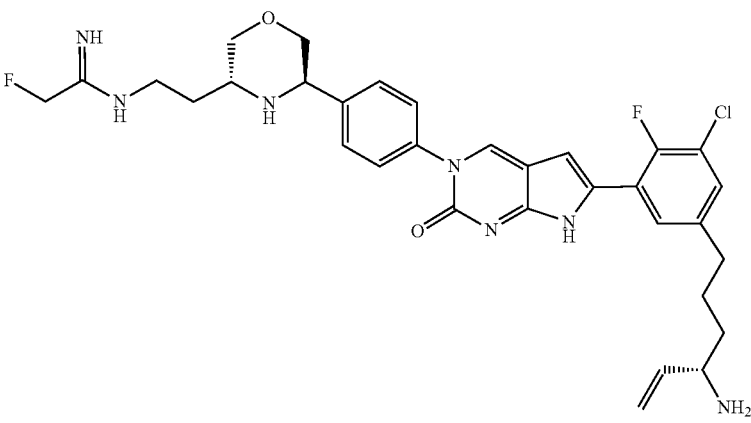 [SMILES: C=C[C@@H](N)CCCc1cc(Cl)c(F)c(-c2cc3cn(-c4ccc([C@@H]5COC[C@@H](CCNC(=N)CF)N5)cc4)c(=O)nc3[nH]2)c1] | 624.6 |
| 58 | 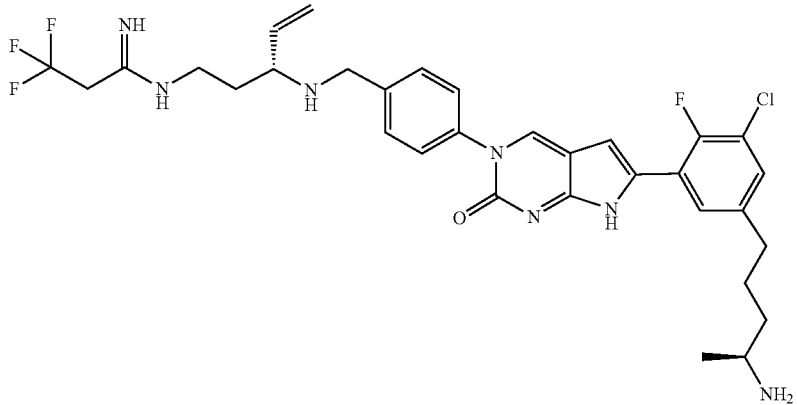 [SMILES: C=C[C@@H](CCNC(=N)CC(F)(F)F)NCc1ccc(-n2cc3cc(-c4cc(CCC[C@H](C)N)cc(Cl)c4F)[nH]c3nc2=O)cc1] | 647.2 |
| 59 | 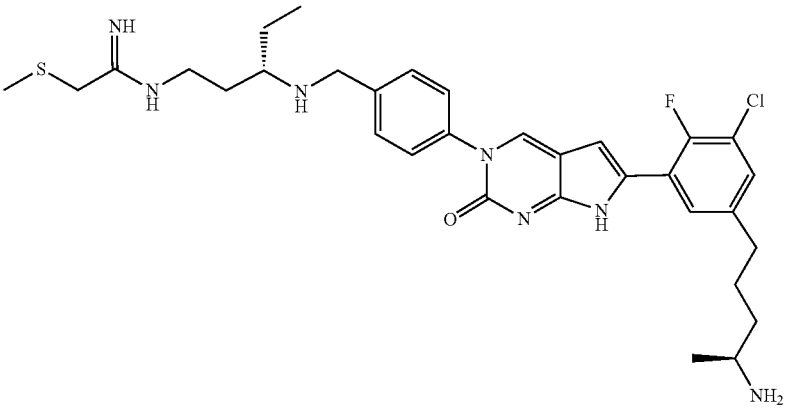 [SMILES: CC[C@@H](CCNC(=N)CSC)NCc1ccc(-n2cc3cc(-c4cc(CCC[C@H](C)N)cc(Cl)c4F)[nH]c3nc2=O)cc1] | 625.2 |

TABLE 2-continued

| # | Structure | ESI, m/z [M + H]+ |
|---|---|---|
| 60 | 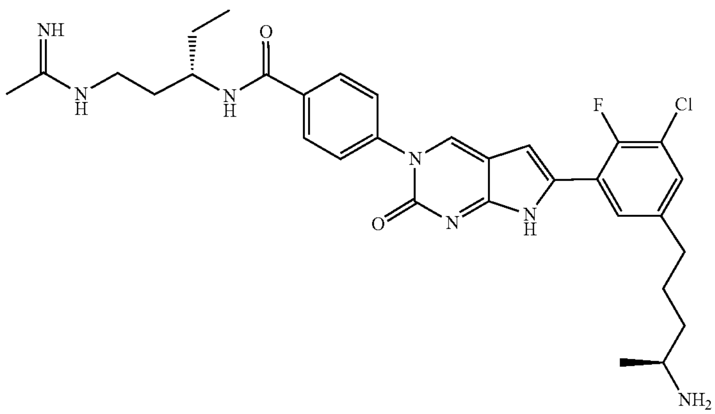 [SMILES: CC[C@@H](CCNC(C)=N)NC(=O)c1ccc(-n2cc3cc(-c4cc(CCC[C@H](C)N)cc(Cl)c4F)[nH]c3nc2=O)cc1] | 592 |
| 61 | 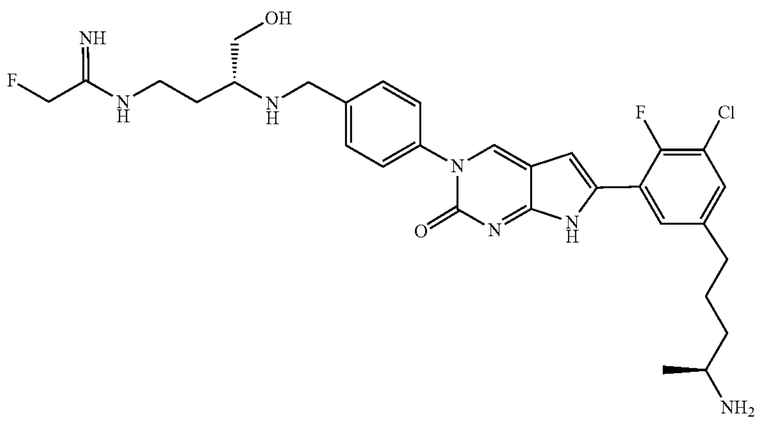 [SMILES: C[C@H](N)CCCc1cc(Cl)c(F)c(-c2cc3cn(-c4ccc(CN[C@@H](CO)CCNC(=N)CF)cc4)c(=O)nc3[nH]2)c1] | 600 |
| 62 | 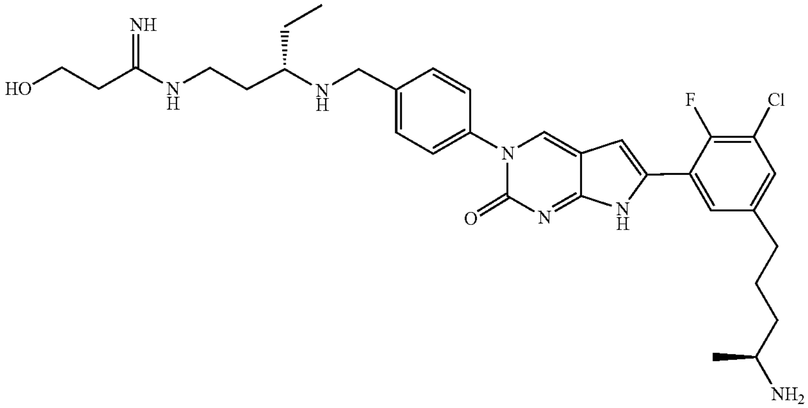 [SMILES: CC[C@@H](CCNC(=N)CCO)NCc1ccc(-n2cc3cc(-c4cc(CCC[C@H](C)N)cc(Cl)c4F)[nH]c3nc2=O)cc1] | 608. |

TABLE 2-continued
| # | Structure | ESI, m/z [M + H]+ |
|---|---|---|
| 63 | 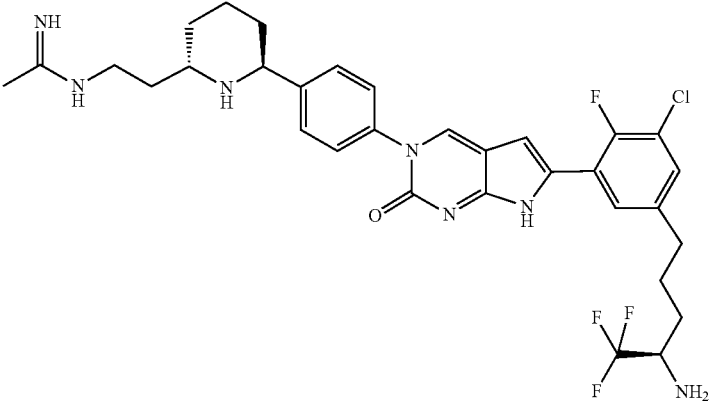 [SMILES: CC(=N)NCC[C@@H]1CCC[C@@H](c2ccc(-n3cc4cc(-c5cc(CCC[C@@H](N)C(F)(F)F)cc(Cl)c5F)[nH]c4nc3=O)cc2)N1] | 647.1 |
| 64 | 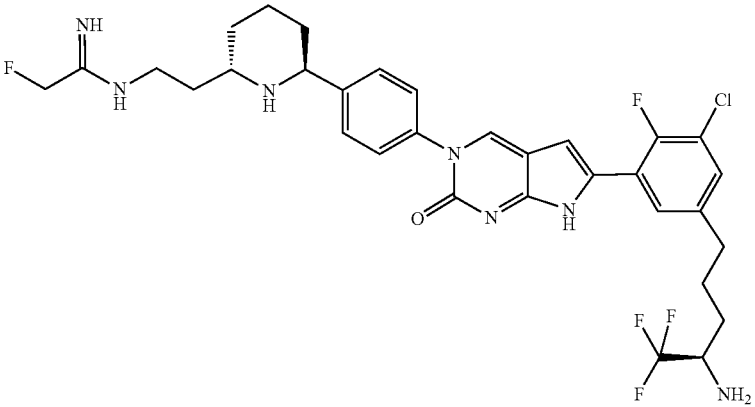 [SMILES: N=C(CF)NCC[C@@H]1CCC[C@@H](c2ccc(-n3cc4cc(-c5cc(CCC[C@@H](N)C(F)(F)F)cc(Cl)c5F)[nH]c4nc3=O)cc2)N1] | 665.1 |
| 65 | 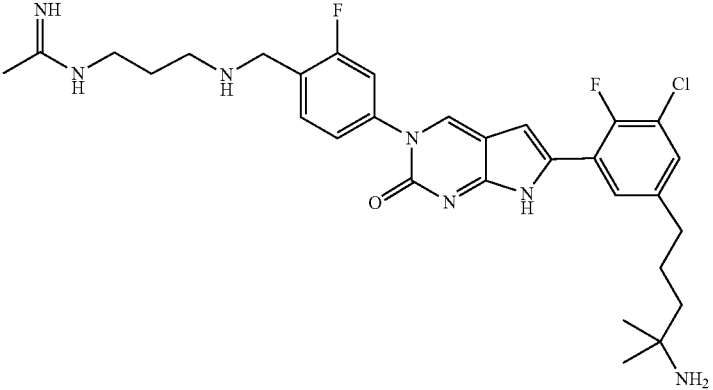 [SMILES: CC(=N)NCCCNCc1ccc(-n2cc3cc(-c4cc(CCCC(C)(C)N)cc(Cl)c4F)[nH]c3nc2=O)cc1F] | 586.6 |

TABLE 2-continued

| # | Structure | ESI, m/z [M + H]+ |
|---|---|---|
| 66 | 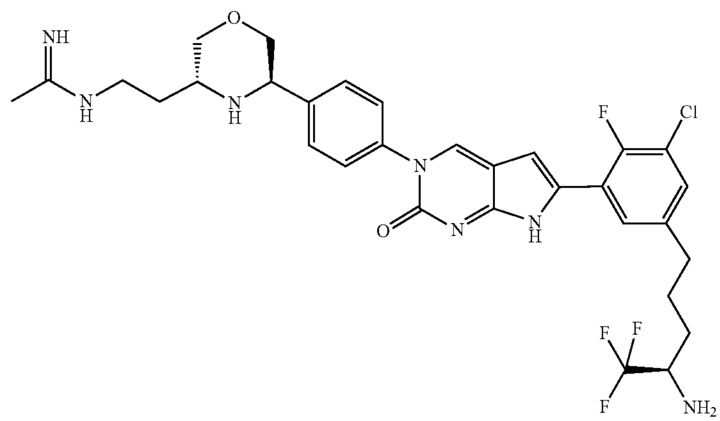 [SMILES: CC(=N)NCC[C@@H]1COC[C@@H](c2ccc(-n3cc4cc(-c5cc(CCC[C@@H](N)C(F)(F)F)cc(Cl)c5F)[nH]c4nc3=O)cc2)N1] | 648.6 |
| 67 | 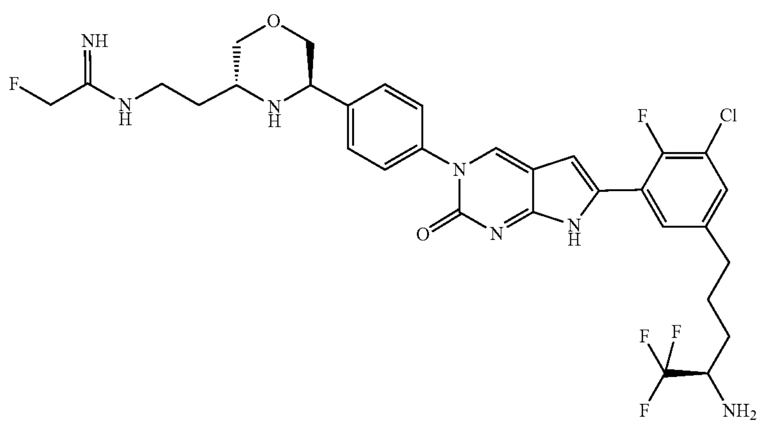 [SMILES: N=C(CF)NCC[C@@H]1COC[C@@H](c2ccc(-n3cc4cc(-c5cc(CCC[C@@H](N)C(F)(F)F)cc(Cl)c5F)[nH]c4nc3=O)cc2)N1] | 666.6 |
| 68 | 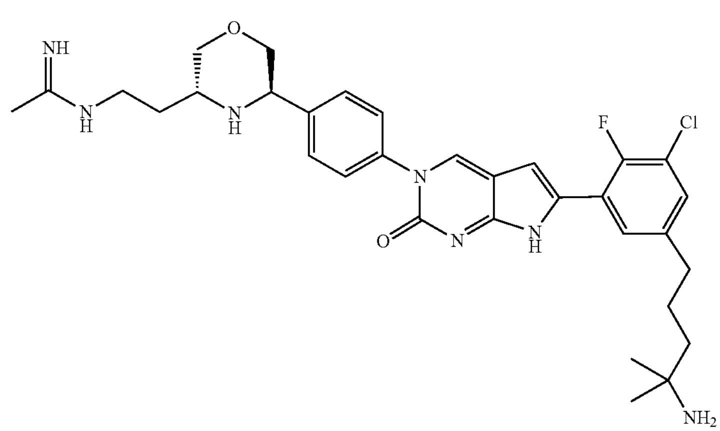 [SMILES: CC(=N)NCC[C@@H]1COC[C@@H](c2ccc(-n3cc4cc(-c5cc(CCCC(C)(C)N)cc(Cl)c5F)[nH]c4nc3=O)cc2)N1] | 608.6 |

TABLE 2-continued
| # | Structure | ESI, m/z [M + H]+ |
|---|-----------|-------------------|
| 69 | 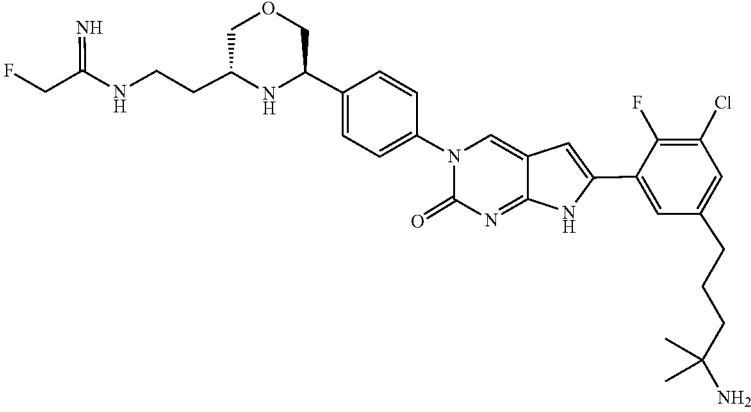 [SMILES: CC(C)(N)CCCc1cc(Cl)c(F)c(-c2cc3cn(-c4ccc([C@@H]5COC[C@@H](CCNC(=N)CF)N5)cc4)c(=O)nc3[nH]2)c1] | 626.6 |
| 70 | 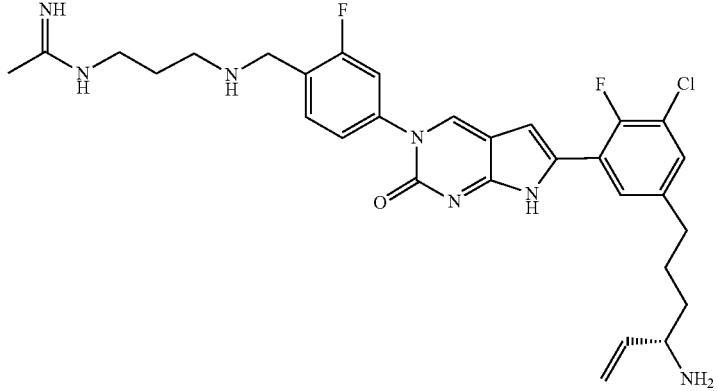 [SMILES: C=C[C@@H](N)CCCc1cc(Cl)c(F)c(-c2cc3cn(-c4ccc(CNCCCNC(C)=N)c(F)c4)c(=O)nc3[nH]2)c1] | 582.6 |
| 71 | 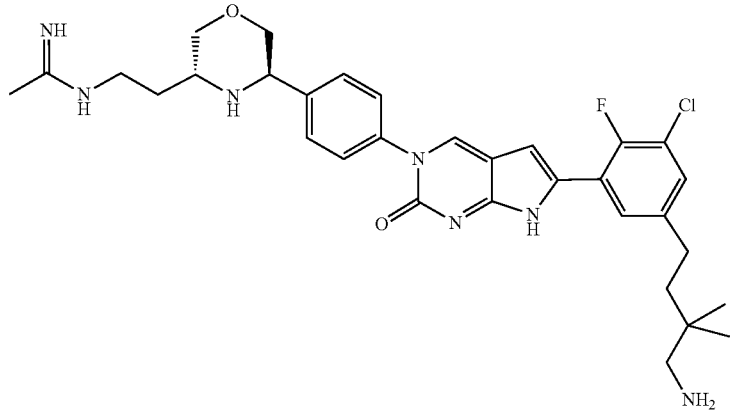 [SMILES: CC(=N)NCC[C@@H]1COC[C@@H](c2ccc(-n3cc4cc(-c5cc(CCC(C)(C)CN)cc(Cl)c5F)[nH]c4nc3=O)cc2)N1] | 608.6 |

TABLE 2-continued
| # | Structure | ESI, m/z [M + H]+ |
|---|-----------|-------------------|
| 72 | 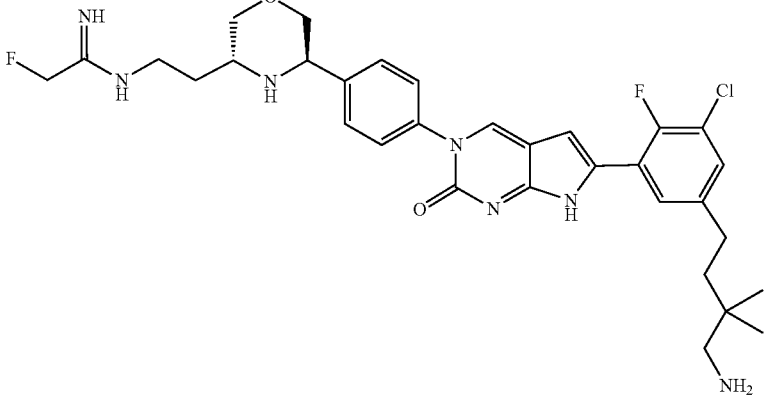 | 626.6 |
| 73 | 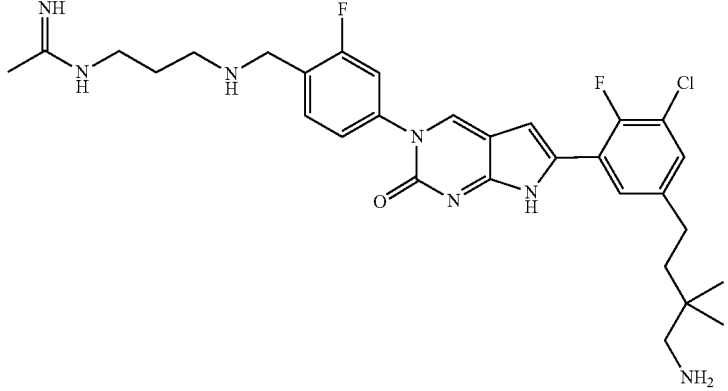 [SMILES: CC(=N)NCCCNCc1ccc(-n2cc3cc(-c4cc(CCC(C)(C)CN)cc(Cl)c4F)[nH]c3nc2=O)cc1F] | 584.6 |
| 74 | 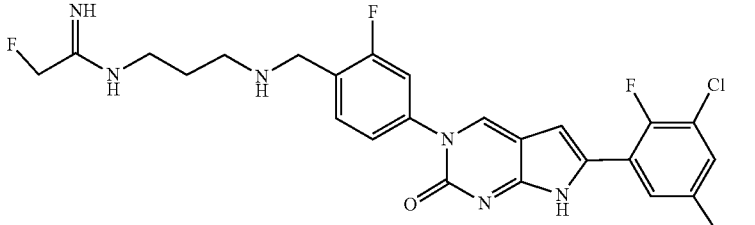 | 602.6 |

TABLE 2-continued

| # | Structure | ESI, m/z [M + H]+ |
|---|---|---|
| 75 | 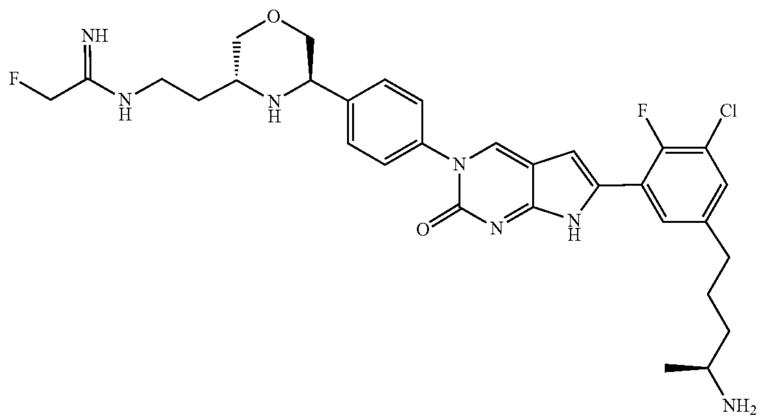 [SMILES: C[C@H](N)CCCc1cc(Cl)c(F)c(-c2cc3cn(-c4ccc([C@@H]5COC[C@@H](CCNC(=N)CF)N5)cc4)c(=O)nc3[nH]2)c1] | 612.6 |
| 76 | 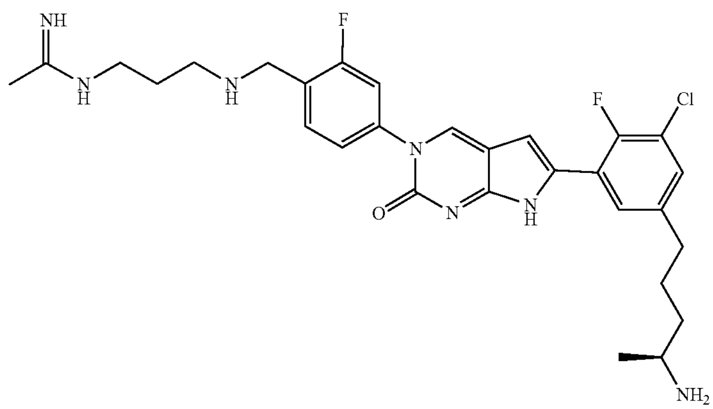 [SMILES: CC(=N)NCCCNCc1ccc(-n2cc3cc(-c4cc(CCC[C@H](C)N)cc(Cl)c4F)[nH]c3nc2=O)cc1F] | 570 |
| 77 | 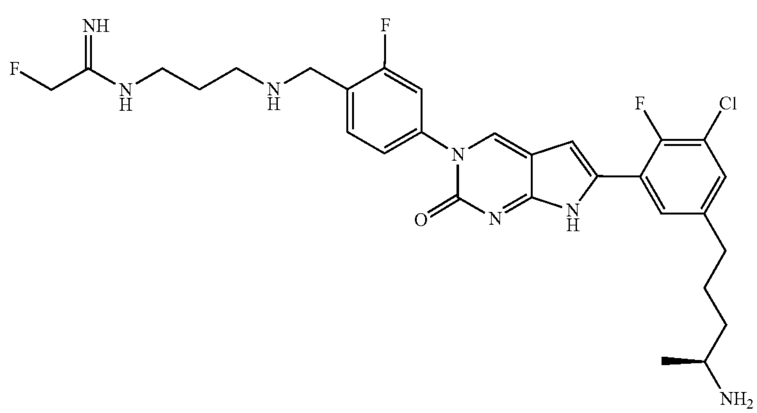 [SMILES: C[C@H](N)CCCc1cc(Cl)c(F)c(-c2cc3cn(-c4ccc(CNCCCNC(=N)CF)c(F)c4)c(=O)nc3[nH]2)c1] | 588 |

TABLE 2-continued

| # | Structure | ESI, m/z [M + H]+ |
|---|---|---|
| 78 | 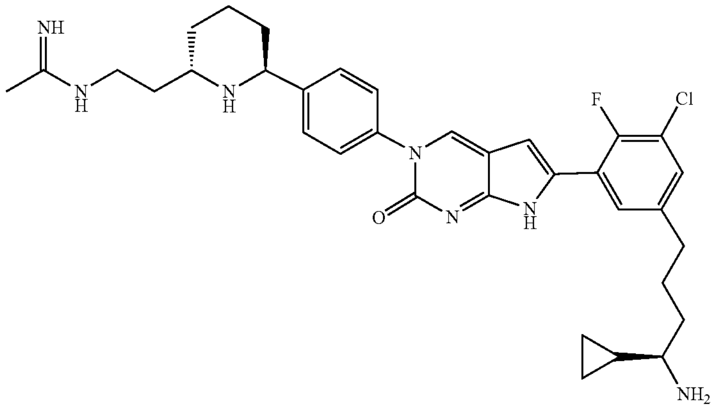 [SMILES: CC(=N)NCC[C@@H]1CCC[C@@H](c2ccc(-n3cc4cc(-c5cc(CCC[C@@H](N)C6CC6)cc(Cl)c5F)[nH]c4nc3=O)cc2)N1] | 620.6 |
| 79 | 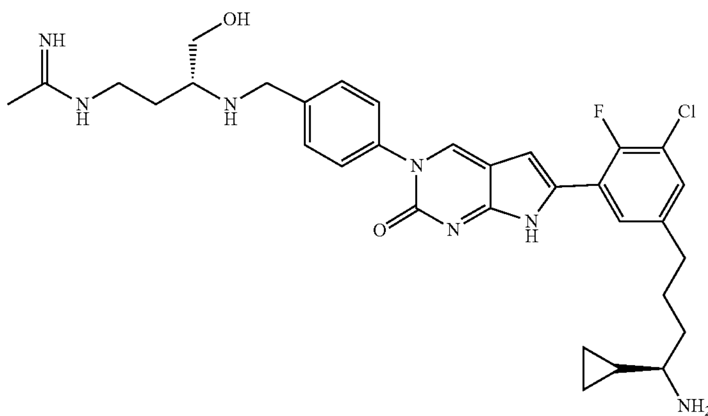 [SMILES: CC(=N)NCC[C@H](CO)NCc1ccc(-n2cc3cc(-c4cc(CCC[C@@H](N)C5CC5)cc(Cl)c4F)[nH]c3nc2=O)cc1] | 608.5 |
| 80 | 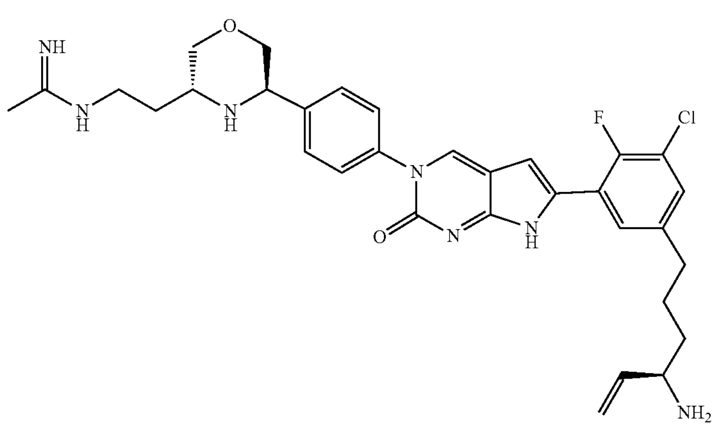 [SMILES: C=C[C@H](N)CCCc1cc(Cl)c(F)c(-c2cc3cn(-c4ccc([C@@H]5COC[C@@H](CCNC(C)=N)N5)cc4)c(=O)nc3[nH]2)c1] | 606.4 |

TABLE 2-continued
| # | Structure | ESI, m/z [M + H]+ |
|---|---|---|
| 81 | 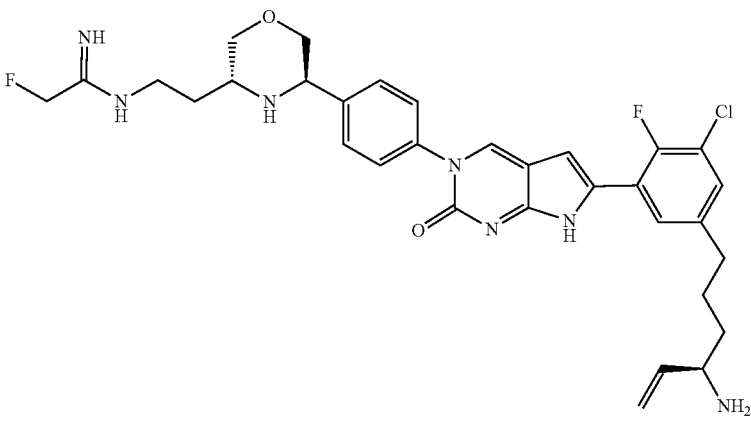 | 624.4 |
| 82 | 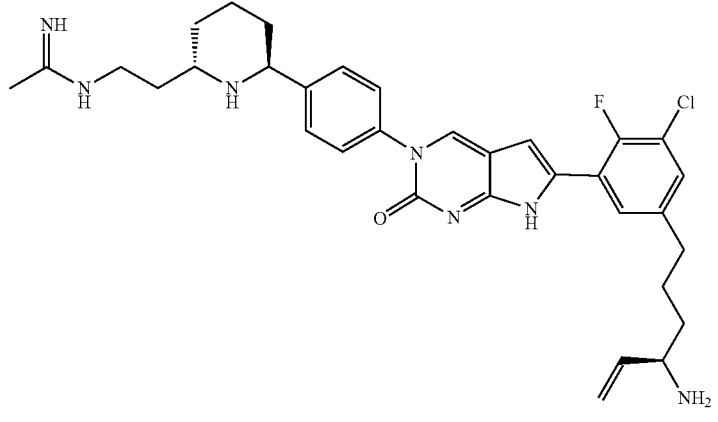 [SMILES: C=C[C@H](N)CCCc1cc(Cl)c(F)c(-c2cc3cn(-c4ccc([C@@H]5CCC[C@@H](CCNC(C)=N)N5)cc4)c(=O)nc3[nH]2)c1] | 606.2 |
| 83 | 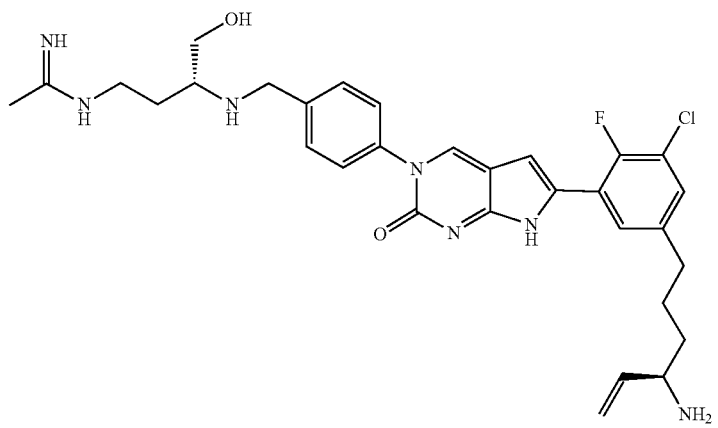 [SMILES: C=C[C@H](N)CCCc1cc(Cl)c(F)c(-c2cc3cn(-c4ccc(CN[C@@H](CO)CCNC(C)=N)cc4)c(=O)nc3[nH]2)c1] | 594.5 |

TABLE 2-continued
| # | Structure | ESI, m/z [M + H]+ |
|---|---|---|
| 84 | 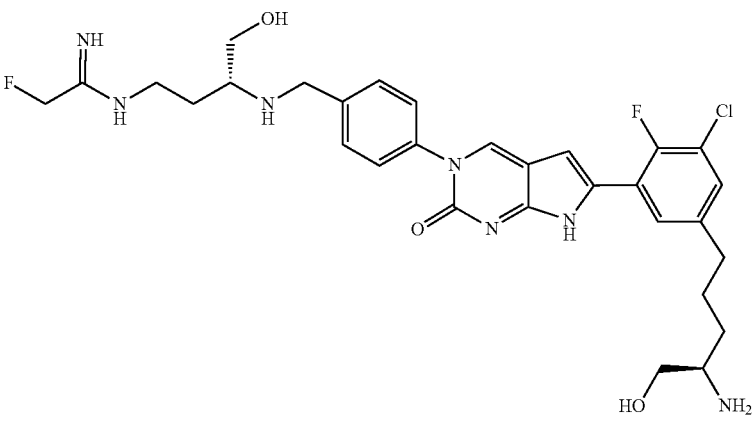 [SMILES: N=C(CF)NCC[C@H](CO)NCc1ccc(-n2cc3cc(-c4cc(CCC[C@@H](N)CO)cc(Cl)c4F)[nH]c3nc2=O)cc1] | 616.4 |
| 85 | 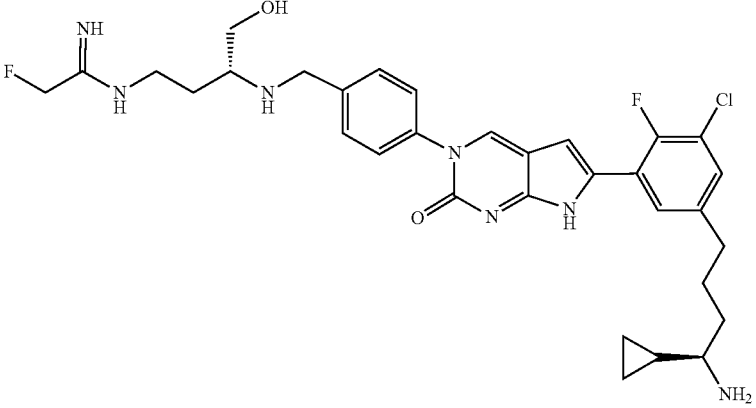 [SMILES: N=C(CF)NCC[C@H](CO)NCc1ccc(-n2cc3cc(-c4cc(CCC[C@@H](N)C5CC5)cc(Cl)c4F)[nH]c3nc2=O)cc1] | 627.7 |
| 86 | 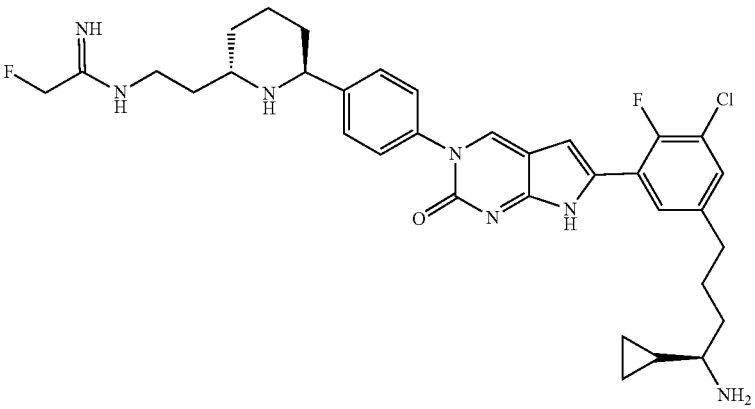 [SMILES: N=C(CF)NCC[C@@H]1CCC[C@@H](c2ccc(-n3cc4cc(-c5cc(CCC[C@@H](N)C6CC6)cc(Cl)c5F)[nH]c4nc3=O)cc2)N1] | 636.5 |

TABLE 2-continued

| # | Structure | ESI, m/z [M + H]+ |
|---|---|---|
| 87 | 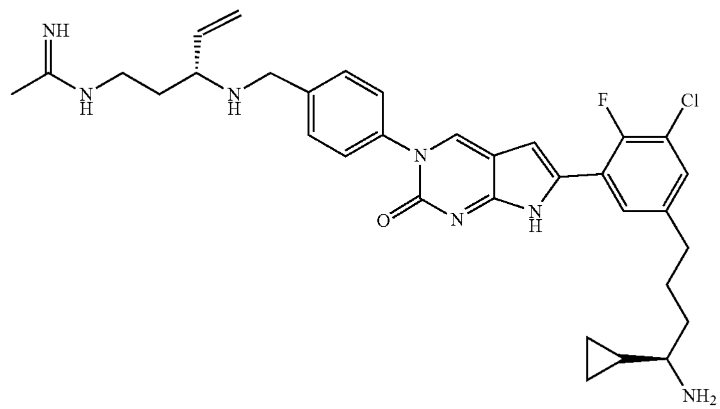 [SMILES: C=C[C@@H](CCNC(C)=N)NCc1ccc(-n2cc3cc(-c4cc(CCC[C@@H](N)C5CC5)cc(Cl)c4F)[nH]c3nc2=O)cc1] | 604.4 |
| 88 | 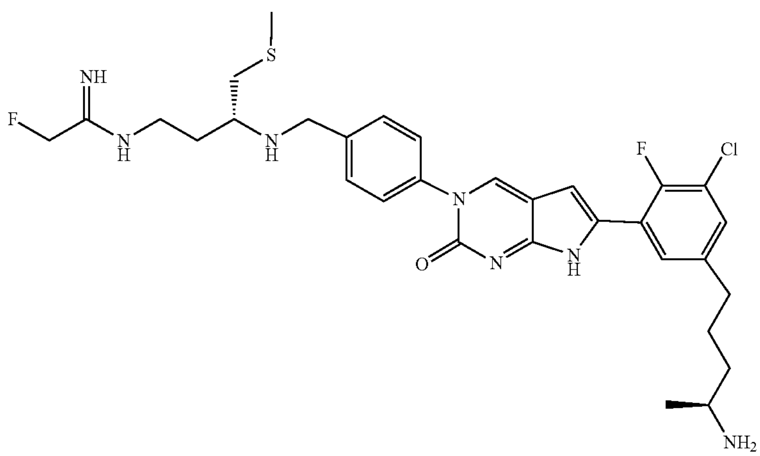 [SMILES: CSC[C@@H](CCNC(=N)CF)NCc1ccc(-n2cc3cc(-c4cc(CCC[C@H](C)N)cc(Cl)c4F)[nH]c3nc2=O)cc1] | 630 |
| 89 | 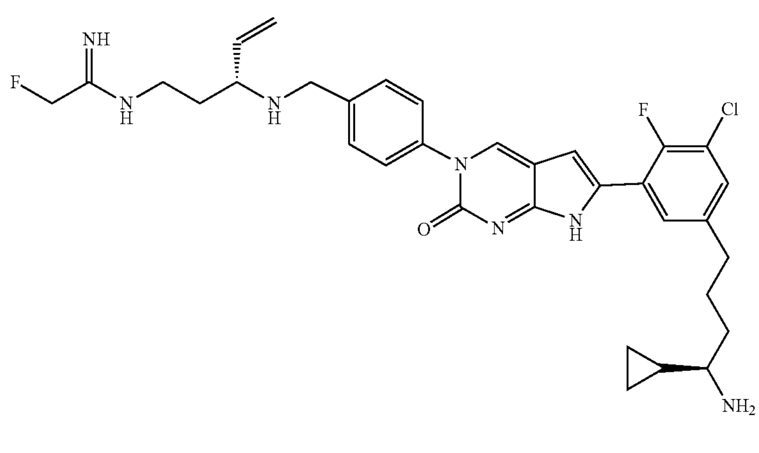 [SMILES: C=C[C@@H](CCNC(=N)CF)NCc1ccc(-n2cc3cc(-c4cc(CCC[C@@H](N)C5CC5)cc(Cl)c4F)[nH]c3nc2=O)cc1] | 622.4 |

TABLE 2-continued
| # | Structure | ESI, m/z [M + H]+ |
|---|-----------|---------------------|
| 90 | 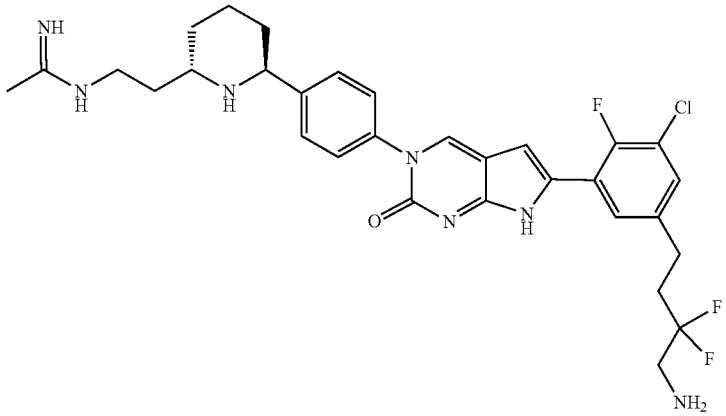 [SMILES: CC(=N)NCC[C@@H]1CCC[C@@H](c2ccc(-n3cc4cc(-c5cc(CCC(F)(F)CN)cc(Cl)c5F)[nH]c4nc3=O)cc2)N1] | 614.4 |
| 91 | 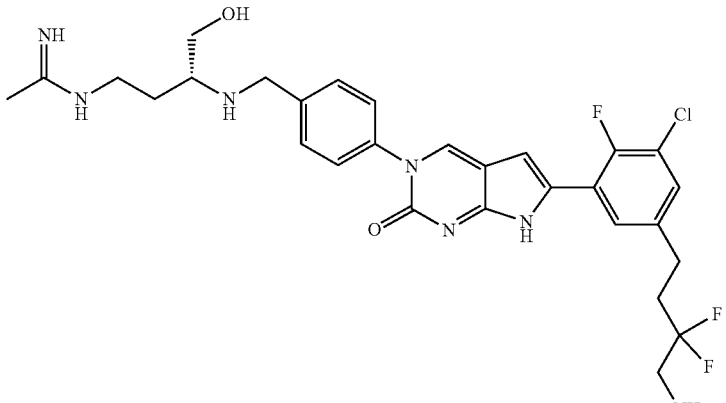 | 604.4 |
| 92 | 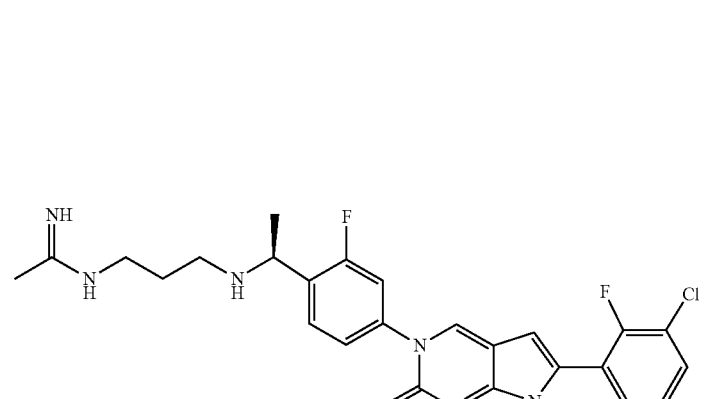 | 596.5 |

TABLE 2-continued
| # | Structure | ESI, m/z [M + H]+ |
|---|-----------|-------------------|
| 93 | 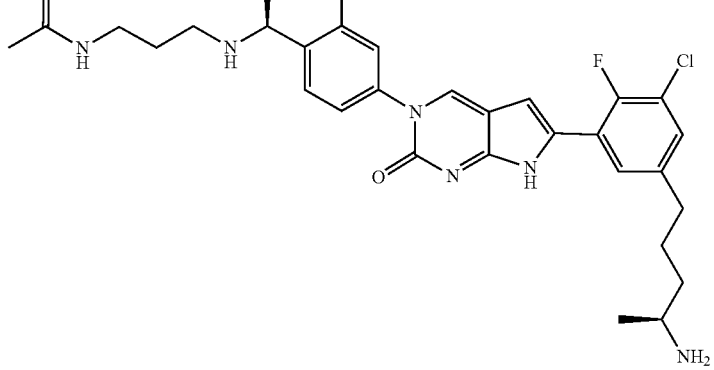 | 584 |
| 94 | 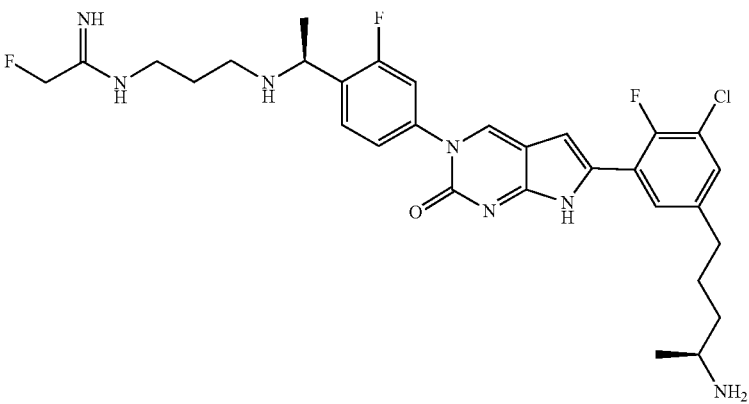 [SMILES: C[C@H](N)CCCc1cc(Cl)c(F)c(-c2cc3cn(-c4ccc([C@H](C)NCCCNC(=N)CF)c(F)c4)c(=O)nc3[nH]2)c1] | 602 |
| 95 | 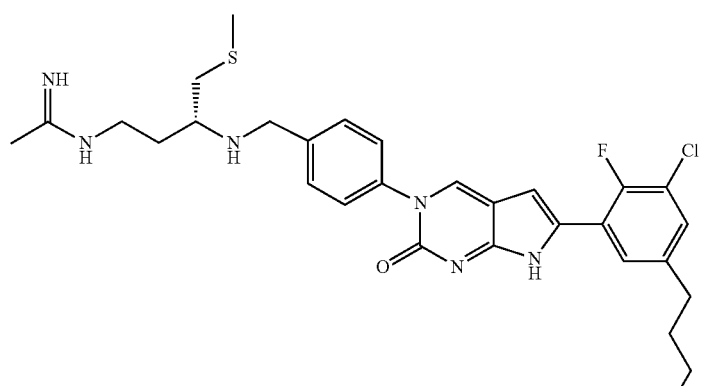 | 612 |

TABLE 2-continued

| # | Structure | ESI, m/z [M + H]+ |
|---|---|---|
| 96 | 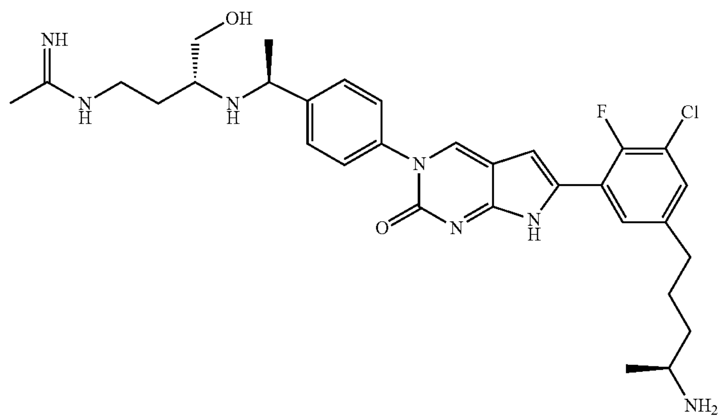 [SMILES: CC(=N)NCC[C@H](CO)N[C@@H](C)c1ccc(-n2cc3cc(-c4cc(CCC[C@H](C)N)cc(Cl)c4F)[nH]c3nc2=O)cc1] | 596.5 |
| 97 | 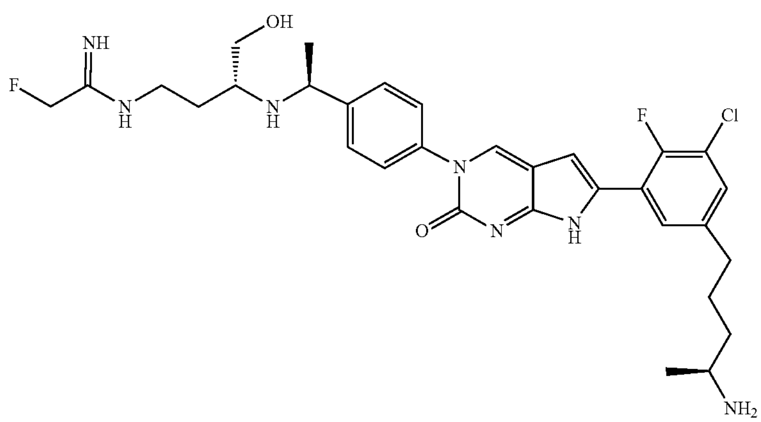 [SMILES: C[C@H](N)CCCc1cc(Cl)c(F)c(-c2cc3cn(-c4ccc([C@H](C)N[C@@H](CO)CCNC(=N)CF)cc4)c(=O)nc3[nH]2)c1] | 614.5 |
| 98 | 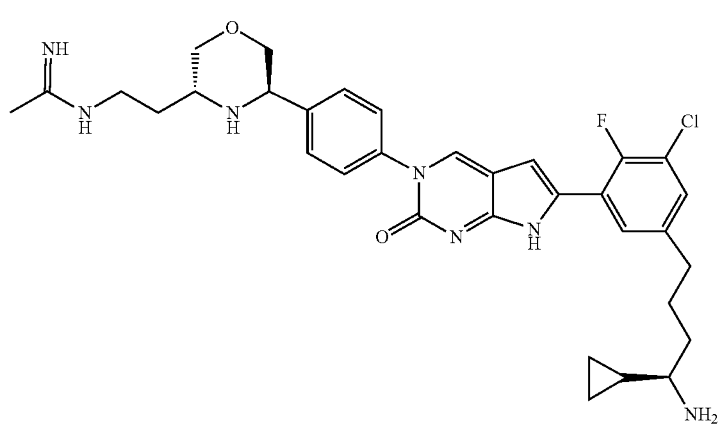 [SMILES: CC(=N)NCC[C@@H]1COC[C@@H](c2ccc(-n3cc4cc(-c5cc(CCC[C@@H](N)C6CC6)cc(Cl)c5F)[nH]c4nc3=O)cc2)N1] | 620.4 |

TABLE 2-continued

| # | Structure | ESI, m/z [M + H]+ |
|---|---|---|
| 99 | 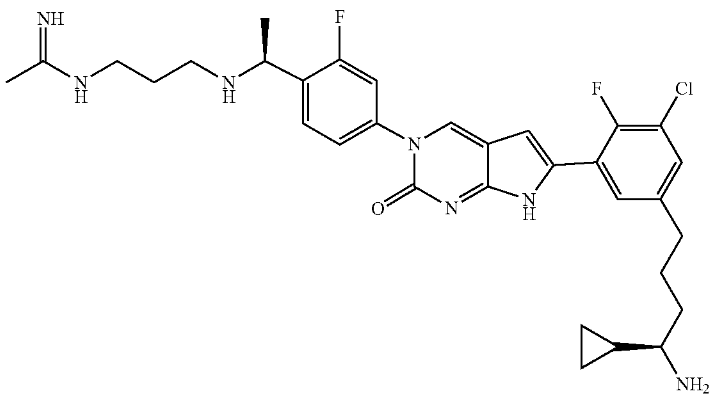 [SMILES: CC(=N)NCCCN[C@@H](C)c1ccc(-n2cc3cc(-c4cc(CCC[C@@H](N)C5CC5)cc(Cl)c4F)[nH]c3nc2=O)cc1F] | 610.5 |
| 100 | 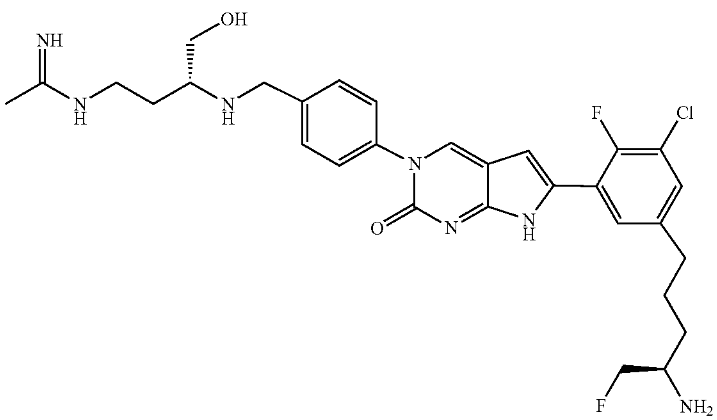 [SMILES: CC(=N)NCC[C@H](CO)NCc1ccc(-n2cc3cc(-c4cc(CCC[C@@H](N)CF)cc(Cl)c4F)[nH]c3nc2=O)cc1] | 600.4 |
| 101 | 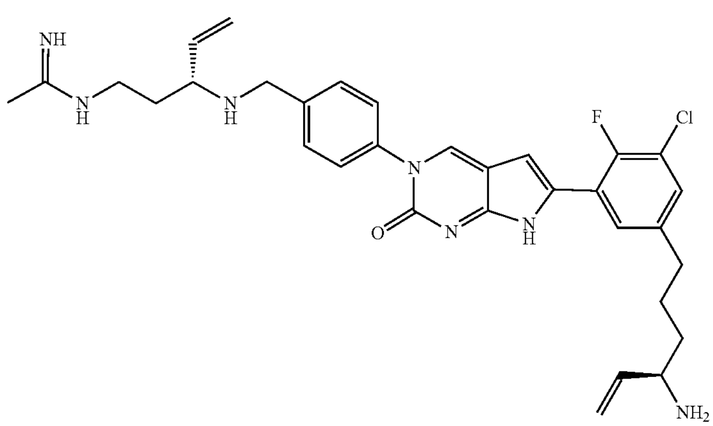 [SMILES: C=C[C@H](N)CCCc1cc(Cl)c(F)c(-c2cc3cn(-c4ccc(CN[C@@H](C=C)CCNC(C)=N)cc4)c(=O)nc3[nH]2)c1] | 590.5 |

TABLE 2-continued

| # | Structure | ESI, m/z [M + H]+ |
|---|---|---|
| 102 | 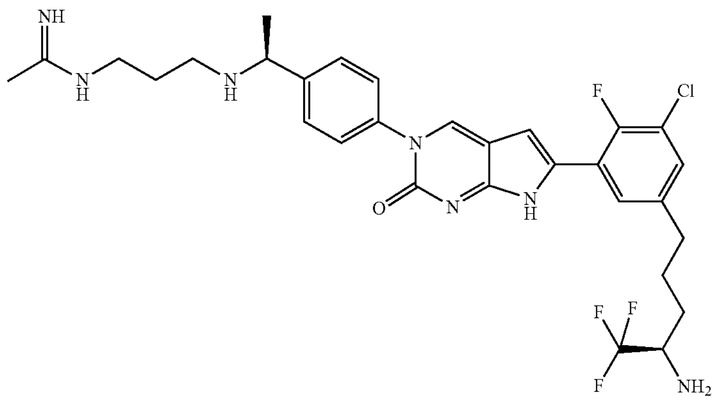 [SMILES: CC(=N)NCCCN[C@@H](C)c1ccc(-n2cc3cc(-c4cc(CCC[C@@H](N)C(F)(F)F)cc(Cl)c4F)[nH]c3nc2=O)cc1] | 620.4 |
| 103 | 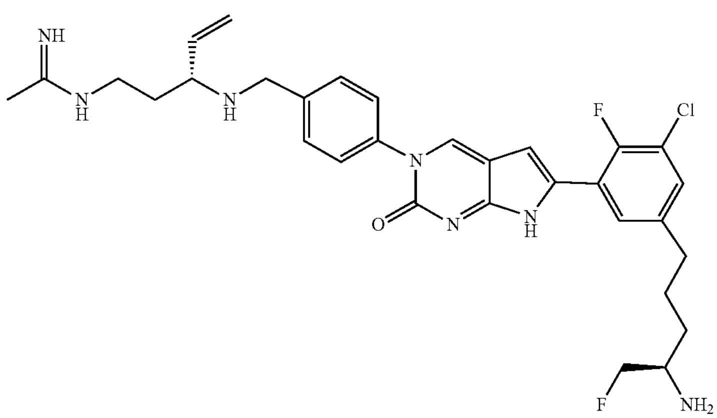 [SMILES: C=C[C@@H](CCNC(C)=N)NCc1ccc(-n2cc3cc(-c4cc(CCC[C@@H](N)CF)cc(Cl)c4F)[nH]c3nc2=O)cc1] | 596.5 |
| 104 | 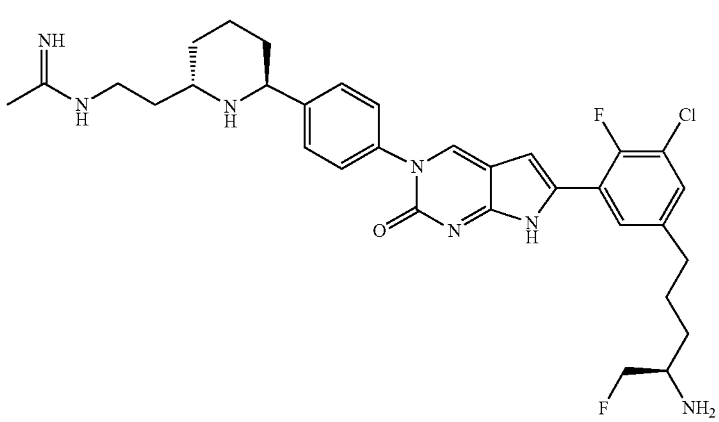 [SMILES: CC(=N)NCC[C@@H]1CCC[C@@H](c2ccc(-n3cc4cc(-c5cc(CCC[C@@H](N)CF)cc(Cl)c5F)[nH]c4nc3=O)cc2)N1] | 610.5 |

TABLE 2-continued

| # | Structure | ESI, m/z [M + H]+ |
|---|---|---|
| 105 | 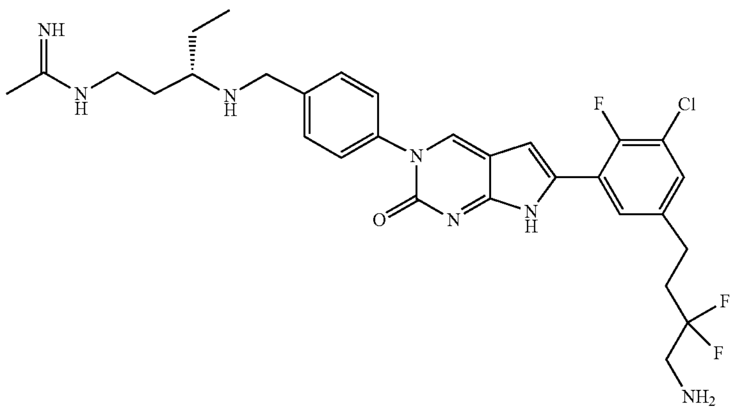 [SMILES: CC[C@@H](CCNC(C)=N)NCc1ccc(-n2cc3cc(-c4cc(CCC(F)(F)CN)cc(Cl)c4F)[nH]c3nc2=O)cc1] | 600.4 |
| 106 | 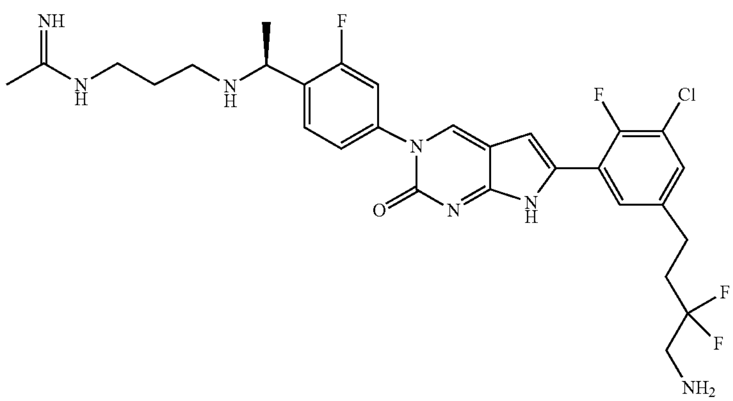 [SMILES: CC(=N)NCCCN[C@@H](C)c1ccc(-n2cc3cc(-c4cc(CCC(F)(F)CN)cc(Cl)c4F)[nH]c3nc2=O)cc1F] | 606.4 |
| 107 | 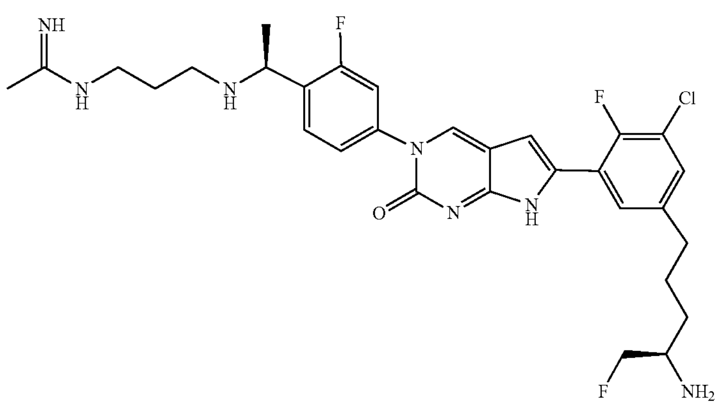 [SMILES: CC(=N)NCCCN[C@@H](C)c1ccc(-n2cc3cc(-c4cc(CCC[C@@H](N)CF)cc(Cl)c4F)[nH]c3nc2=O)cc1F] | 602.4 |

TABLE 2-continued
| # | Structure | ESI, m/z [M + H]+ |
|---|---|---|
| 108 | 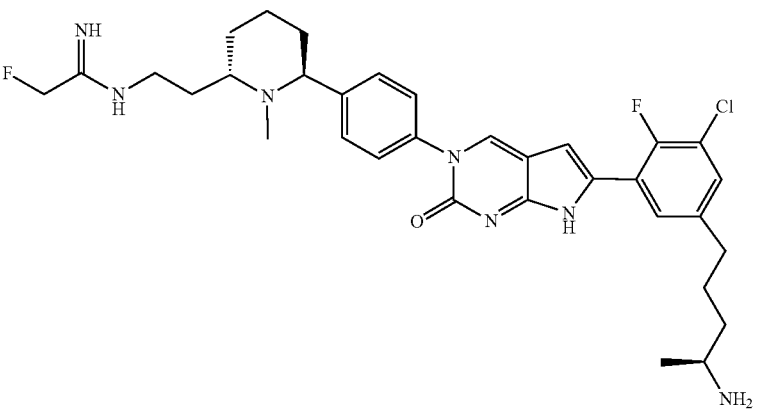 [SMILES: C[C@H](N)CCCc1cc(Cl)c(F)c(-c2cc3cn(-c4ccc([C@@H]5CCC[C@@H](CCNC(=N)CF)N5C)cc4)c(=O)nc3[nH]2)c1] | 624.5 |
| 109 | 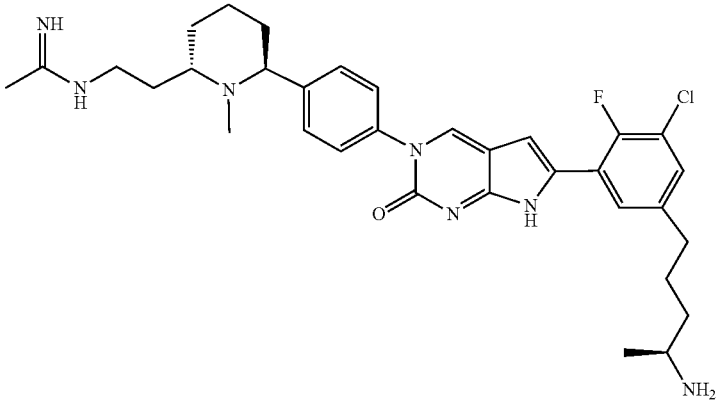 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1C] | 606.5 |
| 110 | 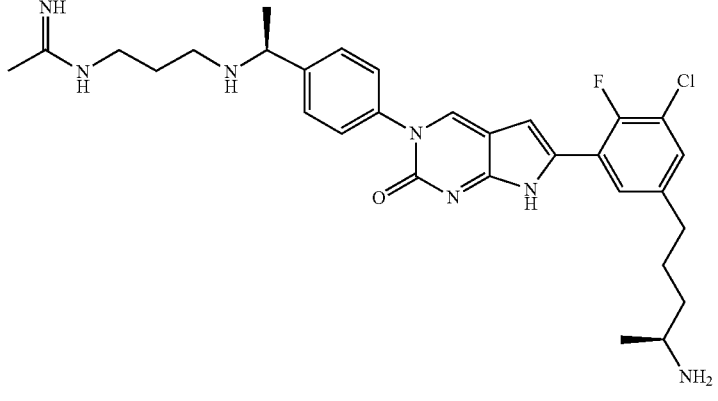 [SMILES: CC(=N)NCCCN[C@@H](C)c1ccc(-n2cc3cc(-c4cc(CCC[C@H](C)N)cc(Cl)c4F)[nH]c3nc2=O)cc1] | 566.4 |

TABLE 2-continued
| # | Structure | ESI, m/z [M + H]+ |
|---|---|---|
| 111 | 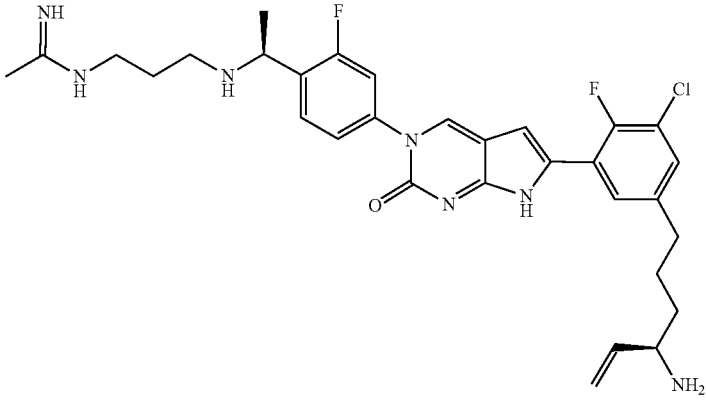 [SMILES: C=C[C@H](N)CCCc1cc(Cl)c(F)c(-c2cc3cn(-c4ccc([C@H](C)NCCCNC(C)=N)c(F)c4)c(=O)nc3[nH]2)c1] | 596.5 |
| 112 | 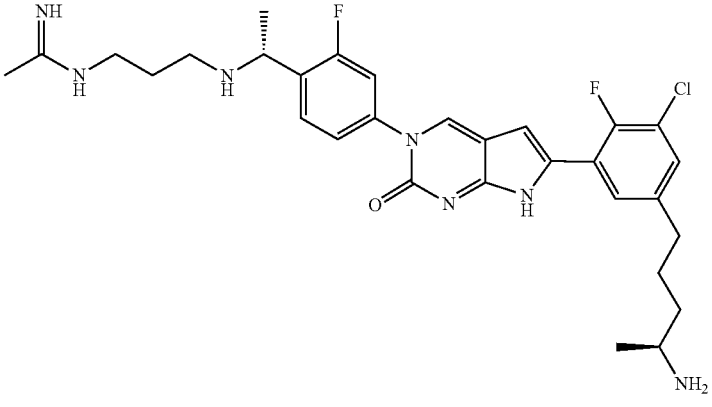 [SMILES: CC(=N)NCCCN[C@H](C)c1ccc(-n2cc3cc(-c4cc(CCC[C@H](C)N)cc(Cl)c4F)[nH]c3nc2=O)cc1F] | 584 |
| 113 | 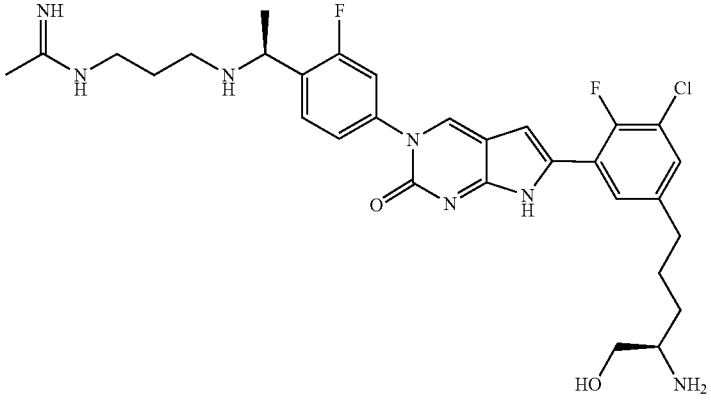 [SMILES: CC(=N)NCCCN[C@@H](C)c1ccc(-n2cc3cc(-c4cc(CCC[C@@H](N)CO)cc(Cl)c4F)[nH]c3nc2=O)cc1F] | 600 |

TABLE 2-continued

| # | Structure | ESI, m/z [M + H]+ |
|---|---|---|
| 114 | 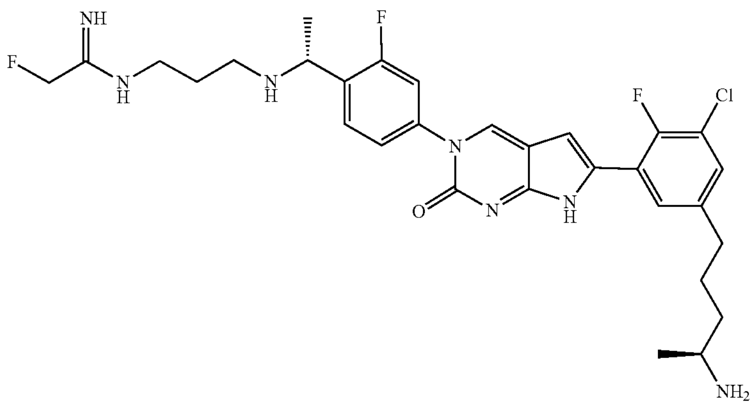 [SMILES: C[C@H](N)CCCc1cc(Cl)c(F)c(-c2cc3cn(-c4ccc([C@@H](C)NCCCNC(=N)CF)c(F)c4)c(=O)nc3[nH]2)c1] | 602 |
| 115 | 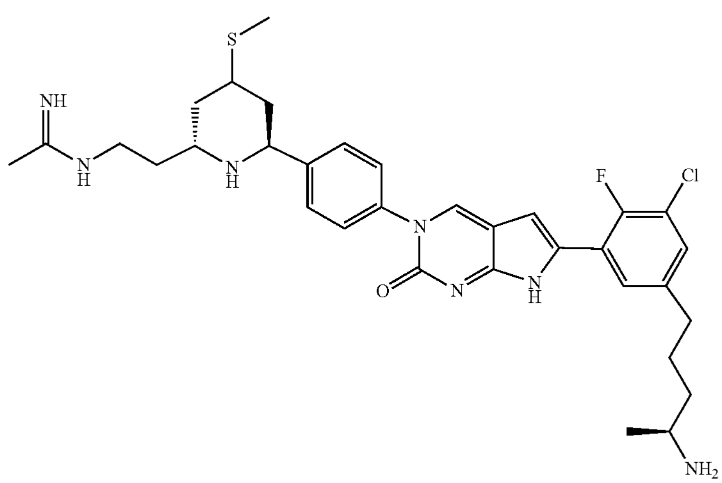 | 638.5 |
| 116 | 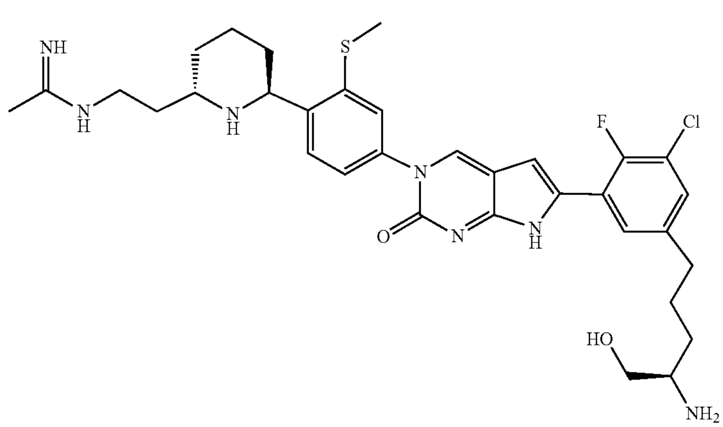 | 654.5 |

TABLE 2-continued
| # | Structure | ESI, m/z [M + H]+ |
|---|-----------|---------------------|
| 117 | 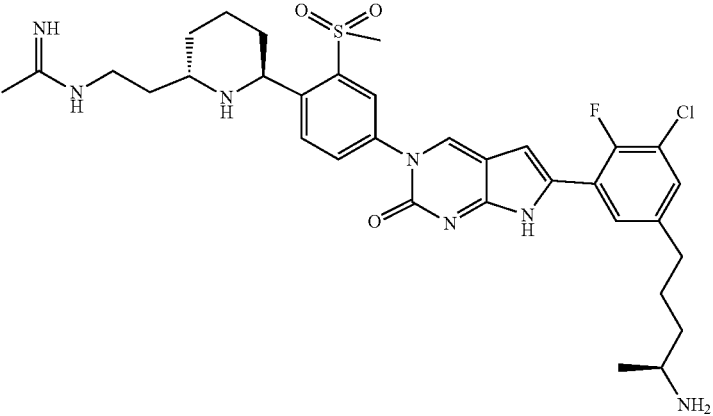 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2S(C)(=O)=O)N1] | 670.5 |
| 118 | 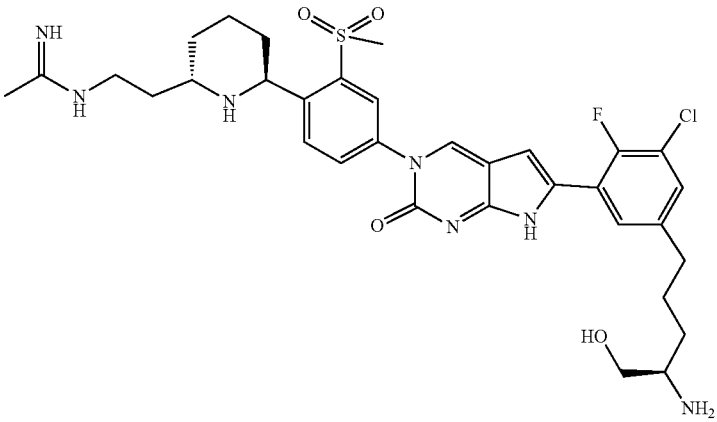 [SMILES: CC(=N)NCC[C@@H]1CCC[C@@H](c2ccc(-n3cc4cc(-c5cc(CCC[C@@H](N)CO)cc(Cl)c5F)[nH]c4nc3=O)cc2S(C)(=O)=O)N1] | 686.1 |
| 119 | 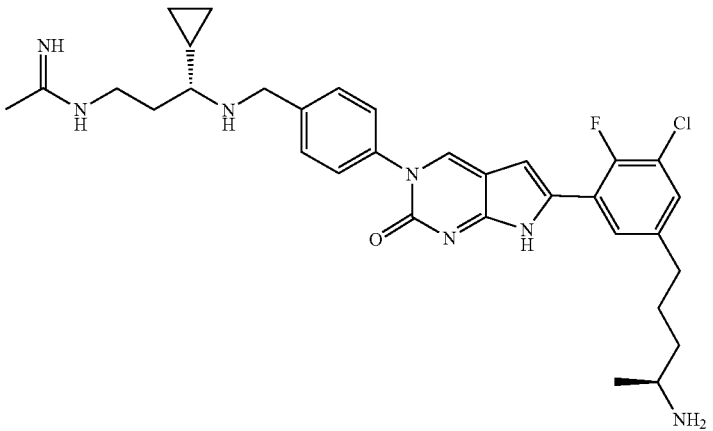 [SMILES: CC(=N)NCC[C@@H](NCc1ccc(-n2cc3cc(-c4cc(CCC[C@H](C)N)cc(Cl)c4F)[nH]c3nc2=O)cc1)C1CC1] | 592.5 |

TABLE 2-continued
| # | Structure | ESI, m/z [M + H]+ |
|---|---|---|
| 120 | 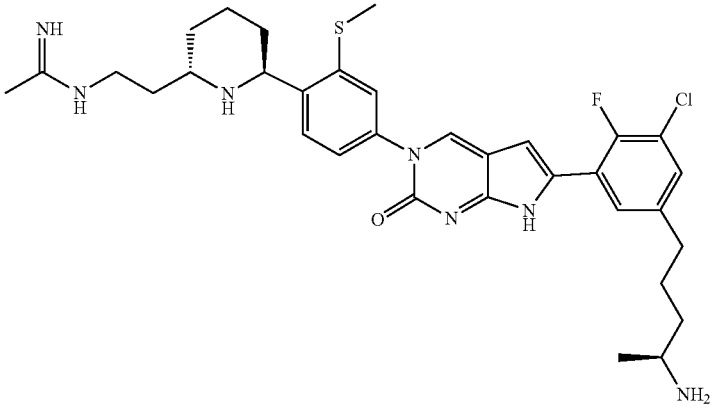 [SMILES: CSc1cc(-n2cc3cc(-c4cc(CCC[C@H](C)N)cc(Cl)c4F)[nH]c3nc2=O)ccc1[C@@H]1CCC[C@@H](CCNC(C)=N)N1] | 664.5 |
| 121 | 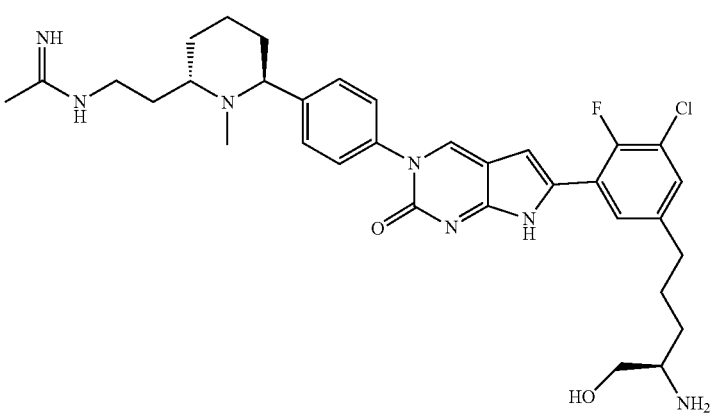 [SMILES: CC(=N)NCC[C@@H]1CCC[C@@H](c2ccc(-n3cc4cc(-c5cc(CCC[C@@H](N)CO)cc(Cl)c5F)[nH]c4nc3=O)cc2)N1C] | 622.5 |
| 122 | 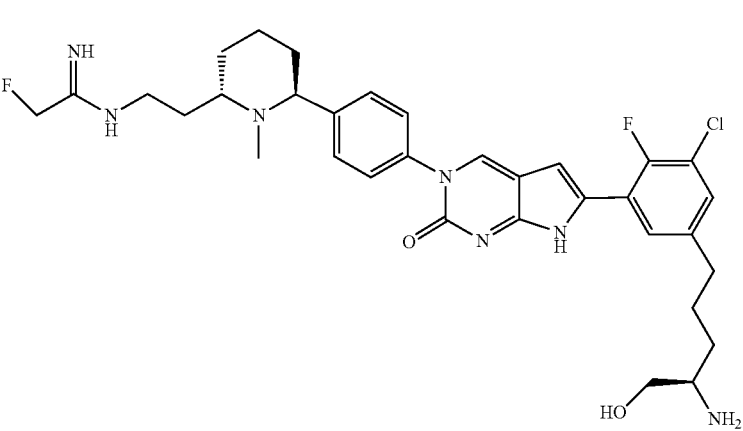 [SMILES: CN1[C@H](CCNC(=N)CF)CCC[C@H]1c1ccc(-n2cc3cc(-c4cc(CCC[C@@H](N)CO)cc(Cl)c4F)[nH]c3nc2=O)cc1] | 640.5 |

TABLE 2-continued
| # | Structure | ESI, m/z [M + H]+ |
|---|---|---|
| 123 | 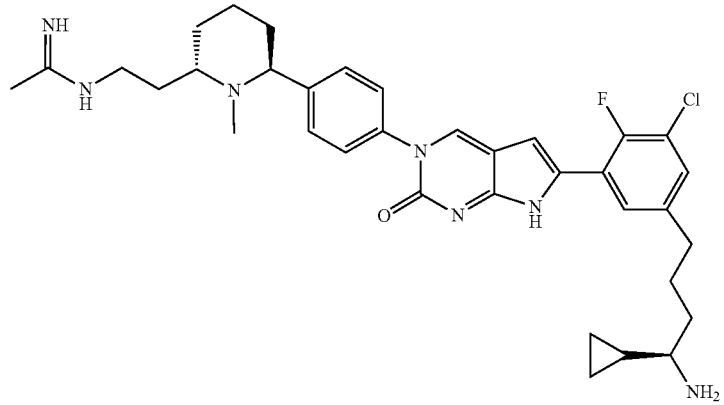 [SMILES: CC(=N)NCC[C@@H]1CCC[C@@H](c2ccc(-n3cc4cc(-c5cc(CCC[C@@H](N)C6CC6)cc(Cl)c5F)[nH]c4nc3=O)cc2)N1C] | 632.5 |
| 124 | 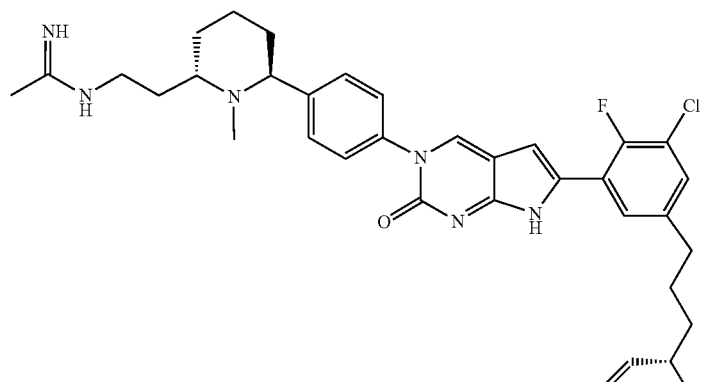 | 618.5 |
| 125 | 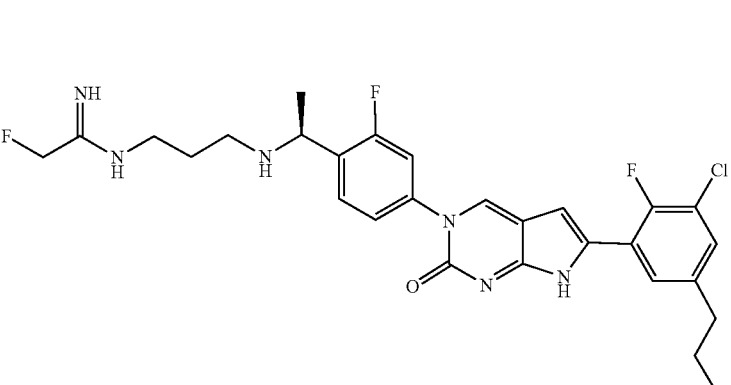 | 618 |

TABLE 2-continued
| # | Structure | ESI, m/z [M + H]+ |
|---|---|---|
| 126 | 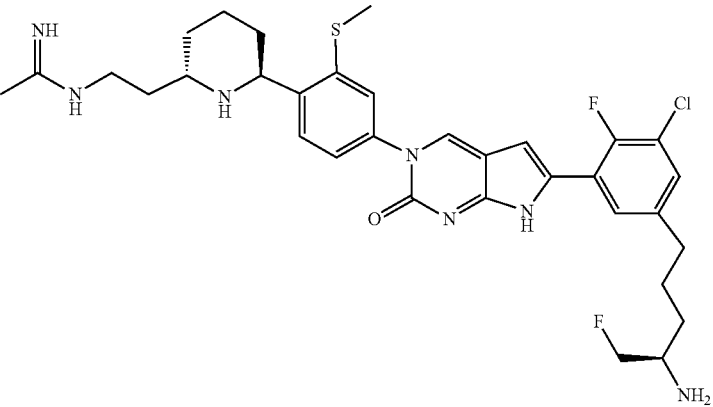 [SMILES: CSc1cc(-n2cc3cc(-c4cc(CCC[C@@H](N)CF)cc(Cl)c4F)[nH]c3nc2=O)ccc1[C@@H]1CCC[C@@H](CCNC(C)=N)N1] | 656.5 |
| 127 | 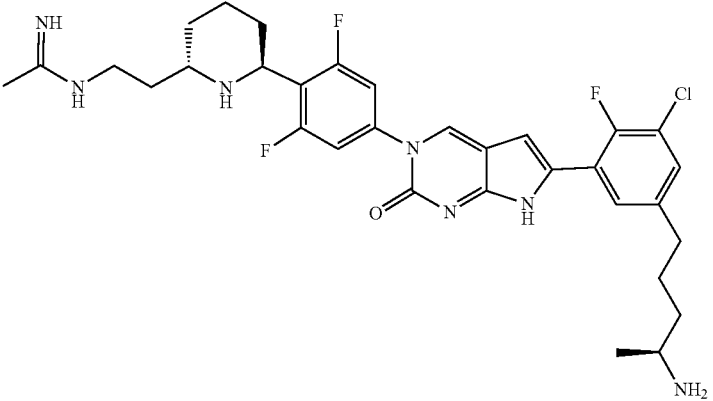 [SMILES: CC(=N)NCC[C@@H]1CCC[C@@H](c2c(F)cc(-n3cc4cc(-c5cc(CCC[C@H](C)N)cc(Cl)c5F)[nH]c4nc3=O)cc2F)N1] | 628.5 |
| 128 | 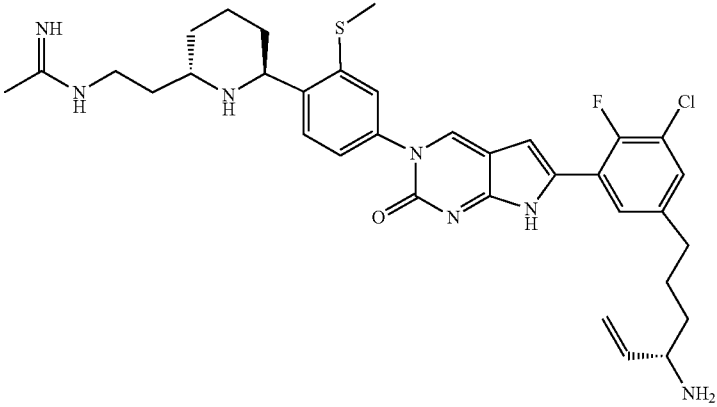 [SMILES: C=C[C@@H](N)CCCc1cc(Cl)c(F)c(-c2cc3cn(-c4ccc([C@@H]5CCC[C@@H](CCNC(C)=N)N5)c(SC)c4)c(=O)nc3[nH]2)c1] | 650.5 |

TABLE 2-continued

| # | Structure | ESI, m/z [M + H]+ |
|---|---|---|
| 129 | 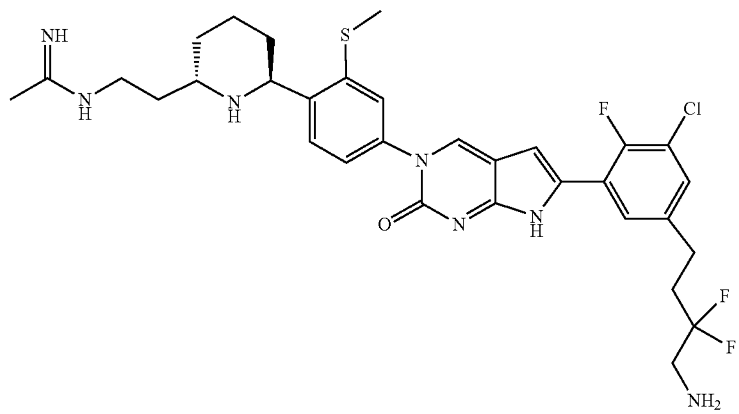 [SMILES: CSc1cc(-n2cc3cc(-c4cc(CCC(F)(F)CN)cc(Cl)c4F)[nH]c3nc2=O)ccc1[C@@H]1CCC[C@@H](CCNC(C)=N)N1] | 660.5 |
| 130 | 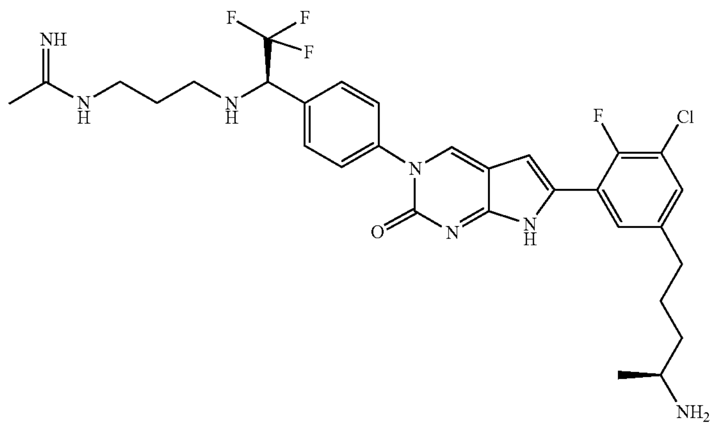 [SMILES: CC(=N)NCCCN[C@H](c1ccc(-n2cc3cc(-c4cc(CCC[C@H](C)N)cc(Cl)c4F)[nH]c3nc2=O)cc1)C(F)(F)F] | 620.4 |
| 131 | 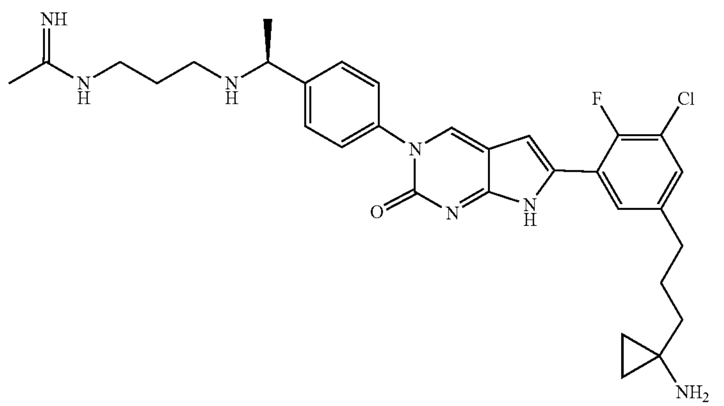 [SMILES: CC(=N)NCCCN[C@@H](C)c1ccc(-n2cc3cc(-c4cc(CCCC5(N)CC5)cc(Cl)c4F)[nH]c3nc2=O)cc1] | 578.5 |

TABLE 2-continued
| # | Structure | ESI, m/z [M + H]+ |
|---|---|---|
| 132 | 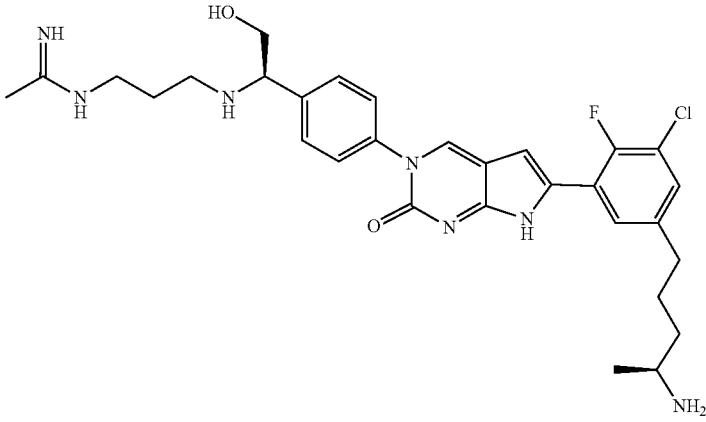 [SMILES: CC(=N)NCCCN[C@@H](CO)c1ccc(-n2cc3cc(-c4cc(CCC[C@H](C)N)cc(Cl)c4F)[nH]c3nc2=O)cc1] | 582.5 |
| 133 | 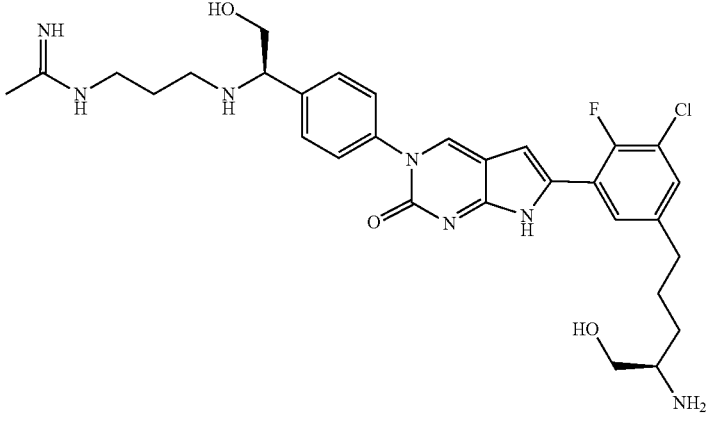 [SMILES: CC(=N)NCCCN[C@@H](CO)c1ccc(-n2cc3cc(-c4cc(CCC[C@@H](N)CO)cc(Cl)c4F)[nH]c3nc2=O)cc1] | 598.5 |
| 134 | 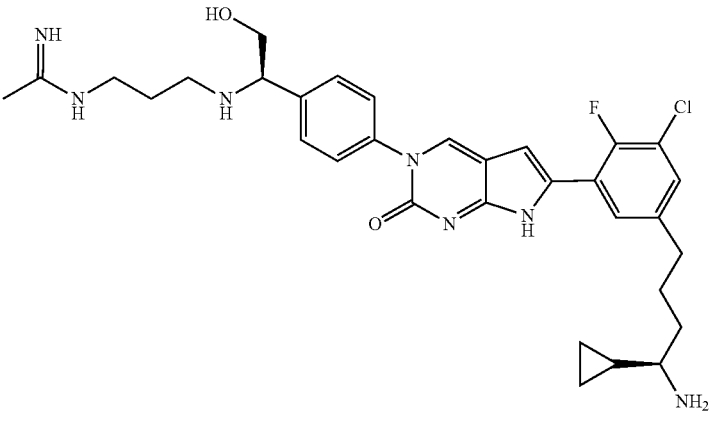 [SMILES: CC(=N)NCCCN[C@@H](CO)c1ccc(-n2cc3cc(-c4cc(CCC[C@@H](N)C5CC5)cc(Cl)c4F)[nH]c3nc2=O)cc1] | 608.5 |

TABLE 2-continued

| # | Structure | ESI, m/z [M + H]+ |
|---|-----------|-------------------|
| 135 | 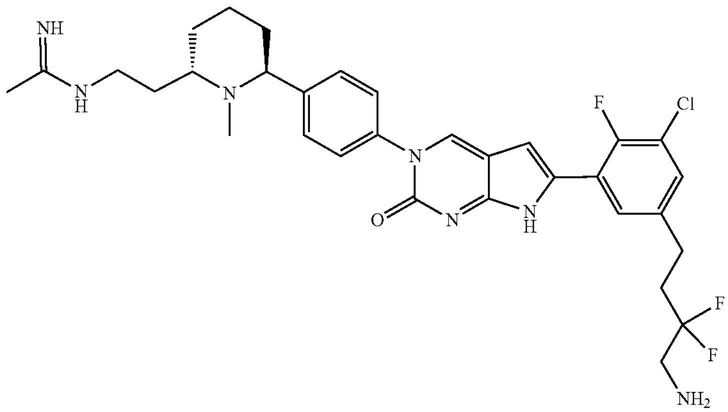 [SMILES: CC(=N)NCC[C@@H]1CCC[C@@H](c2ccc(-n3cc4cc(-c5cc(CCC(F)(F)CN)cc(Cl)c5F)[nH]c4nc3=O)cc2)N1C] | 628.5 |
| 136 | 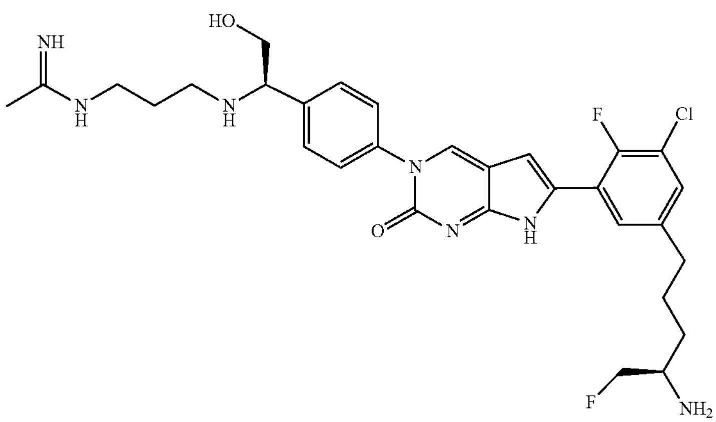 [SMILES: CC(=N)NCCCN[C@@H](CO)c1ccc(-n2cc3cc(-c4cc(CCC[C@@H](N)CF)cc(Cl)c4F)[nH]c3nc2=O)cc1] | 600.5 |
| 137 | 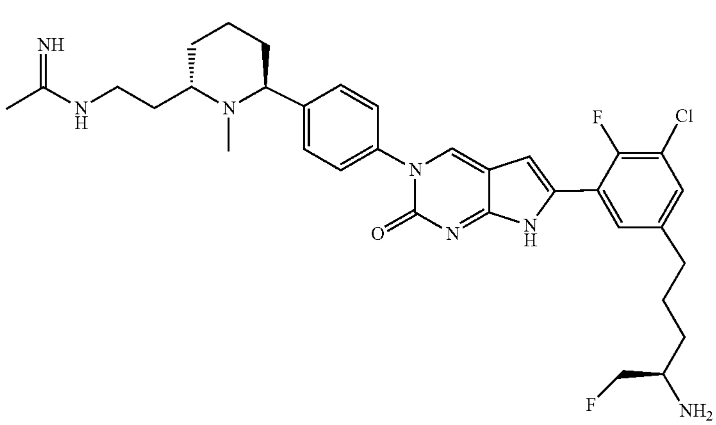 [SMILES: CC(=N)NCC[C@@H]1CCC[C@@H](c2ccc(-n3cc4cc(-c5cc(CCC[C@@H](N)CF)cc(Cl)c5F)[nH]c4nc3=O)cc2)N1C] | 624.5 |

TABLE 2-continued
| # | Structure | ESI, m/z [M + H]+ |
|---|---|---|
| 138 | 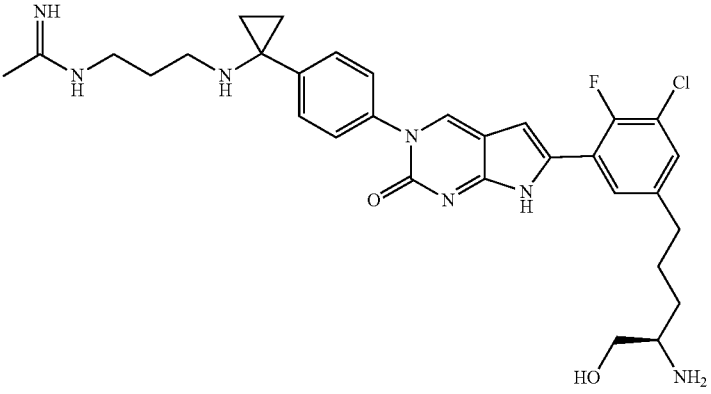 [SMILES: CC(=N)NCCCNC1(c2ccc(-n3cc4cc(-c5cc(CCC[C@@H](N)CO)cc(Cl)c5F)[nH]c4nc3=O)cc2)CC1] | 594.5 |
| 139 | 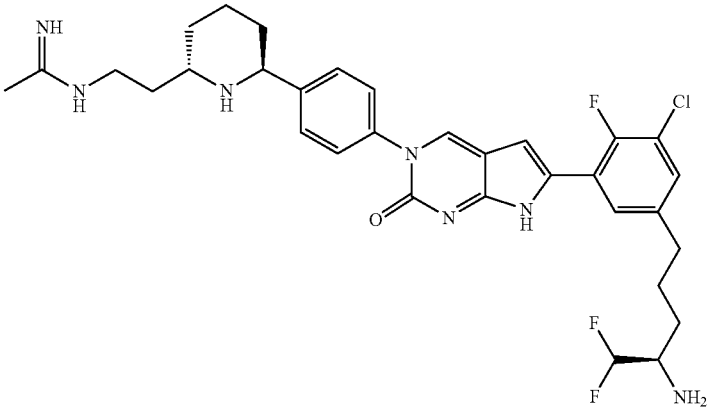 [SMILES: CC(=N)NCC[C@@H]1CCC[C@@H](c2ccc(-n3cc4cc(-c5cc(CCC[C@@H](N)C(F)F)cc(Cl)c5F)[nH]c4nc3=O)cc2)N1] | 628.5 |
| 140 | 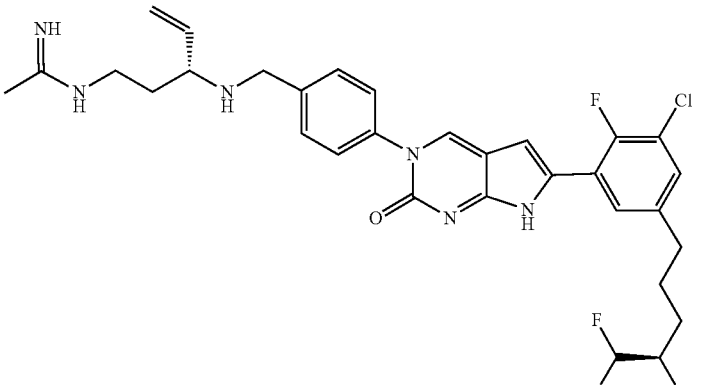 | 614.4 |

TABLE 2-continued

| # | Structure | ESI, m/z [M + H]+ |
|---|---|---|
| 141 | 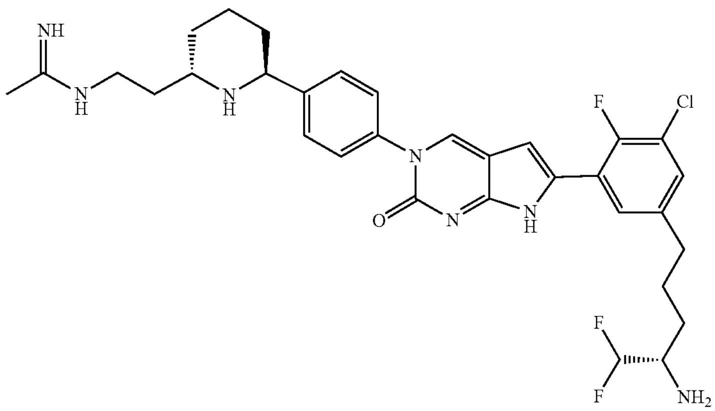 [SMILES: CC(=N)NCC[C@@H]1CCC[C@@H](c2ccc(-n3cc4cc(-c5cc(CCC[C@H](N)C(F)F)cc(Cl)c5F)[nH]c4nc3=O)cc2)N1] | 628.5 |
| 142 | 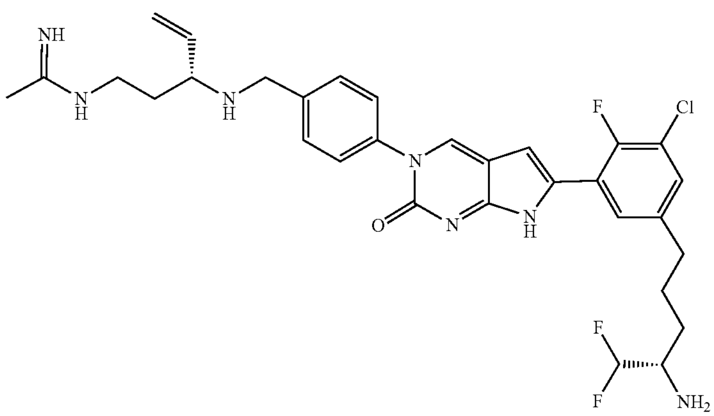 [SMILES: C=C[C@@H](CCNC(C)=N)NCc1ccc(-n2cc3cc(-c4cc(CCC[C@H](N)C(F)F)cc(Cl)c4F)[nH]c3nc2=O)cc1] | 614.5 |
| 143 | 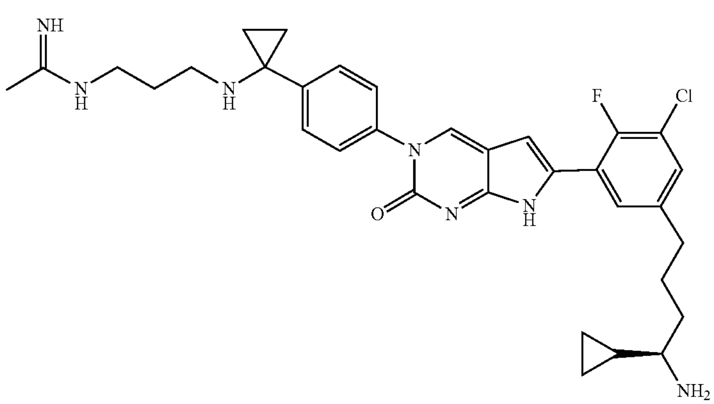 [SMILES: CC(=N)NCCCNC1(c2ccc(-n3cc4cc(-c5cc(CCC[C@@H](N)C6CC6)cc(Cl)c5F)[nH]c4nc3=O)cc2)CC1] | 604.4 |

TABLE 2-continued
| # | Structure | ESI, m/z [M + H]+ |
|---|---|---|
| 144 | 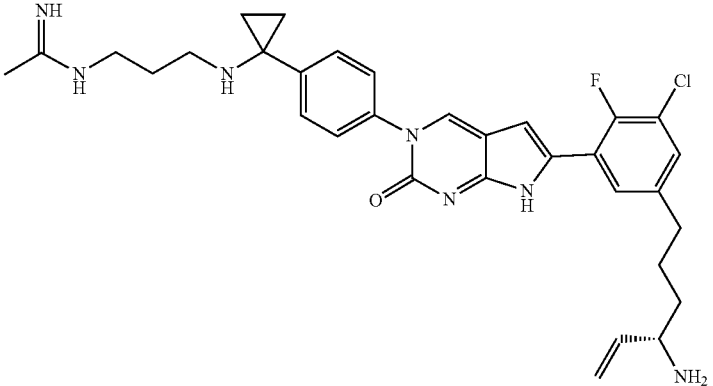 [SMILES: C=C[C@@H](N)CCCc1cc(Cl)c(F)c(-c2cc3cn(-c4ccc(C5(NCCCNC(C)=N)CC5)cc4)c(=O)nc3[nH]2)c1] | 590.5 |
| 145 | 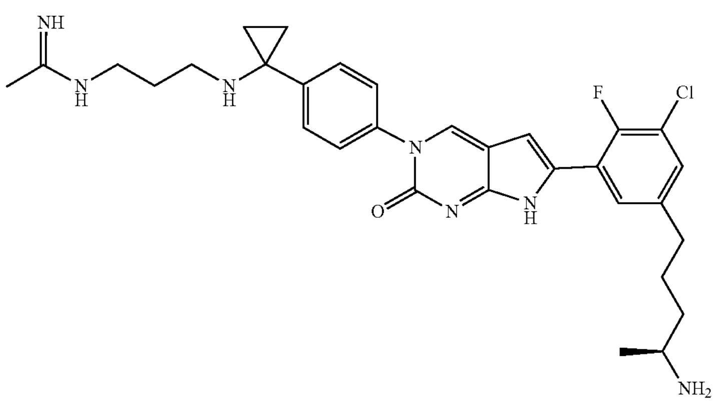 [SMILES: CC(=N)NCCCNC1(c2ccc(-n3cc4cc(-c5cc(CCC[C@H](C)N)cc(Cl)c5F)[nH]c4nc3=O)cc2)CC1] | 578.4 |
| 146 | 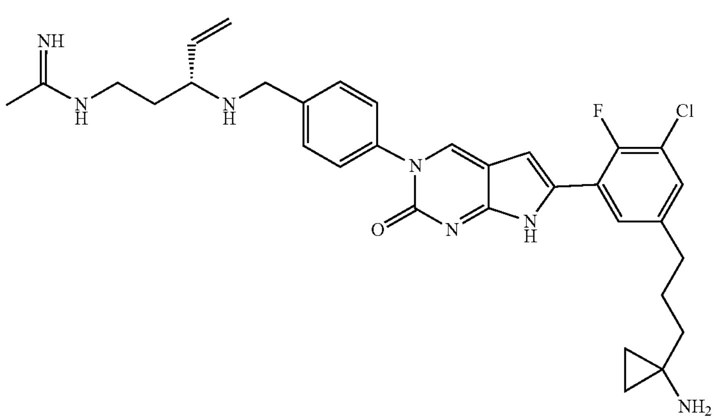 [SMILES: C=C[C@@H](CCNC(C)=N)NCc1ccc(-n2cc3cc(-c4cc(CCCC5(N)CC5)cc(Cl)c4F)[nH]c3nc2=O)cc1] | 590.4 |

TABLE 2-continued
| # | Structure | ESI, m/z [M + H]+ |
|---|---|---|
| 147 | 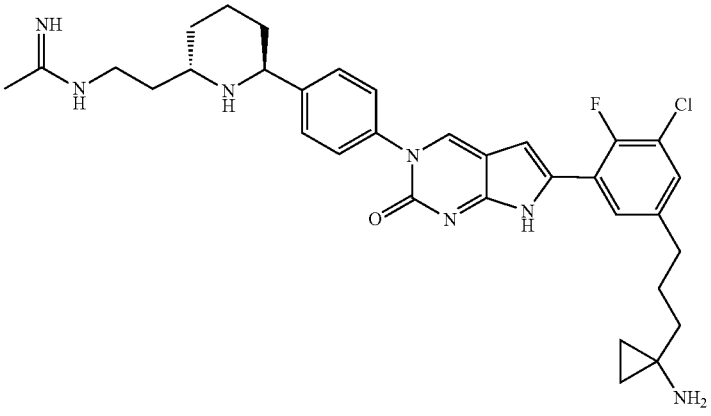 [SMILES: CC(=N)NCC[C@@H]1CCC[C@@H](c2ccc(-n3cc4cc(-c5cc(CCCC6(N)CC6)cc(Cl)c5F)[nH]c4nc3=O)cc2)N1] | 604.5 |
| 148 | 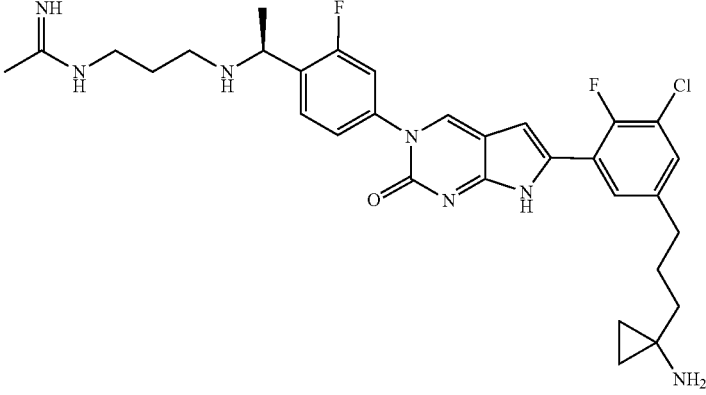 [SMILES: CC(=N)NCCCN[C@@H](C)c1ccc(-n2cc3cc(-c4cc(CCCC5(N)CC5)cc(Cl)c4F)[nH]c3nc2=O)cc1F] | 596.5 |
| 149 | 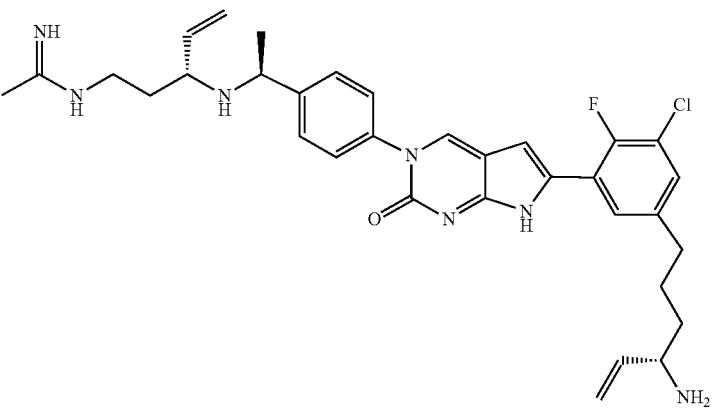 [SMILES: C=C[C@@H](N)CCCc1cc(Cl)c(F)c(-c2cc3cn(-c4ccc([C@H](C)N[C@@H](C=C)CCNC(C)=N)cc4)c(=O)nc3[nH]2)c1] | 604.5 |

TABLE 2-continued
| # | Structure | ESI, m/z [M + H]+ |
|---|-----------|-------------------|
| 150 | 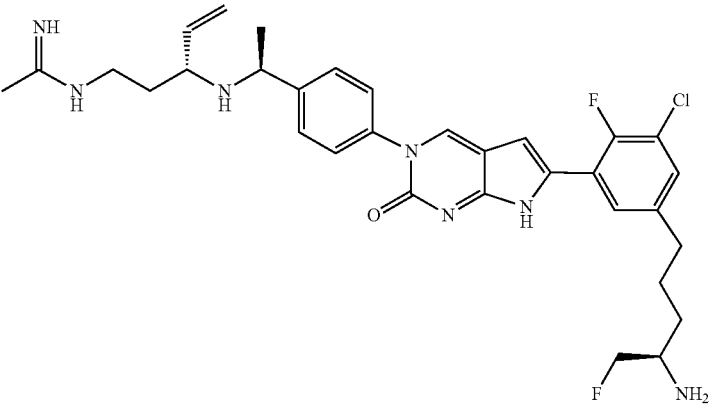 [SMILES: C=C[C@@H](CCNC(C)=N)N[C@@H](C)c1ccc(-n2cc3cc(-c4cc(CCC[C@@H](N)CF)cc(Cl)c4F)[nH]c3nc2=O)cc1] | 610.5 |
| 151 | 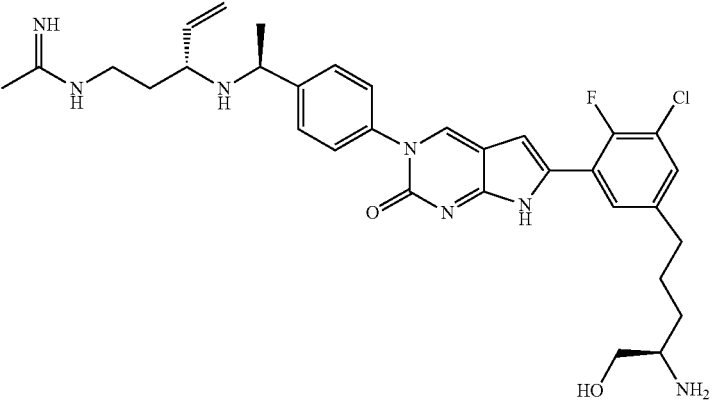 [SMILES: C=C[C@@H](CCNC(C)=N)N[C@@H](C)c1ccc(-n2cc3cc(-c4cc(CCC[C@@H](N)CO)cc(Cl)c4F)[nH]c3nc2=O)cc1] | 608.5 |
| 152 | 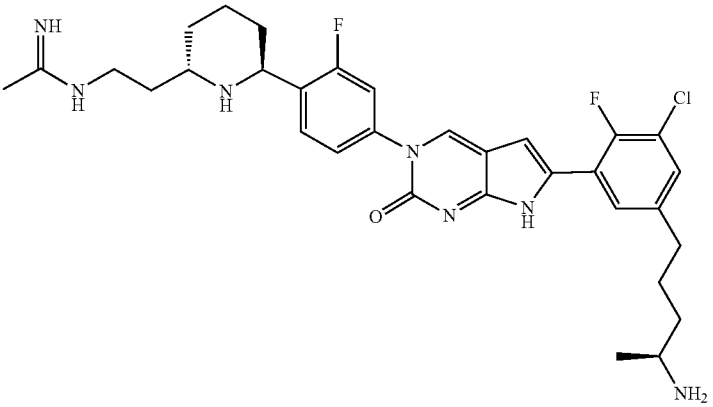 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2F)N1] | 610 |

TABLE 2-continued

| # | Structure | ESI, m/z [M + H]+ |
|---|---|---|
| 153 | 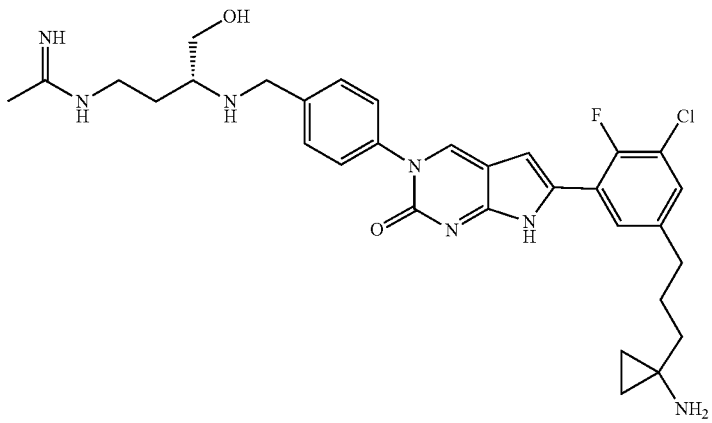 [SMILES: CC(=N)NCC[C@H](CO)NCc1ccc(-n2cc3cc(-c4cc(CCCC5(N)CC5)cc(Cl)c4F)[nH]c3nc2=O)cc1] | 594.5 |
| 154 | 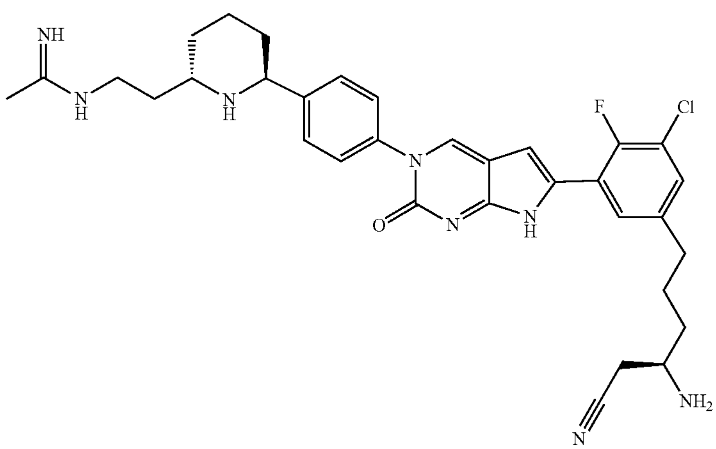 [SMILES: CC(=N)NCC[C@@H]1CCC[C@@H](c2ccc(-n3cc4cc(-c5cc(CCC[C@@H](N)CC#N)cc(Cl)c5F)[nH]c4nc3=O)cc2)N1] | 617.5 |
| 155 | 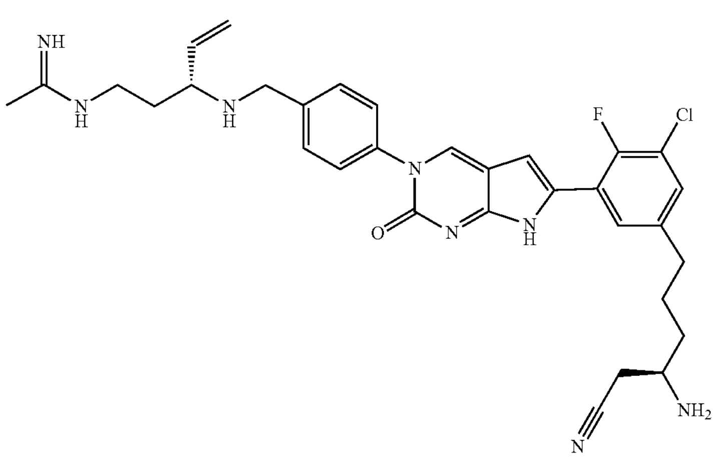 [SMILES: C=C[C@@H](CCNC(C)=N)NCc1ccc(-n2cc3cc(-c4cc(CCC[C@@H](N)CC#N)cc(Cl)c4F)[nH]c3nc2=O)cc1] | 603.4 |

TABLE 2-continued
| # | Structure | ESI, m/z [M + H]+ |
|---|---|---|
| 156 | 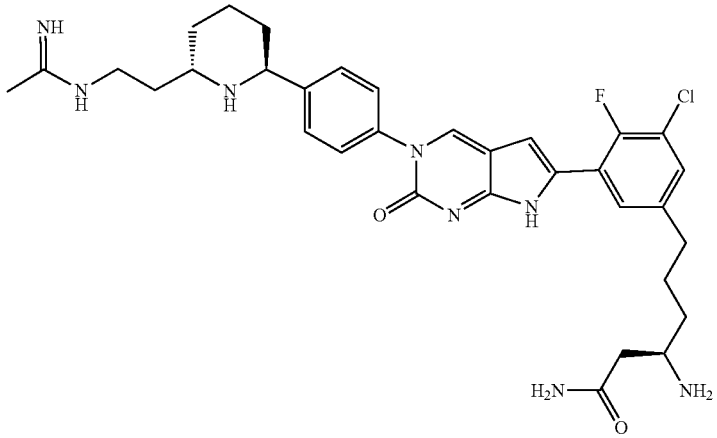 [SMILES: CC(=N)NCC[C@@H]1CCC[C@@H](c2ccc(-n3cc4cc(-c5cc(CCC[C@@H](N)CC(N)=O)cc(Cl)c5F)[nH]c4nc3=O)cc2)N1] | 635.5 |
| 157 | 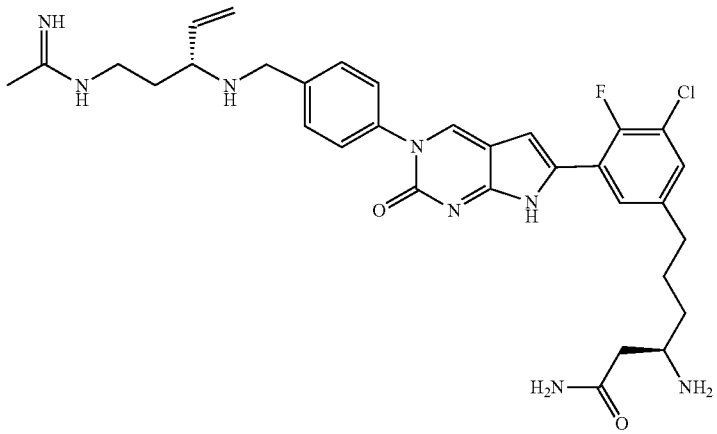 [SMILES: C=C[C@@H](CCNC(C)=N)NCc1ccc(-n2cc3cc(-c4cc(CCC[C@@H](N)CC(N)=O)cc(Cl)c4F)[nH]c3nc2=O)cc1] | 621.5 |
| 158 | 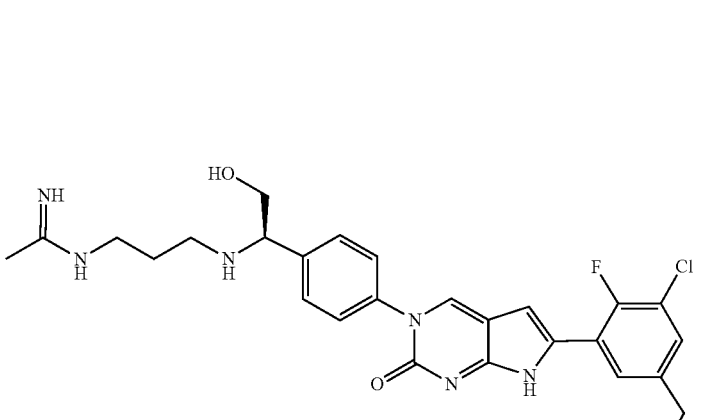 | 594.5 |

TABLE 2-continued

| # | Structure | ESI, m/z [M + H]+ |
|---|---|---|
| 159 | 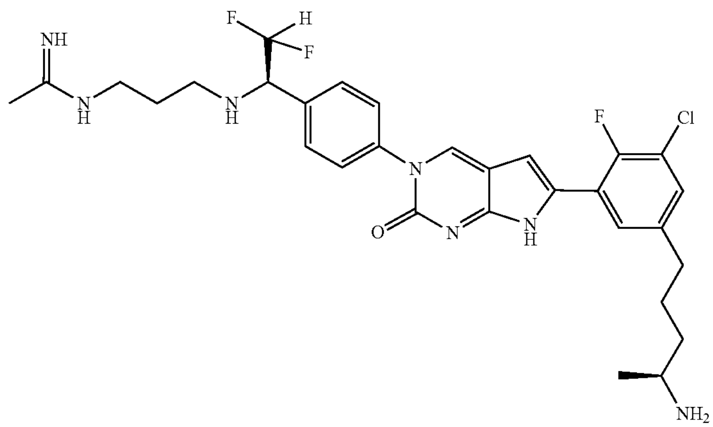 | 602.4 |
| 160 | 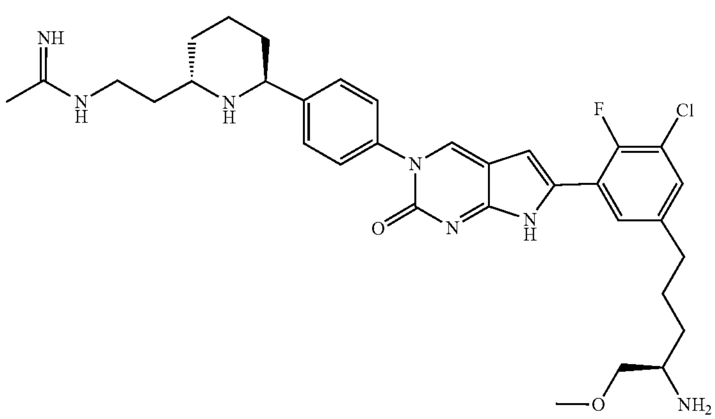 | 622.5 |
| 161 | 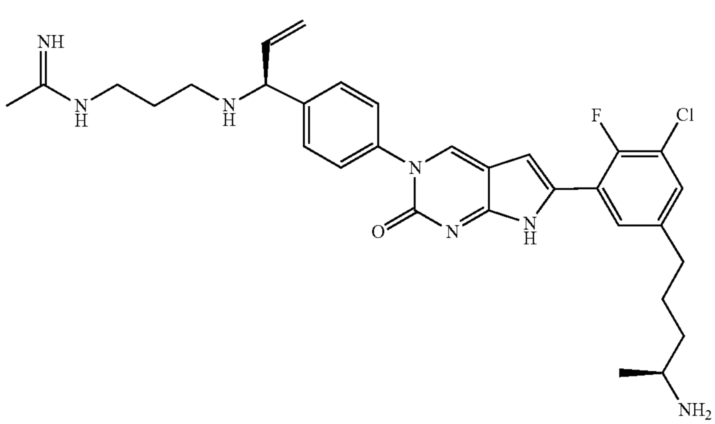 [SMILES: C=C[C@H](NCCCNC(C)=N)c1ccc(-n2cc3cc(-c4cc(CCC[C@H](C)N)cc(Cl)c4F)[nH]c3nc2=O)cc1] | 579 |

TABLE 2-continued

| # | Structure | ESI, m/z [M + H]+ |
|---|---|---|
| 162 | 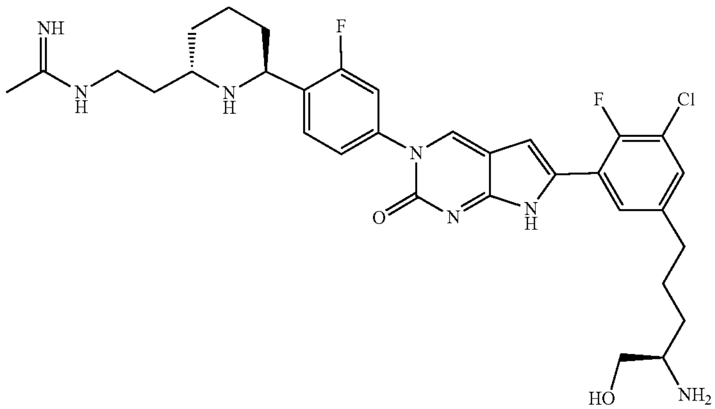 [SMILES: CC(=N)NCC[C@@H]1CCC[C@@H](c2ccc(-n3cc4cc(-c5cc(CCC[C@@H](N)CO)cc(Cl)c5F)[nH]c4nc3=O)cc2F)N1] | 626 |
| 163 | 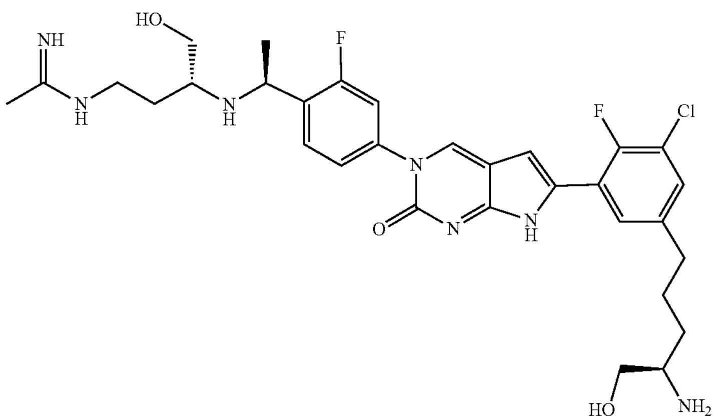 [SMILES: CC(=N)NCC[C@H](CO)N[C@@H](C)c1ccc(-n2cc3cc(-c4cc(CCC[C@@H](N)CO)cc(Cl)c4F)[nH]c3nc2=O)cc1F] | 630 |
| 164 | 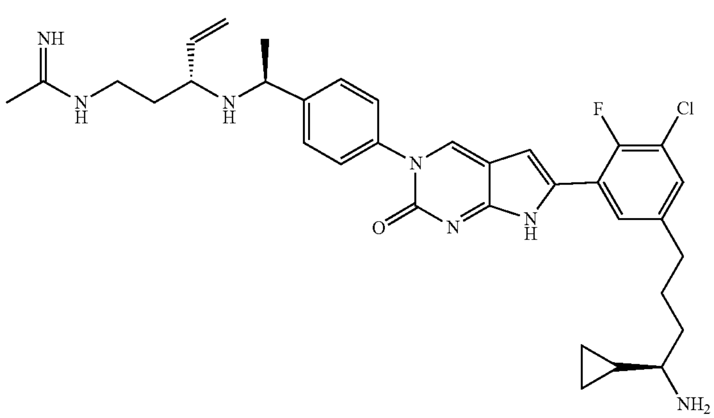 [SMILES: C=C[C@@H](CCNC(C)=N)N[C@@H](C)c1ccc(-n2cc3cc(-c4cc(CCC[C@@H](N)C5CC5)cc(Cl)c4F)[nH]c3nc2=O)cc1] | 618.5 |

TABLE 2-continued

| # | Structure | ESI, m/z [M + H]+ |
|---|-----------|-------------------|
| 165 | 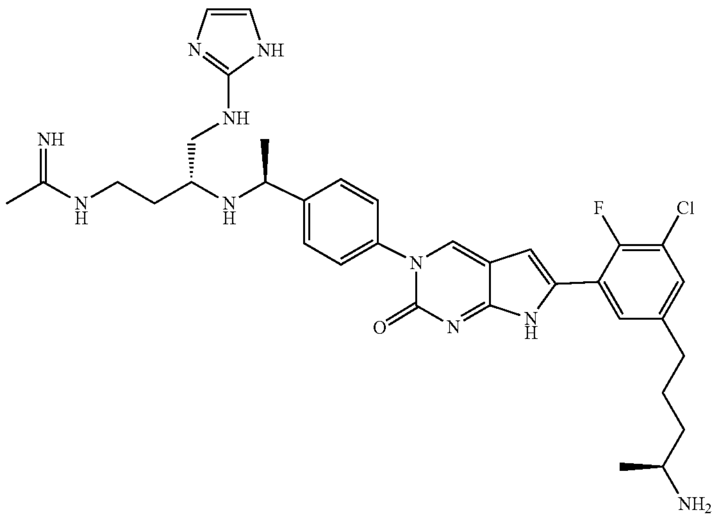 [SMILES: CC(=N)NCC[C@H](CNc1ncc[nH]1)N[C@@H](C)c1ccc(-n2cc3cc(-c4cc(CCC[C@H](C)N)cc(Cl)c4F)[nH]c3nc2=O)cc1] | 661.7 |
| 166 | 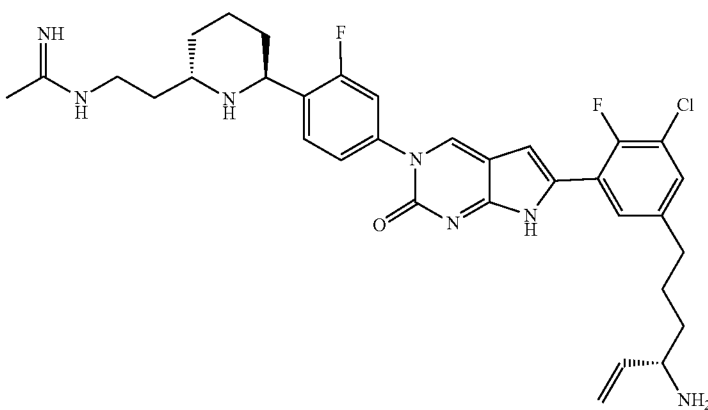 [SMILES: C=C[C@@H](N)CCCc1cc(Cl)c(F)c(-c2cc3cn(-c4ccc([C@@H]5CCC[C@@H](CCNC(C)=N)N5)c(F)c4)c(=O)nc3[nH]2)c1] | 622.6 |
| 167 | 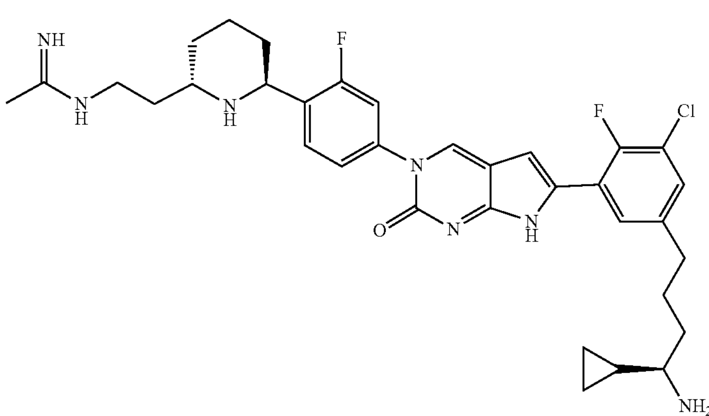 [SMILES: CC(=N)NCC[C@@H]1CCC[C@@H](c2ccc(-n3cc4cc(-c5cc(CCC[C@@H](N)C6CC6)cc(Cl)c5F)[nH]c4nc3=O)cc2F)N1] | 637.2 |

TABLE 2-continued
| # | Structure | ESI, m/z [M + H]+ |
|---|-----------|-------------------|
| 168 | 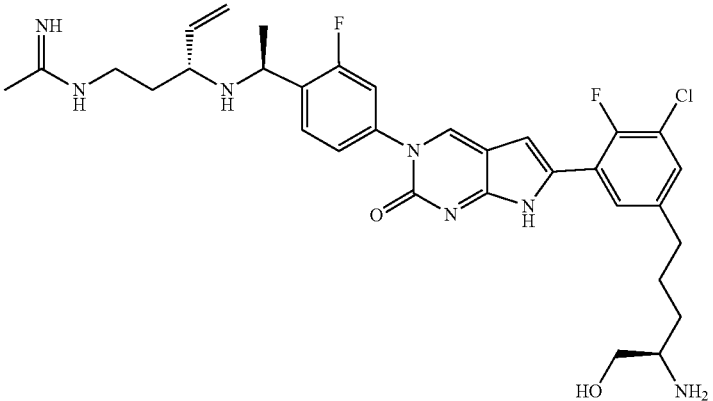 [SMILES: C=C[C@@H](CCNC(C)=N)N[C@@H](C)c1ccc(-n2cc3cc(-c4cc(CCC[C@@H](N)CO)cc(Cl)c4F)[nH]c3nc2=O)cc1F] | 626 |
| 169 | 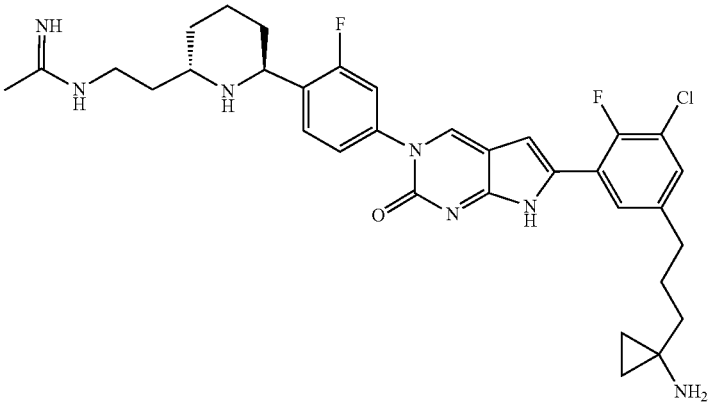 [SMILES: CC(=N)NCC[C@@H]1CCC[C@@H](c2ccc(-n3cc4cc(-c5cc(CCCC6(N)CC6)cc(Cl)c5F)[nH]c4nc3=O)cc2F)N1] | 622.5 |
| 170 | 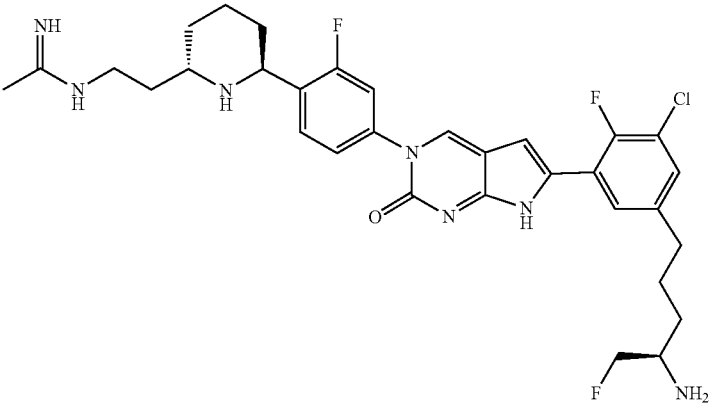 [SMILES: CC(=N)NCC[C@@H]1CCC[C@@H](c2ccc(-n3cc4cc(-c5cc(CCC[C@@H](N)CF)cc(Cl)c5F)[nH]c4nc3=O)cc2F)N1] | 628.3 |

TABLE 2-continued
| # | Structure | ESI, m/z [M + H]+ |
|---|---|---|
| 171 | 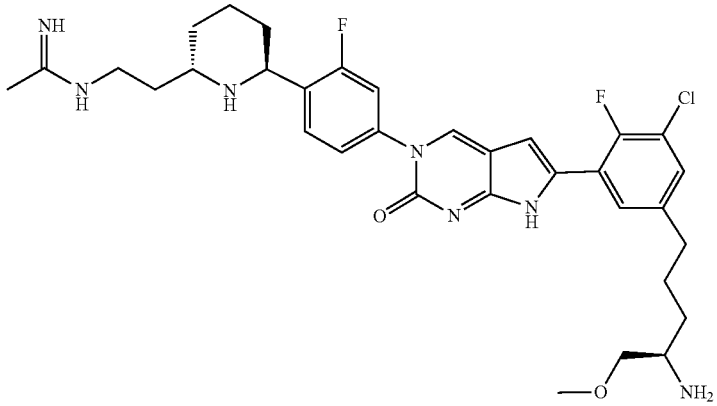 [SMILES: COC[C@H](N)CCCc1cc(Cl)c(F)c(-c2cc3cn(-c4ccc([C@@H]5CCC[C@@H](CCNC(C)=N)N5)c(F)c4)c(=O)nc3[nH]2)c1] | 640.6 |
| 172 | 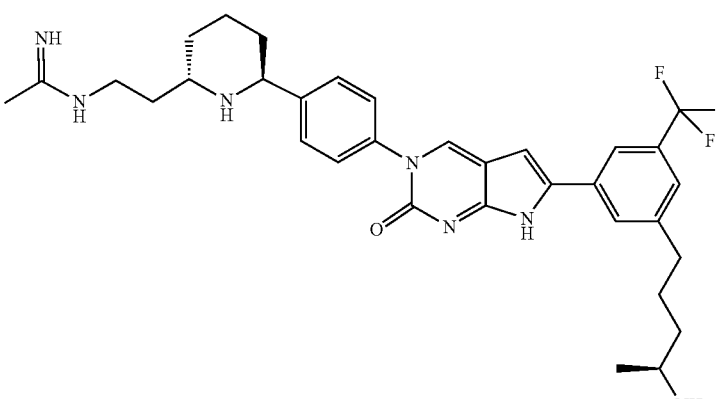 | 608.4 |
| 173 | 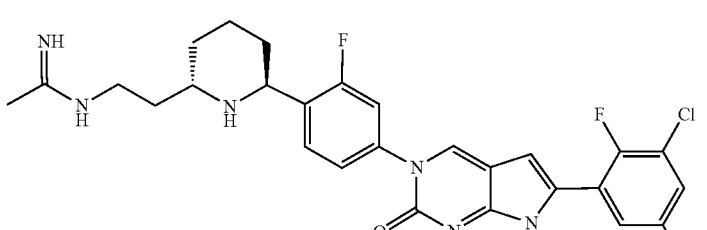 | 622.5 |

TABLE 2-continued
| # | Structure | ESI, m/z [M + H]+ |
|---|---|---|
| 174 | 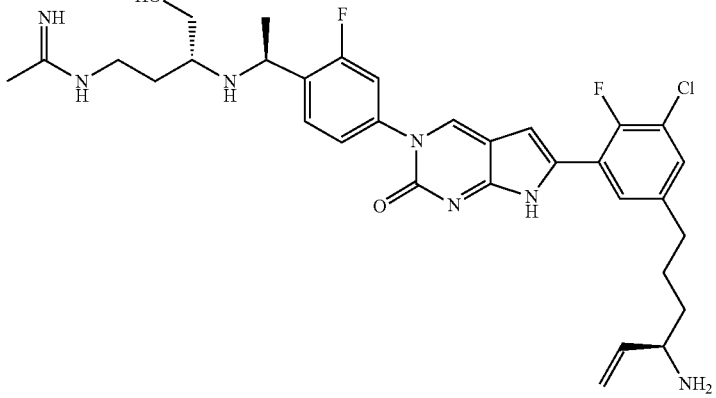 | 626.4 |
| 175 | 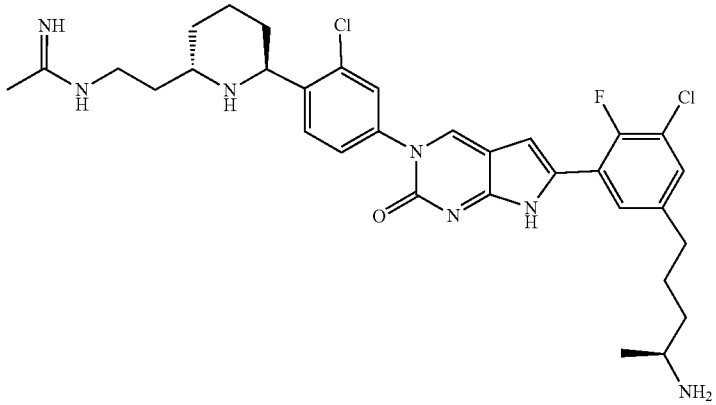 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2Cl)N1] | 626.6 |
| 176 | 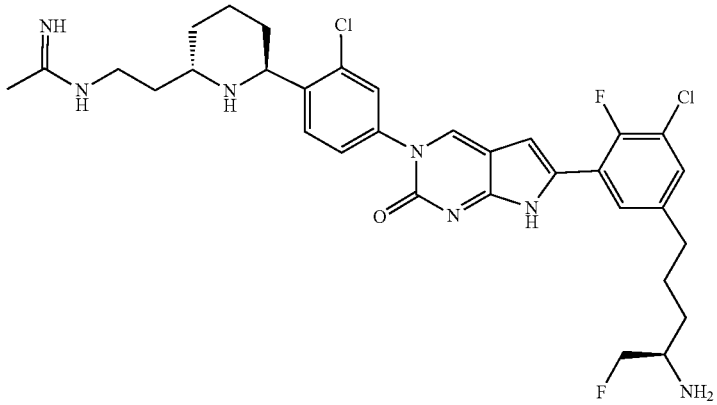 | 646.0 |

TABLE 2-continued

| # | Structure | ESI, m/z [M + H]+ |
|---|---|---|
| 177 | 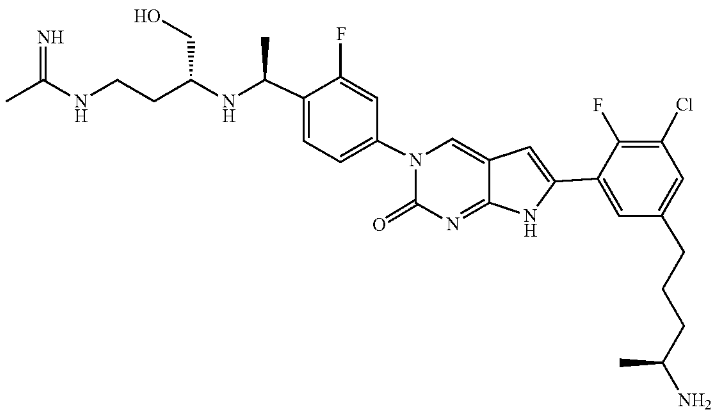 [SMILES: CC(=N)NCC[C@H](CO)N[C@@H](C)c1ccc(-n2cc3cc(-c4cc(CCC[C@H](C)N)cc(Cl)c4F)[nH]c3nc2=O)cc1F] | 614.4 |
| 178 | 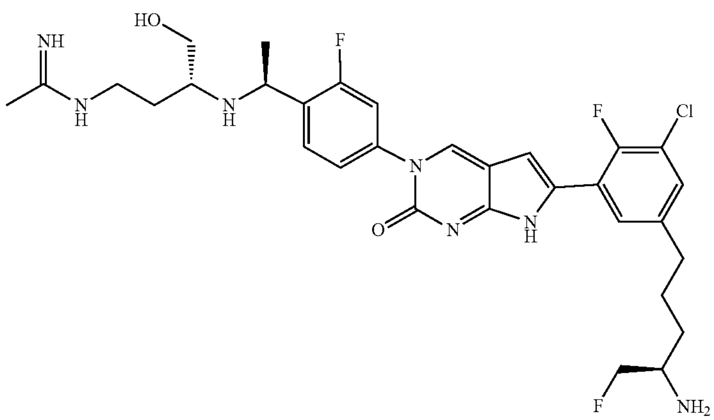 [SMILES: CC(=N)NCC[C@H](CO)N[C@@H](C)c1ccc(-n2cc3cc(-c4cc(CCC[C@@H](N)CF)cc(Cl)c4F)[nH]c3nc2=O)cc1F] | 632.3 |
| 179 | 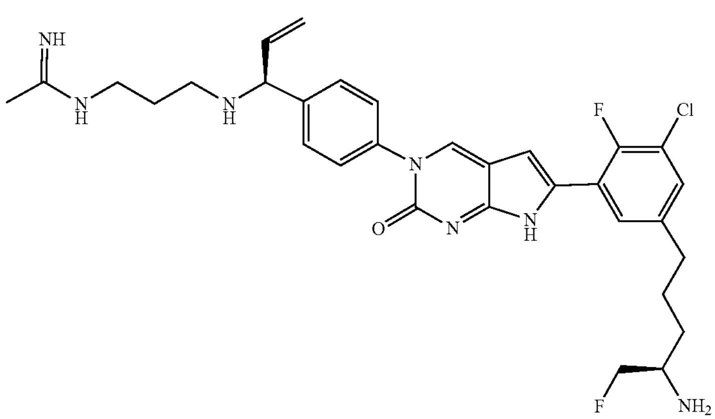 [SMILES: C=C[C@H](NCCCNC(C)=N)c1ccc(-n2cc3cc(-c4cc(CCC[C@@H](N)CF)cc(Cl)c4F)[nH]c3nc2=O)cc1] | 597 |

TABLE 2-continued
| # | Structure | ESI, m/z [M + H]+ |
|---|---|---|
| 180 | 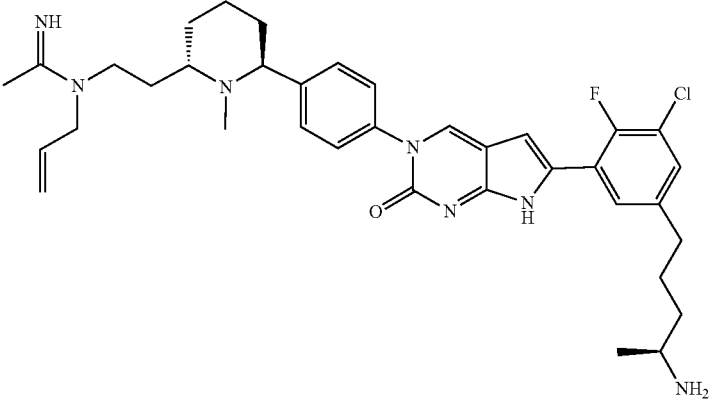 [SMILES: C=CCN(CC[C@@H]1CCC[C@@H](c2ccc(-n3cc4cc(-c5cc(CCC[C@H](C)N)cc(Cl)c5F)[nH]c4nc3=O)cc2)N1C)C(C)=N] | 646.5 |
| 181 | 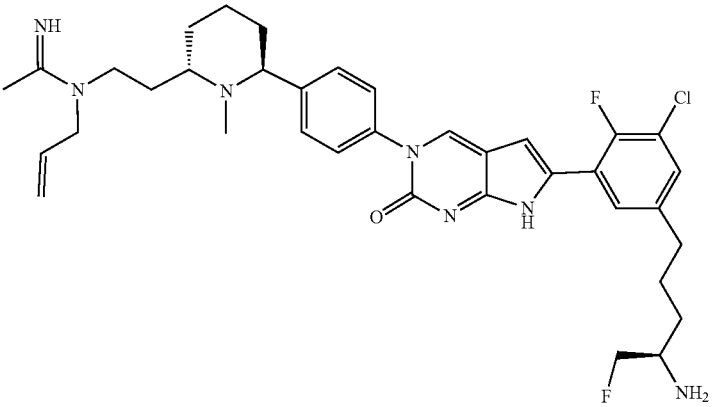 [SMILES: C=CCN(CC[C@@H]1CCC[C@@H](c2ccc(-n3cc4cc(-c5cc(CCC[C@@H](N)CF)cc(Cl)c5F)[nH]c4nc3=O)cc2)N1C)C(C)=N] | 664.5 |
| 182 | 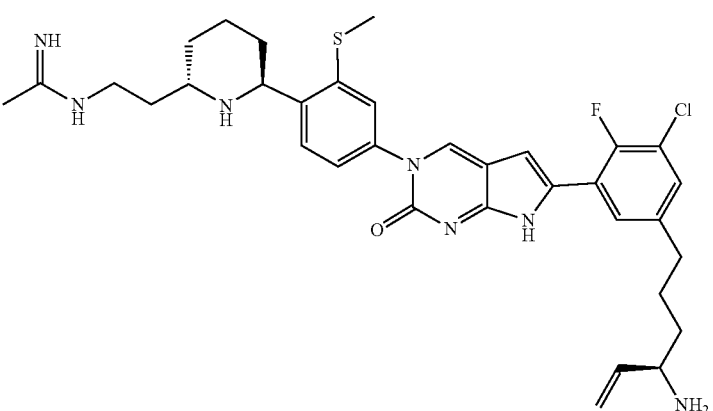 | 650.4 |

TABLE 2-continued

| # | Structure | ESI, m/z [M + H]+ |
|---|---|---|
| 183 | 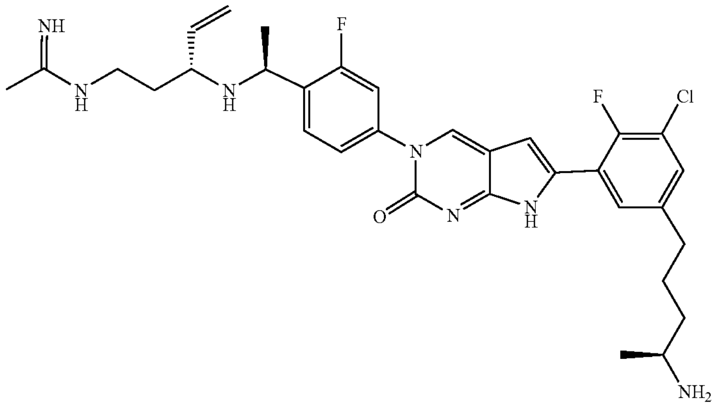 [SMILES: C=C[C@@H](CCNC(C)=N)N[C@@H](C)c1ccc(-n2cc3cc(-c4cc(CCC[C@H](C)N)cc(Cl)c4F)[nH]c3nc2=O)cc1F] | 610.4 |
| 184 | 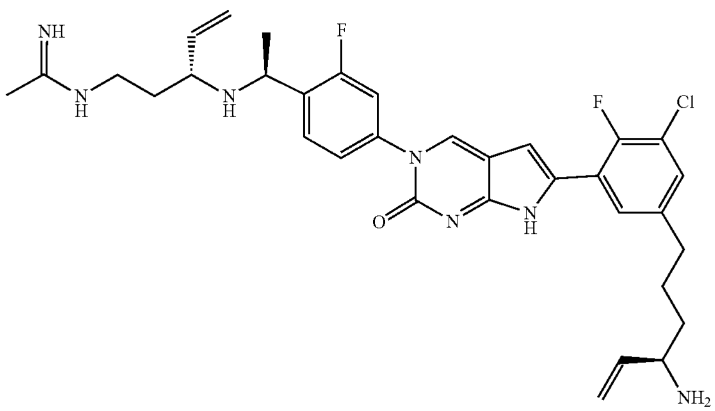 [SMILES: C=C[C@H](N)CCCc1cc(Cl)c(F)c(-c2cc3cn(-c4ccc([C@H](C)N[C@@H](C=C)CCNC(C)=N)c(F)c4)c(=O)nc3[nH]2)c1] | 622.5 |
| 185 | 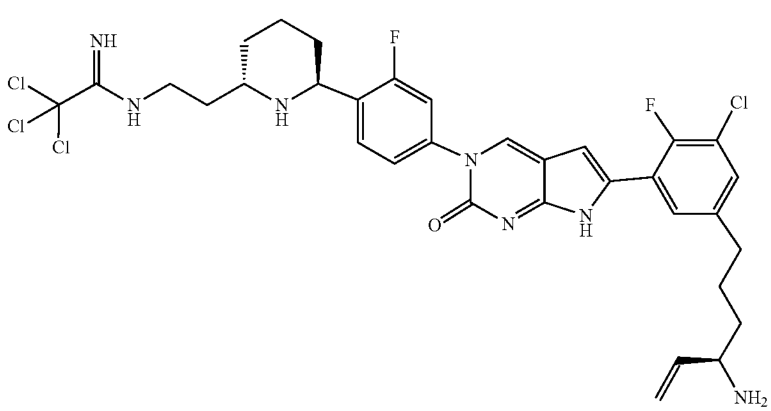 [SMILES: C=C[C@H](N)CCCc1cc(Cl)c(F)c(-c2cc3cn(-c4ccc([C@@H]5CCC[C@@H](CCNC(=N)C(Cl)(Cl)Cl)N5)c(F)c4)c(=O)nc3[nH]2)c1] | 727.4 |

TABLE 2-continued
| # | Structure | ESI, m/z [M + H]+ |
|---|---|---|
| 186 | 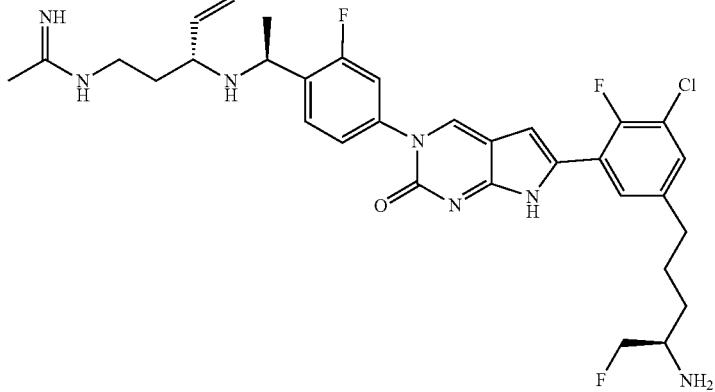 [SMILES: COC[C@@H](CCNC(C)=N)NCc1ccc(-n2cc3cc(-c4cc(CCC[C@@H](N)CF)cc(Cl)c4F)[nH]c3nc2=O)cc1] | 628.4 |
| 187 | 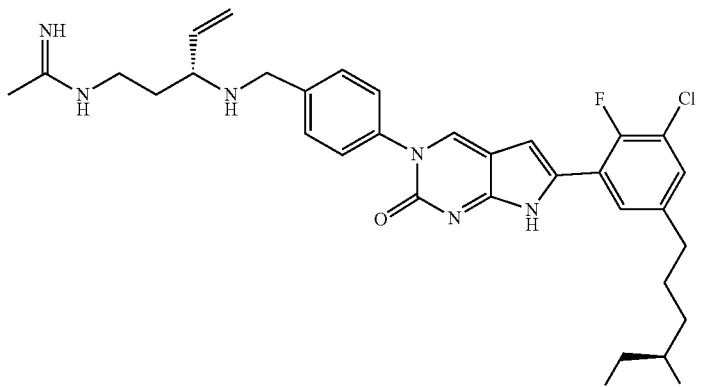 | 608.4 |
| 188 | 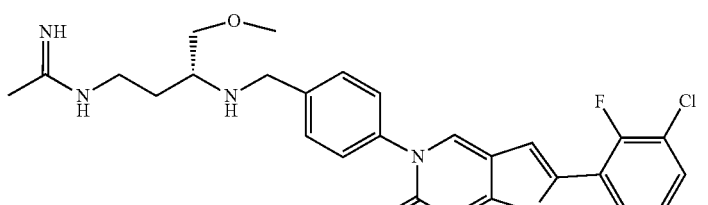 | 614.4 |

TABLE 2-continued
| # | Structure | ESI, m/z [M + H]+ |
|---|---|---|
| 189 | 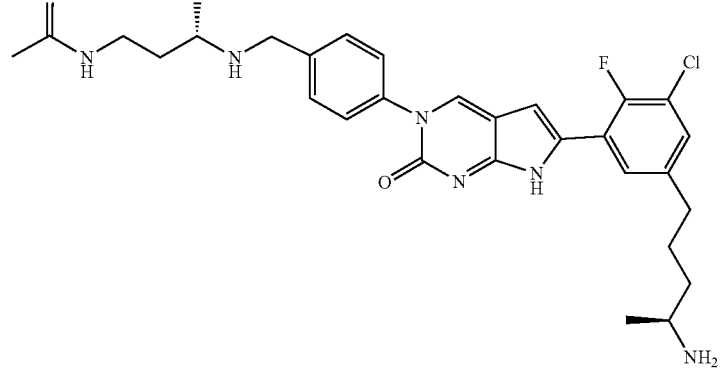 | 596.4 |
| 190 | 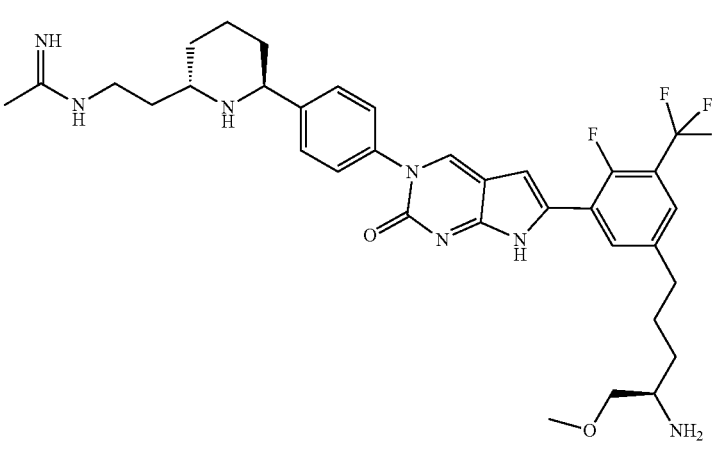 | 656.6 |
| 191 | 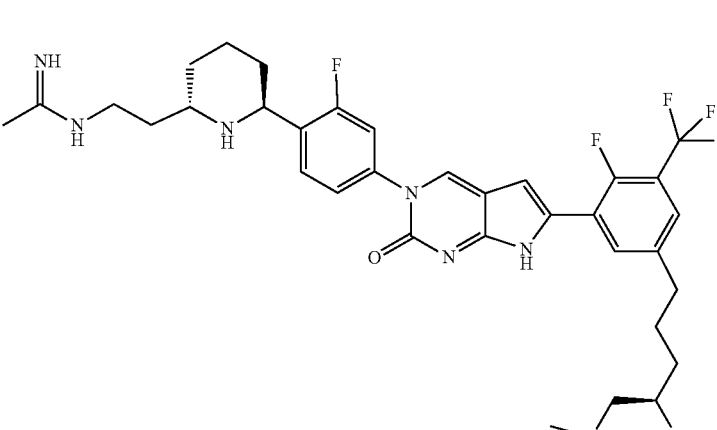 | 674.6 |

TABLE 2-continued

| # | Structure | ESI, m/z [M + H]+ |
|---|---|---|
| 192 | 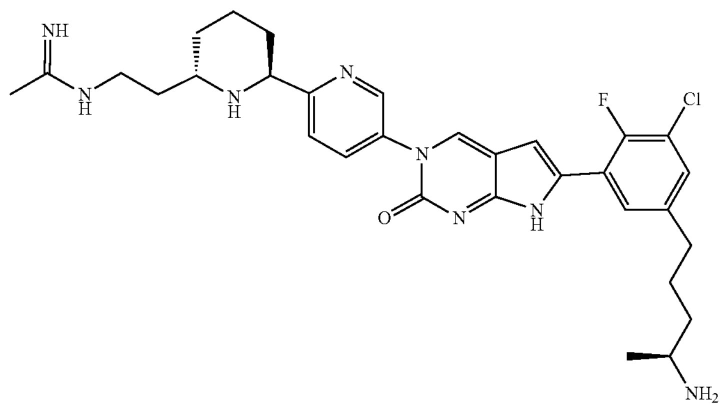 [SMILES: CC(=N)NCC[C@@H]1CCC[C@@H](c2ccc(-n3cc4cc(-c5cc(CCC[C@H](C)N)cc(Cl)c5F)[nH]c4nc3=O)cn2)N1] | 593.4 |
| 193 | 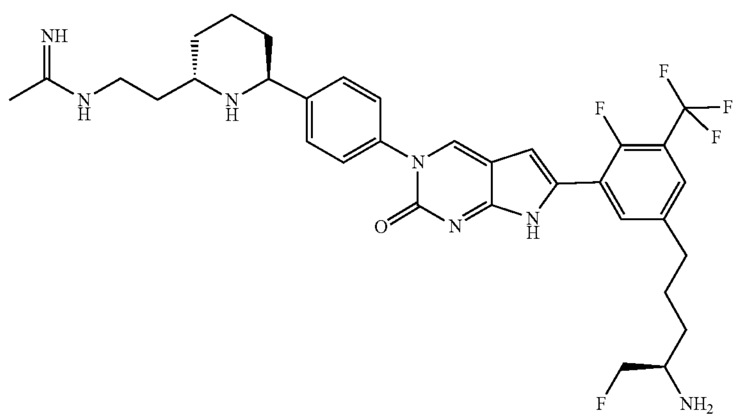 [SMILES: CC(=N)NCC[C@@H]1CCC[C@@H](c2ccc(-n3cc4cc(-c5cc(CCC[C@@H](N)CF)cc(C(F)(F)F)c5F)[nH]c4nc3=O)cc2)N1] | 644.5 |
| 194 | 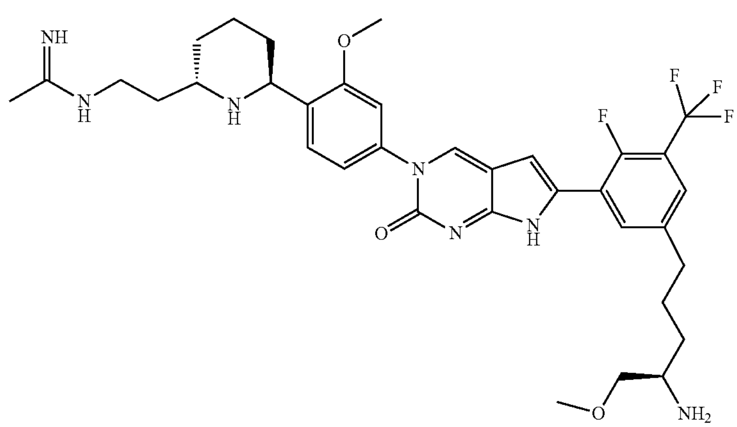 | 686.5 |

TABLE 2-continued

| # | Structure | ESI, m/z [M + H]+ |
|---|---|---|
| 195 | 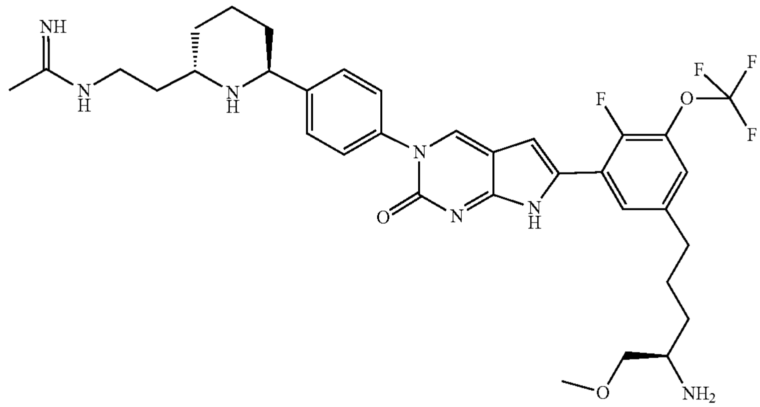 [SMILES: COC[C@H](N)CCCc1cc(OC(F)(F)F)c(F)c(-c2cc3cn(-c4ccc([C@@H]5CCC[C@@H](CCNC(C)=N)N5)cc4)c(=O)nc3[nH]2)c1] | 672 |
| 196 | 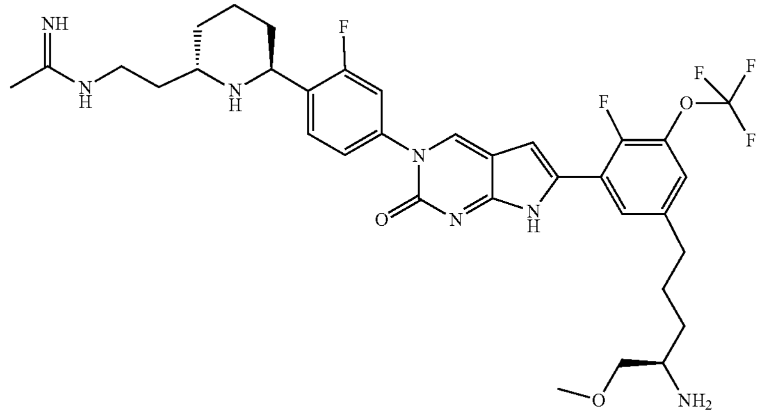 [SMILES: COC[C@H](N)CCCc1cc(OC(F)(F)F)c(F)c(-c2cc3cn(-c4ccc([C@@H]5CCC[C@@H](CCNC(C)=N)N5)c(F)c4)c(=O)nc3[nH]2)c1] | 690 |
| 197 | 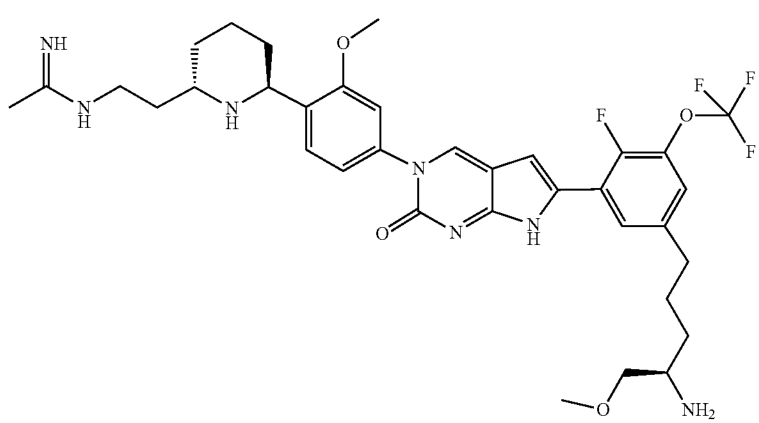 [SMILES: COC[C@H](N)CCCc1cc(OC(F)(F)F)c(F)c(-c2cc3cn(-c4ccc([C@@H]5CCC[C@@H](CCNC(C)=N)N5)c(OC)c4)c(=O)nc3[nH]2)c1] | 702 |

TABLE 2-continued
| # | Structure | ESI, m/z [M + H]+ |
|---|-----------|-------------------|
| 198 | 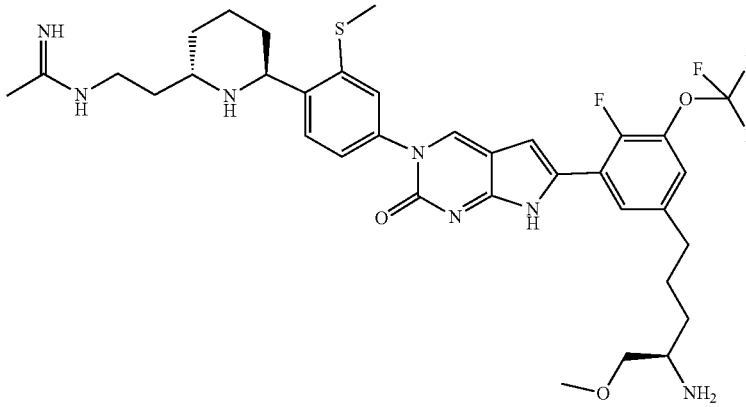 | 718.4 |
| 199 | 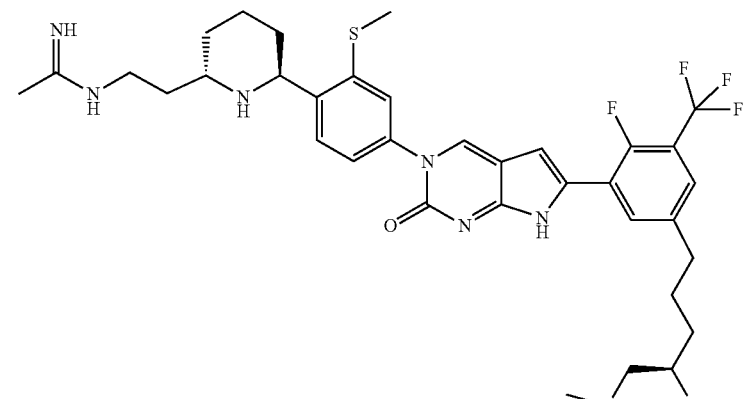 | 702.5 |
| 200 | 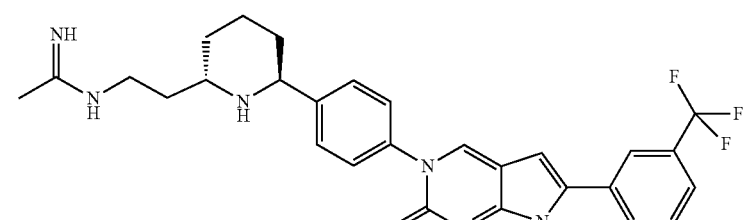 | 638.5 |

TABLE 2-continued
| # | Structure | ESI, m/z [M + H]+ |
|---|---|---|
| 201 | 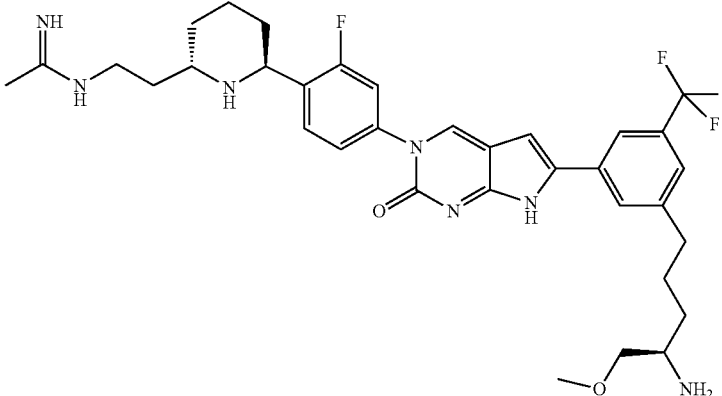 | 656.5 |
| 202 | 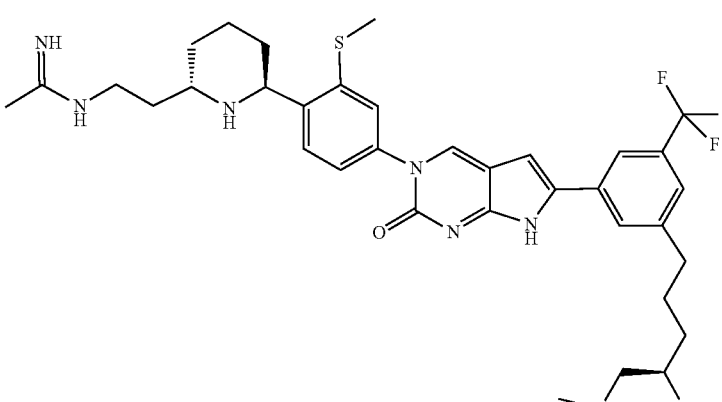 | 684.5 |
| 203 | 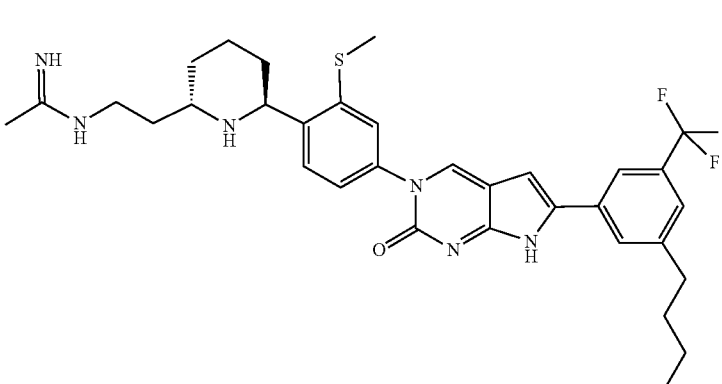 | 672.5 |

TABLE 2-continued

| # | Structure | ESI, m/z [M + H]+ |
|---|---|---|
| 204 | 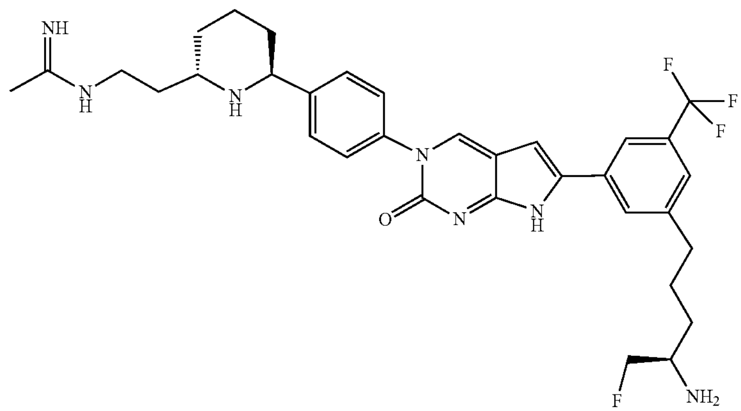 [SMILES: CC(=N)NCC[C@@H]1CCC[C@@H](c2ccc(-n3cc4cc(-c5cc(CCC[C@@H](N)CF)cc(C(F)(F)F)c5)[nH]c4nc3=O)cc2)N1] | 626.5 |
| 205 | 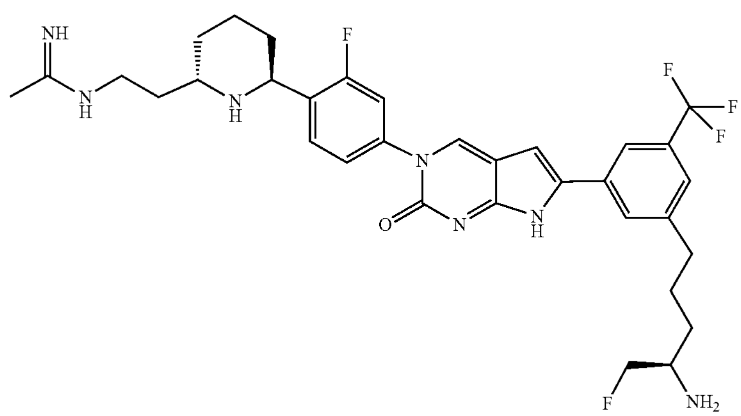 [SMILES: CC(=N)NCC[C@@H]1CCC[C@@H](c2ccc(-n3cc4cc(-c5cc(CCC[C@@H](N)CF)cc(C(F)(F)F)c5)[nH]c4nc3=O)cc2F)N1] | 644.5 |
| 206 | 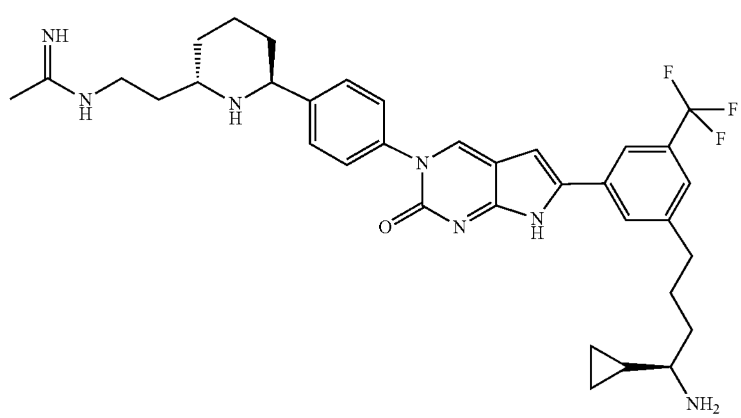 [SMILES: CC(=N)NCC[C@@H]1CCC[C@@H](c2ccc(-n3cc4cc(-c5cc(CCC[C@@H](N)C6CC6)cc(C(F)(F)F)c5)[nH]c4nc3=O)cc2)N1] | 634 |

TABLE 2-continued
| # | Structure | ESI, m/z [M + H]+ |
|---|-----------|-------------------|
| 207 | 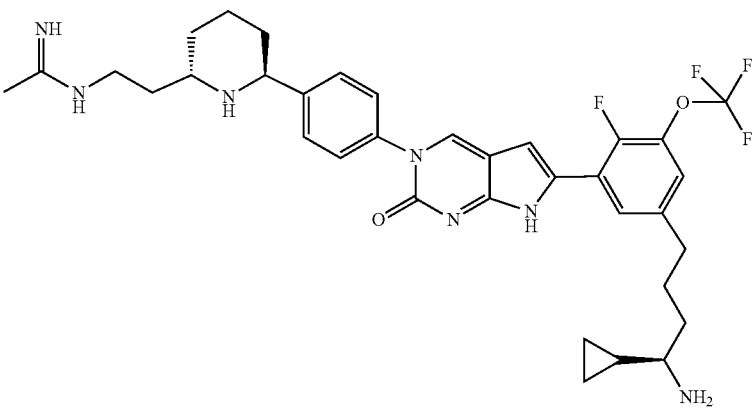 [SMILES: CC(=N)NCC[C@@H]1CCC[C@@H](c2ccc(-n3cc4cc(-c5cc(CCC[C@@H](N)C6CC6)cc(OC(F)(F)F)c5F)[nH]c4nc3=O)cc2)N1] | 668 |
| 208 | 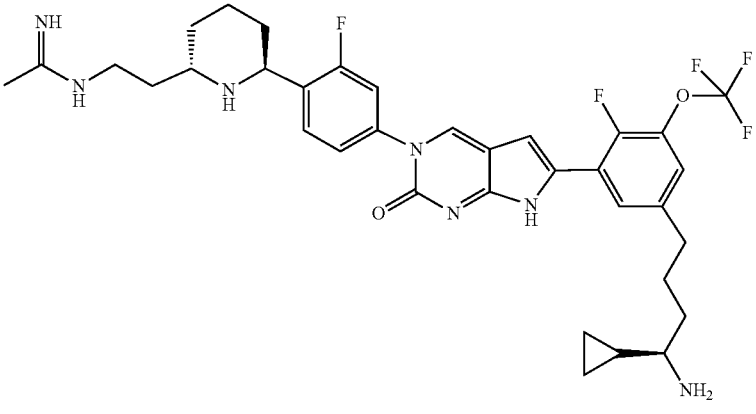 [SMILES: CC(=N)NCC[C@@H]1CCC[C@@H](c2ccc(-n3cc4cc(-c5cc(CCC[C@@H](N)C6CC6)cc(OC(F)(F)F)c5F)[nH]c4nc3=O)cc2F)N1] | 686 |
| 209 | 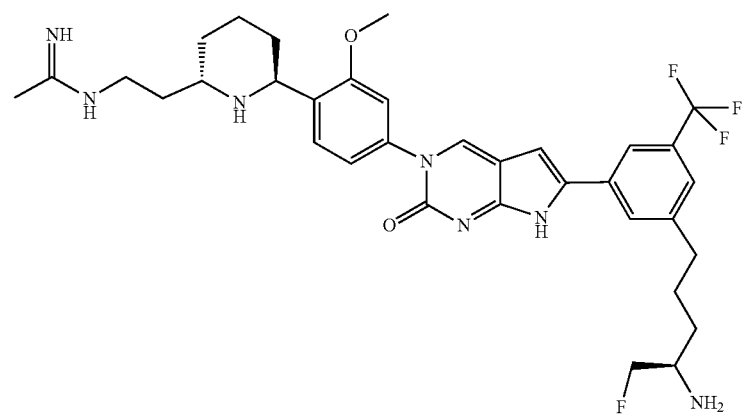 [SMILES: COc1cc(-n2cc3cc(-c4cc(CCC[C@@H](N)CF)cc(C(F)(F)F)c4)[nH]c3nc2=O)ccc1[C@@H]1CCC[C@@H](CCNC(C)=N)N1] | 656.5 |

TABLE 2-continued
| # | Structure | ESI, m/z [M + H]+ |
|---|-----------|-------------------|
| 210 | 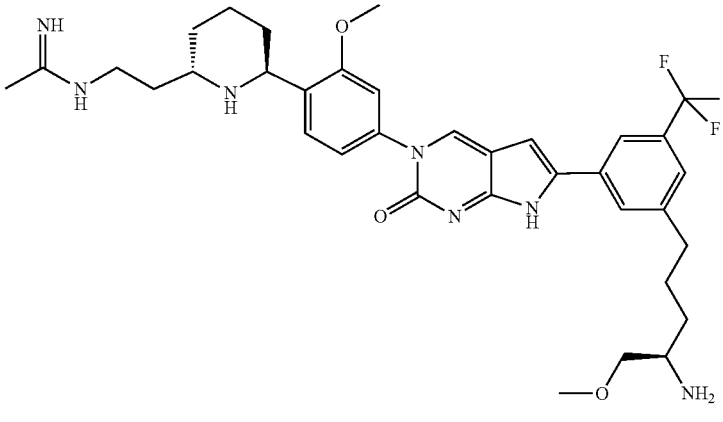 | 668.5 |
| 211 | 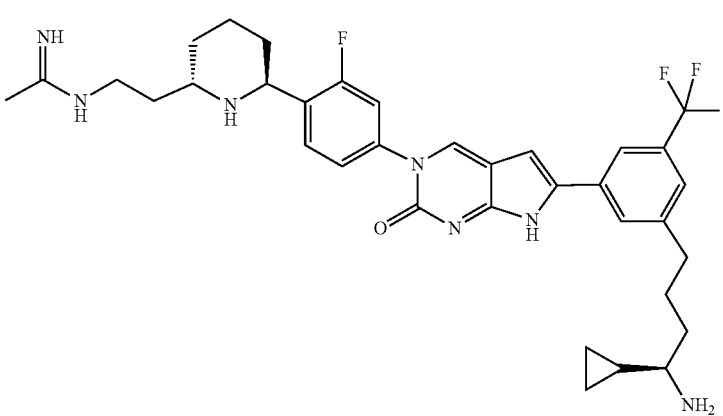 | 652 |
| 212 | 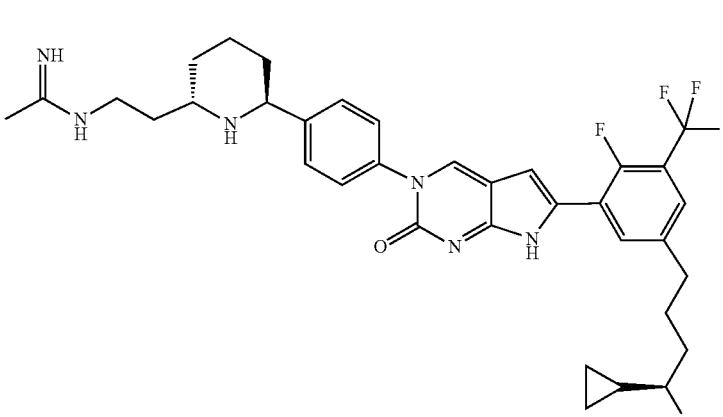 | 652 |

TABLE 2-continued

| # | Structure | ESI, m/z [M + H]+ |
|---|---|---|
| 213 | 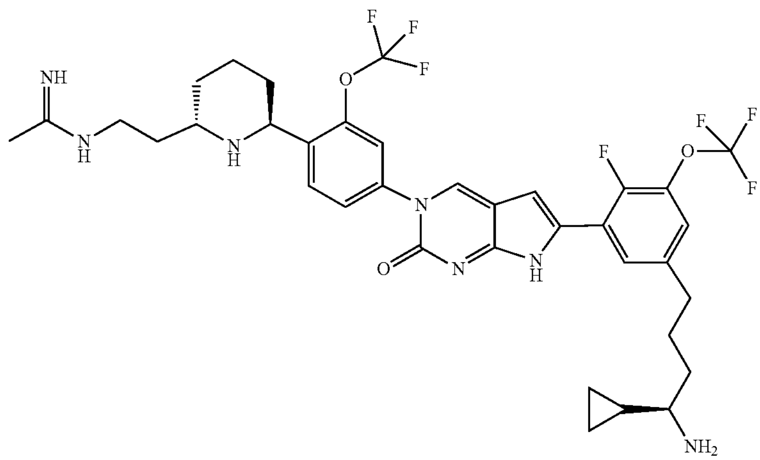 [SMILES: CC(=N)NCC[C@@H]1CCC[C@@H](c2ccc(-n3cc4cc(-c5cc(CCC[C@@H](N)C6CC6)cc(OC(F)(F)F)c5F)[nH]c4nc3=O)cc2OC(F)(F)F)N1] | 752 |
| 214 | 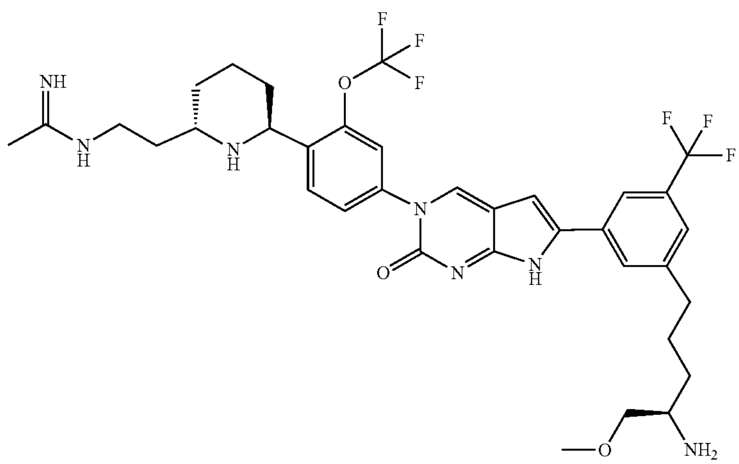 [SMILES: COC[C@H](N)CCCc1cc(-c2cc3cn(-c4ccc([C@@H]5CCC[C@@H](CCNC(C)=N)N5)c(OC(F)(F)F)c4)c(=O)nc3[nH]2)cc(C(F)(F)F)c1] | 722.4 |
| 215 | 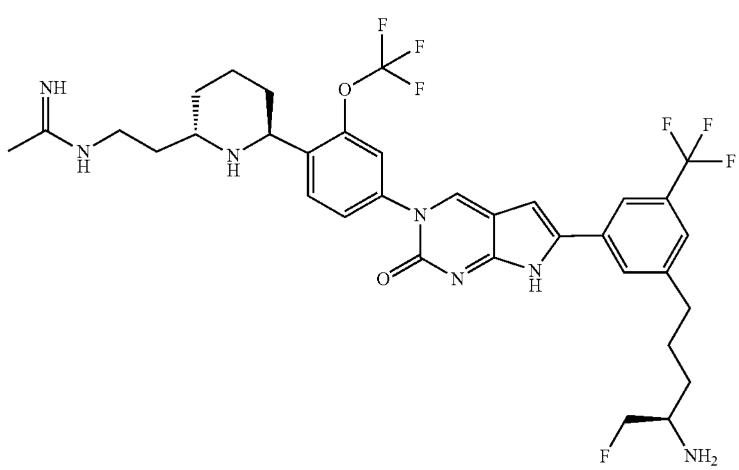 [SMILES: CC(=N)NCC[C@@H]1CCC[C@@H](c2ccc(-n3cc4cc(-c5cc(CCC[C@@H](N)CF)cc(C(F)(F)F)c5)[nH]c4nc3=O)cc2OC(F)(F)F)N1] | 710.4 |

TABLE 2-continued

| # | Structure | ESI, m/z [M + H]+ |
|---|---|---|
| 216 | 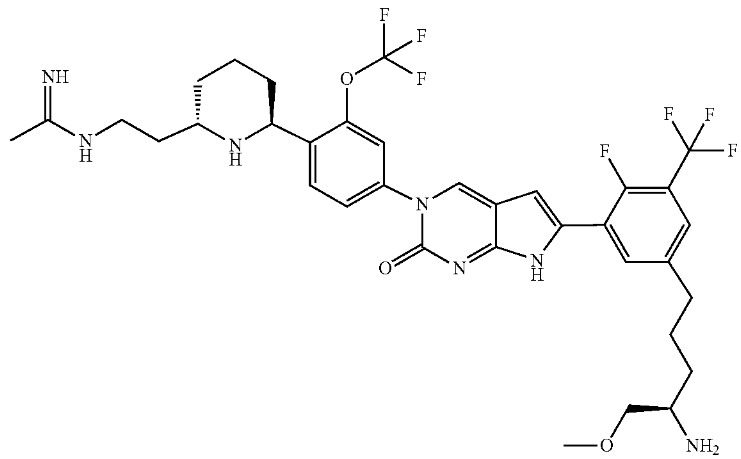 [SMILES: COC[C@H](N)CCCc1cc(-c2cc3cn(-c4ccc([C@@H]5CCC[C@@H](CCNC(C)=N)N5)c(OC(F)(F)F)c4)c(=O)nc3[nH]2)c(F)c(C(F)(F)F)c1] | 740.3 |
| 217 | 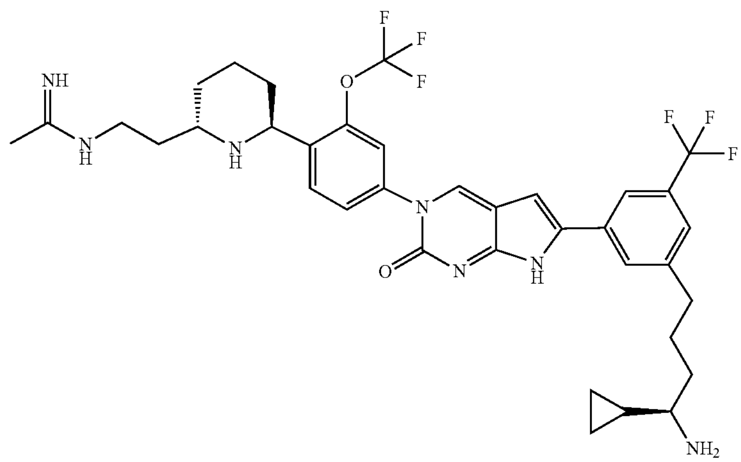 [SMILES: CC(=N)NCC[C@@H]1CCC[C@@H](c2ccc(-n3cc4cc(-c5cc(CCC[C@@H](N)C6CC6)cc(C(F)(F)F)c5)[nH]c4nc3=O)cc2OC(F)(F)F)N1] | 718 |
| 218 | 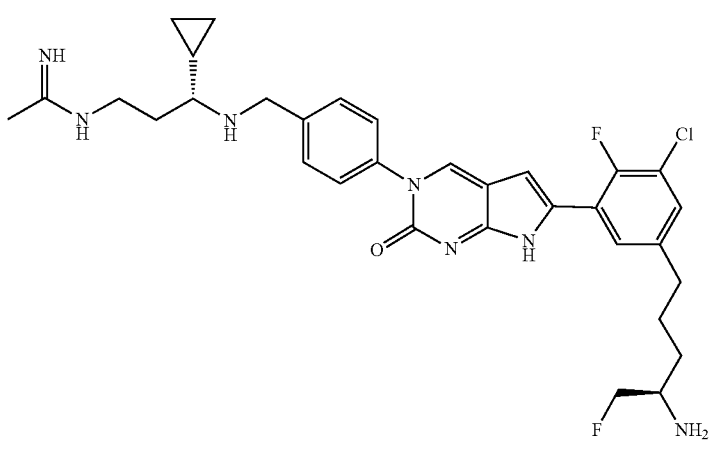 [SMILES: CC(=N)NCC[C@@H](NCc1ccc(-n2cc3cc(-c4cc(CCC[C@@H](N)CF)cc(Cl)c4F)[nH]c3nc2=O)cc1)C1CC1] | 611.3 |

TABLE 2-continued
| # | Structure | ESI, m/z [M + H]+ |
|---|---|---|
| 219 | 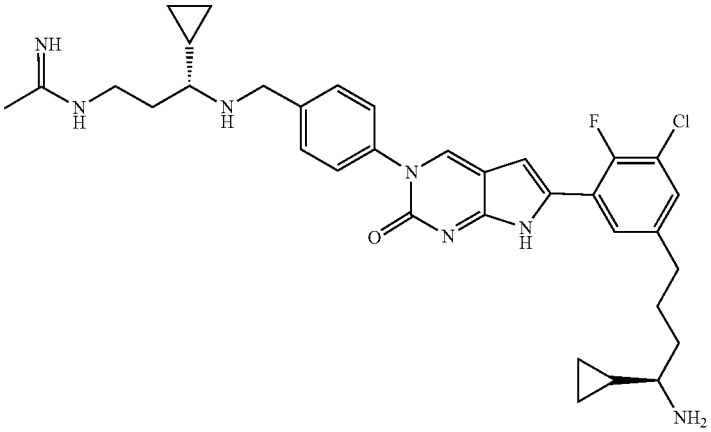 [SMILES: CC(=N)NCC[C@@H](NCc1ccc(-n2cc3cc(-c4cc(CCC[C@@H](N)C5CC5)cc(Cl)c4F)[nH]c3nc2=O)cc1)C1CC1] | 618.7 |
| 220 | 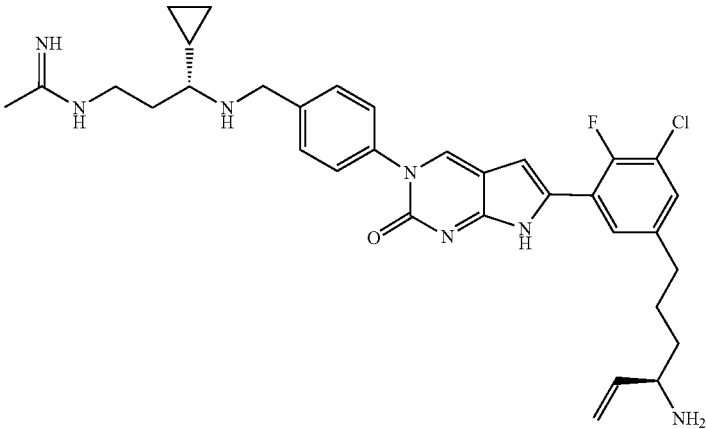 [SMILES: C=C[C@H](N)CCCc1cc(Cl)c(F)c(-c2cc3cn(-c4ccc(CN[C@H](CCNC(C)=N)C5CC5)cc4)c(=O)nc3[nH]2)c1] | 604.4 |
| 221 | 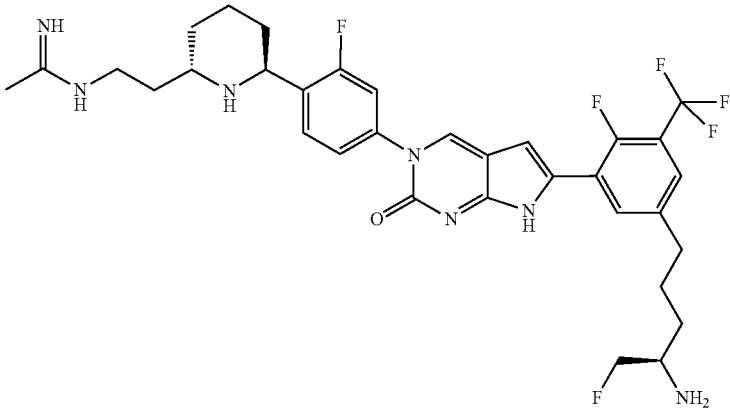 [SMILES: CC(=N)NCC[C@@H]1CCC[C@@H](c2ccc(-n3cc4cc(-c5cc(CCC[C@@H](N)CF)cc(C(F)(F)F)c5F)[nH]c4nc3=O)cc2F)N1] | 662.7 |

TABLE 2-continued
| # | Structure | ESI, m/z [M + H]+ |
|---|-----------|-------------------|
| 222 | 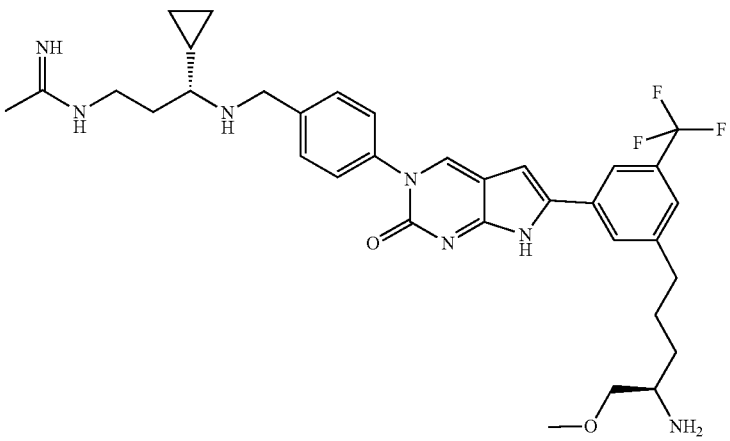 [SMILES: COC[C@H](N)CCCc1cc(-c2cc3cn(-c4ccc(CN[C@H](CCNC(C)=N)C5CC5)cc4)c(=O)nc3[nH]2)cc(C(F)(F)F)c1] | 638.8 |
| 223 | 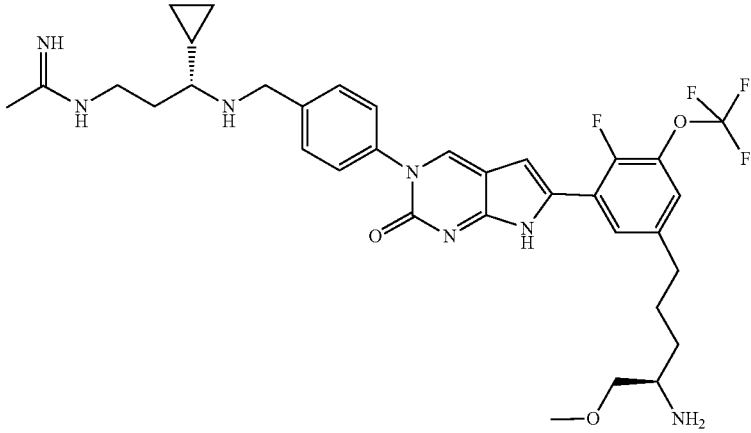 [SMILES: COC[C@H](N)CCCc1cc(OC(F)(F)F)c(F)c(-c2cc3cn(-c4ccc(CN[C@H](CCNC(C)=N)C5CC5)cc4)c(=O)nc3[nH]2)c1] | 672.8 |
| 224 | 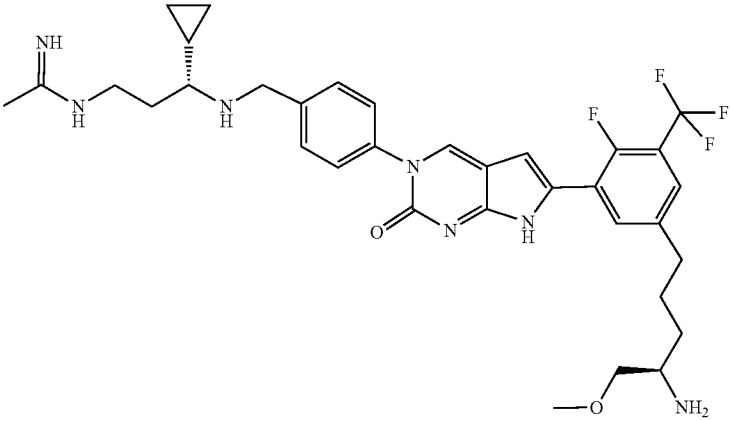 [SMILES: COC[C@H](N)CCCc1cc(-c2cc3cn(-c4ccc(CN[C@H](CCNC(C)=N)C5CC5)cc4)c(=O)nc3[nH]2)c(F)c(C(F)(F)F)c1] | 656.8 |

TABLE 2-continued
| # | Structure | ESI, m/z [M + H]+ |
|---|---|---|
| 225 | 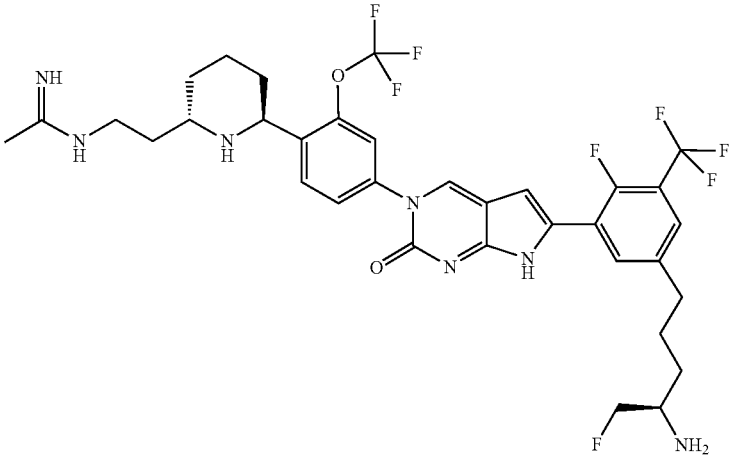 [SMILES: CC(=N)NCC[C@@H]1CCC[C@@H](c2ccc(-n3cc4cc(-c5cc(CCC[C@@H](N)CF)cc(C(F)(F)F)c5F)[nH]c4nc3=O)cc2OC(F)(F)F)N1] | 728.6 |
| 226 | 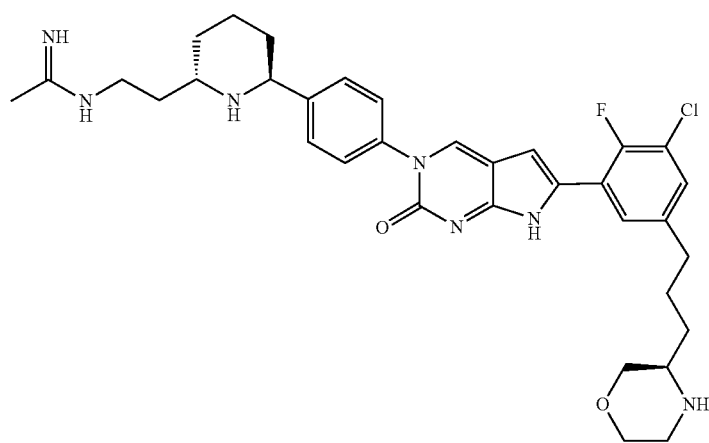 [SMILES: CC(=N)NCC[C@@H]1CCC[C@@H](c2ccc(-n3cc4cc(-c5cc(CCC[C@@H]6COCCN6)cc(Cl)c5F)[nH]c4nc3=O)cc2)N1] | 635.3 |
| 227 | 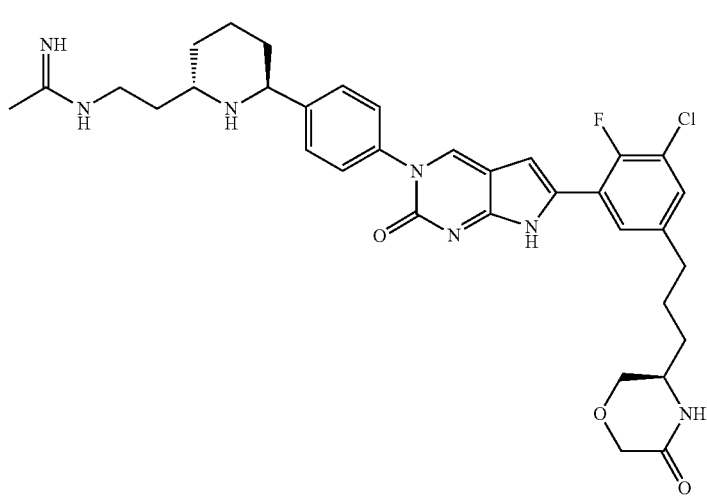 [SMILES: CC(=N)NCC[C@@H]1CCC[C@@H](c2ccc(-n3cc4cc(-c5cc(CCC[C@@H]6COCC(=O)N6)cc(Cl)c5F)[nH]c4nc3=O)cc2)N1] | 649.2 |

TABLE 2-continued
| # | Structure | ESI, m/z [M + H]+ |
|---|---|---|
| 228 | 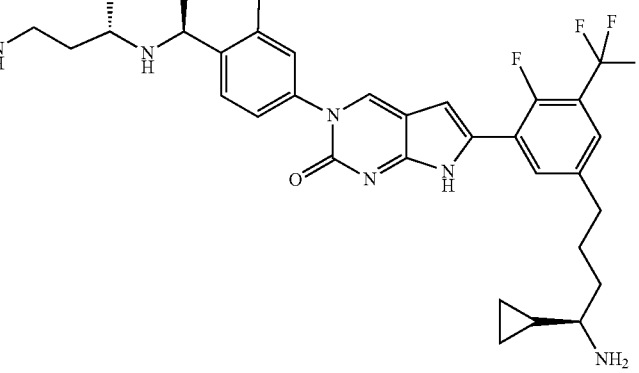 | n/a |
| 229 | 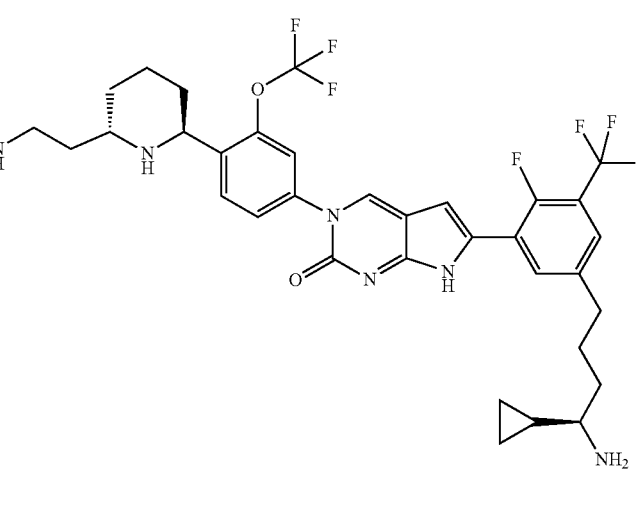 | n/a |
| 230 | 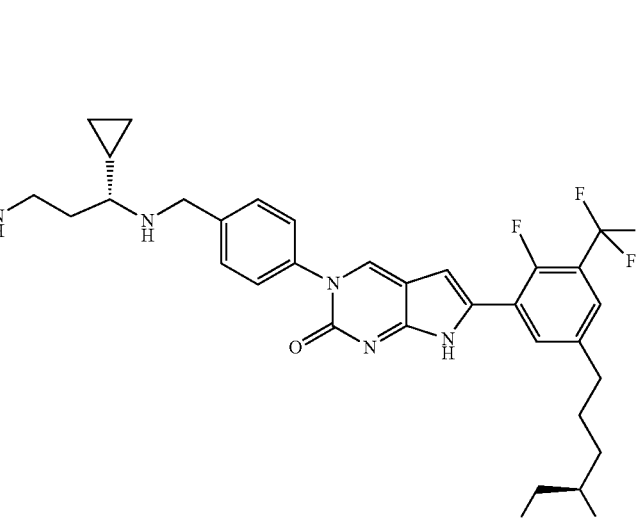 | 644.8 |

TABLE 2-continued
| # | Structure | ESI, m/z [M + H]+ |
|---|---|---|
| 231 | 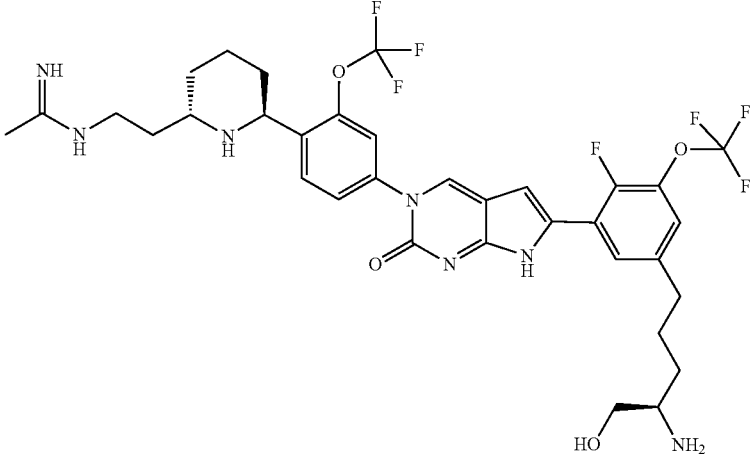 [SMILES: CC(=N)NCC[C@@H]1CCC[C@@H](c2ccc(-n3cc4cc(-c5cc(CCC[C@@H](N)CO)cc(OC(F)(F)F)c5F)[nH]c4nc3=O)cc2OC(F)(F)F)N1] | 742 |
| 232 | 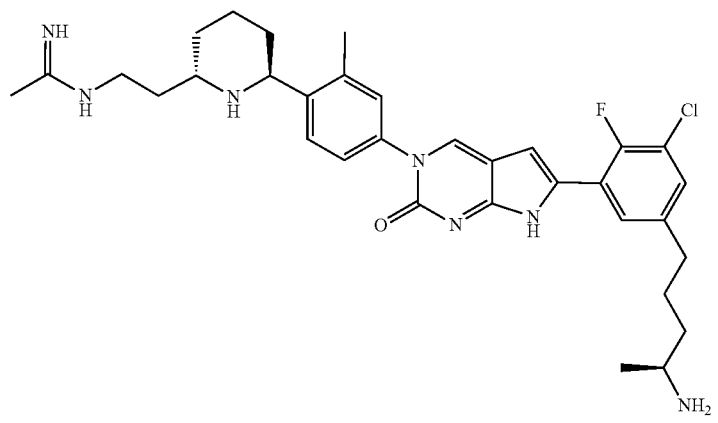 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2C)N1] | 606.4 |
| 233 | 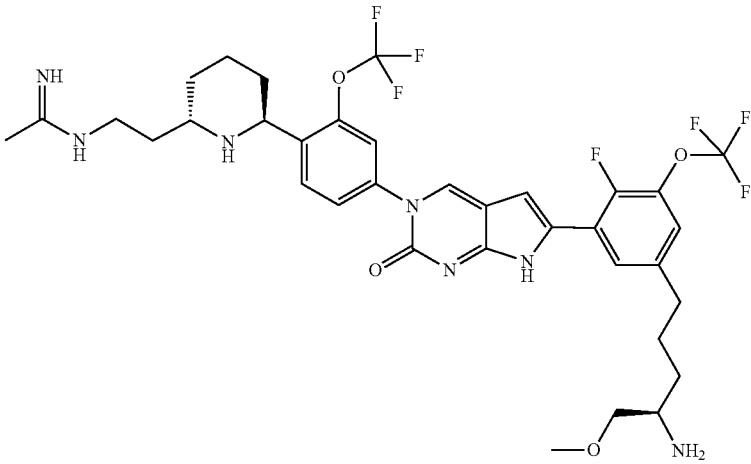 | 756 |

TABLE 2-continued
| # | Structure | ESI, m/z [M + H]+ |
|---|-----------|-------------------|
| 234 | 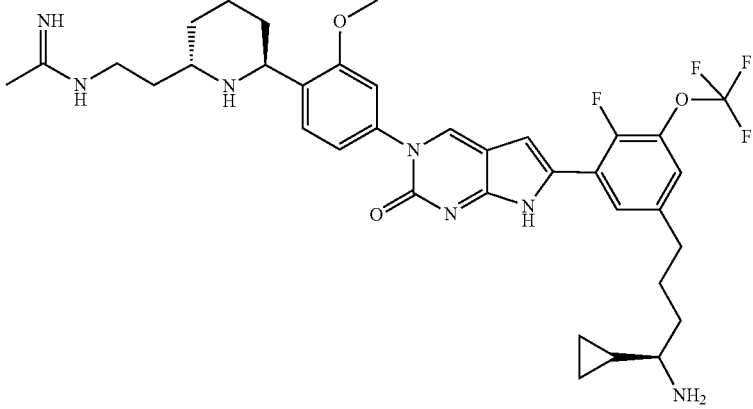 [SMILES: COc1cc(-n2cc3cc(-c4cc(CCC[C@@H](N)C5CC5)cc(OC(F)(F)F)c4F)[nH]c3nc2=O)ccc1[C@@H]1CCC[C@@H](CCNC(C)=N)N1] | 698.4 |
| 235 | 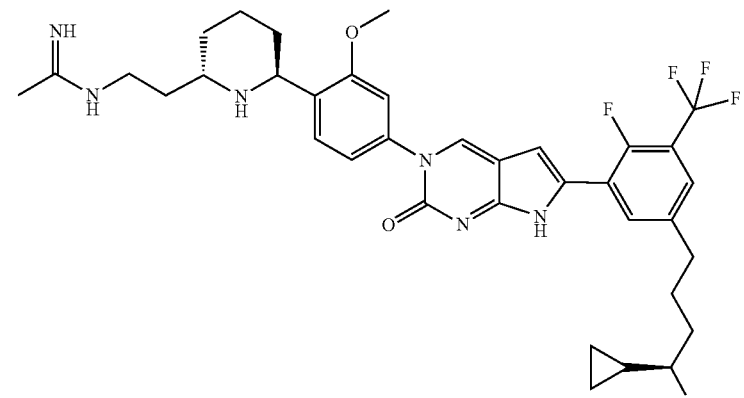 | 682.4 |
| 236 | 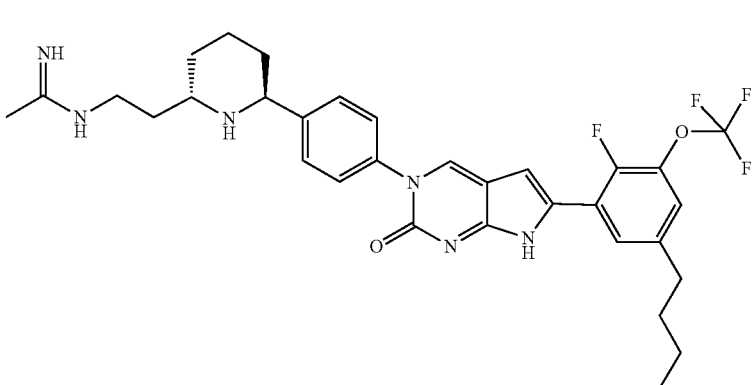 | 660.7 |

TABLE 2-continued
| # | Structure | ESI, m/z [M + H]+ |
|---|-----------|-------------------|
| 237 | 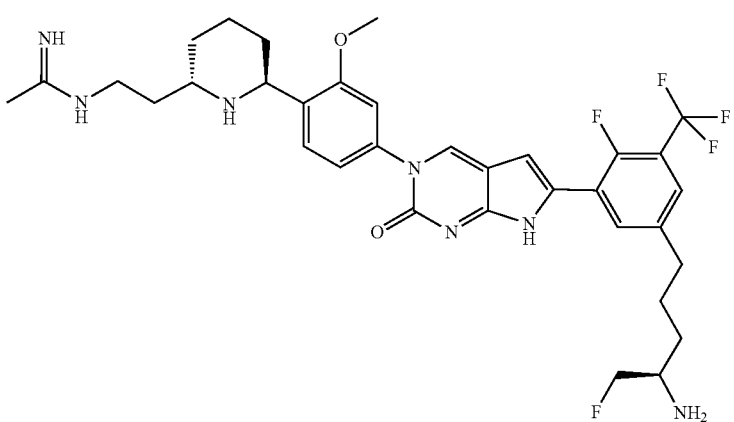 [SMILES: COc1cc(-n2cc3cc(-c4cc(CCC[C@@H](N)CF)cc(C(F)(F)F)c4F)[nH]c3nc2=O)ccc1[C@@H]1CCC[C@@H](CCNC(C)=N)N1] | 674.5 |
| 238 | 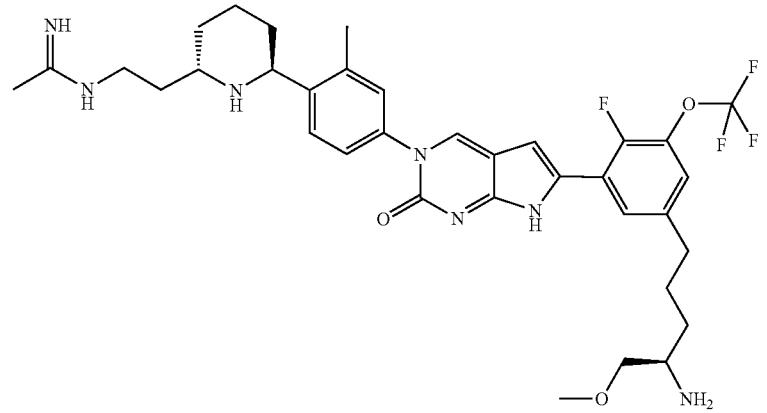 [SMILES: COC[C@H](N)CCCc1cc(OC(F)(F)F)c(F)c(-c2cc3cn(-c4ccc([C@@H]5CCC[C@@H](CCNC(C)=N)N5)c(C)c4)c(=O)nc3[nH]2)c1] | 686.8 |
| 239 | 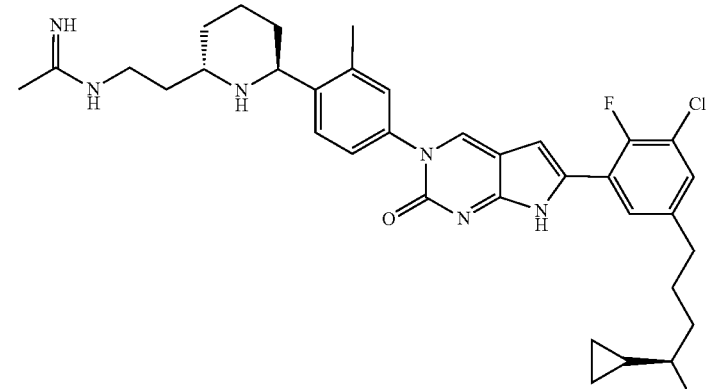 | 632.5 |

TABLE 2-continued
| # | Structure | ESI, m/z [M + H]+ |
|---|---|---|
| 240 | 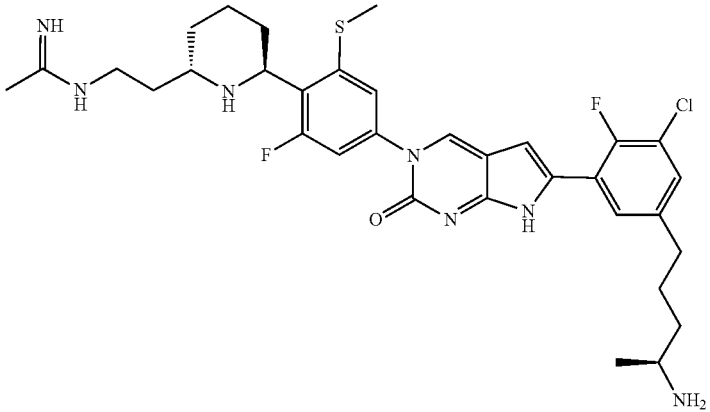 [SMILES: CSc1cc(-n2cc3cc(-c4cc(CCC[C@H](C)N)cc(Cl)c4F)[nH]c3nc2=O)cc(F)c1[C@@H]1CCC[C@@H](CCNC(C)=N)N1] | 656.4 |
| 241 | 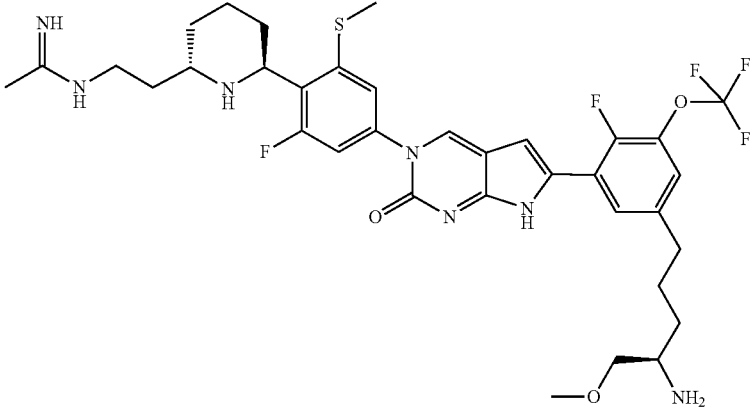 [SMILES: COC[C@H](N)CCCc1cc(OC(F)(F)F)c(F)c(-c2cc3cn(-c4cc(F)c([C@@H]5CCC[C@@H](CCNC(C)=N)N5)c(SC)c4)c(=O)nc3[nH]2)c1] | 736.4 |
| 242 | 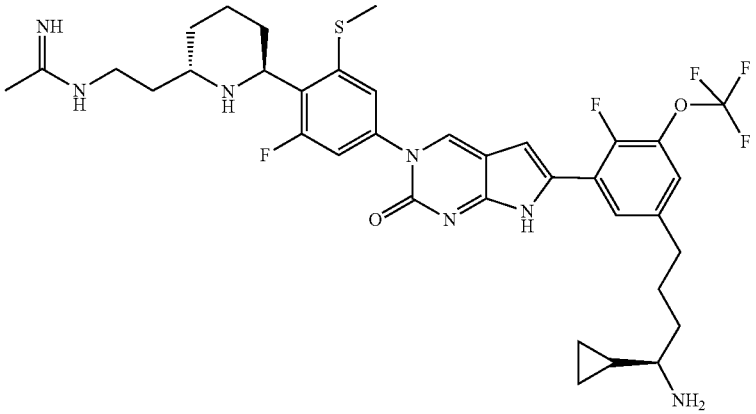 [SMILES: CSc1cc(-n2cc3cc(-c4cc(CCC[C@@H](N)C5CC5)cc(OC(F)(F)F)c4F)[nH]c3nc2=O)cc(F)c1[C@@H]1CCC[C@@H](CCNC(C)=N)N1] | 732.4 |

TABLE 2-continued

| # | Structure | ESI, m/z [M + H]+ |
|---|---|---|
| 243 | 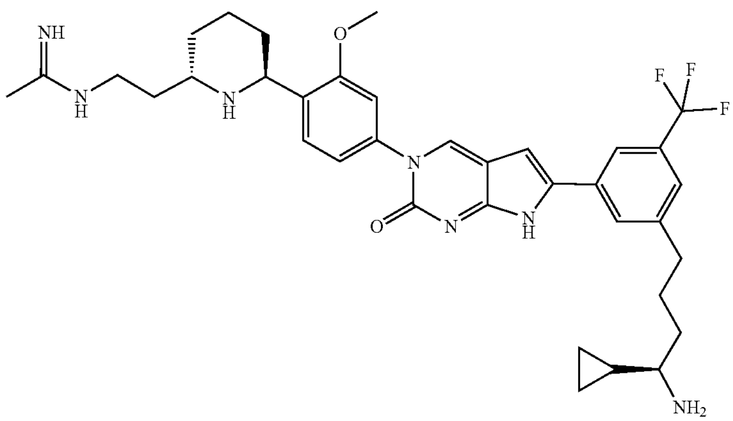 [SMILES: COc1cc(-n2cc3cc(-c4cc(CCC[C@@H](N)C5CC5)cc(C(F)(F)F)c4)[nH]c3nc2=O)ccc1[C@@H]1CCC[C@@H](CCNC(C)=N)N1] | 664.6 |
| 244 | 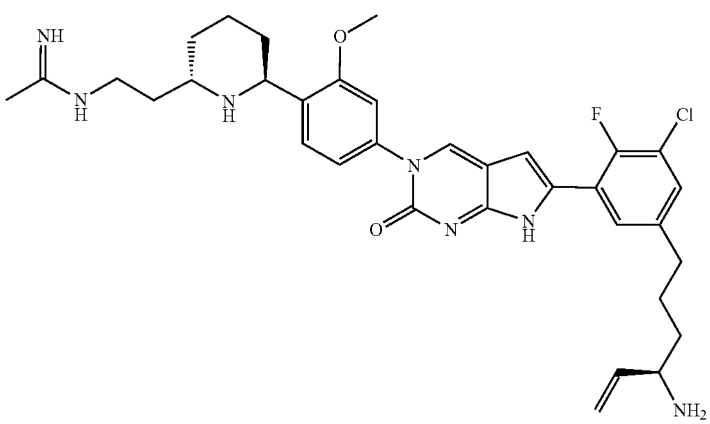 [SMILES: C=C[C@H](N)CCCc1cc(Cl)c(F)c(-c2cc3cn(-c4ccc([C@@H]5CCC[C@@H](CCNC(C)=N)N5)c(OC)c4)c(=O)nc3[nH]2)c1] | 634.4 |
| 245 | 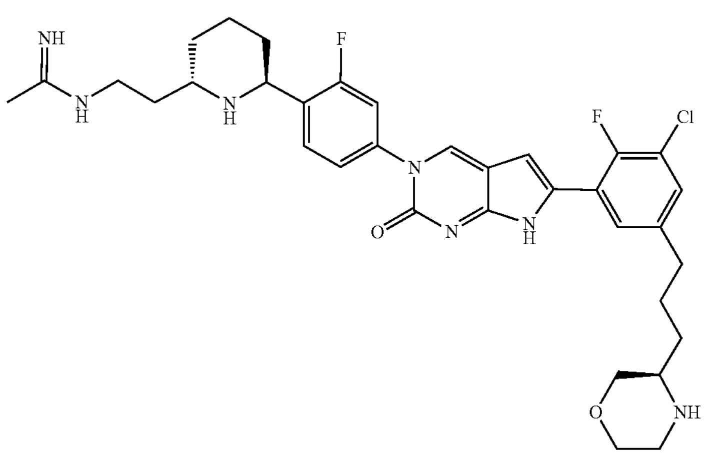 [SMILES: CC(=N)NCC[C@@H]1CCC[C@@H](c2ccc(-n3cc4cc(-c5cc(CCC[C@@H]6COCCN6)cc(Cl)c5F)[nH]c4nc3=O)cc2F)N1] | 652.4 |

TABLE 2-continued
| # | Structure | ESI, m/z [M + H]+ |
|---|---|---|
| 246 | 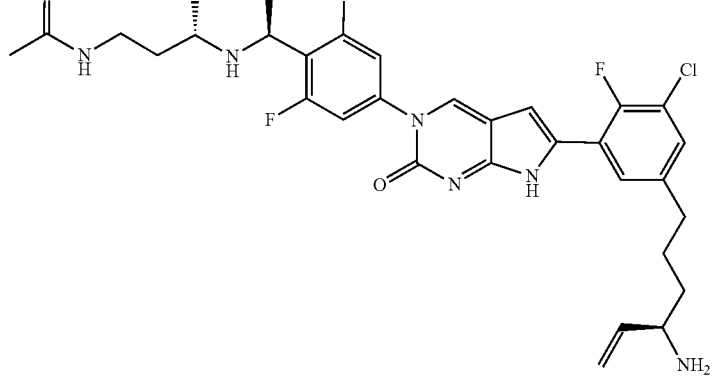 | 640.4 |
| 247 | 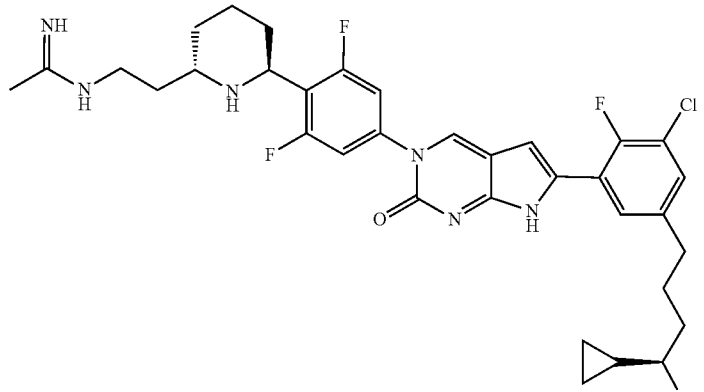 | 654.4 |
| 248 | 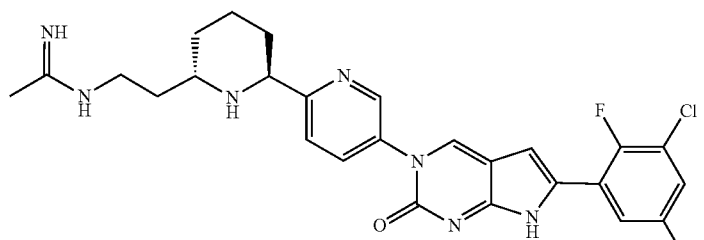 | 619.4 |

TABLE 2-continued
| # | Structure | ESI, m/z [M + H]+ |
|---|---|---|
| 249 | 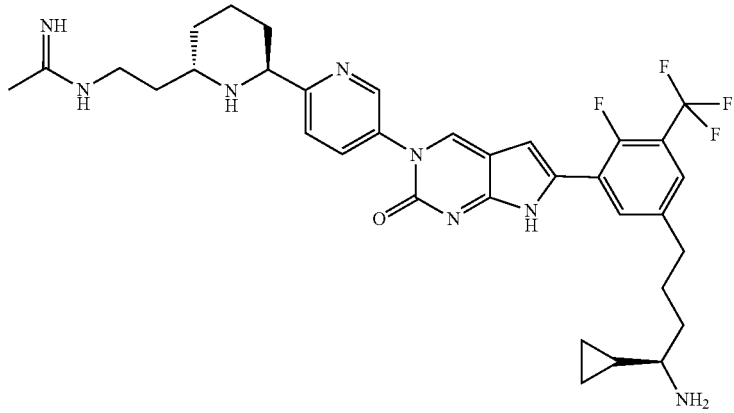 [SMILES: CC(=N)NCC[C@@H]1CCC[C@@H](c2ccc(-n3cc4cc(-c5cc(CCC[C@@H](N)C6CC6)cc(C(F)(F)F)c5F)[nH]c4nc3=O)cn2)N1] | 653.5 |
| 250 | 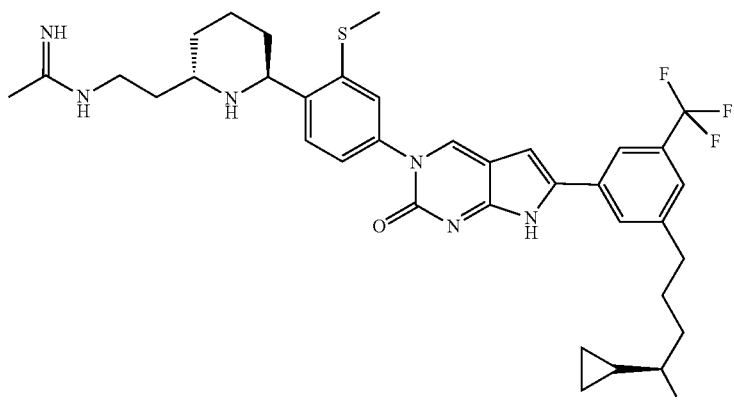 | 680.85 |
| 251 | 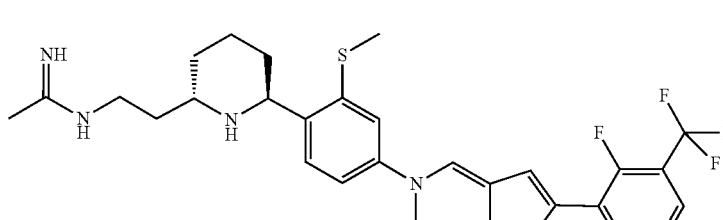 | 698.84 |

TABLE 2-continued

| # | Structure | ESI, m/z [M + H]+ |
|---|---|---|
| 252 | 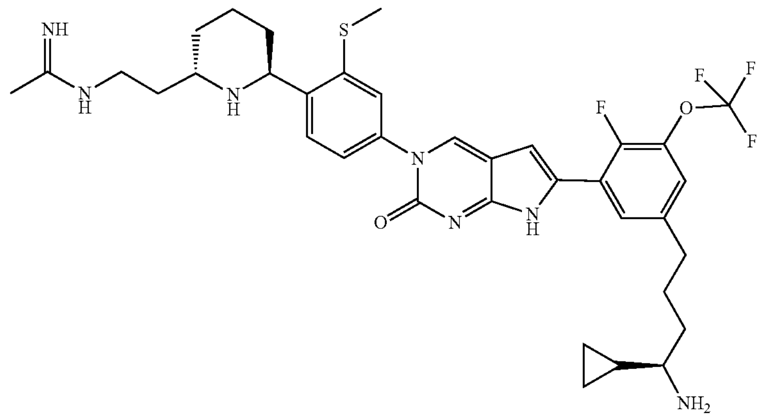 [SMILES: CSc1cc(-n2cc3cc(-c4cc(CCC[C@@H](N)C5CC5)cc(OC(F)(F)F)c4F)[nH]c3nc2=O)ccc1[C@@H]1CCC[C@@H](CCNC(C)=N)N1] | 714.84 |
| 253 | 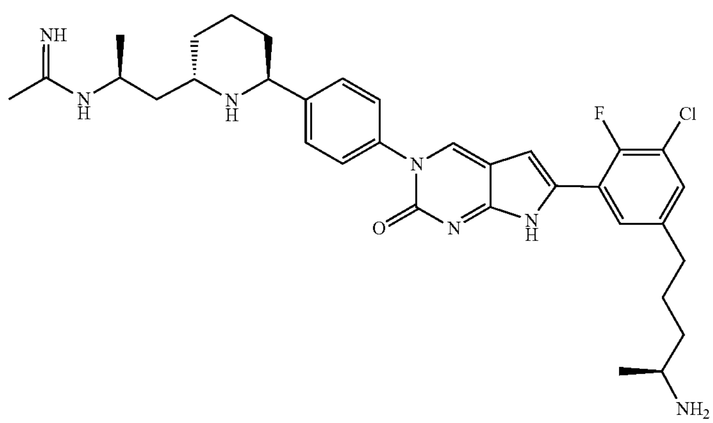 [SMILES: CC(=N)N[C@@H](C)C[C@@H]1CCC[C@@H](c2ccc(-n3cc4cc(-c5cc(CCC[C@H](C)N)cc(Cl)c5F)[nH]c4nc3=O)cc2)N1] | 606.4 |
| 254 | 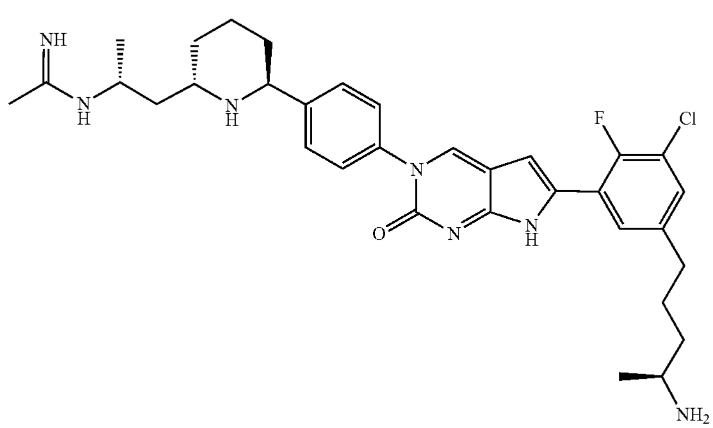 [SMILES: CC(=N)N[C@H](C)C[C@@H]1CCC[C@@H](c2ccc(-n3cc4cc(-c5cc(CCC[C@H](C)N)cc(Cl)c5F)[nH]c4nc3=O)cc2)N1] | 606.4 |

TABLE 2-continued
| # | Structure | ESI, m/z [M + H]+ |
|---|---|---|
| 255 | 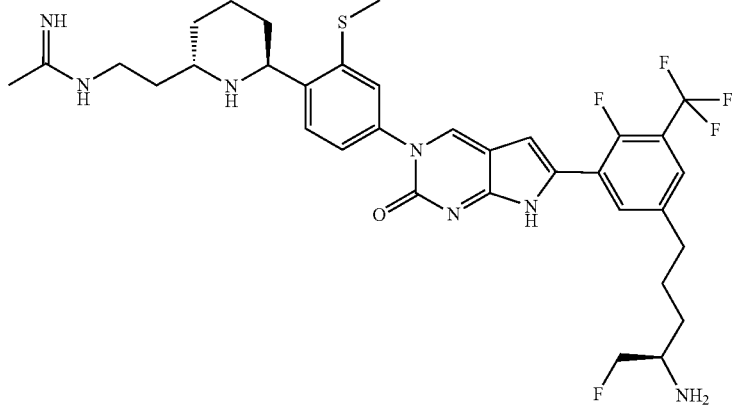 | 690.4 |
| 256 | 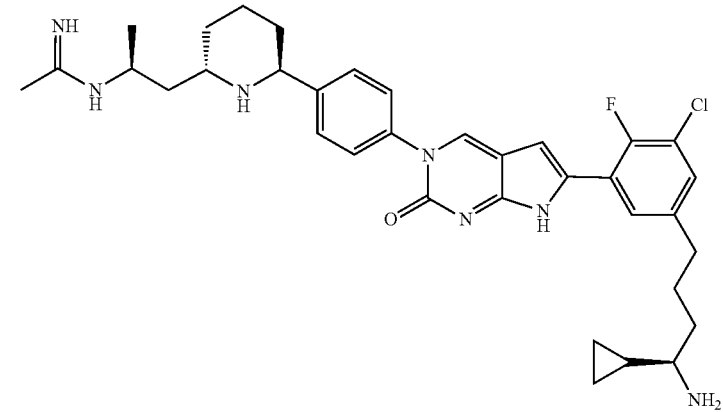 [SMILES: CC(=N)N[C@@H](C)C[C@@H]1CCC[C@@H](c2ccc(-n3cc4cc(-c5cc(CCC[C@@H](N)C6CC6)cc(Cl)c5F)[nH]c4nc3=O)cc2)N1] | 632.4 |
| 257 | 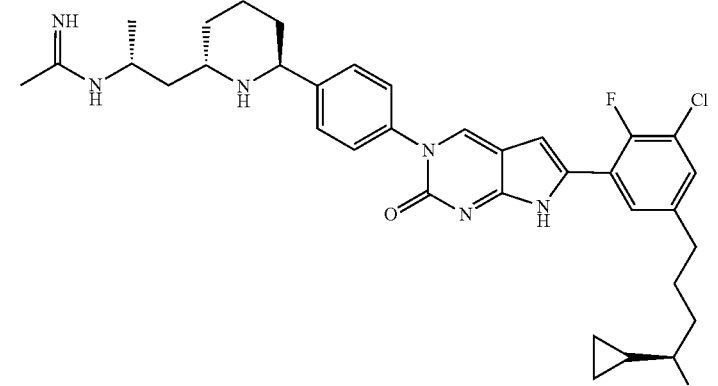 | 632.4 |

TABLE 2-continued

| # | Structure | ESI, m/z [M + H]+ |
|---|---|---|
| 258 | 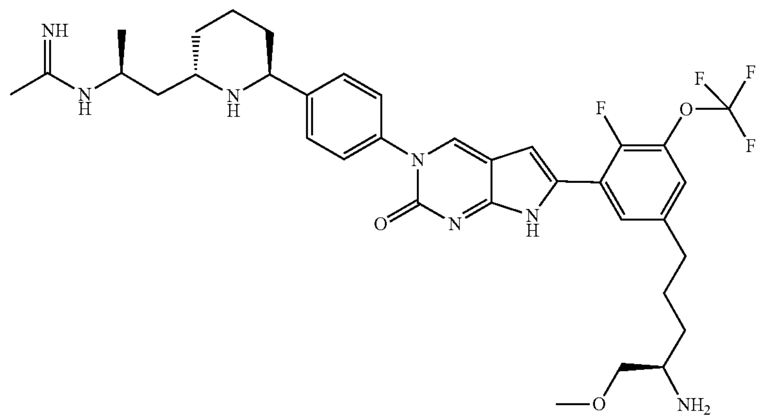 [SMILES: COC[C@H](N)CCCc1cc(OC(F)(F)F)c(F)c(-c2cc3cn(-c4ccc([C@@H]5CCC[C@@H](C[C@H](C)NC(C)=N)N5)cc4)c(=O)nc3[nH]2)c1] | 686.5 |
| 259 | 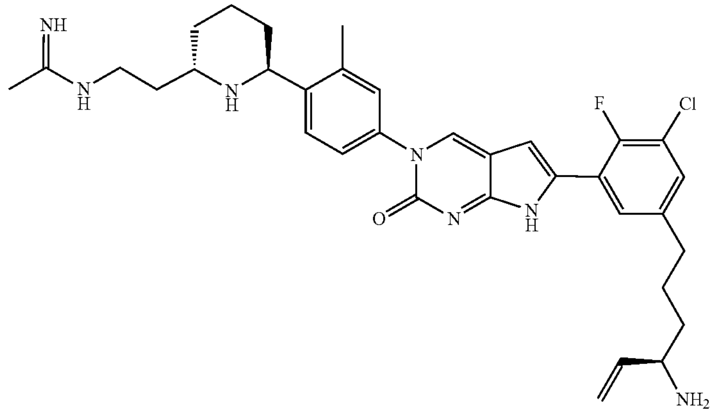 [SMILES: C=C[C@H](N)CCCc1cc(Cl)c(F)c(-c2cc3cn(-c4ccc([C@@H]5CCC[C@@H](CCNC(C)=N)N5)c(C)c4)c(=O)nc3[nH]2)c1] | 618.4 |
| 260 | 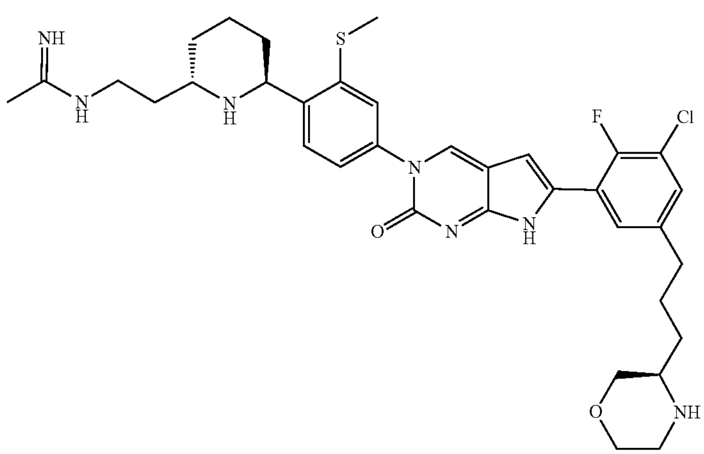 [SMILES: CSc1cc(-n2cc3cc(-c4cc(CCC[C@@H]5COCCN5)cc(Cl)c4F)[nH]c3nc2=O)ccc1[C@@H]1CCC[C@@H](CCNC(C)=N)N1] | 682.1 |

TABLE 2-continued
| # | Structure | ESI, m/z [M + H]+ |
|---|---|---|
| 261 | 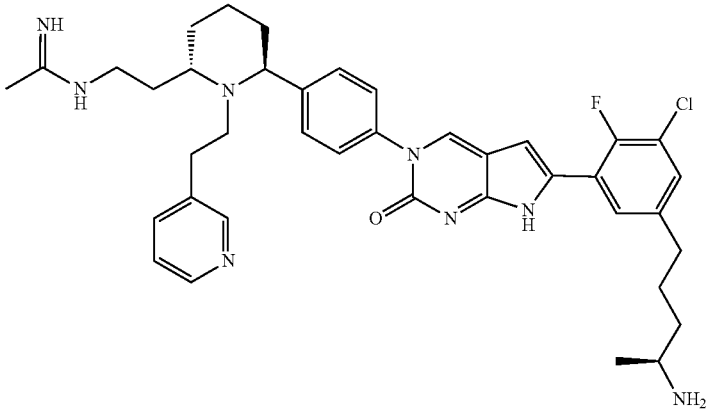 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1CCc1cccnc1] | 697 |
| 262 | 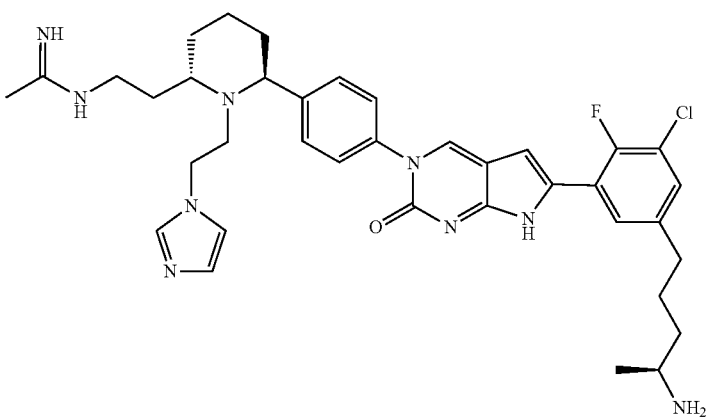 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1CCn1ccnc1] | 686 |
| 263 | 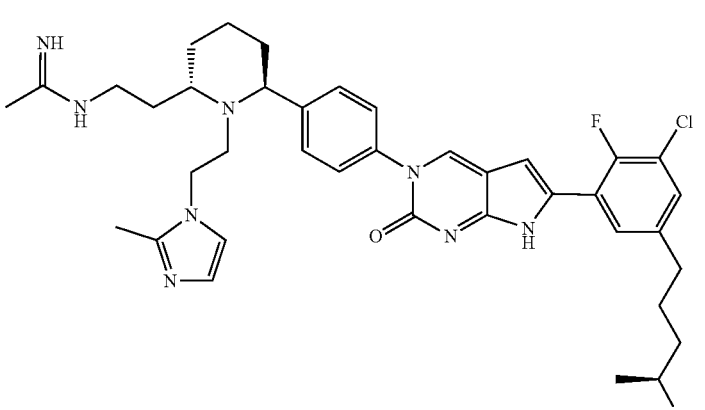 | 700 |

TABLE 2-continued

| # | Structure | ESI, m/z [M + H]+ |
|---|---|---|
| 264 | 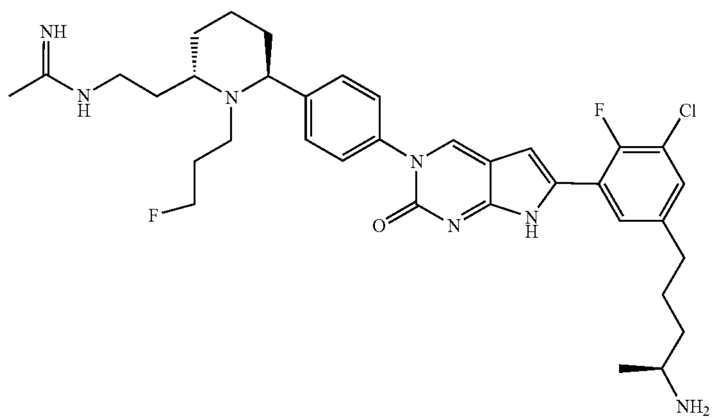 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1CCCF] | 652 |
| 265 | 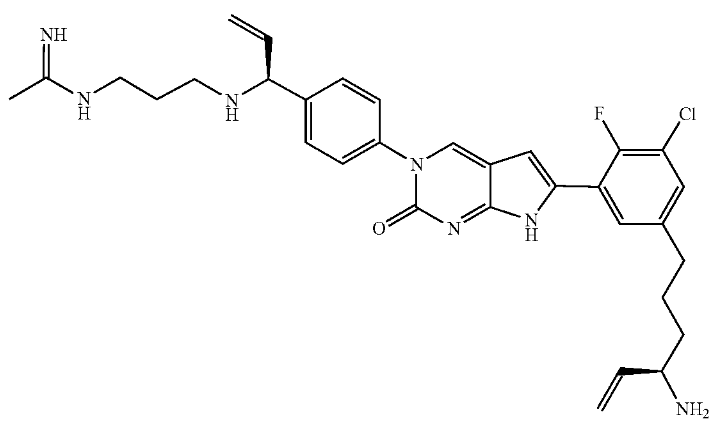 [SMILES: C=C[C@H](NCCCNC(C)=N)c1ccc(-n2cc3cc(-c4cc(CCC[C@@H](N)C=C)cc(Cl)c4F)[nH]c3nc2=O)cc1] | 590.4 |
| 266 | 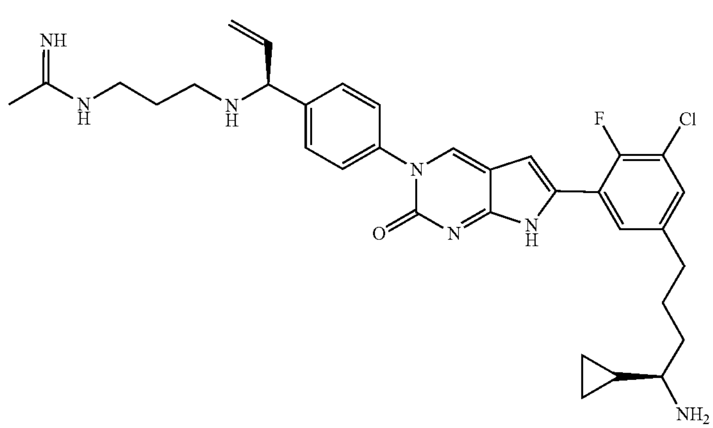 [SMILES: C=C[C@H](NCCCNC(C)=N)c1ccc(-n2cc3cc(-c4cc(CCC[C@@H](N)C5CC5)cc(Cl)c4F)[nH]c3nc2=O)cc1] | 604.4 |

TABLE 2-continued

| # | Structure | ESI, m/z [M + H]+ |
|---|---|---|
| 267 | 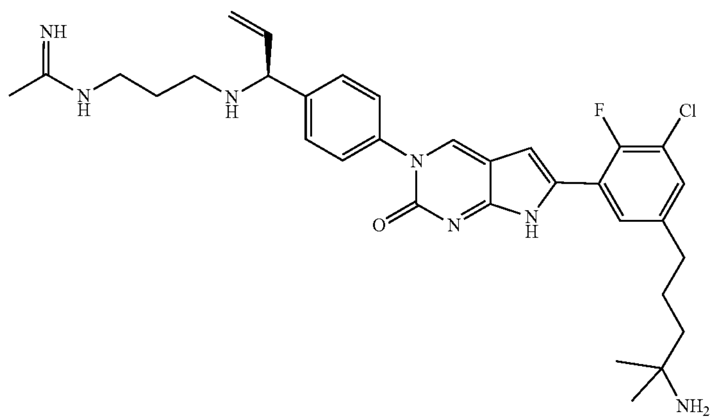 [SMILES: C=C[C@H](NCCCNC(C)=N)c1ccc(-n2cc3cc(-c4cc(CCCC(C)(C)N)cc(Cl)c4F)[nH]c3nc2=O)cc1] | 592.4 |
| 268 | 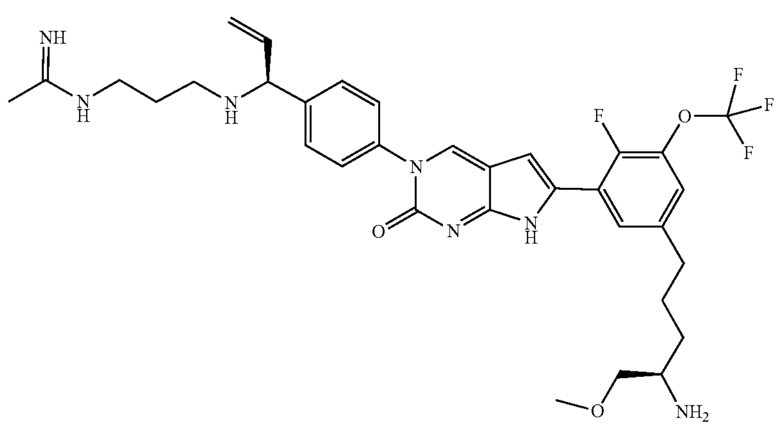 [SMILES: C=C[C@H](NCCCNC(C)=N)c1ccc(-n2cc3cc(-c4cc(CCC[C@@H](N)COC)cc(OC(F)(F)F)c4F)[nH]c3nc2=O)cc1] | 658.4 |
| 269 | 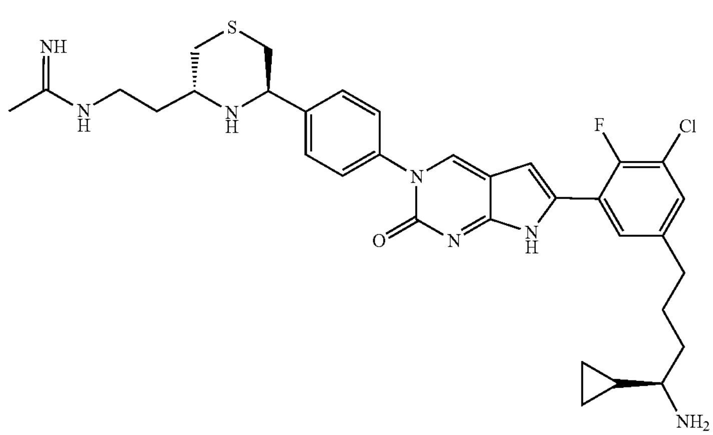 [SMILES: CC(=N)NCC[C@@H]1CSC[C@@H](c2ccc(-n3cc4cc(-c5cc(CCC[C@@H](N)C6CC6)cc(Cl)c5F)[nH]c4nc3=O)cc2)N1] | 636.4 |

TABLE 2-continued

| # | Structure | ESI, m/z [M + H]+ |
|---|---|---|
| 270 | 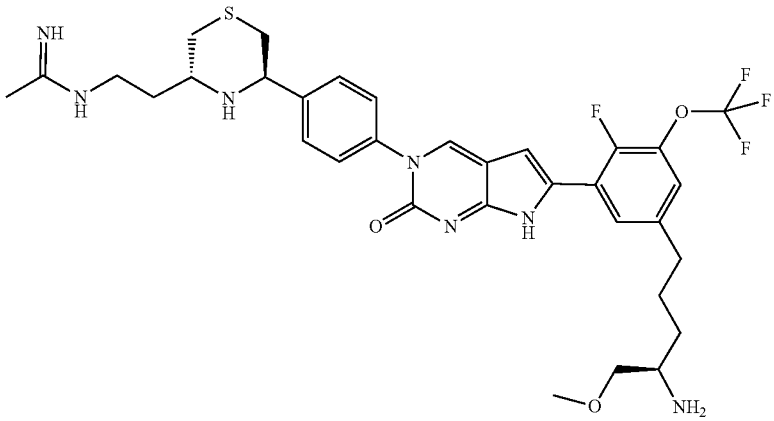 [SMILES: COC[C@H](N)CCCc1cc(OC(F)(F)F)c(F)c(-c2cc3cn(-c4ccc([C@@H]5CSC[C@@H](CCNC(C)=N)N5)cc4)c(=O)nc3[nH]2)c1] | 690.4 |
| 271 | 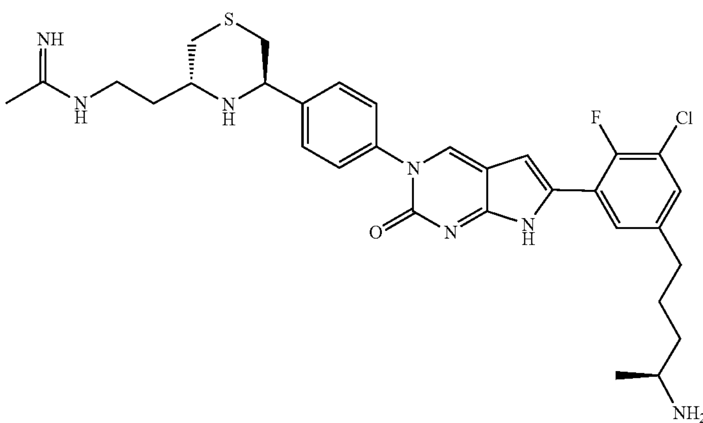 [SMILES: CC(=N)NCC[C@@H]1CSC[C@@H](c2ccc(-n3cc4cc(-c5cc(CCC[C@H](C)N)cc(Cl)c5F)[nH]c4nc3=O)cc2)N1] | 610.4 |
| 272 | 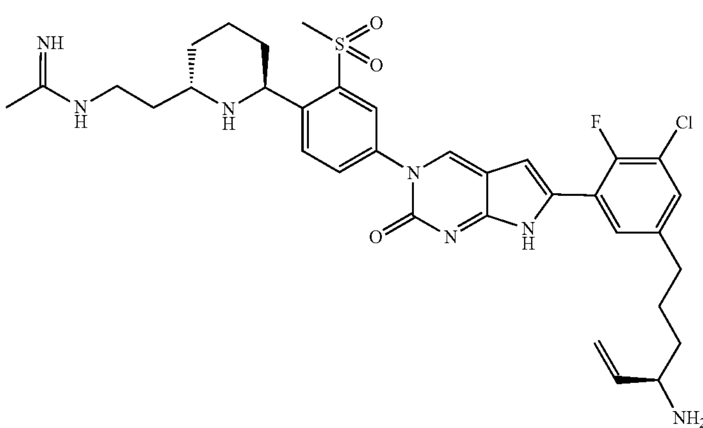 [SMILES: C=C[C@H](N)CCCc1cc(Cl)c(F)c(-c2cc3cn(-c4ccc([C@@H]5CCC[C@@H](CCNC(C)=N)N5)c(S(C)(=O)=O)c4)c(=O)nc3[nH]2)c1] | 682.3 |

TABLE 2-continued
| # | Structure | ESI, m/z [M + H]+ |
|---|---|---|
| 273 | 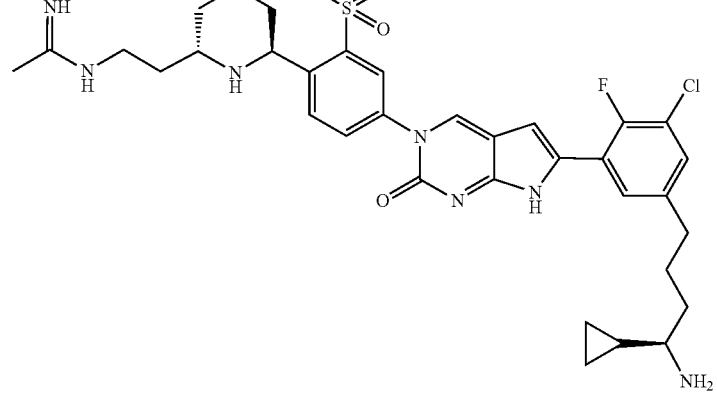 | 696.3 |
| 274 | 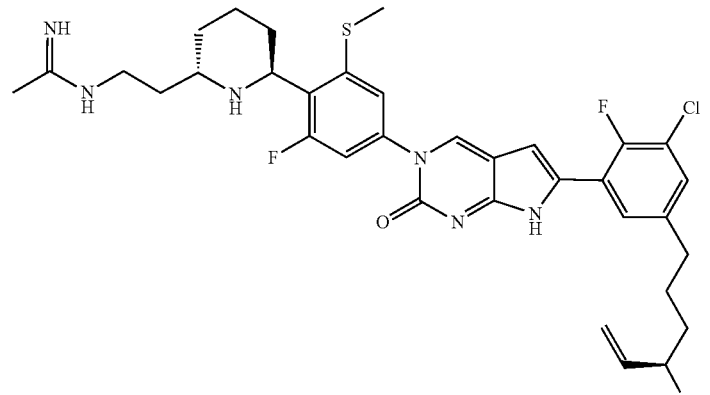 | 668.3 |
| 275 | 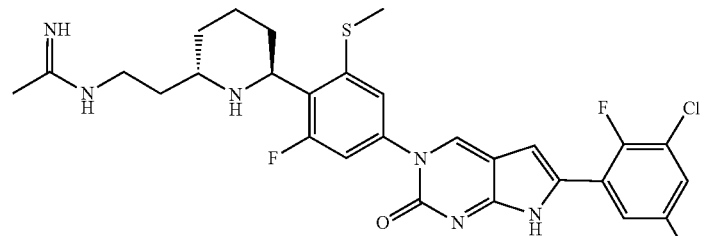 | 682.4 |

TABLE 2-continued
| # | Structure | ESI, m/z [M + H]+ |
|---|-----------|-------------------|
| 276 | 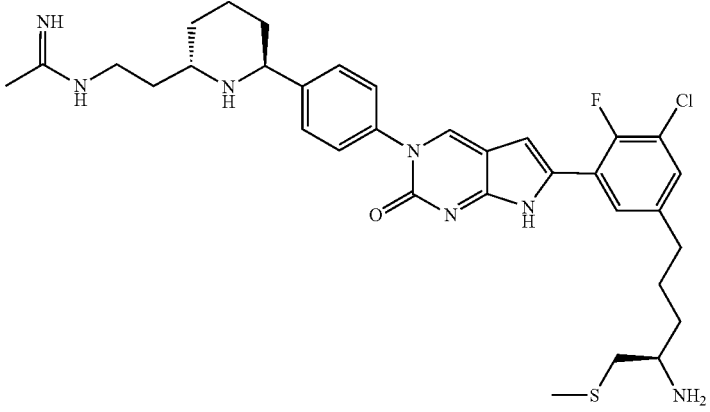 [SMILES: CSC[C@H](N)CCCc1cc(Cl)c(F)c(-c2cc3cn(-c4ccc([C@@H]5CCC[C@@H](CCNC(C)=N)N5)cc4)c(=O)nc3[nH]2)c1] | 638.4 |
| 277 | 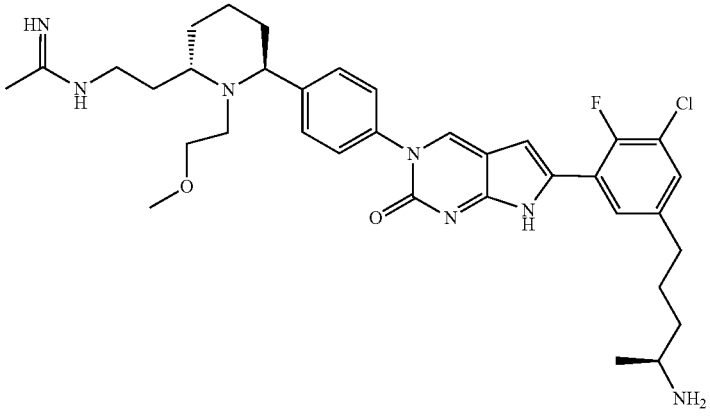 [SMILES: COCCN1[C@H](CCNC(C)=N)CCC[C@H]1c1ccc(-n2cc3cc(-c4cc(CCC[C@H](C)N)cc(Cl)c4F)[nH]c3nc2=O)cc1] | 650 |
| 278 | 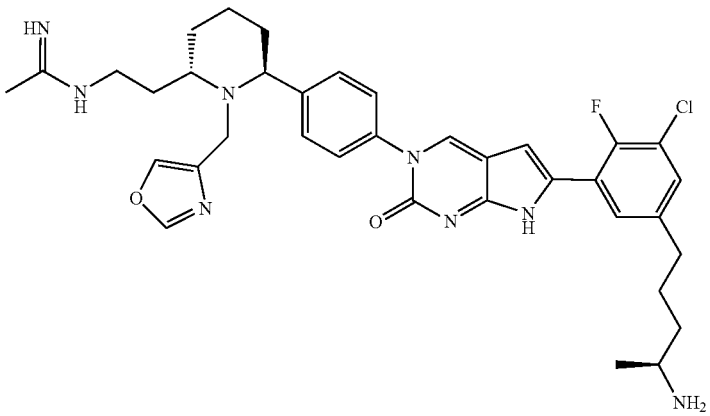 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1Cc1cocn1] | 673 |

TABLE 2-continued
| # | Structure | ESI, m/z [M + H]+ |
|---|---|---|
| 279 | 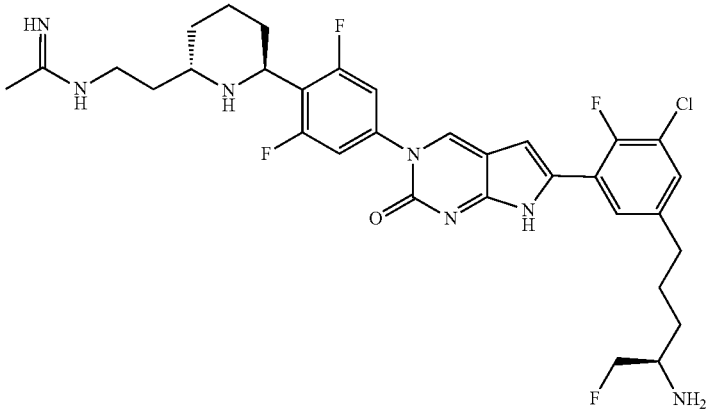 [SMILES: CC(=N)NCC[C@@H]1CCC[C@@H](c2c(F)cc(-n3cc4cc(-c5cc(CCC[C@@H](N)CF)cc(Cl)c5F)[nH]c4nc3=O)cc2F)N1] | 646.4 |
| 280 | 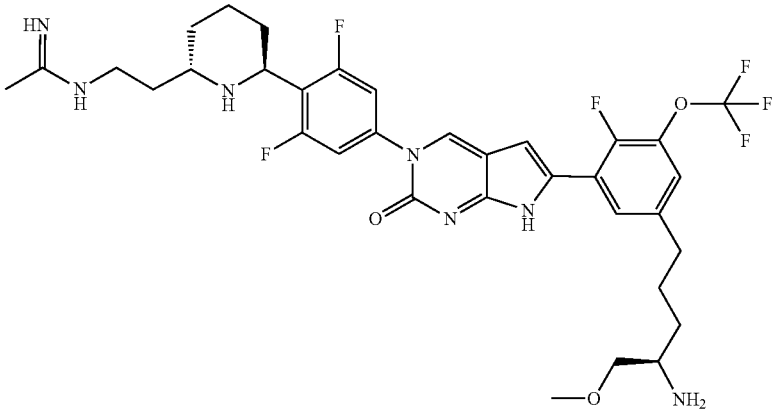 [SMILES: COC[C@H](N)CCCc1cc(OC(F)(F)F)c(F)c(-c2cc3cn(-c4cc(F)c([C@@H]5CCC[C@@H](CCNC(C)=N)N5)c(F)c4)c(=O)nc3[nH]2)c1] | 708.7 |
| 281 | 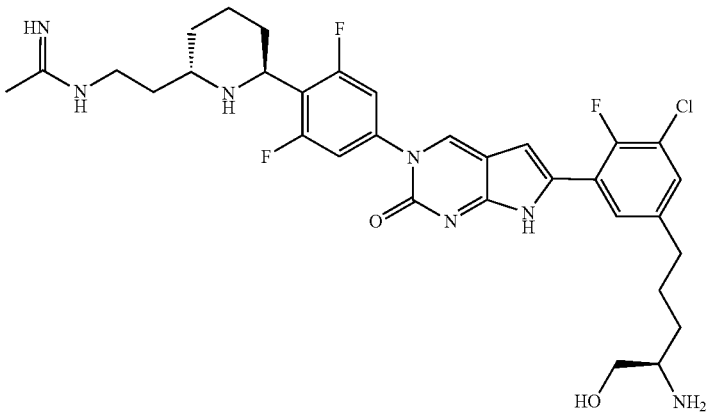 | 644.4 |

TABLE 2-continued

| # | Structure | ESI, m/z [M + H]+ |
|---|---|---|
| 282 | 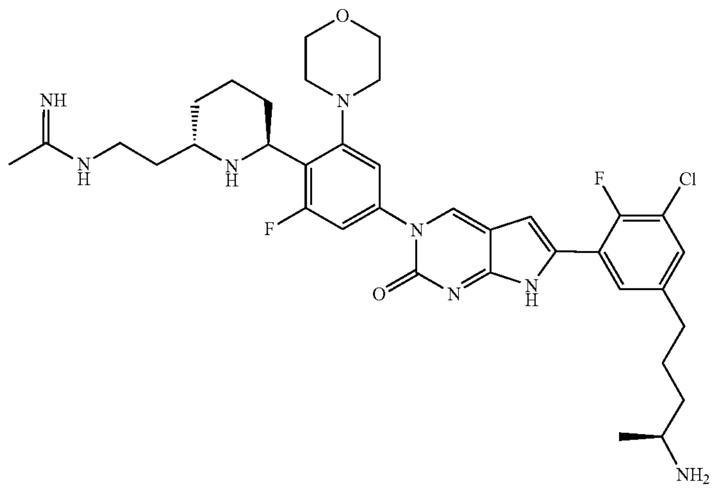 [SMILES: CC(=N)NCC[C@@H]1CCC[C@@H](c2c(F)cc(-n3cc4cc(-c5cc(CCC[C@H](C)N)cc(Cl)c5F)[nH]c4nc3=O)cc2N2CCOCC2)N1] | 695 |
| 283 | 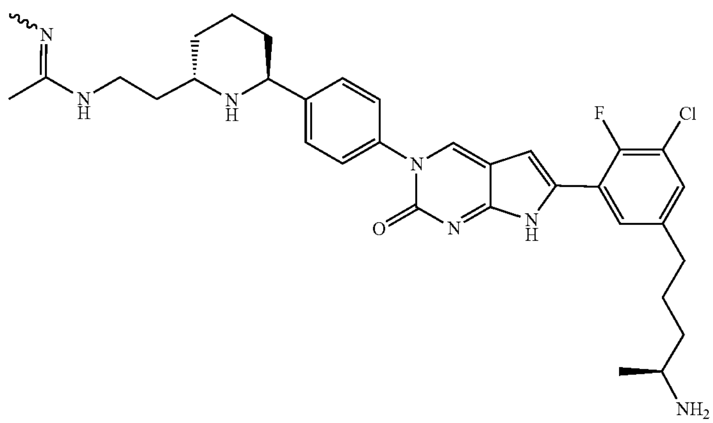 | 606.4 |
| 284 | 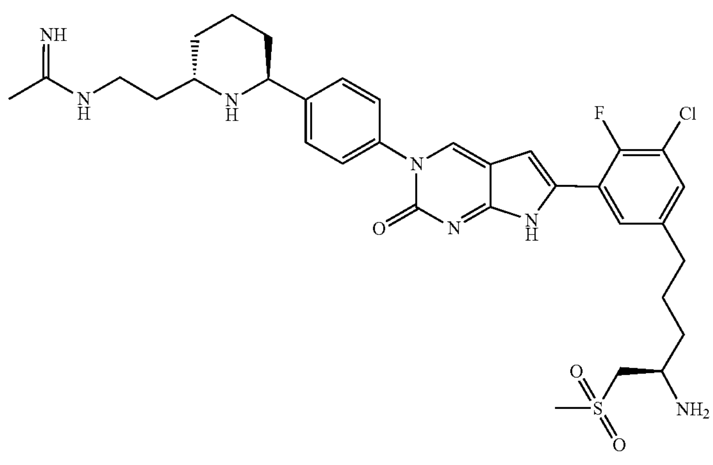 [SMILES: CC(=N)NCC[C@@H]1CCC[C@@H](c2ccc(-n3cc4cc(-c5cc(CCC[C@@H](N)CS(C)(=O)=O)cc(Cl)c5F)[nH]c4nc3=O)cc2)N1] | 670.3 |

TABLE 2-continued
| # | Structure | ESI, m/z [M + H]+ |
|---|---|---|
| 285 | 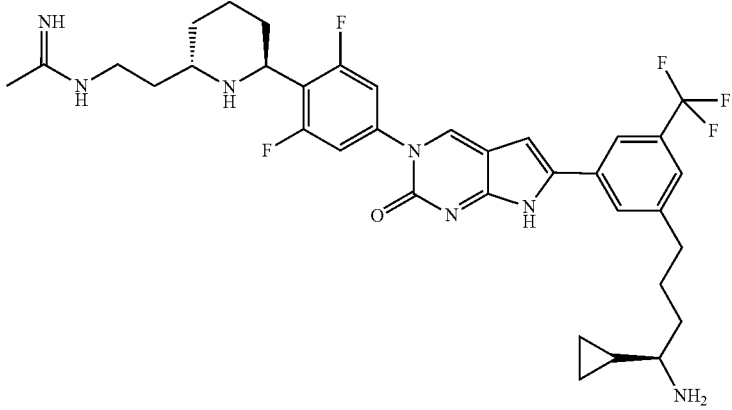 [SMILES: CC(=N)NCC[C@@H]1CCC[C@@H](c2c(F)cc(-n3cc4cc(-c5cc(CCC[C@@H](N)C6CC6)cc(C(F)(F)F)c5)[nH]c4nc3=O)cc2F)N1] | 670.7 |
| 286 | 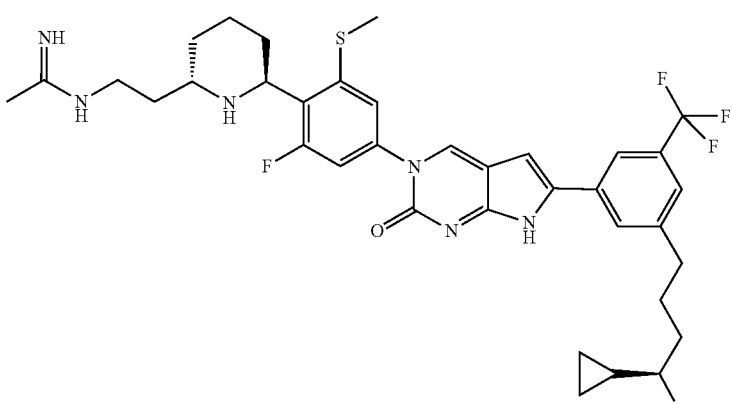 | 698.5 |
| 287 | 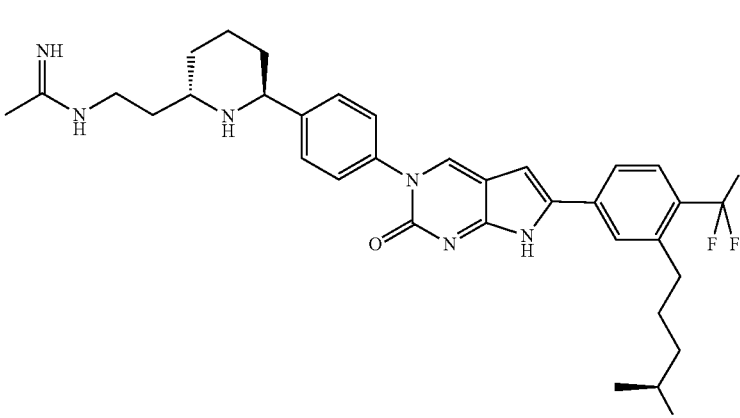 | 608.4 |

TABLE 2-continued

| # | Structure | ESI, m/z [M + H]+ |
|---|---|---|
| 288 | 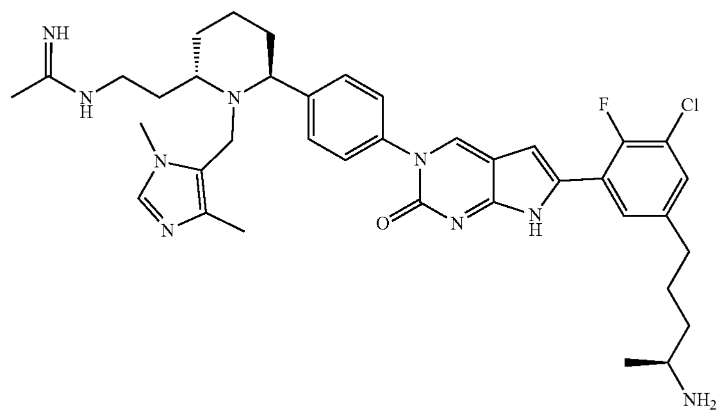 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1Cc1c(C)ncn1C] | 700 |
| 289 | 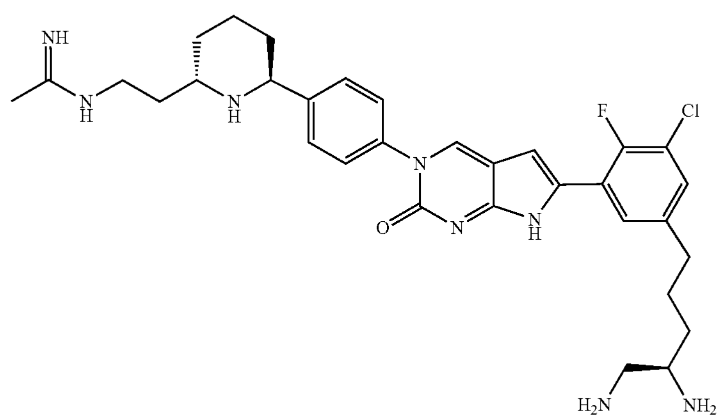 [SMILES: CC(=N)NCC[C@@H]1CCC[C@@H](c2ccc(-n3cc4cc(-c5cc(CCC[C@@H](N)CN)cc(Cl)c5F)[nH]c4nc3=O)cc2)N1] | 607.4 |
| 290 | 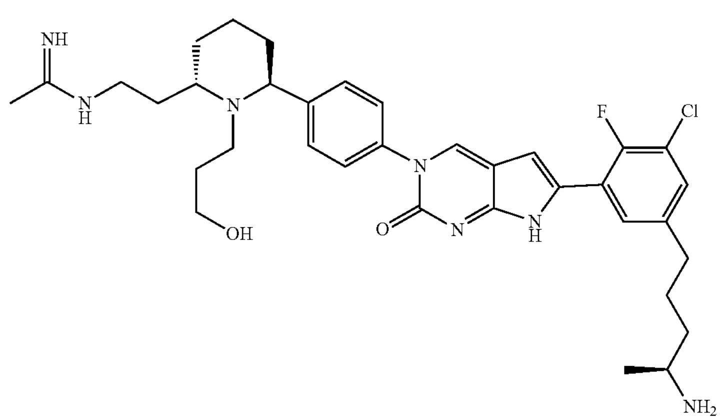 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1CCCO] | 650 |

TABLE 2-continued

| # | Structure | ESI, m/z [M + H]+ |
|---|---|---|
| 291 | 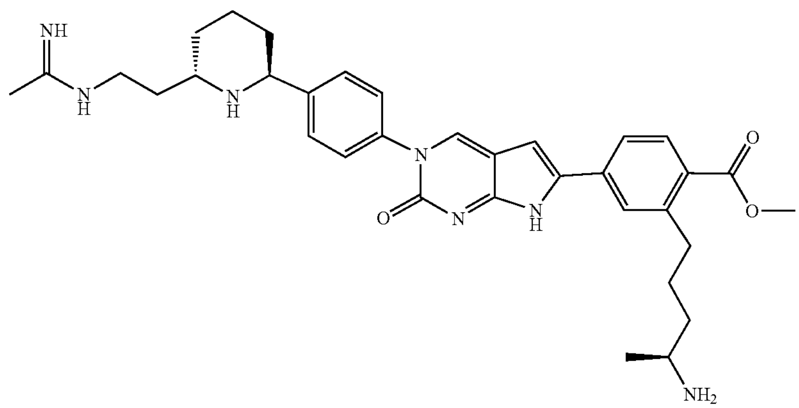 [SMILES: COC(=O)c1ccc(-c2cc3cn(-c4ccc([C@@H]5CCC[C@@H](CCNC(C)=N)N5)cc4)c(=O)nc3[nH]2)cc1CCC[C@H](C)N] | 598.4 |
| 292 | 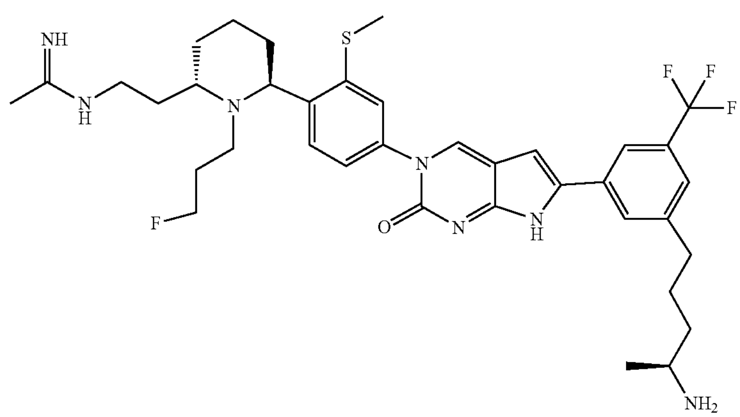 [SMILES: CSc1cc(-n2cc3cc(-c4cc(CCC[C@H](C)N)cc(C(F)(F)F)c4)[nH]c3nc2=O)ccc1[C@@H]1CCC[C@@H](CCNC(C)=N)N1CCCF] | 714 |
| 293 | 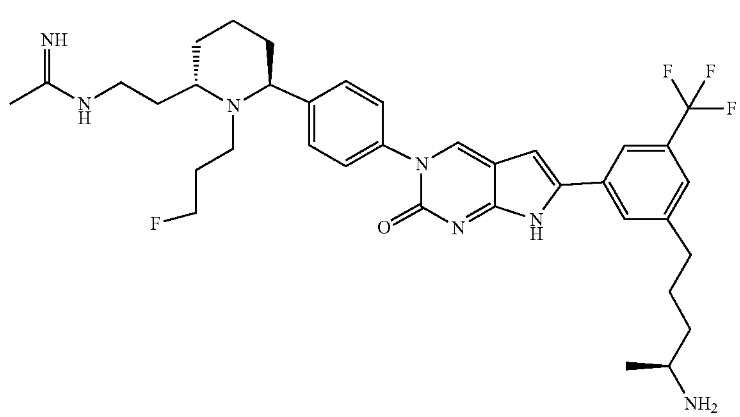 [SMILES: CC(=N)NCC[C@@H]1CCC[C@@H](c2ccc(-n3cc4cc(-c5cc(CCC[C@H](C)N)cc(C(F)(F)F)c5)[nH]c4nc3=O)cc2)N1CCCF] | 668 |

In some embodiments of the disclosed methods, the compound of Formula (II) or Formula (II-1) includes any one of the compounds listed in Table 2a, or a tautomer thereof or a pharmaceutically acceptable salt of the compound or tautomer.

TABLE 2a

| # | Structure |
|---|---|
| 294 | 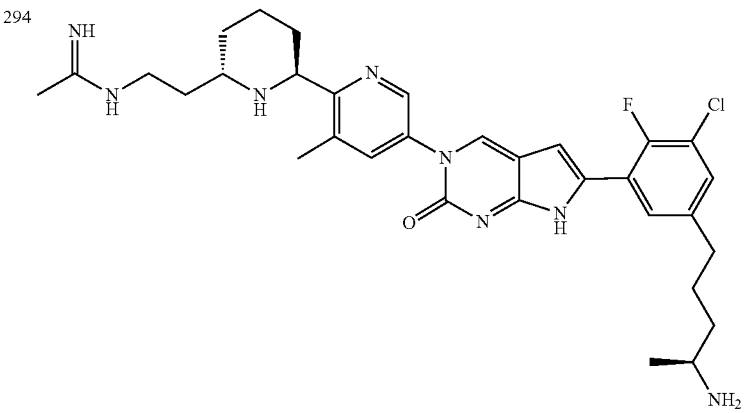 |
| 295 | 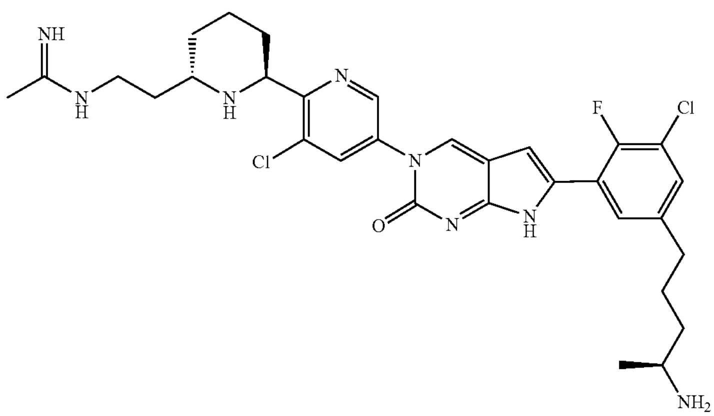 [SMILES: CC(=N)NCC[C@@H]1CCC[C@@H](c2ncc(-n3cc4cc(-c5cc(CCC[C@H](C)N)cc(Cl)c5F)[nH]c4nc3=O)cc2F)N1] |
| 296 | 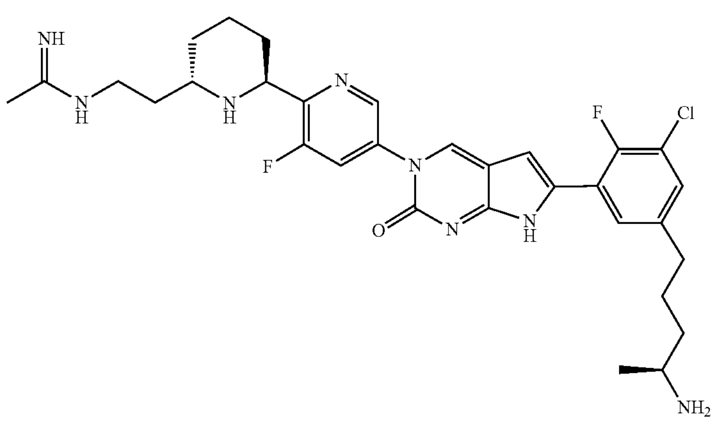 |

TABLE 2a-continued
| # | Structure |
|---|---|
| 297 | 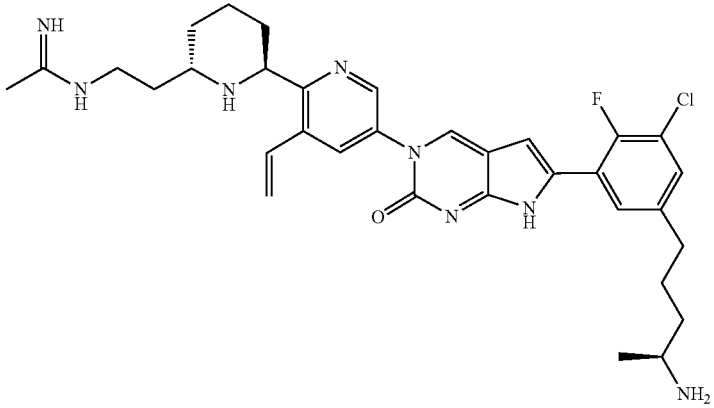 [SMILES: C=Cc1cc(-n2cc3cc(-c4cc(CCC[C@H](C)N)cc(Cl)c4F)[nH]c3nc2=O)cnc1[C@@H]1CCC[C@@H](CCNC(C)=N)N1] |
| 298 | 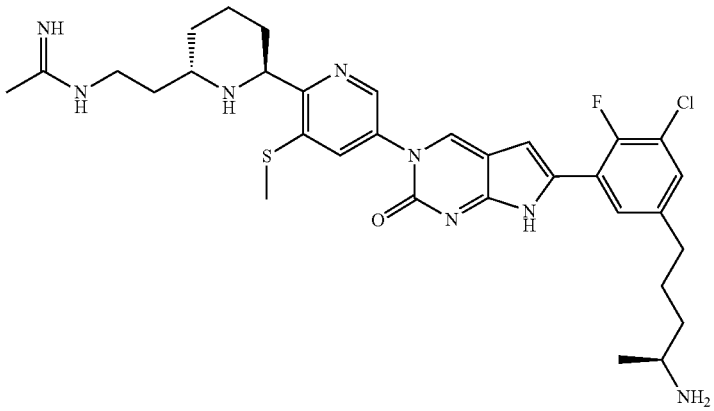 [SMILES: CSc1cc(-n2cc3cc(-c4cc(CCC[C@H](C)N)cc(Cl)c4F)[nH]c3nc2=O)cnc1[C@@H]1CCC[C@@H](CCNC(C)=N)N1] |
| 300 | 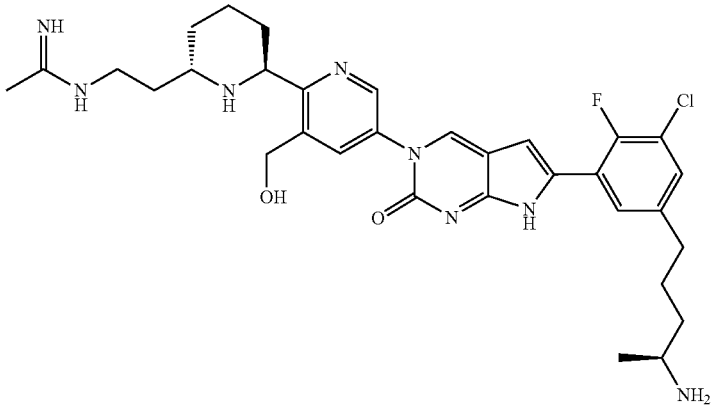 [SMILES: CC(=N)NCC[C@@H]1CCC[C@@H](c2ncc(-n3cc4cc(-c5cc(CCC[C@H](C)N)cc(Cl)c5F)[nH]c4nc3=O)cc2CO)N1] |

TABLE 2a-continued
| # | Structure |
|---|---|
| 305 | 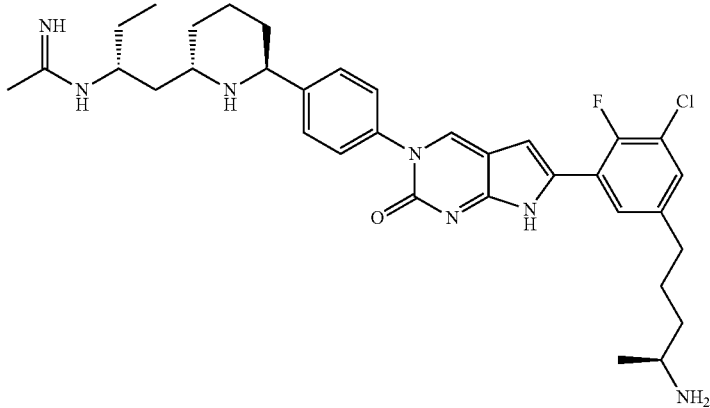 [SMILES: CC[C@H](C[C@@H]1CCC[C@@H](c2ccc(-n3cc4cc(-c5cc(CCC[C@H](C)N)cc(Cl)c5F)[nH]c4nc3=O)cc2)N1)NC(C)=N] |
| 306 | 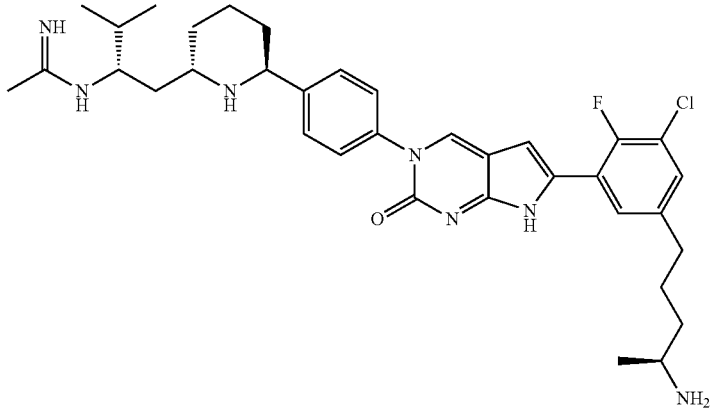 [SMILES: CC(=N)N[C@@H](C[C@@H]1CCC[C@@H](c2ccc(-n3cc4cc(-c5cc(CCC[C@H](C)N)cc(Cl)c5F)[nH]c4nc3=O)cc2)N1)C(C)C] |
| 307 | 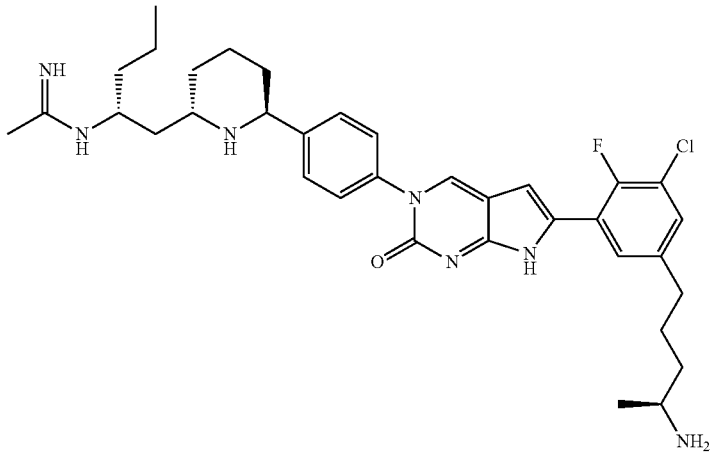 [SMILES: CCC[C@H](C[C@@H]1CCC[C@@H](c2ccc(-n3cc4cc(-c5cc(CCC[C@H](C)N)cc(Cl)c5F)[nH]c4nc3=O)cc2)N1)NC(C)=N] |

TABLE 2a-continued
| # | Structure |
|---|---|
| 308 | 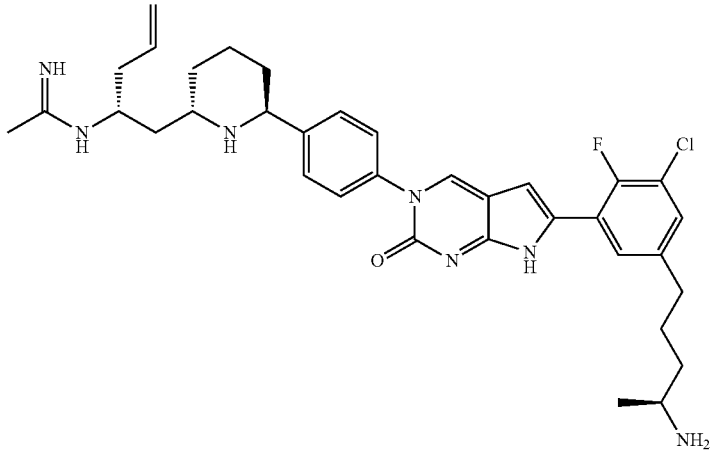 [SMILES: C=CC[C@H](C[C@@H]1CCC[C@@H](c2ccc(-n3cc4cc(-c5cc(CCC[C@H](C)N)cc(Cl)c5F)[nH]c4nc3=O)cc2)N1)NC(C)=N] |
| 309 | 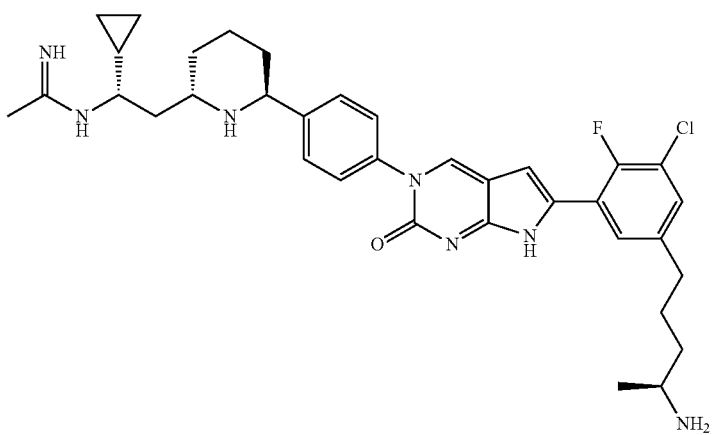 [SMILES: CC(=N)N[C@@H](C[C@@H]1CCC[C@@H](c2ccc(-n3cc4cc(-c5cc(CCC[C@H](C)N)cc(Cl)c5F)[nH]c4nc3=O)cc2)N1)C1CC1] |
| 310 | 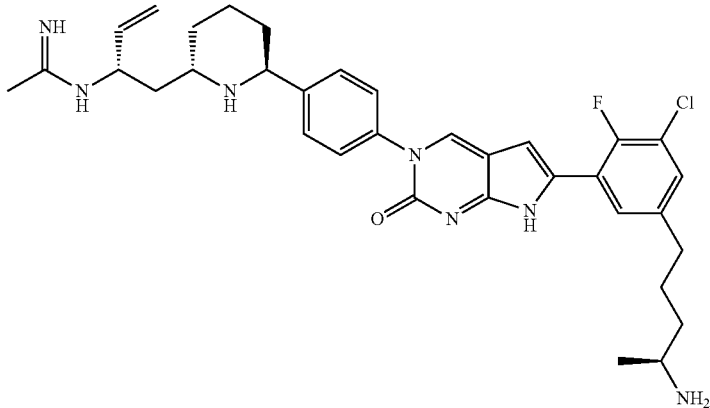 [SMILES: C=C[C@H](C[C@@H]1CCC[C@@H](c2ccc(-n3cc4cc(-c5cc(CCC[C@H](C)N)cc(Cl)c5F)[nH]c4nc3=O)cc2)N1)NC(C)=N] |

TABLE 2a-continued
| # | Structure |
|---|---|
| 311 | 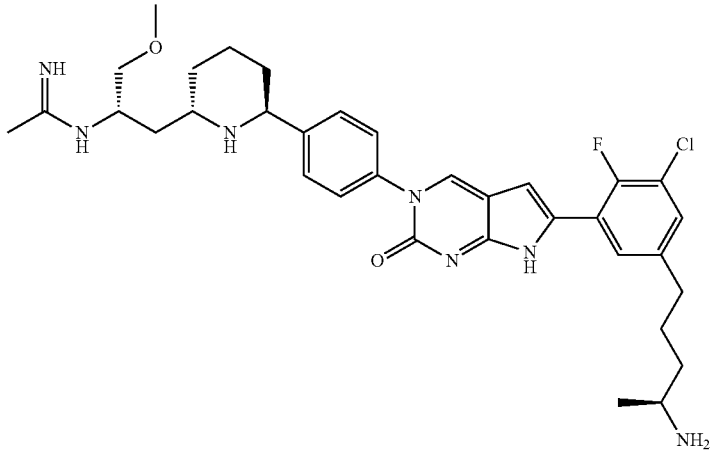 [SMILES: COC[C@H](C[C@@H]1CCC[C@@H](c2ccc(-n3cc4cc(-c5cc(CCC[C@H](C)N)cc(Cl)c5F)[nH]c4nc3=O)cc2)N1)NC(C)=N] |
| 312 | 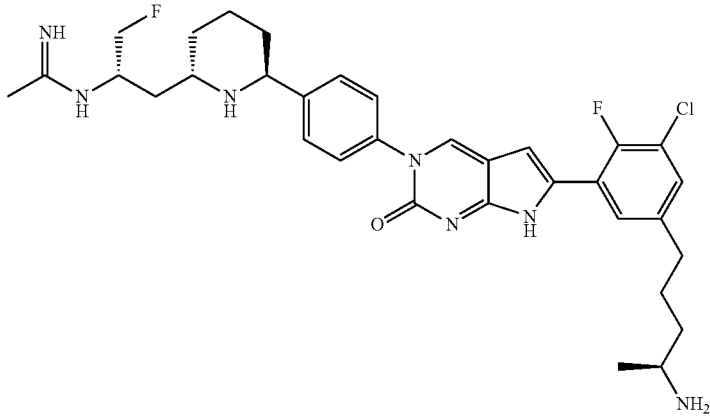 [SMILES: CC(=N)N[C@H](CF)C[C@@H]1CCC[C@@H](c2ccc(-n3cc4cc(-c5cc(CCC[C@H](C)N)cc(Cl)c5F)[nH]c4nc3=O)cc2)N1] |
| 313 | 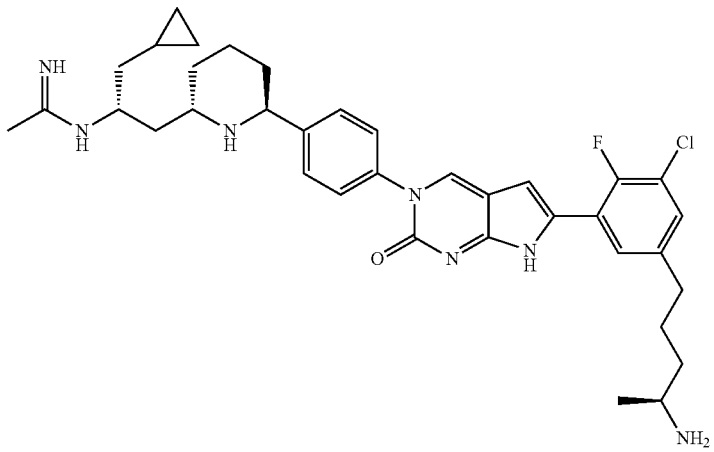 [SMILES: CC(=N)N[C@H](CC1CC1)C[C@@H]1CCC[C@@H](c2ccc(-n3cc4cc(-c5cc(CCC[C@H](C)N)cc(Cl)c5F)[nH]c4nc3=O)cc2)N1] |

TABLE 2a-continued
| # | Structure |
|---|---|
| 314 | 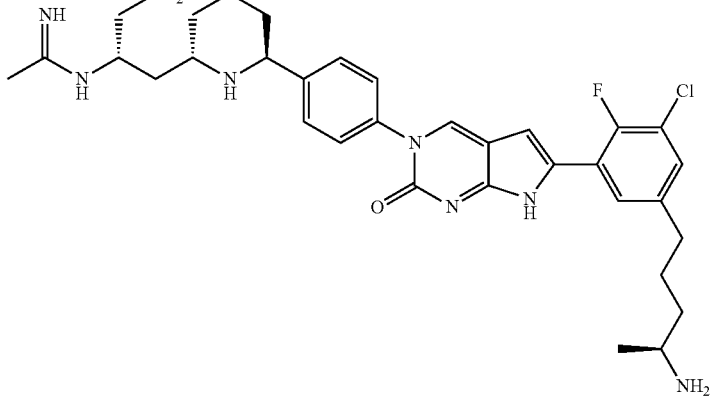 |
| 315 | 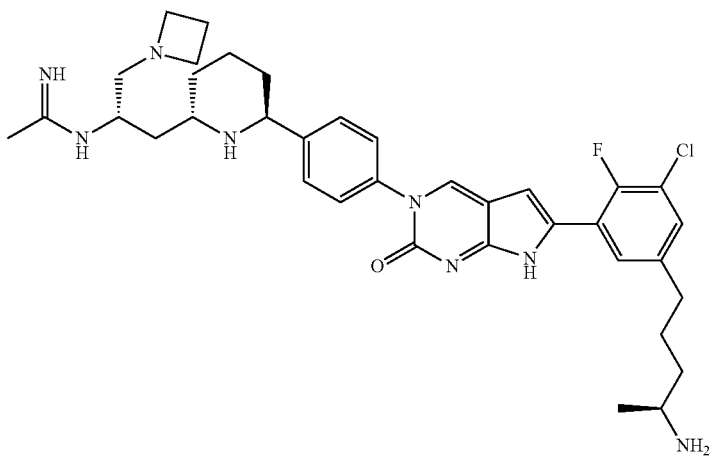 [SMILES: CC(=N)N[C@@H](C[C@@H]1CCC[C@@H](c2ccc(-n3cc4cc(-c5cc(CCC[C@H](C)N)cc(Cl)c5F)[nH]c4nc3=O)cc2)N1)CN1CCC1] |
| 316 | 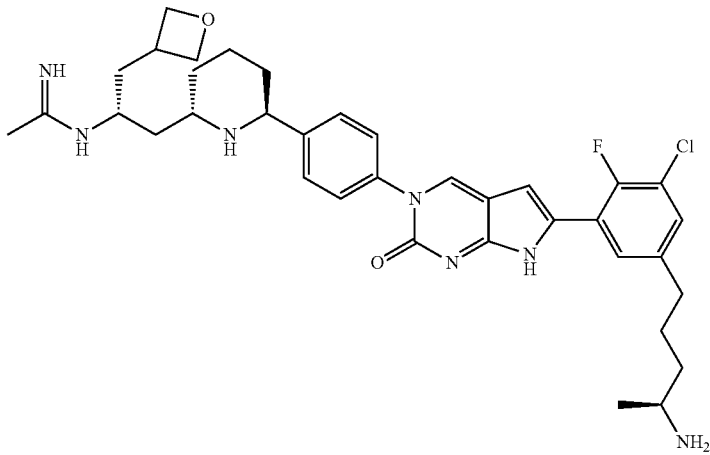 [SMILES: CC(=N)N[C@H](CC1COC1)C[C@@H]1CCC[C@@H](c2ccc(-n3cc4cc(-c5cc(CCC[C@H](C)N)cc(Cl)c5F)[nH]c4nc3=O)cc2)N1] |

In some embodiments of the disclosed methods, the compound of Formula (II) or Formula (II-1) includes any one of the compounds listed in Table 2b, or a tautomer thereof or a pharmaceutically acceptable salt of the compound or tautomer.
TABLE 2b
| # | Structure | ESI, m/z [M + H]+ |
|---|---|---|
| 317 | 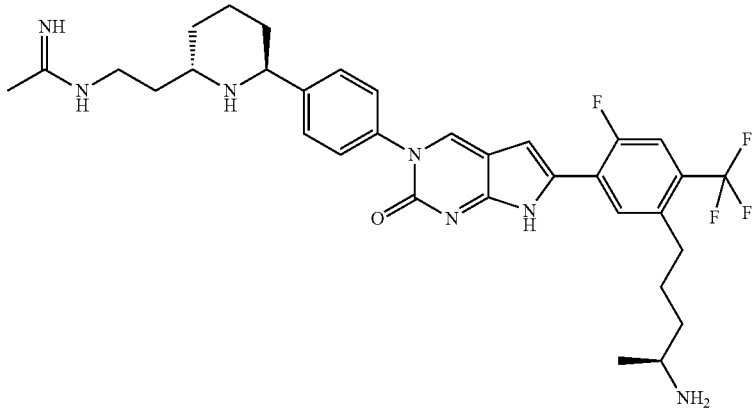 [SMILES: CC(=N)NCC[C@@H]1CCC[C@@H](c2ccc(-n3cc4cc(-c5cc(CCC[C@H](C)N)c(C(F)(F)F)cc5F)[nH]c4nc3=O)cc2)N1] | 626.8 |
| 318 | 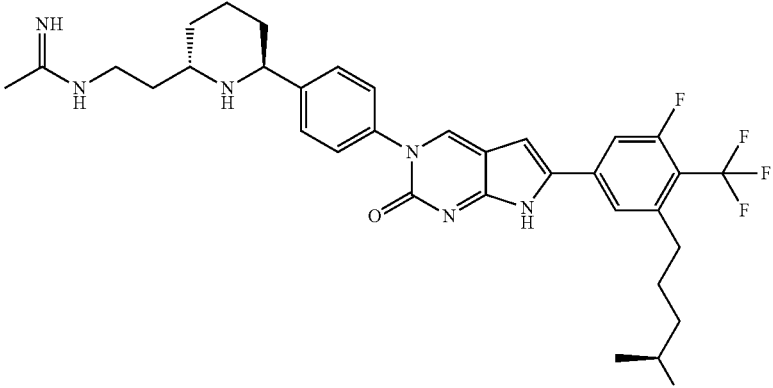 | 626.8 |
| 319 | 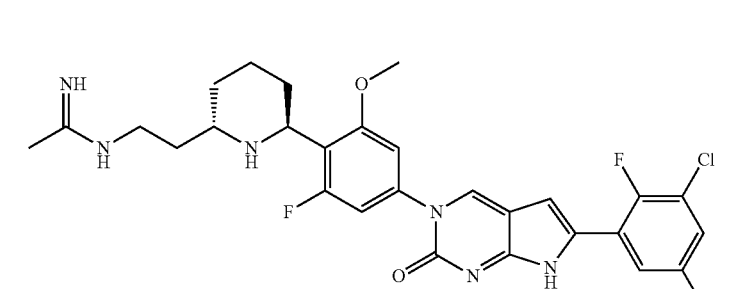 | 640.3 |

TABLE 2b-continued
| # | Structure | ESI, m/z [M + H]+ |
|---|-----------|-------------------|
| 320 | 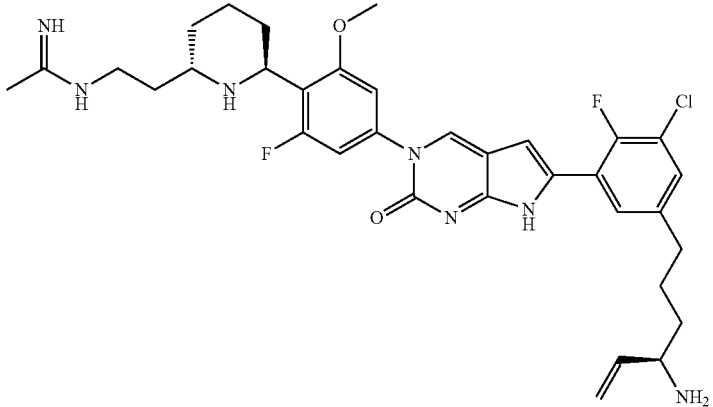 [SMILES: C=C[C@H](N)CCCc1cc(Cl)c(F)c(-c2cc3cn(-c4cc(F)c([C@@H]5CCC[C@@H](CCNC(C)=N)N5)c(OC)c4)c(=O)nc3[nH]2)c1] | 652.3 |
| 321 | 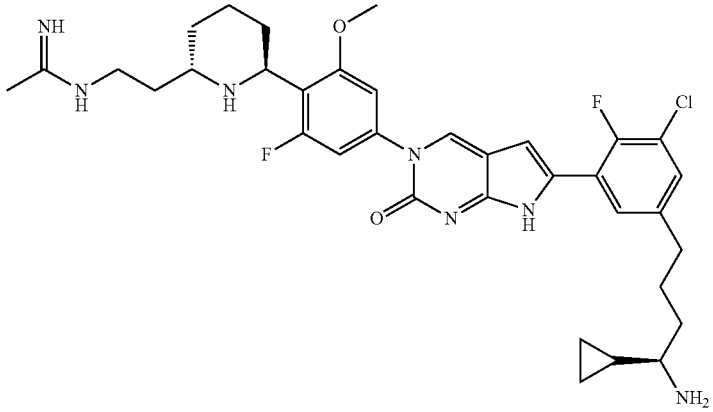 [SMILES: COc1cc(-n2cc3cc(-c4cc(CCC[C@@H](N)C5CC5)cc(Cl)c4F)[nH]c3nc2=O)cc(F)c1[C@@H]1CCC[C@@H](CCNC(C)=N)N1] | 666.4 |
| 322 | 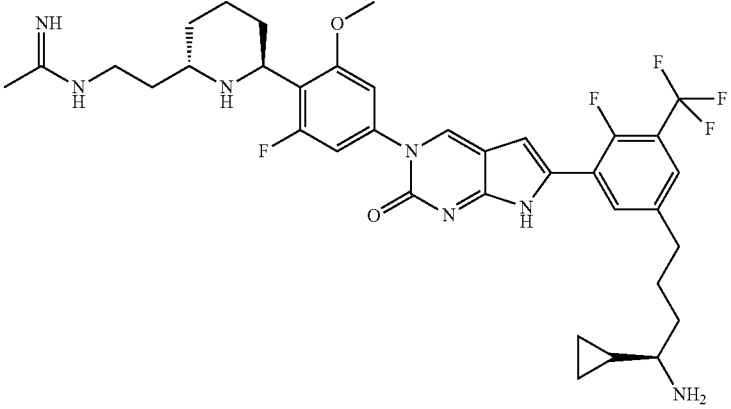 [SMILES: COc1cc(-n2cc3cc(-c4cc(CCC[C@@H](N)C5CC5)cc(C(F)(F)F)c4F)[nH]c3nc2=O)cc(F)c1[C@@H]1CCC[C@@H](CCNC(C)=N)N1] | 700.4 |

TABLE 2b-continued

| # | Structure | ESI, m/z [M + H]+ |
|---|---|---|
| 323 | 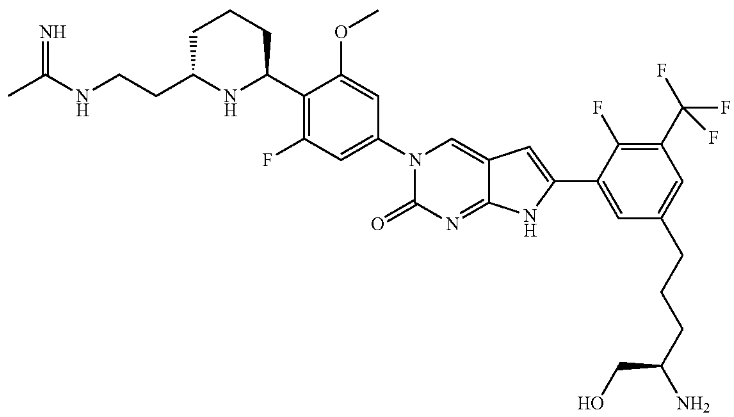 [SMILES: COc1cc(-n2cc3cc(-c4cc(CCC[C@@H](N)CO)cc(C(F)(F)F)c4F)[nH]c3nc2=O)cc(F)c1[C@@H]1CCC[C@@H](CCNC(C)=N)N1] | 690.4 |
| 325 | 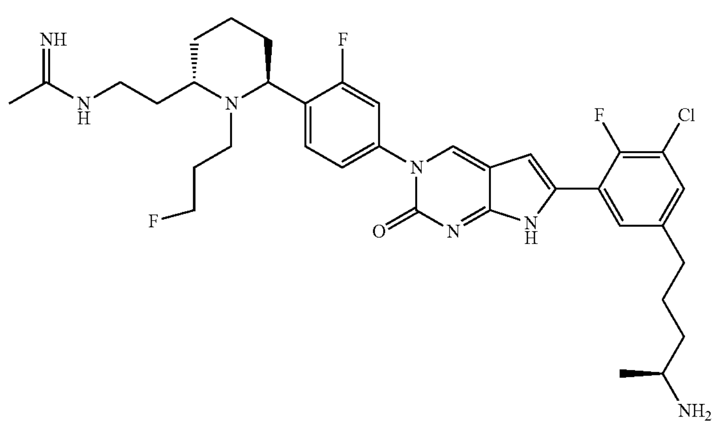 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2F)N1CCCF] | 670 |
| 326 | 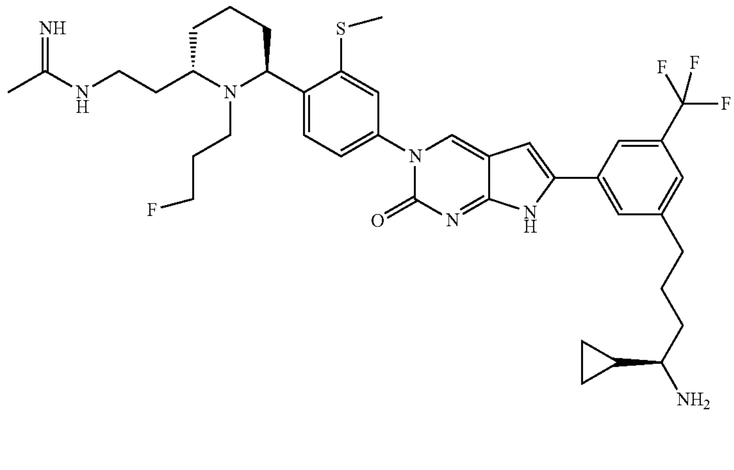 [SMILES: CSc1cc(-n2cc3cc(-c4cc(CCC[C@@H](N)C5CC5)cc(C(F)(F)F)c4)[nH]c3nc2=O)ccc1[C@@H]1CCC[C@@H](CCNC(C)=N)N1CCCF] | 740 |

TABLE 2b-continued
| # | Structure | ESI, m/z [M + H]+ |
|---|---|---|
| 327 | 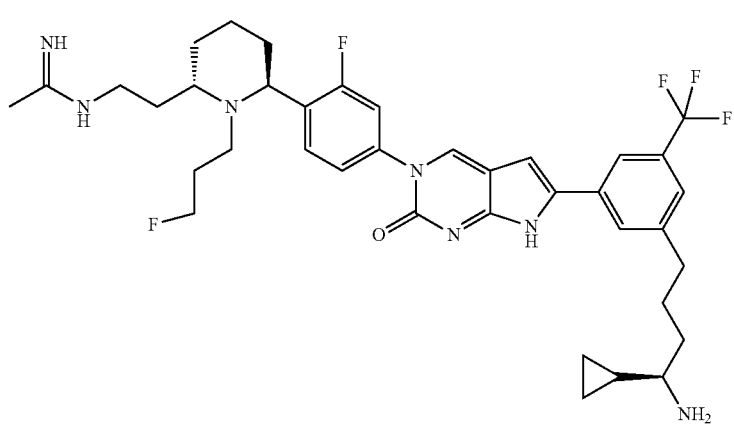 [SMILES: CC(=N)NCC[C@@H]1CCC[C@@H](c2ccc(-n3cc4cc(-c5cc(CCC[C@@H](N)C6CC6)cc(C(F)(F)F)c5)[nH]c4nc3=O)cc2F)N1CCCF] | 712 |
| 328 | 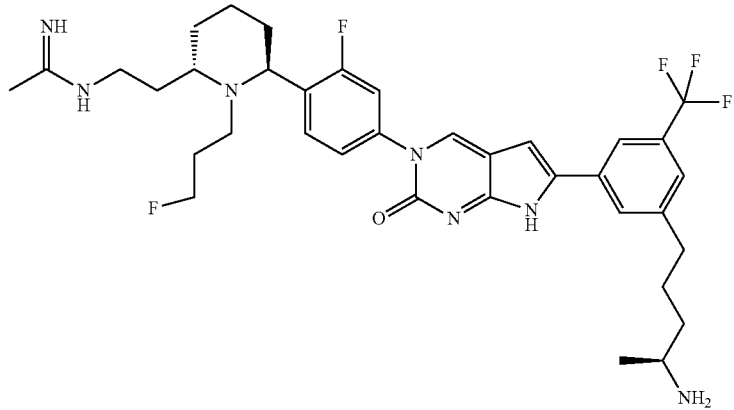 [SMILES: CC(=N)NCC[C@@H]1CCC[C@@H](c2ccc(-n3cc4cc(-c5cc(CCC[C@H](C)N)cc(C(F)(F)F)c5)[nH]c4nc3=O)cc2F)N1CCCF] | 686 |
| 329 | 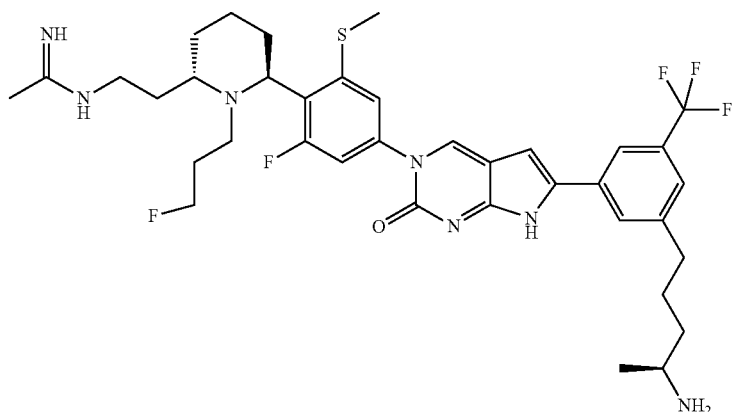 | 732 |

TABLE 2b-continued
| # | Structure | ESI, m/z [M + H]+ |
|---|---|---|
| 330 | 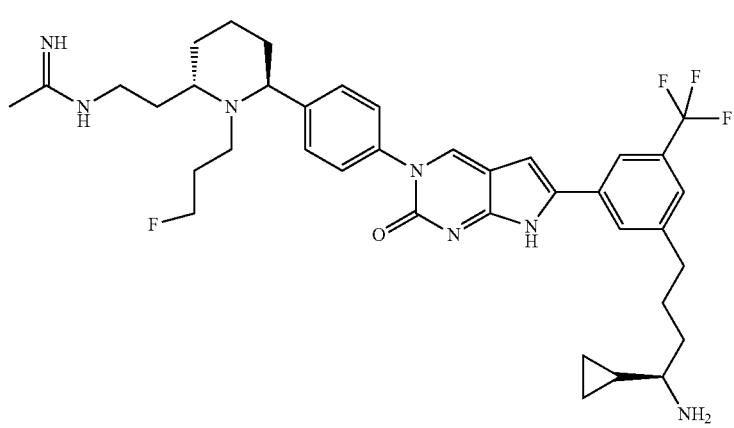 [SMILES: CC(=N)NCC[C@@H]1CCC[C@@H](c2ccc(-n3cc4cc(-c5cc(CCC[C@@H](N)C6CC6)cc(C(F)(F)F)c5)[nH]c4nc3=O)cc2)N1CCCF] | 694 |
| 331 | 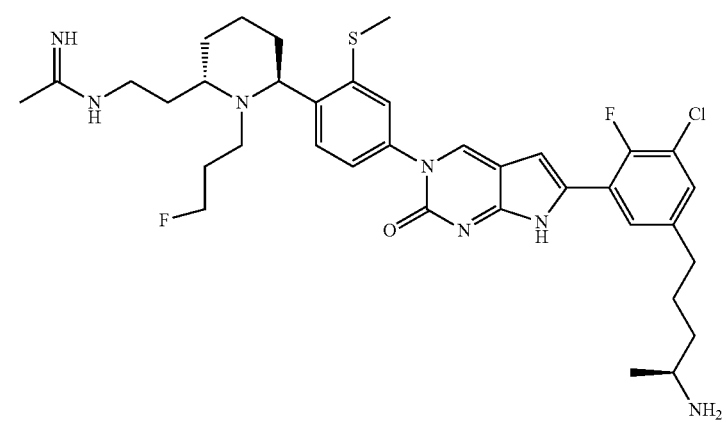 [SMILES: CSc1cc(-n2cc3cc(-c4cc(CCC[C@H](C)N)cc(Cl)c4F)[nH]c3nc2=O)ccc1[C@@H]1CCC[C@@H](CCNC(C)=N)N1CCCF] | 698 |
| 332 | 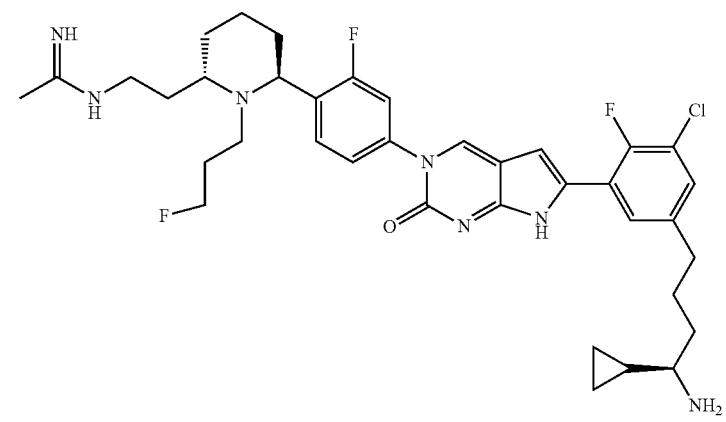 [SMILES: CC(=N)NCC[C@@H]1CCC[C@@H](c2ccc(-n3cc4cc(-c5cc(CCC[C@@H](N)C6CC6)cc(Cl)c5F)[nH]c4nc3=O)cc2F)N1CCCF] | 696 |

TABLE 2b-continued
| # | Structure | ESI, m/z [M + H]+ |
|---|---|---|
| 333 | 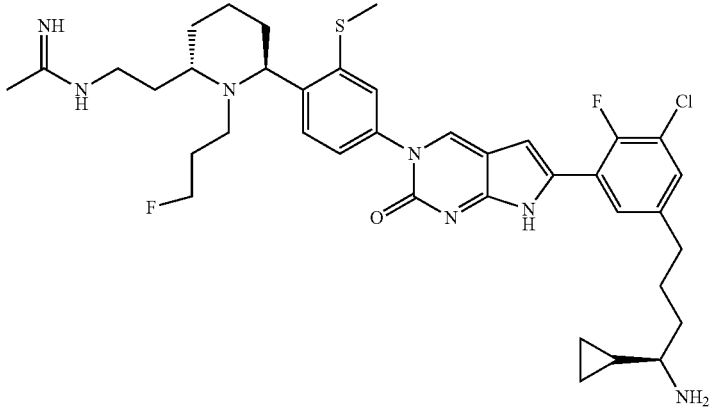 [SMILES: CSc1cc(-n2cc3cc(-c4cc(CCC[C@@H](N)C5CC5)cc(Cl)c4F)[nH]c3nc2=O)ccc1[C@@H]1CCC[C@@H](CCNC(C)=N)N1CCCF] | 724 |
| 334 | 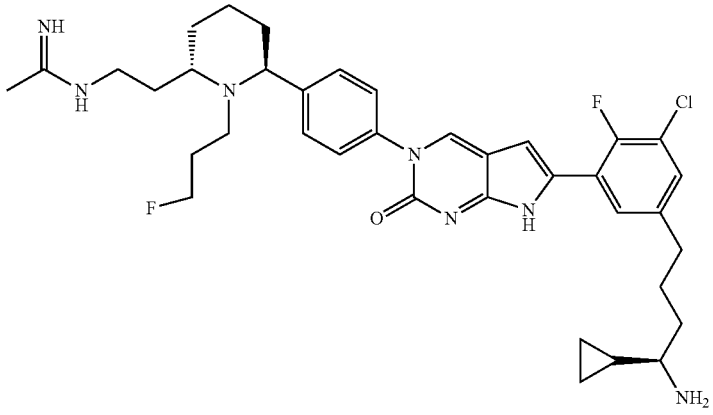 [SMILES: CC(=N)NCC[C@@H]1CCC[C@@H](c2ccc(-n3cc4cc(-c5cc(CCC[C@@H](N)C6CC6)cc(Cl)c5F)[nH]c4nc3=O)cc2)N1CCCF] | 678 |
| 335 | 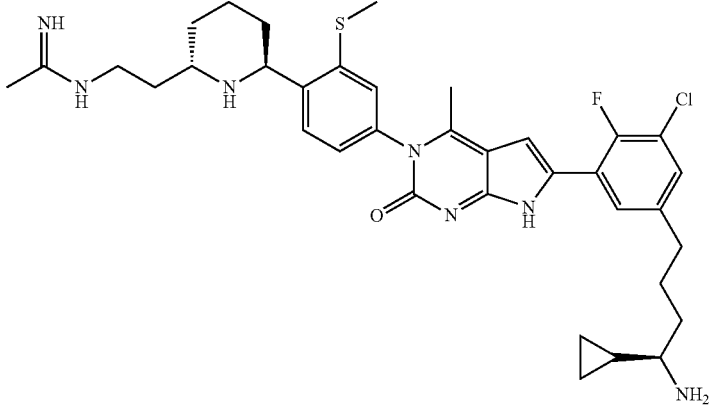 [SMILES: CSc1cc(-n2c(C)c3cc(-c4cc(CCC[C@@H](N)C5CC5)cc(Cl)c4F)[nH]c3nc2=O)ccc1[C@@H]1CCC[C@@H](CCNC(C)=N)N1] | 678.5 |

TABLE 2b-continued
| # | Structure | ESI, m/z [M + H]+ |
|---|---|---|
| 336 | 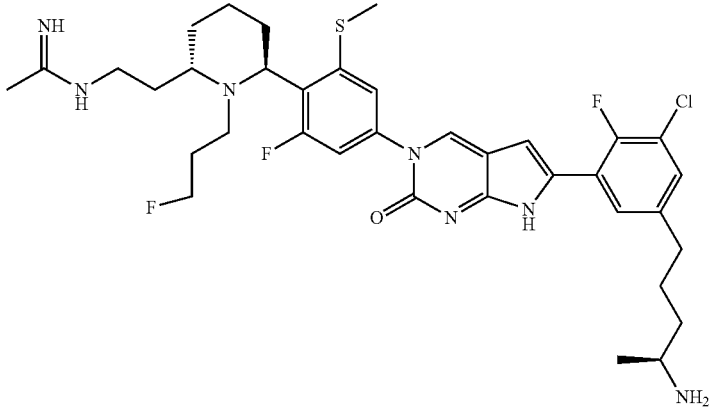 [SMILES: CSc1cc(-n2cc3cc(-c4cc(CCC[C@H](C)N)cc(Cl)c4F)[nH]c3nc2=O)cc(F)c1[C@@H]1CCC[C@@H](CCNC(C)=N)N1CCCF] | 716 |
| 337 | 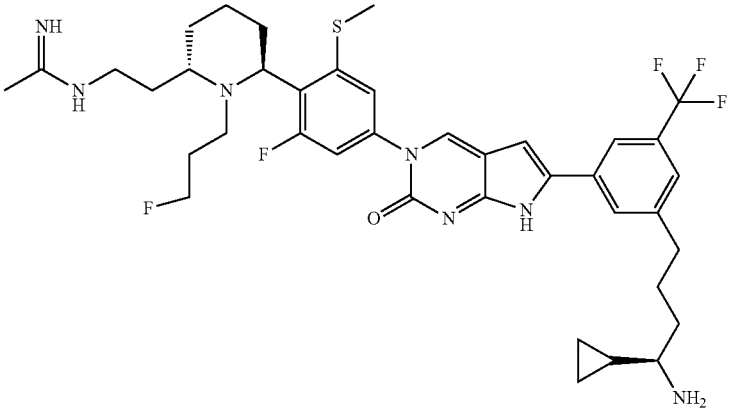 [SMILES: CSc1cc(-n2cc3cc(-c4cc(CCC[C@@H](N)C5CC5)cc(C(F)(F)F)c4)[nH]c3nc2=O)cc(F)c1[C@@H]1CCC[C@@H](CCNC(C)=N)N1CCCF] | 758 |
| 338 | 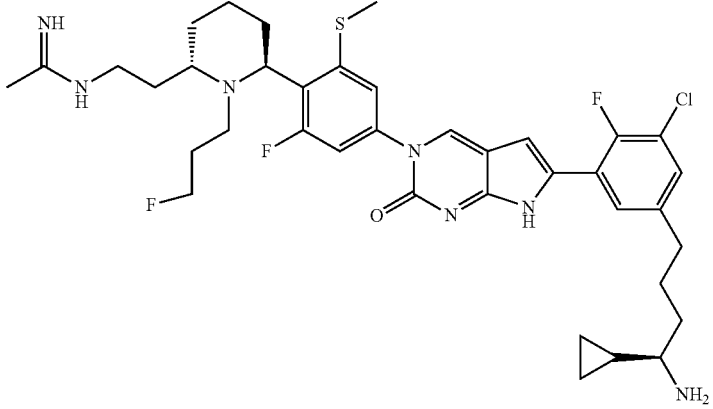 [SMILES: CSc1cc(-n2cc3cc(-c4cc(CCC[C@@H](N)C5CC5)cc(Cl)c4F)[nH]c3nc2=O)cc(F)c1[C@@H]1CCC[C@@H](CCNC(C)=N)N1CCCF] | 742 |

TABLE 2b-continued

| # | Structure | ESI, m/z [M + H]+ |
|---|---|---|
| 339 | 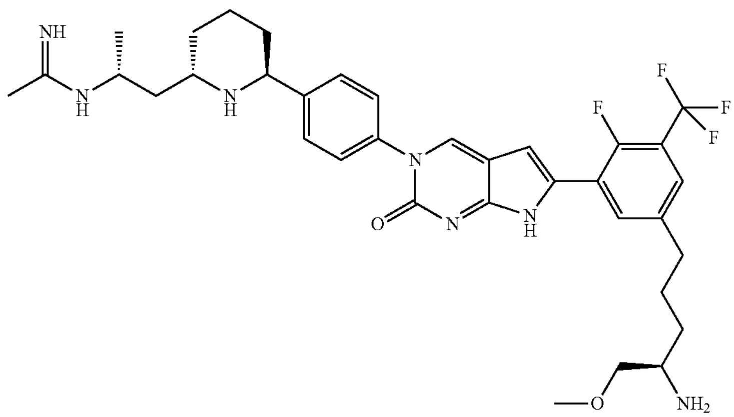 [SMILES: COC[C@H](N)CCCc1cc(-c2cc3cn(-c4ccc([C@@H]5CCC[C@@H](C[C@@H](C)NC(C)=N)N5)cc4)c(=O)nc3[nH]2)c(F)c(C(F)(F)F)c1] | 670.5 |
| 340 | 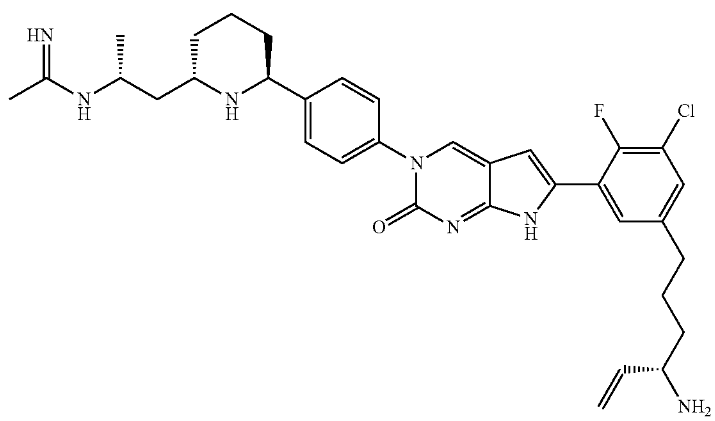 [SMILES: C=C[C@@H](N)CCCc1cc(Cl)c(F)c(-c2cc3cn(-c4ccc([C@@H]5CCC[C@@H](C[C@@H](C)NC(C)=N)N5)cc4)c(=O)nc3[nH]2)c1] | 618.4 |
| 341 | 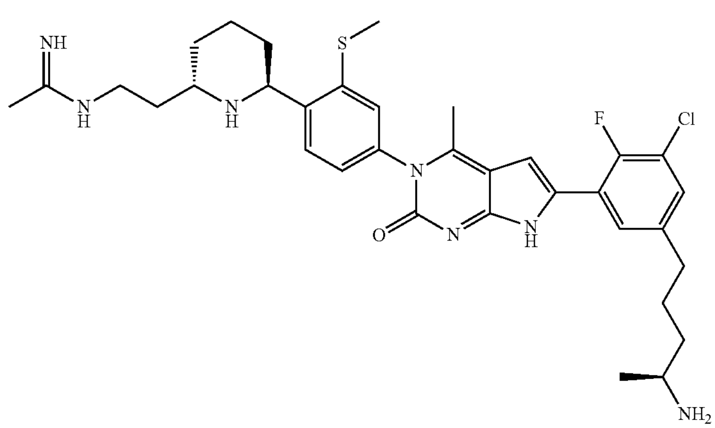 [SMILES: CSc1cc(-n2c(C)c3cc(-c4cc(CCC[C@H](C)N)cc(Cl)c4F)[nH]c3nc2=O)ccc1[C@@H]1CCC[C@@H](CCNC(C)=N)N1] | 652.3 |

TABLE 2b-continued

| # | Structure | ESI, m/z [M + H]+ |
|---|---|---|
| 342 | 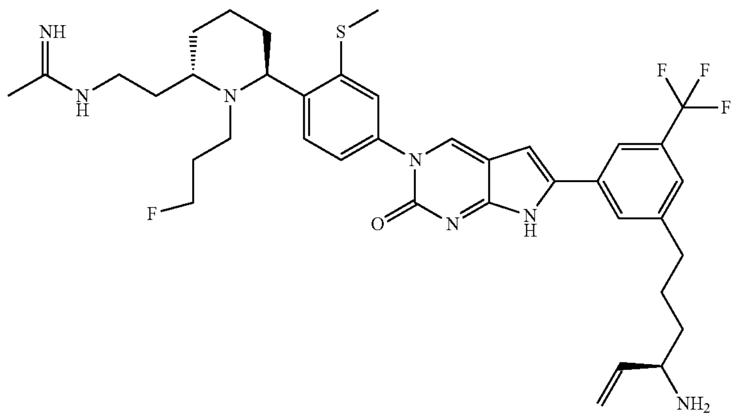 [SMILES: C=C[C@H](N)CCCc1cc(-c2cc3cn(-c4ccc([C@@H]5CCC[C@@H](CCNC(C)=N)N5CCCF)c(SC)c4)c(=O)nc3[nH]2)cc(C(F)(F)F)c1] | 726 |
| 343 | 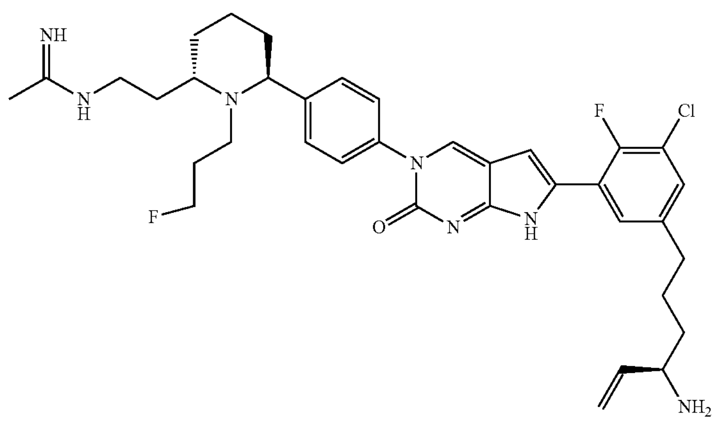 [SMILES: C=C[C@H](N)CCCc1cc(Cl)c(F)c(-c2cc3cn(-c4ccc([C@@H]5CCC[C@@H](CCNC(C)=N)N5CCCF)cc4)c(=O)nc3[nH]2)c1] | 664 |
| 344 | 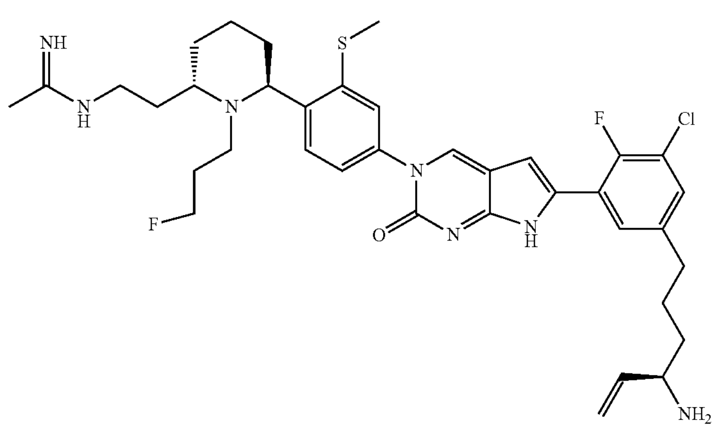 [SMILES: C=C[C@H](N)CCCc1cc(Cl)c(F)c(-c2cc3cn(-c4ccc([C@@H]5CCC[C@@H](CCNC(C)=N)N5CCCF)c(SC)c4)c(=O)nc3[nH]2)c1] | 710 |

TABLE 2b-continued

| # | Structure | ESI, m/z [M + H]+ |
|---|---|---|
| 346 | 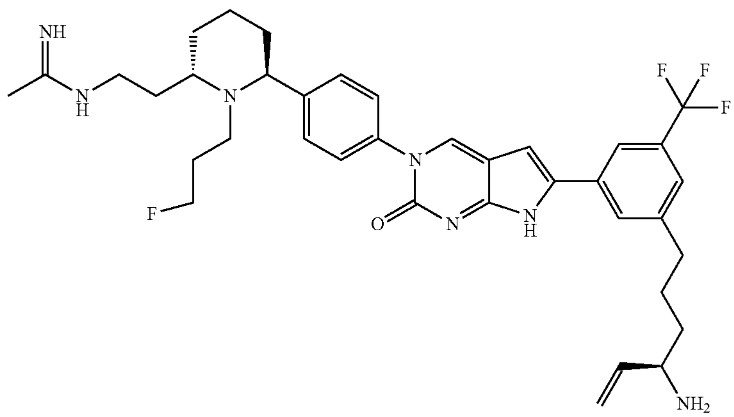 [SMILES: C=C[C@H](N)CCCc1cc(-c2cc3cn(-c4ccc([C@@H]5CCC[C@@H](CCNC(C)=N)N5CCCF)cc4)c(=O)nc3[nH]2)cc(C(F)(F)F)c1] | 680 |
| 347 | 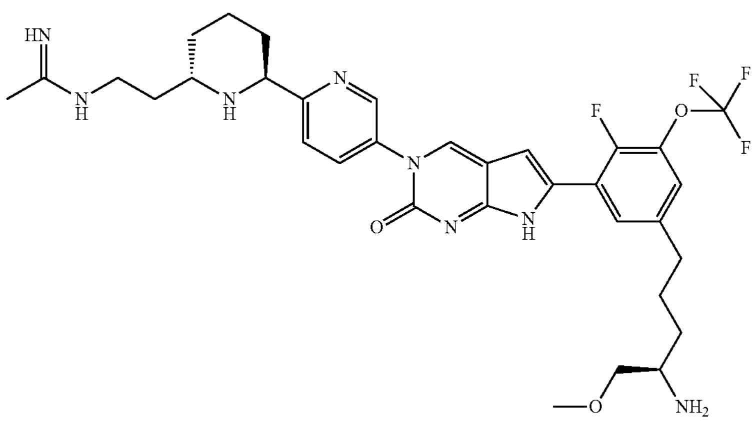 [SMILES: COC[C@H](N)CCCc1cc(OC(F)(F)F)c(F)c(-c2cc3cn(-c4ccc([C@@H]5CCC[C@@H](CCNC(C)=N)N5)nc4)c(=O)nc3[nH]2)c1] | 673.8 |
| 348 | 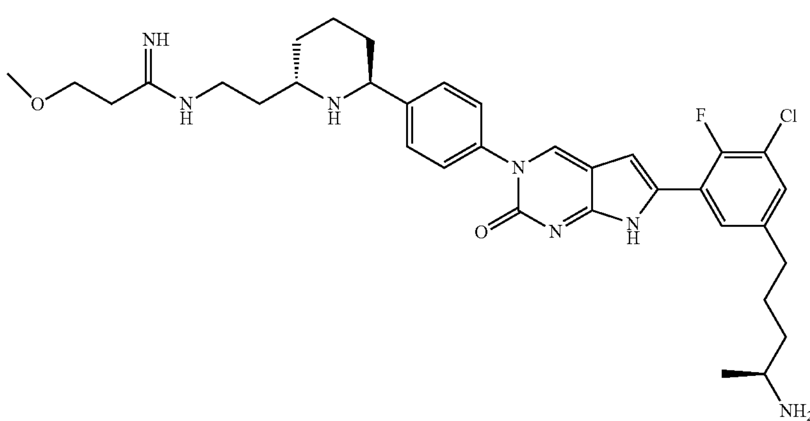 [SMILES: COCCC(=N)NCC[C@@H]1CCC[C@@H](c2ccc(-n3cc4cc(-c5cc(CCC[C@H](C)N)cc(Cl)c5F)[nH]c4nc3=O)cc2)N1] | 636 |

TABLE 2b-continued

| # | Structure | ESI, m/z [M + H]+ |
|---|---|---|
| 349 | 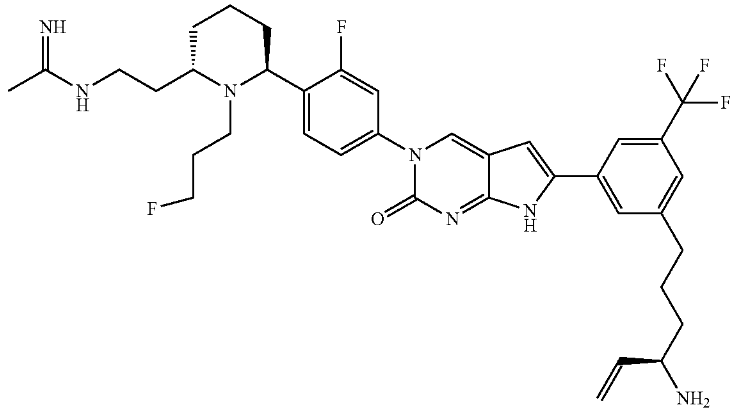 [SMILES: C=C[C@H](N)CCCc1cc(-c2cc3cn(-c4ccc([C@@H]5CCC[C@@H](CCNC(C)=N)N5CCCF)c(F)c4)c(=O)nc3[nH]2)cc(C(F)(F)F)c1] | 698 |
| 350 | 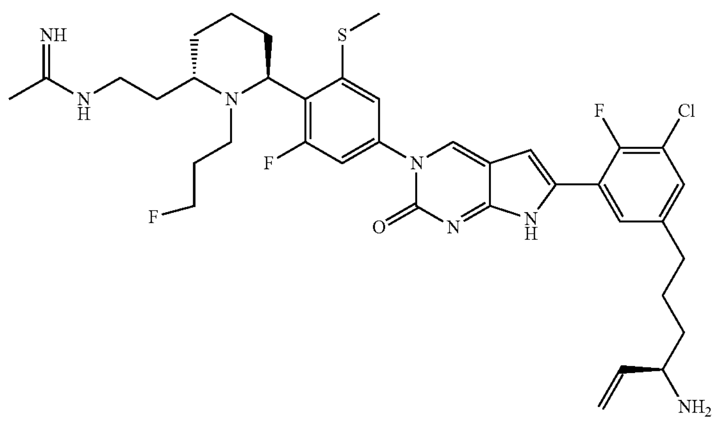 [SMILES: C=C[C@H](N)CCCc1cc(Cl)c(F)c(-c2cc3cn(-c4cc(F)c([C@@H]5CCC[C@@H](CCNC(C)=N)N5CCCF)c(SC)c4)c(=O)nc3[nH]2)c1] | 728 |
| 351 | 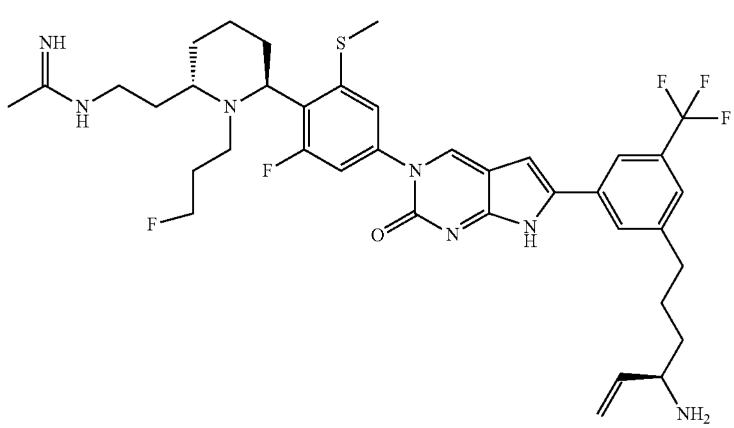 [SMILES: C=C[C@H](N)CCCc1cc(-c2cc3cn(-c4cc(F)c([C@@H]5CCC[C@@H](CCNC(C)=N)N5CCCF)c(SC)c4)c(=O)nc3[nH]2)cc(C(F)(F)F)c1] | 744 |

TABLE 2b-continued
| # | Structure | ESI, m/z [M + H]+ |
|---|---|---|
| 352 | 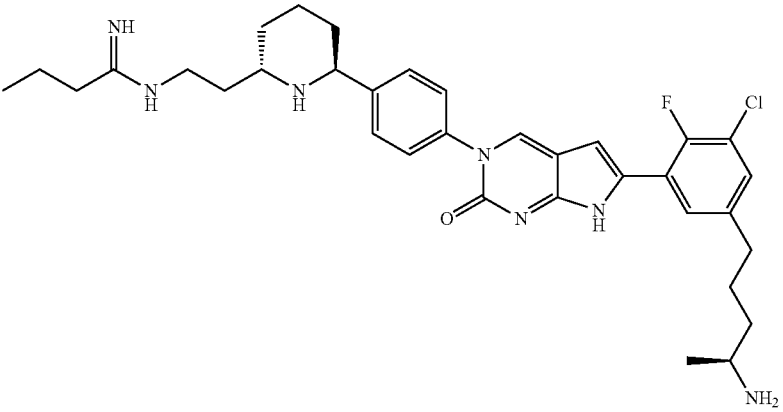 [SMILES: CCCC(=N)NCC[C@@H]1CCC[C@@H](c2ccc(-n3cc4cc(-c5cc(CCC[C@H](C)N)cc(Cl)c5F)[nH]c4nc3=O)cc2)N1] | 620.3 |
| 353 | 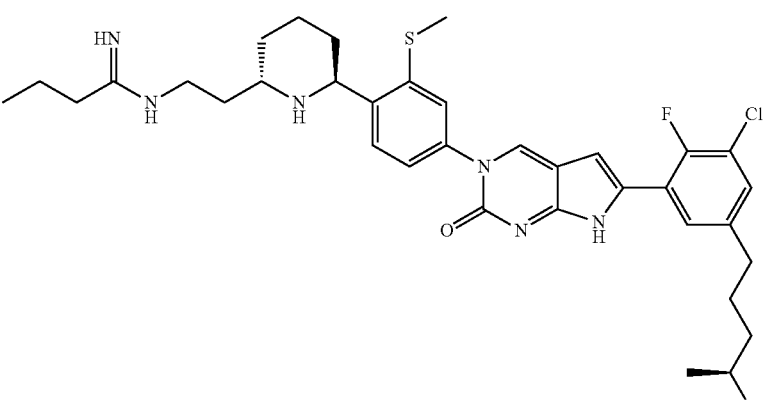 | 666.2 |
| 355 | 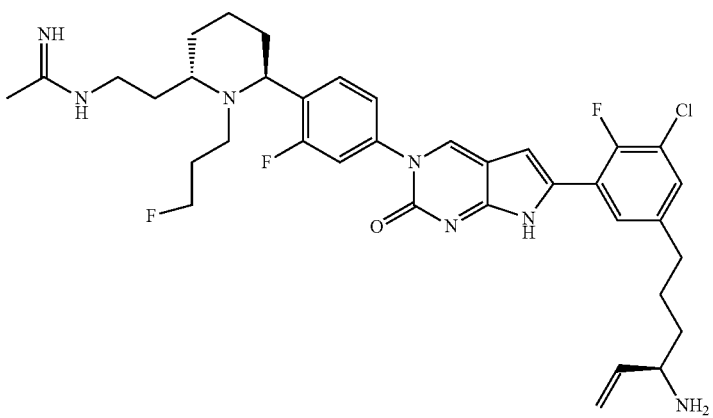 [SMILES: C=C[C@H](N)CCCc1cc(Cl)c(F)c(-c2cc3cn(-c4ccc([C@@H]5CCC[C@@H](CCNC(C)=N)N5CCCF)c(F)c4)c(=O)nc3[nH]2)c1] | 682 |

TABLE 2b-continued
| # | Structure | ESI, m/z [M + H]+ |
|---|---|---|
| 356 | 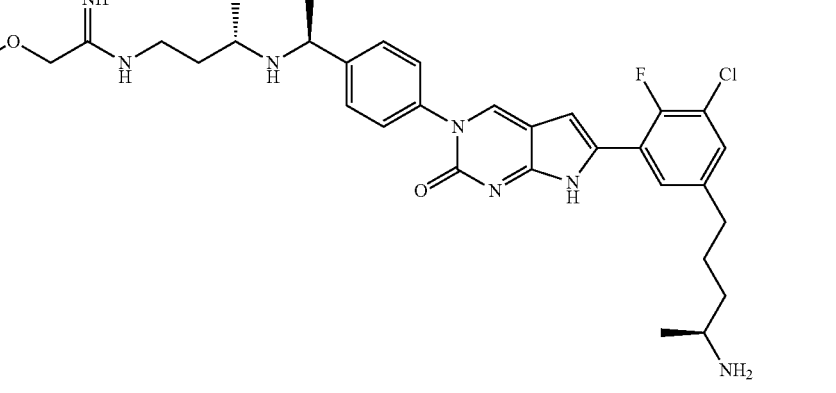 | 622.3 |
| 357 | 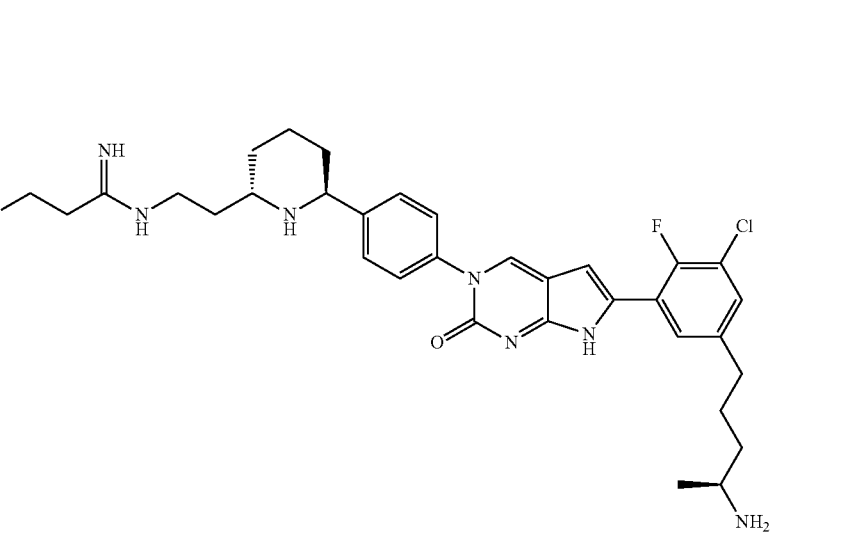 | 622.1 |
| 358 | 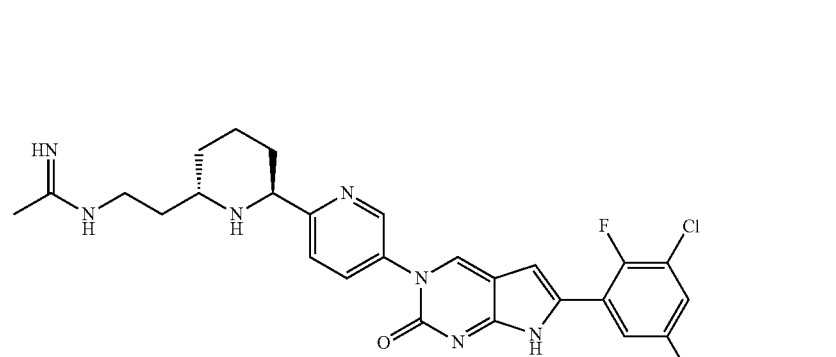 | 623.3 |

TABLE 2b-continued

| # | Structure | ESI, m/z [M + H]+ |
|---|---|---|
| 360 | 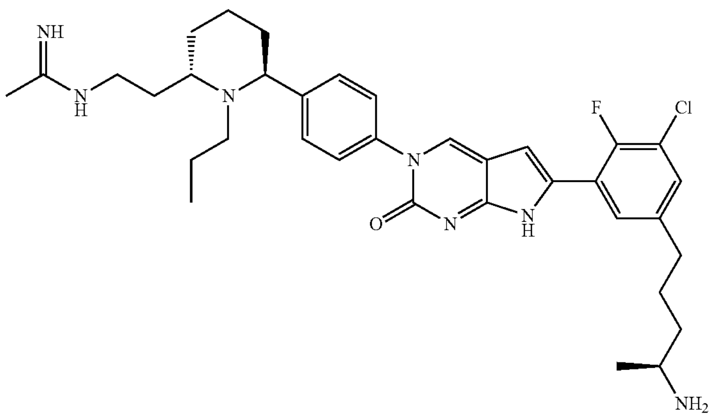 [SMILES: CCCN1[C@H](CCNC(C)=N)CCC[C@H]1c1ccc(-n2cc3cc(-c4cc(CCC[C@H](C)N)cc(Cl)c4F)[nH]c3nc2=O)cc1] | 634 |
| 362 | 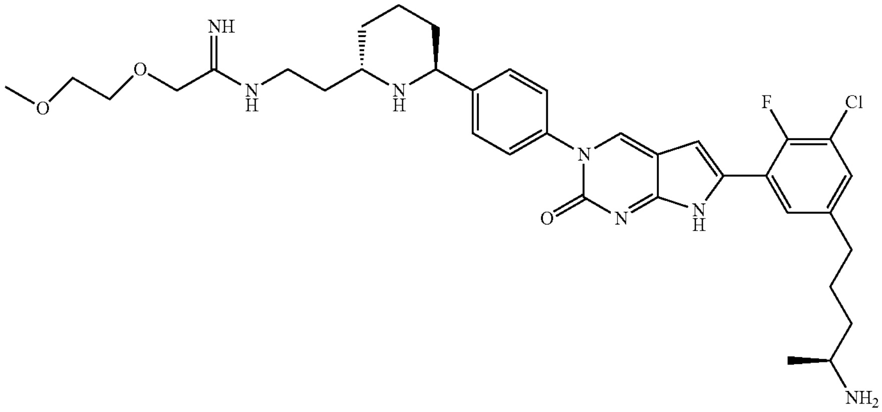 [SMILES: COCCOCC(=N)NCC[C@@H]1CCC[C@@H](c2ccc(-n3cc4cc(-c5cc(CCC[C@H](C)N)cc(Cl)c5F)[nH]c4nc3=O)cc2)N1] | 666 |
| 363 | 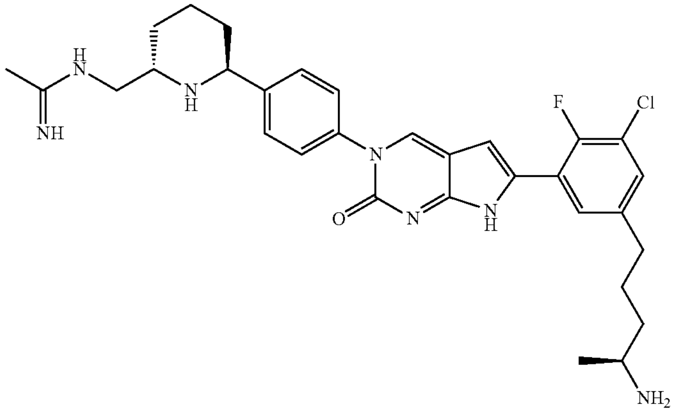 [SMILES: CC(=N)NC[C@@H]1CCC[C@@H](c2ccc(-n3cc4cc(-c5cc(CCC[C@H](C)N)cc(Cl)c5F)[nH]c4nc3=O)cc2)N1] | 578 |

TABLE 2b-continued

| # | Structure | ESI, m/z [M + H]+ |
|---|---|---|
| 364 | 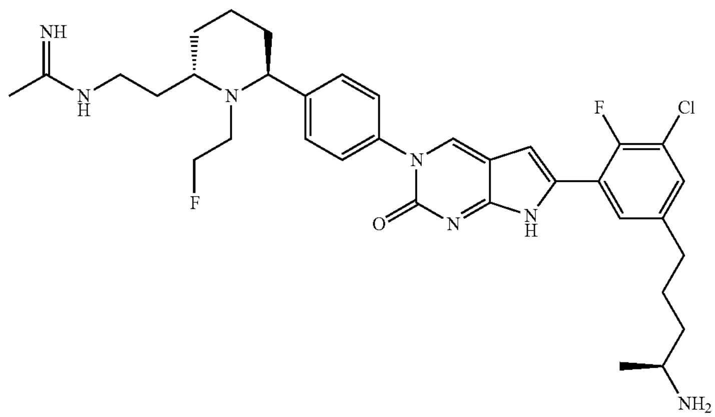 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1CCF] | 638 |
| 365 | 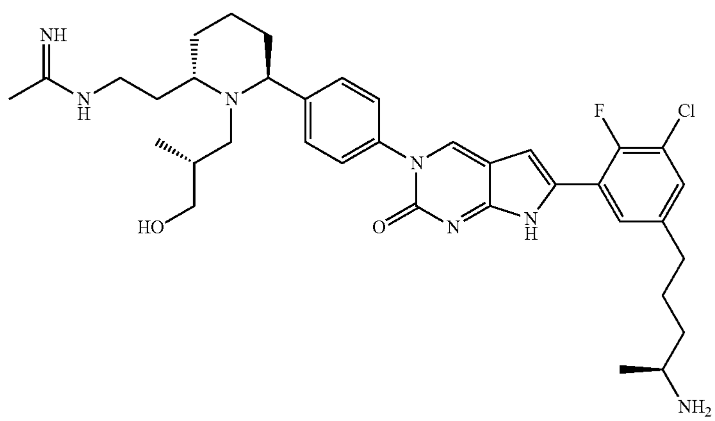 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1C[C@@H](C)CO] | 664 |
| 366 | 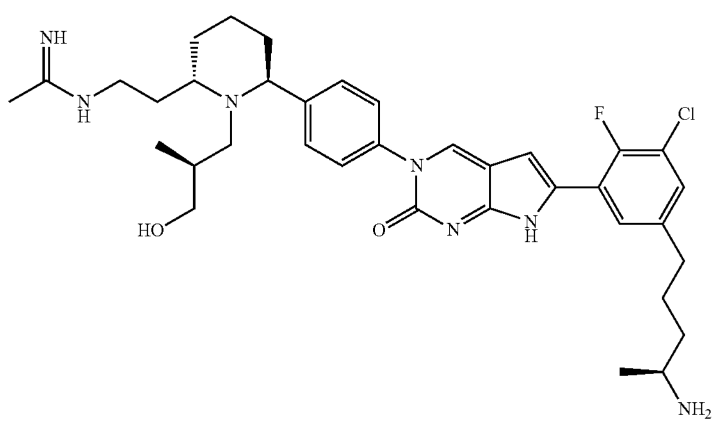 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1C[C@H](C)CO] | 664 |

TABLE 2b-continued

| # | Structure | ESI, m/z [M + H]+ |
|---|---|---|
| 369 | 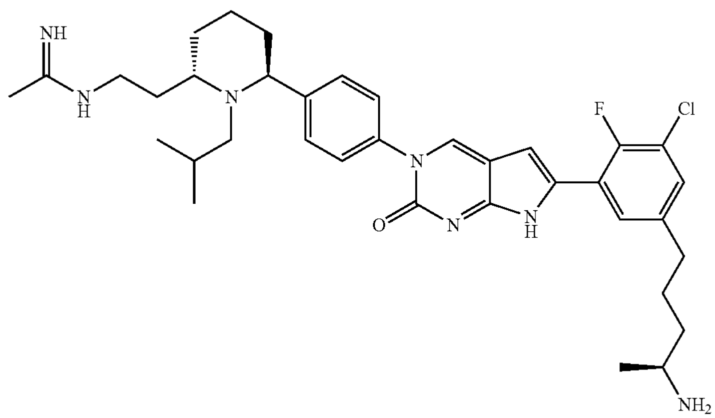 [SMILES: CC(=N)NCC[C@@H]1CCC[C@@H](c2ccc(-n3cc4cc(-c5cc(CCC[C@H](C)N)cc(Cl)c5F)[nH]c4nc3=O)cc2)N1CC(C)C] | 648 |
| 370 | 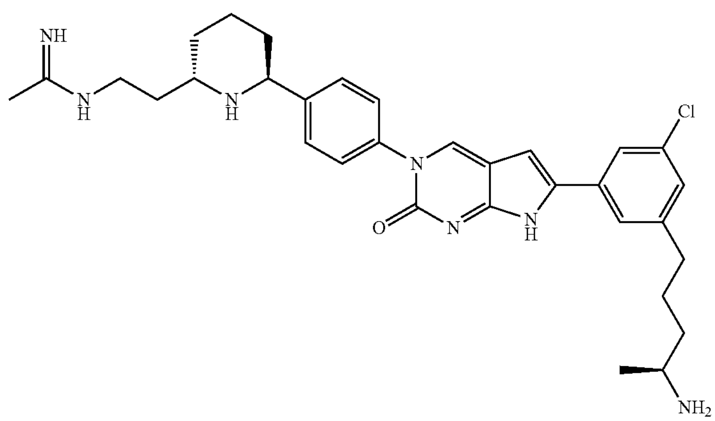 [SMILES: CC(=N)NCC[C@@H]1CCC[C@@H](c2ccc(-n3cc4cc(-c5cc(Cl)cc(CCC[C@H](C)N)c5)[nH]c4nc3=O)cc2)N1] | 574.4 |
| 377 | 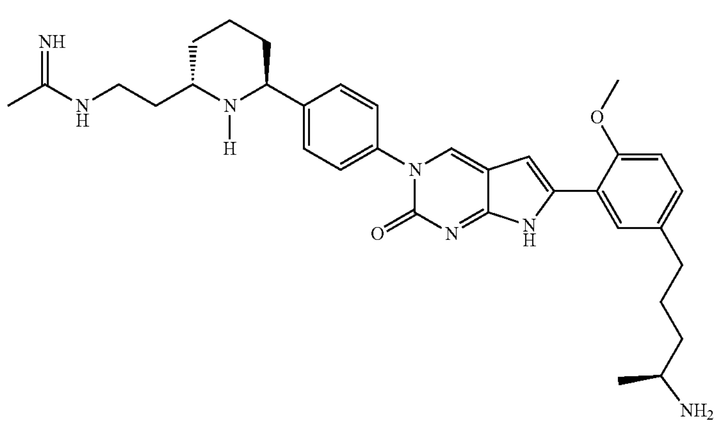 [SMILES: COc1ccc(CCC[C@H](C)N)cc1-c1cc2cn(-c3ccc([C@@H]4CCC[C@@H](CCNC(C)=N)N4)cc3)c(=O)nc2[nH]1] | 570.5 |

In some embodiments, the present application provides a compound of Formula (III):

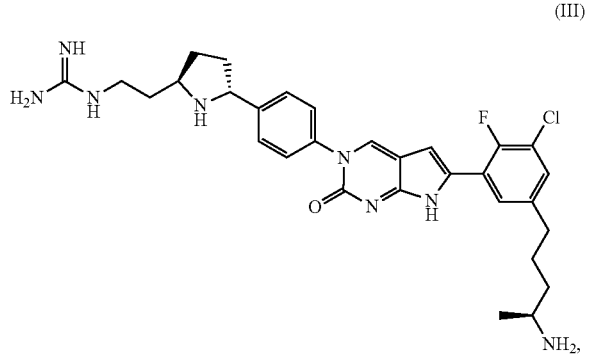 [SMILES: C[C@H](N)CCCc1cc(Cl)c(F)c(-c2cc3cn(-c4ccc([C@H]5CC[C@H](CCNC(=N)N)N5)cc4)c(=O)nc3[nH]2)c1]

(III)

or a tautomer thereof or a pharmaceutically acceptable salt of the compound or tautomer.

In some embodiments, the present disclosure provides a method of treating, preventing, reducing the risk of, or delaying the onset of a microbial infection in a subject, the method comprising administering to the subject a therapeutically effective amount of a compound of Formula (III) or a tautomer thereof or a pharmaceutically acceptable salt of the compound or tautomer.

The compounds or tautomers thereof, or pharmaceutically acceptable salts of the compounds or tautomers disclosed herein can have asymmetric centers. Compounds or tautomers thereof, or pharmaceutically acceptable salts of the compounds or tautomers of the present disclosure containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds or tautomers thereof, or pharmaceutically acceptable salts of the compounds or tautomers disclosed herein, and all such stable isomers are contemplated in the methods of the present disclosure. Cis and trans geometric isomers of the compounds or tautomers thereof, or pharmaceutically acceptable salts of the compounds or tautomers of the present disclosure are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds or tautomers thereof, or pharmaceutically acceptable salts of the compounds or tautomers of the present disclosure and intermediates made herein are considered to be part of the present disclosure. All tautomers of shown or described compounds are also considered to be part of the present disclosure. Furthermore, the disclosure also includes metabolites of the compounds disclosed herein.

The disclosure also comprehends isotopically-labeled compounds or tautomers thereof, or pharmaceutically acceptable salts of the compounds or tautomers, which are identical to those recited in formulae of the disclosure, but for the replacement of one or more atoms by an atom having an atomic mass or mass number different from the atomic mass or mass number most commonly found in nature. Examples of isotopes that can be incorporated into compounds or tautomers thereof, or pharmaceutically acceptable salts of the compounds or tautomers of the disclosure include isotopes of hydrogen, carbon, nitrogen, and fluorine, such as $^3$H, C, $^{14}$C, and $^{18}$F.

The compounds of the present disclosure or tautomers thereof, or pharmaceutically acceptable salts of the compounds or tautomers that contain the aforementioned isotopes and/or isotopes of other atoms are within the scope of the methods of the present disclosure. Isotopically-labeled compounds or tautomers thereof, or pharmaceutically acceptable salts of the compounds or tautomers of the present disclosure, for example, those into which radioactive isotopes such as $^3$H and $^{14}$C are incorporated, are useful in drug and/or substrate tissue distribution assays. Tritium ($^3$H) and carbon-14 ($^{14}$C) isotopes are particularly preferred due to their ease of preparation and detectability. $^{11}$C and $^{18}$F isotopes are particularly useful in PET (positron emission tomography). PET is useful in brain imaging. Further, substitution with heavier isotopes such as deuterium ($^2$H), can afford certain therapeutic advantages resulting from greater metabolic stability, for example, increased in vivo half-life or reduced dosage requirements and, hence, may be preferred in some circumstances. Isotopically labeled compounds or tautomers thereof, or pharmaceutically acceptable salts of the compounds or tautomers having a formula of the disclosed herein can generally be prepared as described in the procedures, Schemes and/or in the Examples disclosed herein, by substituting a non-isotopically labeled reagent with a readily available isotopically labeled reagent. In one embodiment, the compounds or tautomers thereof, or pharmaceutically acceptable salts of the compounds or tautomers disclosed herein are not isotopically labeled.

When any variable (e.g., R) occurs more than one time in any constituent or formulae of the disclosed herein, its definition at each occurrence is independent of its definition at every other occurrence. Thus, for example, if a group is shown to be substituted with one or more R moieties, then R at each occurrence is selected independently from the definition of R. Also, combinations of substituents and/or variables are permissible, but only if such combinations result in stable compounds within a designated atom's normal valence.

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent can be bonded to any atom on the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

In cases wherein compounds of the present disclosure, or tautomers thereof, or pharmaceutically acceptable salts of the compounds or tautomers thereof, contain nitrogen atoms, these, where appropriate, can be converted to N-oxides by treatment with an oxidizing agent (e.g., meta-chloroperoxybenzoic acid (mCPBA) and/or hydrogen peroxides). Thus, shown and claimed nitrogen atoms are considered to cover both the shown nitrogen and its N-oxide (N→O) derivative, as appropriate. In some embodiments, the present disclosure relates to N-oxides of the compounds or tautomers thereof, or pharmaceutically acceptable salts of the compounds or tautomers disclosed herein.

In some embodiments, the present disclosure relates to a compound or a tautomer thereof, or a pharmaceutically acceptable salt of the compound or tautomer that binds the ribosome. In some embodiments, the ribosome is a bacterial ribosome.

In some embodiments, the present disclosure relates to a pharmaceutical composition that includes a compound disclosed herein, or a tautomer thereof, or a pharmaceutically acceptable salt of the compound or tautomer, and a pharmaceutically acceptable carrier. In some embodiments, a pharmaceutically acceptable carrier includes substances capable of being coadministered with a compound described herein and which allows the compound to perform its intended function, for example, treat or prevent a bacterial infection. Suitable pharmaceutically acceptable carriers include, but are not limited to, water, salt solutions, alcohol, vegetable oils, polyethylene glycols, gelatin, lactose, amylase, magnesium stearate, talc, silicic acid, viscous paraffin, perfume oil, fatty acid monoglycerides and diglycerides, petroethral fatty acid esters, hydroxymethyl-cellulose, and polyvinylpyrrolidone. The pharmaceutical preparations can be sterilized and if desired mixed with auxiliary agents, such as lubricants, preservatives, stabilizers, wetting agents, emulsifiers, salts for influencing osmotic pressure, buffers, colorings, flavorings and/or aromatic substances, and the like, which do not deleteriously react with the compounds of the present disclosure.

In some embodiments, the present disclosure relates to a compound or a tautomer thereof, or a pharmaceutically acceptable salt of the compound or tautomer disclosed herein and a means for delivery.

3. METHODS OF THE DISCLOSURE

In some embodiments, the present disclosure provides a method of treating, preventing, reducing the risk of, or delaying the onset of a microbial infection in a human or animal, the method including administering to the human or animal in need thereof an effective amount of one or more compounds disclosed herein, including stereoisomers, tautomers, and salts thereof. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens. In some embodiments, the administered compound is a compound of Formula (I). In some embodiments, the administered compound is a compound of Formula (II). In some embodiments, the administered compound is a compound of Formula (III).

In some embodiments, provided is the use of one or more compounds disclosed herein, including stereoisomers, tautomers, and salts thereof, in the manufacture of a medicament for treating, preventing, reducing the risk of, or delaying the onset of a microbial infection in a human or animal. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens. In some embodiments, the administered compound is a compound of Formula (I). In some embodiments, the administered compound is a compound of Formula (II). In some embodiments, the administered compound is a compound of Formula (III).

In some embodiments, provided are one or more compounds disclosed herein, including stereoisomers, tautomers, and salts thereof, for use in treating, preventing, reducing the risk of, or delaying the onset of a microbial infection in a human or animal. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens. In some embodiments, the administered compound is a compound of Formula (I). In some embodiments, the administered compound is a compound of Formula (II). In some embodiments, the administered compound is a compound of Formula (III).

In one embodiment, provided is a method of treating a microbial infection in a subject, that includes administering to the subject an effective amount of one or more compounds of Formulae (I), (II), and (III) disclosed herein, including stereoisomers, tautomers, and salts thereof, where the infection is caused by or involves one or more microorganisms which are capable of being used as biological weapons. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens. In some embodiments, the administered compound is a compound of Formula (I). In some embodiments, the administered compound is a compound of Formula (II). In some embodiments, the administered compound is a compound of Formula (III).

In one embodiment, provided is a method of preventing a microbial infection in a subject, that includes administering to the subject an effective amount of one or more compounds of Formulae (I), (II), and (III) disclosed herein, including stereoisomers, tautomers, and salts thereof, where the infection is caused by or involves one or more microorganisms which are capable of being used as biological weapons. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens. In some embodiments, the administered compound is a compound of Formula (I). In some embodiments, the administered compound is a compound of Formula (II). In some embodiments, the administered compound is a compound of Formula (III).

In one embodiment, provided is a method of reducing the risk of a microbial infection in a subject, that includes administering to the subject an effective amount of one or more compounds of Formulae (I), (II), and (III) disclosed herein, including stereoisomers, tautomers, and salts thereof, where the infection is caused by or involves one or more microorganisms which are capable of being used as biological weapons. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens. In some embodiments, the administered compound is a compound of Formula (I). In some embodiments, the administered compound is a compound of Formula (II). In some embodiments, the administered compound is a compound of Formula (III).

In one embodiment, provided is a method of delaying the onset of a microbial infection in a subject, that includes administering to the subject an effective amount of one or more compounds of Formulae (I), (II), and (III) disclosed herein, including stereoisomers, tautomers, and salts thereof, where the infection is caused by or involves one or more microorganisms which are capable of being used as biological weapons. In some embodiments, the infection is caused by or involves one or more microorganisms which are capable of being used as biological weapons. In some embodiments, the infection is caused by or involves one or more microorganisms which are extremely-drug resistant Gram-positive or Gram-negative pathogens. In some embodiments, the administered compound is a compound of Formula (I). In some embodiments, the administered compound is a compound of Formula (II). In some embodiments, the administered compound is a compound of Formula (III).

In some embodiments, a bacterium which can be used as a biological weapon possesses one or more characteristics that include, but are not limited to, being easily being produced or disseminated, being easily transmitted from person to person, having the potential for moderate or high morbidity, having the potential for moderate or high mortality, having the potential for causing public panic and social disruption, requiring special action for public health preparedness, and requiring specific enhancements for diagnosis and disease surveillance.

In another embodiment, a bacterium which can be used as a biological weapon is stable or viable, for example, the bacterium is capable of performing all or part of its normal biological functions, such as replicating, forming spores, and infecting a subject, under various conditions. In some embodiments, the bacterium is stable or viable in one or more conditions that include, but are not limited to, heat, cold, high pressure, low pressure, acidic or basic conditions, humidity, dryness, and radiation, including extreme conditions.

In one embodiment, a bacterium which can be used as a biological weapon is stable or viable at a temperature above about 25° C., such as above about 30° C., about 40° C., about 50° C., about 60° C., about 70° C., about 80° C., about 90° C., about 100° C., about 125° C., about 150° C., about 175° C., or above about 200° C. In another embodiment, a bacterium which can be used as a biological weapon is stable or viable at a temperature below about 25° C., such as below about 20° C., about 10° C., about 5° C., about 0° C., about −10° C., about −20° C., about −30° C., about −40° C., about −50° C., about −60° C., about −70° C., about −100° C., or below about −150° C. In one embodiment, a bacterium which can be used as a biological weapon is capable of infecting a subject under various conditions, such as various pressures. In one embodiment, a bacterium which can be used as a biological weapon is stable or viable under pressure above about $5 \times 10^5$ Pa, such as above about $10 \times 10^5$ Pa, about $15 \times 10^5$ Pa, about $20 \times 10^5$ Pa, about $30 \times 10^5$ Pa, about $40 \times 10^5$ Pa, about $50 \times 10^5$ Pa, about $75 \times 10^5$ Pa, or about $100 \times 10^5$ Pa. In another embodiment, a bacterium which can be used as a biological weapon is stable or viable under pressure below about $0.5 \times 10^5$ Pa, such as below about $0.2 \times 10^5$ Pa, about $0.1 \times 10^5$ Pa, about $0.05 \times 10^5$ Pa, about $0.02 \times 10^5$ Pa, about $0.01 \times 10^5$ Pa, about $0.005 \times 10^5$ Pa, about $0.002 \times 10^5$ Pa, or about $0.001 \times 10^5$ Pa.

In one embodiment, a bacterium which can be used as a biological weapon is stable or viable at a pH above about 8.0, such as above about 8.5, about 9.0, about 9.5, about 10.0, about 10.5, about 11.0, about 11.5, about 12.0, about 12.5, about 13.0, about 13.5, or about 14.0. In another embodiment, a bacterium which can be used as a biological weapon is stable or viable at a pH below about 6.0, such as below about 5.5, about 5.0, about 4.5, about 4.0, about 3.5, about 3.0, about 2.5, about 2.0, about 1.5, about 1.0, about 0.5, or about 0.0.

In one embodiment, a bacterium which can be used as a biological weapon is stable or viable under a relative humidity of about 10%, such as about 20%, about 30%, about 40%, about 50%, about 60%, about 70%, about 75%, about 80%, about 85%, about 90%, about 95%, or about 99%.

In another embodiment, a bacterium which can be used as a biological weapon is stable or viable under UV radiation, X-ray radiation, a radiation, R radiation, or y radiation.

In one embodiment, a bacterium which can be used as a biological weapon is able to form spores.

In some embodiments, a bacterium which can be used as a biological weapon can be dispersed in air or in liquid. In one embodiment, the bacterium is in aerosol form, for example, the bacterium is formulated as an aerosol. In another embodiment, the bacterium is in powder form, for example, the bacterium is formulated as powder.

In one embodiment, a bacterium which can be used as a biological weapon includes a bacterium which is resistant to existing antibiotics. In some embodiments, the bacterium is resistant to tetracycline antibiotics, including, but not limited to, tetracycline, doxycycline, minocycline, sancycline, methacycline, chlortetracycline, and deoxytetracycline, and a combination thereof. In some embodiments, the bacterium is resistant to other antibiotics, including, but not limited to, aminoglycosides, such as gentamicin and kanamycin, colistin, methicillin, oxacillin, vancomycin, penicillin, linezolid, fluoroquinolones, such as ciprofloxacin, ceftazidime, and macrolides, such as azithromycin. In some embodiments, a bacterium which can be used as a biological weapon includes a bacterium which is resistant to gentamicin. In some embodiments, a bacterium which can be used as a biological weapon includes a bacterium which is resistant to colistin. In some embodiments, a bacterium which can be used as a biological weapon includes a bacterium which is resistant to gentamicin and colistin.

In some embodiments of the disclosed methods, the one or more microorganisms are biodefense category A or biodefense category B pathogens. Biodefense category A pathogens are those organisms or biological agents that pose the highest risk to national security and public health because they (1) can be easily disseminated or transmitted from person to person, (2) result in high mortality rates and have the potential for major public health impact, (3) might cause public panic and social disruption, and (4) require special action for public health preparedness. Examples of category A pathogens include, but are not limited to, *Bacillus anthracis* (anthrax), *Francisella tularensis* (tularemia), *Yersinia pestis* (plague), Ebola, Marburg, Ebola-like viruses such as Bundibugyo ebolavirus, Sudan ebolavirus, TaiForest ebolavirus, Zaire ebolavirus and Marburg-like viruses such as Marburg virus and Ravn virus. In some embodiments, the one or more microorganisms are selected from the group consisting of biodefense category A pathogens *Bacillus anthracis* (anthrax), *Yersinia pestis* (plague), and *Francisella tularensis* (tularemia).

Biodefense category B pathogens are the second highest priority organisms or biological agents. They are moderately easy to disseminate, result in moderate morbidity rates and low mortality rates, and require specific enhancements for diagnostic capacity and enhanced disease surveillance. Examples of category B pathogens include, but are not limited to, *Burkholderia pseudomallei* (melioidosis), *Coxiella burnetii* (Q fever), *Brucella* species (brucellosis), *Burkholderia mallei* (glanders), *Chlamydia psittaci* (psittacosis), *Rickettsia prowazekii* (typhus fever), diarrheagenic *E. coli*, pathogenic Vibrios, *Shigella* species, *Salmonella*, *Listeria monocytogenes*, *Campylobacter jejuni*, *Yersinia enterocolitica*, *Staphylococcus* enterotoxin B, and Hepatitis A. In some embodiments, the one or more microorganisms are selected from the group consisting of biodefense category B pathogens *Burkholderia pseudomallei* (melioidosis), *Coxiella burnetii* (Q fever), *Brucella* species (brucellosis), *Burkholderia mallei* (glanders), *Chlamydia psittaci* (psittacosis), *Rickettsia prowazekii* (typhus fever), diarrheagenic *E. coli*, pathogenic Vibrios, *Shigella* species, *Salmonella, Listeria monocytogenes, Campylobacter jejuni*, and *Yersinia enterocolitica.*

More examples of category A or B pathogens are provided by the National Institute of Allergy and Infectious Diseases (NIAID) at http://www.niaid.nih.gov/topics/biodefenserelated/biodefense/pages/cata.aspx#, the contents of which are hereby incorporated by reference in its entirety.

In some embodiments, a bacterium which can be used as a biological weapon includes, but is not limited to, a bacterium of the *Bacillus cereus* group. The *Bacillus cereus* group of bacteria includes *Bacillus anthracis* (the etiologic agent of anthrax), *Bacillus cereus, Bacillus* weihenstephanensis (a food borne pathogen), *Bacillus thuringiensis* (an insect pathogen), and *Bacillus mycoides*. In some embodiments, the bacterium is selected from *Bacillus anthracis*, multidrug-resistant (MDR) anthrax, *Francisella tularensis, Clostridium botulinum, Yersinia pestis, Burkholderia mallei, Burkholderia pseudomallei, Brucella species, Shigella species, Coxiella burnetii, Chlamydia psittaci, Clostridium perfringens, Rickettsia prowazekii*, diarrheagenic *E. coli*, pathogenic Vibrios, *Salmonella, Campylobacter jejuni, Yersinia enterocolitica*, and *Listeria monocytogenes*. In some embodiments, the microorganism (bacterium) is selected from *Bacillus anthracis, Franciscella tularensis, Yersinia pestis, Burkholderia mallei*, and *Burkholderia pseudomallei*. In some embodiments, the microorganism (bacterium) is selected from *Burkholderia mallei* and *Burkholderia pseudomallei*. In some embodiments, the microorganism (bacterium) is *Burkholderia pseudomallei.*

In some embodiments, a bacterium which can be used as a biological weapon is *Bacillus anthracis* or multidrug-resistant (MDR) anthrax.

In some embodiments, a bacterium which can be used as a biological weapon is *Burkholderia pseudomallei.*

In some embodiments, a bacterium which can be used as a biological weapon includes, but is not limited to, gram-positive pathogens, gram-negative pathogens, anaerobic pathogens, or atypical pathogens, or a combination thereof. In some embodiments, the bacterium includes methicillin-susceptible *Staphylococcus aureus* (MSSA), methicillin-resistant *Staphylococcus aureus* (MRSA), oxacillin-susceptible *Staphylococcus aureus*, oxacillin-resistant *Staphylococcus aureus*, oxacillin-resistant coagulase-negative *Staphylococcus, Enterococcus faecalis, Enterococcus faecium*, vancomycin-susceptible *Enterococcus faecium*, vancomycin-resistant *Enterococcus faecium*, vancomycin-susceptible *Enterococcus faecalis*, vancomycin-resistant *Enterococcus faecalis, Streptococcus pneumoniae*, penicillin-susceptible *Streptococcus pneumonia*, penicillin-resistant *Streptococcus pneumoniae* (PRSP), *Streptococcus pyogenes, Streptococcus agalactiae, Haemophilus influenzae, Moraxella catarrhalis, Neisseria gonorrhoeae, Escherichia coli, Shigella* spp., *Salmonella* spp., *Klebsiella pneumoniae, Enterobacter aerogenes, Enterobacter cloacae, Serratia marcescens, Acinetobacter baumannii, Stenotrophomonas maltophilia, Bacteroides fragilis, Clostridium perfringens, Chlamydia pneumoniae, Legionella pneumophila, Proteus mirabilis, Pseudomonas aeruginosa*, and *Burkholderia cepacia.*

In some embodiments, the one or more microorganisms are extremely-drug resistant Gram-positive or Gram-negative pathogens.

In some embodiments, provided is a method of treating, preventing, reducing the risk of, or delaying the onset of a microbial infection in a subject that is caused by or involves one or more microorganisms which are capable of being used as biological weapons that includes administering a compound of Formula (I) or a tautomer thereof or a pharmaceutically acceptable salt of the compound or tautomer. In some embodiments, the one or more microorganisms are biodefense category A pathogens. In some embodiments, the one or more microorganisms are biodefense category A pathogens selected from *Bacillus anthracis* (anthrax), *Yersinia pestis* (plague), and *Francisella tularensis* (tularemia).

In some embodiments, provided is a method of treating, preventing, reducing the risk of, or delaying the onset of a microbial infection in a subject that is caused by or involves one or more microorganisms which are capable of being used as biological weapons that includes administering a compound of Formula (I) or a tautomer thereof or a pharmaceutically acceptable salt of the compound or tautomer.

In some embodiments, the one or more microorganisms are biodefense category B pathogens. In some embodiments, the one or more microorganisms are biodefense category B pathogens *Burkholderia pseudomallei* (melioidosis), *Coxiella burnetii* (Q fever), *Brucella* species (brucellosis), *Burkholderia mallei* (glanders), *Chlamydia psittaci* (psittacosis), *Rickettsia prowazekii* (typhus fever), diarrheagenic *E. coli*, pathogenic Vibrios, *Shigella* species, *Salmonella, Listeria monocytogenes, Campylobacter jejuni*, and *Yersinia enterocolitica.*

In some embodiments, provided is a method of treating, preventing, reducing the risk of, or delaying the onset of a microbial infection in a subject that is caused by or involves one or more microorganisms which are capable of being used as biological weapons that includes administering a compound of Formula (I) or a tautomer thereof or a pharmaceutically acceptable salt of the compound or tautomer. In some embodiments, the one or more microorganisms are selected from *Bacillus anthracis, Franciscella tularensis, Yersinia pestis, Burkholderia mallei*, and *Burkholderia pseudomallei*. In some embodiments, the one or more microorganisms are selected from *Burkholderia mallei* and *Burkholderia pseudomallei*. In some embodiments, the one or more microorganisms are *Burkholderia pseudomallei.*

In some embodiments, provided is a method of treating, preventing, reducing the risk of, or delaying the onset of a microbial infection in a subject that is caused by or involves one or more microorganisms which are extremely-drug resistant Gram-positive or Gram-negative pathogens that includes administering a compound of Formula (I) or a tautomer thereof or a pharmaceutically acceptable salt of the compound or tautomer.

In some embodiments, provided is a method of treating, preventing, reducing the risk of, or delaying the onset of a microbial infection in a subject that is caused by or involves one or more microorganisms which are capable of being used as biological weapons that includes administering a compound of Formula (II) or a tautomer thereof or a pharmaceutically acceptable salt of the compound or tautomer.

In some embodiments, the one or more microorganisms are biodefense category A pathogens. In some embodiments, the one or more microorganisms are biodefense category A pathogens selected from *Bacillus anthracis* (anthrax), *Yersinia pestis* (plague), and *Francisella tularensis* (tularemia).

In some embodiments, provided is a method of treating, preventing, reducing the risk of, or delaying the onset of a microbial infection in a subject that is caused by or involves one or more microorganisms which are capable of being used as biological weapons that includes administering a compound of Formula (II) or a tautomer thereof or a pharmaceutically acceptable salt of the compound or tautomer.

In some embodiments, the one or more microorganisms are biodefense category B pathogens. In some embodiments, the one or more microorganisms are biodefense category B pathogens *Burkholderia pseudomallei* (melioidosis), *Coxiella burnetii* (Q fever), *Brucella* species (brucellosis), *Burkholderia mallei* (glanders), *Chlamydia psittaci* (psittacosis), *Rickettsia prowazekii* (typhus fever), diarrheagenic *E. coli*, pathogenic Vibrios, *Shigella* species, *Salmonella*, *Listeria monocytogenes*, *Campylobacter jejuni*, and *Yersinia enterocolitica*.

In some embodiments, provided is a method of treating, preventing, reducing the risk of, or delaying the onset of a microbial infection in a subject that is caused by or involves one or more microorganisms which are capable of being used as biological weapons that includes administering a compound of Formula (II) or a tautomer thereof or a pharmaceutically acceptable salt of the compound or tautomer. In some embodiments, the one or more microorganisms are selected from *Bacillus anthracis, Franciscella tularensis, Yersinia pestis, Burkholderia mallei*, and *Burkholderia pseudomallei*. In some embodiments, the one or more microorganisms are selected from *Burkholderia mallei* and *Burkholderia pseudomallei*. In some embodiments, the one or more microorganisms are *Burkholderia pseudomallei*.

In some embodiments, provided is a method of treating, preventing, reducing the risk of, or delaying the onset of a microbial infection in a subject that is caused by or involves one or more microorganisms which are extremely-drug resistant Gram-positive or Gram-negative pathogens that includes administering a compound of Formula (II) or a tautomer thereof or a pharmaceutically acceptable salt of the compound or tautomer.

In some embodiments, provided is a method of treating, preventing, reducing the risk of, or delaying the onset of a microbial infection in a subject that is caused by or involves one or more microorganisms which are capable of being used as biological weapons that includes administering a compound of Formula (III) or a tautomer thereof or a pharmaceutically acceptable salt of the compound or tautomer.

In some embodiments, the one or more microorganisms are biodefense category A pathogens. In some embodiments, the one or more microorganisms are biodefense category A pathogens selected from *Bacillus anthracis* (anthrax), *Yersinia pestis* (plague), and *Francisella tularensis* (tularemia).

In some embodiments, provided is a method of treating, preventing, reducing the risk of, or delaying the onset of a microbial infection in a subject that is caused by or involves one or more microorganisms which are capable of being used as biological weapons that includes administering a compound of Formula (III) or a tautomer thereof or a pharmaceutically acceptable salt of the compound or tautomer.

In some embodiments, the one or more microorganisms are biodefense category B pathogens. In some embodiments, the one or more microorganisms are biodefense category B pathogens *Burkholderia pseudomallei* (melioidosis), *Coxiella burnetii* (Q fever), *Brucella* species (brucellosis), *Burkholderia mallei* (glanders), *Chlamydia psittaci* (psittacosis), *Rickettsia prowazekii* (typhus fever), diarrheagenic *E. coli*, pathogenic Vibrios, *Shigella* species, *Salmonella*, *Listeria monocytogenes*, *Campylobacter jejuni*, and *Yersinia enterocolitica*.

In some embodiments, provided is a method of treating, preventing, reducing the risk of, or delaying the onset of a microbial infection in a subject that is caused by or involves one or more microorganisms which are capable of being used as biological weapons that includes administering a compound of Formula (III) or a tautomer thereof or a pharmaceutically acceptable salt of the compound or tautomer.

In some embodiments, the one or more microorganisms are selected from *Bacillus anthracis, Franciscella tularensis, Yersinia pestis, Burkholderia mallei*, and *Burkholderia pseudomallei*. In some embodiments, the one or more microorganisms are selected from *Burkholderia mallei* and *Burkholderia pseudomallei*. In some embodiments, the one or more microorganisms are *Burkholderia pseudomallei*.

In some embodiments, provided is a method of treating, preventing, reducing the risk of, or delaying the onset of a microbial infection in a subject that is caused by or involves one or more microorganisms which are extremely-drug resistant Gram-positive or Gram-negative pathogens that includes administering a compound of Formula (III) or a tautomer thereof or a pharmaceutically acceptable salt of the compound or tautomer.

In some embodiments, provided is a method of treating a microbial infection in a subject that includes administering a compound of the present disclosure, for example, a compound of Formulae (I), (II), or (III), after the subject has been exposed to the microorganism, but before the subject develops any symptom of the microbial infection. In some embodiments, the microorganism is a bacterium. In some embodiments, the microbial infection is a bacterial infection. In some embodiments, a compound of Formulae (I), (II), or (III) is administered about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks after the subject has been exposed to the microorganism, but before the subject develops any symptoms. In another embodiment, provided is a method of treating a microbial infection in a subject that includes administering a compound of Formulae (I), (II), or (III) after the subject develops a symptom after the subject has been exposed to the microorganism. In some embodiments, the microorganism is a bacterium. In one embodiment, a compound of Formulae (I), (II), or (III) is administered about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks after the subject develops a symptom.

In another embodiment, provided is a method of treating a microbial infection in a subject that includes administering a compound of the present invention after the subject's suspected exposure to the microorganism, but before the subject develops any symptom of the microbial infection. In one embodiment, the compound of Formulae (I), (II), or (III) is administered about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks after the subject's suspected exposure to the microorganism, but before the subject develops any symptoms. In some embodiments, the microorganism is a bacterium.

In some embodiments, provided is a method of preventing a microbial infection in a subject that includes administering a compound of Formulae (I), (II), or (III) before the subject has been exposed to the microorganism. In some embodiments, the microorganism is a bacterium. In some embodiments, the microbial infection is a bacterial infection. In some embodiments, the compound of Formulae (I), (II), or (III) is administered about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks before the subject has been exposed to the microorganism.

In another embodiment, provided is a method of preventing a microbial infection in a subject that includes administering a compound of Formulae (I), (II), or (III) before or after an event which raises the risk of the subject being exposed to the microorganism. In some embodiments, the microorganism is a bacterium. The event includes, but is not limited to, an attack, for example, a terrorist attack, with a biological weapon and the subject's entry into a risky territory, such as a battlefield. In one embodiment, a compound of Formulae (I), (II), or (III) is administered to the subject about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks before the event. In another embodiment, a compound of Formulae (I), (II), or (III) is administered to the subject about 10 min, about 20 min, about 30 min, about 40 min, about 50 min, about 1 hr, about 2 hrs, about 3 hrs, about 6 hrs, about 12 hrs, about 18 hrs, about 24 hrs, about 36 hrs, about 48 hrs, about 72 hrs, about 96 hrs, about 1 week, or about 2 weeks after the event.

In another embodiment, the method of the present disclosure includes, before administering a compound of Formulae (I), (II), or (III), identifying a subject at risk of being exposed to a microorganism which can be used as a biological weapon. In some embodiments, the microorganism is a bacterium. In some embodiments, the subject at risk of being exposed to a microorganism which can be used as a biological weapon includes, but is not limited to, a subject travelling to, entering, or being in a conflict region, for example, a battlefield or combat zone, including military personnel, intelligence personnel, and animals used in the military, a subject engaged or about to be engaged in a security operation, such as governmental authorities (for example, police, governmental investigators, and secret service members) and other personnel (for example, doctors, nurses, and rescue workers), and animals used in such an operation, and a subject in an geographical area that can be a target of a terrorist attack, for example, a metropolitan area, a city, an area where there is a large population (for example, above 100,000, above 200,000, above 500,000, above 1 million, above 2 million, above 5 million, or above 10 million), or a location or area to which damage is likely to cause a threat to national security or public health (for example, a nuclear power plant, a chemical plant, an airport, or a hospital).

In some embodiments, provided is a method of treating a bacterial infection in a subject, where the subject is exposed or suspected of being exposed to a bacterium or a component thereof, that includes administering to the subject an effective amount of a compound of Formulae (I), (II), or (III). In another embodiment, provided is a method a method of preventing a bacterial infection in a subject, where the subject is at a risk of being exposed to a bacterium or a component thereof, that includes administering to the subject an effective amount of a compound of Formulae (I), (II), or (III). In one embodiment, the bacterium or a component thereof is formulated as an aerosol or power. In another embodiment, the bacterial component is a bacterial spore.

In some embodiments, the effective amount of the compound of Formulae (I), (II), or (III) used in the disclosed methods ranges from about 0.1 mg to about 1500 mg, such as about 0.25 mg, about 0.5 mg, about 1 mg, about 1.5 mg, about 2.5 mg, about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050, mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, or about 1500 mg.

The efficacy of the compounds of Formulae (I), (II), or (III) in treating, preventing, reducing the risk of, or delaying the onset of a bacterial infection can be assessed by using common methods known in the art. In one embodiment, the efficacy is determined by a Minimum Inhibition Concentration (MIC) assay. For example, a compound of Formulae (I), (II), or (III) is serially diluted and then added to the growth medium of the bacterial culture. In some embodiments, the growth medium is cation-adjusted Mueller Hinton broth (CAMHB). The lowest concentration of the compound of Formulae (I), (II), or (III) that inhibits 50% or 90% bacterial growth ($MIC_{50}$ or $MIC_{90}$, respectively) is determined and, if necessary, is compared with the $MIC_{50}$ or $MIC_{90}$ of other antibiotics. In another embodiment, the efficacy is determined through in vivo assays known in the art. In some embodiments, efficacy is determined through in vivo animal experiments. For example, a compound of the present invention is administered to experimental animals, such as mice and rats, in decreasing amounts. The lowest amount of the compound of Formulae (I), (II), or (III) that treats the experimental animal or prevents the experimental animals from being infected by the bacterium or developing any symptoms of the infection is determined and, if necessary, is compared with the lowest amount of other antibiotics which achieves the same results. In some embodiments, treating refers to ameliorating symptoms of a bacterial infection, prolonging the survival time of the animal, or allowing the animal to survive the bacterial infection.

4. FORMULATION AND ADMINISTRATION

The compositions and methods of the present disclosure can be practiced by delivering the compounds of the present disclosure using any means for delivery (any suitable carrier). The dose of active compound, mode of administration and use of suitable carrier will depend upon the intended patient or subject and the targeted microorganism, for example, the target bacterial organism. The formulations, both for human medical use and veterinary use, of compounds according to the present disclosure typically include such compounds in association with a pharmaceutically acceptable carrier.

The compounds of Formulae (I), (II), or (III) disclosed herein can be administered by any route which allows the compounds to perform their intended function, for example, treat or prevent a bacterial infection. Examples of routes of administrant include, but are not limited to, orally, intravenously, and topically. In some embodiments, the compounds of Formulae (I), (II), or (III) described herein are administered optically, ophthalmically, nasally, orally, parenterally, topically, or intravenously to a subject in need thereof. In one embodiment, a compound of Formulae (I), (II), or (III) is administered orally. In another embodiment, a compound of Formulae (I), (II), or (III) is administered intravenously.

The carrier(s) should be "acceptable" in the sense of being compatible with compounds of the present disclosure and not deleterious to the recipient. Pharmaceutically acceptable carriers, in this regard, are intended to include any and all solvents, dispersion media, coatings, absorption delaying agents, and the like, compatible with pharmaceutical administration. Supplementary active compounds (identified or designed according to the disclosure and/or known in the art) also can be incorporated into the compositions. In some embodiments, formulations are prepared by bringing the compound into association with a liquid carrier or a finely divided solid carrier or both, and then, if necessary, shaping the product into the desired formulation.

A pharmaceutical composition of the disclosure should be formulated to be compatible with its intended route of administration. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

For parenteral administration (including intraperitoneal, subcutaneous, intravenous, intradermal, or intramuscular injection), solutions of the compounds of Formulae (I), (II), or (III) in either sesame or peanut oil or in aqueous propylene glycol can be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all of these solutions under sterile conditions is readily accomplished by standard pharmaceutical techniques well known to those skilled in the art. For parenteral application, examples of suitable preparations include solutions, such as oily or aqueous solutions, as well as suspensions, emulsions, or implants, including suppositories. Therapeutic compounds can be formulated in sterile form in multiple or single dose formats, such as being dispersed in a fluid carrier, e.g., sterile physiological saline or 5% saline dextrose solutions, commonly used with injectables.

Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present disclosure suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients, such as microcrystalline cellulose, sodium citrate, calcium carbonate, dicalcium phosphate, and glycine, can be employed along with various disintegrants, such as starch (including corn, potato or tapioca starch), alginic acid, and certain complex silicates, together with granulation binders like polyvinylpyrrolidone, sucrose, gelatin, and acacia. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Additionally, lubricating agents such as magnesium stearate, sodium lauryl sulfate, and talc can be used for tableting purposes. Solid compositions of a similar type can also be employed as fillers in gelatin capsules, including lactose or milk sugar as well as high molecular weight polyethylene glycols.

When aqueous suspensions and/or elixirs are desired for oral administration, the active ingredient can be combined with various sweetening or flavoring agents, coloring matter or dyes, and, if so desired, emulsifying and/or suspending agents as well, together with diluents such as water, ethanol, propylene glycol, glycerin, and various like combinations thereof.

Sustained release compositions can be formulated including those wherein the active component is protected with differentially degradable coatings, e.g., by microencapsulation, multiple coatings, etc.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants can include, for example, for transmucosal administration, detergents and bile salts. Transmucosal administration can be accomplished through the use of nasal sprays or suppositories. For transdermal administration, the active compounds typically are formulated into ointments, salves, gels, or creams.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Liposomal suspensions can also be used as pharmaceutically acceptable carriers.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

In some embodiments, the present invention relates to a medical device containing a compound of Formulae (I), (II), or (III) described herein. In some embodiments, the device is a stent.

Where the active compound is to be used as part of a transplant procedure, it can be provided to the living tissue or organ to be transplanted prior to removal of tissue or organ from the donor. The compound can be provided to the donor host. Alternatively, or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations disclosed herein. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

Generally, an effective amount of dosage of active compound will be in the range of from about 0.1 to about 100 mg/kg of body weight/day, more preferably from about 1.0 to about 50 mg/kg of body weight/day. The amount administered will also likely depend on such variables as the type of surgery or invasive medical procedure, the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

Nonlimiting doses of active compound comprise from about 0.1 to about 1500 mg per dose.

As is understood by one of ordinary skill in the art, generally, when dosages are described for a pharmaceutical active, the dosage is given on the basis of the parent or active moiety. Therefore, if a salt, hydrate, or another form of the parent or active moiety is used, a corresponding adjustment in the weight of the compound is made, although the dose is still referred to on the basis of the parent or active moiety delivered. As a nonlimiting example, if the parent or active moiety of interest is a monocarboxylic acid having a molecular weight of 250, and if the monosodium salt of the acid is desired to be delivered to be delivered at the same dosage, then an adjustment is made recognizing that the monosodium salt would have a molecular weight of approximately 272 (minus 1H or 1.008 atomic mass units and plus 1 Na or 22.99 atomic mass units). Therefore, a 250 mg dosage of the parent or active compound would correspond to about 272 mg of the monosodium salt, which would also deliver 250 mg of the parent or active compound. Said another way, about 272 mg of the monosodium salt would be equivalent to a 250 mg dosage of the parent or active compound.

FORMULATION EXAMPLES

IA. Formulation for Intravenous Administration

| Ingredients | Amount |
| --- | --- |
| Antimicrobial Compound of the present disclosure | 0.1-1500 total mg |
| Dextrose, USP | 50 mg/mL |
| Sodium citrate, USP | 1.60-1.75 mg/mL |
| Citric Acid, USP | 0.80-0.90 mg/mL |
| Water, USP | q.s |

This formulation for intravenous administration is formulated by heating water for injection to about 60° C. Next the sodium citrate, citric acid and dextrose are added and stirred until dissolved. A solution or aqueous slurry of the antimicrobial compound is added to the previous mixture and stirred until dissolved. The mixture is cooled to 25° C. with stirring. The pH is measured and adjusted if necessary. Lastly the mixture is brought to the desired volume, if necessary, with water for injection. The mixture is filtered, filled into the desired container (vial, syringe, infusion container, etc.), over wrapped and terminally moist heat sterilized.

This formulation is useful for intravenous administration, either bolus or infusion, to a patient for treating, preventing, reducing the risk of, or delaying the onset of infection.

IB. Formulation for Intravenous Administration

This formulation for intravenous administration utilizes 6.5 nM tartaric acid buffer in 5% dextrose, and has a pH of 4.4. This formulation is useful for intravenous administration, either bolus or infusion, to a patient for treating, preventing, reducing the risk of, or delaying the onset of infection.

II. Lyophilisate for Reconstitution

Alternatively, the antimicrobial compound can be provided as a lyophilisate which can be reconstituted before intravenous or intramuscular administration.

| Ingredient | mg per injection vial |
| --- | --- |
| Antimicrobial Compound of the present disclosure | 0.1-1500 |
| Cyclodextrin | 1500 |

Reconstitution solution for a volume to be administered of 50 mL (infusion): 5% aqueous glucose solution.

Reconstitution solution for a volume to be administered of 15 mL (bolus): 3.3% aqueous glucose solution.

The foregoing lyophilisate is useful for reconstitution and intravenous administration, either bolus or infusion, to a patient for treating, preventing, reducing the risk of, or delaying the onset of infection.

III. Lyophilisate for Reconstitution

| Ingredient | mg per injection vial |
|---|---|
| Antimicrobial Compound of the present disclosure | 0.1-1500 |
| soya lecithin | 2250 |
| Sodium cholate | 1500 |

Reconstitution solution for a volume to be administered of 50 mL (infusion): 4% aqueous glucose solution.

Reconstitution solution for a volume to be administered of 15 mL (bolus): 2% aqueous glucose solution The foregoing lyophilisate is useful for reconstitution and intravenous administration, either bolus or infusion, to a patient for treating, preventing, reducing the risk of, or delaying the onset of infection.

IV. Lyophilisate for Reconstitution

| Ingredient | mg per injection vial |
|---|---|
| Antimicrobial Compound of the present disclosure | 0.1-1500 |
| soya lecithin | 900 |
| Sodium glycholate | 540 |

Reconstitution solution for a volume to be administered of 15 mL (bolus): 3.3% aqueous glucose solution.

The foregoing lyophilisate is useful for reconstitution and intravenous administration, either bolus or infusion, to a patient for treating, preventing, reducing the risk of, or delaying the onset of infection.

V. Tablet for Oral Administration

| Ingredients | Per Tablet | Per 4000 Tablets |
|---|---|---|
| Antimicrobial Compound of the present disclosure | 0.1-1500 mg | 0.4-6000 g |
| Anhydrous Lactose, NF | 110.45 mg | 441.8 g |
| Microcrystalline Cellulose NF | 80.0 mg | 320.0 g |
| Magnesium Stearate Impalpable Powder NF | 1.00 mg | 4.0 g |
| Croscarmellose Sodium NF Type A | 2.00 mg | 8.0 g |

The antimicrobial compound (any of the compounds equivalent to the desired delivery strength, e.g., 50 to 1500 mg per tablet) is premixed with ⅓ of the microcrystalline cellulose NF and ½ of the anhydrous lactose NF in a ribbon blender for 5 minutes at 20 RPM. To the premix is added the remaining ⅔ of the microcrystalline cellulose NF and the remaining ½ of the anhydrous lactose NF. This is blended for 10 minutes at 20 RPM. Croscarmellose sodium is added to the blended powders and mixed for 5 minutes at 20 RPM. Finally the magnesium stearate is added to the mixture by passing through a 90 mesh screen and blended for an additional 5 minutes at 20 RPM. The lubricated mixture is compressed to provide tablets of 500 mg active ingredient.

These tablets are useful for oral administration to a patient for treating, prevention, reducing the risk of, or delaying the onset of infection.

In some embodiments of the methods, the compounds of Formulae (I), (II), or (III) described herein are administered alone. In some embodiments of the methods, the compounds of Formulae (I), (II), or (III) described herein are administered in combination with other known compositions for treating a microbial infection in a subject. In some embodiments, the compound of Formulae (I), (II), or (III) is administered simultaneously with a known composition. In some embodiments, the compound of Formulae (I), (II), or (III) is administered first, followed by administration of a known composition. In some embodiments, a known composition is administered first, followed by administration of a compound of Formulae (I), (II), or (III). Any therapeutic compositions known in the art for treating a microbial infection can be used in the disclosed methods. The compounds of Formulae (I), (II), or (III) can also be used in combination therapy, for example, in combination with any other treatment modality.

In the disclosed methods, the compound of Formulae (I), (II), or (III) can be administered alone or in combination with pharmaceutically acceptable carriers, diluents or carriers by any of the routes disclosed herein. In some embodiments, the administration is carried out in a single dose. In some embodiments, the administration is carried out in multiple doses. The compound of Formulae (I), (II), or (III), administered alone or in combination with pharmaceutically acceptable carriers, diluents or excipients, can be readily administered in a variety of dosage forms, such tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. In some embodiments, oral pharmaceutical compositions can be suitably sweetened and/or flavored. In some embodiments, the compounds of Formulae (I), (II), or (III) are present in such dosage forms at concentration levels ranging from about 5.0% by weight to about 70% by weight.

In one embodiment, provided is a kit that includes a container, a compound selected from compounds of Formulae (I), (II), and (III) and stereoisomers, tautomers, and salts thereof, and instructions for use in the treatment of a microbial infection that is caused by or involves one or more microorganisms which are capable of being used as biological weapons. In some embodiments, the microorganisms are biodefense category A pathogens or biodefense category B pathogens. In one embodiment, the one or more microorganisms are selected from *Bacillus anthracis, Francisella tularensis, Yersinia pestis, Burkholderia mallei*, and *Burkholderia pseudomallei*.

In another embodiment, provided is a kit that includes a container, a compound selected from compounds of Formulae (I), (II), and (III) and stereoisomers, tautomers, and salts thereof, and instructions for use in the prevention of a microbial infection that is caused by or involves one or more microorganisms which are capable of being used as biological weapons. In some embodiments, the microorganisms are biodefense category A pathogens or biodefense category B pathogens. In one embodiment, the one or more microorganisms are selected from *Bacillus anthracis, Francisella tularensis, Yersinia pestis, Burkholderia mallei*, and *Burkholderia pseudomallei*.

In yet another embodiment, provided is a kit that includes a container, a compound selected from compounds of Formulae (I), (II), and (III) and stereoisomers, tautomers, and salts thereof, and instructions for use in reducing the risk of a microbial infection that is caused by or involves one or more microorganisms which are capable of being used as biological weapons. In some embodiments, the microorganisms are biodefense category A pathogens or biodefense category B pathogens. In one embodiment, the one or more microorganisms are selected from *Bacillus anthracis, Francisella tularensis, Yersinia pestis, Burkholderia mallei,* and *Burkholderia pseudomallei.*

In another embodiment, provided is a kit that includes a container, a compound selected from compounds of Formulae (I), (II), and (III) and stereoisomers, tautomers, and salts thereof, and instructions for use in delaying the onset of a microbial infection that is caused by or involves one or more microorganisms which are capable of being used as biological weapons. In some embodiments, the microorganisms are biodefense category A pathogens or biodefense category B pathogens. In one embodiment, the one or more microorganisms are selected from *Bacillus anthracis, Francisella tularensis, Yersinia pestis, Burkholderia mallei,* and *Burkholderia pseudomallei.*

5. SYNTHESIS OF THE COMPOUNDS OF THE DISCLOSURE

The compounds of the present disclosure can be synthesized by using art recognized techniques, such as those described in US 2012-0220566, WO 2012/173689, or PCT/US2014/054869, the contents of each of which are incorporated herein by reference in their entireties. The compounds thus obtained can be further purified, for example, by flash column chromatography, high performance liquid chromatography, crystallization, or any known purification method.

In one embodiment, compounds of Formula (I) of the present disclosure can be synthesized according to the synthetic Schemes 1-3 below:

Scheme 1

-continued
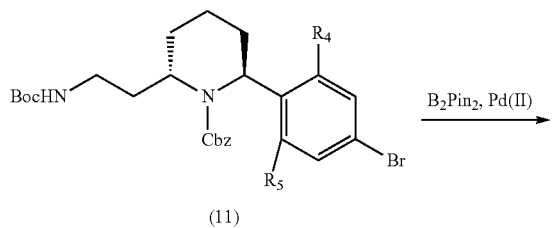
(11)
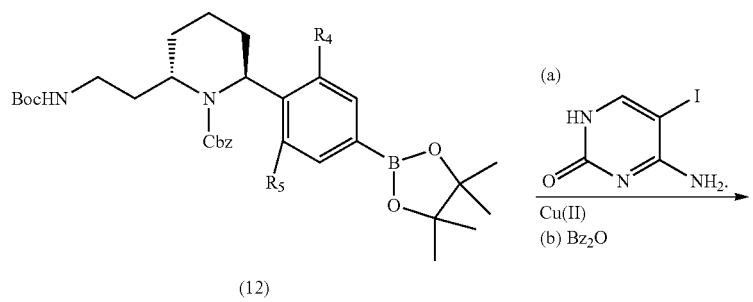
(12)
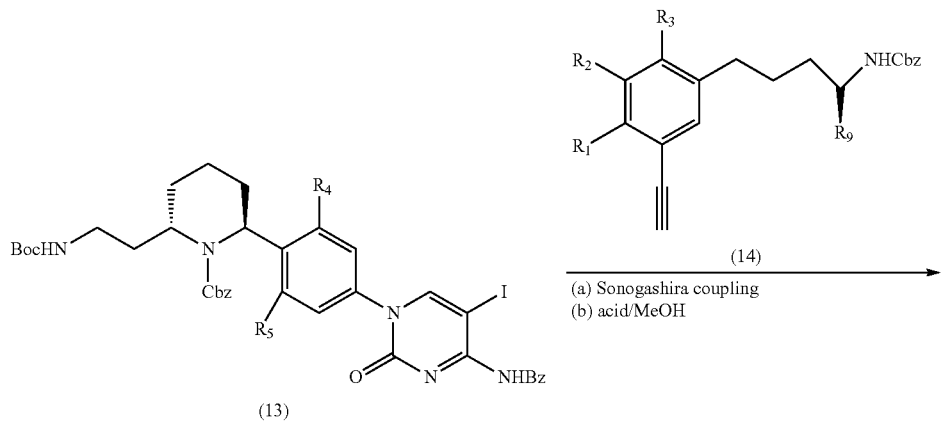
(13)
(14)
(a) Sonogashira coupling
(b) acid/MeOH
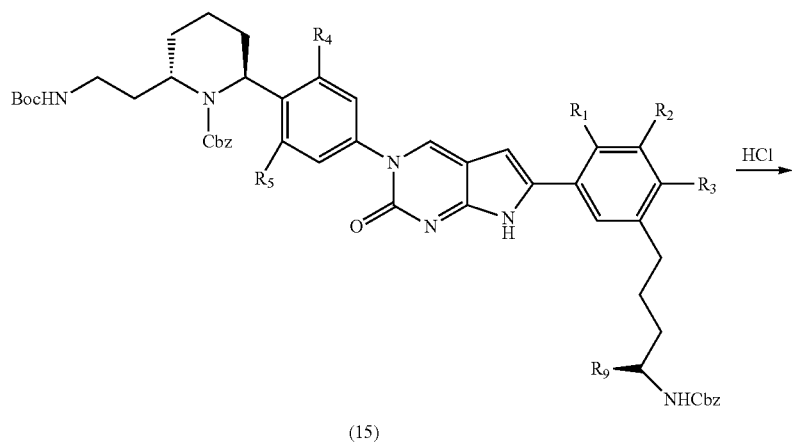
(15)

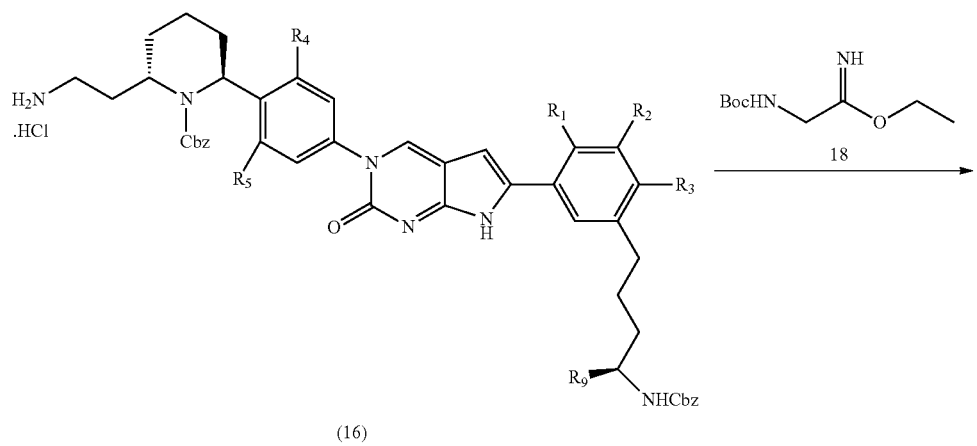

(16)

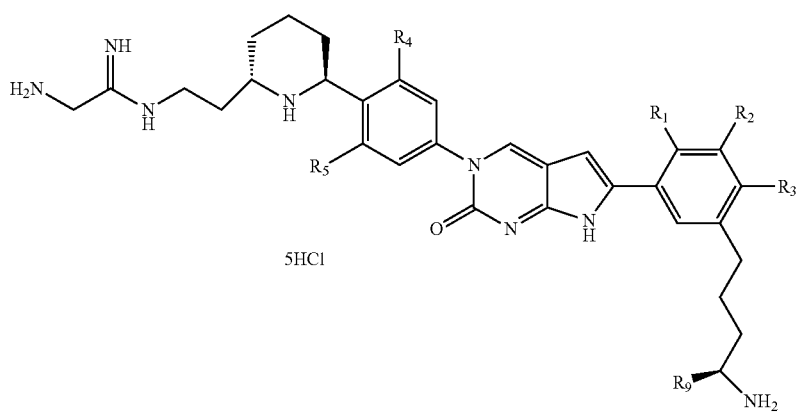

Formula I

Referring to Scheme 1, (S)-(−)-2-methyl-2-propanesulfinamide (1) and aldehyde (2) are reacted to yield 3. 3 is treated with allyl bromide to obtain 4. 4 is treated with iodoacrylate 5 to yield 6, which is treated with a base such as cesium carbonate to afford 7. 7 is reduced to 8 by reacting with a reducing agent such as DIBAL. 8 is reacted with an azide such as diphenylphosphoryl azide (DPPA) to afford intermediate 9. 9 is treated with acid such as aqueous HCl and the resulting mixture treated with Cbz-Cl to yield 10. 10 is treated with triphenylphosphine, followed by Boc anhydride to provide 11. 11 is converted to 12 by treating with bispinacolatodiborane and a Pd(II) reagent such as PdCl$_2$(dppf)·CH$_2$Cl$_2$. 12 is treated with 5-iodocytosine and a Cu(II) reagent such as copper acetate monohydrate, followed by treatment with benzoic anhydride to provide 13. Sonogashira coupling of 13 and alkyne 14 (prepared as disclosed in Scheme 4 herein), for example in the presence of N—N-diisopropylethylamine, Pd(PPh$_3$)$_4$ and CuI in DMF, followed by treatment with methanol, delivers compound 15. Intermediate 15 is treated with acids such as HCl to form a mono-salt 16. Addition of 18 to 16 gives a compound of Formula (I). An analogous scheme may be used starting with 2', shown below, instead of 2, to obtain a compound of Formula I wherein W is N.

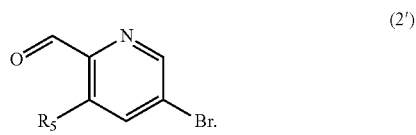

(2')

Scheme 2

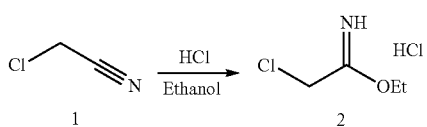

-continued
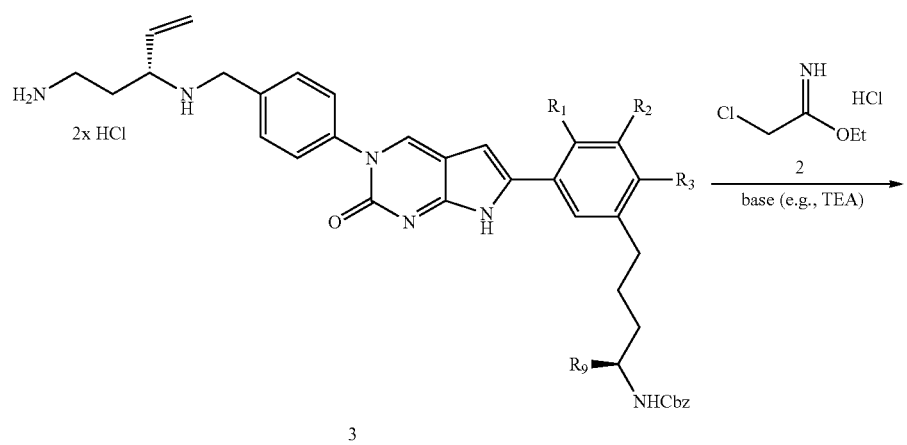
3
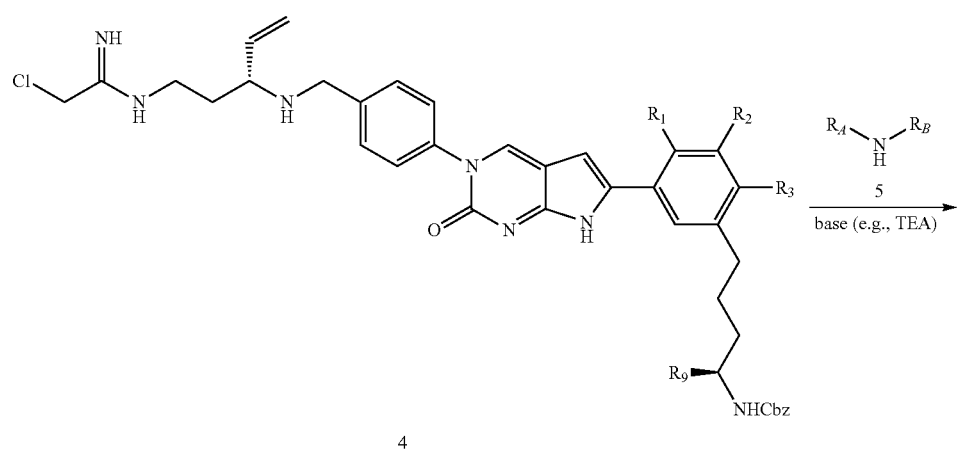
4
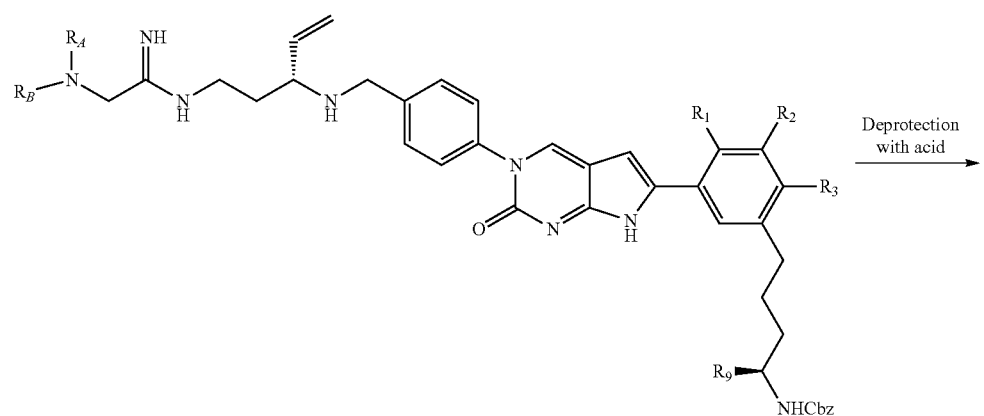
6

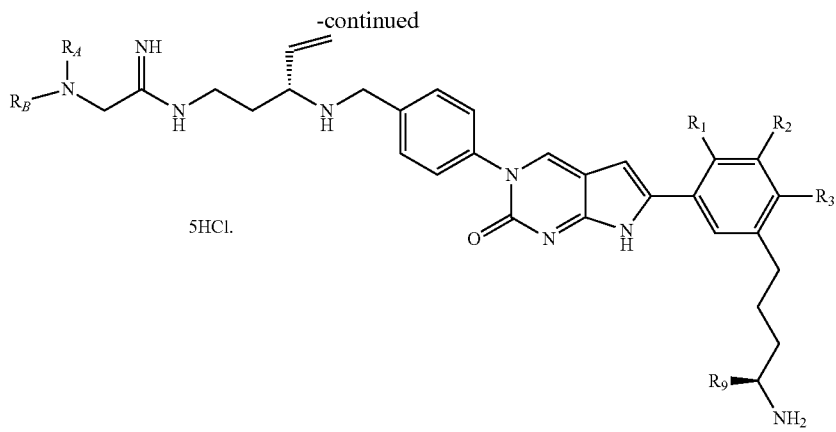

Formula I

Referring to scheme 2, chloro-acetonitrile (1) in anhydrous ethanol is treated with HCl to afford 2. 2 is added to 3 (synthesized as shown in Scheme 3 herein) to yield 4. 4 is treated with 5 to afford 6 taken as is to the next step. Deprotection of 6 with acid such as HBr/AcOH affords a compound of Formula (I).

Intermediate 3 of Scheme 2 can be prepared, for example, as shown in Scheme 3.

Scheme 3

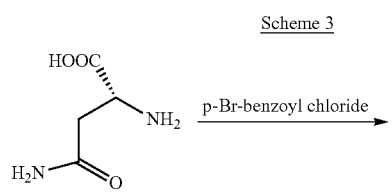

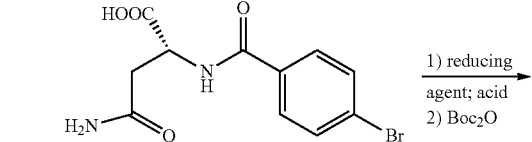

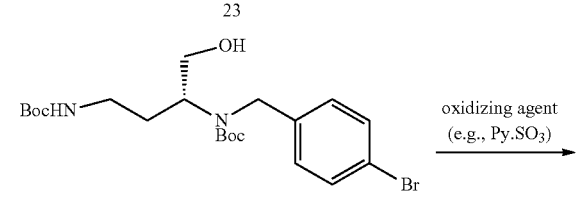

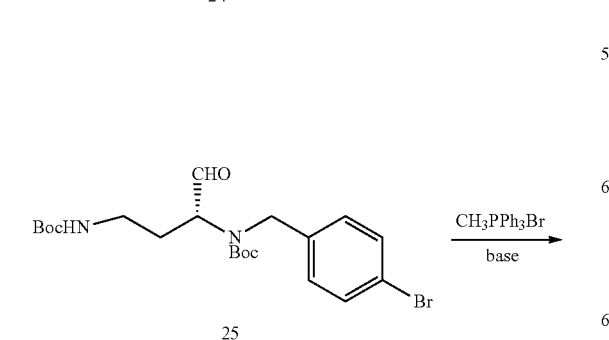

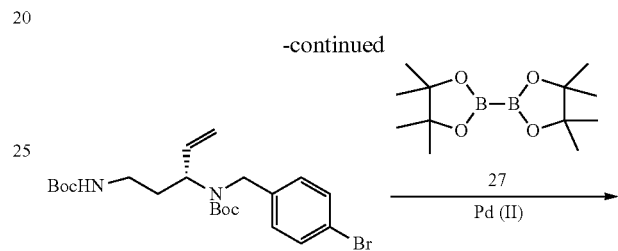

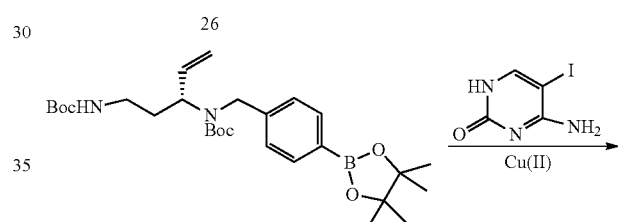

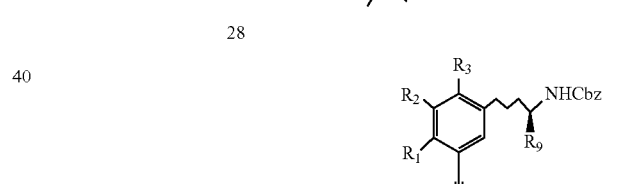

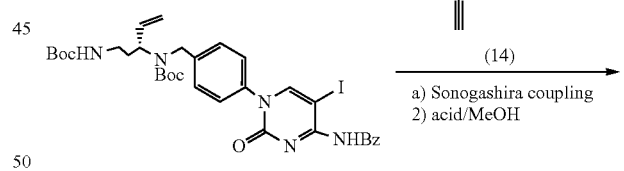

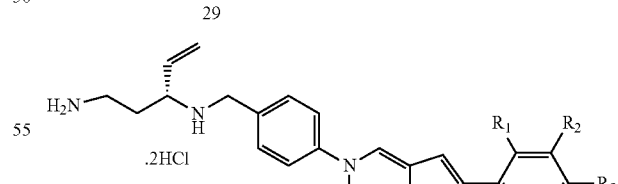

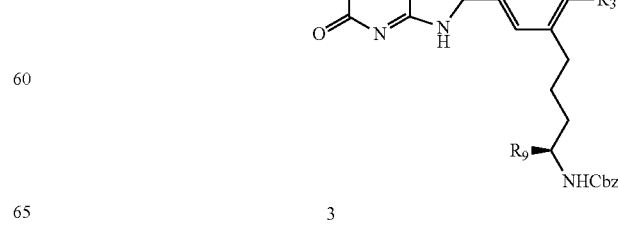

Commercially available D-asparagine hydrate is treated with p-bromo benzoylchloride to afford 23. Intermediate 23 is reduced with a reducing agent such as BH$_3$·THF complex and the product is treated with boc-anhydride to give 24. 24 is oxidized with an oxidizing agent such as pyridine·SO$_3$ complex in DMSO to yield 25. Methyl triphenyl phosphonium bromide is treated with a base such as potassium tertiary butoxide and 25 is added to the resulting mixture to yield 26. 26 is converted to intermediate 3 in a manner analogous to the conversion of 11 to 16 disclosed in Scheme 1 above.

Intermediate 14 of Scheme 1 can be prepared, for example, as shown in Scheme 4.

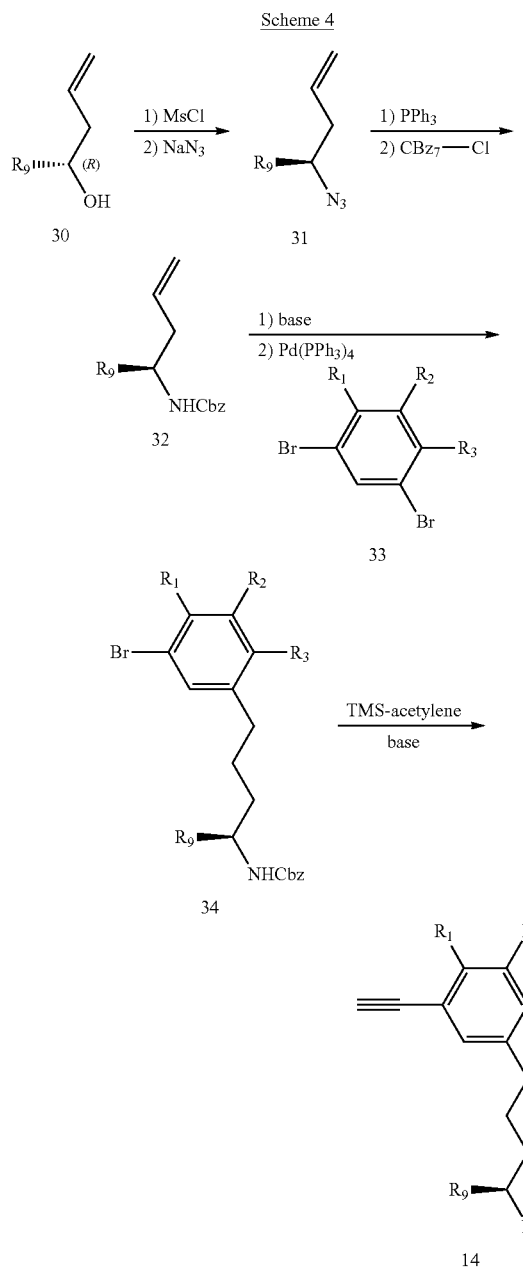

Intermediate 14 can be prepared in a manner analogous to what is described in PCT/US2014/054869.

In one embodiment, compounds of Formula (II) of the present disclosure can be synthesized according to the synthetic Schemes 5-7 below:

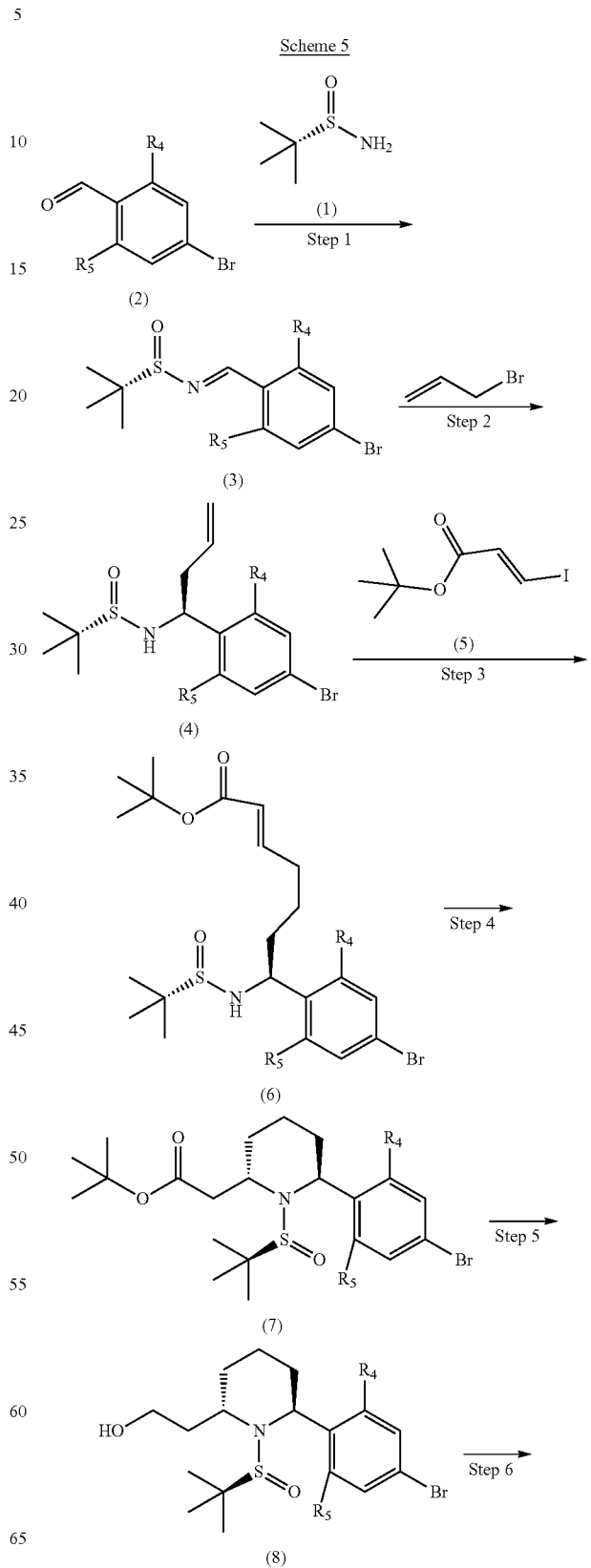

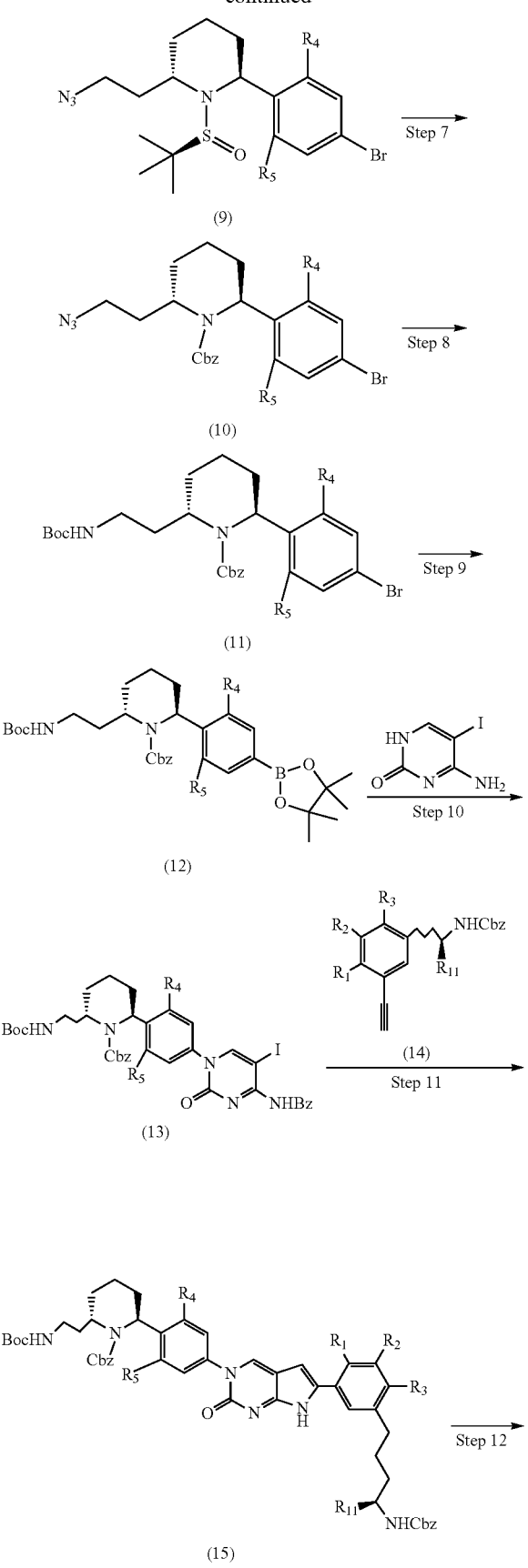

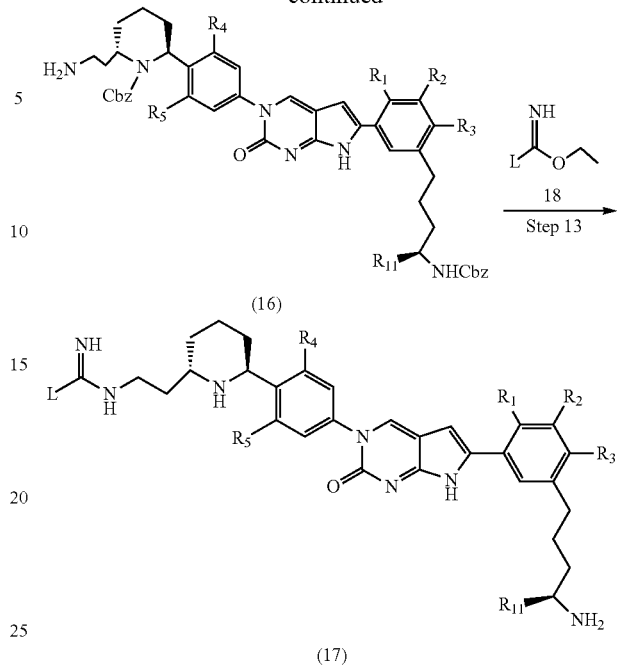

Referring to Scheme 5:

Step 1: (S)-(−)-2-methyl-2-propanesulfinamide (1) and aldehyde 2 are reacted to yield 3. In some embodiments, the reaction is carried out is a solvent (e.g., dichloromethane). In some embodiments, the reaction is carried out at a temperature from about 30° C. to about 50° C. (e.g., at 40° C.). In some embodiments, the reaction is carried out in the presence of a base (e.g., cesium carbonate).

Step 2: Intermediate 3 is reacted with allyl bromide to obtain 4. In some embodiments, the reaction is carried out in a solvent (e.g., N—N'-dimethylformamide). In some embodiments, the reaction is carried out in the presence of activated zinc.

Step 3: Intermediate 4 is reacted with iodoacrylate 5 to yield 6. In some embodiments, the reaction is carried out in the presence of a catalyst. In some embodiments, the catalyst is Pd(PPh$_3$)$_4$.

Step 4: Intermediate 6 is reacted with a base to afford 7. In some embodiments, the base is cesium carbonate. n some embodiments, the reaction is carried out in a solvent (e.g., N—N'-dimethylformamide).

Step 5: Intermediate 7 is reacted with a reducing agent to obtain 8. In some embodiments, the reducing agent is DIBAL.

Step 6: Intermediate 8 is reacted with azide-containing reagent to obtain 9. In some embodiments, the azide-containing reagent is diphenylphosphoryl azide (DPPA). In some embodiments, the reaction is carried out in the presence of a base (e.g., DBU). In some embodiments, the reaction is carried out at a temperature from about 40° C. to about 120° C. (e.g., at about 80° C.).

Step 7: Intermediate 9 is treated with an acid (e.g., HCl)) to remove tert-butylsulfinyl auxiliary group. The resultant NH-containing intermediate is reacted with a protecting group (e.g., Cbz-Cl) to yield intermediate 10.

Step 8: Intermediate 10 is reacted with triphenylphosphine to reduce the azide group. In some embodiments, the reaction is carried out at a temperature from about 35° C. to about 75° C. (e.g., at about 55° C.). The resultant NH$_2$- containing intermediate is reacted with a protecting group (e.g., Boc anhydride) to yield 11.

Step 9: Intermediate 11 is reacted with bispinacolatodiborane to obtain 12. In some embodiments, the reaction is carried out in the presence of a catalyst (e.g., $PdCl_2(dppf)\cdot CH_2Cl_2$). In some embodiments, the reaction is carried out in a solvent (e.g., dimethyl sulfoxide (DMSO)). In some embodiments, the reaction is carried out in the presence of a base (e.g., potassium acetate).

Step 10: Intermediate 12 is reacted with 5-iodocytosine to yield the free amine intermediate. In some embodiments, the reaction is carried out in presence of a catalyst and a ligand (e.g., copper acetate monohydrate and tetramethylehtylenediamine). The free amine intermediate is reacted with a protecting group (e.g., benzoic anhydride) to yield 13.

Step 11: Intermediate 13 is reacted with 14 to yield a protected intermediate. In some embodiments, the reaction is carried out under Sonogashira coupling conditions. In some embodiments, the reaction is carried in the presence of catalyst (e.g., $Pd(PPh_3)_4$ and CuI) and a ligand (e.g., N—N-diisopropylethylamine). The protecyted intermediate is hydrolyzed in the presence of an alcohol (e.g., methanol) to yield 15.

Step 12: Intermediate 15 is reacted with an acid (e.g., HCl) to yield 16. In some embodiments, the reaction is carried out in the presence of Charcoal-siliathiol.

Step 13: Intermediate 16 is reacted with ethoxyimine 18 to a protected intermediate. In some embodiments, the reaction is carried out in the presence of diisopropylethyl amine (DIPEA). The resultant Cbz-protected intermediate was reacted with an acid (e.g., HBr or HBr solution in acetic acid) to yield 17.

An analogous scheme may be used starting with 2', shown below, instead of 2, to obtain a compound of Formula (II) or Formula (II-1) wherein W is N.

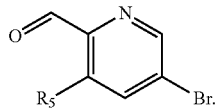

(2')

Scheme 6

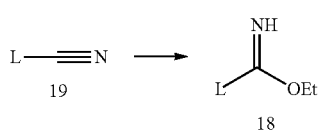

Referring to Scheme 6:

Substituted acetonitrile 19 is reacted with ethanol in the presence of an acid (e.g., HCl) to obtain 18. In some embodiments, the reaction is carried out 0° C. In some embodiments, the reaction is carried out in 4N HCl solution in organic solvent (e.g., 1,4-dioxane).

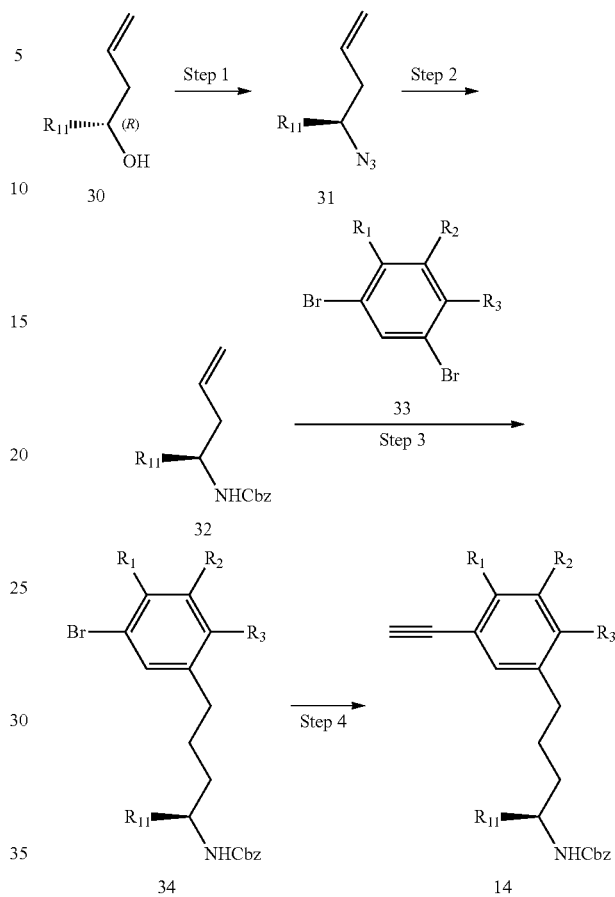

Referring to Scheme 7:

Step 1: Alcohol 30 is reacted with an azide-containing reagent to obtain an azide 31. In some embodiments, the azide-containing reagent is $NaN_3$. In some embodiments, the alcohol 30 is reacted with methanesulfonyl chloride prior to reaction with $NaN_3$.

Step 2: The azide 31 is reacted with triphenylphosphine to reduce the azide group and obtain the free amine-containing intermediate. The free-amine containing intermediate is reacted with a protecting group (e.g., Cbz-Cl) to yield 32.

Step 3: Alkene 32 is reacted with a boron reagent (e.g., 9-BBN) to obtain a boron intermediate which is further reacted with bromobenzene 33 to yield 34. In some embodiments, the reaction in carried out in the presence of a catalyst (e.g., $Pd(PPh_3)_4$). In some embodiments, the reaction is carried out at a temperature from about 40° C. to about 80° C. (e.g., about 60° C.).

Step 4: bromobenzene 34 is reacted with an acetylene reagent (e.g., TMS-acetylene) to yield 14. In some embodiments, the reaction is carried out in the presence of a base (e.g., $K_2CO_3$).

In some embodiments, intermediate 14 can be prepared using methods and procedures analogous to those described in PCT/US2014/054869 and U.S. provisional application 61/875,643, the disclosures of which are incorporated herein by reference in their entireties.

In one embodiment, the compound of Formula (III) of the present disclosure can be synthesized according to the synthetic Scheme 8 below:
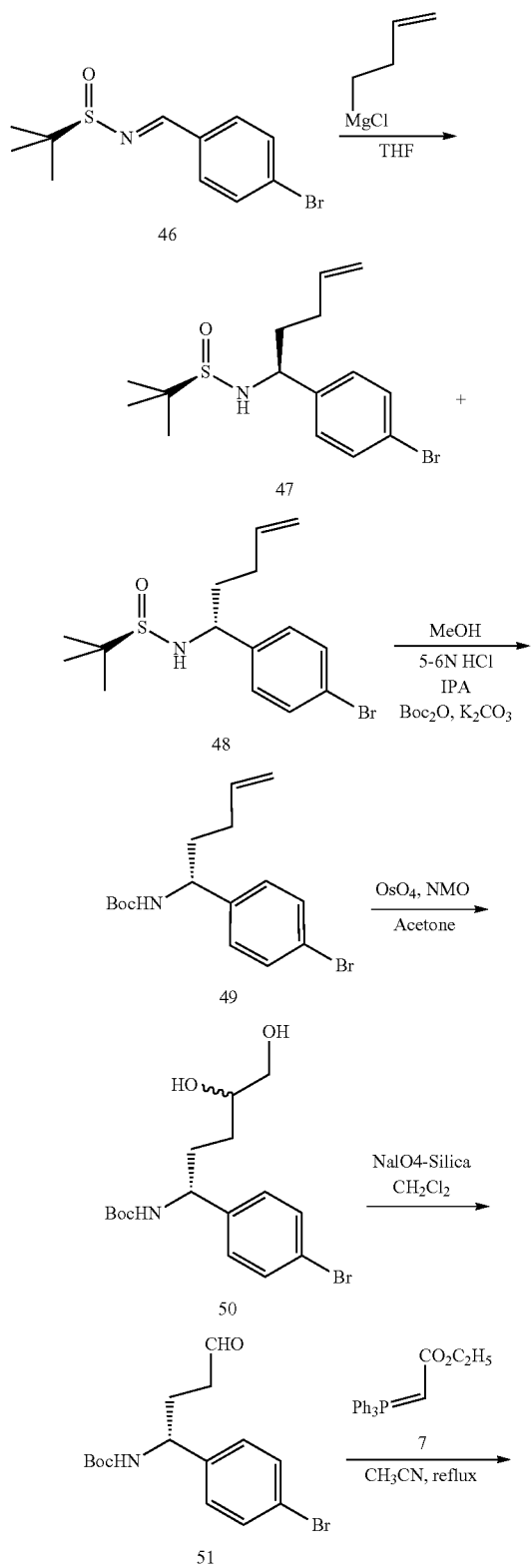
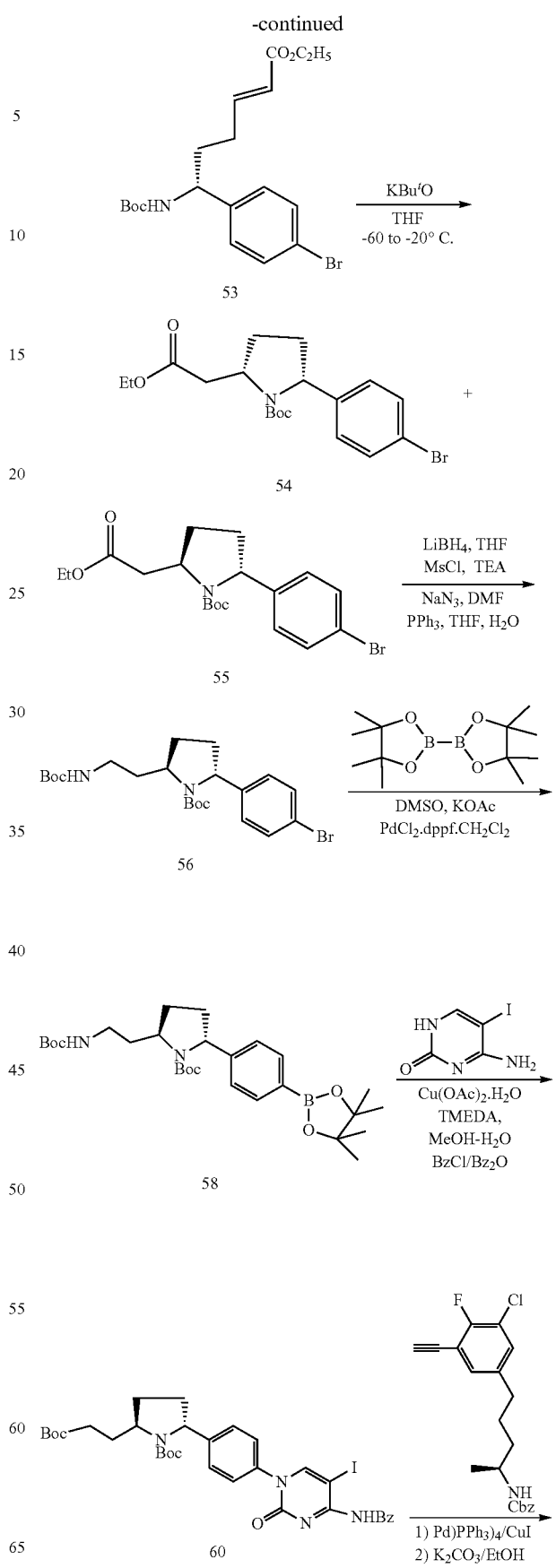

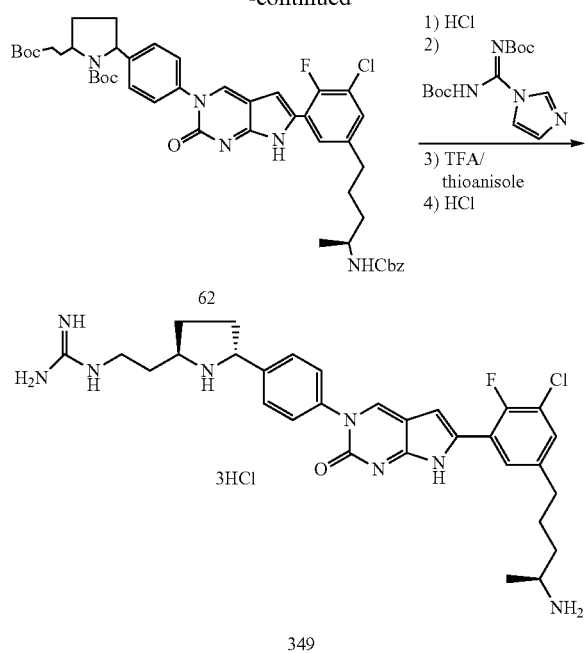

To a solution of (R)-(+)-2-methyl-2-propanesulfinamide and 4-bromobenzaldehyde in, e.g., dichloromethane is added pyridine para-toluenesulfonate and magnesium sulfate and the resulting mixture is stirred overnight at, e.g., ambient temperature. The mixture is then filtered, concentrated, and purified by, e.g., flash chromatography over silica gel to afford compound 46. A solution of compound 46 in tetrahydrofuran is then treated with 3-butenyl magnesium bromide at, e.g., −75° C. The resulting mixture is slowly warmed up to ambient temperature and stirred overnight. The reaction is then quenched with saturated ammonium chloride solution, extracted with ethyl acetate and the combined organic layers are dried (with, e.g., anhydrous sodium sulfate), concentrated, and purified by, e.g., flash chromatography over silica gel to yield 47 and 48.

Compound 48 in methanol is treated with 5-6 N HCl in isopropanol to afford the intermediate amine which is then treated with a saturated solution of $K_2CO_3$ and with di-tert-butyl dicarbonate (($Boc)_2O$) and stirred for, e.g., 72 hours. The resulting solution is then concentrated and extracted with EtOAc. The combined organic layers are washed with brine, dried, concentrated, and purified by, e.g., flash chromatography over silica gel to yield 49.

To a mixture of 49 and N-methyl morpholine oxide (NMO) is added acetone followed by osmium tetroxide ($OsO_4$) and the resulting mixture is stirred overnight at ambient temperature. The reaction mixture is then quenched with saturated of sodium thiosulphate solution, extracted with ethyl acetate, washed with brine, dried, concentrated, and purified by, e.g., flash chromatography over silica gel to afford 50 quantitatively. A mixture of 50 and sodium periodate-silica gel ($NaIO_4$—$SiO_2$) in $CH_2Cl_2$ is stirred for, e.g., 5 hours, filtered, and, concentrated to afford 51. A mixture of 51 and Wittig salt 52 is placed in a sealed tube with $CH_3CN$ and heated to reflux for, e.g., 72 hours. The solution is then concentrated, extracted with EtOAc, washed with brine, dried, and purified by, e.g., flash chromatography over silica gel to afford 53.

To a solution of 53 in, e.g., THF cooled in an acetone-dry ice bath −60° C. is added potassium tert-butoxide ($KO^tBu$) in one portion and the resulting mixture is stirred at, e.g., −60° C. The acetone-dry ice bath temperature is allowed to warm to, e.g., ∼−20° C. and it is maintained at ∼−20° C. by addition of dry ice as required. After 2 hours of stirring at that temperature, the reaction is quenched by the addition of water and the resulting solution is allowed to warm to room temperature. The reaction mixture is then diluted with, e.g., ether, the layers are separated, and the aqueous layer is extracted with ethyl acetate. The combined organic layers are then dried over, e.g., anhydrous $Na_2SO_4$, filtered, and concentrated afford a pale yellow crude viscous liquid which is purified using, e.g., Combiflash chromatography to afford 54 and 55.

To a solution of 55 in THF cooled in ice bath is added $LiBH_4$ in one portion and the resulting solution is allowed to warm to room temperature and stir under an atmosphere of argon. If the reaction is not complete by LC/MS (liquid chromatography/mass spectroscopy), additional $LiBH_4$ can be added to push the reaction to completion. Upon reaction completion, the reaction is cooled in ice bath and slowly quenched by the slow addition of ice and HCl solution (*caution: add HCl very slowly as there is exothermic reaction with vigorous effervescences). The reaction mixture is then extracted with EtOAc and the combined organic layers are dried over anhydrous $Na_2SO_4$, filtered and concentrated to afford a pale yellow viscous liquid (the alcohol) which can be used in next step without any further purification.

The primary alcohol is dissolved in, e.g., $CH_2Cl_2$ and $Et_3N$ is added. The mixture is cooled in ice bath (e.g., 0° C.) and MsCl is added. The resulting solution is allowed to warm to room temperature and stirred for, e.g., 24 hours under argon (additional equivalents of MsCl and $Et_3N$ are added if necessary to push the reaction to completion; reaction monitored by LC/MS and TLC). The reaction is then quenched with cold water, the layers are separated and the aqueous layer is extracted with $CH_2Cl_2$. The combined organic layers are then dried over anhydrous, e.g., $Na_2SO_4$ and concentrated on to afford the mesylate which can be used for next step without any further purification.

A solution of the mesylate obtained in the prior step and $NaN_3$ in DMF is heated to, e.g., 70-75° C. in an oil bath under an atmosphere of argon. Once LC/MS shows complete conversion of starting material, the reaction mixture is cooled to room temperature, diluted with water, and extracted with EtOAc. The combined organic layers are then dried (e.g., $Na_2SO_4$) and concentrated to afford a viscous liquid (the azide) which can be used in next step without any further purification.

To solution of the crude azide in THF and water at room temperature is added triphenylphosphine and the resulting mixture is heated to, e.g., 60-65° C. in an oil bath for, e.g., 16 hours (monitored by LC/MS for conversion of starting material). Once reaction is complete, the heating is stopped and the reaction mixture is cooled to room temperature. Saturated $NaHCO_3$ solution and $EtN^iPr_2$ is added followed by di-tert-butyl dicarbonate (($Boc)_2O$) and the resulting mixture is heated to, e.g., 45-50° C. in oil bath for, e.g., 46 hours. The reaction mixture is then cooled to room temperature, diluted with water and EtOAc, and the layers are separated. The aqueous layer is extracted with EtOAc and the combined organic layers are dried (e.g., $Na_2SO_4$) and concentrated to afford a viscous liquid which is purified using, e.g., Combiflash chromatography to afford 56.

To a solution of 56 in DMSO under an atmosphere of argon is added bispinacalatodiborane 7a and potassium acetate (KOAc) followed by $PdCl_2$(dppf)-$CH_2Cl_2$. The resulting mixture is heated with stirring under an atmosphere of argon to, e.g., 80-85° C. for, e.g., 20 hours. Once LC/MS shows reaction completion, the reaction mixture is cooled to room temperature, diluted with water and 60-70% EtOAc in heptane. The layers are then separated and the aqueous layer is extracted with 60% EtOAc in heptane. The combined organic layers are dried (e.g., $Na_2SO_4$) and concentrated to provide a dark brown viscous liquid which is purified using, e.g., Combiflash chromatography to afford 58.

To a solution of 58 in, e.g., MeOH:$H_2O$ is added iodocytosine, 9a, followed by Cu(OAc)$_2$, $H_2O$ and TMEDA. The resulting solution is stirred at room temperature and air is bubbled very slowly through reaction mixture. After stirring for, e.g., 19 hours at room temperature, the reaction mixture is concentrated to remove any MeOH and diluted with water. The $CH_2Cl_2$, layers are separated and the aqueous later is extracted two more times with $CH_2Cl_2$. The combined organic layers are then dried (e.g., anhydrous $Na_2SO_4$) and concentrated to afford the coupled product which can be used in next step without further purification.

To a solution in EtOAc is added $Bz_2O$ and the resulting solution is heated in an oil bath to, e.g., 70-75° C. under argon atmosphere for, e.g., 3 hours. Once LC/MS shows reaction completion, the reaction mixture is cooled to room temperature and diluted with saturated $NaHCO_3$ solution. The layers are separated and the aqueous layer is extracted with EtOAc. The combined organics are then dried (e.g., $Na_2SO_4$) and concentrated to provide a viscous liquid which is purified using, e.g., Combiflash chromatography to afford 60.

To a degassed solution of 60 in DMF under an atmosphere of argon is added alkyne 11a and EtN$^i$Pr$_2$ followed by Pd(PPh$_3$)$_4$ and CuI. The resulting solution is flushed with argon and heated to, e.g., 70-75° C. with stirring under an atmosphere of argon for, e.g., 16 hours. Once LC/MS shows complete conversion of 60, the reaction mixture is cooled to room temperature and MeOH is added. The resulting solution is then heated under argon to, e.g., 75-80° C. for, e.g., 9 hours (and checked by LC/MS for complete conversion of intermediate). The reaction mixture is cooled to room temperature, concentrated to remove MeOH, and diluted with water. The EtOAc layer is separated and the organic layer is extracted once with EtOAc. The combined organic layers are washed with NH$_4$OH, water and brine, dried (e.g., $Na_2SO_4$), and concentrated to provide a dark brown viscous liquid which is purified by using, e.g., prep TLC to afford protected intermediate 62.

To a solution of 62 in $CH_2Cl_2$ is added an acid, e.g., 4N solution of HCl in dioxane and the resulting solution is stirred at room temperature for, e.g., 2 hours. Once LC/MS shows complete conversion of starting material, the reaction mixture is concentrated and dried under vacuum to provide the deprotected amine intermediate as a foam which can be used in next step without any further purification.

To a solution of the deprotected amine intermediate in MeOH at room temperature is added EtN$^i$Pr$_2$ and bis-boc-guanylpyrazole 13a and the resulting reaction mixture is stirred at room temperature. Once LC/MS shows reaction completion, the reaction mixture is concentrated to afford a viscous liquid which can be used in next step without any further purification.

To a solution of the above compound in trifluoroacetic acid is added thioanisole and the resulting mixture is stirred with heating to, e.g., 45° C. in an oil bath for, e.g., 3 hours. Once LC/MS shows reaction completion, the reaction mixture is cooled to room temperature, concentrated, and purified using, e.g., Varian prep HPLC. HPLC fractions are collected and concentrated and the obtained TFA salt is converted to the HCl salt by treatment with, e.g., 6 N HCl (2×). The resulting solid is then lyophilized to afford 349 (Formula (III)).

The specific approaches and compounds shown in the schemes above are not intended to be limiting. The chemical structures in the schemes herein depict variables that are hereby defined commensurately with chemical group definitions (moieties, atoms, etc.) of the corresponding position in the compound formulae herein, whether identified by the same variable name (for example, $R_1$, $R_2$, $R_3$) or not. The suitability of a chemical group in a compound structure for use in the synthesis of another compound is within the knowledge of one of ordinary skill in the art.

Additional methods of synthesizing compounds of the formulae herein and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R., *Comprehensive Organic Transformations*, VCH Publishers (1989); Fieser L. et al., *Fieser and Fieser's Reagents for Organic Synthesis*, John Wiley and Sons (1994); and Paquette L., ed., *Encyclopedia of Reagents for Organic Synthesis*, John Wiley and Sons (1995) and subsequent editions thereof.

6. CHARACTERIZATION OF COMPOUNDS OF THE DISCLOSURE

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules disclosed herein for activity, for example, as anti-cancer, anti-bacterial, anti-fungal, anti-parasitic or anti-viral agents. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

(1) Surface Binding Studies. A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor® from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization. Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis. It is contemplated that, in addition to characterization by the foregoing biochemical assays, the compound of interest can also be characterized as a modulator (for example, an inhibitor of protein synthesis) of the functional activity of the ribosome or ribosomal subunit.

Furthermore, more specific protein synthesis inhibition assays can be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of 3H leucine or $^{35}$S methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is an inhibitor of protein synthesis.

(4) Antimicrobial assays and other evaluation. Furthermore, the compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule can be acting as a protein synthesis inhibitor. More specifically, the activity of the compounds of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms.

(5) The translation-only assay for ribosomal protein production uses purified 70S ribosomes, corresponding 5100 extracts containing the biological molecules necessary to support protein translation, and mRNA encoding firefly luciferase or another protein reporter. The resulting luminescence signal is proportional to protein translation and is determined by a luminescence assay plate reader (Victor2V Multilabel Reader). This assay is performed with varying concentrations of potential translation inhibitors in the assay. The resulting data are used to calculate IC50 values of inhibition for the compounds using appropriate software (MDL Assay Explorer with a one-site competition model of binding).

The in vitro activity of the compounds of the present disclosure can be determined. Antimicrobial testing is typically performed to determine the minimum inhibitory concentration (MIC). Minimum inhibitory concentrations (MICs) are determined by the microdilution method in a final volume of 100 µl according to protocols outlined by The Clinical and Laboratory Standards Institute (CLSI). Performance standards for reference strains are assessed within the same experimental design to maintain quality control. See, for example, Clinical Laboratory Standards Institute: Methods for dilution antimicrobial susceptibility tests for bacteria that grow aerobically M7-A8. Approved Standard-Eighth Edition. Wayne, PA: CLSI; December 2008; and Clinical Laboratory Standards Institute: Performance Standards for Antimicrobial Susceptibility Testing M100-S20; Approved Standard-Twentieth Edition. Wayne, PA: CLSI; June 2010.

For example, an agar-dilution MIC assay could be run using the following protocol. Pure cultures of isolates to be tested are grown on Chocolate Agar at 35° C. to 36.5° C. in a $CO_2$ enriched (5%) atmosphere for 16-18 hours. Using a cotton applicator or a bacteriologic loop, isolated colonies (or cells from less dense areas of growth on the plate) are suspended in 5 mL saline. The density of the suspension is then adjusted to contain $10^8$ colony forming units (CFU)/mL by comparison with a 0.5 McFarland $BaSO_4$ turbidity standard. This suspension is then diluted in 1:10 in MH broth to give $10^7$ CFU/mL. Using a multichannel pipettor, 0.002 mL spots of the bacterial suspension is dispensed onto the surface of the medium (104 CFU). Each plate of the set of antibiotic containing media plus a plate of Chocolate Agar or GCS medium (as a control to determine that all isolates grew) is inoculated. The inoculated plates are air-dried at room temperature for approximately 15 minutes. The plates are then inverted and incubated at 35° C. to 36.5° C. in a $CO_2$-enriched (5%) atmosphere for 24 hours. The plates are then examined for growth.

Another in vitro assay that can be performed is a time-kill kinetic assay. Using this assay, bactericidal activity can be determined by time-kill methodology as described by Clinical Laboratory Standards Institute. For example, the compounds to be tested are added to test flasks at concentrations of 2×-32× the MIC (determined, for example, using the assays described herein). Once dissolved, compounds are diluted in Giolitti Cantoni (GC) broth to a volume of 1 mL at the 25× desired final concentration; a flask containing 1 mL of GC broth without compound is prepared as a growth control. A 0.5 McFarland equivalent is prepared for the test organism, diluted 1:200 in pre-warmed GC broth, and incubated in 5% $CO_2$-enriched atmosphere at 35° C. for 30 minutes prior to exposure to the test compound. After the 30-minute pre-incubation, 24 mL is removed and added to each test flask for a final volume of 25 mL. A sample is removed from the growth control flask, diluted in Phosphate Buffered Saline (PBS) and plated on Chocolate Agar (CA) to confirm an inoculum of approximately $5 \times 10^5$ CFU/mL. Samples are then removed from all flasks at 1, 2, 4, 6, 8, and 24 hours, diluted in PBS and plated on CA to determine the number of viable cells in each flask. Plate counts are incubated at 35° C. in 5% $CO_2$-enriched atmosphere for 48 hours and colonies are counted. Plate counts are then graphed.

The antimicrobial and other drug properties of the compounds can further be evaluated in various in vivo mammalian assays, such as a mouse or rat peritonitis infectious models, skin and soft tissue models (often referred to as the thigh model), or a mouse pneumonia model. There are septicemia or organ infection models known to those skilled in the art. These efficacy models can be used as part of the evaluation process and can be used as a guide of potential efficacy in humans. Endpoints can vary from reduction in bacterial burden to lethality. For the latter endpoint, results are often expressed as a $PD_{50}$ value, or the dose of drug that protects 50% of the animals from mortality.

To further assess a compound's drug-like properties, measurements of inhibition of cytochrome P450 enzymes and phase II metabolizing enzyme activity can also be measured either using recombinant human enzyme systems or more complex systems like human liver microsomes. Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

(5) Animal Pharmacology and Toxicology. The compounds of the present disclosure can be evaluated for efficacy in well-known animal models. The following table provides representative animal models for various infection indications.

| Target Infection Indication | Animal Model of Efficacy |
| --- | --- |
| HAP/VAP | Efficacy in mouse and/or rat pneumoniae model vs. respiratory tract infection pathogens of interest (*Streptococcus pneumoniae*, including multi-drug resistant *Streptococcus pneumoniae*, *H. influenzae*, methicillin resistant *Staphylococcus aureus* (MRSA), and *Pseudomonas aeruginosa*) |
| cSSSI | Efficacy in mouse model against pathogens of interest (MRSA, *K. pneumoniae*) |
| Sepsis | Efficacy in mouse peritonitis model vs. pathogens of interest (*E. coli*, *K. pneumoniae*, *E. faecalis*, MRSA) |
| cUTI | Efficacy in mouse model against *E. coli*, *K. pneumoniae* and/or MRSA |
| Febrile neutropenia | Efficacy in mouse peritonitis model against *S. aureus*, *S. epidermidis*, *S. pneumoniae*, *S. pyogenes*, *P. aeruginosa* |

Animal Model for Complicated Skin and Skin Structure Infections (cSSSI): Murine Skin and Soft Tissue Infection Model of *Klebsiella pneumoniae* 1705966 in Thighs of Neutropenic Female CD-1 Mice This model is useful to assess the efficacy of compounds of the present disclosure in a *Klebsiella pneumoniae* 1705966 neutropenic mouse thigh infection model using female ICR (CD-1) mice.

Study Design:

Species: Female ICR (CD-1) Mice, 8 to 9 weeks old, weighting 25-29 g.

Inoculum: *Klebsiella pneumoniae* 17059663 was streaked from frozen stock onto Blood agar (Tryptic Soy Agar+5% Sheep Blood), BD, #221261) and incubated overnight at 35° C. After overnight incubation, enough bacteria (approx. 1 full loop) to measure $OD_{625}=0.990$ was transferred from plate and diluted into 10 mL pre-warmed Mueller-Hinton broth. This culture was further diluted 1:1000 into pre-warmed MH broth and grown for approximately 2 hours at 35° C. with shaking. Each mouse was given 0.1 mL of 1:1000 dilution culture injected into both caudal thigh muscles under isoflurane inhalation anesthesia.

| Dilution incubation) | Initial. O.D | Final O.D. (after ~2 hr. |
|---|---|---|
| 1:10 | 0.135 | 0.424 |
| 1:100 | 0.014 | 0.215 |
| 1:1000 | 0.001 | 0.035 |

Neutropenia is induced by intraperitoneal (I.P.) administration of Cyclophosphamide monohydrate on Day −4 (150 mg/kg) and Day −1 (100 mg/kg).
Vehicle: 0.9% sodium chloride
Dosing: Each mouse in the treated groups was given the appropriate dose of the compound to be tested in a volume of 0.2 mL, 2 and 8 hrs post bacterial inoculation.
Time Points:
Controls: 0, 2, 6, and 24 hrs.
Treated: 24 hrs.
Sampling: 2 or 3 mice/time point were euthanized via $CO_2$, and their caudal thigh muscles excised and homogenized. The thigh muscles were placed in 5 mL sterile PBS in Stomacher Filter bag and homogenized with MicroBiomaster80 (Brinkmann) for 60 seconds, normal setting and 1:10 dilutions were made per standard protocol in a 96-well plate. Aliquots of 25 ul for each dilution, as well as the homogenate, were plated on blood agar plates and incubated at 35° C. to determine the CFU/mL over the time course. After overnight incubation, colonies were counted.
Animal Model for Sepsis:
Murine Peritonitis Model (*E. coli, K. Pneumoniae, E. faecalis*, MRSA)
This model is used to evaluate the effect of subcutaneous (SC) treatment with compounds of the present disclosure on growth of *Escherichia coli* ATCC 25922 in a mouse peritonitis model using female Swiss Webster mice.
Controls:
Negative: Inoculum only
Inoculum Vehicle Intraperitoneal
Positive: Ciprofloxacin
Study Design:
Species: Female Swiss Webster Mice
Inoculation: *Escherichia coli* ATCC 25922 is made by adding 1 mL (4/6/07) stock to 9 mL 0.25% Brewer's Yeast to make (1:10), then 1 mL of the (1:10) will be added to 9 mL 0.25% Brewer's Yeast to make (1:100), then 1 mL of the (1:100) will be added to 9 mL 0.25% Brewer's Yeast to make (1:1000), then 2.5 mL of the (1:1000) will be added to 122.5 mL 0.25% Brewer's Yeast to make (1:50,000), 1 mL/mouse will be inoculated intraperitoneally (IP).
Route of Administration: SC
Dosing: Vehicle for compounds of the present disclosure: Saline or 50 mM Sodium phosphate buffer in 10% Captisol in water, pH=7.2.
Dose Administration: Q3H×3 beginning at 30 min post bacterial inoculation
Study Duration: 24 hrs. 0.25% Brewer's Yeast Extract (BYE): Dilute 2% prepared on 11/12/09 (Lot.2158K, MP Biomedicals) 25 mL 2%+175 mL 1×PBS.
Outcome Measures: Colony Forming Unit's from peritoneal wash and spleen homogenate and drug levels from wash, spleen homogenate, and plasma.
Blood is collected via cardiac puncture while mouse is under $CO_2$ narcosis. The whole blood sample is placed in heparinized eppendorf tubes and kept on wet ice until centrifuged (4 min @ 14,000 rpm). Plasma is transferred to 96 deep-well block on dry ice and stored at −20° C. Immediately following blood collection, 2 mL of sterile PBS (phosphate buffered saline) was injected into the peritoneal cavity with a 25 G needle. The abdomen was gently massaged, and a small incision was made to allow access to the peritoneal cavity. The peritoneal wash fluid was collected using sterile technique, serially diluted 1:10, plated on blood agar plates, and incubated overnight at 35° C.

Spleens were harvested and placed in 1 mL sterile PBS in Stomacher bag and homogenized with MicroBiomaster80 (Brinkmann) for 60 seconds, normal setting and 1:10 dilutions were made. 25 µl of each dilution, as well as the homogenate, was plated on blood agar plates and incubated at 35° C. to determine the CFU/mL over the time course. After overnight incubation, colonies were counted.
Other Animal Models Similarly, other animal infection models can be used for hospital acquired pneumonia (HAP)/ventilator acquired pneumonia (VAP), complicated urinary tract infections (cUTI), and febrile neutropenia.

7. EXAMPLES

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

The compounds or tautomers thereof, or pharmaceutically acceptable salts of said compounds or tautomers of the present disclosure can be prepared using known chemical transformations adapted to the particular situation at hand.

Some of the abbreviations used in the following experimental details of the synthesis of the examples are defined below: h or hr=hour(s); min=minute(s); mol=mole(s); mmol=millimole(s); M=molar; M=micromolar; g=gram(s); µg=microgram(s); rt=room temperature; L=liter(s); mL=milliliter(s); $Et_2O$=diethyl ether; THF=tetrahydrofuran; DMSO=dimethyl sulfoxide; EtOAc=ethyl acetate; $Et_3N$=triethylamine; i-$Pr_2NEt$ or DIPEA=diisopropylethylamine; $CH_2Cl_2$=methylene chloride; $CHCl_3$=chloroform; $CDCl_3$=deuterated chloroform; $CCl_4$=carbon tetrachloride; MeOH=methanol; $CD_3OD$=deuterated methanol; EtOH=ethanol; DMF=dimethylformamide; BOC=t-butoxycarbonyl; CBZ=benzyloxycarbonyl; TBS=t-butyldimethylsilyl; TBSCl=t-butyldimethylsilyl chloride; TFA=trifluoroacetic acid; DBU=diazabicycloundecene; TBDPSCl=t-butyldiphenylchlorosilane; Hunig's Base=N,N-diisopropylethylamine; DMAP=4-dimethylaminopyridine; CuI=copper (I) iodide; MsCl=methanesulfonyl chloride; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; Pd(dppf)$Cl_2$=dichloro[1,1'-bis(diphenylphosphino)ferrocene] palladium (II).

Exemplary compounds synthesized in accordance with the disclosure are listed in Tables 1, 1a, 1b, 1c, 2, 2a, and 2b. A bolded or dashed bond is shown to indicate a particular stereochemistry at a chiral center, whereas a wavy bond indicates that the substituent can be in either orientation or that the compound is a mixture thereof.

The compounds of the present disclosure can be prepared, formulated, and delivered as salts. For convenience, the compounds are generally shown without indicating a particular salt form.

The compounds of the present disclosure can be made using synthetic chemical techniques well known to those of skill in the art. The compounds of Formula (I) (compounds 1-69 from Tables 1, 1a, 1b, and 1c, above) were synthesized according to the methods and procedures similar to those described in Schemes 1-4-3 and in PCT Pub. No. WO 2017/193017, which is incorporated by reference in its entirety. The compounds of Formula (II) (compounds 1-293 from Tables 2, 2a, and 2b, above) can be prepared according to the methods and procedures described in Schemes 5-7 and in PCT Pub. No. WO 2017/193016, which is incorporated by reference in its entirety. The compound of Formula (III) can be prepared according to the methods and procedures described in Scheme 8 and in U.S. Pub. No. 2016/0214988, which is incorporated by reference in its entirety.

Example 1: Activity of Pyrrolocytosine Protein Synthesis Inhibitors Against Multiresistant Gram-Negative Bacteria The four compounds shown in Table 3 below were tested against (i) multiresistant Enterobacteriaceae and *Acinetobacter* with carbapenemases; (ii) Enterobacteriaceae with MCR-1; and (iii) *P. aeruginosa* with altered efflux (see Tables 3 and 4). The compounds included: RX-04A (1-(2-((2S,6S)-6-(4-(6-(5-((S)-4-aminopentyl)-3-(tert-butoxy)-2-fluorophenyl)-2-oxo-2,7-dihydro-3H-pyrrolo[2,3-d]pyrimidin-3-yl)phenyl)piperidin-2-yl)ethyl)guanidine; RX-04B (N-(2-((2S,6S)-6-(4-(6-(5-((R)-4-amino-4-cyclopropylbutyl)-3-chloro-2-fluorophenyl)-2-oxo-2,7-dihydro-3H-pyrrolo[2,3-d]pyrimidin-3-yl)-2-(methylthio)phenyl)piperidin-2-yl)ethyl)acetimidamide; compound 120 of Formula (II) from Table 2, above); RX-04C (N-(2-((2S,6S)-6-(4-(6-(5-((R)-4-amino-5-hydroxypentyl)-3-chloro-2-fluorophenyl)-2-oxo-2,7-dihydro-3H-pyrrolo[2,3-d]pyrimidin-3-yl)-2-fluorophenyl)piperidin-2-yl)ethyl)acetimidamide; compound 162 of Formula (II) from Table 2, above); and RX-04D (N-(3-((4-(6-(5-((R)-4-amino-5-hydroxypentyl)-3-chloro-2-fluorophenyl)-2-oxo-2,7-dihydro-3H-pyrrolo[2,3-d]pyrimidin-3-yl)benzyl)amino)pent-4-en-1-yl)acetimidamide; compound 8 of Formula (I) from Table 1, above); In this case, MCR-1 is relevant because its activity reduces the negative charge of lipopolysaccharides, potentially affecting binding of poly-basic molecules such as the compounds tested herein, as well as polymyxins.

TABLE 3

Compounds Tested

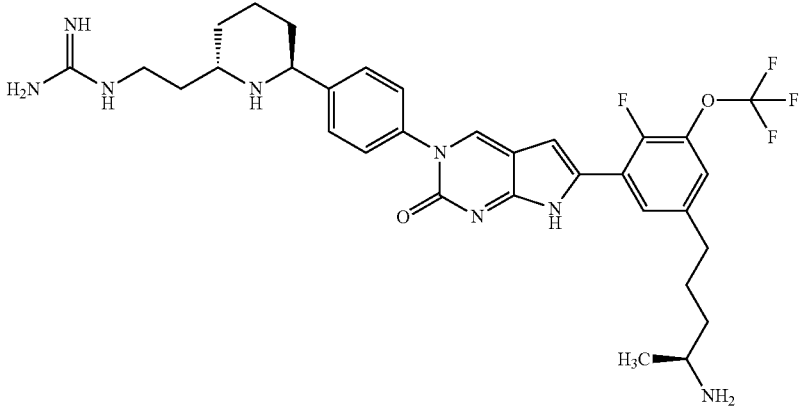 [SMILES: C[C@H](N)CCCc1cc(OC(F)(F)F)c(F)c(-c2cc3cn(-c4ccc([C@@H]5CCC[C@@H](CCNC(=N)N)N5)cc4)c(=O)nc3[nH]2)c1]

RX-04A

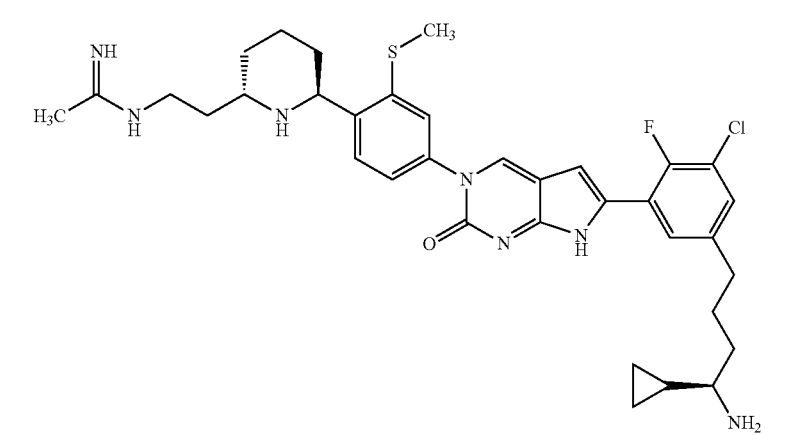 [SMILES: CSc1cc(-n2cc3cc(-c4cc(CCC[C@@H](N)C5CC5)cc(Cl)c4F)[nH]c3nc2=O)ccc1[C@@H]1CCC[C@@H](CCNC(C)=N)N1]

RX-04B

TABLE 3-continued

Compounds Tested

RX-04C

RX-04D

TABLE 4

Test Panel
Resistance mechanism/phenotype*

| Species | Carbapenem + cephalosporin susceptible controls | KPC | SME | MBL | OXA-48 | OXA-23 | Low efflux | Normal efflux | Raised efflux | MCR-1 | E. coli DH10B recipient | DH10B mcr-1 transformant |
|---|---|---|---|---|---|---|---|---|---|---|---|---|
| E. coli | 5 | 5 | — | 5 | 5 | — | — | — | — | 3 | 1 | 1 |
| S. enterica | — | — | — | — | — | — | — | — | — | 11 | — | — |
| K. pneumoniae | 5 | 5 | — | 5 | 5 | — | — | — | — | — | — | — |
| Enterobacter spp. | 4 | 2 | — | 1 | 1 | — | — | — | — | — | — | — |
| S. marcescens | 2 | — | 1 | — | 1 | — | — | — | — | — | — | — |
| P. aeruginosa | — | — | — | 5 | — | — | 5 | 5 | 5 | — | — | — |
| A. baumannii | 5 | — | — | — | — | 5 | — | — | — | — | — | — |

E. coli ATCC 25922 and P. aeruginosa ATCC 27853 were controls throughout

*numbers in the table refer to the number of each species that exhibit the particular resistance/genotype.

MICs of the four tested compounds and comparators (amikacin, cefepime, colistin, meropenem and tigecycline) were determined by CLSI broth microdilution using pre-prepared plates (Trek Diagnostic Systems) (CLSI Approved Standard M7-A10). Carbapenemase and mcr-1 genes were detected by PCR or sequencing. Efflux levels in *P. aeruginosa* isolates were inferred by interpretive reading of antibiogram data.

MICs for the 68 Enterobacteriaceae were unimodal, with peaks at 1 mg/L for analogues RX-04A and RX-04B and 2 mg/L for RX-04C and RX-04D (FIG. 1). For RX-04A, the most active of the tested analogues, 67/68 (>98%) MICs were 0.25-2 mg/L. For all of the tested compounds, MICs were lowest for *E. Coli* and highest for *S. marcescens* (MICs from 8 to greater than 16 mg/L were seen for one *Serratia*).

Figure 2:
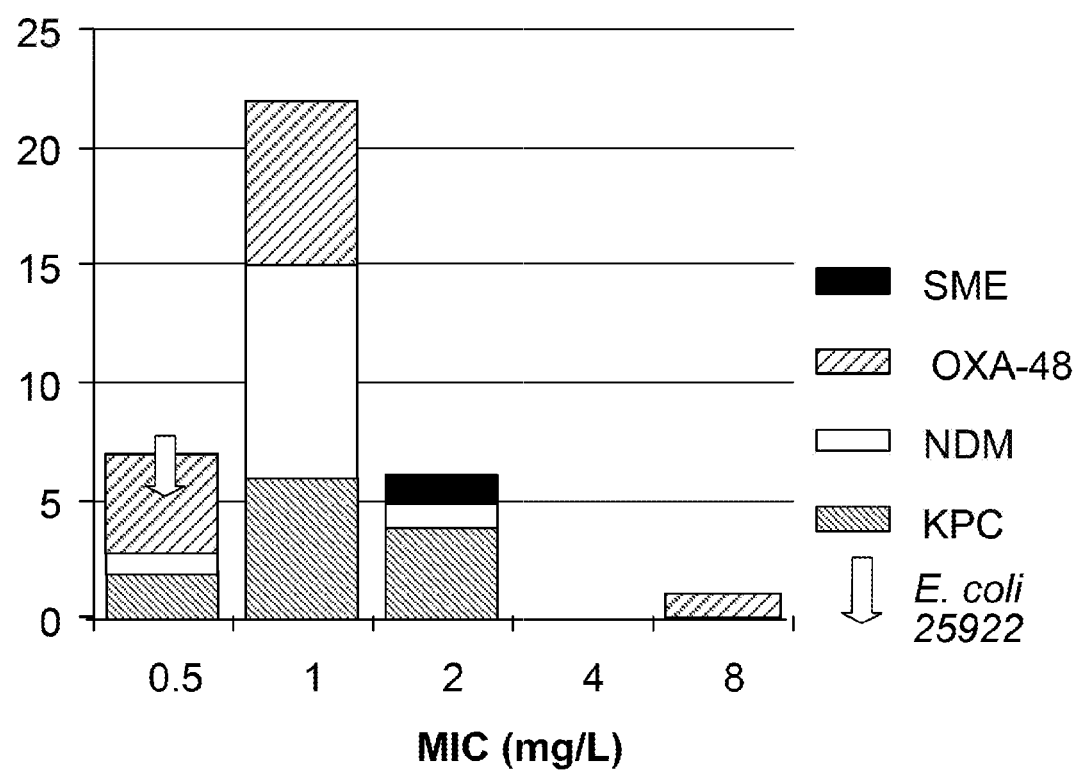
FIG. 2 provides a bar graph illustrating the MIC distributions of RX-04A for CPE (n=36).
Figure 3:
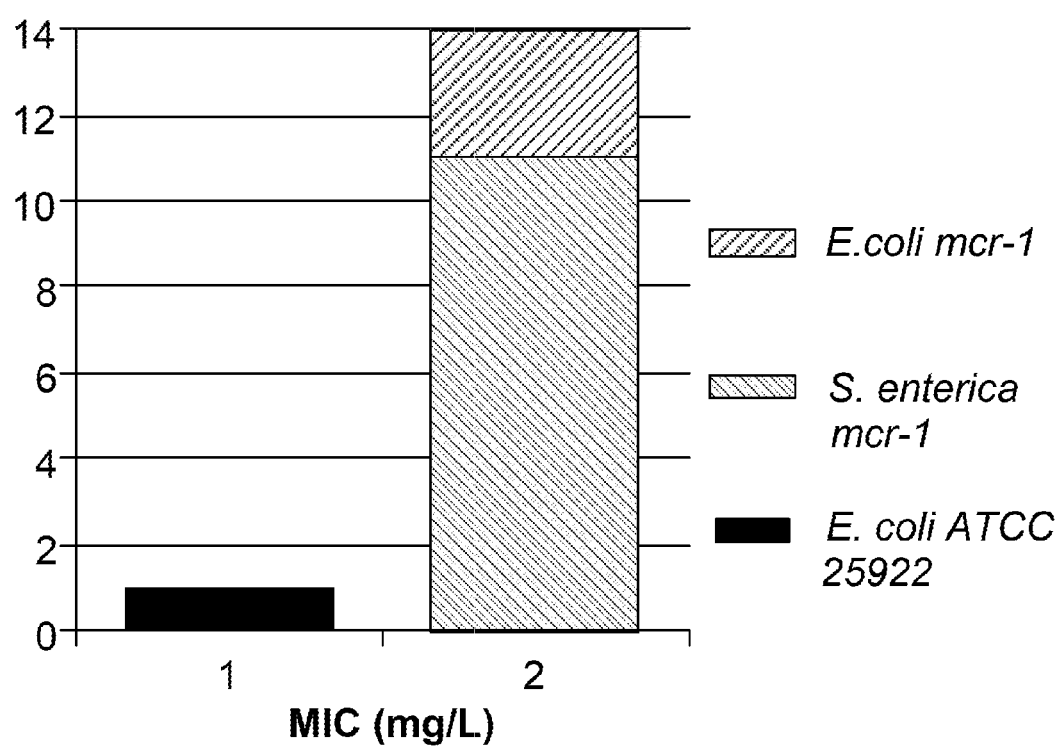
FIG. 3 provides a bar graph illustrating the MIC distributions of RX-04A for MCR-1 isolates (n=14).

MICs of RX-04A for 35/36 (97%) of CPE were within 4-fold of the MIC for *E. coli* ATCC 25922 (FIG. 2). MIC differentials for analogues RX-04B-D were similarly small. MICs of RX-04A for all MCR-1 isolates (n=14) were within 2-fold of that for *E. coli* ATCC 25922 (FIG. 3). MIC differentials for analogues RX-04B-D were similarly small. Acquisition of mcr-1 did not raise RX-04 MICs for *E. coli* DH10B (Table 5).

TABLE 5

MICs of RX04-A-D and colistin for *E. coli* DH10B and its mcr-1 transformant

| Strain | MIC (mg/L) | | | | |
| --- | --- | --- | --- | --- | --- |
| | RX-04A | RX-04B | RX-04C | RX-04D | COL |
| DH10B Recipient | 0.25 | 0.5 | 0.5 | 1 | 0.25 |
| MCR-1 Transformant | 0.25 | 0.5 | 0.5 | 1 | 4 |

Figure 4:
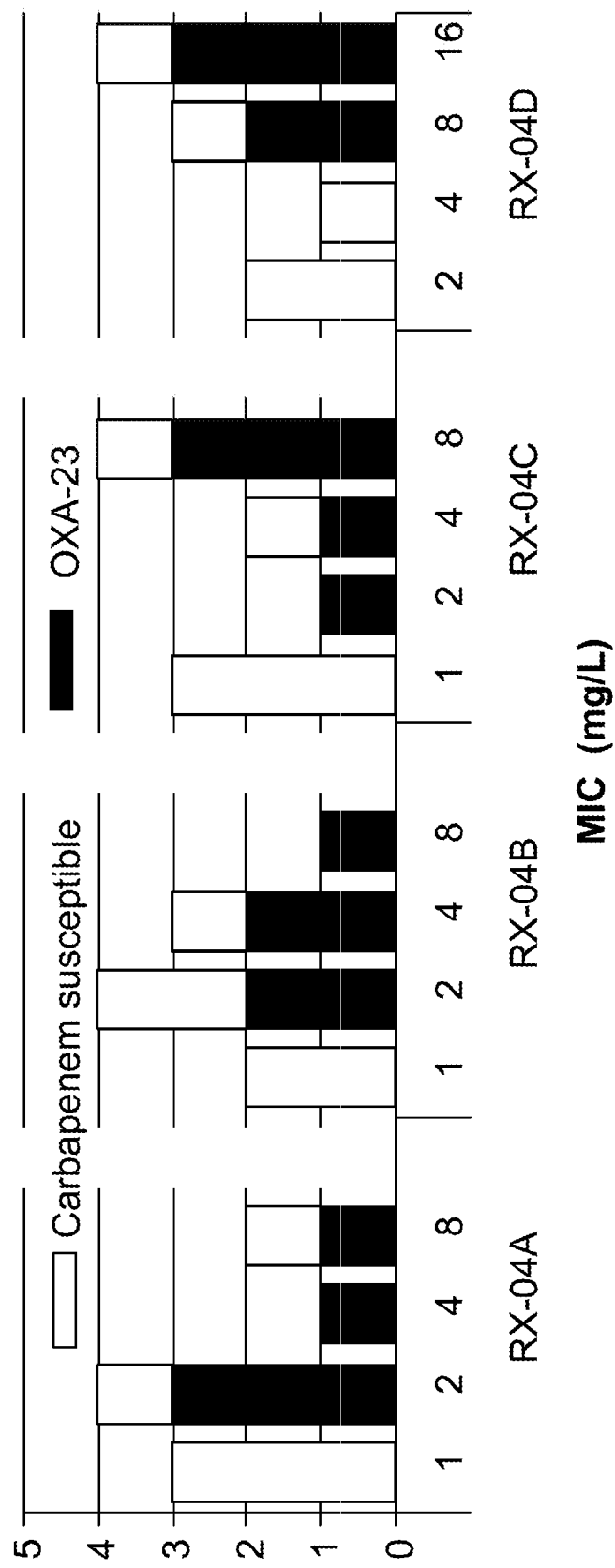
FIG. 4 provides a bar graph illustrating the MIC distributions of RX-04A-D for *A. baumannii* isolates (n=10).
Figure 5:
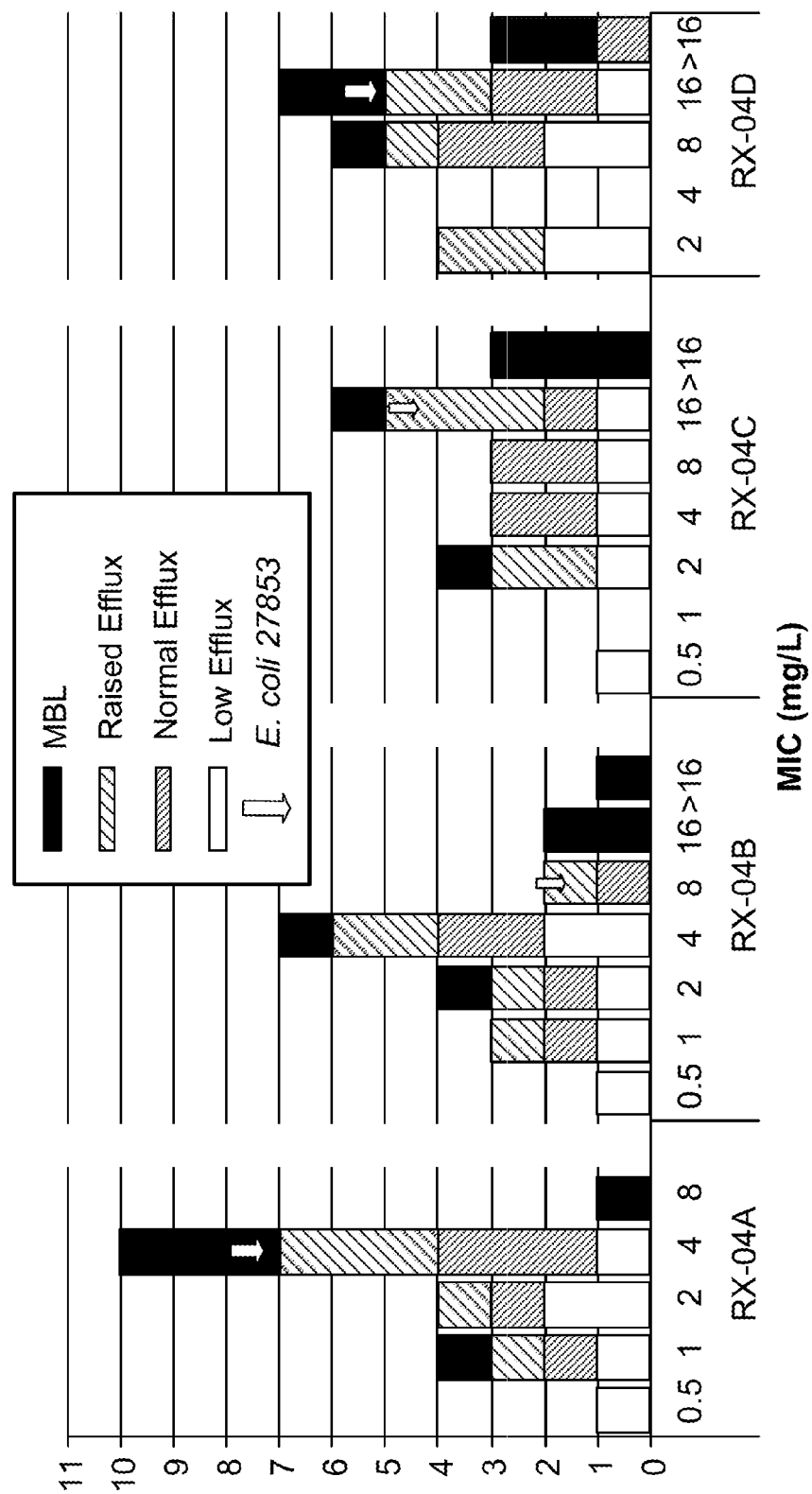
FIG. 5 provides bar graphs illustrating MIC distributions of RX-04A-D for *P. aeruginosa* (n=20).

MIC distributions of RX-04 analogues A-C straddled 1-8 mg/L for the 10 *A. baumannii*. RX-04A had the lowest MICs, with 7/10 values from 1-2 mg/L, D was the least active analogue (FIG. 4). MICs for *A. baumannii* with OXA-23 carbapenemases were mostly higher than carbapenem-susceptible isolates, but numbers were small and 3/5 OXA-23 isolates belonged to the same lineage (International Clone II; the other 2 were unique pulsotypes). RX-04A again was the most active analogue against *P. aeruginosa* isolates, with MICs from 1-4 mg/L for 19/20 (95%) isolates. Almost half (48%) of the MICs were ≥16 mg/L for analogues C and D (FIG. 5). MICs of all analogues tended to be higher for *P. aeruginosa* with 'normal' vs. low efflux, but not further raised for those with elevated efflux.

The four analogues had broad activity against Enterobacteriaceae and non-fermenters. RX-04A was the most active analogue with MICs mostly 1-2 mg/L for Enterobacteriaceae and *A. baumannii* and 1-4 mg/L for *P. aeruginosa*. Among Enterobacteriaceae, *E. coli* was the most susceptible species and *S. marcescens* the least susceptible. MICs for carbapenemase producers and MCR-1 isolates were only 2-4-fold above a highly susceptible control. Acquisition of MCR-1 did not affect susceptibility to these basic molecules, despite affective surface charge. RX-04A MICs were not raised in *P. aeruginosa* isolates with elevated efflux. MICs were slightly raised against multiresistant *A. baumannii*. Pyrrolocytosines showed promising activity against this challenging collection of multiresistant Gram-negative bacteria.

Example 2: In Vitro Antibacterial Susceptibility Testing

Antimicrobial susceptibility testing following Clinical Laboratory Standard Institute (CLSI) standards were performed for pyrrolocytosine compounds with reference licensed compounds against 30 strain diversity sets of Category A and B Bacterial pathogens *Burkholderia pseudomallei, Francisella tularensis, Burkholderia mallei, Bacillus anthracis*, and *Yersinia pestis*.

Experimental

Bacterial inoculums were prepared by suspending colonies into cation-adjusted Mueller-Hinton broth (CAMHB) from 18-24 h *B. anthracis, B. pseudomallei* and *B. mallei* plates; or 42-48 h *F. tularensis* and *Y. pestis* plates that were incubated at 35° C. Sheep Blood agar (SBA) plates were used for *B. anthracis* and *Y. pestis*, and chocolate agar for *F. tularensis, B. pseudomallei* and *B. mallei*. Suspended cultures were diluted with CAMHB to a bacterial cell density of $10^5$ CFU/mL adjusted based on comparison to 0.5 McFarland standard.

Experimental Protocol

MICs were determined by the microdilution method in 96-well plates according to CLSI guidelines. Antibiotics were serially diluted two-fold in 50 μL of CAMHB. For all steps with *F. tularensis*, CAMHB was supplemented with 2% Isovitalex (Becton Dickinson). The antibiotic ranges used for the compounds was 8-0.004 μg/mL for the diversity strains of *F. tularensis* (FT), *Y. pestis* (YP), *B. mallei* (BM), and *B. pseudomallei* (BP), and 16-0.008 μg/mL for *B. anthracis* (BA) diversity set, based on a final well volume of 100 μL after inoculation. Plates were incubated at 35° C. MICs were determined visually at 18-24 h or 42-48 h (*F. tularensis* and *Y. pestis*).

Quality control of antibiotic stocks were established by using *E. coli* ATCC 25922 (EC), *P. aeruginosa* ATCC 27853 (PA), and *S. aureus* ATCC 29213 (SA). Inoculums were prepared as described above from 18-24 h SBA plates. Conversion factors; *E. coli* $6.83\times10^8$ CFU/ml/OD, *P. aeruginosa* $5.74\times10^{10}$ CFU/ml/OD and *S. aureus* $2.07\times10^{10}$ CFU/ml/OD.

Drugs and Materials

The compounds tested (shown in Table 6 below) were: RX-D1 (10.9 mg), RX-D2 (11 mg), RX-D3 (12.1 mg), RX-D4 (10.9 mg), RX-D5 (10.5 mg), RX-D6 (12.4 mg), RX-D7 (11.5 mg), RX-D8 (11.2 mg), RX-D9 (10.7 mg), RX-D10 (11.7 mg), RX-D11 (11 mg), and RX-D13 (Formula (III); 10.3 mg). The compounds were provided in powder form and stocks of 5.12 mg/mL were made in 100% DMSO after considering the purity. Prior to use, this solution was further diluted in CAMHB for loading onto 96 microwell plates as described in the experimental protocol section above. Comparator antibiotics ciprofloxacin, ceftazidime, and azithromycin were all purchased from USP, made into 5.12 mg/mL stocks according to the CLSI M100-S18 Table 4 guidelines and stored at −70° C. until use.

TABLE 6

Tested compounds

RX-D1

RX-D2

RX-D3

TABLE 6-continued
Tested compounds
RX-D4
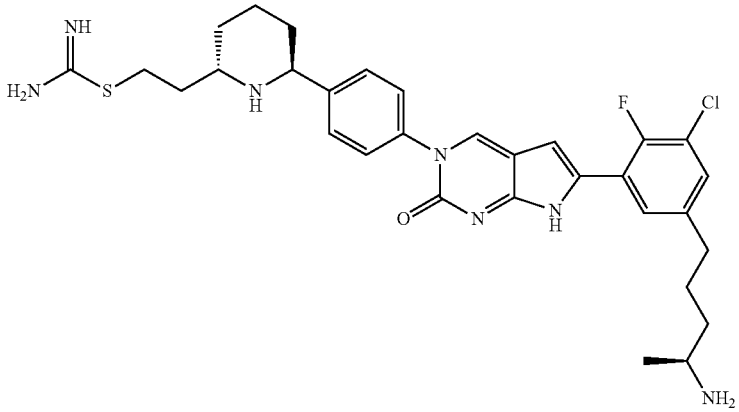 [SMILES: C[C@H](N)CCCc1cc(Cl)c(F)c(-c2cc3cn(-c4ccc([C@@H]5CCC[C@@H](CCSC(=N)N)N5)cc4)c(=O)nc3[nH]2)c1]
RX-D5
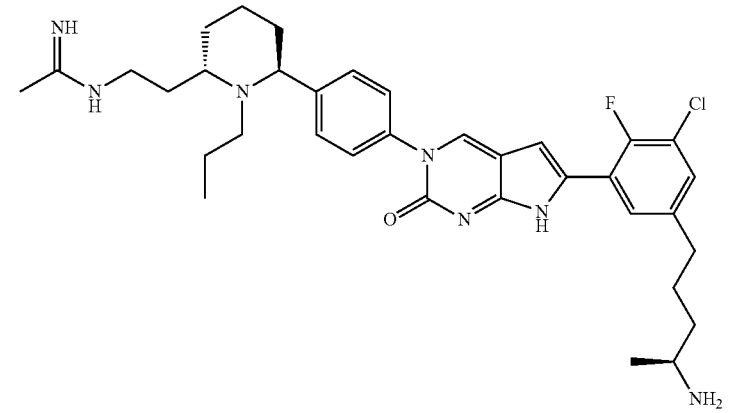 [SMILES: CCCN1[C@H](CCNC(C)=N)CCC[C@H]1c1ccc(-n2cc3cc(-c4cc(CCC[C@H](C)N)cc(Cl)c4F)[nH]c3nc2=O)cc1]
RX-D6
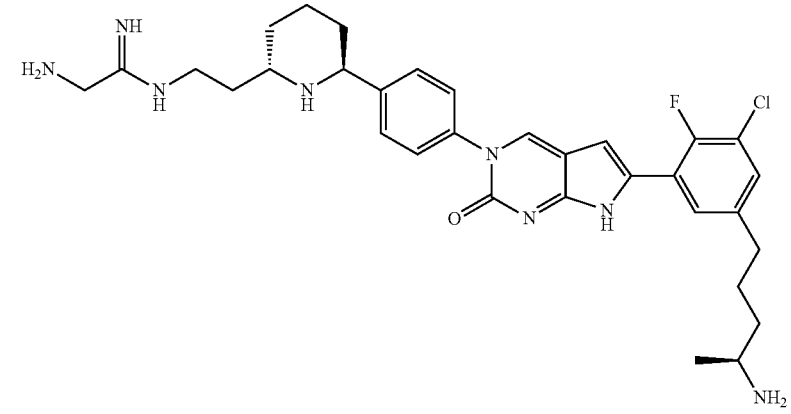 [SMILES: C[C@H](N)CCCc1cc(Cl)c(F)c(-c2cc3cn(-c4ccc([C@@H]5CCC[C@@H](CCNC(=N)CN)N5)cc4)c(=O)nc3[nH]2)c1]

TABLE 6-continued

Tested compounds

RX-D7

RX-D8

RX-D9

TABLE 6-continued

Tested compounds

RX-D10

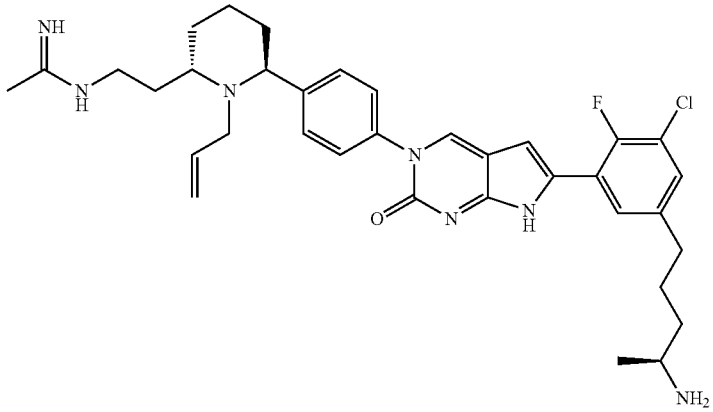 [SMILES: C=CCN1[C@H](CCNC(C)=N)CCC[C@H]1c1ccc(-n2cc3cc(-c4cc(CCC[C@H](C)N)cc(Cl)c4F)[nH]c3nc2=O)cc1]

RX-D11

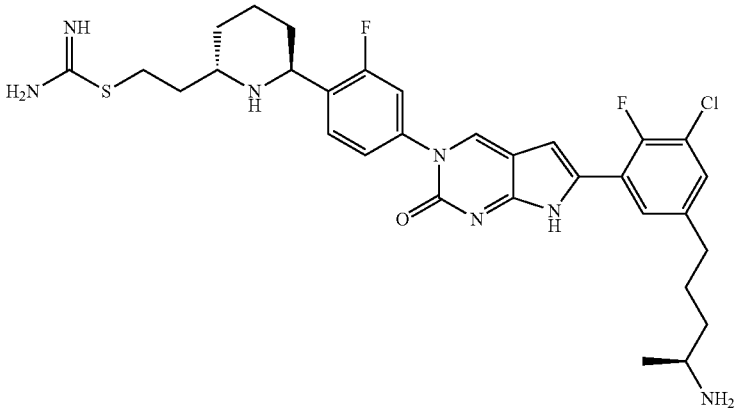 [SMILES: C[C@H](N)CCCc1cc(Cl)c(F)c(-c2cc3cn(-c4ccc([C@@H]5CCC[C@@H](CCSC(=N)N)N5)c(F)c4)c(=O)nc3[nH]2)c1]

RX-D13
(Formula (III))

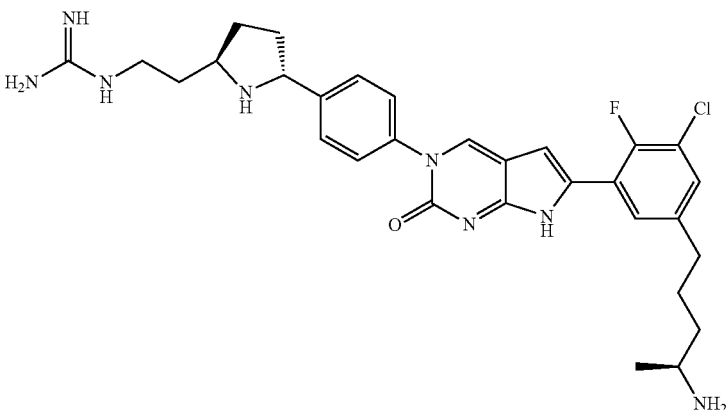

Results

Results are summarized in Tables 7 and 8 MIC data acceptance for the three compounds was based on CLSI approved MIC ranges for *E. coli* ATCC 25922, *S. aureus* ATCC 29213 and *P. aeruginosa* ATCC 27853. The MIC results for ciprofloxacin, azithromycin, and ceftazidime were compared to published CLSI ranges (Clinical and Laboratory Standards Institute. 2013). MICs for comparator compounds (Table 7) met acceptable criteria for EC and SA, while with PA the MIC value was a dilution lower than acceptable range. However, since two out of the three QC's fell in range, the results are considered valid and are accepted.

Overall most compounds were effective against the BA, FT, YP and BM diversity sets with MIC90 values between ≤0.008 to of 1 µg/mL. While these compounds did better than the comparator for the BM diversity, the $MIC_{90}$ against the BP diversity set was between 4→8 µg/mL for

TABLE 7

| MIC summary against Category A pathogens | | | | | | | | | |
|---|---|---|---|---|---|---|---|---|---|
| | *B. anthracis* (n = 30) | | | *Y. pestis* (n = 30) | | | *F. tulerensis* (n = 30) | | |
| | MIC range | $MIC_{50}$ | $MIC_{90}$ | MIC range | $MIC_{50}$ | $MIC_{90}$ | MIC range | $MIC_{50}$ | $MIC_{90}$ |
| RX-D1 | ≤0.008-0.12 | 0.06 | 0.06 | 0.008-0.25 | 0.12 | 0.25 | 0.06-0.5 | 0.12 | 0.25 |
| RX-D2 | 0.03-0.12 | 0.06 | 0.12 | 0.03-1 | 0.25 | 1 | 0.015-1 | 0.12 | 0.25 |
| RX-D3 | 0.03-0.25 | 0.12 | 0.12 | 0.06-0.5 | 0.12 | 0.25 | 0.015-2 | 0.12 | 0.25 |
| RX-D4 | 0.015-0.12 | 0.06 | 0.12 | ≤0.004-0.5 | 0.12 | 0.25 | ≤0.004-0.5 | 0.03 | 0.06 |
| RX-D5 | 0.015-0.12 | 0.06 | 0.06 | 0.03-0.5 | 0.12 | 0.25 | ≤0.004-1 | 0.06 | 0.12 |
| RX-D6 | 0.06-0.25 | 0.12 | 0.25 | 0.015-1 | 0.5 | 1 | 0.03-0.5 | 0.06 | 0.25 |
| RX-D7 | ≤0.008-0.06 | ≤0.008 | 0.03 | 0.03-1 | 0.25 | 0.5 | 0.06-0.5 | 0.12 | 0.25 |
| RX-D8 | ≤0.008-0.015 | ≤0.008 | ≤0.008 | 0.06-0.5 | 0.25 | 0.5 | ≤0.004-0.12 | 0.03 | 0.06 |
| RX-D9 | ≤0.008-0.12 | 0.06 | 0.12 | 0.06-0.5 | 0.12 | 0.25 | 0.03-2 | 0.12 | 0.25 |
| RX-D10 | ≤0.008-0.25 | 0.12 | 0.25 | 0.03-0.5 | 0.12 | 0.5 | 0.03-2 | 0.12 | 0.5 |
| RX-D11 | ≤0.008-0.5 | 0.12 | 0.25 | ≤0.004-0.25 | 0.12 | 0.25 | 0.008-1 | 0.06 | 0.12 |
| RX-D13 | ≤0.008-0.12 | 0.06 | 0.06 | 0.03-0.25 | 0.06 | 0.25 | ≤0.004-0.12 | 0.015 | 0.06 |
| Ciproflo-xacin | 0.015-0.06 | 0.03 | 0.06 | ≤0.004-0.06 | 0.015 | 0.03 | 0.008-0.5 | 0.015 | 0.03 |

TABLE 8

| MIC summary against Category B pathogens | | | | | | |
|---|---|---|---|---|---|---|
| | *B. mallei* (n = 30) | | | *B. pseudomallei* (n = 30) | | |
| | MIC range | $MIC_{50}$ | $MIC_{90}$ | MIC range | $MIC_{50}$ | $MIC_{90}$ |
| RX-D1 | 0.06-0.25 | 0.12 | 0.12 | 0.5-4 | 1 | 4 |
| RX-D2 | 0.06-0.5 | 0.12 | 0.25 | 0.25->8 | >8 | >8 |
| RX-D3 | 0.03-0.25 | 0.12 | 0.25 | 0.5-8 | 2 | 4 |
| RX-D4 | 0.03-0.12 | 0.12 | 0.12 | 0.25-8 | 1 | 4 |
| RX-D5 | 0.03-0.12 | 0.06 | 0.12 | 0.5->8 | 4 | 8 |
| RX-D6 | 0.12-0.25 | 0.12 | 0.25 | 1->8 | >8 | >8 |
| RX-D7 | 0.06-0.5 | 0.25 | 0.25 | 1->8 | 4 | 8 |
| RX-D8 | 0.03-0.25 | 0.06 | 0.12 | 0.5->8 | 8 | >8 |
| RX-D9 | 0.03-0.5 | 0.12 | 0.25 | 0.5-4 | 2 | 4 |
| RX-D10 | 0.06-0.25 | 0.12 | 0.25 | 0.25-8 | 2 | 4 |
| RX-D11 | 0.03-0.25 | 0.06 | 0.12 | 0.25-8 | 1 | 2 |
| RX-D13 | 0.008-0.12 | 0.06 | 0.12 | 0.25-8 | 1 | 4 |
| Azithromycin | 0.06-1 | 0.5 | 1 | — | — | — |
| Ceftazidime | — | — | — | ≤0.03-32 | 1 | 1 |

INCORPORATION BY REFERENCE

The entire disclosure of each of the patent documents and scientific articles referred to herein is incorporated by reference for all purposes.

EQUIVALENTS

The disclosure can be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

What is claimed is:

1. A method of treating, preventing, reducing the risk of, or delaying the onset of a microbial infection in a subject, the method comprising administering to the subject a therapeutically effective amount of a compound of Formula (I):

(I)

or a tautomer thereof or a pharmaceutically acceptable salt of the compound or tautomer, wherein:

$R_1$ is selected from H and halo;

$R_2$ is selected from H, halo, $C_{1-6}$ alkyl, $C_{1-4}$ haloalkyl, and $OR^{a1}$;

$R_3$ is selected from H, $C_{1-6}$ alkyl, and $C_{1-4}$ haloalkyl;

W is selected from N and $CR_4$;

$R_4$ is selected from H, halo, $OR^{a2}$, $SR^{a2}$, 5-6 membered heterocycloalkyl, $S(O)_2R^{b2}$, $C_{1-6}$ alkyl, $C_{1-4}$ alkylthio, and $C_{2-6}$ alkenyl, wherein the $C_{1-6}$ alkyl is optionally substituted with a substituent selected from $OR^{a2}$;

$R_5$ is selected from H, halo, $C_{1-6}$ alkyl, and $C_{2-6}$ alkenyl, wherein the $C_{1-6}$ alkyl is optionally substituted with a substituent selected from $OR^{a2}$;

$R_6$ is selected from H, $C_{1-6}$ alkyl, and $C_{2-6}$ alkenyl, wherein the $C_{1-6}$ alkyl is optionally substituted with $OR^{a3}$;

$R_7$ is selected from H and $C_{1-6}$ alkyl; or $R_6$ and $R_7$ together with the carbon atoms to which they are attached and the nitrogen atom connecting the two carbon atoms forms a ring of the formula:

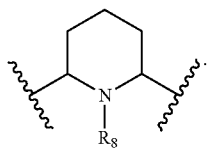

$R_8$ is selected from H, $C_{1-6}$ alkyl, and $C_{1-4}$ haloalkyl;
X is selected from O and $NR^N$;
$R^N$ is selected from H and $C_{1-4}$ alkyl;
$R_A$ is H;
$R_B$ is H; or
$R_A$ and $R_B$ together with the nitrogen atom to which they are attached form a 5- to 6-membered heterocycloalkyl ring containing 1 or 2 heteroatoms selected from N, O and S, wherein the 5- to 6-membered heterocycloalkyl is optionally substituted with halo;
$R_9$ is selected from $C_{1-6}$ alkyl, $C_{2-6}$ alkenyl, $C_{3-5}$ cycloalkyl, wherein the $C_{1-6}$ alkyl is optionally substituted with a substituent selected from $OR^{a3}$ and $SR^{a3}$;
$R_{10}$ is selected from H, $C_{2-4}$ alkenyl, $C_{1-4}$ haloalkyl and $C_{1-4}$ alkyl optionally substituted with a substituent selected from amino, $C_{1-4}$ alkoxy, $C_{3-5}$ cycloalkyl, and 3- to 6-membered heterocycloalkyl;
$R_{11}$ is H or $C_{1-3}$ alkyl, wherein the $C_{1-3}$ alkyl is optionally substituted with OH; and
each of $R^{a1}$, $R^{a2}$, $R^{a3}$, and $R^{b2}$ is independently selected from H, $C_{1-6}$ alkyl and $C_{1-4}$ haloalkyl;
wherein the infection is caused by or involves one or more microorganisms which are capable of being used as biological weapons or which are extremely-drug resistant Gram-positive or Gram-negative pathogens.

2. The method of claim 1, wherein $R_1$ is selected from H and fluoro.

3. The method of claim 1, wherein $R_2$ is selected from H, halo, $C_{1-4}$ haloalkyl, and $C_{1-4}$ haloalkoxy.

4. The method of claim 1, wherein $R_2$ is selected from H, chloro, trifluoromethyl, and trifluoromethoxy.

5. The method of claim 1, wherein $R_3$ is selected from H and trifluoromethyl.

6. The method of claim 1, wherein $R_4$ is selected from H, 6-membered heterocycloalkyl, $S(O)_2 C_{1-4}$ alkyl, fluoro, chloro, methylthio, methoxy, methyl, $S(=O)_2$(methyl), trifluoromethoxy, and N-morpholino.

7. The method of claim 1, wherein W is $CR_4$ and $R_4$ is selected from H, halo, $S(C_{1-6}$ alkyl), fluoro, and methylthio.

8. The method of claim 1, wherein $R_5$ is selected from H and fluoro.

9. The method of claim 1, wherein $R_6$ is selected from H, ethenyl, and hydroxymethyl.

10. The method of claim 1, wherein $R_7$ is selected from H and methyl.

11. The method of claim 1, wherein $R_6$ and $R_7$ form a ring of the formula:

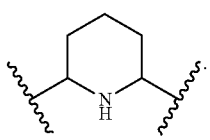 [SMILES: *C1CCCC(*)N1]

12. The method of claim 1, wherein $R_6$ and $R_7$ form a ring of the formula:

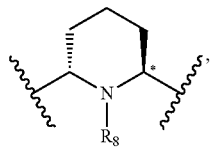

wherein the * indicates the ring carbon that is attached to the ring containing W.

13. The method of claim 1, wherein $R_8$ is selected from H and 3-fluoropropyl.

14. The method of claim 1, wherein $R_8$ is $C_{1-4}$ haloalkyl.

15. The method of claim 1, wherein $R^N$ is selected from H and methyl.

16. The method of claim 1, wherein $R_A$ is H and $R_B$ is H.

17. The method of claim 1, wherein $R_A$ and $R_B$ together with the nitrogen atom to which they are attached form a ring selected from the formulae:

(i)

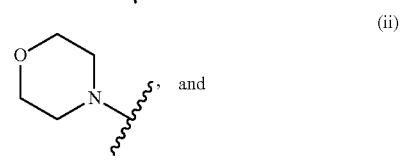

(ii)

and

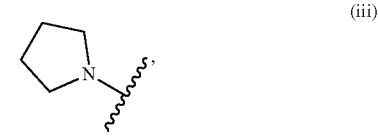

(iii)

wherein any one of the formulae (i)-(iii) is optionally substituted with halo.

18. The method of claim 1, wherein $R_A$ and $R_B$ together with the nitrogen atom to which they are attached form a ring of the formula:

(iiia)

19. The method of claim 1, wherein $R_9$ is selected from $C_{1-6}$ alkyl, $C_{1-6}$ hydroxyalkyl, methyl, $C_{2-6}$ alkenyl, ethenyl $C_{1-6}$ hydroxymethyl, methoxymethyl, methylthiomethyl, cyclopropyl and $C_{3-5}$ cycloalkyl, wherein the $C_{1-6}$ alkyl is optionally substituted with a substituent selected from $C_{1-6}$ alkoxy and $S(C_{1-6}$ alkyl).

20. The method of claim 1, wherein $R_{10}$ is selected from H and $C_{1-4}$ alkyl optionally substituted with a substituent selected from amino, $C_{1-4}$ alkoxy, $C_{3-5}$ cycloalkyl, and 3- to 6-membered heterocycloalkyl.

21. The method of claim 1, wherein:
$R_1$ is selected from H and fluoro;
$R_2$ is selected from H, halo, $C_{1-4}$ haloalkyl, and $C_{1-4}$ haloalkoxy;
$R_3$ is selected from H and $C_{1-4}$ haloalkyl;
W is $CR_4$ and $R_4$ is selected from H, halo, $C_{1-6}$ alkyl, $C_{1-4}$ alkoxy, $C_{1-4}$ haloalkoxy, $S(C_{1-4}$ alkyl), 6-membered heterocycloalkyl, and $S(O)_2C_{1-4}$ alkyl;
$R_5$ is selected from H and fluoro;
$R_6$ is selected from H, ethenyl, and $C_{1-6}$ hydroxyalkyl;
$R_7$ is selected from H and methyl; or
$R_6$ and $R_7$ form a ring of the formula:

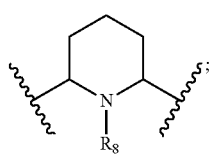

$R_8$ is selected from H and $C_{1-4}$ haloalkyl;
$R^N$ is selected from H and methyl;
$R_A$ is H and $R_B$ is H; or
$R_A$ and $R_B$ together with the nitrogen atom to which they are attached form a ring selected from the formulae:

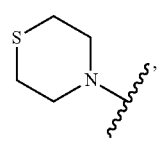 (i)

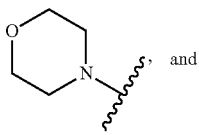 (ii) and

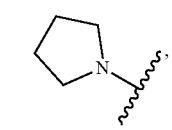 (iii)

wherein any one of the formulae (i)-(iii) is optionally substituted with halo;
$R_9$ is selected from $C_{1-6}$ alkyl, $C_{1-6}$ hydroxyalkyl, and $C_{3-5}$ cycloalkyl, wherein the $C_{1-6}$ alkyl is optionally substituted with a substituent selected from $C_{1-6}$ alkoxy and $S(C_{1-6}$ alkyl);
$R_{10}$ is selected from H, methyl, ethyl, n-propyl and i-propyl; and
$R_{11}$ is H.

22. The method of claim 1, wherein:
$R_1$ is selected from H and fluoro;
$R_2$ is selected from H, chloro, trifluoromethyl, and trifluoromethoxy;
$R_3$ is selected from H and trifluoromethyl;
W is $CR_4$ and $R_4$ is selected from H, fluoro, chloro, methylthio, methoxy, methyl, $S(=O)_2$(methyl), trifluoromethoxy, and N-morpholino;
$R_5$ is selected from H and fluoro;
$R_6$ is selected from H, ethenyl, and hydroxymethyl;
$R_7$ is selected from H and methyl; or
$R_6$ and $R_7$ form a ring of the formula:

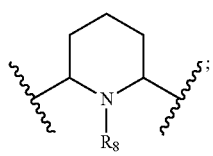

$R_8$ is selected from H and 3-fluoropropyl;
$R^N$ is selected from H and methyl;
$R_A$ is H and $R_B$ is H;
$R_9$ is selected from methyl, $C_{1-6}$ hydroxymethyl, methoxymethyl, methylthiomethyl, ethenyl, and cyclopropyl;
$R_{10}$ is selected from H, methyl, ethyl, n-propyl and i-propyl; and
$R_{11}$ is H.

23. The method of claim 1, wherein:
$R_1$ is selected from H and fluoro;
$R_2$ is selected from chloro and trifluoromethyl;
$R_3$ is H;
W is $CR_4$ and $R_4$ is selected from H and fluoro;
$R_5$ is H;
$R_6$ and $R_7$ form a ring of the formula:

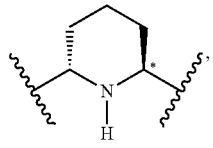 [SMILES: *[C@@H]1CCC[C@@H](*)N1]

wherein the * indicates the ring carbon that is attached to the ring containing W;
X is NH;
$R_A$ is H and $R_B$ is H;
$R_9$ is selected from methyl, and methylthiomethyl;
$R_{10}$ is selected from H, methyl, ethyl, n-propyl and i-propyl; and
$R_{11}$ is H.

24. The method of claim 1, wherein the compound of Formula (I) has the Formula (A):

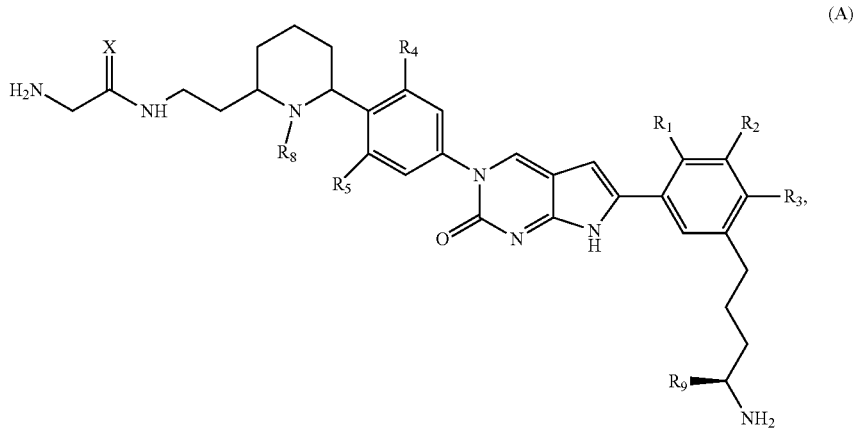

(A)

or a tautomer thereof or a pharmaceutically acceptable salt of the compound or tautomer.

25. The method of claim 1, wherein the compound of Formula (I) has the Formula (Ia):

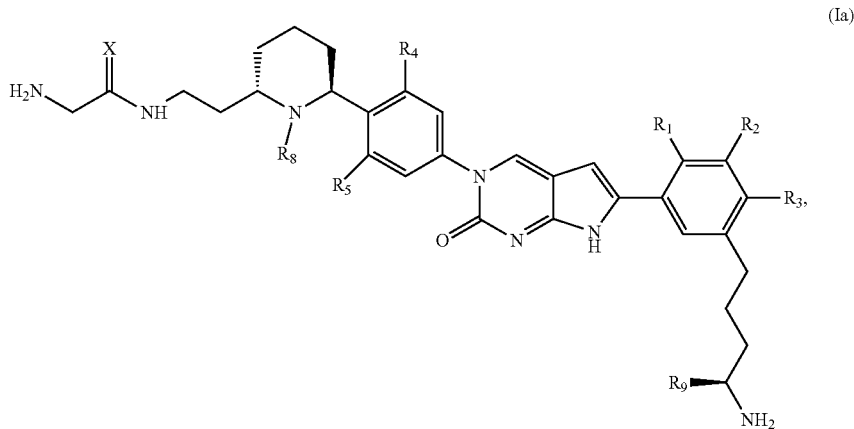

(Ia)

or a tautomer thereof or a pharmaceutically acceptable salt of the compound or tautomer.

26. The method of claim 1, wherein the compound of Formula (I) has a formula selected from Formulae (Ib)-(Id):

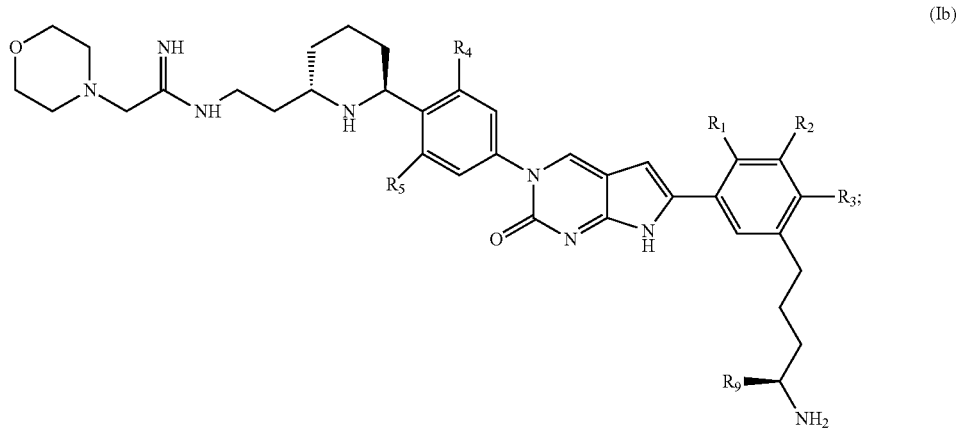

(Ib)

or a tautomer thereof or a pharmaceutically acceptable salt of the compound or tautomer.

27. The method of claim 1, wherein the compound of Formula (I) is selected from any one of the compounds listed in Table 1, Table 1a, Table 1b, or Table 1c, or a tautomer thereof or a pharmaceutically acceptable salt of the compound or tautomer.

28. The method of claim 1, wherein the one or more microorganisms are categorized in biodefense category A or biodefense category B.

29. The method of claim 1, wherein the one or more microorganisms are selected from the group consisting of *Bacillus anthracis* (anthrax), *Yersinia pestis* (plague), and *Francisella tularensis* (tularemia), *Burkholderia pseudomallei* (melioidosis), *Coxiella burnetii* (Q fever), *Brucella* species (brucellosis), *Burkholderia mallei* (glanders), *Chlamydia psittaci* (psittacosis), *Rickettsia prowazekii* (typhus fever), diarrheagenic *E. coli*, pathogenic Vibrios, *Shigella* species, *Salmonella*, *Listeria monocytogenes*, *Campylobacter jejuni*, and *Yersinia enterocolitica*.

* * * * *